US012370194B2

(12) United States Patent
Yates

(10) Patent No.: US 12,370,194 B2
(45) Date of Patent: *Jul. 29, 2025

(54) METALLOENZYME INHIBITOR COMPOUNDS

(71) Applicant: Eikonizo Therapeutics, Inc., Cambridge, MA (US)

(72) Inventor: Christopher M. Yates, Belmont, MA (US)

(73) Assignee: Eikonizo Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/443,509

(22) Filed: Feb. 16, 2024

(65) Prior Publication Data

US 2024/0307391 A1    Sep. 19, 2024

Related U.S. Application Data

(63) Continuation of application No. 17/336,444, filed on Jun. 2, 2021, now Pat. No. 11,938,134, which is a continuation of application No. 16/518,279, filed on Jul. 22, 2019, now abandoned, which is a continuation of application No. 15/917,555, filed on Mar. 9, 2018, now Pat. No. 10,357,493.

(60) Provisional application No. 62/513,145, filed on May 31, 2017, provisional application No. 62/469,565, filed on Mar. 10, 2017.

(51) Int. Cl.
*C07D 413/14* (2006.01)
*A61K 31/506* (2006.01)
*C07D 413/04* (2006.01)

(52) U.S. Cl.
CPC .......... *A61K 31/506* (2013.01); *C07D 413/04* (2013.01); *C07D 413/14* (2013.01)

(58) Field of Classification Search
CPC ........................... A61K 31/506; C07D 413/04
See application file for complete search history.

(56) References Cited

U.S. PATENT DOCUMENTS

| | | | |
|---|---|---|---|
| 4,205,085 A | 5/1980 | Shepherd | |
| 5,231,097 A | 7/1993 | Klausener et al. | |
| 5,272,158 A | 12/1993 | Hartman et al. | |
| 5,686,018 A | 11/1997 | Demus et al. | |
| 5,728,844 A | 3/1998 | Muller et al. | |
| 5,728,845 A | 3/1998 | Muller et al. | |
| 8,778,931 B2 | 7/2014 | Gould | |
| 9,096,518 B2 | 8/2015 | Blackburn et al. | |
| 9,145,405 B2 | 9/2015 | Luo et al. | |
| 9,650,379 B2 | 5/2017 | Lee et al. | |
| 10,357,493 B2 | 7/2019 | Yates | |
| 10,774,179 B2 | 9/2020 | Kember et al. | |
| 11,938,134 B2 * | 3/2024 | Yates | C07D 413/14 |
| 2005/0165015 A1 | 7/2005 | Ncube et al. | |
| 2006/0052599 A1 | 3/2006 | Ishibashi et al. | |
| 2006/0142321 A1 | 6/2006 | Jover et al. | |
| 2006/0142332 A1 | 6/2006 | Torrens Jover et al. | |
| 2008/0214603 A1 | 9/2008 | Torrens Jover et al. | |
| 2009/0036480 A1 | 2/2009 | Torrens Jover et al. | |
| 2009/0074717 A1 | 3/2009 | Leivers et al. | |
| 2009/0197880 A1 | 8/2009 | Leivers et al. | |
| 2009/0247757 A1 | 10/2009 | Li et al. | |
| 2010/0130499 A1 | 5/2010 | Tafesse | |
| 2011/0039827 A1 | 2/2011 | Blackburn et al. | |
| 2011/0212969 A1 | 9/2011 | Blackburn et al. | |
| 2011/0251184 A1 | 10/2011 | Blackburn et al. | |
| 2011/0288117 A1 | 11/2011 | Gould et al. | |
| 2012/0040953 A1 | 2/2012 | Barba et al. | |
| 2012/0053201 A1 | 3/2012 | Blackburn et al. | |
| 2012/0094997 A1 | 4/2012 | England et al. | |
| 2012/0121502 A1 | 5/2012 | van Duzer et al. | |
| 2012/0202834 A1 | 8/2012 | Aspnes et al. | |
| 2014/0275093 A1 | 9/2014 | Blackburn et al. | |
| 2014/0329825 A1 | 11/2014 | Hebach et al. | |
| 2015/0197497 A1 | 7/2015 | Abeywickrama et al. | |
| 2015/0359794 A1 | 12/2015 | Benz et al. | |
| 2016/0039789 A1 | 2/2016 | England et al. | |
| 2017/0096405 A1 | 4/2017 | Song et al. | |
| 2017/0183325 A1 | 6/2017 | Chen et al. | |
| 2017/0313698 A1 | 11/2017 | Shuttleworth et al. | |
| 2017/0349540 A1 | 12/2017 | Hooker et al. | |
| 2018/0215726 A1 | 8/2018 | Holson et al. | |
| 2018/0215743 A1 | 8/2018 | Lee et al. | |
| 2018/0256572 A1 | 9/2018 | Yates | |
| 2018/0273495 A1 | 9/2018 | Kim et al. | |
| 2019/0077786 A1 | 3/2019 | Ueng et al. | |
| 2019/0135799 A1 | 5/2019 | Ito et al. | |
| 2020/0171028 A1 | 6/2020 | Yates | |

(Continued)

FOREIGN PATENT DOCUMENTS

CN    101573333 A    11/2009
CN    105884767 A    8/2016

(Continued)

OTHER PUBLICATIONS

International Preliminary Report on Patentability mailed Aug. 15, 2024 for Application No. PCT/US2023/012174.
International Preliminary Report on Patentability mailed Oct. 17, 2024 for Application No. PCT/US2023/017894.
International Preliminary Report on Patentability mailed Oct. 17, 2024 for Application No. PCT/US2023/017900.
James et al., Development of EKZ-102, a potent and selective CNS-penetrant HDAC6 inhibitor with the potential to benefit a broad population of people with ALS. Eikonizo Therapeutics. Oct. 23, 2024. Poster. 3 pages.
Partial Supplementary European Search Report mailed Jul. 6, 2023 for European Application No. 20847655.6.

(Continued)

*Primary Examiner* — Paul V Ward
(74) *Attorney, Agent, or Firm* — Wolf, Greenfield & Sacks, P.C.

(57) ABSTRACT

Provided are compounds having HDAC6 modulating activity, and methods of treating diseases, disorders or symptoms thereof mediated by HDAC6.

21 Claims, No Drawings

(56) References Cited

U.S. PATENT DOCUMENTS

| | | |
|---|---|---|
| 2021/0188831 A1 | 6/2021 | Lee et al. |
| 2021/0253555 A1 | 8/2021 | Zheng et al. |
| 2022/0041584 A1 | 2/2022 | Piscopio et al. |
| 2022/0088018 A1 | 3/2022 | Yates |
| 2022/0098180 A1 | 3/2022 | Ito et al. |
| 2022/0144815 A1 | 5/2022 | Brunet et al. |
| 2022/0251043 A1 | 8/2022 | Pan et al. |
| 2022/0281814 A1 | 9/2022 | Wagner et al. |
| 2024/0174616 A1 | 5/2024 | Wagner et al. |

FOREIGN PATENT DOCUMENTS

| | | |
|---|---|---|
| CN | 108976223 A | 12/2018 |
| CN | 109651357 A | 4/2019 |
| CN | 110950860 A | 4/2020 |
| CN | 112794860 A | 5/2021 |
| DE | 3929233 A1 | 3/1991 |
| DE | 4029466 A1 | 3/1991 |
| DE | 4307243 A1 | 10/1993 |
| DE | 10312963 A1 | 10/2004 |
| EP | 540334 A1 | 5/1993 |
| EP | 625513 A1 | 11/1994 |
| EP | 2624832 B1 | 9/2017 |
| JP | S58-170780 A | 10/1983 |
| JP | H04-272989 A | 9/1992 |
| JP | H07-206829 A | 8/1995 |
| JP | H10-251255 A | 9/1998 |
| JP | 2002-305083 A | 10/2002 |
| JP | 2011-8205 A | 1/2011 |
| JP | 2011-148714 A | 8/2011 |
| JP | 2013-542994 A | 11/2013 |
| JP | 2017-190296 A | 10/2017 |
| WO | WO 1995/11228 A1 | 4/1995 |
| WO | WO 97/40017 A2 | 10/1997 |
| WO | WO 1998/45268 A1 | 10/1998 |
| WO | WO 1999/019419 A1 | 4/1999 |
| WO | WO 2000/015637 A1 | 3/2000 |
| WO | WO 2000/068230 A1 | 11/2000 |
| WO | WO 2001/072712 A1 | 10/2001 |
| WO | WO 2001/085695 A1 | 11/2001 |
| WO | WO 2002/002530 A1 | 1/2002 |
| WO | WO 2002/026696 A1 | 4/2002 |
| WO | WO 2002/026703 A1 | 4/2002 |
| WO | WO 2002/030879 A2 | 4/2002 |
| WO | WO 2002/098426 A1 | 12/2002 |
| WO | WO 2003/024448 A2 | 3/2003 |
| WO | WO 2003/041641 A2 | 5/2003 |
| WO | WO 2003/074038 A1 | 9/2003 |
| WO | WO 2003/082288 A1 | 10/2003 |
| WO | WO 2004/065354 A1 | 8/2004 |
| WO | WO 2004/069823 A1 | 8/2004 |
| WO | WO 2004/076386 A2 | 9/2004 |
| WO | WO 2004/082638 A2 | 9/2004 |
| WO | WO 2004/098609 A1 | 11/2004 |
| WO | WO 2005/000300 A1 | 1/2005 |
| WO | WO 2005/020921 A2 | 3/2005 |
| WO | WO 2005/051300 A2 | 6/2005 |
| WO | WO 2005/065681 A2 | 7/2005 |
| WO | WO 2005/066151 A1 | 7/2005 |
| WO | WO 2005/092899 A1 | 10/2005 |
| WO | WO 2006/018308 A1 | 2/2006 |
| WO | WO 2006/018309 A1 | 2/2006 |
| WO | WO 2006/044958 A1 | 4/2006 |
| WO | WO 2006/065842 A2 | 6/2006 |
| WO | WO 2006/066133 A2 | 6/2006 |
| WO | WO 2006/084186 A2 | 8/2006 |
| WO | WO 2006/087309 A1 | 8/2006 |
| WO | WO 2007/003604 A2 | 1/2007 |
| WO | WO 2007/011626 A2 | 1/2007 |
| WO | WO 2007/029035 A2 | 3/2007 |
| WO | WO 2007/056593 A2 | 5/2007 |
| WO | WO 2007/084390 A2 | 7/2007 |
| WO | WO 2007/084455 A1 | 7/2007 |
| WO | WO 2007/093827 A1 | 8/2007 |
| WO | WO 2007/098608 A1 | 9/2007 |
| WO | WO 2007/115408 A1 | 10/2007 |
| WO | WO 2008/016123 A1 | 2/2008 |
| WO | WO 2008/060721 A1 | 5/2008 |
| WO | WO 2008/064265 A2 | 5/2008 |
| WO | WO 2008/074132 A1 | 6/2008 |
| WO | WO 2008/097428 A2 | 8/2008 |
| WO | WO 2008/128335 A1 | 10/2008 |
| WO | WO 2009/011787 A1 | 1/2009 |
| WO | WO 2009/011876 A1 | 1/2009 |
| WO | WO 2009/027349 A2 | 3/2009 |
| WO | WO 2009/079011 A1 | 6/2009 |
| WO | WO 2009/112550 A1 | 9/2009 |
| WO | WO 2009/129036 A1 | 10/2009 |
| WO | WO 2009/129335 A2 | 10/2009 |
| WO | WO 2009/137462 A2 | 11/2009 |
| WO | WO 2010/028192 A1 | 3/2010 |
| WO | WO 2010/033906 A2 | 3/2010 |
| WO | WO 2010/043953 A2 | 4/2010 |
| WO | WO 2010/054278 A2 | 5/2010 |
| WO | WO 2010/075551 A1 | 7/2010 |
| WO | WO 2010/078449 A2 | 7/2010 |
| WO | WO 2010/081145 A1 | 7/2010 |
| WO | WO 2010/083141 A1 | 7/2010 |
| WO | WO 2010/086311 A1 | 8/2010 |
| WO | WO 2010/088414 A2 | 8/2010 |
| WO | WO 2010/122151 A1 | 10/2010 |
| WO | WO 2010/139966 A1 | 12/2010 |
| WO | WO 2010/151318 A1 | 12/2010 |
| WO | WO 2011/002520 A2 | 1/2011 |
| WO | WO 2011/038185 A1 | 3/2011 |
| WO | WO 2011/058582 A1 | 5/2011 |
| WO | WO 2011/088181 A1 | 7/2011 |
| WO | WO 2011/088187 A1 | 7/2011 |
| WO | WO 2011/088192 A1 | 7/2011 |
| WO | WO 2011/106632 A1 | 9/2011 |
| WO | WO 2011/133888 A1 | 10/2011 |
| WO | WO 2011/133920 A1 | 10/2011 |
| WO | WO 2011/137320 A2 | 11/2011 |
| WO | WO 2011/154374 A1 | 12/2011 |
| WO | WO 2011/154431 A1 | 12/2011 |
| WO | WO 2012/012320 A1 | 1/2012 |
| WO | WO 2012/027564 A1 | 3/2012 |
| WO | WO 2012/038438 A1 | 3/2012 |
| WO | WO 2012/045804 A1 | 4/2012 |
| WO | WO 2012/047852 A2 | 4/2012 |
| WO | WO 2012/068109 A2 | 5/2012 |
| WO | WO 2012/076898 A1 | 6/2012 |
| WO | WO 2012/085038 A1 | 6/2012 |
| WO | WO 2012/088015 A2 | 6/2012 |
| WO | WO 2012/103008 A1 | 8/2012 |
| WO | WO 2012/117027 A1 | 9/2012 |
| WO | WO 2012/120023 A1 | 9/2012 |
| WO | WO 2012/123916 A2 | 9/2012 |
| WO | WO 2012/136111 A1 | 10/2012 |
| WO | WO 2012/157984 A2 | 11/2012 |
| WO | WO 2012/158957 A2 | 11/2012 |
| WO | WO 2012/170867 A1 | 12/2012 |
| WO | WO 2013/006408 A1 | 1/2013 |
| WO | WO 2013/008162 A1 | 1/2013 |
| WO | WO 2013/009810 A1 | 1/2013 |
| WO | WO 2013/009812 A1 | 1/2013 |
| WO | WO 2013/009827 A1 | 1/2013 |
| WO | WO 2013/009830 A1 | 1/2013 |
| WO | WO 2013/059582 A2 | 4/2013 |
| WO | WO 2013/062344 A1 | 5/2013 |
| WO | WO 2013/063549 A1 | 5/2013 |
| WO | WO 2013/066831 A1 | 5/2013 |
| WO | WO 2013/066832 A1 | 5/2013 |
| WO | WO 2013/066833 A1 | 5/2013 |
| WO | WO 2013/066834 A1 | 5/2013 |
| WO | WO 2013/066835 A2 | 5/2013 |
| WO | WO 2013/066836 A1 | 5/2013 |
| WO | WO 2013/066838 A1 | 5/2013 |
| WO | WO 2013/066839 A2 | 5/2013 |
| WO | WO 2013/080120 A1 | 6/2013 |
| WO | WO 2013/085890 A1 | 6/2013 |
| WO | WO 2013/101600 A1 | 7/2013 |
| WO | WO 2013/155262 A2 | 10/2013 |
| WO | WO 2013/169574 A2 | 11/2013 |

(56) References Cited

FOREIGN PATENT DOCUMENTS

| | | |
|---|---|---|
| WO | WO 2013/185353 A1 | 12/2013 |
| WO | WO 2014/014900 A1 | 1/2014 |
| WO | WO 2014/049107 A1 | 4/2014 |
| WO | WO 2014/059306 A1 | 4/2014 |
| WO | WO 2014/159210 A1 | 10/2014 |
| WO | WO 2014/159214 A1 | 10/2014 |
| WO | WO 2014/159218 A1 | 10/2014 |
| WO | WO 2014/159224 A1 | 10/2014 |
| WO | WO 2014/172191 A1 | 10/2014 |
| WO | WO 2014/178606 A1 | 11/2014 |
| WO | WO 2014/179528 A2 | 11/2014 |
| WO | WO 2014/180984 A1 | 11/2014 |
| WO | WO 2014/181137 A1 | 11/2014 |
| WO | WO 2014/194280 A2 | 12/2014 |
| WO | WO 2014/202827 A1 | 12/2014 |
| WO | WO 2015/017546 A1 | 2/2015 |
| WO | WO 2015/052160 A1 | 4/2015 |
| WO | WO 2015/058106 A1 | 4/2015 |
| WO | WO 2015/087151 A1 | 6/2015 |
| WO | WO 2015/102426 A1 | 7/2015 |
| WO | WO 2015/137750 A1 | 9/2015 |
| WO | WO 2015/154064 A2 | 10/2015 |
| WO | WO 2015/165960 A1 | 11/2015 |
| WO | WO 2015/187542 A1 | 12/2015 |
| WO | WO 2016/012485 A1 | 1/2016 |
| WO | WO 2016/018795 A1 | 2/2016 |
| WO | WO 2016/031815 A1 | 3/2016 |
| WO | WO 2016/040223 A1 | 3/2016 |
| WO | WO 2016/055786 A1 | 4/2016 |
| WO | WO 2016/087257 A1 | 6/2016 |
| WO | WO 2016/087265 A1 | 6/2016 |
| WO | WO 2016/100619 A2 | 6/2016 |
| WO | WO 2016/105518 A1 | 6/2016 |
| WO | WO 2016/120182 A1 | 8/2016 |
| WO | WO 2016/126721 A1 | 8/2016 |
| WO | WO 2016/126722 A1 | 8/2016 |
| WO | WO 2016/126724 A1 | 8/2016 |
| WO | WO 2016/126725 A1 | 8/2016 |
| WO | WO 2016/126726 A1 | 8/2016 |
| WO | WO 2016/128541 A1 | 8/2016 |
| WO | WO 2016/168598 A1 | 10/2016 |
| WO | WO 2016/168660 A1 | 10/2016 |
| WO | WO 2016/179550 A1 | 11/2016 |
| WO | WO 2016/179554 A1 | 11/2016 |
| WO | WO 2016/183331 A1 | 11/2016 |
| WO | WO 2016/190630 A1 | 12/2016 |
| WO | WO 2016/196771 A1 | 12/2016 |
| WO | WO 2017/011323 A1 | 1/2017 |
| WO | WO 2017/014321 A1 | 1/2017 |
| WO | WO 2017/018803 A1 | 2/2017 |
| WO | WO 2017/018804 A1 | 2/2017 |
| WO | WO 2017/018805 A1 | 2/2017 |
| WO | WO 2017/023133 A2 | 2/2017 |
| WO | WO 2017/024009 A1 | 2/2017 |
| WO | WO 2017/029514 A1 | 2/2017 |
| WO | WO 2017/033946 A1 | 3/2017 |
| WO | WO 2017/060854 A1 | 4/2017 |
| WO | WO 2017/065473 A1 | 4/2017 |
| WO | WO 2017/076757 A1 | 5/2017 |
| WO | WO 2017/081310 A1 | 5/2017 |
| WO | WO 2017/081311 A1 | 5/2017 |
| WO | WO 2017/083368 A1 | 5/2017 |
| WO | WO 2017/093019 A1 | 6/2017 |
| WO | WO 2017/109044 A1 | 6/2017 |
| WO | WO 2017/110861 A1 | 6/2017 |
| WO | WO 2017/110862 A1 | 6/2017 |
| WO | WO 2017/111152 A1 | 6/2017 |
| WO | WO 2017/123568 A2 | 7/2017 |
| WO | WO 2017/142883 A1 | 8/2017 |
| WO | WO 2017/156350 A1 | 9/2017 |
| WO | WO 2017/162834 A1 | 9/2017 |
| WO | WO 2017/165256 A1 | 9/2017 |
| WO | WO 2017/090109 A1 | 11/2017 |
| WO | WO 2017/193030 A1 | 11/2017 |
| WO | WO 2017/197046 A1 | 11/2017 |
| WO | WO 2017/208032 A1 | 12/2017 |
| WO | WO 2017/213252 A1 | 12/2017 |
| WO | WO 2017/222950 A1 | 12/2017 |
| WO | WO 2017/222951 A1 | 12/2017 |
| WO | WO 2017/222952 A1 | 12/2017 |
| WO | WO 2018/005192 A1 | 1/2018 |
| WO | WO 2018/050656 A2 | 3/2018 |
| WO | WO 2018/055135 A1 | 3/2018 |
| WO | WO 2018/075959 A1 | 4/2018 |
| WO | WO 2018/085170 A1 | 5/2018 |
| WO | WO 2018/129533 A1 | 7/2018 |
| WO | WO 2018/154466 A1 | 8/2018 |
| WO | WO 2018/165520 A1 | 9/2018 |
| WO | WO 2018/187553 A1 | 10/2018 |
| WO | WO 2018/188962 A1 | 10/2018 |
| WO | WO 2018/189340 A1 | 10/2018 |
| WO | WO 2018/191360 A1 | 10/2018 |
| WO | WO 2018/202491 A1 | 11/2018 |
| WO | WO 2018/213364 A1 | 11/2018 |
| WO | WO 2018/219356 A1 | 12/2018 |
| WO | WO 2019/027054 A1 | 2/2019 |
| WO | WO 2019/060210 A1 | 3/2019 |
| WO | WO 2019/100735 A1 | 5/2019 |
| WO | WO 2019/101709 A1 | 5/2019 |
| WO | WO 2019/109046 A1 | 6/2019 |
| WO | WO 2019/110663 A1 | 6/2019 |
| WO | WO 2019/122323 A1 | 6/2019 |
| WO | WO 2019/139921 A1 | 7/2019 |
| WO | WO 2019/164222 A1 | 8/2019 |
| WO | WO 2019/166824 A1 | 9/2019 |
| WO | WO 2019/171234 A1 | 9/2019 |
| WO | WO 2019/200238 A1 | 10/2019 |
| WO | WO 2019/204550 A1 | 10/2019 |
| WO | WO 2019/212927 A1 | 11/2019 |
| WO | WO 2019/228289 A1 | 12/2019 |
| WO | WO 2020/011816 A1 | 1/2020 |
| WO | WO 2020/022794 A1 | 1/2020 |
| WO | WO 2020/028150 A1 | 2/2020 |
| WO | WO 2020/029908 A1 | 2/2020 |
| WO | WO 2020/039028 A1 | 2/2020 |
| WO | WO 2020/061112 A1 | 3/2020 |
| WO | WO 2020/061118 A1 | 3/2020 |
| WO | WO 2020/061216 A1 | 3/2020 |
| WO | WO 2020/070610 A1 | 4/2020 |
| WO | WO 2020/096916 A2 | 5/2020 |
| WO | WO 2020/106119 A1 | 5/2020 |
| WO | WO 2020/127974 A1 | 6/2020 |
| WO | WO 2020/132561 A1 | 6/2020 |
| WO | WO 2020/158762 A1 | 8/2020 |
| WO | WO 2020/194272 A1 | 10/2020 |
| WO | WO 2020/201773 A1 | 10/2020 |
| WO | WO 2020/207941 A1 | 10/2020 |
| WO | WO 2020/212479 A1 | 10/2020 |
| WO | WO 2020/219650 A1 | 10/2020 |
| WO | WO 2020/223136 A1 | 11/2020 |
| WO | WO 2020/240492 A1 | 12/2020 |
| WO | WO 2020/240493 A1 | 12/2020 |
| WO | WO 2020/245381 A1 | 12/2020 |
| WO | WO 2020/254494 A1 | 12/2020 |
| WO | WO 2020/264437 A1 | 12/2020 |
| WO | WO 2021/021979 A2 | 2/2021 |
| WO | WO 2021/022076 A1 | 2/2021 |
| WO | WO 2021/046183 A1 | 3/2021 |
| WO | WO 2021/048242 A1 | 3/2021 |
| WO | WO 2021/057872 A1 | 4/2021 |
| WO | WO 2021/060567 A1 | 4/2021 |
| WO | WO 2021/067859 A1 | 4/2021 |
| WO | WO 2021/092151 A1 | 5/2021 |
| WO | WO 2021/092153 A1 | 5/2021 |
| WO | WO 2021/092174 A1 | 5/2021 |
| WO | WO 2021/127643 A1 | 6/2021 |
| WO | WO 2021/133957 A1 | 7/2021 |
| WO | WO 2021/172886 A1 | 9/2021 |
| WO | WO 2021/172887 A1 | 9/2021 |
| WO | WO 2021/208945 A1 | 10/2021 |
| WO | WO 2021/210857 A1 | 10/2021 |
| WO | WO 2021/236491 A1 | 11/2021 |
| WO | WO 2021/244416 A1 | 12/2021 |
| WO | WO 2021/263171 A1 | 12/2021 |

(56) References Cited

FOREIGN PATENT DOCUMENTS

| | | |
|---|---|---|
| WO | WO 2022/013728 A1 | 1/2022 |
| WO | WO 2022/029041 A1 | 2/2022 |
| WO | WO 2022/049496 A1 | 3/2022 |
| WO | WO 2022/081928 A1 | 4/2022 |
| WO | WO 2022/133551 A1 | 6/2022 |
| WO | WO 2022/169985 A1 | 8/2022 |
| WO | WO 2022/174193 A1 | 8/2022 |
| WO | WO 2022/187690 A1 | 9/2022 |
| WO | WO 2022/197690 A1 | 9/2022 |
| WO | WO 2022/215020 A1 | 10/2022 |
| WO | WO 2022/216616 A1 | 10/2022 |
| WO | WO 2022/226388 A1 | 10/2022 |
| WO | WO 2022/235842 A1 | 11/2022 |
| WO | WO 2023/097386 A1 | 6/2023 |
| WO | WO 2023/118507 A2 | 6/2023 |
| WO | WO 2023/195809 A1 | 10/2023 |

OTHER PUBLICATIONS

Extended European Search Report mailed Oct. 10, 2023 for European Application No. 20847655.6.
Invitation to Pay Additional Fees mailed Sep. 24, 2020 for Application No. PCT/US2020/044148.
International Search Report and Written Opinion mailed Feb. 16, 2021 for Application No. PCT/US2020/044148.
International Preliminary Report on Patentability mailed Feb. 10, 2022 for Application No. PCT/US2020/044148.
International Search Report and Written Opinion mailed May 10, 2018 for Application No. PCT/US2018/021696.
International Preliminary Report on Patentability mailed Sep. 19, 2021 for Application No. PCT/US2018/021696.
Invitation to Pay Additional Fees mailed Apr. 29, 2022 for Application No. PCT/US2022/015129.
International Search Report and Written Opinion mailed Jun. 24, 2022 for Application No. PCT/US2022/015129.
International Preliminary Report on Patentability mailed Aug. 17, 2023 for Application No. PCT/US2022/015129.
Invitation to Pay Additional Fees mailed Apr. 3, 2023 for Application No. PCT/US2023/012174.
International Search Report and Written Opinion mailed Jun. 29, 2023 for Application No. PCT/US2023/012174.
International Search Report and Written Opinion mailed Aug. 25, 2023 for Application No. PCT/US2023/017894.
Invitation to Pay Additional Fees mailed Jun. 9, 2023 for Application No. PCT/US2023/017900.
International Search Report and Written Opinion mailed Aug. 23, 2023 for Application No. PCT/US2023/017900.
[No Author Listed], 1,4-Dimethyl-7-(pyridin-2-ylmethoxy)indole-2-carboxylic acid. PubChem CID No. 140972344. Accessed May 25, 2023. Created Dec. 6, 2019. https://pubchem.ncbi.nlm.nih.gov/compound/140972344. 10 pages.
[No Author Listed], 2-(Difluoromethyl)-5-[2-(4-fluorophenoxy)pyrimidin-5-yl]-1,3,4-oxadiazole. PubChem CID No. 162351258. Accessed May 25, 2023. Created Dec. 13, 2021. https://pubchem.ncbi.nlm.nih.gov/compound/162351258. 10 pages.
[No Author Listed], 2-(Phenoxymethyl)pyrimidine. PubChem CID No. 19371420. Accessed May 25, 2023. Created Dec. 4, 2017. https://pubchem.ncbi.nlm.nih.gov/compound/19371420. 11 pages.
[No Author Listed], Augustine Therapeutics Showcase Presentation. Recorded at the 2022 Investival Showcase in London, England on Nov. 14, 2022. Accessed Feb. 7, 2023 from <https://www.youtube.com/watch?v=8wJXGd2CgQU>. Selected screenshots. 6 pages.
[No Author Listed], Bringing NHA HDAC6 inhibitors to the clinic for cardiovascular and neurodegenerative disorders. Chong Kun Dang Pharmaceutical Corp. Nature Research Custom Media. Jun. 2022;B41.
[No Author Listed], Cancer Innovates, accelerating early cancer drug discovery. Cancer Innova. Feb. 2022. Accessed from <https://www-cancerinnova-com.translate.goog/en/cancer-innova-acelerando-el-descubrimiento-temprano-de-farmacos-en-cancer/?_x_tr_sl=auto&_x_tr_tl=en&_x_tr_hl=en&_x_tr_pto=wapp>. 10 pages.
[No Author Listed], CAS Registration No. 1111575-80-4. Registry (STN). Feb. 25, 2009. 1 page.
[No Author Listed], CAS Registration No. 1332894-18-4. Registry (STN). Sep. 20, 2011. 1 page.
[No Author Listed], CAS Registration No. 1860746-44-6. Registry (STN). Feb. 5, 2016. 1 page.
[No Author Listed], CAS Registration No. 1875612-53-5. Registry (STN). Feb. 28, 2016. 1 page.
[No Author Listed], CAS Registration No. 1940897-22-2. Registry (STN). Jun. 28, 2016. 1 page.
[No Author Listed], CAS Registration No. 73779-41-6. Registry (STN). Nov. 16, 1984. 1 page.
[No Author Listed], CAY10603: Catalog No. S7596; Synonyms: BML-281. Apr. 2015. 4 pages. Accessed Jul. 19, 2022 from <https://www.selleckchem.com/products/cay10603.html?gclid=CjwKCAjwoMSWBhAdEiwAVJ2ndvOI8KYzzn0XiWLIF5DRM50crFNHcVSDwVsA6XALwr0yzmIKn10muxoCgkcQAvD_BwE>.
[No Author Listed], HDAC: Inhibitory Selectivity. AdooQ Bioscience. 21 pages. Accessed May 18, 2022 from <https://www.adooq.com/epigenetics-histone-deacetylase-hdac.html?gclid=EAIaIQobChMI4K_CiJzk9AIVpQaICR2_rgPTEAMYASAAEgKHnvD_BWE >.
[No Author Listed], Jubilant Therapeutics Inc. receives Orphan Drug Designation for JBI-802 for Acute Myeloid Leukemia (AML) and Small Cell Lung Cancer (SCLC). Jubilant Therapeutics. Jan. 5, 2023. Accessed from <https://www.prnewswire.com/news-releases/jubilant-therapeutics-inc-receives-orphan-drug-designation-for-jbi-802-for-acute-myeloid-leukemia-aml-and-small-cell-lung-cancer-sclc-301714552.html>. 3 pages.
[No Author Listed], NCT03713892: CKD-504 in SAD and MAD in Healthy Korean and Caucasian Adult Male and Female Subjects. Last Update Posted Feb. 24, 2020. 6 pages. Accessed Feb. 7, 2023 from <https://clinicaltrials.gov/ct2/show/NCT03713892>.
[No Author Listed], NCT04746287: Evaluation of the Safety and Tolerability of CKD-510 in Healthy Subjects. Last Update Posted May 4, 2022. 8 pages. Accessed Feb. 7, 2023 from <https://clinicaltrials.gov/ct2/show/NCT04746287>.
[No Author Listed], NCT05526742: A Study to Evaluate the Relative Bioavailability of Formulations of CKD-510 and to Assess the Effect of Food on the CKD-510 Tablet Formulation in Healthy Subjects. Last Update Posted Sep. 8, 2022. 7 pages. Accessed Feb. 7, 2023 from <https://clinicaltrials.gov/ct2/show/NCT05526742>.
[No Author Listed], OnKure Expands Executive Team with the Addition of Chief Scientific Officer and Chief Development Officer. OnKure Therapeutics. Aug. 3, 2021. Accessed from <https://onkuretherapeutics.com/press-release/onkure-expands-executive-team-and-appoints-head-of-discovery-chief-financial-officer-and-general-counsel-2/>. 4 pages.
[No Author Listed], OnKure Therapeutics Appoints Jennifer R. Diamond, M.D., as Chief Medical Officer. OnKure Therapeutics. Oct. 1, 20214. Accessed from <https://onkuretherapeutics.com/year/2021/onkure-therapeutics-appoints-jennifer-r-diamond-m-d-as-chief-medical-officer/>. 3 pages.
[No Author Listed], ORYZON collaborates with the CMT Research Foundation in the US. Oryzon Press Release. Jul. 26, 2022. 2 pages.
[No Author Listed], Pharmacology review for belinostat. Center for Drug Evaluation and Research. Application No. 206256Orig1s000. May 22, 2014. 98 pages.
[No Author Listed], Pharmacology review for panobinostat. Center for Drug Evaluation and Research. Application No. 205353Orig1s000. Sep. 2, 2014. 125 pages.
[No Author Listed], Pharmacology review for vorinostat. Center for Drug Evaluation and Research. Application No. 21-991. Oct. 5, 2006. 106 pages.
[No Author Listed], Pipeline Program and Development Status. OnKure Therapeutics. May 13, 2021. Accessed from <https://web.archive.org/web/20210513123624/https:/onkuretherapeutics.com/pipeline/>. 2 pages.

(56) References Cited

OTHER PUBLICATIONS

[No Author Listed], Pipeline Program and Development Status. OnKure Therapeutics. Oct. 8, 2021. Accessed from <https://web.archive.org/web/20210513123624/https:/onkuretherapeutics.com/pipeline/>. 2 pages.

[No Author Listed], Precision oral medicines with enhanced therapeutic index. Jubilant Therapeutics. Corporate Presentation. Jan. 2023. 38 pages.

[No Author Listed], PubChem Substance Record for PubChem SID 227322283, SCHEMBL1075847. Accessed Sep. 21, 2020. 9 pages.

[No Author Listed], PubChem Substance Record for PubChem SID 274711921, 2-[5-(3-Nitrophenyl)furfuryl]-1,2,3,4-tetrahydroisoquinoline-7-carbohydroximic acid. Accessed Sep. 21, 2020. 8 pages.

[No Author Listed], Scaling New Heights in the Fight Against Heart Disease. Tenaya Therapeutics. Corporate Presentation. Sep. 2022. 38 pages.

[No Author Listed], Tenaya Therapeutics Announces TN-201 IND Clearance and Anticipated 2023 Milestones. GlobeNewswire. Jan. 9, 2023. Accessed from <https://www.globenewswire.com/news-release/2023/01/09/2585026/0/en/Tenaya-Therapeutics-Announces-TN-201-IND-Clearance-and-Anticipated-2023-Milestones.html>. 7 pages.

[No Author Listed], The basque-based company Quimatryx licenses a cancer drug for 92 million dollars. Basque Press. Jul. 29, 2022. Accessed from <https://basque.press/the-guipuzcoa-based-company-quimatryx-licenses-a-cancer-drug-for-92-million-dollars-la-empresa-guipuzcoana-quimatryx-licencia-un-farmaco-contra-el-cancer-por-92-millones-de-dolares/>. 5 pages.

[No Author Listed], The McQuade Center for Strategic Research and Development and Eikonizo Therapeutics Enter Agreement to Develop Treatments for Patients with Rare Diseases. Feb. 9, 2021.

Adalbert et al., Novel HDAC6 Inhibitors Increase Tubulin Acetylation and Rescue Axonal Transport of Mitochondria in a Model of Charcot-Marie-Tooth Type 2F. ACS Chem Neurosci. Feb. 5, 2020;11(3):258-267. doi: 10.1021/acschemneuro.9b00338. Epub Jan. 8, 2020.

Aleksandrova et al., Elaboration of the Effective Multi-Target Therapeutic Platform for the Treatment of Alzheimer's Disease Based on Novel Monoterpene-Derived Hydroxamic Acids. Int J Mol Sci. Jun. 4, 2023;24(11):9743. doi: 10.3390/ijms24119743.

Bae et al., CKD-506: A novel HDAC6-selective inhibitor that exerts therapeutic effects in a rodent model of multiple sclerosis. Sci Rep. Jul. 14, 2021;11(1):14466. doi: 10.1038/s41598-021-93232-6.

Bae et al., CKD-510, a novel non-hydroxamic acid histone deacetylase 6 (HDAC6) inhibitor for Charcot-Marie-Tooth disease type 1A. J Peripher Nerv Syst.2022;27(Suppl. 3):S4. Abstract Only.

Beshore et al., Redefining the Histone Deacetylase Inhibitor Pharmacophore: High Potency with No Zinc Cofactor Interaction. ACS Med Chem Lett. Mar. 7, 2021;12(4):540-547. doi: 10.1021/acsmedchemlett.1c00074.

Blackburn et al., Histone deacetylase inhibitors derived from 1,2,3,4-tetrahydropyrrolo[1,2-a]pyrazine and related heterocycles selective for the HDAC6 isoform. Bioorg Med Chem Lett. Dec. 1, 2014;24(23):5450-4. doi: 10.1016/j.bmcl.2014.10.022.

Blackburn et al., Potent histone deacetylase inhibitors derived from 4-(aminomethyl)-N-hydroxybenzamide with high selectivity for the HDAC6 isoform. J Med Chem. Sep. 26, 2013;56(18):7201-11. doi: 10.1021/jm400385r. Epub Sep. 4, 2013.

Bondarev et al., Recent developments of HDAC inhibitors: Emerging indications and novel molecules. Br J Clin Pharmacol. 2021; 87(12): 4577-4597. https://doi.org/10.1111/bcp.14889.

Buommino et al., Synergism of a Novel 1,2,4-oxadiazole-containing Derivative with Oxacillin against Methicillin-Resistant *Staphylococcus aureus*. Antibiotics (Basel). Oct. 16, 2021;10(10):1258. doi: 10.3390/antibiotics10101258.

Chang et al., The Role of HDAC6 in Autophagy and NLRP3 Inflammasome. Front Immunol. Oct. 27, 2021;12:763831. doi: 10.3389/fimmu.2021.763831.

Choi et al., Acetylation changes tau interactome to degrade tau in Alzheimer's disease animal and organoid models. Aging Cell. Jan. 2020;19(1):e13081. doi: 10.1111/acel.13081. Epub Nov. 25, 2019.

Choi et al., CKD-506, a novel HDAC6-selective inhibitor, improves renal outcomes and survival in a mouse model of systemic lupus erythematosus. Sci Rep. Nov. 23, 2018;8(1):17297. doi: 10.1038/s41598-018-35602-1.

Cragin et al., A Novel Zinc Binding Group for HDAC6 Inhibition. FASEB J. May 2022;36 Suppl 1. doi: 10.1096/fasebj.2022.36.S1.R3604. Abstract Only.

Faridoon et al., Medicinal chemistry insights into non-hydroxamate HDAC6 selective inhibitors. Med Chem Res. Oct. 31, 2022;32(1):1-14. doi: 10.1007/s00044-022-02987-8.

Fazal et al., HDAC6 inhibition restores TDP-43 pathology and axonal transport defects in human motor neurons with TARDBP mutations. EMBO J. 2021;40:e106177.

Gaisina et al., Activation of Nrf2 and Hypoxic Adaptive Response Contribute to Neuroprotection Elicited by Phenylhydroxamic Acid Selective HDAC6 Inhibitors. ACS Chem Neurosci. May 16, 2018;9(5):894-900. doi: 10.1021/acschemneuro.7b00435. Epub Jan. 17, 2018.

Gajendran et al., Novel dual LSD1/HDAC6 inhibitor for the treatment of cancer. PLoS One. Jan. 3, 2023;18(1):e0279063. doi: 10.1371/journal.pone.0279063.

Guo et al., Design, synthesis and biological evaluation of brain penetrant benzazepine-based histone deacetylase 6 inhibitors for alleviating stroke-induced brain infarction. Eur J Med Chem. Jun. 5, 2021;218:113383. doi: 10.1016/j.ejmech.2021.113383. Epub Mar. 17, 2021.

Ha et al., A novel histone deacetylase 6 inhibitor improves myelination of Schwann cells in a model of Charcot-Marie-Tooth disease type 1A. Br J Pharmacol. Nov. 2020;177(22):5096-5113. doi: 10.1111/bph.15231. Epub Sep. 27, 2020.

Hendricks et al., In vivo PET imaging of histone deacetylases by 18F-suberoylanilide hydroxamic acid (18F-SAHA). J Med Chem. Aug. 11, 2011;54(15):5576-82. doi: 10.1021/jm200620f. Epub Jul. 18, 2011.

Hong et al., CKD-510, a novel selective HDAC6 inhibitor, is well-tolerated and increased acetyl-tubulin in healthy volunteers. J Peripher Nerv Syst.2022;27(Suppl. 3):S76-7. Abstract Only.

Hu et al., 3D-QSAR Studies of HDAC6 Inhibitors Using Docking-Based Alignment. Lett Drug Des Discov. Jul. 2017;14(7):798-810. doi: 10.2174/1570180813666161028165151.

Hubbert et al., HDAC6 is a microtubule-associated deacetylase. Nature. May 23, 2002;417(6887):455-8. doi: 10.1038/417455a.

Jeong et al., Therapeutic Potential of CKD-504, a Novel Selective Histone Deacetylase 6 Inhibitor, in a Zebrafish Model of Neuromuscular Junction Disorders. Mol Cells. Apr. 30, 2022;45(4):231-242. doi: 10.14348/molcells.2022.5005.

Kattar, et al., Parallel medicinal chemistry approaches to selective HDAC1/HDAC2 inhibitor (SHI-1:2) optimization. Bioorg Med Chem Lett. Feb. 15, 2009;19(4):1168-72. doi: 10.1016/j.bmcl.2008.12.083. Epub Dec. 25, 2008.

Kim et al., HDAC6 inhibitor blocks amyloid beta-induced impairment of mitochondrial transport in hippocampal neurons. PLoS One. 2012;7(8):e42983. doi: 10.1371/journal.pone.0042983. Epub Aug. 22, 2012.

Kim et al., HDAC6 Inhibitors Rescued the Defective Axonal Mitochondrial Movement in Motor Neurons Derived from the Induced Pluripotent Stem Cells of Peripheral Neuropathy Patients with HSPB1 Mutation. Stem Cells Int. 2016;2016:9475981. doi: 10.1155/2016/9475981. Epub Dec. 26, 2016.

Kleinschek et al., Potent and Selective Non-hydroxamate Histone Deacetylase 8 Inhibitors. ChemMedChem. Dec. 6, 2016;11(23):2598-2606. doi: 10.1002/cmdc.201600528. Epub Nov. 9, 2016.

Kozikowski et al., Brain Penetrable Histone Deacetylase 6 Inhibitor SW-100 Ameliorates Memory and Learning Impairments in a Mouse Model of Fragile X Syndrome. ACS Chem Neurosci. Mar. 20, 2019;10(3):1679-1695. doi: 10.1021/acschemneuro.8b00600. Epub Dec. 14, 2018.

Kozikowski, A.P., Application for Federal Assistance for Study of the New HDAC6i SW-100 as a Treatment for Alzheimer's Disease and Other Tauopathies; Title: Study of the New HDAC6i SW-100

(56) References Cited

OTHER PUBLICATIONS as a Treatment for Alzheimer's Disease and Other Tauopathies for StarWise Therapeutics LLC and University of South Florida. FOA: PAS17-065. Received Mar. 31, 2017. 62 pages.

Krukowski et al., HDAC6 inhibition effectively reverses chemotherapy-induced peripheral neuropathy. Pain. Jun. 2017;158(6):1126-1137. doi: 10.1097/j.pain.0000000000000893.

Lechner et al., Target deconvolution of HDAC pharmacopoeia reveals MBLAC2 as common off-target. Nat Chem Biol. Aug. 2022;18(8):812-820. doi: 10.1038/s41589-022-01015-5. Epub Apr. 28, 2022. Erratum in: Nat Chem Biol. Jul. 15, 2022.

Lee et al., Novel Histone Deacetylase 6 Inhibitor CKD-506 Inhibits NF-κB Signaling in Intestinal Epithelial Cells and Macrophages and Ameliorates Acute and Chronic Murine Colitis. Inflamm Bowel Dis. May 12, 2020;26(6):852-862. doi: 10.1093/ibd/izz317.

Lee et al., Novel Histone Deacetylase 6 Inhibitor Confers Anti-inflammatory Effects and Enhances Gut Barrier Function. Gut Liver. Sep. 27, 2022. doi: 10.5009/gnl220159. Epub ahead of print.

Li et al., A Novel HDAC6 Inhibitor, CKD-504, is Effective in Treating Preclinical Models of Huntington's Disease. BMB Rep. Jan. 3, 2023:5747. Epub ahead of print.

Li et al., Abstract 4441: CS3003, an HDAC6-selective inhibitor, improves anti-PD-1 immune checkpoint blockade therapy efficacy. Proceedings of the Annual Meeting of the American Association for Cancer Research. Apr. 27-28 and Jun 22-24, 2022. Philadelphia, PA. Cancer Res 2020;80(16 Suppl). Poster. 1 page.

Lipczynska-Kochany et al., Mutagenicity of pyridine- and quinoline-carbohydroxamic acid derivatives. Mutat Res. Mar. 1984;135(3):139-48. doi: 10.1016/0165-1218(84)90114-9.

Liu et al., MiR-222-3p Inhibits Trophoblast Cell Migration and Alleviates Preeclampsia in Rats Through Inhibiting HDAC6 and Notch1 Signaling. Reprod Sci. Nov. 18, 2021. doi: 10.1007/s43032-021-00793-y. Epub ahead of print.

Mahmoud et al., Nimbolide inhibits 2D and 3D prostate cancer cells migration, affects microtubules and angiogenesis and suppresses B-RAF/p.ERK-mediated in vivo tumor growth. Phytomedicine. Jan. 2022;94:153826. doi: 10.1016/j.phymed.2021.153826. Epub Nov. 1, 2021.

Martin et al., Discovery of novel N-hydroxy-2-arylisoindoline-4-carboxamides as potent and selective inhibitors of HDAC11. Bioorg Med Chem Lett. Jul. 1, 2018;28(12):2143-2147. doi: 10.1016/j.bmcl.2018.05.021. Epub May 9, 2018.

McMahon, VEGF receptor signaling in tumor angiogenesis. The Oncologist. 2000;5(suppl 1):3-10.

Munakata et al., Mutagenicity of N-acylglycinohydroxamic acids and related compounds. J Pharmacobiodyn. Nov. 1980;3(11):557-61. doi: 10.1248/bpb1978.3.557.

Neidle, Cancer Drug Design and Discovery. Elsevier/Academic Press. 2008; 427-431.

Onishi et al., A novel orally active HDAC6 inhibitor T-518 shows a therapeutic potential for Alzheimer's disease and tauopathy in mice. Sci Rep. Jul. 29, 2021;11(1):15423. doi: 10.1038/s41598-021-94923-w.

Park et al., Therapeutic potential of CKD-506, a novel selective histone deacetylase 6 inhibitor, in a murine model of rheumatoid arthritis. Arthritis Res Ther. Jul. 25, 2020;22(1):176. doi: 10.1186/s13075-020-02258-0.

Pinedo et al., Translational Research: The Role of VEGF in Tumor Angiogenesis. The Oncologist. 2000;5(Suppl 1):1-2.

Rivieccio et al., HDAC6 is a target for protection and regeneration following injury in the nervous system. Proc Natl Acad Sci U S A. Nov. 17, 2009;106(46):19599-604. doi: 10.1073/pnas.0907935106. Epub Nov. 2, 2009.

Sandrone et al., Role of Fluorination in the Histone Deacetylase 6 (HDAC6) Selectivity of Benzohydroxamate-Based Inhibitors. ACS Med Chem Lett. Oct. 11, 2021;12(11):1810-1817. doi: 10.1021/acsmedchemlett.1c00425.

Selenica et al., Histone deacetylase 6 inhibition improves memory and reduces total tau levels in a mouse model of tau deposition. Alzheimers Res Ther. Feb. 27, 2014;6(1):12. doi: 10.1186/alzrt241.

Shen et al., A patent review of histone deacetylase 6 inhibitors in neurodegenerative diseases (2014-2019). Expert Opin Ther Pat. Feb. 2020;30(2):121-136. doi: 10.1080/13543776.2019.1708901. Epub Dec. 25, 2019.

Shen et al., A patent review of histone deacetylase 6 inhibitors in neurodegenerative diseases (2014-2019). Expert Opin Ther Pat. 2020;30(2):121-136. doi: 10.1080/13543776.2019.1708901.

Shen et al., Bicyclic-Capped Histone Deacetylase 6 Inhibitors with Improved Activity in a Model of Axonal Charcot-Marie-Tooth Disease. ACS Chem Neurosci. Feb. 17, 2016;7(2):240-58. doi: 10.1021/acschemneuro.5b00286. Epub Dec. 7, 2015.

Shen et al., Structural and in Vivo Characterization of Tubastatin A, a Widely Used Histone Deacetylase 6 Inhibitor. ACS Med Chem Lett. Jan. 15, 2020;11(5):706-712. doi: 10.1021/acsmedchemlett.9b00560.

Shen et al., Why Hydroxamates May Not Be the Best Histone Deacetylase Inhibitors—What Some May Have Forgotten or Would Rather Forget? ChemMedChem. Jan. 5, 2016;11(1):15-21. doi: 10.1002/cmdc.201500486. Epub Nov. 25, 2015.

Shidore et al., 3-Substituted 1-methyl-3-benzazepin-2-ones as 5-HT2C receptor agonists. RSC Adv. Oct. 19, 2015;5(111):91908-21. doi: 10.1039/C5RA17718A.

Shukla et al., Histone Deacetylases Inhibitors in Neurodegenerative Diseases, Neuroprotection and Neuronal Differentiation. Front Pharmacol. Apr. 24, 2020;11:537. doi: 10.3389/fphar.2020.00537.

Simoes-Pires et al., HDAC6 as a target for neurodegenerative diseases: what makes it different from the other HDACs? Mol Neurodegener. Jan. 29, 2013;8:7. doi: 10.1186/1750-1326-8-7.

Sixto-Lopez et al., silico design of HDAC6 inhibitors with neuroprotective effects. J Biomol Struct Dyn. Nov. 16, 2021:1-19. doi: 10.1080/07391102.2021.2001378. Epub ahead of print.

Wang et al., Mutagenicity and antibacterial activity of hydroxamic acids. Antimicrob Agents Chemother. Apr. 1977; 11(4):753-5. doi: 10.1128/AAC.11.4.753.

Wang, C.Y., Mutagenicity of hydroxamic acids for *Salmonella typhimurium*. Mutat Res. Sep. 1977;56(1):7-12. doi: 10.1016/0027-5107(77)90235-4.

Watson et al., Aromatic C—F Interactions Influence Binding Mode of Inhibitors in HDAC6. FASEB J. May 2022;36 Suppl 1. doi: 10.1096/fasebj.2022.36.S1.R2257. Abstract Only.

Wei et al., Mutagenicity of some monoaromatic hydroxamic acids. Toxicol Lett. Jan. 1985;24(1):111-6. doi: 10.1016/0378-4274(85)90148-1.

Xu et al., Design, Synthesis, Bioactivity Evaluation, Crystal Structures, and In Silico Studies of New α-Amino Amide Derivatives as Potential Histone Deacetylase 6 Inhibitors. Molecules. May 22, 2022;27(10):3335. doi: 10.3390/molecules27103335.

Yang et al., Phenotypic screening with deep learning identifies HDAC6 inhibitors as cardioprotective in a BAG3 mouse model of dilated cardiomyopathy. Sci Transl Med. Jul. 6, 2022;14(652):1-15. doi: 10.1126/scitranslmed.ab15654.

Yang et al., Phenotypic screening with deep learning identifies HDAC6 inhibitors as cardioprotective in a BAG3 mouse model of dilated cardiomyopathy. Sci Transl Med. Jul. 6, 2022;14(652):1-15. doi: 10.1126/scitranslmed.ab15654. Supplementary Materials, 44 pages.

Yu et al., Quinazolin-2,4-dione-Based Hydroxamic Acids as Selective Histone Deacetylase-6 Inhibitors for Treatment of Non-Small Cell Lung Cancer. J Med Chem. Jan. 24, 2019;62(2):857-874. doi: 10.1021/acs.jmedchem.8b01590. Epub Dec. 20, 2018.

Zhang et al., Design, synthesis, and biological evaluation of novel histone deacetylase 6 selective inhibitors. J Saudi Chem Soc. May 2022;26(3):101450. doi: 10.1016/j.jscs.2022.101450.

Zhang et al., Tubastatin A/ACY-1215 improves cognition in Alzheimer's disease transgenic mice. J Alzheimers Dis. 2014;41(4):1193-205. doi: 10.3233/JAD-140066.

U.S. Appl. No. 18/835,194, filed Aug. 1, 2024, Wagner et al.
U.S. Appl. No. 18/854,932, filed Oct. 7, 2024, Wagner.
U.S. Appl. No. 18/854,938, filed Oct. 7, 2024, Wagner et al.
PCT/US2023/012174, Aug. 15, 2024, International Preliminary Report on Patentability.
PCT/US2023/017894, Oct. 17, 2024, International Preliminary Report on Patentability.

(56) References Cited

OTHER PUBLICATIONS

PCT/US2023/017900, Oct. 17, 2024, International Preliminary Report on Patentability.

* cited by examiner

METALLOENZYME INHIBITOR COMPOUNDS

CROSS-REFERENCE TO RELATED APPLICATIONS

The present application is a Continuation Application of and claims priority under 35 U.S.C. § 120 to U.S. application Ser. No. 17/336,444, filed Jun. 2, 2021, which is a Continuation Application of and claims priority under 35 U.S.C. § 120 to U.S. application Ser. No. 16/518,279, filed Jul. 22, 2019, which is a Continuation Application of and claims priority under 35 U.S.C. § 120 to U.S. application Ser. No. 15/917,555, filed Mar. 9, 2018, now issued U.S. Pat. No. 10,357,493, which claims priority under 35 U.S.C. § 119(e) to U.S. Provisional Patent Application Ser. No. 62/469,565, filed Mar. 10, 2017, and U.S. Provisional Patent Application Ser. No. 62/513,145, filed May 31, 2017. The entirety of each is incorporated herein by reference.

BACKGROUND

Living organisms have developed tightly regulated processes that specifically import metals, transport them to intracellular storage sites and ultimately transport them to sites of use. One of the most useful functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the azole antifungals fluconazole and voriconazole contain a 1-(1,2,4-triazole) group that binds to the heme iron present in the active site of the target enzyme lanosterol demethylase and thereby inactivates the enzyme. Another example includes the zinc-binding hydroxamic acid group that has been incorporated into most published inhibitors of matrix metalloproteinases and histone deacetylases. Another example is the zinc-binding carboxylic acid group that has been incorporated into most published angiotensin-converting enzyme inhibitors.

In the design of clinically safe and effective metalloenzyme inhibitors, use of appropriate metal-binding groups for any particular target and clinical indication is desirable. If a weakly binding metal-binding group is utilized, potency may be ineffective. On the other hand, if a very tightly binding metal-binding group is utilized, non-selectivity for the target enzyme versus related metalloenzymes may result. The lack of effective selectivity can be a cause for clinical toxicity due to unintended inhibition of these off-target metalloenzymes. One example of such clinical toxicity is the unintended inhibition of human drug metabolizing enzymes such as CYP2C9, CYP2C19 and CYP3A4 by the currently-available azole antifungal agents such as fluconazole and voriconazole. It is believed that this off-target inhibition is caused primarily by the indiscriminate binding of the currently utilized 1-(1,2,4-triazole) to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof.

Post-translational lysine acetylation of proteins is a critical process in regulating many cellular functions. This modification is a dynamic process controlled by two enzyme families: histone acetyltransferases (HAT) and histone deacetylases (HDAC). HDACs are responsible for the deacetylation of lysine residues on a variety of substrates including histone and non-histone (e.g. α-tubulin) proteins. There are 18 mammalian HDAC enzymes which are divided into four classes based on sequence identity and catalytic activity. Class I, II, and IV HDAC enzymes are $Zn^{2+}$ dependent metalloenzymes whereas the sirtuins, HDAC class III, are nicotinomide adenine dinucleotide ($NAD^+$) dependent. Class I includes HDAC1, 2, 3, and 8 and these enzymes are primarily located in the nucleus where they are involved in histone modification and regulation of gene expression. Class II is divided into two subgroups: class IIa containing HDAC4, 5, 7, and 9 and class IIB containing HDAC6 and 10. Class IV is made up of only HDAC11 (Mazitschek et al., *Nat Chem Bio.* 2010, 6, 238-243).

For many years, HDAC enzymes have been targeted with small molecule inhibitors due to their therapeutic potential in oncology, neurology, immunology, and infections (Kuilenburg et al., *Biochem J,* 2003, 370, 737-749; Johnstone et al., *Nature Reviews Drug Discovery,* 2014, 13, 673-691). Many HDAC inhibitors have progressed into clinical development for the treatment of cancer but there has been limited success with the approval of only a few pan-HDAC inhibitors (SAHA, Belinostat and Panobinostat) and the class I selective romidepsin (Wang et al., *Molecules,* 2015, 20, 3898-3941). A challenge to develop HDAC inhibitors has been the management of toxicities, many of which are dose limiting in the clinic (Piekarz et al., Pharmaceuticals, 2010, 3, 2751-2767; Witt et al., Cancer Letters, 2009, 277, 8-21). Some of the side effects can be attributed to the hydroxamic acid metal-binding group, a common motif in many of the HDAC inhibitors. The hydroxamic acid is a potent metal binding group that has been associated with toxicity alone but use of this metal binding group amplifies the problem by leading to limited HDAC isoform selectivity and poor pharmacokinetic properties (Kozikowski et al., *Chem Med Chem,* 2016, 11, 15-21; Deprez-Poulain et al., *J Med Chem,* 2009, 52, 6790-6802).

Efforts in recent years have been focused on the pharmacology associated with the different HDAC classes and specific isoforms. HDAC6 is an isoform that has been of particular interest partly because it has been shown that mice deficient in HDAC6 are viable and develop normally (Matthias et al., *Molecular and Cellular Biology,* 2008, 28, 1688-1701). This is in stark contrast to the lethality associated with HDAC1, 2, and 3 knock outs (Witt et al., *Cancer Letters,* 2009, 277, 8-21). HDAC6 is a class IIb enzyme that has a unique protein structure containing two catalytic domains, nuclear localization and export signal sequences, a cytoplasmic retention domain, and a ubiquitin binding domain. HDAC6 is also the largest HDAC enzyme with 1215 amino acids. HDAC6 is predominantly located in the cytoplasm except in certain instances and has been shown to have many different non-histone protein substrates including α-tubulin, HSP90, cortactin, Foxp3, etc. HDAC6 inhibitors are expected to have significant therapeutic potential in oncology, immunology, and neurology (Kalin et al., *J Med Chem*, 2013, 56, 6297-6313; Diederich et al., *Epigenomics*, 2015, 7, 103-118).

There has been significant research focused on the discovery of selective HDAC6 inhibitors but reported inhibitors still retain moderate to strong inhibition of one or more off-target HDAC isoforms. The lack of selectivity for HDAC6 leads to mixed and often difficult to interpret results in preclinical models. There is a significant need for the development of non-hydroxamic acid HDAC6 inhibitors with an improved pharmacokinetic profile that have selectivity over class I and other class II HDAC isoforms.

BRIEF SUMMARY OF THE INVENTION

The invention is directed towards compounds (e.g., any of those delineated herein), methods of modulating activity of metalloenzymes, and methods of treating diseases, disorders or symptoms thereof. The methods can comprise the compounds herein.

It is understood that the embodiments of the invention discussed below with respect to the preferred variable selections can be taken alone or in combination with one or more embodiments, or preferred variable selections, of the invention, as if each combination were explicitly listed herein.

In one aspect, provided are compounds of Formula I:

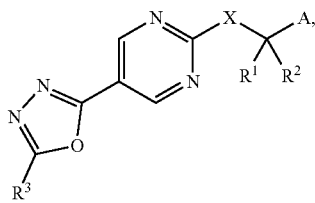

I or pharmaceutically acceptable salts, co-crystals, tautomers, stereoisomers, solvates, hydrates, polymorphs, isotopically enriched derivatives, or prodrugs thereof, wherein:

A is aryl, heteroaryl, cycloalkyl, heterocycloalkyl, arylalkyl, or alkyl, wherein A is optionally substituted with 1-3 independent substituents $R^5$;

X is $NR^4$ or O;

each of $R^1$ and $R^2$ is, independently, hydrogen, cyano, alkyl, alkenyl, alkynyl, cycloalkyl, aryl, heteroaryl, heterocycloalkyl, —$(CH_2)_nNR^aC(O)R^b$, —$C(O)NR^aR^b$, —$(CH_2)_nNR^dSO_2R^d$, —$CO_2R^e$, —$COR^f$, or —$CH_2OR^f$, wherein $R^1$ and $R^2$ are optionally substituted with 1-3 independent substituents $R^5$;

or $R^1$ and $R^2$ together with the atoms to which they are attached form a heterocycloalkyl or cycloalkyl ring, wherein said heterocycloalkyl and cycloalkyl are optionally substituted with 1-3 independent substituents $R^5$;

or $R^1$ and A together with the atoms to which they are attached form a heterocycloalkyl ring or fused bicyclic ring;

$R^3$ is haloalkyl or —$OR^g$;

$R^4$ is hydrogen or alkyl;

each occurrence of $R^5$ is, independently, halogen, cyano, alkyl, haloalkyl, —$NR^aR^b$, —$NHSO_2R^c$, —$(CH_2)_nNR^aR^b$, —$(CH_2)_nC(O)NR^aR^b$, —$(CH_2)_nNR^dSO_2R^d$, —$S(O)R^d$, —$S(O)_2R^d$, —$CO_2R^e$, —$COR^f$, —$(CR^eR^f)_nOR^f$, —$OR^f$, or aryl substituted with 0-3 independent halogen, —$NR^aR^b$, —$NHSO_2R^c$, —$(CH_2)_nNR^aR^b$, —$(CH_2)_nC(O)NR^aR^b$, —$(CH_2)_nNHSO_2R^d$, —$S(O)R^d$, —$S(O)_2R^d$, —$CO_2R^e$, —$COR^f$, —$(CR^eR^f)_nOR^f$, or —$OR^f$; or two occurrences of $R^5$, together with the atoms to which they are attached, form a cycloalkyl, heterocycloalkyl, aryl, or heteroaryl ring;

each n is independently 1, 2, 3, 4, 5, 6, 7, 8, 9, or 10;

each occurrence of $R^a$, $R^b$, $R^c$, $R^d$, $R^e$, and $R^f$ is, independently, hydrogen, acyl, alkoxyalkyl, alkyl, alkenyl, alkynyl, heteroalkyl, haloalkyl, cycloalkyl, heterocycloalkyl, aryl, heteroaryl, arylalkyl, heteroarylalkyl, heterocycloalkylalkyl, a nitrogen protecting group when attached to a nitrogen atom, or an oxygen protecting group when attached to an oxygen atom; or $R^a$ and $R^b$ together with the atoms to which they are attached form a heterocycloalkyl ring; or $R^e$ and $R^f$ together with the atoms to which they are attached form a cycloalkyl ring; and $R^g$ is haloalkyl.

In certain embodiments, A is aryl, heteroaryl, cycloalkyl, heterocycloalkyl, or arylalkyl.

In certain embodiments, A is aryl, heteroaryl, cycloalkyl, or heterocycloalkyl.

In certain embodiments, A is aryl, heteroaryl, or cycloalkyl. In certain embodiments, A is aryl, heteroaryl, or $C_{3-6}$ cycloalkyl.

In certain embodiments, A is aryl or heteroaryl.

In certain embodiments, A is aryl. In certain embodiments, A is phenyl or naphthyl. In certain embodiments, A is phenyl. In certain embodiments, A is unsubstituted phenyl. In certain embodiments, A is phenyl substituted with 1-3 independent substituents $R^5$. In certain embodiments, A is phenyl substituted with 1-3 independent substituents $R^5$, wherein each occurrence of $R^5$ is, independently, halogen, cyano, alkyl, haloalkyl, or —$OR^f$; and $R^f$ is haloalkyl or alkyl.

In certain embodiments, A is

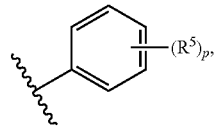

wherein p is 0, 1, 2, or 3. In certain embodiments, A is

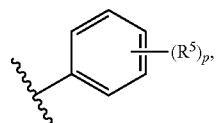

wherein p is 1, 2, or 3. In certain embodiments, A is

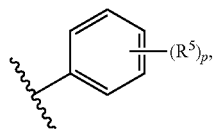

wherein p is 1 or 2. In certain embodiments, A is

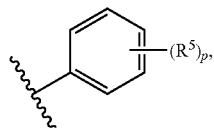

wherein p is 1.

In certain embodiments, A is

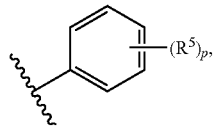

wherein p is 2. In certain embodiments, A is

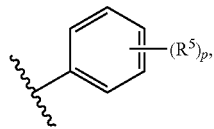

wherein p is 3.

In certain embodiments, A is

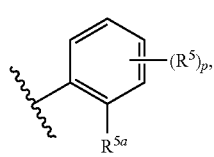

wherein $R^{5a}$ is any group as defined for $R^5$ herein, and p is 0, 1, or 2. In certain embodiments, $R^{5a}$ is halogen. In certain embodiments, $R^{5a}$ is F, Cl, or Br. In certain embodiments, $R^{5a}$ is F or $C_1$. In certain embodiments, $R^{5a}$ is F. In certain embodiments, $R^{5a}$ is $C_1$. In certain embodiments, $R^{5a}$ is halogen; each occurrence of $R^5$ is, independently, halogen, cyano, alkyl, haloalkyl, or —$OR^f$; $R^f$ is alkyl or haloalkyl; and p is 0, 1, or 2. In certain embodiments, $R^{5a}$ is F or $C_1$; each occurrence of $R^5$ is, independently, halogen, cyano, alkyl, haloalkyl, or —$OR^f$; $R^f$ is alkyl or haloalkyl; and p is 0 or 1.

In certain embodiments, A is

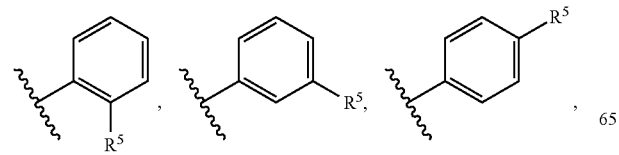

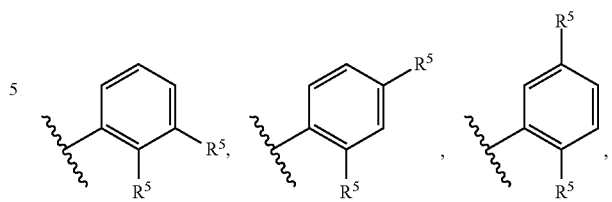

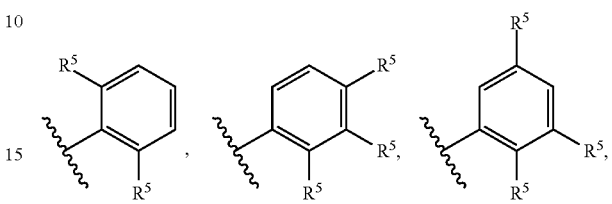


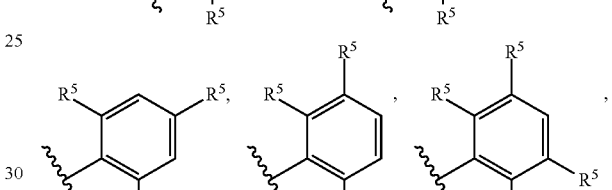

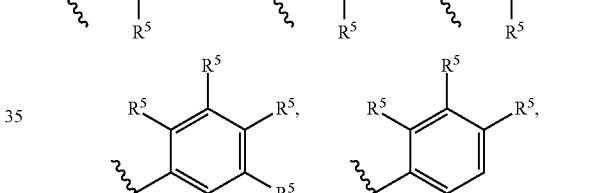

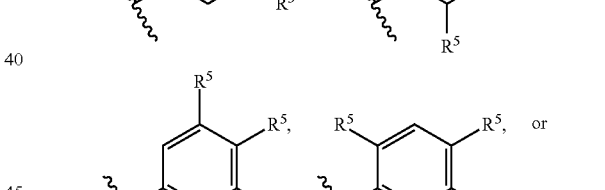

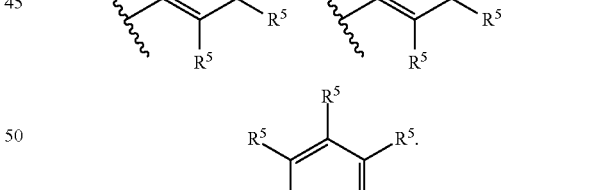

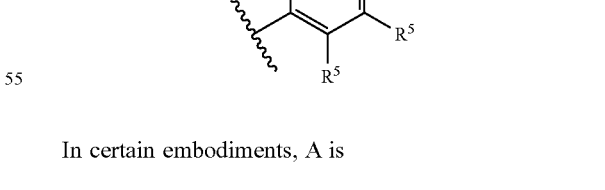

In certain embodiments, A is

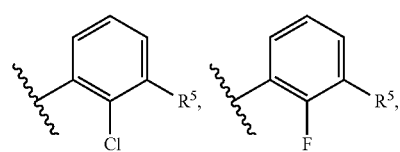

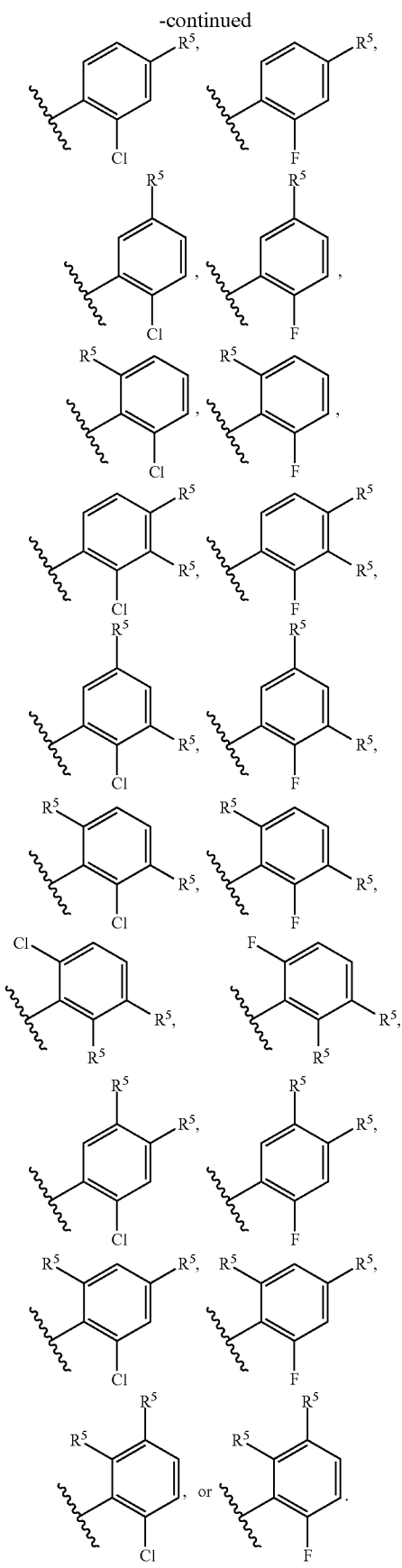
In certain embodiments, A is
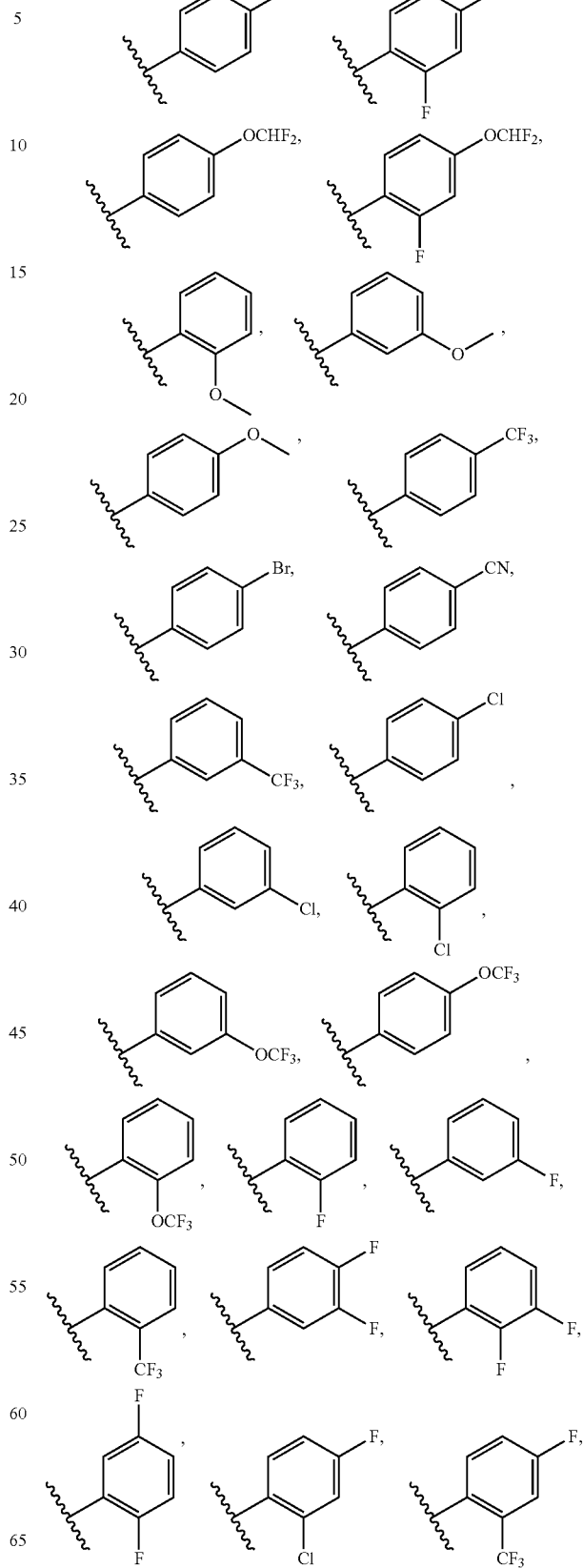

-continued

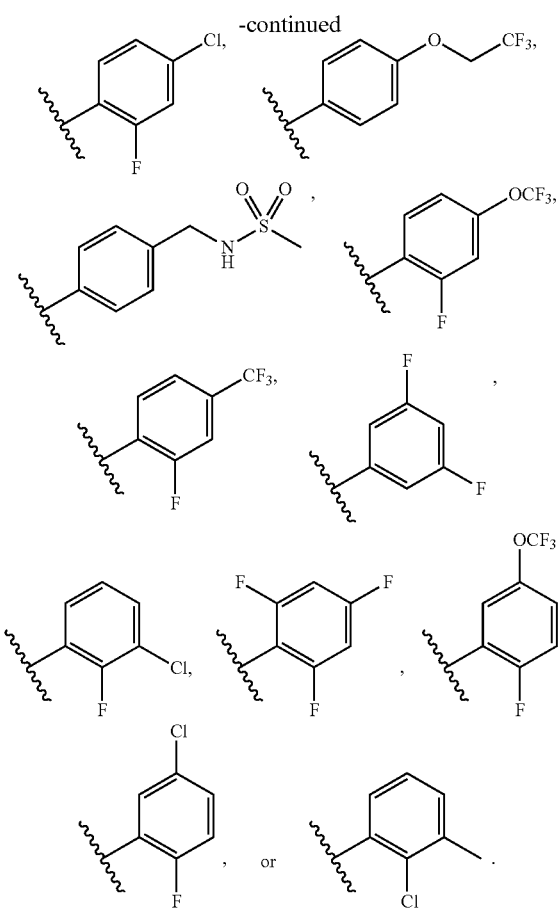

In certain embodiments, A is heteroaryl. In certain embodiments, A is monocyclic or bicyclic heteroaryl. In certain embodiments, A is bicyclic heteroaryl. In certain embodiments, A is monocyclic heteroaryl. In certain embodiments, A is pyridyl. In certain embodiments, A is 2-pyridyl, 3-pyridyl, or 4-pyridyl. In certain embodiments, A is 2-pyridyl or 3-pyridyl substituted with 1-3 independent substituents $R^5$, wherein each occurrence of $R^5$ is, independently, halogen, cyano, alkyl, haloalkyl, or —$OR^f$; and R is haloalkyl or alkyl.

In certain embodiments, A is

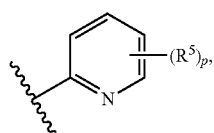

wherein p is 0, 1, 2, or 3. In certain embodiments, A is

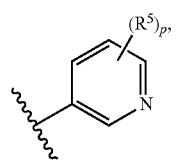

wherein p is 0, 1, 2, or 3. In certain embodiments, A is

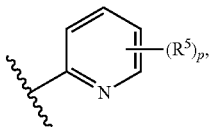

wherein p is 0 or 1. In certain embodiments, A is

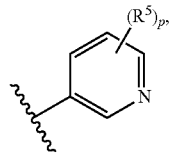

wherein p is 0 or 1.

In certain embodiments, A is

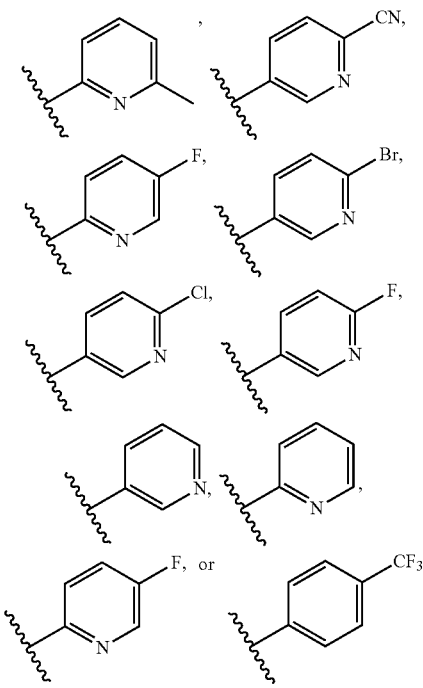

In certain embodiments, A is cycloalkyl. In certain embodiments, A is $C_{3-6}$ cycloalkyl. In certain embodiments, A is unsubstituted $C_{3-6}$ cycloalkyl. In certain embodiments, A is $C_{3-6}$ cycloalkyl substituted with 0-3 independent substituents $R^5$, wherein each occurrence of $R^5$ is, independently, halogen, cyano, alkyl, haloalkyl, or —$OR^f$; and $R^f$ is haloalkyl or alkyl. In certain embodiments, A is cyclopropyl. In certain embodiments, A is cyclobutyl. In certain embodiments, A is cyclopentyl. In certain embodiments, A is cyclohexyl.

In certain embodiments, A is arylalkyl. In certain embodiments, A is benzyl. In certain embodiments, A is benzyl substituted with 1-3 independent substituents $R^5$, wherein each occurrence of $R^5$ is, independently, halogen, cyano, alkyl, haloalkyl, or —$OR^f$; and $R^f$ is haloalkyl or alkyl.

In certain embodiments, X is $NR^4$; and $R^4$ is hydrogen or alkyl. In certain embodiments, X is NH. In certain embodiments, X is O.

In certain embodiments, $R^1$ is hydrogen, cyano, alkyl, alkenyl, alkynyl, cycloalkyl, aryl, heteroaryl, heterocycloalkyl, —$(CH_2)_nNR^aC(O)R^b$, —$C(O)NR^aR^b$, —$(CH_2)_nNR^dSO_2R^d$, —$CO_2R^e$, —$COR^f$, or —$CH_2OR^f$, wherein $R^1$ is optionally substituted with 1-3 independent substituents $R^5$.

In certain embodiments, $R^1$ is hydrogen, alkyl, haloalkyl, aryl, cycloalkyl, —$CH_2OR^f$, —$C(O)NR^aR^b$, or —$CH_2NHSO_2R^d$. In certain embodiments, $R^1$ is hydrogen, alkyl, haloalkyl, aryl, cycloalkyl, —$CH_2OR^f$, —$C(O)NR^aR^b$, or —$CH_2NHSO_2R^d$, wherein each occurrence of $R^a$, $R^b$, $R^d$, and $R^f$ is, independently, alkyl, haloalkyl, or aryl; or $R^a$ and $R^b$ together with the atoms to which they are attached form a heterocycloalkyl ring.

In certain embodiments, $R^1$ is hydrogen, alkyl, haloalkyl, or —$CH_2OR^f$. In certain embodiments, $R^1$ is hydrogen, alkyl, haloalkyl, or —$CH_2OR^f$; and $R^f$ is alkyl, haloalkyl, or aryl.

In certain embodiments, $R^1$ is alkyl, haloalkyl, or —$CH_2OR^f$. In certain embodiments, $R^1$ is alkyl, haloalkyl, or —$CH_2OR^f$; and $R^f$ is alkyl, haloalkyl, or aryl.

In certain embodiments, $R^1$ is alkyl. In certain embodiments, $R^1$ is $C_{1-6}$ alkyl. In certain embodiments, $R^1$ is $C_{1-4}$ alkyl. In certain embodiments, $R^1$ is methyl, ethyl, propyl, butyl, isopropyl, or isobutyl. In certain embodiments, $R^1$ is methyl. In certain embodiments, $R^1$ is ethyl.

In certain embodiments, $R^1$ is —$CH_2OR^f$. In certain embodiments, $R^1$ is —$CH_2OR^f$; and $R^f$ is hydrogen, alkyl, haloalkyl, arylalkyl, or aryl. In certain embodiments, $R^1$ is —$CH_2OH$, —$CH_2O\ CH_2Ph$, or —$CH_2OCH_3$.

In certain embodiments, $R^1$ is haloalkyl. In certain embodiments, $R^1$ is $C_{1-6}$ haloalkyl. In certain embodiments, $R^1$ is $C_{1-3}$ haloalkyl. In certain embodiments, $R^1$ is —$CH_2F$, —$CF_2H$, —$CF_3$, or —$CH_2CF_3$. In certain embodiments, $R^1$ is —$CF_3$ or —$CH_2CF_3$.

In certain embodiments, $R^1$ is —$(CH_2)_nNR^dSO_2R^d$. In certain embodiments, $R^1$ is —$(CH_2)_nNR^dSO_2R^d$; and each occurrence of $R^d$ is, independently, hydrogen, aryl, heteroaryl, cycloalkyl, or alkyl. In certain embodiments, $R^1$ is —$(CH_2)_nNHSO_2R^d$. In certain embodiments, $R^1$ is —$(CH_2)_nNHSO_2R^d$, wherein $R^d$ is aryl, heteroaryl, cycloalkyl, or alkyl. In certain embodiments, $R^1$ is —$CH_2NHSO_2R^d$, wherein $R^d$ is aryl or alkyl. In certain embodiments, $R^1$ is —$CH_2NHSO_2Me$, —$CH_2NMeSO_2Me$, —$CH_2NHSO_2Et$, —$CH_2NHSO_2Pr$, —$CH_2NHSO_2iPr$, —$CH_2NHSO_2iBu$, —$CH_2NHSO_2$-cyclopropyl, or —$CH_2NHSO_2Ph$. In certain embodiments, $R^1$ is —$CH_2NHSO_2Me$ or —$CH_2NHSO_2Ph$.

In certain embodiments, $R^1$ is hydrogen, methyl, ethyl, propyl, isopropyl, phenyl, —$CH_2CF_3$, trifluoromethyl, —$CH_2OCH_3$, —$CH_2OPh$, —$C(O)$-morpholinyl, —$C(O)NHPh$, —$CH_2NHSO_2Me$, or —$CH_2NHSO_2Ph$.

In certain embodiments, $R^1$ and A together with the atoms to which they are attached form a heterocycloalkyl ring or fused bicyclic ring. In certain embodiments, $R^1$ and A together with the atoms to which they are attached form a heterocycloalkyl ring or fused bicyclic ring; and $R^2$ is hydrogen.

In certain embodiments, $R^1$ and A together with the atoms to which they are attached form a heterocycloalkyl ring. In certain embodiments, $R^1$ and A together with the atoms to which they are attached form a heterocycloalkyl ring; and $R^2$ is hydrogen. In certain embodiments, $R^1$ and A together with the atoms to which they are attached form a pyrrolidinyl, piperidinyl, tetrahydrofuranyl, or tetrahydropyranyl ring. In certain embodiments, $R^1$ and A together with the atoms to which they are attached form a pyrrolidinyl, piperidinyl, tetrahydrofuranyl, or tetrahydropyranyl ring; and $R^2$ is hydrogen.

In certain embodiments, $R^1$ and A together with the atoms to which they are attached form a fused bicyclic ring. In certain embodiments, $R^1$ and A together with the atoms to which they are attached form a fused bicyclic ring; and $R^2$ is hydrogen. In certain embodiments, $R^1$ and A together with the atoms to which they are attached form an indanyl or tetrahydronaphthalenyl ring. In certain embodiments, $R^1$ and A together with the atoms to which they are attached form an indanyl or tetrahydronaphthalenyl ring; and $R^2$ is hydrogen.

In certain embodiments, $R^2$ is hydrogen, cyano, alkyl, alkenyl, alkynyl, cycloalkyl, aryl, heteroaryl, heterocycloalkyl, —$(CH_2)_nNR^aC(O)R^b$, —$C(O)NR^aR^b$, —$(CH_2)_nNHSO_2R^d$, —$CO_2R^e$, —$COR^f$, or —$CH_2OR^f$, wherein $R^2$ is optionally substituted with 1-3 independent substituents $R^5$.

In certain embodiments, $R^2$ is hydrogen, alkyl, haloalkyl, aryl, cycloalkyl, —$CH_2OR^f$, —$C(O)NR^aR^b$, or —$CH_2NHSO_2R^d$. In certain embodiments, $R^2$ is hydrogen, alkyl, haloalkyl, aryl, cycloalkyl, —$CH_2OR^f$, —$C(O)NR^aR^b$, or —$CH_2NHSO_2R^d$, wherein each occurrence of $R^a$, $R^b$, $R^d$, and $R^f$ is, independently, alkyl, haloalkyl, or aryl; or $R^a$ and $R^b$ together with the atoms to which they are attached form a heterocycloalkyl ring.

In certain embodiments, $R^2$ is hydrogen, alkyl, haloalkyl, or —$CH_2OR^f$. In certain embodiments, $R^2$ is hydrogen, alkyl, haloalkyl, or —$CH_2OR^f$; and $R^f$ is alkyl, haloalkyl, or aryl.

In certain embodiments, $R^2$ is alkyl, haloalkyl, or —$CH_2OR^f$. In certain embodiments, $R^2$ is alkyl, haloalkyl, or —$CH_2OR^f$; and $R^f$ is alkyl, haloalkyl, or aryl.

In certain embodiments, $R^2$ is alkyl. In certain embodiments, $R^2$ is $C_{1-6}$ alkyl. In certain embodiments, $R^2$ is $C_{1-4}$ alkyl. In certain embodiments, $R^2$ is methyl, ethyl, propyl, butyl, isopropyl, or isobutyl. In certain embodiments, $R^2$ is methyl. In certain embodiments, $R^2$ is ethyl.

In certain embodiments, $R^2$ is —$CH_2OR^f$. In certain embodiments, $R^2$ is —$CH_2OR^f$; and $R^f$ is hydrogen, alkyl, haloalkyl, arylalkyl, or aryl. In certain embodiments, $R^2$ is —$CH_2OH$, —$CH_2O\ CH_2Ph$, or —$CH_2OCH_3$.

In certain embodiments, $R^2$ is haloalkyl. In certain embodiments, $R^2$ is $C_{1-6}$ haloalkyl. In certain embodiments, $R^2$ is $C_{1-3}$ haloalkyl. In certain embodiments, $R^2$ is —$CH_2F$, —$CF_2H$, —$CF_3$, or —$CH_2CF_3$. In certain embodiments, $R^2$ is —$CF_3$ or —$CH_2CF_3$.

In certain embodiments, $R^2$ is —$(CH_2)_nNR^dSO_2R^d$. In certain embodiments, $R^2$ is —$(CH_2)_nNR^dSO_2R^d$; and each occurrence of $R^d$ is, independently, hydrogen, aryl, heteroaryl, cycloalkyl, or alkyl. In certain embodiments, $R^2$ is —$(CH_2)_nNHSO_2R^d$. In certain embodiments, $R^2$ is —$(CH_2)_nNHSO_2R^d$, wherein $R^d$ is aryl, heteroaryl, cycloalkyl, or alkyl. In certain embodiments, $R^2$ is —$CH_2NHSO_2R^d$, wherein $R^d$ is aryl or alkyl. In certain embodiments, $R^2$ is —$CH_2NHSO_2Me$, —$CH_2NMeSO_2Me$, —$CH_2NHSO_2Et$, —$CH_2NHSO_2Pr$, —$CH_2NHSO_2iPr$, —$CH_2NHSO_2iBu$, —$CH_2NHSO_2$-cyclopropyl, or —$CH_2NHSO_2Ph$. In certain embodiments, $R^2$ is —$CH_2NHSO_2Me$ or —$CH_2NHSO_2Ph$.

In certain embodiments, $R^2$ is hydrogen, methyl, ethyl, propyl, isopropyl, phenyl, —$CH_2CF_3$, trifluoromethyl, —$CH_2OCH_3$, —$CH_2OPh$, —$C(O)$-morpholinyl, —$C(O)NHPh$, —$CH_2NHSO_2Me$, or —$CH_2NHSO_2Ph$. In certain embodiments, $R^2$ is hydrogen.

In certain embodiments, each of $R^1$ and $R^2$ is, independently, hydrogen, alkyl, haloalkyl, aryl, cycloalkyl, —CH$_2$OR$^f$, —C(O)NR$^a$R$^b$, —CH$_2$NHSO$_2$R$^d$. In certain embodiments, each of R$^1$ and R$^2$ is, independently, hydrogen, alkyl, haloalkyl, or —CH$_2$OR$^f$.

In certain embodiments, R$^1$ is alkyl, haloalkyl, or —CH$_2$OR$^f$; and R$^2$ is hydrogen. In certain embodiments, R$^2$ is alkyl, haloalkyl, or —CH$_2$OR$^f$; and R$^2$ is hydrogen.

In certain embodiments, R$^1$ is methyl, haloalkyl, or —CH$_2$OR$^f$; and R$^2$ is hydrogen. In certain embodiments, R$^2$ is alkyl, haloalkyl, or —CH$_2$OR$^f$; and R$^2$ is hydrogen.

In certain embodiments, R$^1$ is methyl, ethyl, propyl, isopropyl, phenyl, —CH$_2$CF$_3$, trifluoromethyl, —CH$_2$OCH$_3$, —CH$_2$OPh, —C(O)-morpholinyl, —C(O)NHPh, —CH$_2$NHSO$_2$Me, or —CH$_2$NHSO$_2$Ph; and R$^2$ is hydrogen. In certain embodiments, R$^1$ is hydrogen, methyl, ethyl, propyl, isopropyl, —CH$_2$CF$_3$, trifluoromethyl, —CH$_2$OCH$_3$, or —CH$_2$OPh; and R$^2$ is hydrogen.

In certain embodiments, R$^1$ and R$^2$ together with the atoms to which they are attached form a heterocycloalkyl or cycloalkyl ring, wherein said heterocycloalkyl and cycloalkyl are optionally substituted with 1-3 independent substituents R$^5$. In certain embodiments, R$^1$ and R$^2$ together with the atoms to which they are attached form a heterocycloalkyl or cycloalkyl ring, wherein said heterocycloalkyl and cycloalkyl are optionally substituted with 1-3 independent substituents R$^5$, wherein each occurrence of R$^5$ is, independently, halogen, aryl, or acyl.

In certain embodiments, R$^1$ and R$^2$ together with the atoms to which they are attached form a heterocycloalkyl ring substituted with 1-3 independent substituents R$^5$, wherein each occurrence of R$^5$ is, independently, halogen, aryl, or acyl. In certain embodiments, R$^1$ and R$^2$ together with the atoms to which they are attached form a piperidine ring optionally substituted with aryl or acyl.

In certain embodiments, R$^1$ and R$^2$ together with the atoms to which they are attached form a cycloalkyl ring. In certain embodiments, R$^1$ and R$^2$ together with the atoms to which they are attached form a cycloalkyl ring optionally substituted with 1-3 independent substituents R$^5$. In certain embodiments, R$^1$ and R$^2$ together with the atoms to which they are attached form a cycloalkyl ring optionally substituted with 1-3 independent substituents R$^5$, wherein each occurrence of R$^5$ is halogen. In certain embodiments, R$^1$ and R$^2$ together with the atoms to which they are attached form a C$_{3-6}$ cycloalkyl ring. In certain embodiments, R$^1$ and R$^2$ together with the atoms to which they are attached form a C$_{3-6}$ cycloalkyl ring optionally substituted with 1-3 independent substituents R$^5$. In certain embodiments, R$^1$ and R$^2$ together with the atoms to which they are attached form a C$_{3-6}$ cycloalkyl ring optionally substituted with 1-3 independent substituents R$^5$, wherein each occurrence of R$^5$ is halogen. In certain embodiments, R$^1$ and R$^2$ together with the atoms to which they are attached form a C$_{3-4}$ cycloalkyl ring. In certain embodiments, R$^1$ and R$^2$ together with the atoms to which they are attached form a C$_{3-4}$ cycloalkyl ring optionally substituted with 1-3 independent substituents R$^5$. In certain embodiments, R$^1$ and R$^2$ together with the atoms to which they are attached form a C$_{3-4}$ cycloalkyl ring optionally substituted with 1-3 independent substituents R$^5$, wherein each occurrence of R$^5$ is halogen.

In certain embodiments, R$^3$ is haloalkyl. In certain embodiments, R$^3$ is C$_{1-6}$ haloalkyl. In certain embodiments, R$^3$ is C$_{1-4}$ haloalkyl. In certain embodiments, R$^3$ is C$_{1-3}$ haloalkyl. In certain embodiments, R$^3$ is Cl$_2$ haloalkyl. In certain embodiments, R$^3$ is —CF$_3$, —CHF$_2$, or CH$_2$F.

In certain embodiments, the compound of Formula I is a compound of Formula I-a:

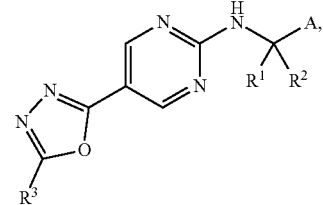

or a pharmaceutically acceptable salt, co-crystal, tautomer, stereoisomer, solvate, hydrate, polymorph, isotopically enriched derivative, or prodrug thereof, wherein R$^1$, R$^2$, R$^3$, and A are as defined herein.

In certain embodiments of the compound of Formula I-a, A is aryl or heteroaryl. In certain embodiments of the compound of Formula I-a, A is phenyl. In certain embodiments of the compound of Formula I-a, A is phenyl substituted with 1-3 independent substituents R$^5$, wherein each occurrence of R$^5$ is, independently, halogen, cyano, alkyl, haloalkyl, or —OR$^f$; and R$^f$ is haloalkyl or alkyl.

In certain embodiments of the compound of Formula I-a, R$^1$ is alkyl, haloalkyl, or —CH$_2$OR$^f$; R$^f$ is aryl, alkyl, or haloalkyl; and R$^2$ is hydrogen.

In certain embodiments of the compound of Formula I-a, R$^1$ and R$^2$ together with the atoms to which they are attached form a C$_{3-6}$ cycloalkyl ring.

In certain embodiments of the compound of Formula I-a, R$^3$ is haloalkyl.

In certain embodiments of the compound of Formula I-a, A is aryl or heteroaryl; R$^1$ is alkyl, haloalkyl, or —CH$_2$OR$^f$; R$^f$ is aryl, alkyl, or haloalkyl; R$^2$ is hydrogen; and R$^3$ is haloalkyl.

In certain embodiments of the compound of Formula I-a, A is aryl or heteroaryl; R$^1$ and R$^2$ together with the atoms to which they are attached form a C$_{3-6}$ cycloalkyl ring; and R$^3$ is haloalkyl.

In certain embodiments of the compound of Formula I-a, A is phenyl substituted with 1-3 independent substituents R$^5$, wherein each occurrence of R$^5$ is, independently, halogen, cyano, alkyl, haloalkyl, or —OR$^f$; R$^f$ is haloalkyl or alkyl; R$^1$ is alkyl, haloalkyl, or —CH$_2$OR$^f$; R$^f$ is aryl, alkyl, or haloalkyl; R$^2$ is hydrogen; and R$^3$ is haloalkyl.

In certain embodiments of the compound of Formula I-a, A is phenyl substituted with 1-3 independent substituents R$^5$, wherein each occurrence of R$^5$ is, independently, halogen, cyano, alkyl, haloalkyl, or —OR$^f$; R$^f$ is haloalkyl or alkyl; R$^1$ and R$^2$ together with the atoms to which they are attached form a C$_{3-6}$ cycloalkyl ring; and R$^3$ is haloalkyl.

In certain embodiments, the compound of Formula I is a compound of Formula I-b:

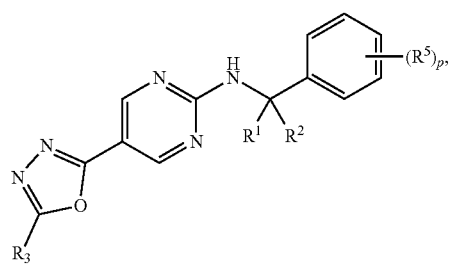

or a pharmaceutically acceptable salt, co-crystal, tautomer, stereoisomer, solvate, hydrate, polymorph, isotopically enriched derivative, or prodrug thereof, wherein p is 0, 1, 2, or 3; and $R^1$, $R^2$, $R^3$, and $R^5$ are as defined herein.

In certain embodiments of the compound of Formula I-b, $R^1$ is alkyl, haloalkyl, or —$CH_2OR^f$; $R^f$ is aryl, alkyl, or haloalkyl; and $R^2$ is hydrogen.

In certain embodiments of the compound of Formula I-b, $R^1$ and $R^2$ together with the atoms to which they are attached form a $C_{3-6}$ cycloalkyl ring.

In certain embodiments of the compound of Formula I-b, $R^3$ is haloalkyl.

In certain embodiments of the compound of Formula I-b, each $R^5$ is, independently, halogen, cyano, alkyl, haloalkyl, or —$OR^f$.

In certain embodiments of the compound of Formula I-b, $R^1$ is alkyl, haloalkyl, or —$CH_2OR^f$, wherein $R^f$ is aryl, alkyl, or haloalkyl; $R^2$ is hydrogen; $R^3$ is haloalkyl; and each $R^5$ is, independently, halogen, cyano, alkyl, haloalkyl, or —$OR^f$.

In certain embodiments of the compound of Formula I-b, $R^1$ and $R^2$ together with the atoms to which they are attached form a $C_{3-6}$ cycloalkyl ring; $R^3$ is haloalkyl; and each $R^5$ is, independently, halogen, cyano, alkyl, haloalkyl, or —$OR^f$.

In certain embodiments, the compound of Formula I is a compound of Formula I-c:

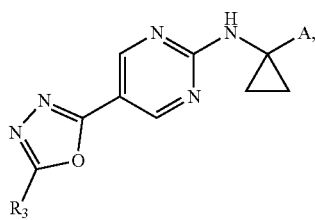

I-c or a pharmaceutically acceptable salt, co-crystal, tautomer, stereoisomer, solvate, hydrate, polymorph, isotopically enriched derivative, or prodrug thereof, wherein $R^3$ and A are as defined herein.

In certain embodiments of the compound of Formula I-a, A is aryl or heteroaryl. In certain embodiments of the compound of Formula I-a, A is phenyl. In certain embodiments of the compound of Formula I-a, A is phenyl substituted with 1-3 independent substituents $R^5$, wherein each occurrence of $R^5$ is, independently, halogen, cyano, alkyl, haloalkyl, or —$OR^f$; and $R^f$ is haloalkyl or alkyl.

In certain embodiments of the compound of Formula I-c, $R^3$ is haloalkyl. In certain embodiments of the compound of Formula I-c, $R^3$ is $C_{1-3}$ haloalkyl. In certain embodiments of the compound of Formula I-c, $R^3$ is —$CF_3$, —$CHF_2$, or $CH_2F$. In certain embodiments of the compound of Formula I-c, $R^3$ is —$CHF_2$.

In certain embodiments of the compound of Formula I-c, A is aryl or heteroaryl; and $R^3$ is haloalkyl.

In certain embodiments of the compound of Formula I-c, A is aryl or heteroaryl; and $R^3$ is $C_{1-3}$ haloalkyl.

In certain embodiments of the compound of Formula I-c, A is phenyl substituted with 1-3 independent substituents $R^5$, wherein each occurrence of $R^5$ is, independently, halogen, cyano, alkyl, haloalkyl, or —$OR^f$; $R^f$ is haloalkyl or alkyl; and $R^3$ is haloalkyl.

In certain embodiments of the compound of Formula I-a, A is phenyl substituted with 1-3 independent substituents $R^5$, wherein each occurrence of $R^5$ is, independently, halogen, cyano, alkyl, haloalkyl, or —$OR^f$; $R^f$ is haloalkyl or alkyl; and $R^3$ is $C_{1-3}$ haloalkyl.

In certain embodiments, the compound of Formula I is a compound of Formula I-d:

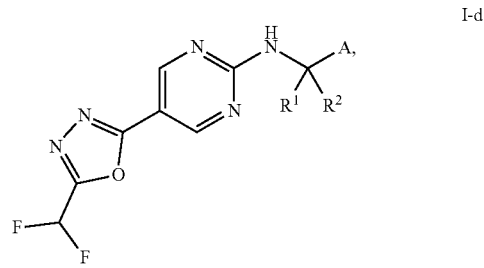

I-d or a pharmaceutically acceptable salt, co-crystal, tautomer, stereoisomer, solvate, hydrate, polymorph, isotopically enriched derivative, or prodrug thereof, wherein $R^1$, $R^2$, and A are as defined herein.

In certain embodiments of the compound of Formula I-a, A is aryl or heteroaryl. In certain embodiments of the compound of Formula I-a, A is phenyl. In certain embodiments of the compound of Formula I-a, A is phenyl substituted with 1-3 independent substituents $R^5$, wherein each occurrence of $R^5$ is, independently, halogen, cyano, alkyl, haloalkyl, or —$OR^f$; and $R^f$ is haloalkyl or alkyl.

In certain embodiments of the compound of Formula I-d, $R^1$ is alkyl, haloalkyl, or —$CH_2OR^f$, wherein $R^f$ is aryl, alkyl, or haloalkyl; and $R^2$ is hydrogen.

In certain embodiments of the compound of Formula I-d, $R^1$ and $R^2$ together with the atoms to which they are attached form a $C_{3-6}$ cycloalkyl ring.

In certain embodiments of the compound of Formula I-d, A is aryl or heteroaryl; $R^1$ is alkyl, haloalkyl, or —$CH_2OR^f$; $R^f$ is aryl, alkyl, or haloalkyl; and $R^2$ is hydrogen.

In certain embodiments of the compound of Formula I-d, A is aryl or heteroaryl; and $R^1$ and $R^2$ together with the atoms to which they are attached form a $C_{3-6}$ cycloalkyl ring.

In certain embodiments of the compound of Formula I-d, A is phenyl substituted with 1-3 independent substituents $R^5$, wherein each occurrence of $R^5$ is, independently, halogen, cyano, alkyl, haloalkyl, or —$OR^f$, wherein $R^f$ is haloalkyl or alkyl; $R^1$ is alkyl, haloalkyl, or —$CH_2OR^f$, wherein $R^f$ is aryl, alkyl, or haloalkyl; and $R^2$ is hydrogen.

In certain embodiments of the compound of Formula I-d, A is phenyl substituted with 1-3 independent substituents $R^5$, wherein each occurrence of $R^5$ is, independently, halogen, cyano, alkyl, haloalkyl, or —$OR^f$; $R^f$ is haloalkyl or alkyl; and $R^1$ and $R^2$ together with the atoms to which they are attached form a $C_{3-6}$ cycloalkyl ring.

In certain embodiments, the compound of Formula I is a compound of Formula I-e:

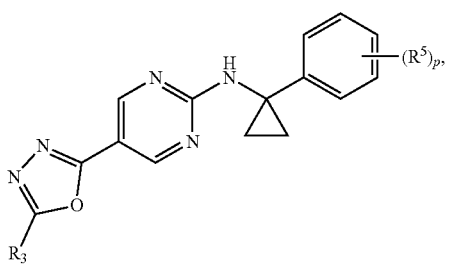

or a pharmaceutically acceptable salt, co-crystal, tautomer, stereoisomer, solvate, hydrate, polymorph, isotopically enriched derivative, or prodrug thereof, wherein p is 0, 1, 2, or 3; and $R^3$ and $R^5$ are as defined herein.

In certain embodiments of the compound of Formula I-e, $R^3$ is haloalkyl. In certain embodiments of the compound of Formula I-e, $R^3$ is $C_{1-3}$ haloalkyl. In certain embodiments of the compound of Formula I-e, $R^3$ is —$CF_3$, —$CHF_2$, or $CH_2F$. In certain embodiments of the compound of Formula I-e, $R^3$ is —$CHF_2$.

In certain embodiments of the compound of Formula I-e, each occurrence of $R^5$ is, independently, halogen, cyano, alkyl, haloalkyl, or —$OR^f$. In certain embodiments of the compound of Formula I-e, each occurrence of $R^5$ is, independently, halogen, cyano, alkyl, haloalkyl, or —$OR^f$; and $R^f$ is haloalkyl or alkyl.

In certain embodiments of the compound of Formula I-e, $R^3$ is haloalkyl; and each occurrence of $R^5$ is, independently, halogen, cyano, alkyl, haloalkyl, or —$OR^f$.

In certain embodiments of the compound of Formula I-e, $R^3$ is haloalkyl; each occurrence of $R^5$ is, independently, halogen, cyano, alkyl, haloalkyl, or —$OR^f$; and $R^f$ is haloalkyl or alkyl.

In certain embodiments, the compound of Formula I is a compound of Formula I-f:

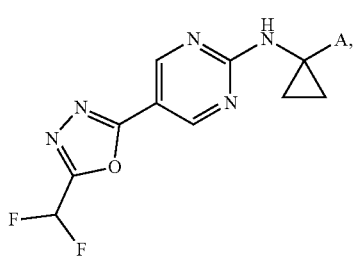

or a pharmaceutically acceptable salt, co-crystal, tautomer, stereoisomer, solvate, hydrate, polymorph, isotopically enriched derivative, or prodrug thereof, wherein A is as defined herein.

In certain embodiments of the compound of Formula I-f, A is aryl, heteroaryl, or cycloalkyl. In certain embodiments of the compound of Formula I-f, A is aryl or heteroaryl.

In certain embodiments of the compound of Formula I-f, A is heteroaryl. In certain embodiments of the compound of Formula I-f, A is monocyclic or bicyclic heteroaryl. In certain embodiments of the compound of Formula I-f, A is pyridyl. In certain embodiments of the compound of Formula I-f, A is 2-pyridyl or 3-pyridyl substituted with 1-3 independent substituents $R^5$; each occurrence of $R^5$ is, independently, halogen, cyano, alkyl, haloalkyl, or —$OR^f$; and $R^f$ is haloalkyl or alkyl In certain embodiments of the compound of Formula I-f, A is aryl. In certain embodiments of the compound of Formula I-f, A is phenyl. In certain embodiments of the compound of Formula I-f, A is phenyl substituted with 1-3 independent substituents $R^5$, wherein each occurrence of $R^5$ is, independently, halogen, cyano, alkyl, haloalkyl, or —$OR^f$; and $R^f$ is haloalkyl or alkyl.

In certain embodiments of the compound of Formula I-f, A is,

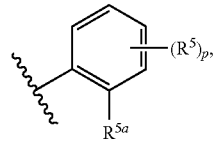

wherein $R^{5a}$ is halogen; each occurrence of $R^5$ is, independently, halogen, cyano, alkyl, haloalkyl, or —$OR^f$; $R^f$ is alkyl or haloalkyl; and p is 0, 1, or 2.

In certain embodiments, the compound of Formula I is a compound of Formula I-g:

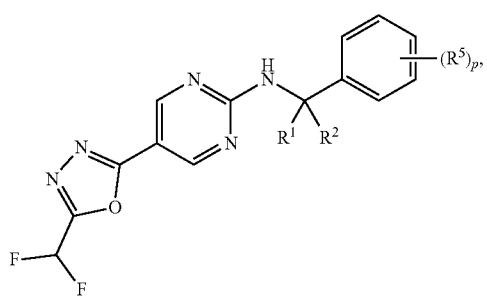

or a pharmaceutically acceptable salt, co-crystal, tautomer, stereoisomer, solvate, hydrate, polymorph, isotopically enriched derivative, or prodrug thereof, wherein $R^1$, $R^2$, $R^5$, and p are as defined herein.

In certain embodiments of the compound of Formula I-g, $R^1$ is alkyl, haloalkyl, or —$CH_2OR^f$; $R^f$ is aryl, alkyl, or haloalkyl; and $R^2$ is hydrogen.

In certain embodiments of the compound of Formula I-g, $R^1$ and $R^2$ together with the atoms to which they are attached form a $C_{3-6}$ cycloalkyl ring.

In certain embodiments of the compound of Formula I-g, p is 1, 2, or 3.

In certain embodiments of the compound of Formula I-g, p is 1, 2, or 3; each occurrence of $R^5$ is, independently, halogen, cyano, alkyl, haloalkyl, or —$OR^f$; $R^f$ is haloalkyl or alkyl. In certain embodiments of the compound of Formula I-g, at least one $R^5$ is halogen.

In certain embodiments of the compound of Formula I-g, p is 1, 2, or 3; each occurrence of $R^5$ is, independently, halogen, cyano, alkyl, haloalkyl, or —$OR^f$, wherein $R^f$ is haloalkyl or alkyl;
  $R^1$ is alkyl, haloalkyl, or —$CH_2OR^f$, wherein $R^f$ is aryl, alkyl, or haloalkyl; and $R^2$ is hydrogen.

In certain embodiments of the compound of Formula I-g, p is 1, 2, or 3; each occurrence of $R^5$ is, independently, halogen, cyano, alkyl, haloalkyl, or —$OR^f$, wherein $R^f$ is haloalkyl or alkyl, and at least one $R^5$ is halogen; $R^1$ is alkyl, haloalkyl, or —$CH_2OR^f$, wherein $R^f$ is aryl, alkyl, or haloalkyl; and $R^2$ is hydrogen.

In certain embodiments of the compound of Formula I-g, p is 1, 2, or 3; each occurrence of $R^5$ is, independently, halogen, cyano, alkyl, haloalkyl, or —$OR^f$; $R^f$ is haloalkyl or alkyl; and $R^1$ and $R^2$ together with the atoms to which they are attached form a $C_{3-6}$ cycloalkyl ring.

In certain embodiments of the compound of Formula I-g, p is 1, 2, or 3; each occurrence of $R^5$ is, independently, halogen, cyano, alkyl, haloalkyl, or —$OR^f$; $R^f$ is haloalkyl or alkyl; wherein at least one $R^5$ is halogen; and $R^1$ and $R^2$ together with the atoms to which they are attached form a $C_{3-6}$ cycloalkyl ring.

In certain embodiments, the compound of Formula I is a compound of Formula I-h:

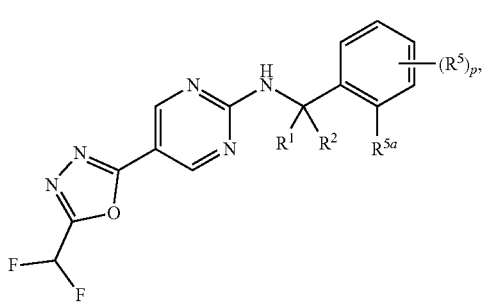

I-h or a pharmaceutically acceptable salt, co-crystal, tautomer, stereoisomer, solvate, hydrate, polymorph, isotopically enriched derivative, or prodrug thereof, wherein $R^1$, $R^2$, $R^5$, $R^{5a}$, and p are as defined herein.

In certain embodiments of the compound of Formula I-h, $R^1$ is alkyl, haloalkyl, or —$CH_2OR^f$; $R^f$ is aryl, alkyl, or haloalkyl; and $R^2$ is hydrogen.

In certain embodiments of the compound of Formula I-h, $R^1$ and $R^2$ together with the atoms to which they are attached form a $C_{3-6}$ cycloalkyl ring.

In certain embodiments of the compound of Formula I-h, p is 0, 1, or 2. In certain embodiments of the compound of Formula I-h, p is 0 or 1.

In certain embodiments of the compound of Formula I-h, $R^{5a}$ is halogen. In certain embodiments of the compound of Formula I-h, $R^{5a}$ is —F or —$C_1$.

In certain embodiments of the compound of Formula I-h, p is 0 or 1; $R^{5a}$ is halogen; $R^5$ is halogen, cyano, alkyl, haloalkyl, or —$OR^f$; and $R^f$ is haloalkyl or alkyl.

In certain embodiments of the compound of Formula I-h, p is 0 or 1; $R^{5a}$ is halogen; $R^5$ is halogen, cyano, alkyl, haloalkyl, or —$OR^f$, wherein $R^f$ is haloalkyl or alkyl; $R^1$ is alkyl, haloalkyl, or —$CH_2OR^f$, wherein $R^f$ is aryl, alkyl, or haloalkyl; and $R^2$ is hydrogen.

In certain embodiments of the compound of Formula I-h, p is 0 or 1; $R^{5a}$ is halogen; $R^5$ is halogen, cyano, alkyl, haloalkyl, or —$OR^f$; $R^f$ is haloalkyl or alkyl; and $R^1$ and $R^2$ together with the atoms to which they are attached form a $C_{3-6}$ cycloalkyl ring.

In certain embodiments, the compound of Formula I is a compound of Formula I-i:

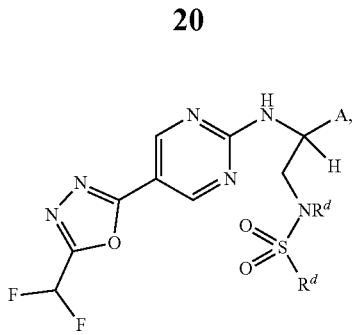

I-i or a pharmaceutically acceptable salt, co-crystal, tautomer, stereoisomer, solvate, hydrate, polymorph, isotopically enriched derivative, or prodrug thereof, wherein each $R^d$ is, independently, hydrogen, alkyl, aryl, or heteroaryl; and A is as defined herein.

In certain embodiments of the compound of Formula I-i, A is aryl, heteroaryl, or cycloalkyl. In certain embodiments of the compound of Formula I-i, A is aryl or heteroaryl.

In certain embodiments of the compound of Formula I-i, A is heteroaryl. In certain embodiments of the compound of Formula I-i, A is monocyclic or bicyclic heteroaryl. In certain embodiments of the compound of Formula I-i, A is pyridyl. In certain embodiments of the compound of Formula I-i, A is 2-pyridyl or 3-pyridyl substituted with 1-3 independent substituents $R^5$, wherein each occurrence of $R^5$ is, independently, halogen, cyano, alkyl, haloalkyl, or —$OR^f$; and $R^f$ is haloalkyl or alkyl In certain embodiments of the compound of Formula I-i, A is aryl. In certain embodiments of the compound of Formula I-i, A is phenyl. In certain embodiments of the compound of Formula I-i, A is phenyl substituted with 1-3 independent substituents $R^5$; each occurrence of $R^5$ is, independently, halogen, cyano, alkyl, haloalkyl, or —$OR^f$; and $R^f$ is haloalkyl or alkyl.

In certain embodiments of the compound of Formula I-i, A is

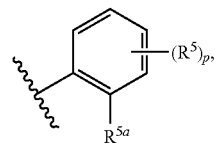

wherein $R^{5a}$ is halogen; each occurrence of $R^5$ is, independently, halogen, cyano, alkyl, haloalkyl, or —$OR^f$; $R^f$ is alkyl or haloalkyl; and p is 0, 1, or 2.

In another aspect, provided are compounds of Formula I:

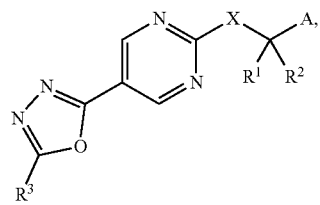

I or pharmaceutically acceptable salts, co-crystals, tautomers, stereoisomers, solvates, hydrates, polymorphs, isotopically enriched derivatives, or prodrugs thereof, wherein:

A is aryl, heteroaryl, cycloalkyl, heterocycloalkyl, arylalkyl, or alkyl, wherein A is optionally substituted with 1-3 independent substituents $R^5$;

X is $NR^4$ or O;

each of $R^1$ and $R^2$ is, independently, hydrogen, cyano, alkyl, alkenyl, alkynyl, cycloalkyl, aryl, heteroaryl, heterocycloalkyl, —$(CR^hR^i)_n$-E-$NR^aC(O)R^b$, —$C(O)NR^aR^b$, —$(CR^hR^i)_n$-E-$NR^dSO_2R^d$, —$(CR^hR^i)_n$-G-$SO_2R^d$, —$CO_2R^e$, —$COR^f$, or —$CH_2OR^f$, wherein $R^1$ and $R^2$ are optionally substituted with 1-3 independent substituents $R^5$;

or $R^1$ and $R^2$ together with the atoms to which they are attached form a heterocycloalkyl or cycloalkyl ring, wherein said heterocycloalkyl and cycloalkyl are optionally substituted with 1-3 independent substituents $R^5$;

or $R^1$ and A together with the atoms to which they are attached form a heterocycloalkyl ring or fused bicyclic ring;

$R^3$ is haloalkyl or —$OR^g$;

$R^4$ is hydrogen or alkyl;

each occurrence of $R^5$ is, independently, halogen, cyano, alkyl, haloalkyl, —$NR^aR^b$, —$NHSO_2R^c$, —$(CH_2)_n$-$NR^aR^b$, —$(CH_2)_nC(O)NR^aR^b$, —$(CH_2)_nNR^dSO_2R^d$, —$S(O)R^d$, —$S(O)_2R^d$, —$CO_2R^e$, —$COR^f$, —$(CR^eR^f)_nOR^f$, —$OR^f$, or aryl substituted with 0-3 independent halogen, —$NR^aR^b$, —$NHSO_2R^c$, —$(CH_2)_nNR^aR^b$, —$(CH_2)_nC(O)NR^aR^b$, —$(CH_2)_nNHSO_2R^d$, —$S(O)R^d$, —$S(O)_2R^d$, —$CO_2R^e$, —$COR^f$, —$(CR^eR^f)_nOR^f$, or —$OR^f$; or two occurrences of $R^5$, together with the atoms to which they are attached, form a cycloalkyl, heterocycloalkyl, aryl, or heteroaryl ring;

each n is independently 1, 2, 3, 4, 5, 6, 7, 8, 9, or 10;

E is a bond, aryl, heteroaryl, cycloalkyl, or heterocycloalkyl;

G is heteroaryl or heterocycloalkyl;

each occurrence of $R^a$, $R^b$, $R^c$, $R^d$, $R^e$, and $R^f$ is, independently, hydrogen, acyl, alkoxyalkyl, alkyl, alkenyl, alkynyl, heteroalkyl, haloalkyl, cycloalkyl, heterocycloalkyl, aryl, heteroaryl, arylalkyl, heteroarylalkyl, heterocycloalkylalkyl, a nitrogen protecting group when attached to a nitrogen atom, or an oxygen protecting group when attached to an oxygen atom; or $R^a$ and $R^b$ together with the atoms to which they are attached form a heterocycloalkyl ring; or $R^e$ and $R^f$ together with the atoms to which they are attached form a cycloalkyl ring; or 2 instances of $R^d$ together with the atoms to which they are attached form a heterocycloalkyl ring;

$R^g$ is haloalkyl; and each occurrence of $R^h$ and $R^i$ is, independently, hydrogen, halogen, alkyl, alkenyl, alkynyl, heteroalkyl, haloalkyl, cycloalkyl, heterocycloalkyl, aryl, heteroaryl, arylalkyl, heteroarylalkyl, or heterocycloalkylalkyl.

In certain embodiments, A is aryl, heteroaryl, cycloalkyl, heterocycloalkyl, arylalkyl, or alkyl, wherein A is optionally substituted with 1-3 independent substituents $R^5$;

X is $NR^4$ or O;

each of $R^1$ and $R^2$ is, independently, hydrogen, cyano, alkyl, alkenyl, alkynyl, cycloalkyl, aryl, heteroaryl, heterocycloalkyl, —$(CR^hR^i)_n$-E-$NR^aC(O)R^b$, —$C(O)NR^aR^b$, —$(CR^hR^i)_n$-E-$NR^dSO_2R^d$, —$(CR^hR^i)_n$-G-$SO_2R^d$, —$CO_2R^e$, —$COR^f$, or —$CH_2OR^f$, wherein $R^1$ and $R^2$ are optionally substituted with 1-3 independent substituents $R^5$;

or $R^1$ and A together with the atoms to which they are attached form a heterocycloalkyl ring or fused bicyclic ring;

$R^3$ is haloalkyl or —$OR^g$;

$R^4$ is hydrogen or alkyl;

each occurrence of $R^5$ is, independently, halogen, cyano, alkyl, haloalkyl, —$NR^aR^b$, —$NHSO_2R^c$, —$(CH_2)_n$-$NR^aR^b$, —$(CH_2)_nC(O)NR^aR^b$, —$(CH_2)_nNR^dSO_2R^d$, —$S(O)R^d$, —$S(O)_2R^d$, —$CO_2R^e$, —$COR^f$, —$(CR^eR^f)_nOR^f$, —$OR^f$, or aryl substituted with 0-3 independent halogen, —$NR^aR^b$, —$NHSO_2R^c$, —$(CH_2)_nNR^aR^b$, —$(CH_2)_nC(O)NR^aR^b$, —$(CH_2)_nNHSO_2R^d$, —$S(O)R^d$, —$S(O)_2R^d$, —$CO_2R^e$, —$COR^f$, —$(CR^eR^f)_nOR^f$, or —$OR^f$; or two occurrences of $R^5$, together with the atoms to which they are attached, form a cycloalkyl, heterocycloalkyl, aryl, or heteroaryl ring;

each n is independently 1, 2, 3, 4, 5, 6, 7, 8, 9, or 10;

E is a bond, aryl, heteroaryl, cycloalkyl, or heterocycloalkyl;

G is heteroaryl or heterocycloalkyl;

each occurrence of $R^a$, $R^b$, $R^c$, $R^d$, $R^e$, and $R^f$ is, independently, hydrogen, acyl, alkoxyalkyl, alkyl, alkenyl, alkynyl, heteroalkyl, haloalkyl, cycloalkyl, heterocycloalkyl, aryl, heteroaryl, arylalkyl, heteroarylalkyl, heterocycloalkylalkyl, a nitrogen protecting group when attached to a nitrogen atom, or an oxygen protecting group when attached to an oxygen atom; or $R^a$ and $R^b$ together with the atoms to which they are attached form a heterocycloalkyl ring; or $R^e$ and $R^f$ together with the atoms to which they are attached form a cycloalkyl ring; or 2 instances of $R^d$ together with the atoms to which they are attached form a heterocycloalkyl ring;

$R^g$ is haloalkyl; and each occurrence of $R^h$ and $R^i$ is, independently, hydrogen, halogen, alkyl, alkenyl, alkynyl, heteroalkyl, haloalkyl, cycloalkyl, heterocycloalkyl, aryl, heteroaryl, arylalkyl, heteroarylalkyl, or heterocycloalkylalkyl.

In certain embodiments, A is aryl, heteroaryl, cycloalkyl, heterocycloalkyl, or arylalkyl.

In certain embodiments, A is aryl, heteroaryl, cycloalkyl, or heterocycloalkyl.

In certain embodiments, A is aryl, heteroaryl, or cycloalkyl. In certain embodiments, A is aryl, heteroaryl, or $C_{3-6}$ cycloalkyl.

In certain embodiments, A is aryl or heteroaryl.

In certain embodiments, A is aryl. In certain embodiments, A is phenyl or naphthyl. In certain embodiments, A is phenyl. In certain embodiments, A is unsubstituted phenyl. In certain embodiments, A is phenyl substituted with 1-3 independent substituents $R^5$. In certain embodiments, A is phenyl substituted with 1-3 independent substituents $R^5$, wherein each occurrence of $R^5$ is, independently, halogen, cyano, alkyl, haloalkyl, or —$OR^f$; and $R^f$ is haloalkyl or alkyl.

In certain embodiments, A is

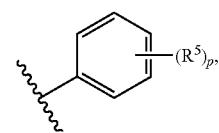

wherein p is 0, 1, 2, or 3. In certain embodiments, A is

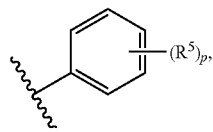

wherein p is 1, 2, or 3. In certain embodiments, A is

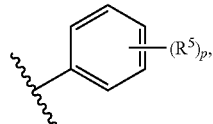

wherein p is 1 or 2. In certain embodiments, A is

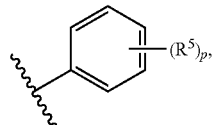

wherein p is 1. In certain embodiments, A is

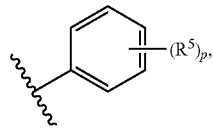

wherein p is 2. In certain embodiments, A is

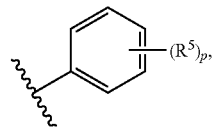

wherein p is 3.

In certain embodiments, A is

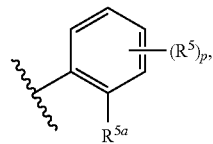

wherein $R^{5a}$ is any group as defined for $R^5$ herein, and p is 0, 1, or 2. In certain embodiments, $R^{5a}$ is halogen. In certain embodiments, $R^{5a}$ is F, Cl, or Br. In certain embodiments, $R^{5a}$ is F or $C_1$. In certain embodiments, $R^{5a}$ is F. In certain embodiments, $R^{5a}$ is $C_1$. In certain embodiments, $R^{5a}$ is halogen; each occurrence of $R^5$ is, independently, halogen, cyano, alkyl, haloalkyl, or —$OR^f$; $R^f$ is alkyl or haloalkyl; and p is 0, 1, or 2. In certain embodiments, $R^{5a}$ is F or $C_1$; each occurrence of $R^5$ is, independently, halogen, cyano, alkyl, haloalkyl, or —$OR^f$; $R^f$ is alkyl or haloalkyl; and p is 0 or 1.

In certain embodiments, A is

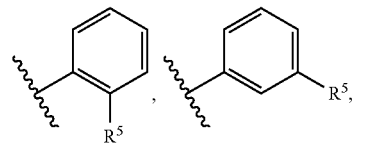

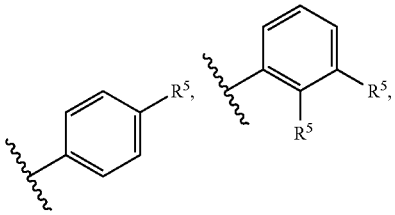

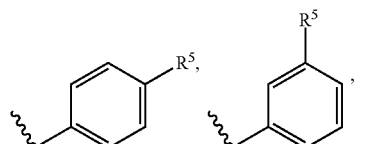

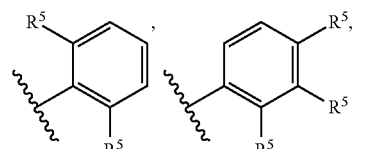

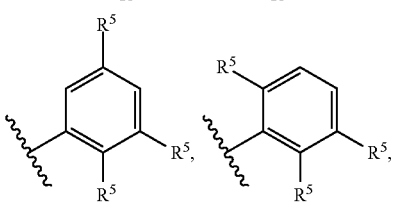

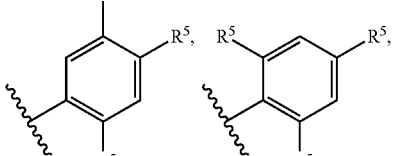

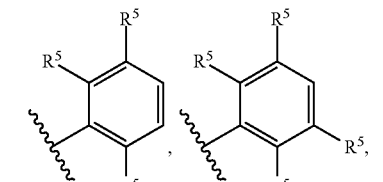

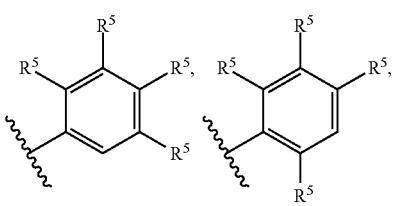

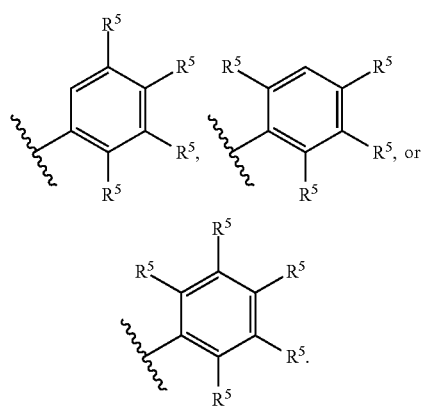
In certain embodiments, A is
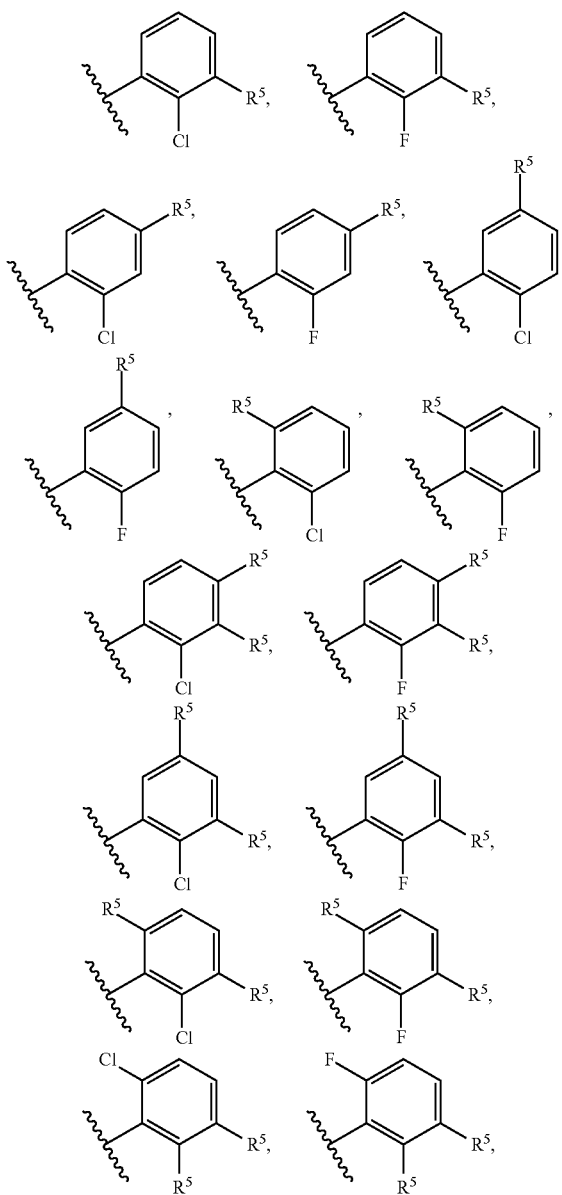
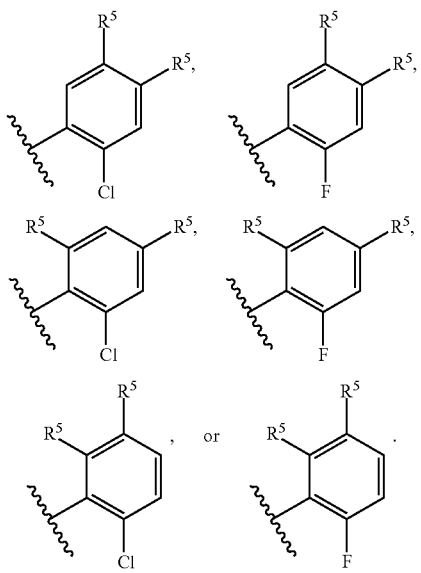
In certain embodiments, A is
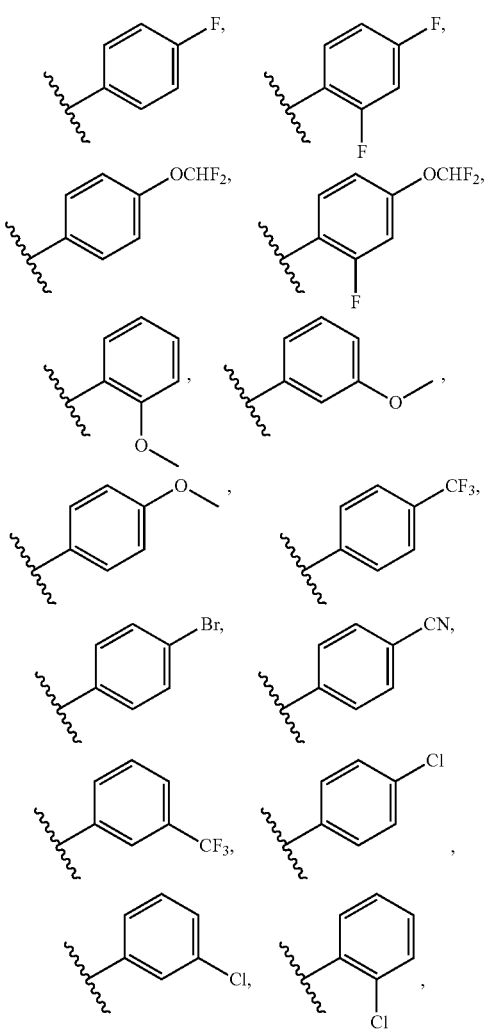

-continued

[structures shown]

In certain embodiments, A is heteroaryl. In certain embodiments, A is monocyclic or bicyclic heteroaryl. In certain embodiments, A is bicyclic heteroaryl. In certain embodiments, A is monocyclic heteroaryl. In certain embodiments, A is pyridyl. In certain embodiments, A is 2-pyridyl, 3-pyridyl, or 4-pyridyl. In certain embodiments, A is 2-pyridyl or 3-pyridyl substituted with 1-3 independent substituents $R^5$, wherein each occurrence of $R^5$ is, independently, halogen, cyano, alkyl, haloalkyl, or —$OR^f$; and $R^f$ is haloalkyl or alkyl.

In certain embodiments, A is

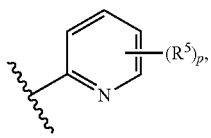

wherein p is 0 or 1. In certain embodiments, A is

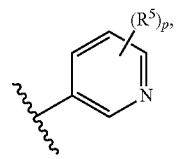

wherein p is 0, 1, 2 or 3. In certain embodiments, A is

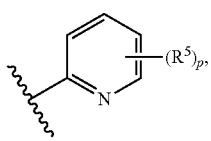

wherein p is 0 or 1. In certain embodiments, A is

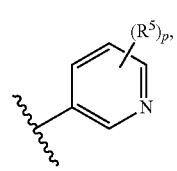

wherein p is 0 or 1.

In certain embodiments, A

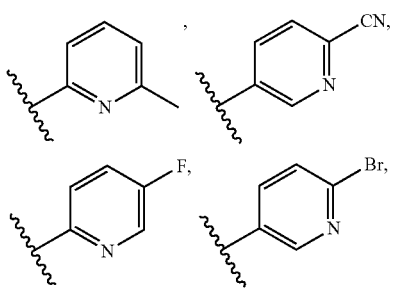

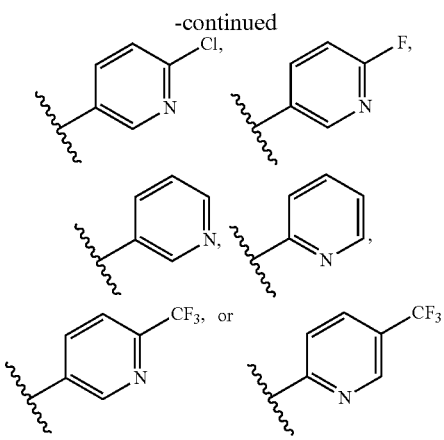

In certain embodiments, A is $C_{3-6}$ cycloalkyl. In certain embodiments, A is unsubstituted $C_{3-6}$ cycloalkyl. In certain embodiments, A is $C_{3-6}$ cycloalkyl substituted with 0-3 independent substituents $R^5$, wherein each occurrence of $R^5$ is, independently, halogen, cyano, alkyl, haloalkyl, or —$OR^f$; and $R^f$ is haloalkyl or alkyl. In certain embodiments, A is cyclopropyl. In certain embodiments, A is cyclobutyl. In certain embodiments, A is cyclopentyl. In certain embodiments, A is cyclohexyl.

In certain embodiments, A is heterocycloalkyl. In certain embodiments, A is a 4-7 membered heterocycloalkyl. In certain embodiments, A is a 4-7 membered heterocycloalkyl. In certain embodiments, A is a 5-6 membered heterocycloalkyl. In certain embodiments, A is a 5 membered heterocycloalkyl. In certain embodiments, A is a 6 membered heterocycloalkyl. In certain embodiments, A is oxepanyl, tetrahydropyranyl, dihydropyranyl, tetrahydrofuranyl, oxetanyl, azepanyl, piperidinyl, piperazinyl, morpholinyl, pyrrolidinyl, or azetidinyl. In certain embodiments, A is tetrahydropyranyl, tetrahydrofuranyl, piperidinyl, or pyrrolidinyl.

In certain embodiments, A is arylalkyl. In certain embodiments, A is benzyl. In certain embodiments, A is benzyl substituted with 1-3 independent substituents $R^5$, wherein each occurrence of $R^5$ is, independently, halogen, cyano, alkyl, haloalkyl, or —$OR^f$; and $R^f$ is haloalkyl or alkyl.

In certain embodiments, X is $NR^4$; and $R^4$ is hydrogen or alkyl. In certain embodiments, X is NH. In certain embodiments, X is O.

In certain embodiments, $R^1$ is hydrogen, cyano, alkyl, alkenyl, alkynyl, cycloalkyl, aryl, heteroaryl, heterocycloalkyl, —$(CR^hR^i)_n$-E-$NR^aC(O)R^b$, —$C(O)NR^aR^b$, —$(CR^hR^i)_n$-E-$NR^dSO_2R^d$, —$(CR^hR^i)_n$-G-$SO_2R^d$, —$CO_2R^e$, —$COR^f$, or —$CH_2OR^f$, wherein $R^1$ is optionally substituted with 1-3 independent substituents $R^5$.

In certain embodiments, $R^1$ is hydrogen, alkyl, haloalkyl, aryl, cycloalkyl, —$CH_2OR^f$, —$(CR^hR^i)_n$-E-$NR^aC(O)R^b$, —$C(O)NR^aR^b$, —$(CR^hR^i)_n$-E-$NR^dSO_2R^d$, or —$(CR^hR^i)_n$-G-$SO_2R^d$. In certain embodiments, $R^1$ is hydrogen, alkyl, haloalkyl, aryl, cycloalkyl, —$CH_2OR^f$, —$(CH_2)_nNR^aC(O)R^b$, —$C(O)NR^aR^b$, —$(CH_2)_nNR^dSO_2R^d$, or -G-$SO_2R^d$. In certain embodiments, $R^1$ is hydrogen, alkyl, haloalkyl, aryl, cycloalkyl, —$CH_2OR^f$, —$(CH_2)_nNR^aC(O)R^b$, —$C(O)NR^aR^b$, —$(CH_2)_n$-E-$NR^dSO_2R^d$, or -G-$SO_2R^d$, wherein each occurrence of $R^a$, $R^b$, $R^d$, and $R^f$ is, independently, alkyl, haloalkyl, or aryl; or $R^a$ and $R^b$ together with the atoms to which they are attached form a heterocycloalkyl ring; or 2 instances of $R^d$ together with the atoms to which they are attached form a heterocycloalkyl ring; E is aryl; and G is heterocycloalkyl. In certain embodiments, $R^1$ is —$CH_2OR^f$, —$(CH_2)_nNR^aC(O)R^b$, —$C(O)NR^aR^b$, —$(CH_2)_n$-E-$NR^dSO_2R^d$, or -G-$SO_2R^d$, wherein each occurrence of $R^a$, $R^b$, $R^d$, and $R^f$ is, independently, alkyl, haloalkyl, or aryl; or $R^a$ and $R^b$ together with the atoms to which they are attached form a heterocycloalkyl ring; or 2 instances of $R^d$ together with the atoms to which they are attached form a heterocycloalkyl ring; E is aryl; and G is heterocycloalkyl. In certain embodiments, $R^1$ is —$(CH_2)_nNR^aC(O)R^b$, —$(CH_2)_n$-E-$NR^dSO_2R^d$, or -G-$SO_2R^d$, wherein each occurrence of $R^a$, $R^b$, and $R^d$ is, independently, alkyl, haloalkyl, or aryl; or $R^a$ and $R^b$ together with the atoms to which they are attached form a heterocycloalkyl ring; or 2 instances of $R^d$ together with the atoms to which they are attached form a heterocycloalkyl ring; E is aryl; and G is heterocycloalkyl.

In certain embodiments, $R^1$ is hydrogen, alkyl, haloalkyl, or —$CH_2OR^f$. In certain embodiments, $R^1$ is hydrogen, alkyl, haloalkyl, or —$CH_2OR^f$; and $R^f$ is alkyl, haloalkyl, or aryl.

In certain embodiments, $R^1$ is alkyl, haloalkyl, or —$CH_2OR^f$. In certain embodiments, $R^1$ is alkyl, haloalkyl, or —$CH_2OR^f$; and $R^f$ is alkyl, haloalkyl, or aryl.

In certain embodiments, $R^1$ is alkyl. In certain embodiments, $R^1$ is $C_{1-6}$ alkyl. In certain embodiments, $R^1$ is $C_{1-4}$ alkyl. In certain embodiments, $R^1$ is methyl, ethyl, propyl, butyl, isopropyl, or isobutyl. In certain embodiments, $R^1$ is methyl. In certain embodiments, $R^1$ is ethyl.

In certain embodiments, $R^1$ is —$CH_2OR^f$. In certain embodiments, $R^1$ is —$CH_2OR^f$; and $R^f$ is hydrogen, alkyl, haloalkyl, arylalkyl, or aryl. In certain embodiments, $R^1$ is —$CH_2OH$, —$CH_2O\ CH_2Ph$, or —$CH_2OCH_3$.

In certain embodiments, $R^1$ is haloalkyl. In certain embodiments, $R^1$ is $C_{1-6}$ haloalkyl. In certain embodiments, $R^1$ is $C_{1-3}$ haloalkyl. In certain embodiments, $R^1$ is —$CH_2F$, —$CF_2H$, —$CF_3$, or —$CH_2CF_3$. In certain embodiments, $R^1$ is —$CF_3$ or —$CH_2CF_3$.

In certain embodiments, $R^1$ is —$(CR^hR^i)_n$-E-$NR^aC(O)R^b$. In certain embodiments, $R^1$ is —$(CR^hR^i)_n$-E-$NR^aC(O)R^b$; and E is a bond, aryl, or heteroaryl. In certain embodiments, $R^1$ is —$(CR^hR^i)_nNR^aC(O)R^b$. In certain embodiments, $R^1$ is —$(CR^hR^i)_nNR^aC(O)R^b$; each occurrence of $R^h$ and $R^i$ is, independently, hydrogen, halogen, haloalkyl, or alkyl; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring. In certain embodiments, $R^1$ is —$(CH_2)_nNR^aC(O)R^b$. In certain embodiments, $R^1$ is —$(CH_2)_nNR^aC(O)R^b$; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring. In certain embodiments, $R^1$ is —$(CH_2)_nNHC(O)R^b$. In certain embodiments, $R^1$ is —$(CH_2)_nNHC(O)R^b$; and $R^b$ is aryl, heteroaryl, cycloalkyl, haloalkyl, or alkyl. In certain embodiments, $R^1$ is —$(CH_2)_nNHC(O)R^b$; and $R^b$ is haloalkyl or alkyl. In certain embodiments, $R^1$ is —$CH_2NHC(O)R^b$; and $R^b$ is haloalkyl or alkyl. In certain embodiments, $R^1$ is —$CH_2NHC(O)CF_3$.

In certain embodiments, $R^1$ is —$(CR^hR^i)_n$-G-$SO_2R^d$. In certain embodiments, $R^i$ is —$(CR^hR^i)_n$-G-$SO_2R^d$; G is heterocycloalkyl or heteroaryl; each occurrence of $R^h$ and $R^i$ is, independently, hydrogen, halogen, haloalkyl, or alkyl; and $R^d$ is aryl, heteroaryl, cycloalkyl, haloalkyl, or alkyl. In certain embodiments, $R^1$ is —$(CH_2)_n$-G-$SO_2R^d$. In certain embodiments, $R^i$ is —$(CH_2)_n$-G-$SO_2R^d$; G is heterocycloalkyl or heteroaryl; and $R^d$ is hydrogen, aryl, heteroaryl, cycloalkyl, haloalkyl, or alkyl. In certain embodiments, $R^1$ is -G-SO$_2$R$^d$. In certain embodiments, R$^1$ is -G-SO$_2$R$^d$; G is heterocycloalkyl; and R$^d$ is, independently, aryl, heteroaryl, cycloalkyl, haloalkyl, or alkyl. In certain embodiments, R$^1$ is -G-SO$_2$R$^d$; G is azepanyl, piperidinyl, pyrrolidinyl, azetidinyl, or aziridinyl; and R$^d$ is, independently, aryl, heteroaryl, cycloalkyl, haloalkyl, or alkyl.

In certain embodiments, R$^1$ is —(CR$^h$R$^i$)$_n$-E-NR$^d$SO$_2$R$^d$. In certain embodiments, R$^1$ is —(CR$^h$R$^i$)$_n$-E-NR$^d$SO$_2$R$^d$; E is a bond, aryl, or heteroaryl; each occurrence of R$^h$ and R$^i$ is, independently, hydrogen, halogen, haloalkyl, or alkyl; and each occurrence of R$^d$ is, independently, hydrogen, aryl, heteroaryl, cycloalkyl, haloalkyl, or alkyl; or 2 instances of R$^d$ together with the atoms to which they are attached form a heterocycloalkyl ring. In certain embodiments, R$^1$ is —(CR$^h$R$^i$)$_n$NR$^d$SO$_2$R$^d$. In certain embodiments, R$^1$ is —(CR$^h$R$^i$)$_n$NR$^d$SO$_2$R$^d$; each occurrence of R$^h$ and R$^i$ is, independently, hydrogen, halogen, haloalkyl, or alkyl; and each occurrence of R$^d$ is, independently, hydrogen, aryl, heteroaryl, cycloalkyl, haloalkyl, or alkyl; or 2 instances of R$^d$ together with the atoms to which they are attached form a heterocycloalkyl ring.

In certain embodiments, R$^1$ is —(CH$_2$)$_n$-E-NR$^d$SO$_2$R$^d$. In certain embodiments, R$^1$ is —(CH$_2$)$_n$-E-NR$^d$SO$_2$R$^d$; E is a bond or aryl; and each occurrence of R$^d$ is, independently, hydrogen, aryl, heteroaryl, cycloalkyl, haloalkyl, or alkyl; or 2 instances of R$^d$ together with the atoms to which they are attached form a heterocycloalkyl ring. In certain embodiments, R$^1$ is —(CH$_2$)$_n$NR$^d$SO$_2$R$^d$. In certain embodiments, R$^1$ is —(CH$_2$)$_n$NR$^d$SO$_2$R$^d$; and each occurrence of R$^d$ is, independently, hydrogen, aryl, heteroaryl, cycloalkyl, haloalkyl, or alkyl; or 2 instances of R$^d$ together with the atoms to which they are attached form a heterocycloalkyl ring. In certain embodiments, R$^1$ is —(CH$_2$)$_n$NHSO$_2$R$^d$. In certain embodiments, R$^1$ is —(CH$_2$)$_n$NHSO$_2$R$^d$, wherein R$^d$ is aryl, heteroaryl, cycloalkyl, haloalkyl, or alkyl. In certain embodiments, R$^1$ is —CH$_2$NHSO$_2$R$^d$, wherein R$^d$ is aryl or alkyl.

In certain embodiments, R$^1$ is —CH$_2$CH$_2$NHSO$_2$Me, —CH(CH$_3$)NHSO$_2$Me, —CH$_2$NHSO$_2$Me, —CH$_2$NMeSO$_2$Me, —CH$_2$NHSO$_2$Et, —CH$_2$NHSO$_2$Pr, —CH$_2$NHSO$_2$iPr, —CH$_2$NHSO$_2$iBu, —CH$_2$NHSO$_2$CH$_2$CF$_3$, CH$_2$N(CH$_2$CF$_3$)SO$_2$CH$_3$, —CH$_2$NHSO$_2$-cyclopropyl, —CH$_2$NHSO$_2$Ph

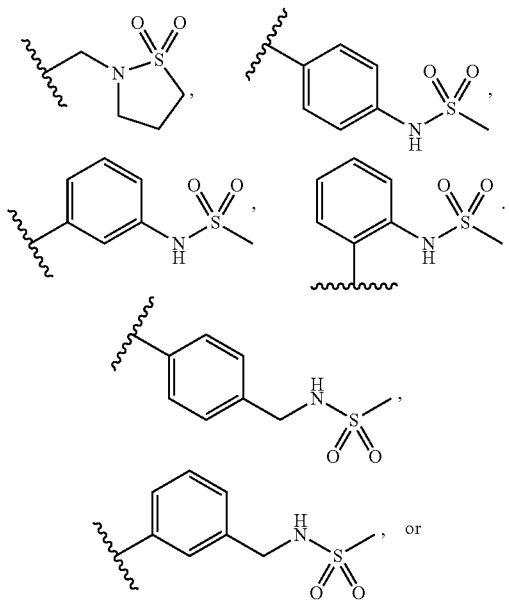

or

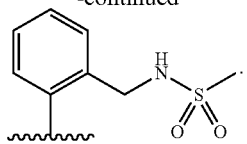

In certain embodiments, R$^1$ is —CH$_2$CH$_2$NHSO$_2$Me, —CH(CH$_3$)NHSO$_2$Me, —CH$_2$NHSO$_2$Me, —CH$_2$NMeSO$_2$Me, —CH$_2$NHSO$_2$Et, —CH$_2$NHSO$_2$Pr, —CH$_2$NHSO$_2$iPr, —CH$_2$NHSO$_2$iBu, —CH$_2$NHSO$_2$CH$_2$CF$_3$, CH$_2$N(CH$_2$CF$_3$)SO$_2$CH$_3$, —CH$_2$NHSO$_2$-cyclopropyl, —CH$_2$NHSO$_2$Ph, or

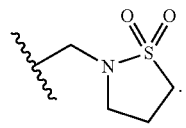 [SMILES: *CN1CCCS1(=O)=O]

In certain embodiments, R$^1$ is —CH$_2$NHSO$_2$Me, —CH$_2$NMeSO$_2$Me, —CH$_2$NHSO$_2$Et, —CH$_2$NHSO$_2$Pr, —CH$_2$NHSO$_2$iPr, —CH$_2$NHSO$_2$iBu, —CH$_2$NHSO$_2$-cyclopropyl, or —CH$_2$NHSO$_2$Ph.

In certain embodiments, R$^1$ is hydrogen, methyl, ethyl, propyl, isopropyl, phenyl, —CH$_2$CF$_3$, trifluoromethyl, —CH$_2$OCH$_3$, —CH$_2$OPh, —C(O)-morpholinyl, —CH$_2$NHC(O)CF$_3$, —C(O)NHPh, —CH$_2$NHSO$_2$Me, —CH$_2$NMeSO$_2$Me, —CH$_2$NHSO$_2$Et, —CH$_2$NHSO$_2$Pr, —CH$_2$NHSO$_2$iPr, —CH$_2$NHSO$_2$iBu, —CH$_2$NHSO$_2$-cyclopropyl, or —CH$_2$NHSO$_2$Ph.

In certain embodiments, R$^1$ and A together with the atoms to which they are attached form a heterocycloalkyl ring or fused bicyclic ring. In certain embodiments, R$^1$ and A together with the atoms to which they are attached form a heterocycloalkyl ring or fused bicyclic ring; and R$^2$ is hydrogen.

In certain embodiments, R$^1$ and A together with the atoms to which they are attached form a heterocycloalkyl ring. In certain embodiments, R$^1$ and A together with the atoms to which they are attached form a heterocycloalkyl ring; and R$^2$ is hydrogen. In certain embodiments, R$^1$ and A together with the atoms to which they are attached form a pyrrolidinyl, piperidinyl, tetrahydrofuranyl, or tetrahydropyranyl ring. In certain embodiments, R$^1$ and A together with the atoms to which they are attached form a pyrrolidinyl, piperidinyl, tetrahydrofuranyl, or tetrahydropyranyl ring; and R$^2$ is hydrogen.

In certain embodiments, R$^1$ and A together with the atoms to which they are attached form a fused bicyclic ring. In certain embodiments, R$^1$ and A together with the atoms to which they are attached form a fused bicyclic ring; and R$^2$ is hydrogen. In certain embodiments, R$^1$ and A together with the atoms to which they are attached form an indanyl or tetrahydronaphthalenyl ring. In certain embodiments, R$^1$ and A together with the atoms to which they are attached form an indanyl or tetrahydronaphthalenyl ring; and R$^2$ is hydrogen.

In certain embodiments, R$^2$ is hydrogen, cyano, alkyl, alkenyl, alkynyl, cycloalkyl, aryl, heteroaryl, heterocycloalkyl, —(CR$^h$R$^i$)$_n$-E-NR$^a$C(O)R$^b$, —C(O)NR$^a$R$^b$, —(CR$^h$R$^i$)$_n$-E-NR$^d$SO$_2$R$^d$, —(CR$^h$R$^i$)$_n$-G-SO$_2$R$^d$, —CO$_2$R$^e$, —COR$^f$, or —CH$_2$OR$^f$, wherein R$^2$ is optionally substituted with 1-3 independent substituents R$^5$.

In certain embodiments, $R^2$ is hydrogen, alkyl, haloalkyl, aryl, cycloalkyl, —$CH_2OR^f$, —$(CR^hR^i)_n$-E-$NR^aC(O)R^b$, —$C(O)NR^aR^b$, —$(CR^hR^i)_n$-E-$NR^dSO_2R^d$, or —$(CR^hR^i)_n$-G-$SO_2R^d$. In certain embodiments, $R^2$ is hydrogen, alkyl, haloalkyl, aryl, cycloalkyl, —$CH_2OR^f$, —$(CH_2)_nNR^aC(O)R^b$, —$C(O)NR^aR^b$, —$(CH_2)_nNR^dSO_2R^d$, or -G-$SO_2R^d$. In certain embodiments, $R^2$ is hydrogen, alkyl, haloalkyl, aryl, cycloalkyl, —$CH_2OR^f$, —$(CH_2)_nNR^aC(O)R^b$, —$C(O)NR^aR^b$, —$(CH_2)_n$-E-$NR^dSO_2R^d$, or -G-$SO_2R^d$, wherein each occurrence of $R^a$, $R^b$, $R^d$, and $R^f$ is, independently, alkyl, haloalkyl, or aryl; or $R^a$ and $R^b$ together with the atoms to which they are attached form a heterocycloalkyl ring; or 2 instances of $R^d$ together with the atoms to which they are attached form a heterocycloalkyl ring; E is aryl; and G is heterocycloalkyl. In certain embodiments, $R^2$ is —$CH_2OR^f$, —$(CH_2)_nNR^aC(O)R^b$, —$C(O)NR^aR^b$, —$(CH_2)_n$-E-$NR^dSO_2R^d$, or -G-$SO_2R^d$, wherein each occurrence of $R^a$, $R^b$, $R^d$, and $R^f$ is, independently, alkyl, haloalkyl, or aryl; or $R^a$ and $R^b$ together with the atoms to which they are attached form a heterocycloalkyl ring; or 2 instances of $R^d$ together with the atoms to which they are attached form a heterocycloalkyl ring; E is aryl; and G is heterocycloalkyl. In certain embodiments, $R^2$ is —$(CH_2)_nNR^aC(O)R^b$, —$(CH_2)_n$-E-$NR^dSO_2R^d$, or -G-$SO_2R^d$, wherein each occurrence of $R^a$, $R^b$, and $R^d$ is, independently, alkyl, haloalkyl, or aryl; or $R^a$ and $R^b$ together with the atoms to which they are attached form a heterocycloalkyl ring; or 2 instances of $R^d$ together with the atoms to which they are attached form a heterocycloalkyl ring; E is aryl; and G is heterocycloalkyl.

In certain embodiments, $R^2$ is hydrogen, alkyl, haloalkyl, or —$CH_2OR^f$. In certain embodiments, $R^2$ is hydrogen, alkyl, haloalkyl, or —$CH_2OR^f$; and $R^f$ is alkyl, haloalkyl, or aryl.

In certain embodiments, $R^2$ is alkyl, haloalkyl, or —$CH_2OR^f$. In certain embodiments, $R^2$ is alkyl, haloalkyl, or —$CH_2OR^f$; and $R^f$ is alkyl, haloalkyl, or aryl.

In certain embodiments, $R^2$ is alkyl. In certain embodiments, $R^2$ is $C_{1-6}$ alkyl. In certain embodiments, $R^2$ is $C_{1-4}$ alkyl. In certain embodiments, $R^2$ is methyl, ethyl, propyl, butyl, isopropyl, or isobutyl. In certain embodiments, $R^2$ is methyl. In certain embodiments, $R^2$ is ethyl.

In certain embodiments, $R^2$ is —$CH_2OR^f$. In certain embodiments, $R^2$ is —$CH_2OR^f$; and $R^f$ is hydrogen, alkyl, haloalkyl, arylalkyl, or aryl. In certain embodiments, $R^2$ is —$CH_2OH$, —$CH_2O CH_2Ph$, or —$CH_2OCH_3$.

In certain embodiments, $R^2$ is haloalkyl. In certain embodiments, $R^2$ is $C_{1-6}$ haloalkyl. In certain embodiments, $R^2$ is $C_{1-3}$ haloalkyl. In certain embodiments, $R^2$ is —$CH_2F$, —$CF_2H$, —$CF_3$, or —$CH_2CF_3$. In certain embodiments, $R^2$ is —$CF_3$ or —$CH_2CF_3$.

In certain embodiments, $R^2$ is —$(CR^hR^i)_n$-E-$NR^aC(O)R^b$. In certain embodiments, $R^2$ is —$(CR^hR^i)_n$-E-$NR^aC(O)R^b$; and E is a bond, aryl, or heteroaryl. In certain embodiments, $R^2$ is —$(CR^hR^i)_nNR^aC(O)R^b$. In certain embodiments, $R^2$ is —$(CR^hR^i)_nNR^aC(O)R^b$; each occurrence of $R^h$ and $R^i$ is, independently, hydrogen, halogen, haloalkyl, or alkyl; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring. In certain embodiments, $R^2$ is —$(CH_2)_nNR^aC(O)R^b$. In certain embodiments, $R^2$ is —$(CH_2)_nNR^aC(O)R^b$; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring. In certain embodiments, $R^2$ is —$(CH_2)_nNHC(O)R^b$. In certain embodiments, $R^2$ is —$(CH_2)_nNHC(O)R^b$; and $R^b$ is aryl, heteroaryl, cycloalkyl, haloalkyl, or alkyl. In certain embodiments, $R^2$ is —$(CH_2)_nNHC(O)R^b$; and $R^b$ is haloalkyl or alkyl. In certain embodiments, $R^2$ is —$CH_2NHC(O)R^b$; and $R^b$ is haloalkyl or alkyl. In certain embodiments, $R^2$ is —$CH_2NHC(O)CF_3$.

In certain embodiments, $R^2$ is —$(CR^hR^i)_n$-G-$SO_2R^d$. In certain embodiments, $R^2$ is —$(CR^hR^i)_n$-G-$SO_2R^d$; G is heterocycloalkyl or heteroaryl; each occurrence of $R^h$ and $R^i$ is, independently, hydrogen, halogen, haloalkyl, or alkyl; and $R^d$ is aryl, heteroaryl, cycloalkyl, haloalkyl, or alkyl. In certain embodiments, $R^2$ is —$(CH_2)_n$-G-$SO_2R^d$. In certain embodiments, $R^2$ is —$(CH_2)_n$-G-$SO_2R^d$; G is heterocycloalkyl or heteroaryl; and $R^d$ is hydrogen, aryl, heteroaryl, cycloalkyl, haloalkyl, or alkyl. In certain embodiments, $R^2$ is -G-$SO_2R^d$. In certain embodiments, $R^2$ is -G-$SO_2R^d$; G is heterocycloalkyl; and $R^d$ is, independently, aryl, heteroaryl, cycloalkyl, haloalkyl, or alkyl. In certain embodiments, $R^2$ is -G-$SO_2R^d$; G is azepanyl, piperidinyl, pyrrolidinyl, azetidinyl, or aziridinyl; and $R^d$ is, independently, aryl, heteroaryl, cycloalkyl, haloalkyl, or alkyl.

In certain embodiments, $R^2$ is —$(CR^hR^i)_n$-E-$NR^dSO_2R^d$. In certain embodiments, $R^2$ is —$(CR^hR^i)_n$-E-$NR^dSO_2R^d$; E is a bond, aryl, or heteroaryl; each occurrence of $R^h$ and $R^i$ is, independently, hydrogen, halogen, haloalkyl, or alkyl; and each occurrence of $R^d$ is, independently, hydrogen, aryl, heteroaryl, cycloalkyl, haloalkyl, or alkyl; or 2 instances of $R^d$ together with the atoms to which they are attached form a heterocycloalkyl ring. In certain embodiments, $R^2$ is —$(CR^hR^i)_nNR^dSO_2R^d$. In certain embodiments, $R^2$ is —$(CR^hR^i)_nNR^dSO_2R^d$; each occurrence of $R^h$ and $R^i$ is, independently, hydrogen, halogen, haloalkyl, or alkyl; and each occurrence of $R^d$ is, independently, hydrogen, aryl, heteroaryl, cycloalkyl, haloalkyl, or alkyl; or 2 instances of $R^d$ together with the atoms to which they are attached form a heterocycloalkyl ring.

In certain embodiments, $R^2$ is —$(CH_2)_n$-E-$NR^dSO_2R^d$. In certain embodiments, $R^2$ is —$(CH_2)_n$-E-$NR^dSO_2R^d$; E is a bond or aryl; and each occurrence of $R^d$ is, independently, hydrogen, aryl, heteroaryl, cycloalkyl, haloalkyl, or alkyl; or 2 instances of $R^d$ together with the atoms to which they are attached form a heterocycloalkyl ring. In certain embodiments, $R^2$ is —$(CH_2)_nNR^dSO_2R^d$. In certain embodiments, $R^2$ is —$(CH_2)_nNR^dSO_2R^d$; and each occurrence of $R^d$ is, independently, hydrogen, aryl, heteroaryl, cycloalkyl, haloalkyl, or alkyl; or 2 instances of $R^d$ together with the atoms to which they are attached form a heterocycloalkyl ring. In certain embodiments, $R^2$ is —$(CH_2)_nNHSO_2R^d$. In certain embodiments, $R^2$ is —$(CH_2)_nNHSO_2R^d$, wherein $R^d$ is aryl, heteroaryl, cycloalkyl, haloalkyl, or alkyl. In certain embodiments, $R^2$ is —$CH_2NHSO_2R^d$, wherein $R^d$ is aryl or alkyl.

In certain embodiments, $R^2$ is —$CH_2CH_2NHSO_2Me$, —$CH(CH_3)NHSO_2Me$, —$CH_2NHSO_2Me$, —$CH_2NMeSO_2Me$, —$CH_2NHSO_2Et$, —$CH_2NHSO_2Pr$, —$CH_2NHSO_2iPr$, —$CH_2NHSO_2iBu$, —$CH_2NHSO_2CH_2CF_3$, $CH_2N(CH_2CF_3)SO_2CH_3$, —$CH_2NHSO_2$-cyclopropyl, —$CH_2NHSO_2Ph$,

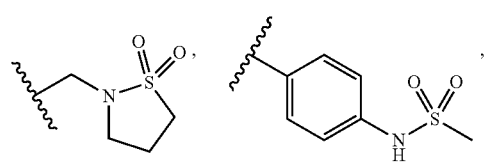

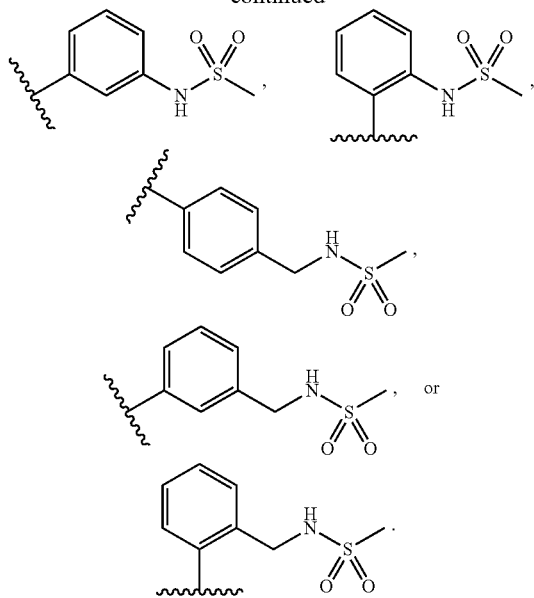

In certain embodiments, R² is —CH₂CH₂NHSO₂Me, —CH(CH₃)NHSO₂Me, —CH₂NHSO₂Me, —CH₂NMeSO₂Me, —CH₂NHSO₂Et, —CH₂NHSO₂Pr, —CH₂NHSO₂iPr, —CH₂NHSO₂iBu, —CH₂NHSO₂CH₂CF₃, CH₂N(CH₂CF₃)SO₂CH₃, —CH₂NHSO₂-cyclopropyl, —CH₂NHSO₂Ph, or

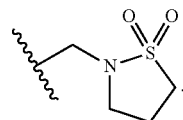

In certain embodiments, R² is —CH₂NHSO₂Me, —CH₂NMeSO₂Me, —CH₂NHSO₂Et, —CH₂NHSO₂Pr, —CH₂NHSO₂iPr, —CH₂NHSO₂iBu, —CH₂NHSO₂-cyclopropyl, or —CH₂NHSO₂Ph.

In certain embodiments, R² is hydrogen, methyl, ethyl, propyl, isopropyl, phenyl, —CH₂CF₃, trifluoromethyl, —CH₂OCH₃, —CH₂OPh, —C(O)-morpholinyl, —CH₂NHC(O)CF₃, —C(O)NHPh, —CH₂NHSO₂Me, —CH₂NMeSO₂Me, —CH₂NHSO₂Et, —CH₂NHSO₂Pr, —CH₂NHSO₂iPr, —CH₂NHSO₂iBu, —CH₂NHSO₂-cyclopropyl, or —CH₂NHSO₂Ph. In certain embodiments, R² is hydrogen.

In certain embodiments, each of R¹ and R² is, independently, hydrogen, alkyl, haloalkyl, aryl, cycloalkyl, —(CR$^h$R$^i$)$_n$-E-NR$^a$C(O)R$^b$, —C(O)NR$^a$R$^b$, —(CR$^h$R$^i$)$_n$-E-NR$^d$SO₂R$^d$, —(CR$^h$R$^i$)$_n$-G-SO₂R$^d$, or —CH₂OR$^f$. In certain embodiments, each of R¹ and R² is, independently, hydrogen, alkyl, haloalkyl, aryl, cycloalkyl, —CH₂OR$^f$, —C(O)NR$^a$R$^b$, —CH₂NR$^a$C(O)R$^b$, or —(CR$^h$R$^i$)$_n$-E-NR$^d$SO₂R$^d$. In certain embodiments, each of R¹ and R² is, independently, hydrogen, alkyl, haloalkyl, aryl, cycloalkyl, —CH₂OR$^f$, —C(O)NR$^a$R$^b$, or —CH₂NHSO₂R$^d$. In certain embodiments, each of R¹ and R² is, independently, hydrogen, alkyl, haloalkyl, —CH₂OR$^f$, or —CH₂NHSO₂R$^d$.

In certain embodiments, R¹ is alkyl, haloalkyl, aryl, cycloalkyl, —(CR$^h$R$^i$)$_n$-E-NR$^a$C(O)R$^b$, —C(O)NR$^a$R$^b$, —(CR$^h$R$^i$)$_n$-E-NR$^d$SO₂R$^d$, —(CR$^h$R$^i$)$_n$-G-SO₂R$^d$, or —CH₂OR$^f$; and R² is hydrogen. In certain embodiments, R¹ is alkyl, haloalkyl, aryl, cycloalkyl, —CH₂OR$^f$, —C(O)NR$^a$R$^b$, or —(CR$^h$R$^i$)$_n$-E-NR$^d$SO₂R$^d$; and R² is hydrogen. In certain embodiments, R¹ is alkyl, haloalkyl, aryl, cycloalkyl, —CH₂OR$^f$, —C(O)NR$^a$R$^b$, or —CH₂NHSO₂R$^d$; and R² is hydrogen. In certain embodiments, R¹ is alkyl, haloalkyl, —CH₂OR$^f$, or —CH₂NHSO₂R$^d$; and R² is hydrogen. In certain embodiments, R¹ is —CH₂OR$^f$, —(CH₂)$_n$NR$^a$C(O)R$^b$, —C(O)NR$^a$R$^b$, —(CH₂)$_n$-E-NR$^d$SO₂R$^d$, or -G-SO₂R$^d$; and R² is hydrogen. In certain embodiments, R¹ is —(CR$^h$R$^i$)$_n$-E-NR$^a$C(O)R$^b$, —(CR$^h$R$^i$)$_n$-E-NR$^d$SO₂R$^d$, or —(CR$^h$R$^i$)$_n$)-G-SO₂R$^d$; and R² is hydrogen. In certain embodiments, R¹ is —(CH₂)$_n$NR$^a$C(O)R$^b$, —(CH₂)$_n$-E-NR$^d$SO₂R$^d$, or -G-SO₂R$^d$; and R² is hydrogen. In certain embodiments, R¹ is —(CR$^h$R$^i$)$_n$-E-NR$^d$SO₂R$^d$ or —(CR$^h$R$^i$)$_n$)-G-SO₂R$^d$; and R² is hydrogen. In certain embodiments, each of R¹ is —CH₂OR$^f$ or —CH₂NHSO₂R$^d$; and R² is hydrogen.

In certain embodiments, R¹ is alkyl, haloalkyl, or —CH₂OR$^f$; and R² is hydrogen. In certain embodiments, R² is alkyl, haloalkyl, or —CH₂OR$^f$; and R² is hydrogen.

In certain embodiments, R¹ is methyl, haloalkyl, or —CH₂OR$^f$; and R² is hydrogen. In certain embodiments, R² is alkyl, haloalkyl, or —CH₂OR$^f$; and R² is hydrogen.

In certain embodiments, R¹ is methyl, ethyl, propyl, isopropyl, phenyl, —CH₂CF₃, trifluoromethyl, —CH₂OCH₃, —CH₂OPh, —C(O)-morpholinyl, —CH₂NHC(O)CF₃, —C(O)NHPh, —CH₂NHSO₂Me, —CH₂NMeSO₂Me, —CH₂NHSO₂Et, —CH₂NHSO₂Pr, —CH₂NHSO₂iPr, —CH₂NHSO₂iBu, —CH₂NHSO₂-cyclopropyl, or —CH₂NHSO₂Ph; and R² is hydrogen. In certain embodiments, R¹ is —CH₂NHSO₂Me, —CH₂NMeSO₂Me, —CH₂NHSO₂Et, —CH₂NHSO₂Pr, —CH₂NHSO₂iPr, —CH₂NHSO₂iBu, —CH₂NHSO₂-cyclopropyl, or —CH₂NHSO₂Ph; and R² is hydrogen. In certain embodiments, R¹ is hydrogen, methyl, ethyl, propyl, isopropyl, —CH₂CF₃, trifluoromethyl, —CH₂OCH₃, or —CH₂OPh; and R² is hydrogen.

In certain embodiments, R³ is haloalkyl. In certain embodiments, R³ is $C_{1-6}$ haloalkyl. In certain embodiments, R³ is $C_{1-4}$ haloalkyl. In certain embodiments, R³ is $C_{1-3}$ haloalkyl. In certain embodiments, R³ is Cl₂ haloalkyl. In certain embodiments, R³ is —CF₃, —CHF₂, or CH₂F.

In certain embodiments, the compound of Formula I is a compound of Formula I-a:

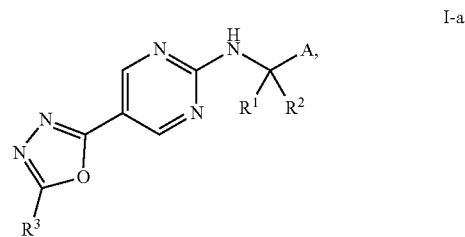

or a pharmaceutically acceptable salt, co-crystal, tautomer, stereoisomer, solvate, hydrate, polymorph, isotopically enriched derivative, or prodrug thereof, wherein R¹, R², R³, and A are as defined herein.

In certain embodiments of the compound of Formula I-a, A is aryl or heteroaryl. In certain embodiments of the compound of Formula I-a, A is phenyl. In certain embodiments of the compound of Formula I-a, A is phenyl substituted with 1-3 independent substituents R⁵, wherein each occurrence of $R^5$ is, independently, halogen, cyano, alkyl, haloalkyl, or —$OR^f$; and $R^f$ is haloalkyl or alkyl.

In certain embodiments of the compound of Formula I-a, $R^1$ is alkyl, haloalkyl, or —$CH_2OR^f$; $R^f$ is aryl, alkyl, or haloalkyl; and $R^2$ is hydrogen.

In certain embodiments of the compound of Formula I-a, $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments of the compound of Formula I-a, $R^1$ is —$(CR^hR^i)_n$$NR^aC(O)R^b$; each occurrence of $R^h$ and $R^i$ is, independently, hydrogen, halogen, haloalkyl, or alkyl; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring; and $R^2$ is hydrogen.

In certain embodiments of the compound of Formula I-a, $R^3$ is haloalkyl.

In certain embodiments of the compound of Formula I-a, A is aryl or heteroaryl; $R^1$ is alkyl, haloalkyl, or —$CH_2OR^f$; $R^f$ is aryl, alkyl, or haloalkyl; $R^2$ is hydrogen; and $R^3$ is haloalkyl.

In certain embodiments of the compound of Formula I-a, A is aryl or heteroaryl; $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; $R^2$ is hydrogen; and $R^3$ is haloalkyl.

In certain embodiments of the compound of Formula I-a, A is phenyl substituted with 1-3 independent substituents $R^5$, wherein each occurrence of $R^5$ is, independently, halogen, cyano, alkyl, haloalkyl, or —$OR^f$; $R^f$ is haloalkyl or alkyl; $R^1$ is alkyl, haloalkyl, or —$CH_2OR^f$; $R^f$ is aryl, alkyl, or haloalkyl; $R^2$ is hydrogen; and $R^3$ is haloalkyl.

In certain embodiments of the compound of Formula I-a, A is phenyl substituted with 1-3 independent substituents $R^5$, wherein each occurrence of $R^5$ is, independently, halogen, cyano, alkyl, haloalkyl, or —$OR^f$; $R^f$ is haloalkyl or alkyl; $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; $R^2$ is hydrogen; and $R^3$ is haloalkyl.

In certain embodiments, the compound of Formula I is a compound of Formula I-b:

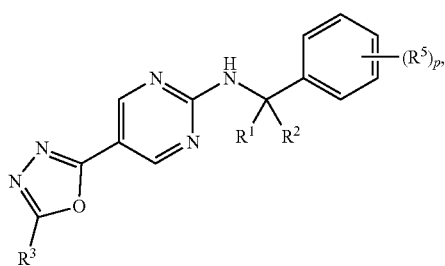

I-b or a pharmaceutically acceptable salt, co-crystal, tautomer, stereoisomer, solvate, hydrate, polymorph, isotopically enriched derivative, or prodrug thereof, wherein p is 0, 1, 2, or 3; and $R^1$, $R^2$, $R^3$, and $R^5$ are as defined herein.

In certain embodiments of the compound of Formula I-b, $R^1$ is alkyl, haloalkyl, or —$CH_2OR^f$; $R^f$ is aryl, alkyl, or haloalkyl; and $R^2$ is hydrogen.

In certain embodiments of the compound of Formula I-b, $R^1$ is —$(CR^hR^i)_n$$NR^aC(O)R^b$; each occurrence of $R^h$ and $R^i$ is, independently, hydrogen, halogen, haloalkyl, or alkyl; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring; and $R^2$ is hydrogen.

In certain embodiments of the compound of Formula I-b, $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments of the compound of Formula I-b, $R^3$ is haloalkyl.

In certain embodiments of the compound of Formula I-b, each $R^5$ is, independently, halogen, cyano, alkyl, haloalkyl, or —$OR^f$.

In certain embodiments of the compound of Formula I-b, $R^1$ is alkyl, haloalkyl, or —$CH_2OR^f$, wherein $R^f$ is aryl, alkyl, or haloalkyl; $R^2$ is hydrogen; $R^3$ is haloalkyl; and each $R^5$ is, independently, halogen, cyano, alkyl, haloalkyl, or —$OR^f$.

In certain embodiments of the compound of Formula I-b, $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; $R^2$ is hydrogen; $R^3$ is haloalkyl; and each $R^5$ is, independently, halogen, cyano, alkyl, haloalkyl, or —$OR^f$.

In certain embodiments, the compound of Formula I is a compound of Formula I-d:

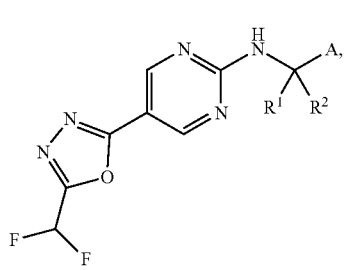

I-d or a pharmaceutically acceptable salt, co-crystal, tautomer, stereoisomer, solvate, hydrate, polymorph, isotopically enriched derivative, or prodrug thereof, wherein $R^1$, $R^2$, and A are as defined herein.

In certain embodiments of the compound of Formula I-d, A is aryl or heteroaryl. In certain embodiments of the compound of Formula I-d, A is phenyl. In certain embodiments of the compound of Formula I-d, A is phenyl substituted with 1-3 independent substituents $R^5$, wherein each occurrence of $R^5$ is, independently, halogen, cyano, alkyl, haloalkyl, or —$OR^f$; and $R^f$ is haloalkyl or alkyl.

In certain embodiments of the compound of Formula I-d, $R^1$ is alkyl, haloalkyl, or —$CH_2OR^f$, wherein $R^f$ is aryl, alkyl, or haloalkyl; and $R^2$ is hydrogen.

In certain embodiments of the compound of Formula I-d, $R^1$ is —$(CR^hR^i)_nNR^aC(O)R^b$; each occurrence of $R^h$ and $R^i$ is, independently, hydrogen, halogen, haloalkyl, or alkyl; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring; and $R^2$ is hydrogen.

In certain embodiments of the compound of Formula I-d, $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments of the compound of Formula I-d, A is aryl or heteroaryl; $R^1$ is alkyl, haloalkyl, or —$CH_2OR^f$; $R^f$ is aryl, alkyl, or haloalkyl; and $R^2$ is hydrogen.

In certain embodiments of the compound of Formula I-d, A is aryl or heteroaryl; $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments of the compound of Formula I-d, A is phenyl substituted with 1-3 independent substituents $R^5$, wherein each occurrence of $R^5$ is, independently, halogen, cyano, alkyl, haloalkyl, or —$OR^f$, wherein $R^f$ is haloalkyl or alkyl; $R^1$ is alkyl, haloalkyl, or —$CH_2OR^f$, wherein $R^f$ is aryl, alkyl, or haloalkyl; and $R^2$ is hydrogen.

In certain embodiments of the compound of Formula I-d, A is phenyl substituted with 1-3 independent substituents $R^5$, wherein each occurrence of $R^5$ is, independently, halogen, cyano, alkyl, haloalkyl, or —$OR^f$, wherein $R^f$ is haloalkyl or alkyl; $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments, the compound of Formula I is a compound of Formula I-g:

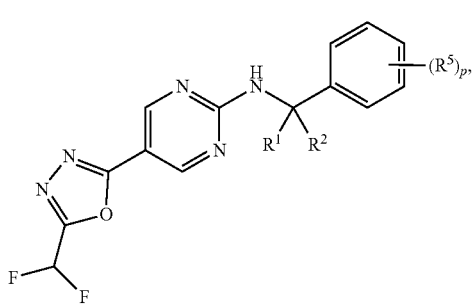

I-g or a pharmaceutically acceptable salt, co-crystal, tautomer, stereoisomer, solvate, hydrate, polymorph, isotopically enriched derivative, or prodrug thereof, wherein $R^1$, $R^2$, $R^5$, and p are as defined herein.

In certain embodiments of the compound of Formula I-g, $R^1$ is alkyl, haloalkyl, or —$CH_2OR^f$; $R^f$ is aryl, alkyl, or haloalkyl; and $R^2$ is hydrogen.

In certain embodiments of the compound of Formula I-g, $R^1$ is —$(CR^hR^i)_nNR^aC(O)R^b$; each occurrence of $R^h$ and $R^i$ is, independently, hydrogen, halogen, haloalkyl, or alkyl; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring; and $R^2$ is hydrogen.

In certain embodiments of the compound of Formula I-g, $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments of the compound of Formula I-g, p is 1, 2, or 3.

In certain embodiments of the compound of Formula I-g, p is 1, 2, or 3; each occurrence of $R^5$ is, independently, halogen, cyano, alkyl, haloalkyl, or —$OR^f$; $R^f$ is haloalkyl or alkyl. In certain embodiments of the compound of Formula I-g, at least one $R^5$ is halogen.

In certain embodiments of the compound of Formula I-g, p is 1, 2, or 3; each occurrence of $R^5$ is, independently, halogen, cyano, alkyl, haloalkyl, or —$OR^f$, wherein $R^f$ is haloalkyl or alkyl; $R^1$ is alkyl, haloalkyl, or —$CH_2OR^f$, wherein $R^f$ is aryl, alkyl, or haloalkyl; and $R^2$ is hydrogen.

In certain embodiments of the compound of Formula I-g, p is 1, 2, or 3; each occurrence of $R^5$ is, independently, halogen, cyano, alkyl, haloalkyl, or —$OR^f$, wherein $R^f$ is haloalkyl or alkyl, and at least one $R^5$ is halogen; $R^1$ is alkyl, haloalkyl, or —$CH_2OR^f$, wherein $R^f$ is aryl, alkyl, or haloalkyl; and $R^2$ is hydrogen.

In certain embodiments of the compound of Formula I-g, p is 1, 2, or 3; each occurrence of $R^5$ is, independently, halogen, cyano, alkyl, haloalkyl, or —$OR^f$, wherein $R^f$ is haloalkyl or alkyl; $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, haloalkyl, or alkyl; and $R^2$ is hydrogen.

In certain embodiments of the compound of Formula I-g, p is 1, 2, or 3; each occurrence of $R^5$ is, independently, halogen, cyano, alkyl, haloalkyl, or —$OR^f$, wherein $R^f$ is haloalkyl or alkyl, and at least one $R^5$ is halogen; $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments, the compound of Formula I is a compound of Formula I-h:

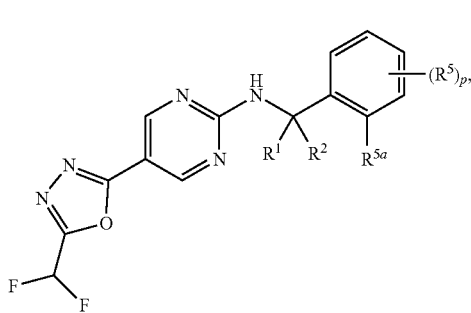

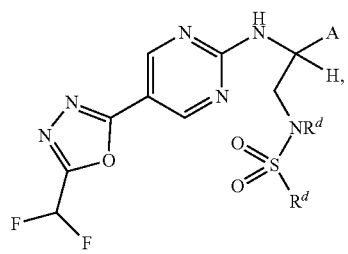

or a pharmaceutically acceptable salt, co-crystal, tautomer, stereoisomer, solvate, hydrate, polymorph, isotopically enriched derivative, or prodrug thereof, wherein $R^1$, $R^2$, $R^5$, $R^{5a}$, and p are as defined herein.

In certain embodiments of the compound of Formula I-h, $R^1$ is alkyl, haloalkyl, or —CH$_2$OR$^f$; $R^f$ is aryl, alkyl, or haloalkyl; and $R^2$ is hydrogen.

In certain embodiments of the compound of Formula I-h, $R^1$ is —(CR$^h$R$^i$)$_n$NR$^a$C(O)R$^b$; each occurrence of R$^h$ and R$^i$ is, independently, hydrogen, halogen, haloalkyl, or alkyl; and each occurrence of R$^a$ and R$^b$ is, independently, hydrogen, aryl, heteroaryl, cycloalkyl, haloalkyl, or alkyl; or R$^a$ and R$^b$ together with the atoms to which they are attached form a heterocycloalkyl ring; and $R^2$ is hydrogen.

In certain embodiments of the compound of Formula I-h, $R^1$ is —(CR$^h$R$^i$)$_n$-E-NR$^d$SO$_2$R$^d$; E is a bond, aryl, or heteroaryl; each occurrence of R$^d$ is, independently, hydrogen, alkyl, haloalkyl, cycloalkyl, aryl, or heteroaryl; or 2 instances of R$^d$ together with the atoms to which they are attached form a heterocycloalkyl ring; each occurrence of R$^h$ and R$^i$ is, independently, hydrogen, halogen, haloalkyl, or alkyl; and $R^2$ is hydrogen.

In certain embodiments of the compound of Formula I-h, p is 0, 1, or 2. In certain embodiments of the compound of Formula I-h, p is 0 or 1.

In certain embodiments of the compound of Formula I-h, $R^{5a}$ is halogen. In certain embodiments of the compound of Formula I-h, $R^{5a}$ is —F or —C$_1$.

In certain embodiments of the compound of Formula I-h, p is 0 or 1; $R^{5a}$ is halogen; $R^5$ is halogen, cyano, alkyl, haloalkyl, or —OR$^f$; and R$^f$ is haloalkyl or alkyl.

In certain embodiments of the compound of Formula I-h, p is 0 or 1; $R^{5a}$ is halogen; $R^5$ is halogen, cyano, alkyl, haloalkyl, or —OR$^f$, wherein R$^f$ is haloalkyl or alkyl; $R^1$ is alkyl, haloalkyl, or —CH$_2$OR$^f$, wherein R$^f$ is aryl, alkyl, or haloalkyl; and $R^2$ is hydrogen.

In certain embodiments of the compound of Formula I-h, p is 0 or 1; $R^{5a}$ is halogen; $R^5$ is halogen, cyano, alkyl, haloalkyl, or —OR$^f$, wherein R$^f$ is haloalkyl or alkyl; $R^1$ is —(CR$^h$R$^i$)$_n$-E-NR$^d$SO$_2$R$^d$; E is a bond, aryl, or heteroaryl; each occurrence of R$^d$ is, independently, hydrogen, alkyl, haloalkyl, cycloalkyl, aryl, or heteroaryl; or 2 instances of R$^d$ together with the atoms to which they are attached form a heterocycloalkyl ring; each occurrence of R$^h$ and R$^i$ is, independently, hydrogen, halogen, haloalkyl, or alkyl; and $R^2$ is hydrogen.

In certain embodiments, the compound of Formula I is a compound of Formula I-i:

or a pharmaceutically acceptable salt, co-crystal, tautomer, stereoisomer, solvate, hydrate, polymorph, isotopically enriched derivative, or prodrug thereof, wherein R$^d$ and A are as defined herein.

In certain embodiments of the compound of Formula I-i, A is aryl, heteroaryl, or cycloalkyl. In certain embodiments of the compound of Formula I-i, A is aryl or heteroaryl.

In certain embodiments of the compound of Formula I-i, A is heteroaryl. In certain embodiments of the compound of Formula I-i, A is monocyclic or bicyclic heteroaryl. In certain embodiments of the compound of Formula I-i, A is pyridyl. In certain embodiments of the compound of Formula I-i, A is 2-pyridyl or 3-pyridyl substituted with 1-3 independent substituents $R^5$, wherein each occurrence of $R^5$ is, independently, halogen, cyano, alkyl, haloalkyl, or —OR$^f$; and R$^f$ is haloalkyl or alkyl In certain embodiments of the compound of Formula I-i, A is aryl. In certain embodiments of the compound of Formula I-i, A is phenyl. In certain embodiments of the compound of Formula I-i, A is phenyl substituted with 1-3 independent substituents $R^5$; each occurrence of $R^5$ is, independently, halogen, cyano, alkyl, haloalkyl, or —OR$^f$; and R$^f$ is haloalkyl or alkyl.

In certain embodiments of the compound of Formula I-i, A is

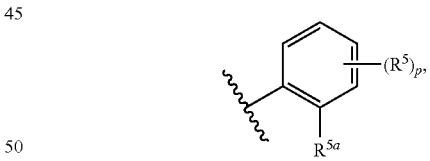

wherein $R^{5a}$ is halogen; each occurrence of $R^5$ is, independently, halogen, cyano, alkyl, haloalkyl, or —OR$^f$; R$^f$ is alkyl or haloalkyl; and p is 0, 1, or 2.

In certain embodiments of the compound of Formula I-i, each occurrence of R$^d$ is, independently, hydrogen, alkyl, haloalkyl, cycloalkyl, aryl, or heteroaryl; or 2 instances of R$^d$ together with the atoms to which they are attached form a heterocycloalkyl ring. In certain embodiments of the compound of Formula I-i, each occurrence of R$^d$ is, independently, hydrogen, alkyl, haloalkyl, cycloalkyl, or aryl; or 2 instances of R$^d$ together with the atoms to which they are attached form a heterocycloalkyl ring.

In certain embodiments, the compound of Formula I is a compound of Formula I-j:

I-j

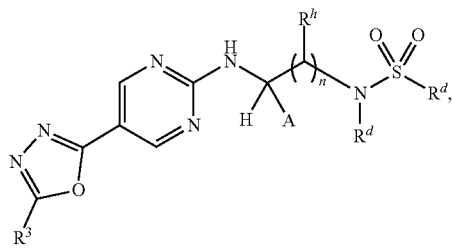

or a pharmaceutically acceptable salt, co-crystal, tautomer, stereoisomer, solvate, hydrate, polymorph, isotopically enriched derivative, or prodrug thereof, wherein $R^d$, $R^h$, n, $R^3$, and A are as defined herein.

In certain embodiments of the compound of Formula I-j, A is aryl, heteroaryl, or cycloalkyl. In certain embodiments of the compound of Formula I-j, A is aryl or heteroaryl.

In certain embodiments of the compound of Formula I-j, A is heteroaryl. In certain embodiments of the compound of Formula I-j, A is monocyclic or bicyclic heteroaryl. In certain embodiments of the compound of Formula I-j, A is pyridyl. In certain embodiments of the compound of Formula I-j, A is 2-pyridyl or 3-pyridyl substituted with 1-3 independent substituents $R^5$, wherein each occurrence of $R^5$ is, independently, halogen, cyano, alkyl, haloalkyl, or —$OR^f$; and $R^f$ is haloalkyl or alkyl In certain embodiments of the compound of Formula I-j, A is aryl. In certain embodiments of the compound of Formula I-j, A is phenyl. In certain embodiments of the compound of Formula I-j, A is phenyl substituted with 1-3 independent substituents $R^5$; each occurrence of $R^5$ is, independently, halogen, cyano, alkyl, haloalkyl, or —$OR^f$; and $R^f$ is haloalkyl or alkyl.

In certain embodiments of the compound of Formula I-j, A is

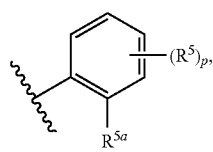

wherein $R^{5a}$ is halogen; each occurrence of $R^5$ is, independently, halogen, cyano, alkyl, haloalkyl, or —$OR^f$; $R^f$ is alkyl or haloalkyl; and p is 0, 1, or 2.

In certain embodiments of the compound of Formula I-j, each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; n is 1, 2, or 3; and $R^h$ is, hydrogen, halogen, haloalkyl, or alkyl. In certain embodiments of the compound of Formula I-j, each occurrence of $R^d$ is, independently, hydrogen, alkyl, haloalkyl, cycloalkyl, or aryl; or 2 instances of $R^d$ together with the atoms to which they are attached form a heterocycloalkyl ring; n is 1, 2, or 3; and $R^h$ is, hydrogen, halogen, haloalkyl, or alkyl.

In certain embodiments of the compound of Formula I-j, $R^3$ is haloalkyl. In certain embodiments of the compound of Formula I-j, $R^3$ is $C_{1-3}$ haloalkyl. In certain embodiments of the compound of Formula I-j, $R^3$ is —$CF_3$, —$CHF_2$, or $CH_2F$. In certain embodiments of the compound of Formula I-j, $R^3$ is —$CHF_2$.

In certain embodiments, the compound of Formula I is a compound of Formula I-k:

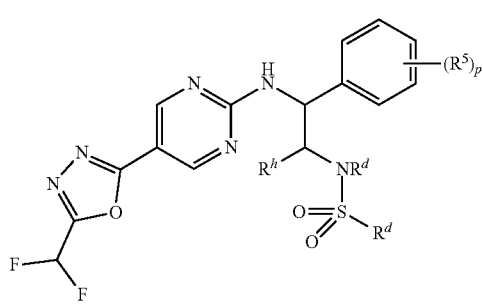

or a pharmaceutically acceptable salt, co-crystal, tautomer, stereoisomer, solvate, hydrate, polymorph, isotopically enriched derivative, or prodrug thereof, wherein $R^d$, $R^h$, $R^5$, and p are as defined herein.

In certain embodiments of the compound of Formula I-k, each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; and $R^h$ is, hydrogen, halogen, haloalkyl, or alkyl.

In certain embodiments of the compound of Formula I-k, p is 1, 2, or 3.

In certain embodiments of the compound of Formula I-k p is 1, 2, or 3; each occurrence of $R^5$ is, independently, halogen, cyano, alkyl, haloalkyl, or —$OR^f$; $R^f$ is haloalkyl or alkyl. In certain embodiments of the compound of Formula I-k, at least one $R^5$ is halogen.

In certain embodiments of the compound of Formula I-k, p is 1, 2, or 3; each occurrence of $R^5$ is, independently, halogen, cyano, alkyl, haloalkyl, or —$OR^f$, wherein $R^f$ is haloalkyl or alkyl;

$R^d$ is, independently, hydrogen, alkyl, haloalkyl, cycloalkyl, aryl, or heteroaryl; or 2 instances of $R^d$ together with the atoms to which they are attached form a heterocycloalkyl ring; and $R^h$ is, hydrogen, halogen, haloalkyl, or alkyl.

In certain embodiments of the compound of Formula I-k, p is 1, 2, or 3; each occurrence of $R^5$ is, independently, halogen, cyano, alkyl, haloalkyl, or —$OR^f$, wherein $R^f$ is haloalkyl or alkyl, and at least one $R^5$ is halogen; $R^d$ is, independently, hydrogen, alkyl, haloalkyl, cycloalkyl, aryl, or heteroaryl; or 2 instances of $R^d$ together with the atoms to which they are attached form a heterocycloalkyl ring; and $R^h$ is, hydrogen, halogen, haloalkyl, or alkyl.

In another aspect, provided are compounds of Formula I:

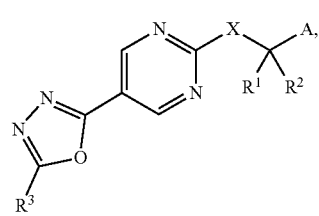

and pharmaceutically acceptable salts, co-crystals, tautomers, stereoisomers, solvates, hydrates, polymorphs, isotopically enriched derivatives, or prodrugs thereof, wherein:

A is aryl, heteroaryl, cycloalkyl, heterocycloalkyl, arylalkyl, or alkyl, wherein each A is optionally substituted with 1-3 independent substituents $R^5$;

X is $NR^4$ or O;

each of $R^1$ and $R^2$ is, independently, hydrogen, cyano, alkyl, alkenyl, alkynyl, cycloalkyl, aryl, heteroaryl, heterocycloalkyl, heteroarylalkyl, heterocycloalkylalkyl, $-(CR^hR^i)_n\text{-E-}NR^aC(O)R^b$, $-C(O)NR^aR^b$, $-(CR^hR^i)_n\text{-E-}NR^dSO_2R^d$, $-(CR^hR^i)\text{-G-}SO_2R^d$, $-CO_2R^e$, $-COR^f$, or $-CH_2OR^f$, wherein each $R^1$ and $R^2$ is optionally substituted with 1-3 independent substituents $R^5$;

or $R^1$ and $R^2$ together with the atoms to which they are attached form a heterocycloalkyl or cycloalkyl ring, wherein said heterocycloalkyl and cycloalkyl are optionally substituted with 1-3 independent substituents $R^5$;

or $R^1$ and A together with the atoms to which they are attached form a heterocycloalkyl ring or fused bicyclic ring;

$R^3$ is haloalkyl or $-OR^g$;

$R^4$ is hydrogen, alkyl, $-(CR^hR^i)_nC(O)NR^aR^b$, $-C(O)(CR^hR^i)_nNR^aR^b$, $-C(O)O(CR^hR^i)_nC(O)NR^aR^b$, or $-(CR^hR^i)_nOP(O)(OR^a)_2$;

each occurrence of $R^5$ is, independently, halogen, cyano, alkyl, haloalkyl, $-NR^aR^b$, $-NHSO_2R^c$, $-(CH_2)_nNR^aR^b$, $-(CH_2)_nC(O)NR^aR^b$, $-(CH_2)_nNR^dSO_2R^d$, $-S(O)R^d$, $-S(O)_2R^d$, $-CO_2R^e$, $-COR^f$, $-(CR^eR^f)_nOR^f$, $-OR^f$, or aryl substituted with 0-3 independent halogen, $-NR^aR^b$, $-NHSO_2R^c$, $-(CH_2)_nNR^aR^b$, $-(CH_2)_nC(O)NR^aR^b$, $-(CH_2)_nNHSO_2R^d$, $-S(O)R^d$, $-S(O)_2R^d$, $-CO_2R^e$, $-COR^f$, $-(CR^eR^f)_nOR^f$, or $-OR^f$; or two occurrences of $R^5$, together with the atoms to which they are attached, form a cycloalkyl, heterocycloalkyl, aryl, or heteroaryl ring;

each n is independently 1, 2, 3, 4, 5, 6, 7, 8, 9, or 10;

each E is independently a bond, aryl, heteroaryl, cycloalkyl, or heterocycloalkyl;

each G is independently heteroaryl or heterocycloalkyl;

each occurrence of $R^a$, $R^b$, $R^c$, $R^d$, $R^e$, and $R^f$ is, independently, hydrogen, acyl, alkoxyalkyl, alkyl, alkenyl, alkynyl, heteroalkyl, haloalkyl, cycloalkyl, heterocycloalkyl, aryl, heteroaryl, arylalkyl, heteroarylalkyl, heterocycloalkylalkyl, a nitrogen protecting group when attached to a nitrogen atom, or an oxygen protecting group when attached to an oxygen atom; or $R^a$ and $R^b$ together with the atoms to which they are attached form a heterocycloalkyl ring; or $R^e$ and $R^f$ together with the atoms to which they are attached form a cycloalkyl ring; or 2 instances of $R^d$ together with the atoms to which they are attached form a heterocycloalkyl ring;

$R^g$ is haloalkyl; and each occurrence of $R^h$ and $R^i$ is, independently, hydrogen, halogen, alkyl, alkenyl, alkynyl, heteroalkyl, haloalkyl, cycloalkyl, heterocycloalkyl, aryl, heteroaryl, arylalkyl, heteroarylalkyl, or heterocycloalkylalkyl.

In certain embodiments, A is aryl, heteroaryl, cycloalkyl, heterocycloalkyl, arylalkyl, or alkyl, wherein each A is optionally substituted with 1-3 independent substituents $R^5$;

X is $NR^4$ or O;

each of $R^1$ and $R^2$ is, independently, hydrogen, cyano, alkyl, alkenyl, alkynyl, cycloalkyl, aryl, heteroaryl, heterocycloalkyl, heteroarylalkyl, heterocycloalkylalkyl, $-(CR^hR^i)_n\text{-E-}NR^aC(O)R^b$, $-C(O)NR^aR^b$, $-(CR^hR^i)_n\text{-E-}NR^dSO_2R^d$, $-(CR^hR^i)_n\text{-G-}SO_2R^d$, $-CO_2R^e$, $-COR^f$, or $-CH_2OR^f$, wherein each $R^1$ and $R^2$ is optionally substituted with 1-3 independent substituents $R^5$;

or $R^1$ and A together with the atoms to which they are attached form a heterocycloalkyl ring or fused bicyclic ring;

$R^3$ is haloalkyl or $-OR^g$;

$R^4$ is hydrogen, alkyl, $-(CR^hR^i)_nC(O)NR^aR^b$, $-C(O)(CR^hR^i)_nNR^aR^b$, $-C(O)O(CR^hR^i)_nC(O)NR^aR^b$, or $-(CR^hR^i)_nOP(O)(OR^a)_2$;

each occurrence of $R^5$ is, independently, halogen, cyano, alkyl, haloalkyl, $-NR^aR^b$, $-NHSO_2R^c$, $-(CH_2)_nNR^aR^b$, $-(CH_2)_nC(O)NR^aR^b$, $-(CH_2)_nNR^dSO_2R^d$, $-S(O)R^d$, $-S(O)_2R^d$, $-CO_2R^e$, $-COR^f$, $-(CR^eR^f)_nOR^f$, $-OR^f$, or aryl substituted with 0-3 independent halogen, $-NR^aR^b$, $-NHSO_2R^c$, $-(CH_2)_nNR^aR^b$, $-(CH_2)_nC(O)NR^aR^b$, $-(CH_2)_nNHSO_2R^d$, $-S(O)R^d$, $-S(O)_2R^d$, $-CO_2R^e$, $-COR^f$, $-(CR^eR^f)_nOR^f$, or $-OR^f$; or two occurrences of $R^5$, together with the atoms to which they are attached, form a cycloalkyl, heterocycloalkyl, aryl, or heteroaryl ring;

each n is independently 1, 2, 3, 4, 5, 6, 7, 8, 9, or 10;

each E is independently a bond, aryl, heteroaryl, cycloalkyl, or heterocycloalkyl;

each G is independently heteroaryl or heterocycloalkyl;

each occurrence of $R^a$, $R^b$, $R^c$, $R^d$, $R^e$, and $R^f$ is, independently, hydrogen, acyl, alkoxyalkyl, alkyl, alkenyl, alkynyl, heteroalkyl, haloalkyl, cycloalkyl, heterocycloalkyl, aryl, heteroaryl, arylalkyl, heteroarylalkyl, heterocycloalkylalkyl, a nitrogen protecting group when attached to a nitrogen atom, or an oxygen protecting group when attached to an oxygen atom; or $R^a$ and $R^b$ together with the atoms to which they are attached form a heterocycloalkyl ring; or $R^e$ and $R^f$ together with the atoms to which they are attached form a cycloalkyl ring; or 2 instances of $R^d$ together with the atoms to which they are attached form a heterocycloalkyl ring;

$R^g$ is haloalkyl; and each occurrence of $R^h$ and $R^i$ is, independently, hydrogen, halogen, alkyl, alkenyl, alkynyl, heteroalkyl, haloalkyl, cycloalkyl, heterocycloalkyl, aryl, heteroaryl, arylalkyl, heteroarylalkyl, or heterocycloalkylalkyl.

In certain embodiments, A is aryl, heteroaryl, cycloalkyl, heterocycloalkyl, or arylalkyl, wherein each A is optionally substituted with 1-3 independent substituents $R^5$.

In certain embodiments, A is aryl, heteroaryl, cycloalkyl, or heterocycloalkyl, wherein each A is optionally substituted with 1-3 independent substituents $R^5$.

In certain embodiments, A is aryl, heteroaryl, or cycloalkyl, wherein each A is optionally substituted with 1-3 independent substituents $R^5$. In certain embodiments, A is aryl, heteroaryl, or $C_{3-6}$ cycloalkyl, wherein each A is optionally substituted with 1-3 independent substituents $R^5$.

In certain embodiments, A is aryl or heteroaryl, wherein each A is optionally substituted with 1-3 independent substituents $R^5$.

In certain embodiments, A is aryl optionally substituted with 1-3 independent substituents $R^5$. In certain embodiments, A is phenyl or naphthyl, wherein each A is optionally substituted with 1-3 independent substituents $R^5$. In certain embodiments, A is phenyl optionally substituted with 1-3 independent substituents $R^5$. In certain embodiments, A is unsubstituted phenyl. In certain embodiments, A is phenyl substituted with 1-3 independent substituents $R^5$. In certain embodiments, A is phenyl substituted with 1-3 independent substituents $R^5$, wherein each occurrence of $R^5$ is, independently, halogen, cyano, alkyl, haloalkyl, or —OR$^f$; and each R$^f$ is independently haloalkyl or alkyl.

In certain embodiments, A is

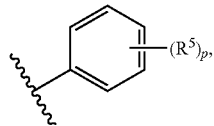

wherein p is 0, 1, 2, or 3. In certain embodiments, A is

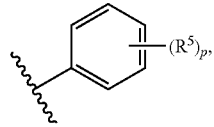

wherein p is 1, 2, or 3. In certain embodiments A is

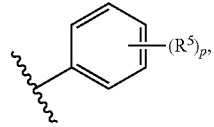

wherein p is 1 or 2. In certain embodiments, A is

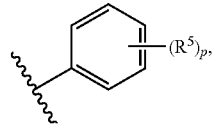

wherein p is 1. In certain embodiments, A is

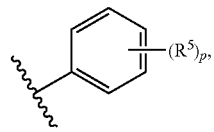

wherein p is 2. In certain embodiments, A is

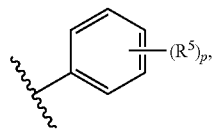

wherein p is 3.

In certain embodiments, A is

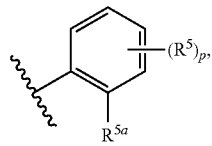

herein R$^{5a}$ is any group as defined for R$^5$ herein, and p is 0, 1, or 2. In certain embodiments, R$^{5a}$ is halogen. In certain embodiments, R$^{5a}$ is F, Cl, or Br. In certain embodiments, R$^{5a}$ is F or C$_1$. In certain embodiments, R$^{5a}$ is F. In certain embodiments, R$^{5a}$ is C$_1$. In certain embodiments, R$^{5a}$ is halogen; each occurrence of R$^5$ is, independently, halogen, cyano, alkyl, haloalkyl, or —OR$^f$; R$^f$ is independently alkyl or haloalkyl; and p is 0, 1, or 2. In certain embodiments, R$^{5a}$ is F or C$_1$; each occurrence of R$^5$ is, independently, halogen, cyano, alkyl, haloalkyl, or —OR$^f$; R is independently alkyl or haloalkyl; and p is 0 or 1.

In certain embodiments, A is

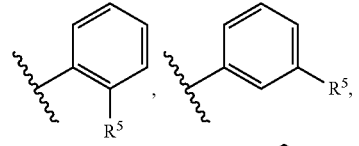

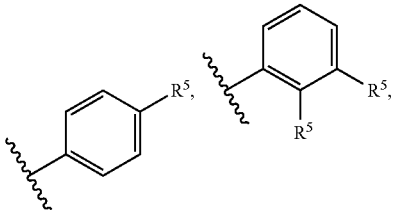

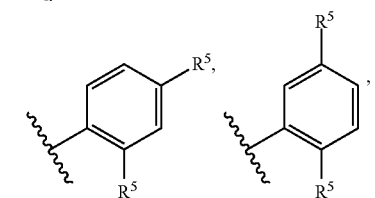

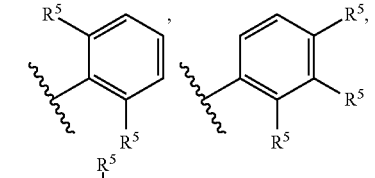

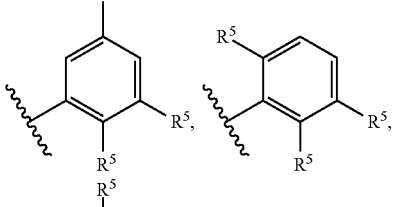

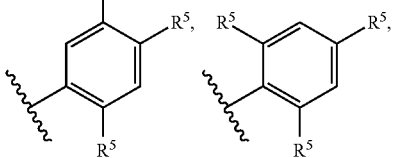

-continued
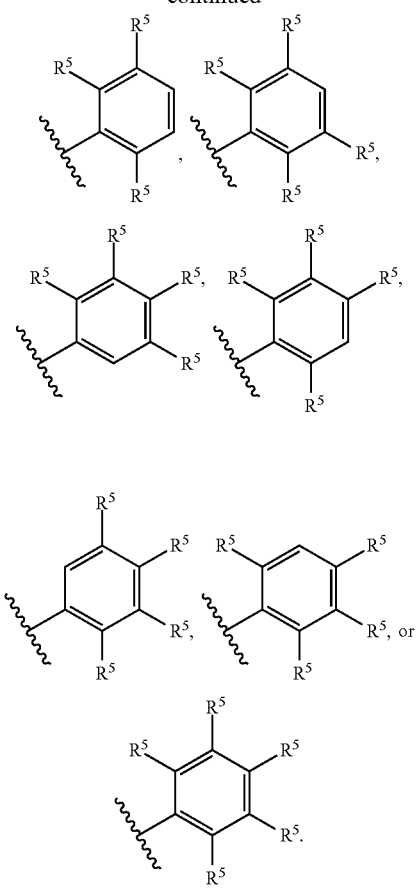
In certain embodiments, A is
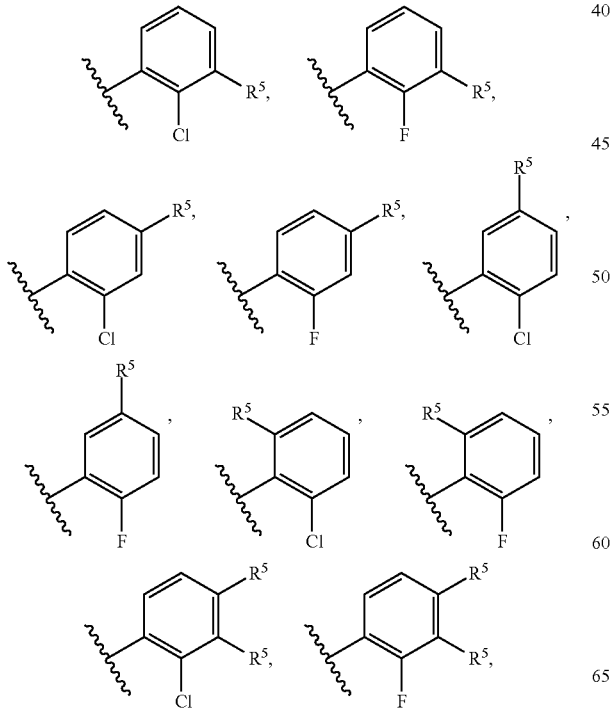
-continued
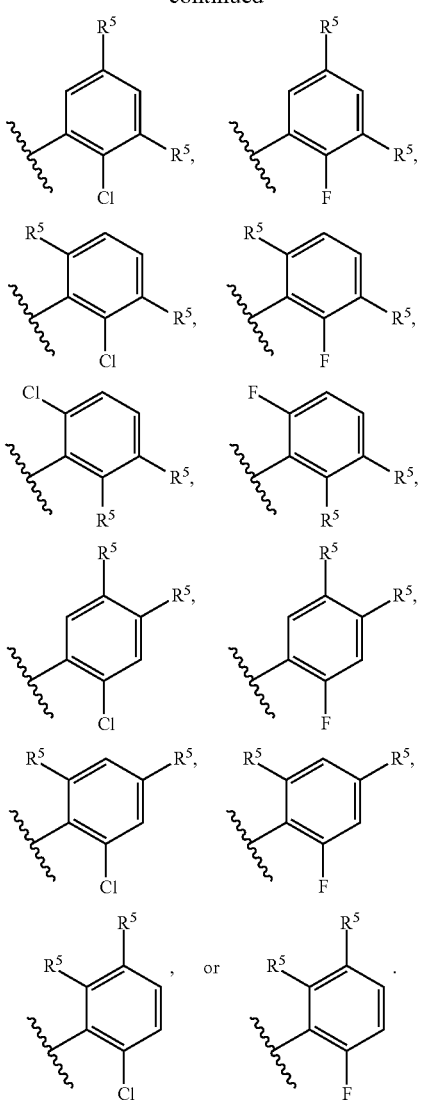
In certain embodiments, A is
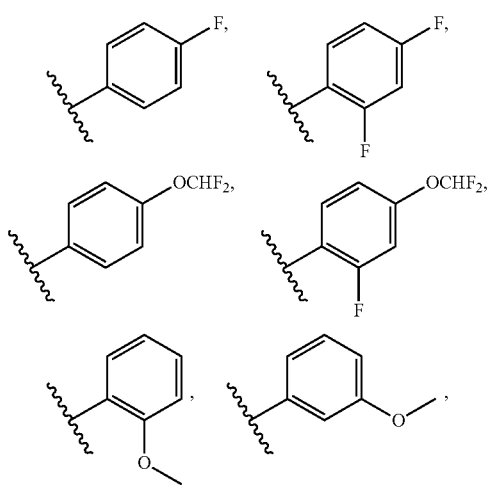

-continued

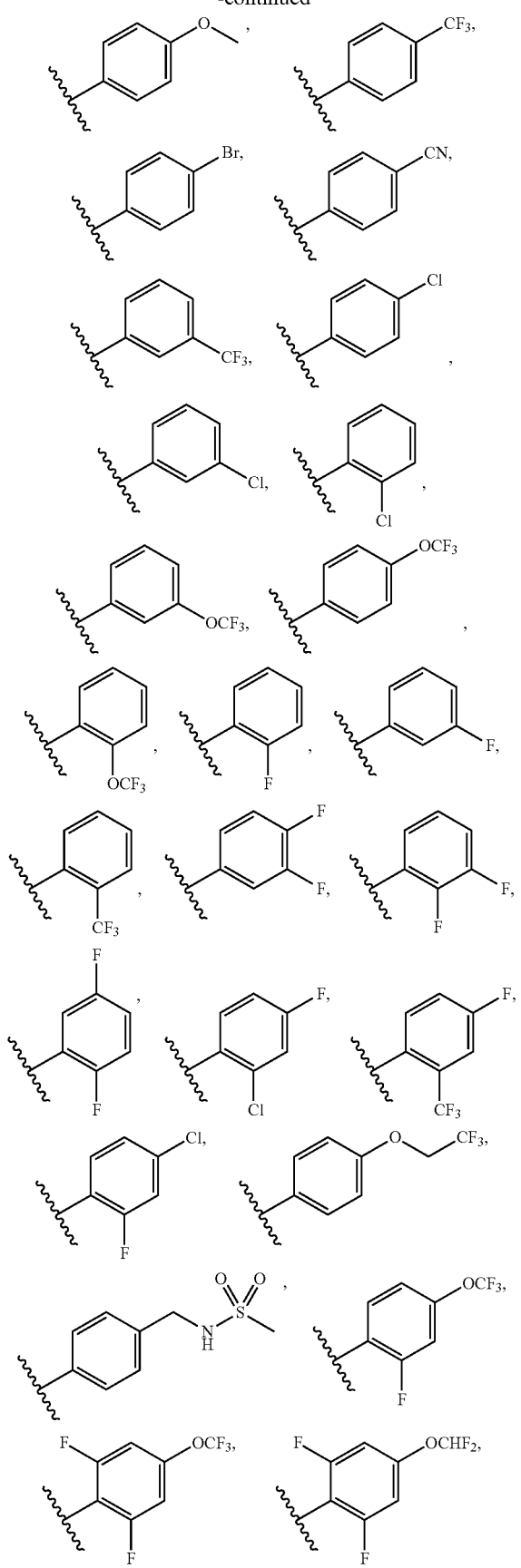

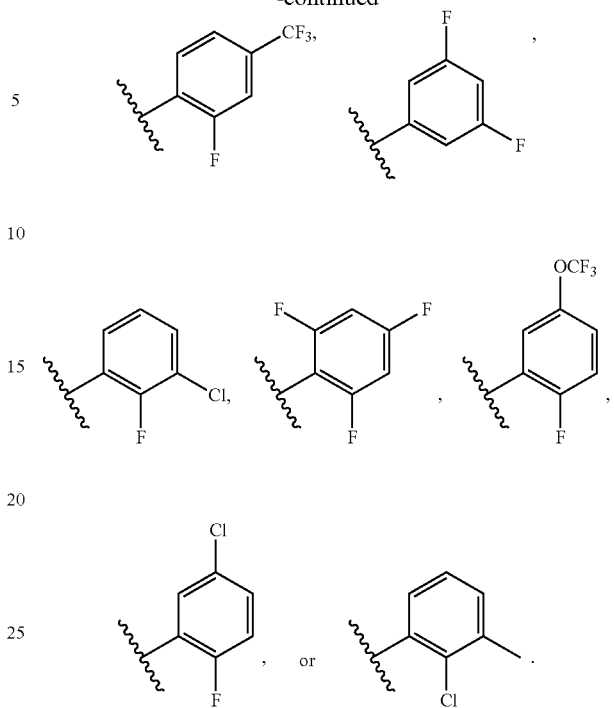

In certain embodiments, A is heteroaryl. In certain embodiments, A is monocyclic or bicyclic heteroaryl, wherein each A is optionally substituted with 1-3 independent substituents $R^5$. In certain embodiments, A is bicyclic heteroaryl optionally substituted with 1-3 independent substituents $R^5$. In certain embodiments, A is monocyclic heteroaryl optionally substituted with 1-3 independent substituents $R^5$. In certain embodiments, A is pyridyl optionally substituted with 1-3 independent substituents $R^5$. In certain embodiments, A is 2-pyridyl, 3-pyridyl, or 4-pyridyl, wherein each A is optionally substituted with 1-3 independent substituents $R^5$. In certain embodiments, A is 2-pyridyl or 3-pyridyl substituted with 1-3 independent substituents $R^5$, wherein each occurrence of $R^5$ is, independently, halogen, cyano, alkyl, haloalkyl, or —$OR^f$; and $R^f$ is independently haloalkyl or alkyl.

In certain embodiments, A is

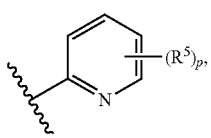

wherein p is 0, 1, 2, or 3. In certain embodiments, A is

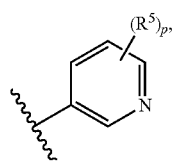

wherein p is 0, 1, 2, or 3. In certain embodiments, A is

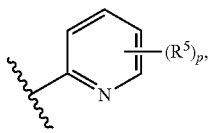

wherein p is 0 or 1. In certain embodiments, A is

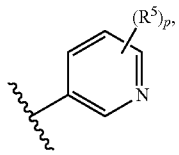

wherein p is 0 or 1.

In certain embodiments, A is

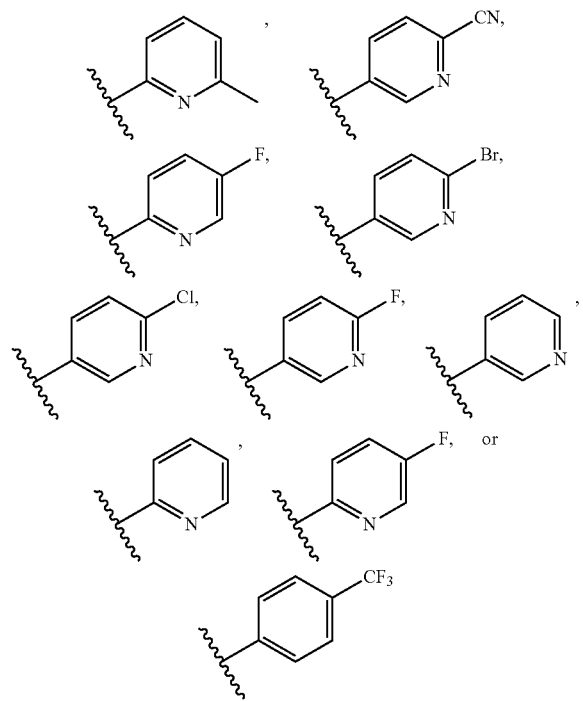

In certain embodiments, A is cycloalkyl optionally substituted with 1-3 independent substituents $R^5$. In certain embodiments, A is $C_{3-6}$ cycloalkyl optionally substituted with 1-3 independent substituents $R^5$. In certain embodiments, A is unsubstituted $C_{3-6}$ cycloalkyl. In certain embodiments, A is $C_{3-6}$ cycloalkyl substituted with 1-3 independent substituents $R^5$, wherein each occurrence of $R^5$ is, independently, halogen, cyano, alkyl, haloalkyl, or —$OR^f$; and $R^f$ is independently haloalkyl or alkyl. In certain embodiments, A is cyclopropyl optionally substituted with 1-3 independent substituents $R^5$. In certain embodiments, A is cyclobutyl optionally substituted with 1-3 independent substituents $R^5$. In certain embodiments, A is cyclopentyl optionally substituted with 1-3 independent substituents $R^5$. In certain embodiments, A is cyclohexyl optionally substituted with 1-3 independent substituents $R^5$.

In certain embodiments, A is heterocycloalkyl optionally substituted with 1-3 independent substituents $R^5$. In certain embodiments, A is a 4-7 membered heterocycloalkyl optionally substituted with 1-3 independent substituents $R^5$. In certain embodiments, A is a 4-7 membered heterocycloalkyl optionally substituted with 1-3 independent substituents $R^5$. In certain embodiments, A is a 5-6 membered heterocycloalkyl optionally substituted with 1-3 independent substituents $R^5$. In certain embodiments, A is a 5 membered heterocycloalkyl optionally substituted with 1-3 independent substituents $R^5$. In certain embodiments, A is a 6 membered heterocycloalkyl optionally substituted with 1-3 independent substituents $R^5$. In certain embodiments, A is oxepanyl, tetrahydropyranyl, dihydropyranyl, tetrahydrofuranyl, oxetanyl, azepanyl, piperidinyl, piperazinyl, morpholinyl, pyrrolidinyl, or azetidinyl, wherein each A is optionally substituted with 1-3 independent substituents $R^5$. In certain embodiments, A is tetrahydropyranyl, tetrahydrofuranyl, piperidinyl, or pyrrolidinyl, wherein each A is optionally substituted with 1-3 independent substituents $R^5$.

In certain embodiments, A is arylalkyl optionally substituted with 1-3 independent substituents $R^5$. In certain embodiments, A is benzyl optionally substituted with 1-3 independent substituents $R^5$. In certain embodiments, A is benzyl substituted with 1-3 independent substituents $R^5$, wherein each occurrence of $R^5$ is, independently, halogen, cyano, alkyl, haloalkyl, or —$OR^f$; and $R^f$ is independently haloalkyl or alkyl.

In certain embodiments, X is $NR^4$; and $R^4$ is hydrogen, alkyl, —$(CR^hR^i)_nC(O)NR^aR^b$, —$C(O)(CR^hR^i)_nNR^aR^b$, —$C(O)O(CR^hR^i)_nC(O)NR^aR^b$, or —$(CR^hR^i)_nOP(O)(OR^a)_2$. In certain embodiments, X is $NR^4$; and $R^4$ is hydrogen, alkyl, —$(CH_2)_nC(O)NR^aR^b$, —$C(O)(CH_2)_nNR^aR^b$, —$C(O)O(CH_2)_nC(O)NR^aR^b$, or —$(CH_2)_nOP(O)(OR^a)_2$. In certain embodiments, X is $NR^4$; and $R^4$ is hydrogen, alkyl, —$CH_2C(O)NR^aR^b$, —$C(O)CH_2NR^aR^b$, —$C(O)OCH_2C(O)NR^aR^b$, or —$CH_2OP(O)(OR^a)_2$; and each occurrence of $R^a$ and $R^b$ is independently hydrogen or alkyl. In certain embodiments, X is $NR^4$; and $R^4$ is hydrogen or alkyl. In certain embodiments, X is NH. In certain embodiments, X is O.

In certain embodiments, $R^1$ is hydrogen, cyano, alkyl, alkenyl, alkynyl, cycloalkyl, aryl, heteroaryl, heterocycloalkyl, heteroarylalkyl, heterocycloalkylalkyl, —$(CR^hR^i)_n$-E-$NR^aC(O)R^b$, —$C(O)NR^aR^b$, —$(CR^hR^i)_n$-E-$NR^dSO_2R^d$, —$(CR^hR^i)_n$-G-$SO_2R^d$, —$CO_2R^e$, —$COR^f$, or —$CH_2OR^f$, wherein each $R^1$ is optionally substituted with 1-3 independent substituents $R^5$.

In certain embodiments, $R^1$ is hydrogen, alkyl, haloalkyl, aryl, cycloalkyl, heteroarylalkyl, heterocycloalkylalkyl, —$CH_2OR^f$, —$(CR^hR^i)_n$-E-$NR^aC(O)R^b$, —$C(O)NR^aR^b$, —$(CR^hR^i)_n$-E-$NR^dSO_2R^d$, or —$(CR^hR^i)_n$-G-$SO_2R^d$, wherein each $R^1$ is optionally substituted with 1-3 independent substituents $R^5$. In certain embodiments, $R^1$ is hydrogen, alkyl, haloalkyl, aryl, cycloalkyl, heteroarylalkyl, heterocycloalkylalkyl, —$CH_2OR^f$, —$(CH_2)_nNR^aC(O)R^b$, —$C(O)NR^aR^b$, —$(CH_2)_nNR^dSO_2R^d$, or -G-$SO_2R^d$, wherein each $R^1$ is optionally substituted with 1-3 independent substituents $R^5$. In certain embodiments, $R^1$ is hydrogen, alkyl, haloalkyl, aryl, cycloalkyl, heteroarylalkyl, heterocycloalkylalkyl, —$CH_2OR^f$, —$(CH_2)_nNR^aC(O)R^b$, —$C(O)NR^aR^b$, —$(CH_2)_n$-E-$NR^dSO_2R^d$, or -G-$SO_2R^d$, wherein each $R^1$ is optionally substituted with 1-3 independent substituents $R^5$; wherein each occurrence of $R^a$, $R^b$, $R^d$, and $R^f$ is, independently, alkyl, haloalkyl, or aryl; or $R^a$ and $R^b$ together with the atoms to which they are attached form a heterocycloalkyl ring; or 2 instances of $R^d$ together with the atoms to which they are attached form a heterocycloalkyl ring; E is aryl; and G is heterocycloalkyl. In certain embodiments, $R^i$ is —CH$_2$OR$^f$, —(CH$_2$)$_n$NR$^a$C(O)R$^b$, —C(O)NR$^a$R$^b$, —(CH$_2$)$_n$-E-NR$^d$SO$_2$R$^d$, or -G-SO$_2$R$^d$, wherein each occurrence of R$^a$, R$^b$, R$^d$, and R$^f$ is, independently, alkyl, haloalkyl, or aryl; or R$^a$ and R$^b$ together with the atoms to which they are attached form a heterocycloalkyl ring; or 2 instances of R$^d$ together with the atoms to which they are attached form a heterocycloalkyl ring; E is aryl; and G is heterocycloalkyl. In certain embodiments, $R^1$ is —(CH$_2$)$_n$NR$^a$C(O)R$^b$, —(CH$_2$)$_n$-E-NR$^d$SO$_2$R$^d$, or -G-SO$_2$R$^d$, wherein each occurrence of R$^a$, R$^b$, and R$^d$ is, independently, alkyl, haloalkyl, or aryl; or R$^a$ and R$^b$ together with the atoms to which they are attached form a heterocycloalkyl ring; or 2 instances of R$^d$ together with the atoms to which they are attached form a heterocycloalkyl ring; E is aryl; and G is heterocycloalkyl.

In certain embodiments, $R^1$ is —(CR$^h$R$^i$)$_n$-G-SO$_2$R$^d$, —(CR$^h$R$^i$)$_n$-E-NR$^d$SO$_2$R$^d$, or —(CR$^h$R$^i$)$_n$-E-NR$^a$C(O)R$^b$. In certain embodiments, $R^1$ is —(CH$_2$)$_n$-G-SO$_2$R$^d$, —(CH$_2$)$_n$-E-NR$^d$SO$_2$R$^d$, or —(CH$_2$)$_n$-E-NR$^a$C(O)R$^b$. In certain embodiments, $R^1$ is —(CH$_2$)$_n$NR$^a$C(O)R$^b$, or —(CH$_2$)$_n$NR$^a$SO$_2$R$^d$, wherein each occurrence of R$^a$, R$^b$, and R$^d$ is, independently, alkyl, haloalkyl, or aryl; or R$^a$ and R$^b$ together with the atoms to which they are attached form a heterocycloalkyl ring; or 2 instances of R$^d$ together with the atoms to which they are attached form a heterocycloalkyl ring.

In certain embodiments, $R^1$ is hydrogen, alkyl, haloalkyl, or —CH$_2$OR$^f$, wherein each $R^1$ is optionally substituted with 1-3 independent substituents $R^5$. In certain embodiments, $R^1$ is hydrogen, alkyl, haloalkyl, or —CH$_2$OR$^f$; and R$^f$ is alkyl, haloalkyl, cycloalkyl, or aryl.

In certain embodiments, $R^1$ is alkyl, haloalkyl, or —CH$_2$OR$^f$, wherein each $R^1$ is optionally substituted with 1-3 independent substituents $R^5$. In certain embodiments, $R^1$ is alkyl, haloalkyl, or —CH$_2$OR$^f$; and R$^f$ is alkyl, haloalkyl, cycloalkyl, or aryl.

In certain embodiments, $R^1$ is alkyl optionally substituted with 1-3 independent substituents $R^5$. In certain embodiments, $R^1$ is C$_{1-6}$ alkyl optionally substituted with 1-3 independent substituents $R^5$. In certain embodiments, $R^1$ is C$_{1-4}$ alkyl optionally substituted with 1-3 independent substituents $R^5$. In certain embodiments, $R^1$ is methyl, ethyl, propyl, butyl, isopropyl, or isobutyl. In certain embodiments, $R^1$ is methyl. In certain embodiments, $R^1$ is ethyl.

In certain embodiments, $R^1$ is —CH$_2$OR$^f$. In certain embodiments, $R^1$ is —CH$_2$OR$^f$; and R$^f$ is hydrogen, alkyl, haloalkyl, arylalkyl, or aryl. In certain embodiments, $R^1$ is —CH$_2$OH, —CH$_2$O CH$_2$Ph, —CH$_2$O-cyclopropyl, —CH$_2$OCH$_2$CF$_3$, or —CH$_2$OCH$_3$.

In certain embodiments, $R^1$ is haloalkyl. In certain embodiments, $R^1$ is C$_{1-6}$ haloalkyl. In certain embodiments, $R^1$ is C$_{1-3}$ haloalkyl. In certain embodiments, $R^1$ is —CH$_2$F, —CF$_2$H, —CF$_3$, or —CH$_2$CF$_3$. In certain embodiments, $R^1$ is —CF$_3$ or —CH$_2$CF$_3$.

In certain embodiments, $R^1$ is —(CR$^h$R$^i$)$_n$-E-NR$^a$C(O)R$^b$. In certain embodiments, $R^1$ is —(CR$^h$R$^i$)$_n$-E-NR$^a$C(O)R$^b$; and E is a bond, aryl, or heteroaryl. In certain embodiments, $R^1$ is —(CR$^h$R$^i$)$_n$NR$^a$C(O)R$^b$. In certain embodiments, $R^1$ is —(CR$^h$R$^i$)$_n$NR$^a$C(O)R$^b$; each occurrence of R$^h$ and R$^i$ is, independently, hydrogen, halogen, haloalkyl, or alkyl; and each occurrence of R$^a$ and R$^b$ is, independently, hydrogen, aryl, heteroaryl, cycloalkyl, haloalkyl, or alkyl; or R$^a$ and R$^b$ together with the atoms to which they are attached form a heterocycloalkyl ring. In certain embodiments, $R^1$ is —(CH$_2$)$_n$NR$^a$C(O)R$^b$. In certain embodiments, $R^1$ is —(CH$_2$)$_n$NR$^a$C(O)R$^b$; and each occurrence of R$^a$ and R$^b$ is, independently, hydrogen, aryl, heteroaryl, cycloalkyl, haloalkyl, or alkyl; or R$^a$ and R$^b$ together with the atoms to which they are attached form a heterocycloalkyl ring. In certain embodiments, $R^1$ is —(CH$_2$)$_n$NHC(O)R$^b$. In certain embodiments, $R^1$ is —(CH$_2$)$_n$NHC(O)R$^b$; and R$^b$ is aryl, heteroaryl, cycloalkyl, haloalkyl, or alkyl. In certain embodiments, $R^1$ is —(CH$_2$)$_n$NHC(O)R$^b$; and R$^b$ is cycloalkyl, haloalkyl, or alkyl. In certain embodiments, $R^1$ is —CH$_2$NHC(O)R$^b$; and R$^b$ is cycloalkyl, haloalkyl, or alkyl. In certain embodiments, $R^1$ is —CH$_2$NHC(O)CF$_3$, —CH$_2$NHC(O)-cyclopropyl, —CH$_2$N(CH$_3$)C(O)-cyclopropyl, —CH$_2$NHC(O)CH$_3$, or —CH$_2$N(CH$_2$CF$_3$)C(O)CH$_3$.

In certain embodiments, $R^1$ is —(CR$^h$R$^i$)$_n$-G-SO$_2$R$^d$. In certain embodiments, $R^1$ is —(CR$^h$R$^i$)$_n$-G-SO$_2$R$^d$; G is heterocycloalkyl or heteroaryl; each occurrence of R$^h$ and R$^i$ is, independently, hydrogen, halogen, haloalkyl, or alkyl; and R$^d$ is aryl, heteroaryl, cycloalkyl, haloalkyl, or alkyl. In certain embodiments, $R^1$ is —(CH$_2$)$_n$-G-SO$_2$R$^d$. In certain embodiments, $R^1$ is —(CH$_2$)$_n$-G-SO$_2$R$^d$; G is heterocycloalkyl or heteroaryl; and R$^d$ is hydrogen, aryl, heteroaryl, cycloalkyl, haloalkyl, or alkyl. In certain embodiments, $R^1$ is -G-SO$_2$R$^d$. In certain embodiments, $R^1$ is -G-SO$_2$R$^d$; G is heterocycloalkyl; and R$^d$ is, independently, aryl, heteroaryl, cycloalkyl, haloalkyl, or alkyl. In certain embodiments, $R^1$ is -G-SO$_2$R$^d$; G is azepanyl, piperidinyl, pyrrolidinyl, azetidinyl, or aziridinyl; and R$^d$ is, independently, aryl, heteroaryl, cycloalkyl, haloalkyl, or alkyl. In certain embodiments, $R^1$ is —(CH$_2$)$_n$SO$_2$R$^d$. In certain embodiments, $R^1$ is —(CH$_2$)$_n$SO$_2$R$^d$, wherein R$^d$ is alkyl or haloalkyl. In certain embodiments, $R^1$ is —(CH$_2$)$_n$SO$_2$R$^d$, wherein R$^d$ is alkyl. In certain embodiments, $R^1$ is —CH$_2$SO$_2$Me.

In certain embodiments, $R^1$ is —(CR$^h$R$^i$)$_n$-E-NR$^d$SO$_2$R$^d$. In certain embodiments, $R^1$ is —(CR$^h$R$^i$)$_n$-E-NR$^d$SO$_2$R$^d$; E is a bond, aryl, or heteroaryl; each occurrence of R$^h$ and R$^i$ is, independently, hydrogen, halogen, haloalkyl, or alkyl; and each occurrence of R$^d$ is, independently, hydrogen, aryl, heteroaryl, cycloalkyl, haloalkyl, or alkyl; or 2 instances of R$^d$ together with the atoms to which they are attached form a heterocycloalkyl ring. In certain embodiments, $R^1$ is —(CR$^h$R$^i$)$_n$NR$^d$SO$_2$R$^d$. In certain embodiments, $R^1$ is —(CR$^h$R$^i$)$_n$NR$^d$SO$_2$R$^d$; each occurrence of R$^h$ and R$^i$ is, independently, hydrogen, halogen, haloalkyl, or alkyl; and each occurrence of R$^d$ is, independently, hydrogen, aryl, heteroaryl, cycloalkyl, haloalkyl, or alkyl; or 2 instances of R$^d$ together with the atoms to which they are attached form a heterocycloalkyl ring. In certain embodiments, $R^1$ is —(CH$_2$)$_n$-E-NR$^d$SO$_2$R$^d$. In certain embodiments, $R^1$ is —(CH$_2$)$_n$-E-NR$^d$SO$_2$R$^d$; E is a bond or aryl; and each occurrence of R$^d$ is, independently, hydrogen, aryl, heteroaryl, cycloalkyl, haloalkyl, or alkyl; or 2 instances of R$^d$ together with the atoms to which they are attached form a heterocycloalkyl ring. In certain embodiments, $R^1$ is —(CH$_2$)$_n$NR$^d$SO$_2$R$^d$. In certain embodiments, $R^1$ is —(CH$_2$)$_n$NR$^d$SO$_2$R$^d$; and each occurrence of R$^d$ is, independently, hydrogen, aryl, heteroaryl, cycloalkyl, haloalkyl, or alkyl; or 2 instances of R$^d$ together with the atoms to which they are attached form a heterocycloalkyl ring. In certain embodiments, $R^1$ is —(CH$_2$)$_n$NHSO$_2$R$^d$. In certain embodiments, $R^1$ is —(CH$_2$)$_n$NHSO$_2$R$^d$, wherein R$^d$ is aryl, heteroaryl, cycloalkyl, haloalkyl, or alkyl. In certain embodiments, $R^1$ is —CH$_2$NHSO$_2$R$^d$, wherein R$^d$ is aryl or alkyl.

In certain embodiments, $R^1$ is —CH$_2$CH$_2$NHSO$_2$Me, —CH(CH$_3$)NHSO$_2$Me, —CH$_2$NHSO$_2$Me, —CH$_2$NMeSO$_2$Me, —CH$_2$NHSO$_2$Et, —CH$_2$NHSO$_2$Pr, —CH$_2$NHSO$_2$iPr, —CH$_2$NHSO$_2$iBu, —CH$_2$NHSO$_2$CH$_2$CF$_3$, —CH$_2$N(CH$_3$)SO$_2$Et, —CH$_2$N (CH₂CF₃)SO₂CH₃, —CH₂N(CH₂CF₃)SO₂Et, —CH₂N(CH₃)SO₂-cyclopropyl, —CH₂N(CH₂CF₃)SO₂-cyclopropyl, —CH₂NHSO₂-cyclopropyl, —CH₂NHSO₂Ph,

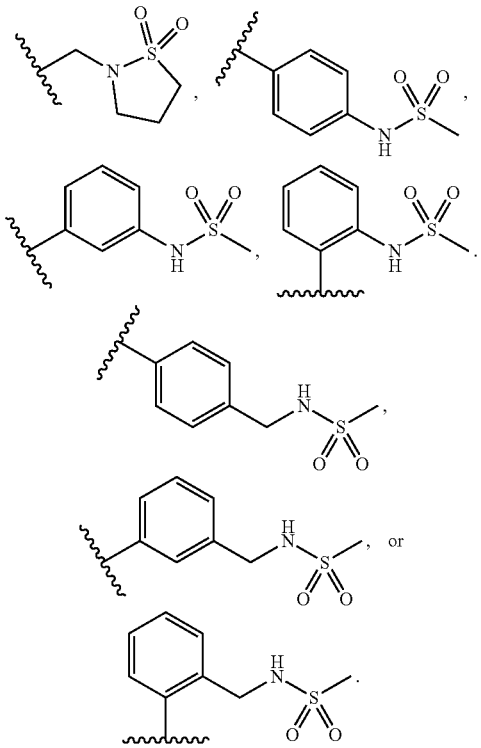

In certain embodiments, R¹ is —CH₂CH₂NHSO₂Me, —CH(CH₃)NHSO₂Me, —CH₂NHSO₂Me, —CH₂NMeSO₂Me, —CH₂NHSO₂Et, —CH₂NHSO₂Pr, —CH₂NHSO₂iPr, —CH₂NHSO₂iBu, —CH₂NHSO₂CH₂CF₃, CH₂N(CH₂CF₃)SO₂CH₃, —CH₂NHSO₂-cyclopropyl, —CH₂NHSO₂Ph, or

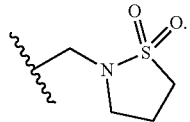 [SMILES: *CN1CCCS1(=O)=O]

In certain embodiments, R¹ is —CH₂NHSO₂Me, —CH₂NMeSO₂Me, —CH₂NHSO₂Et, —CH₂NHSO₂Pr, —CH₂NHSO₂iPr, —CH₂NHSO₂iBu, —CH₂NHSO₂-cyclopropyl, or —CH₂NHSO₂Ph.

In certain embodiments, R¹ is heteroarylalkyl or heterocycloalkylalkyl, wherein each R¹ is optionally substituted with 1-3 independent substituents R⁵. In certain embodiments, R¹ is heteroarylalkyl optionally substituted with 1-3 independent substituents R⁵. In certain embodiments, R¹ is heterocycloalkylalkyl optionally substituted with 1-3 independent substituents R⁵. In certain embodiments, R¹ is 5-membered heteroarylalkyl or 5-membered heterocycloalkylalkyl, wherein each R¹ is optionally substituted with 1-3 independent substituents R⁵. In certain embodiments, R¹ is 5-membered heteroarylalkyl optionally substituted with 1-3 independent substituents R⁵. In certain embodiments, R¹ is 5-membered heterocycloalkylalkyl optionally substituted with 1-3 independent substituents R⁵. In certain embodiments, R¹ is pyrrolylmethyl, imidazolylmethyl, pyrazolylmethyl, or pyrrolidin-2-onylmethyl, wherein each R¹ is optionally substituted with 1-3 independent substituents R⁵. In certain embodiments, R¹ is pyrrolylmethyl, imidazolylmethyl, or pyrazolylmethyl, wherein each R¹ is optionally substituted with 1-3 independent substituents R⁵.

In certain embodiments, R¹ is hydrogen, methyl, ethyl, propyl, isopropyl, phenyl, —CH₂CF₃, trifluoromethyl, —CH₂OCH₃, —CH₂OPh, —C(O)-morpholinyl, —CH₂NHC(O)CF₃, —C(O)NHPh, —CH₂NHSO₂Me, —CH₂NMeSO₂Me, —CH₂NHSO₂Et, —CH₂NHSO₂Pr, —CH₂NHSO₂iPr, —CH₂NHSO₂iBu, —CH₂NHSO₂-cyclopropyl, or —CH₂NHSO₂Ph.

In certain embodiments, R¹ and A together with the atoms to which they are attached form a heterocycloalkyl ring or fused bicyclic ring. In certain embodiments, R¹ and A together with the atoms to which they are attached form a heterocycloalkyl ring or fused bicyclic ring; and R² is hydrogen.

In certain embodiments, R¹ and A together with the atoms to which they are attached form a heterocycloalkyl ring. In certain embodiments, R¹ and A together with the atoms to which they are attached form a heterocycloalkyl ring; and R² is hydrogen. In certain embodiments, R¹ and A together with the atoms to which they are attached form a pyrrolidinyl, piperidinyl, tetrahydrofuranyl, or tetrahydropyranyl ring. In certain embodiments, R¹ and A together with the atoms to which they are attached form a pyrrolidinyl, piperidinyl, tetrahydrofuranyl, or tetrahydropyranyl ring; and R² is hydrogen.

In certain embodiments, R¹ and A together with the atoms to which they are attached form a fused bicyclic ring. In certain embodiments, R¹ and A together with the atoms to which they are attached form a fused bicyclic ring; and R² is hydrogen. In certain embodiments, R¹ and A together with the atoms to which they are attached form an indanyl or tetrahydronaphthalenyl ring. In certain embodiments, R¹ and A together with the atoms to which they are attached form an indanyl or tetrahydronaphthalenyl ring; and R² is hydrogen.

In certain embodiments, R² is hydrogen, cyano, alkyl, alkenyl, alkynyl, cycloalkyl, aryl, heteroaryl, heterocycloalkyl, —(CRʰRⁱ)ₙ-E-NRᵃC(O)Rᵇ, —C(O)NRᵃRᵇ, —(CRʰRⁱ)ₙ-E-NRᵈSO₂Rᵈ, —(CRʰRⁱ)ₙ-G-SO₂Rᵈ, —CO₂Rᵉ, —CORᶠ, or —CH₂ORᶠ, wherein each R² is optionally substituted with 1-3 independent substituents R⁵.

In certain embodiments, R² is hydrogen, alkyl, haloalkyl, aryl, cycloalkyl, —CH₂ORᶠ, —(CRʰRⁱ)ₙ-E-NRᵃC(O)Rᵇ, —C(O)NRᵃRᵇ, —(CRʰRⁱ)ₙ-E-NRᵈSO₂Rᵈ, or —(CRʰRⁱ)ₙ-G-SO₂Rᵈ, wherein each R² is optionally substituted with 1-3 independent substituents R⁵. In certain embodiments, R² is hydrogen, alkyl, haloalkyl, aryl, cycloalkyl, —CH₂ORᶠ, —(CH₂)ₙNRᵃC(O)Rᵇ, —C(O)NRᵃRᵇ, —(CH₂)ₙNRᵈSO₂Rᵈ, or -G-SO₂Rᵈ, wherein each R² is optionally substituted with 1-3 independent substituents R⁵. In certain embodiments, R² is hydrogen, alkyl, haloalkyl, aryl, cycloalkyl, —CH₂ORᶠ, —(CH₂)ₙNRᵃC(O)Rᵇ, —C(O)NRᵃRᵇ, —(CH₂)ₙ-E-NRᵈSO₂Rᵈ, or -G-SO₂Rᵈ, wherein each R² is optionally substituted with 1-3 independent substituents R⁵; wherein each occurrence of Rᵃ, Rᵇ, Rᵈ, and Rᶠ is, independently, alkyl, haloalkyl, or aryl; or Rᵃ and Rᵇ together with the atoms to which they are attached form a heterocycloalkyl ring; or 2 instances of Rᵈ together with the atoms to which they are attached form a heterocycloalkyl ring; E is aryl; and G is heterocycloalkyl. In certain embodiments, R² is —CH₂ORᶠ, —(CH₂)ₙNRᵃC(O)Rᵇ, —C(O)NRᵃRᵇ, —(CH₂)ₙ-E-NRᵈSO₂Rᵈ, or -G-SO₂Rᵈ, wherein each occurrence of $R^a$, $R^b$, $R^d$, and $R^f$ is, independently, alkyl, haloalkyl, or aryl; or $R^a$ and $R^b$ together with the atoms to which they are attached form a heterocycloalkyl ring; or 2 instances of $R^d$ together with the atoms to which they are attached form a heterocycloalkyl ring; E is aryl; and G is heterocycloalkyl. In certain embodiments, $R^2$ is —(CH$_2$)$_n$NR$^a$C(O)R$^b$, —(CH$_2$)$_n$-E-NR$^d$SO$_2$R$^d$, or -G-SO$_2$R$^d$, wherein each occurrence of $R^a$, $R^b$, and $R^d$ is, independently, alkyl, haloalkyl, or aryl; or $R^a$ and $R^b$ together with the atoms to which they are attached form a heterocycloalkyl ring; or 2 instances of $R^d$ together with the atoms to which they are attached form a heterocycloalkyl ring; E is aryl; and G is heterocycloalkyl.

In certain embodiments, $R^2$ is —(CR$^h$R$^i$)$_n$-G-SO$_2$R$^d$, —(CR$^h$R$^i$)$_n$-E-NR$^d$SO$_2$R$^d$, or —(CR$^h$R$^i$)$_n$-E-NR$^a$C(O)R$^b$. In certain embodiments, $R^2$ is —(CH$_2$)$_n$-G-SO$_2$R$^d$, —(CH$_2$)$_n$-E-NR$^d$SO$_2$R$^d$, or —(CH$_2$)$_n$-E-NR$^a$C(O)R$^b$. In certain embodiments, $R^2$ is —(CH$_2$)$_n$NR$^a$C(O)R$^b$ or —(CH$_2$)$_n$NR$^a$SO$_2$R$^d$, wherein each occurrence of $R^a$, $R^b$, and $R^d$ is, independently, alkyl, haloalkyl, or aryl; or $R^a$ and $R^b$ together with the atoms to which they are attached form a heterocycloalkyl ring; or 2 instances of $R^d$ together with the atoms to which they are attached form a heterocycloalkyl ring.

In certain embodiments, $R^2$ is hydrogen, alkyl, haloalkyl, or —CH$_2$OR$^f$, wherein each $R^2$ is optionally substituted with 1-3 independent substituents $R^5$. In certain embodiments, $R^2$ is hydrogen, alkyl, haloalkyl, or —CH$_2$OR$^f$; and $R^f$ is alkyl, haloalkyl, or aryl.

In certain embodiments, $R^2$ is alkyl, haloalkyl, or —CH$_2$OR$^f$, wherein each $R^2$ is optionally substituted with 1-3 independent substituents $R^5$. In certain embodiments, $R^2$ is alkyl, haloalkyl, or —CH$_2$OR$^f$; and $R^f$ is alkyl, haloalkyl, or aryl.

In certain embodiments, $R^2$ is alkyl optionally substituted with 1-3 independent substituents $R^5$. In certain embodiments, $R^2$ is $C_{1-6}$ alkyl optionally substituted with 1-3 independent substituents $R^5$. In certain embodiments, $R^2$ is $C_{1-4}$ alkyl optionally substituted with 1-3 independent substituents $R^5$. In certain embodiments, $R^2$ is methyl, ethyl, propyl, butyl, isopropyl, or isobutyl. In certain embodiments, $R^2$ is methyl. In certain embodiments, $R^2$ is ethyl.

In certain embodiments, $R^2$ is —CH$_2$OR$^f$. In certain embodiments, $R^2$ is —CH$_2$OR$^f$; and $R^f$ is hydrogen, alkyl, haloalkyl, arylalkyl, or aryl. In certain embodiments, $R^2$ is —CH$_2$OH, —CH$_2$O CH$_2$Ph, —CH$_2$O-cyclopropyl, —CH$_2$OCH$_2$CF$_3$, or —CH$_2$OCH$_3$.

In certain embodiments, $R^2$ is haloalkyl. In certain embodiments, $R^2$ is $C_{1-6}$ haloalkyl. In certain embodiments, $R^2$ is $C_{1-3}$ haloalkyl. In certain embodiments, $R^2$ is —CH$_2$F, —CF$_2$H, —CF$_3$, or —CH$_2$CF$_3$. In certain embodiments, $R^2$ is —CF$_3$ or —CH$_2$CF$_3$.

In certain embodiments, $R^2$ is —(CR$^h$R$^i$)$_n$-E-NR$^a$C(O)R$^b$. In certain embodiments, $R^2$ is —(CR$^h$R$^i$)$_n$-E-NR$^a$C(O)R$^b$; and E is a bond, aryl, or heteroaryl. In certain embodiments, $R^2$ is —(CR$^h$R$^i$)$_n$NR$^a$C(O)R$^b$. In certain embodiments, $R^2$ is —(CR$^h$R$^i$)$_n$NR$^a$C(O)R$^b$; each occurrence of $R^h$ and $R^i$ is, independently, hydrogen, halogen, haloalkyl, or alkyl; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring. In certain embodiments, $R^2$ is —(CH$_2$)$_n$NR$^a$C(O)R$^b$. In certain embodiments, $R^2$ is —(CH$_2$)$_n$NR$^a$C(O)R$^b$; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring. In certain embodiments, $R^2$ is —(CH$_2$)$_n$NHC(O)R$^b$. In certain embodiments, $R^2$ is —(CH$_2$)$_n$NHC(O)R$^b$; and $R^b$ is aryl, heteroaryl, cycloalkyl, haloalkyl, or alkyl. In certain embodiments, $R^2$ is —(CH$_2$)$_n$NHC(O)R$^b$; and $R^b$ is haloalkyl or alkyl. In certain embodiments, $R^2$ is —CH$_2$NHC(O)R$^b$; and $R^b$ is haloalkyl or alkyl. In certain embodiments, $R^2$ is —CH$_2$NHC(O)CF$_3$, —CH$_2$NHC(O)-cyclopropyl, —CH$_2$N(CH$_3$)C(O)-cyclopropyl, —CH$_2$NHC(O)CH$_3$, or —CH$_2$N(CH$_2$CF$_3$)C(O)CH$_3$.

In certain embodiments, $R^2$ is —(CR$^h$R$^i$)$_n$-G-SO$_2$R$^d$. In certain embodiments, $R^2$ is —(CR$^h$R$^i$)$_n$-G-SO$_2$R$^d$; G is heterocycloalkyl or heteroaryl; each occurrence of $R^h$ and $R^i$ is, independently, hydrogen, halogen, haloalkyl, or alkyl; and $R^d$ is aryl, heteroaryl, cycloalkyl, haloalkyl, or alkyl. In certain embodiments, $R^2$ is —(CH$_2$)$_n$-G-SO$_2$R$^d$. In certain embodiments, $R^2$ is —(CH$_2$)$_n$-G-SO$_2$R$^d$; G is heterocycloalkyl or heteroaryl; and $R^d$ is hydrogen, aryl, heteroaryl, cycloalkyl, haloalkyl, or alkyl. In certain embodiments, $R^2$ is -G-SO$_2$R$^d$. In certain embodiments, $R^2$ is -G-SO$_2$R$^d$; G is heterocycloalkyl; and $R^d$ is, independently, aryl, heteroaryl, cycloalkyl, haloalkyl, or alkyl. In certain embodiments, $R^2$ is -G-SO$_2$R$^d$; G is azepanyl, piperidinyl, pyrrolidinyl, azetidinyl, or aziridinyl; and $R^d$ is, independently, aryl, heteroaryl, cycloalkyl, haloalkyl, or alkyl. In certain embodiments, $R^2$ is —(CH$_2$)$_n$SO$_2$R$^d$. In certain embodiments, $R^2$ is —(CH$_2$)$_n$SO$_2$R$^d$, wherein $R^d$ is alkyl or haloalkyl. In certain embodiments, $R^2$ is —(CH$_2$)$_n$SO$_2$R$^d$, wherein $R^d$ is alkyl. In certain embodiments, $R^2$ is —CH$_2$SO$_2$Me.

In certain embodiments, $R^2$ is —(CR$^h$R$^i$)$_n$-E-NR$^d$SO$_2$R$^d$. In certain embodiments, $R^2$ is —(CR$^h$R$^i$)$_n$-E-NR$^d$SO$_2$R$^d$; E is a bond, aryl, or heteroaryl; each occurrence of $R^h$ and $R^i$ is, independently, hydrogen, halogen, haloalkyl, or alkyl; and each occurrence of $R^d$ is, independently, hydrogen, aryl, heteroaryl, cycloalkyl, haloalkyl, or alkyl; or 2 instances of $R^d$ together with the atoms to which they are attached form a heterocycloalkyl ring. In certain embodiments, $R^2$ is —(CR$^h$R$^i$)$_n$NR$^d$SO$_2$R$^d$. In certain embodiments, $R^2$ is —(CR$^h$R$^i$)$_n$NR$^d$SO$_2$R$^d$;

each occurrence of $R^h$ and $R^i$ is, independently, hydrogen, halogen, haloalkyl, or alkyl; and each occurrence of $R^d$ is, independently, hydrogen, aryl, heteroaryl, cycloalkyl, haloalkyl, or alkyl; or 2 instances of $R^d$ together with the atoms to which they are attached form a heterocycloalkyl ring.

In certain embodiments, $R^2$ is —(CH$_2$)$_n$-E-NR$^d$SO$_2$R$^d$. In certain embodiments, $R^2$ is —(CH$_2$)$_n$-E-NR$^d$SO$_2$R$^d$; E is a bond or aryl; and each occurrence of $R^d$ is, independently, hydrogen, aryl, heteroaryl, cycloalkyl, haloalkyl, or alkyl; or 2 instances of $R^d$ together with the atoms to which they are attached form a heterocycloalkyl ring. In certain embodiments, $R^2$ is —(CH$_2$)$_n$NR$^d$SO$_2$R$^d$. In certain embodiments, $R^2$ is —(CH$_2$)$_n$NR$^d$SO$_2$R$^d$; and each occurrence of $R^d$ is, independently, hydrogen, aryl, heteroaryl, cycloalkyl, haloalkyl, or alkyl; or 2 instances of $R^d$ together with the atoms to which they are attached form a heterocycloalkyl ring. In certain embodiments, $R^2$ is —(CH$_2$)$_n$NHSO$_2$R$^d$. In certain embodiments, $R^2$ is —(CH$_2$)$_n$NHSO$_2$R$^d$, wherein $R^d$ is aryl, heteroaryl, cycloalkyl, haloalkyl, or alkyl. In certain embodiments, $R^2$ is —CH$_2$NHSO$_2$R$^d$, wherein $R^d$ is aryl or alkyl.

In certain embodiments, $R^2$ is —CH$_2$CH$_2$NHSO$_2$Me, —CH(CH$_3$)NHSO$_2$Me, —CH$_2$NHSO$_2$Me, —CH$_2$NMeSO$_2$Me, —CH$_2$NHSO$_2$Et, —CH$_2$NHSO$_2$Pr, —CH$_2$NHSO$_2$iPr, —CH$_2$NHSO$_2$iBu, —CH$_2$NHSO$_2$CH$_2$CF$_3$, —CH$_2$N(CH$_3$)SO$_2$Et, —CH$_2$N(CH$_2$CF$_3$)SO$_2$CH$_3$, —CH$_2$N(CH$_2$CF$_3$)SO$_2$Et, —CH$_2$N (CH₃)SO₂-cyclopropyl, —CH₂N(CH₂CF₃)SO₂-cyclopropyl, —CH₂NHSO₂-cyclopropyl, —CH₂NHSO₂Ph,

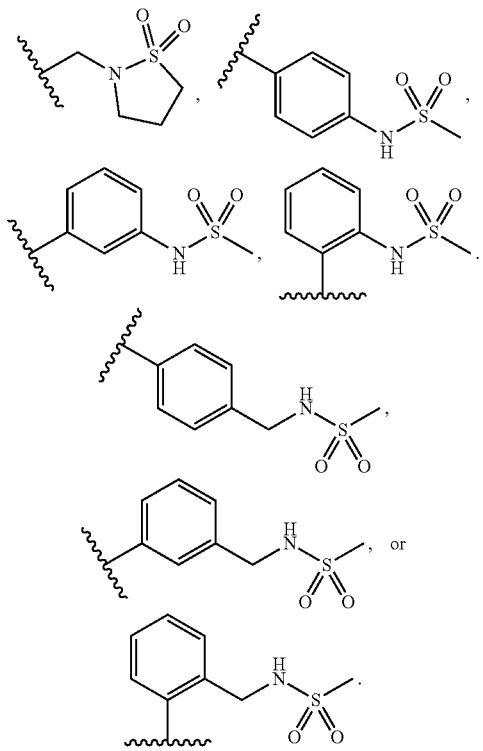

In certain embodiments, R² is —CH₂CH₂NHSO₂Me, —CH(CH₃)NHSO₂Me, —CH₂NHSO₂Me, —CH₂NMeSO₂Me, —CH₂NHSO₂Et, —CH₂NHSO₂Pr, —CH₂NHSO₂iPr, —CH₂NHSO₂iBu, —CH₂NHSO₂CH₂CF₃, CH₂N(CH₂CF₃)SO₂CH₃, —CH₂NHSO₂-cyclopropyl, —CH₂NHSO₂Ph, or

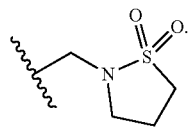 [SMILES: *CN1CCCS1(=O)=O]

In certain embodiments, R² is —CH₂NHSO₂Me, —CH₂NMeSO₂Me, —CH₂NHSO₂Et, —CH₂NHSO₂Pr, —CH₂NHSO₂iPr, —CH₂NHSO₂iBu, —CH₂NHSO₂-cyclopropyl, or —CH₂NHSO₂Ph.

In certain embodiments, R² is hydrogen, methyl, ethyl, propyl, isopropyl, phenyl, —CH₂CF₃, trifluoromethyl, —CH₂OCH₃, —CH₂OPh, —C(O)-morpholinyl, —CH₂NHC(O)CF₃, —C(O)NHPh, —CH₂NHSO₂Me, —CH₂NMeSO₂Me, —CH₂NHSO₂Et, —CH₂NHSO₂Pr, —CH₂NHSO₂iPr, —CH₂NHSO₂iBu, —CH₂NHSO₂-cyclopropyl, or —CH₂NHSO₂Ph. In certain embodiments, R² is hydrogen.

In certain embodiments, each of R¹ and R² is, independently, hydrogen, cyano, alkyl, alkenyl, alkynyl, cycloalkyl, aryl, heteroaryl, heterocycloalkyl, heteroarylalkyl, heterocycloalkylalkyl, —(CRʰRⁱ)ₙ-E-NRᵃC(O)Rᵇ, —C(O)NRᵃRᵇ, —(CRʰRⁱ)ₙ-E-NRᵈSO₂Rᵈ, —(CRʰRⁱ)ₙ-G-SO₂Rᵈ, —CO₂Rᵉ, —CORᶠ, or —CH₂ORᶠ, wherein each R¹ and R² is optionally substituted with 1-3 independent substituents R⁵.

In certain embodiments, each of R¹ and R² is, independently, hydrogen, alkyl, haloalkyl, aryl, cycloalkyl, —(CRʰRⁱ)ₙ-E-NRᵃC(O)Rᵇ, —C(O)NRᵃRᵇ, —(CRʰRⁱ)ₙ-E-NRᵈSO₂Rᵈ, —(CRʰRⁱ)ₙ-G-SO₂Rᵈ, or —CH₂ORᶠ, wherein each R¹ and R² is optionally substituted with 1-3 independent substituents R⁵. In certain embodiments, each of R¹ and R² is, independently, hydrogen, alkyl, haloalkyl, aryl, cycloalkyl, —CH₂ORᶠ, —C(O)NRᵃRᵇ, —CH₂NRᵃC(O)Rᵇ, or —(CRʰRⁱ)ₙ-E-NRᵈSO₂Rᵈ, wherein each R¹ and R² is optionally substituted with 1-3 independent substituents R⁵. In certain embodiments, each of R¹ and R² is, independently, hydrogen, alkyl, haloalkyl, aryl, cycloalkyl, —CH₂ORᶠ, —C(O)NRᵃRᵇ, or —CH₂NHSO₂Rᵈ, wherein each R¹ and R² is optionally substituted with 1-3 independent substituents R⁵. In certain embodiments, each of R¹ and R² is, independently, hydrogen, alkyl, haloalkyl, —CH₂ORᶠ, or —CH₂NHSO₂Rᵈ.

In certain embodiments, R¹ is cyano, alkyl, alkenyl, alkynyl, cycloalkyl, aryl, heteroaryl, heterocycloalkyl, heteroarylalkyl, heterocycloalkylalkyl, —(CRʰRⁱ)ₙ-E-NRᵃC(O)Rᵇ, —C(O)NRᵃRᵇ, —(CRʰRⁱ)ₙ-E-NRᵈSO₂Rᵈ, —(CRʰRⁱ)ₙ-G-SO₂Rᵈ, —CO₂Rᵉ, —CORᶠ, or —CH₂ORᶠ, wherein each R¹ is optionally substituted with 1-3 independent substituents R⁵; and R² is hydrogen.

In certain embodiments, R¹ is alkyl, haloalkyl, aryl, cycloalkyl, —(CRʰRⁱ)ₙ-E-NRᵃC(O)Rᵇ, —C(O)NRᵃRᵇ, —(CRʰRⁱ)ₙ-E-NRᵈSO₂Rᵈ, —(CRʰRⁱ)ₙ-G-SO₂Rᵈ, or —CH₂ORᶠ, wherein each R¹ is optionally substituted with 1-3 independent substituents R⁵; and R² is hydrogen. In certain embodiments, R¹ is alkyl, haloalkyl, aryl, cycloalkyl, —CH₂ORᶠ, —C(O)NRᵃRᵇ, or —(CRʰRⁱ)ₙ-E-NRᵈSO₂Rᵈ, wherein each R¹ is optionally substituted with 1-3 independent substituents R⁵; and R² is hydrogen. In certain embodiments, R¹ is alkyl, haloalkyl, aryl, cycloalkyl, —CH₂ORᶠ, —C(O)NRᵃRᵇ, or —CH₂NHSO₂Rᵈ, wherein each R¹ is optionally substituted with 1-3 independent substituents R⁵; and R² is hydrogen. In certain embodiments, R¹ is alkyl, haloalkyl, —CH₂ORᶠ, or —CH₂NHSO₂Rᵈ; and R² is hydrogen. In certain embodiments, R¹ is —CH₂ORᶠ, —(CH₂)ₙNRᵃC(O)Rᵇ, —C(O)NRᵃRᵇ, —(CH₂)ₙ-E-NRᵈSO₂Rᵈ, or -G-SO₂Rᵈ; and R² is hydrogen. In certain embodiments, R¹ is —(CRʰRⁱ)ₙ-E-NRᵃC(O)Rᵇ, —(CRʰRⁱ)ₙ-E-NRᵈSO₂Rᵈ, or —(CRʰRⁱ)ₙ-G-SO₂Rᵈ; and R² is hydrogen. In certain embodiments, R¹ is —(CH₂)ₙNRᵃC(O)Rᵇ, —(CH₂)ₙ-E-NRᵈSO₂Rᵈ, or -G-SO₂Rᵈ; and R² is hydrogen. In certain embodiments, R¹ is —(CRʰRⁱ)ₙ-E-NRᵈSO₂Rᵈ or —(CRʰRⁱ)ₙ-G-SO₂Rᵈ; and R² is hydrogen. In certain embodiments, each of R¹ is —CH₂ORᶠ or —CH₂NHSO₂Rᵈ; and R² is hydrogen. In certain embodiments, R¹ is —(CRʰRⁱ)ₙ-G-SO₂Rᵈ, —(CRʰRⁱ)ₙ-E-NRᵈSO₂Rᵈ, or —(CRʰRⁱ)ₙ-E-NRᵃC(O)Rᵇ; and R² is hydrogen. In certain embodiments, R¹ is —(CH₂)ₙ-G-SO₂Rᵈ, —(CH₂)ₙ-E-NRᵈSO₂Rᵈ, or —(CH₂)ₙ-E-NRᵃC(O)Rᵇ; and R² is hydrogen. In certain embodiments, R¹ is —(CH₂)ₙNRᵃC(O)Rᵇ or —(CH₂)ₙNRᵈSO₂Rᵈ; and R² is hydrogen, wherein each occurrence of Rᵃ, Rᵇ, and Rᵈ is, independently, alkyl, haloalkyl, or aryl; or Rᵃ and Rᵇ together with the atoms to which they are attached form a heterocycloalkyl ring; or 2 instances of Rᵈ together with the atoms to which they are attached form a heterocycloalkyl ring.

In certain embodiments, R¹ is alkyl, haloalkyl, or —CH₂ORᶠ; and R² is hydrogen. In certain embodiments, R² is alkyl, haloalkyl, or —CH₂ORᶠ; and R² is hydrogen.

In certain embodiments, R¹ is methyl, haloalkyl, or —CH₂ORᶠ; and R² is hydrogen. In certain embodiments, R² is alkyl, haloalkyl, or —CH₂ORᶠ; and R² is hydrogen.

In certain embodiments, $R^1$ is methyl, ethyl, propyl, isopropyl, phenyl, —$CH_2CF_3$, trifluoromethyl, —$CH_2OCH_3$, —$CH_2OPh$, —C(O)-morpholinyl, —$CH_2NHC(O)CF_3$, —C(O)NHPh, —$CH_2NHSO_2Me$, —$CH_2NMeSO_2Me$, —$CH_2NHSO_2Et$, —$CH_2NHSO_2Pr$, —$CH_2NHSO_2iPr$, —$CH_2NHSO_2iBu$, —$CH_2NHSO_2$-cyclopropyl, or —$CH_2NHSO_2Ph$; and $R^2$ is hydrogen. In certain embodiments, $R^1$ is —$CH_2NHSO_2Me$, —$CH_2NMeSO_2Me$, —$CH_2NHSO_2Et$, —$CH_2NHSO_2Pr$, —$CH_2NHSO_2iPr$, —$CH_2NHSO_2iBu$, —$CH_2NHSO_2$-cyclopropyl, or —$CH_2NHSO_2Ph$; and $R^2$ is hydrogen. In certain embodiments, $R^1$ is hydrogen, methyl, ethyl, propyl, isopropyl, —$CH_2CF_3$, trifluoromethyl, —$CH_2OCH_3$, or —$CH_2OPh$; and $R^2$ is hydrogen.

In certain embodiments, $R^3$ is haloalkyl. In certain embodiments, $R^3$ is $C_{1-6}$ haloalkyl. In certain embodiments, $R^3$ is $C_{1-4}$ haloalkyl. In certain embodiments, $R^3$ is $C_{1-3}$ haloalkyl. In certain embodiments, $R^3$ is $Cl_2$ haloalkyl. In certain embodiments, $R^3$ is —$CF_3$, —$CHF_2$, or $CH_2F$.

In certain embodiments, the compound of Formula I is a compound of Formula I-a:

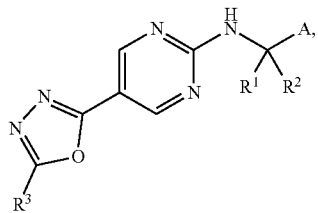

I-a or a pharmaceutically acceptable salt, co-crystal, tautomer, stereoisomer, solvate, hydrate, polymorph, isotopically enriched derivative, or prodrug thereof, wherein $R^1$, $R^2$, $R^3$, and A are as defined herein.

In certain embodiments of the compound of Formula I-a, A is aryl or heteroaryl, wherein each A is optionally substituted with 1-3 independent substituents $R^5$. In certain embodiments of the compound of Formula I-a, A is aryl optionally substituted with 1-3 independent substituents $R^5$. In certain embodiments of the compound of Formula I-a, A is phenyl optionally substituted with 1-3 independent substituents $R^5$. In certain embodiments of the compound of Formula I-a, A is phenyl substituted with 1-3 independent substituents $R^5$, wherein each occurrence of $R^5$ is, independently, halogen, cyano, alkyl, haloalkyl, or —$OR^f$; and $R^f$ is independently haloalkyl or alkyl.

In certain embodiments of the compound of Formula I-a, $R^1$ is alkyl, haloalkyl, or —$CH_2OR^f$; $R^f$ is aryl, alkyl, or haloalkyl; and $R^2$ is hydrogen.

In certain embodiments of the compound of Formula I-a, $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments of the compound of Formula I-a, $R^1$ is —$(CR^hR^i)_nNR^aC(O)R^b$; each occurrence of $R^h$ and $R^i$ is, independently, hydrogen, halogen, haloalkyl, or alkyl; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring; and $R^2$ is hydrogen.

In certain embodiments of the compound of Formula I-a, $R^3$ is haloalkyl.

In certain embodiments of the compound of Formula I-a, A is aryl or heteroaryl; $R^1$ is alkyl, haloalkyl, or —$CH_2OR^f$; $R^f$ is aryl, alkyl, or haloalkyl; $R^2$ is hydrogen; and $R^3$ is haloalkyl.

In certain embodiments of the compound of Formula I-a, A is aryl or heteroaryl, wherein each A is optionally substituted with 1-3 independent substituents $R^5$; $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; $R^2$ is hydrogen; and $R^3$ is haloalkyl.

In certain embodiments of the compound of Formula I-a, A is phenyl substituted with 1-3 independent substituents $R^5$, wherein each occurrence of $R^5$ is, independently, halogen, cyano, alkyl, haloalkyl, or —$OR^f$; $R^f$ is independently haloalkyl or alkyl; $R^1$ is alkyl, haloalkyl, or —$CH_2OR^f$; $R^f$ is aryl, alkyl, or haloalkyl; $R^2$ is hydrogen; and $R^3$ is haloalkyl.

In certain embodiments of the compound of Formula I-a, A is phenyl substituted with 1-3 independent substituents $R^5$, wherein each occurrence of $R^5$ is, independently, halogen, cyano, alkyl, haloalkyl, or —$OR^f$; $R^f$ is independently haloalkyl or alkyl; $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; $R^2$ is hydrogen; and $R^3$ is haloalkyl.

In certain embodiments, the compound of Formula I is a compound of Formula I-b:

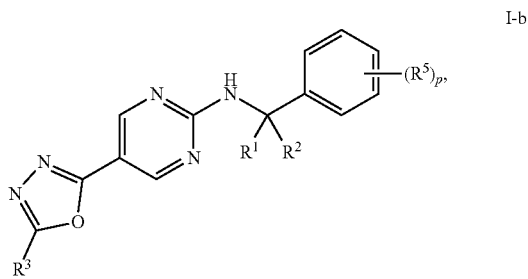

I-b or a pharmaceutically acceptable salt, co-crystal, tautomer, stereoisomer, solvate, hydrate, polymorph, isotopically enriched derivative, or prodrug thereof, wherein p is 0, 1, 2, or 3; and $R^1$, $R^2$, $R^3$, and $R^5$ are as defined herein.

In certain embodiments of the compound of Formula I-b, $R^1$ is alkyl, haloalkyl, or —$CH_2OR^f$; $R^f$ is aryl, alkyl, or haloalkyl; and $R^2$ is hydrogen.

In certain embodiments of the compound of Formula I-b, $R^1$ is —$(CR^hR^i)_nNR^aC(O)R^b$; each occurrence of $R^h$ and $R^i$ is, independently, hydrogen, halogen, haloalkyl, or alkyl; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring; and $R^2$ is hydrogen.

In certain embodiments of the compound of Formula I-b, $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments of the compound of Formula I-b, $R^3$ is haloalkyl.

In certain embodiments of the compound of Formula I-b, each $R^5$ is, independently, halogen, cyano, alkyl, haloalkyl, or —$OR^f$.

In certain embodiments of the compound of Formula I-b, $R^1$ is alkyl, haloalkyl, or —$CH_2OR^f$, wherein $R^f$ is aryl, alkyl, or haloalkyl; $R^2$ is hydrogen; $R^3$ is haloalkyl; and each $R^5$ is, independently, halogen, cyano, alkyl, haloalkyl, or —$OR^f$.

In certain embodiments of the compound of Formula I-b, $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; $R^2$ is hydrogen; $R^3$ is haloalkyl; and each $R^5$ is, independently, halogen, cyano, alkyl, haloalkyl, or —$OR^f$.

In certain embodiments, the compound of Formula I is a compound of Formula I-d:

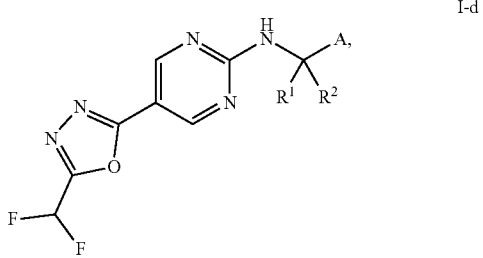

I-d or a pharmaceutically acceptable salt, co-crystal, tautomer, stereoisomer, solvate, hydrate, polymorph, isotopically enriched derivative, or prodrug thereof, wherein $R^1$, $R^2$, and A are as defined herein.

In certain embodiments of the compound of Formula I-d, A is aryl or heteroaryl, wherein each A is optionally substituted with 1-3 independent substituents $R^5$. In certain embodiments of the compound of Formula I-d, A is aryl optionally substituted with 1-3 independent substituents $R^5$. In certain embodiments of the compound of Formula I-d, A is phenyl optionally substituted with 1-3 independent substituents $R^5$. In certain embodiments of the compound of Formula I-d, A is phenyl substituted with 1-3 independent substituents $R^5$, wherein each occurrence of $R^5$ is, independently, halogen, cyano, alkyl, haloalkyl, or —$OR^f$; and $R^f$ is independently haloalkyl or alkyl.

In certain embodiments of the compound of Formula I-d, $R^1$ is alkyl, haloalkyl, or —$CH_2OR^f$, wherein $R^f$ is aryl, alkyl, or haloalkyl; and $R^2$ is hydrogen.

In certain embodiments of the compound of Formula I-d, $R^1$ is —$(CR^hR^i)_nNR^aC(O)R^b$; each occurrence of $R^h$ and $R^i$ is, independently, hydrogen, halogen, haloalkyl, or alkyl; and each occurrence of $R^a$ and $R^b$ is, independently, hydrogen, aryl, heteroaryl, cycloalkyl, haloalkyl, or alkyl; or $R^a$ and $R^b$ together with the atoms to which they are attached form a heterocycloalkyl ring; and $R^2$ is hydrogen.

In certain embodiments of the compound of Formula I-d, $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments of the compound of Formula I-d, A is aryl or heteroaryl, wherein each A is optionally substituted with 1-3 independent substituents $R^5$; $R^1$ is alkyl, haloalkyl, or —$CH_2OR^f$; $R^f$ is aryl, alkyl, or haloalkyl; and $R^2$ is hydrogen.

In certain embodiments of the compound of Formula I-d, A is aryl or heteroaryl, wherein each A is optionally substituted with 1-3 independent substituents $R^5$; $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments of the compound of Formula I-d, A is phenyl substituted with 1-3 independent substituents $R^5$, wherein each occurrence of $R^5$ is, independently, halogen, cyano, alkyl, haloalkyl, or —$OR^f$, wherein $R^f$ is independently haloalkyl or alkyl; $R^1$ is alkyl, haloalkyl, or —$CH_2OR^f$, wherein $R^f$ is aryl, alkyl, or haloalkyl; and $R^2$ is hydrogen.

In certain embodiments of the compound of Formula I-d, A is phenyl substituted with 1-3 independent substituents $R^5$, wherein each occurrence of $R^5$ is, independently, halogen, cyano, alkyl, haloalkyl, or —$OR^f$, wherein $R^f$ is independently haloalkyl or alkyl; $R^1$ is —$(CR^hR^i)_n$-E-$NR^dSO_2R^d$; E is a bond, aryl, or heteroaryl; each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; each occurrence of $R^h$ and $R^i$ is, independently, hydrogen, halogen, haloalkyl, or alkyl; and $R^2$ is hydrogen.

In certain embodiments, the compound of Formula I is a compound of Formula I-g:

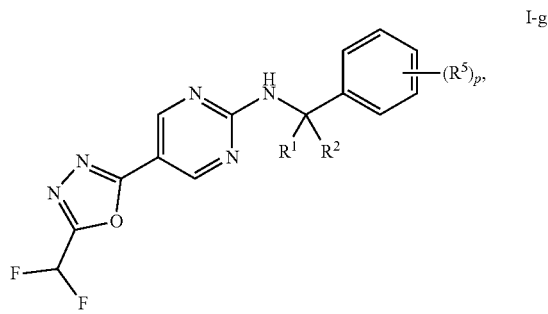

I-g or a pharmaceutically acceptable salt, co-crystal, tautomer, stereoisomer, solvate, hydrate, polymorph, isotopically enriched derivative, or prodrug thereof, wherein p is 0, 1, 2, or 3; and $R^1$, $R^2$, and $R^5$ are as defined herein.

In certain embodiments of the compound of Formula I-g, $R^1$ is alkyl, haloalkyl, or —CH$_2$OR$^f$; R$^f$ is aryl, alkyl, or haloalkyl; and $R^2$ is hydrogen.

In certain embodiments of the compound of Formula I-g, $R^1$ is —(CR$^h$R$^i$)$_n$NR$^a$C(O)R$^b$; each occurrence of R$^h$ and R$^i$ is, independently, hydrogen, halogen, haloalkyl, or alkyl; and each occurrence of R$^a$ and R$^b$ is, independently, hydrogen, aryl, heteroaryl, cycloalkyl, haloalkyl, or alkyl; or R$^a$ and R$^b$ together with the atoms to which they are attached form a heterocycloalkyl ring; and $R^2$ is hydrogen.

In certain embodiments of the compound of Formula I-g, $R^1$ is —(CR$^h$R$^i$)$_n$-E-NR$^d$SO$_2$R$^d$; E is a bond, aryl, or heteroaryl; each occurrence of R$^d$ is, independently, hydrogen, alkyl, haloalkyl, cycloalkyl, aryl, or heteroaryl; or 2 instances of R$^d$ together with the atoms to which they are attached form a heterocycloalkyl ring; each occurrence of R$^h$ and R$^i$ is, independently, hydrogen, halogen, haloalkyl, or alkyl; and $R^2$ is hydrogen.

In certain embodiments of the compound of Formula I-g, p is 1, 2, or 3.

In certain embodiments of the compound of Formula I-g, p is 1, 2, or 3; each occurrence of R$^5$ is, independently, halogen, cyano, alkyl, haloalkyl, or —OR$^f$; R$^f$ is independently haloalkyl or alkyl. In certain embodiments of the compound of Formula I-g, at least one R$^5$ is halogen.

In certain embodiments of the compound of Formula I-g, p is 1, 2, or 3; each occurrence of R$^5$ is, independently, halogen, cyano, alkyl, haloalkyl, or —OR$^f$, wherein R$^f$ is independently haloalkyl or alkyl; $R^1$ is alkyl, haloalkyl, or —CH$_2$OR$^f$, wherein R$^f$ is aryl, alkyl, or haloalkyl; and $R^2$ is hydrogen.

In certain embodiments of the compound of Formula I-g, p is 1, 2, or 3; each occurrence of R$^5$ is, independently, halogen, cyano, alkyl, haloalkyl, or —OR$^f$, wherein R$^f$ is independently haloalkyl or alkyl, and at least one R$^5$ is halogen; $R^1$ is alkyl, haloalkyl, or —CH$_2$OR$^f$, wherein R$^f$ is aryl, alkyl, or haloalkyl; and $R^2$ is hydrogen.

In certain embodiments of the compound of Formula I-g, p is 1, 2, or 3; each occurrence of R$^5$ is, independently, halogen, cyano, alkyl, haloalkyl, or —OR$^f$, wherein R$^f$ is independently haloalkyl or alkyl; $R^1$ is —(CR$^h$R$^i$)$_n$-E-NR$^d$SO$_2$R$^d$; E is a bond, aryl, or heteroaryl; each occurrence of R$^d$ is, independently, hydrogen, alkyl, haloalkyl, cycloalkyl, aryl, or heteroaryl; or 2 instances of R$^d$ together with the atoms to which they are attached form a heterocycloalkyl ring; each occurrence of R$^h$ and R$^i$ is, independently, hydrogen, halogen, haloalkyl, or alkyl; and $R^2$ is hydrogen.

In certain embodiments of the compound of Formula I-g, p is 1, 2, or 3; each occurrence of R$^5$ is, independently, halogen, cyano, alkyl, haloalkyl, or —OR$^f$, wherein R$^f$ is independently haloalkyl or alkyl, and at least one R$^5$ is halogen; $R^1$ is —(CR$^h$R$^i$)$_n$-E-NR$^d$SO$_2$R$^d$; E is a bond, aryl, or heteroaryl; each occurrence of R$^d$ is, independently, hydrogen, alkyl, haloalkyl, cycloalkyl, aryl, or heteroaryl; or 2 instances of R$^d$ together with the atoms to which they are attached form a heterocycloalkyl ring; each occurrence of R$^h$ and R$^i$ is, independently, hydrogen, halogen, haloalkyl, or alkyl; and $R^2$ is hydrogen.

In certain embodiments, the compound of Formula I is a compound of Formula I-h:

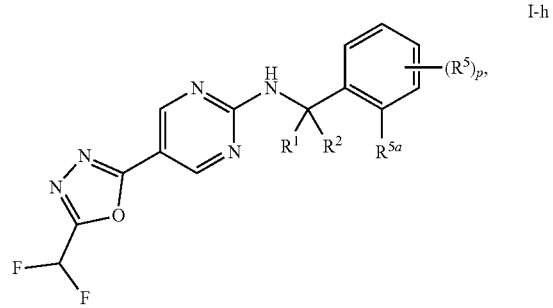

I-h or a pharmaceutically acceptable salt, co-crystal, tautomer, stereoisomer, solvate, hydrate, polymorph, isotopically enriched derivative, or prodrug thereof, wherein p is 0, 1, 2, or 3; and $R^1$, $R^2$, $R^5$, and $R^{5a}$ are as defined herein.

In certain embodiments of the compound of Formula I-h, $R^1$ is alkyl, haloalkyl, or —CH$_2$OR$^f$; R$^f$ is aryl, alkyl, or haloalkyl; and $R^2$ is hydrogen.

In certain embodiments of the compound of Formula I-h, $R^1$ is —(CR$^h$R$^i$)$_n$NR$^a$C(O)R$^b$; each occurrence of R$^h$ and R$^i$ is, independently, hydrogen, halogen, haloalkyl, or alkyl; and each occurrence of R$^a$ and R$^b$ is, independently, hydrogen, aryl, heteroaryl, cycloalkyl, haloalkyl, or alkyl; or R$^a$ and R$^b$ together with the atoms to which they are attached form a heterocycloalkyl ring; and $R^2$ is hydrogen.

In certain embodiments of the compound of Formula I-h, $R^1$ is —(CR$^h$R$^i$)$_n$-E-NR$^d$SO$_2$R$^d$; E is a bond, aryl, or heteroaryl; each occurrence of R$^d$ is, independently, hydrogen, alkyl, haloalkyl, cycloalkyl, aryl, or heteroaryl; or 2 instances of R$^d$ together with the atoms to which they are attached form a heterocycloalkyl ring; each occurrence of R$^h$ and R$^i$ is, independently, hydrogen, halogen, haloalkyl, or alkyl; and $R^2$ is hydrogen.

In certain embodiments of the compound of Formula I-h, p is 0, 1, or 2. In certain embodiments of the compound of Formula I-h, p is 0 or 1.

In certain embodiments of the compound of Formula I-h, $R^{5a}$ is halogen. In certain embodiments of the compound of Formula I-h, $R^{5a}$ is —F or —C$_1$.

In certain embodiments of the compound of Formula I-h, p is 0 or 1; $R^{5a}$ is halogen; $R^5$ is halogen, cyano, alkyl, haloalkyl, or —OR$^f$; and R$^f$ is independently haloalkyl or alkyl.

In certain embodiments of the compound of Formula I-h, p is 0 or 1; $R^{5a}$ is halogen; $R^5$ is halogen, cyano, alkyl, haloalkyl, or —OR$^f$, wherein R$^f$ is independently haloalkyl or alkyl; $R^1$ is alkyl, haloalkyl, or —CH$_2$OR$^f$, wherein R$^f$ is aryl, alkyl, or haloalkyl; and $R^2$ is hydrogen.

In certain embodiments of the compound of Formula I-h, p is 0 or 1; $R^{5a}$ is halogen; $R^5$ is halogen, cyano, alkyl, haloalkyl, or —OR$^f$, wherein R$^f$ is independently haloalkyl or alkyl; $R^1$ is —(CR$^h$R$^i$)$_n$-E-NR$^d$SO$_2$R$^d$; E is a bond, aryl, or heteroaryl; each occurrence of R$^d$ is, independently, hydrogen, alkyl, haloalkyl, cycloalkyl, aryl, or heteroaryl; or 2 instances of R$^d$ together with the atoms to which they are attached form a heterocycloalkyl ring; each occurrence of R$^h$ and R$^i$ is, independently, hydrogen, halogen, haloalkyl, or alkyl; and $R^2$ is hydrogen.

In certain embodiments, the compound of Formula I is a compound of Formula I-i:

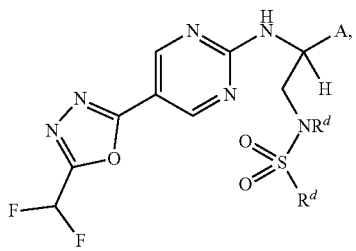

or a pharmaceutically acceptable salt, co-crystal, tautomer, stereoisomer, solvate, hydrate, polymorph, isotopically enriched derivative, or prodrug thereof, wherein $R^d$ and A are as defined herein.

In certain embodiments of the compound of Formula I-i, A is aryl, heteroaryl, or cycloalkyl, wherein each A is optionally substituted with 1-3 independent substituents $R^5$. In certain embodiments of the compound of Formula I-i, A is aryl or heteroaryl, wherein each A is optionally substituted with 1-3 independent substituents $R^5$.

In certain embodiments of the compound of Formula I-i, A is heteroaryl optionally substituted with 1-3 independent substituents $R^5$. In certain embodiments of the compound of Formula I-i, A is monocyclic or bicyclic heteroaryl, wherein each A is optionally substituted with 1-3 independent substituents $R^5$. In certain embodiments of the compound of Formula I-i, A is pyridyl optionally substituted with 1-3 independent substituents $R^5$. In certain embodiments of the compound of Formula I-i, A is 2-pyridyl or 3-pyridyl substituted with 1-3 independent substituents $R^5$, wherein each occurrence of $R^5$ is, independently, halogen, cyano, alkyl, haloalkyl, or $-OR^f$; and $R^f$ is independently haloalkyl or alkyl.

In certain embodiments of the compound of Formula I-i, A is aryl optionally substituted with 1-3 independent substituents $R^5$. In certain embodiments of the compound of Formula I-i, A is phenyl optionally substituted with 1-3 independent substituents $R^5$. In certain embodiments of the compound of Formula I-i, A is phenyl substituted with 1-3 independent substituents $R^5$; each occurrence of $R^5$ is, independently, halogen, cyano, alkyl, haloalkyl, or $-OR^f$; and $R^f$ is independently haloalkyl or alkyl.

In certain embodiments of the compound of Formula I-i, A is

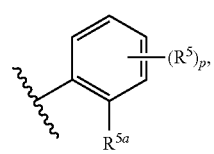

wherein $R^{5a}$ is halogen; each occurrence of $R^5$ is, independently, halogen, cyano, alkyl, haloalkyl, or $-OR^f$; $R^f$ is independently alkyl or haloalkyl; and p is 0, 1, or 2.

In certain embodiments of the compound of Formula I-i, each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring. In certain embodiments of the compound of Formula I-i, each occurrence of $R^d$ is, independently, hydrogen, alkyl, haloalkyl, cycloalkyl, or aryl; or 2 instances of $R^d$ together with the atoms to which they are attached form a heterocycloalkyl ring.

In certain embodiments of the compound of Formula I-i, A is phenyl substituted with halogen or $-OR^f$; $R^f$ is haloalkyl; and each occurrence of $R^d$ is, independently, hydrogen, alkyl, or haloalkyl.

In certain embodiments, the compound of Formula I is a compound of Formula I-j:

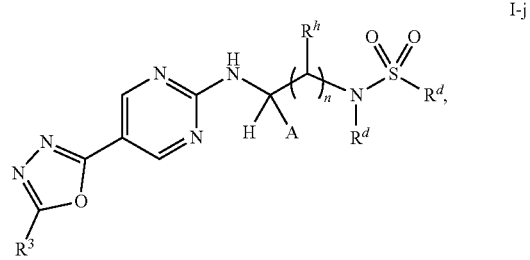

or a pharmaceutically acceptable salt, co-crystal, tautomer, stereoisomer, solvate, hydrate, polymorph, isotopically enriched derivative, or prodrug thereof, wherein $R^d$, $R^h$, n, $R^3$, and A are as defined herein.

In certain embodiments of the compound of Formula I-i, A is aryl, heteroaryl, or cycloalkyl, wherein each A is optionally substituted with 1-3 independent substituents $R^5$. In certain embodiments of the compound of Formula I-i, A is aryl or heteroaryl, wherein each A is optionally substituted with 1-3 independent substituents $R^5$.

In certain embodiments of the compound of Formula I-i, A is heteroaryl optionally substituted with 1-3 independent substituents $R^5$. In certain embodiments of the compound of Formula I-i, A is monocyclic or bicyclic heteroaryl, wherein each A is optionally substituted with 1-3 independent substituents $R^5$. In certain embodiments of the compound of Formula I-i, A is pyridyl optionally substituted with 1-3 independent substituents $R^5$. In certain embodiments of the compound of Formula I-i, A is 2-pyridyl or 3-pyridyl substituted with 1-3 independent substituents $R^5$, wherein each occurrence of $R^5$ is, independently, halogen, cyano, alkyl, haloalkyl, or $-OR^f$; and $R^f$ is independently haloalkyl or alkyl.

In certain embodiments of the compound of Formula I-i, A is aryl optionally substituted with 1-3 independent substituents $R^5$. In certain embodiments of the compound of Formula I-i, A is phenyl optionally substituted with 1-3 independent substituents $R^5$. In certain embodiments of the compound of Formula I-i, A is phenyl substituted with 1-3 independent substituents $R^5$; each occurrence of $R^5$ is, independently, halogen, cyano, alkyl, haloalkyl, or $-OR^f$; and $R^f$ is independently haloalkyl or alkyl.

In certain embodiments of the compound of Formula I-j, A is

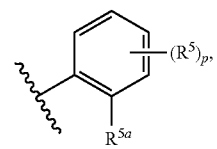

wherein $R^{5a}$ is halogen; each occurrence of $R^5$ is, independently, halogen, cyano, alkyl, haloalkyl, or $-OR^f$; $R^f$ is independently alkyl or haloalkyl; and p is 0, 1, or 2.

In certain embodiments of the compound of Formula I-j, each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; n is 1, 2, or 3; and $R^h$ is, hydrogen, halogen, haloalkyl, or alkyl. In certain embodiments of the compound of Formula I-j, each occurrence of $R^d$ is, independently, hydrogen, alkyl, haloalkyl, cycloalkyl, or aryl; or 2 instances of $R^d$ together with the atoms to which they are attached form a heterocycloalkyl ring; n is 1, 2, or 3; and $R^h$ is, hydrogen, halogen, haloalkyl, or alkyl.

In certain embodiments of the compound of Formula I-j, $R^3$ is haloalkyl. In certain embodiments of the compound of Formula I-j, $R^3$ is $C_{1-3}$ haloalkyl. In certain embodiments of the compound of Formula I-j, $R^3$ is —$CF_3$, —$CHF_2$, or $CH_2F$. In certain embodiments of the compound of Formula I-j, $R^3$ is —$CHF_2$.

In certain embodiments of the compound of Formula I-j, A is phenyl substituted with halogen or —$OR^f$; $R^f$ is haloalkyl; each occurrence of $R^d$ is, independently, hydrogen, alkyl, or haloalkyl; $R^3$ is —$CF_3$, —$CHF_2$, or $CH_2F$; n is 1; and $R^h$ is hydrogen.

In certain embodiments, the compound of Formula I is a compound of Formula I-k:

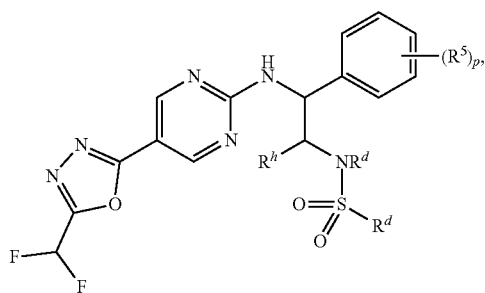

I-k or a pharmaceutically acceptable salt, co-crystal, tautomer, stereoisomer, solvate, hydrate, polymorph, isotopically enriched derivative, or prodrug thereof, wherein p is 0, 1, 2, or 3; and $R^d$, $R^h$, and $R^5$ are as defined herein.

In certain embodiments of the compound of Formula I-k, each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; and $R^h$ is, hydrogen, halogen, haloalkyl, or alkyl.

In certain embodiments of the compound of Formula I-k, p is 1, 2, or 3.

In certain embodiments of the compound of Formula I-k p is 1, 2, or 3; each occurrence of $R^5$ is, independently, halogen, cyano, alkyl, haloalkyl, or —$OR^f$; $R^f$ is independently haloalkyl or alkyl. In certain embodiments of the compound of Formula I-k, at least one $R^5$ is halogen.

In certain embodiments of the compound of Formula I-k, p is 1, 2, or 3; each occurrence of $R^5$ is, independently, halogen, cyano, alkyl, haloalkyl, or —$OR^f$, wherein $R^f$ is independently haloalkyl or alkyl; $R^d$ is, independently, hydrogen, alkyl, haloalkyl, cycloalkyl, aryl, or heteroaryl; or 2 instances of $R^d$ together with the atoms to which they are attached form a heterocycloalkyl ring; and $R^h$ is, hydrogen, halogen, haloalkyl, or alkyl.

In certain embodiments of the compound of Formula I-k, p is 1, 2, or 3; each occurrence of $R^5$ is, independently, halogen, cyano, alkyl, haloalkyl, or —$OR^f$, wherein $R^f$ is independently haloalkyl or alkyl, and at least one $R^5$ is halogen; $R^d$ is, independently, hydrogen, alkyl, haloalkyl, cycloalkyl, aryl, or heteroaryl; or 2 instances of $R^d$ together with the atoms to which they are attached form a heterocycloalkyl ring; and $R^h$ is, hydrogen, halogen, haloalkyl, or alkyl.

In certain embodiments of the compound of Formula I-k, p is 1; $R^5$ is halogen or —$OR^f$; $R^f$ is haloalkyl; each occurrence of $R^d$ is, independently, hydrogen, alkyl, or haloalkyl; and $R^h$ is hydrogen.

In certain embodiments, the compound of Formula I is a compound of Formula I-1:

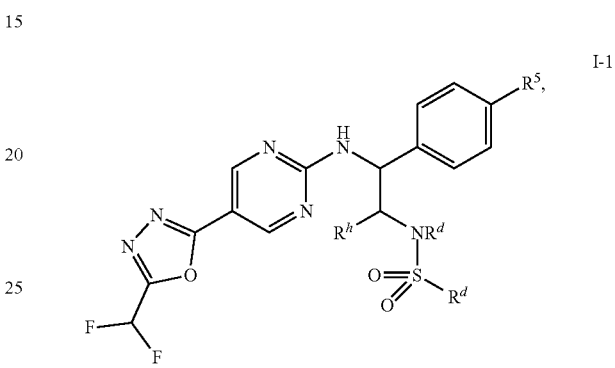

I-1 or a pharmaceutically acceptable salt, co-crystal, tautomer, stereoisomer, solvate, hydrate, polymorph, isotopically enriched derivative, or prodrug thereof, wherein $R^d$, $R^h$, and $R^5$ are as defined herein.

In certain embodiments of the compound of Formula I-1, each occurrence of $R^d$ is, independently, hydrogen, alkyl, haloalkyl, cycloalkyl, aryl, or heteroaryl; or 2 instances of $R^d$ together with the atoms to which they are attached form a heterocycloalkyl ring; and $R^h$ is, hydrogen, halogen, haloalkyl, or alkyl.

In certain embodiments of the compound of Formula I-1, $R^5$ is halogen, cyano, alkyl, haloalkyl, or —$OR^f$; $R^f$ is independently haloalkyl or alkyl. In certain embodiments of the compound of Formula I-k, $R^5$ is halogen or —$OR^f$; and $R^f$ is haloalkyl.

In certain embodiments of the compound of Formula I-1, $R^5$ is halogen, cyano, alkyl, haloalkyl, or —$OR^f$, wherein $R^f$ is independently haloalkyl or alkyl; $R^d$ is, independently, hydrogen, alkyl, haloalkyl, cycloalkyl, aryl, or heteroaryl; or 2 instances of $R^d$ together with the atoms to which they are attached form a heterocycloalkyl ring; and $R^h$ is, hydrogen, halogen, haloalkyl, or alkyl.

In certain embodiments of the compound of Formula I-1, $R^5$ is halogen or —$OR^f$; $R^f$ is haloalkyl; each occurrence of $R^d$ is, independently, hydrogen, alkyl, or haloalkyl; and $R^h$ is hydrogen.

In certain embodiments, the compound of Formula I is a compound selected from the group consisting of:
N-(1-phenylethyl)-5-(5-(trifluoromethyl)-1,3,4-oxadiazol-2-yl)pyrimidin-2-amine (2);
N-((6-methylpyridin-2-yl)methyl)-5-(5-(trifluoromethyl)-1,3,4-oxadiazol-2-yl)pyrimidin-2-amine (3);
5-(5-(difluoromethyl)-1,3,4-oxadiazol-2-yl)-N-(1-phenylethyl)pyrimidin-2-amine (6); N-benzhydryl-5-(5-(difluoromethyl)-1,3,4-oxadiazol-2-yl)pyrimidin-2-amine (7);
5-(5-(difluoromethyl)-1,3,4-oxadiazol-2-yl)-N-(1-(4-fluorophenyl)cyclopropyl)-N-methylpyrimidin-2-amine (8);

5-(5-(difluoromethyl)-1,3,4-oxadiazol-2-yl)-N-(2-(4-fluorophenyl)propan-2-yl)pyrimidin-2-amine (9);
5-(5-(difluoromethyl)-1,3,4-oxadiazol-2-yl)-N-(1-(2,6-difluorophenyl)cyclopropyl)pyrimidin-2-amine (11);
2-(difluoromethyl)-5-(2-(1-phenylcyclopropoxy)pyrimidin-5-yl)-1,3,4-oxadiazole (12);
5-(5-(difluoromethyl)-1,3,4-oxadiazol-2-yl)-N-(3,3,3-trifluoro-1-(4-fluorophenyl)propyl)pyrimidin-2-amine (13);
(+)-5-(5-(difluoromethyl)-1,3,4-oxadiazol-2-yl)-N-(3,3,3-trifluoro-1-(4-fluorophenyl)propyl)pyrimidin-2-amine (13(+));
(−)-5-(5-(difluoromethyl)-1,3,4-oxadiazol-2-yl)-N-(3,3,3-trifluoro-1-(4-fluorophenyl)propyl)pyrimidin-2-amine (13(−));
5-(5-(difluoromethyl)-1,3,4-oxadiazol-2-yl)-N-(1-(4'-fluoro-[1,1'-biphenyl]-2-yl)cyclopropyl)pyrimidin-2-amine (14);
5-(5-(difluoromethyl)-1,3,4-oxadiazol-2-yl)-N-(2,2,2-trifluoro-1-(4-fluorophenyl)ethyl)pyrimidin-2-amine (15);
5-(5-(difluoromethyl)-1,3,4-oxadiazol-2-yl)-N-(1-(4'-fluoro-[1,1'-biphenyl]-4-yl)cyclopropyl)pyrimidin-2-amine (16);
5-(5-(difluoromethyl)-1,3,4-oxadiazol-2-yl)-N-(4-(4-fluorophenyl)-1-phenylpiperidin-4-yl)pyrimidin-2-amine (17);
5-(5-(difluoromethyl)-1,3,4-oxadiazol-2-yl)-N-(1-(4'-fluoro-[1,1'-biphenyl]-3-yl)cyclopropyl)pyrimidin-2-amine (18);
5-(5-(difluoromethyl)-1,3,4-oxadiazol-2-yl)-N-(1-(4-fluorophenyl)-2-phenoxyethyl)pyrimidin-2-amine (19);
5-(5-(difluoromethyl)-1,3,4-oxadiazol-2-yl)-N-(1-(4-fluorophenyl)ethyl)pyrimidin-2-amine (20);
(+)-5-(5-(difluoromethyl)-1,3,4-oxadiazol-2-yl)-N-(1-(4-fluorophenyl)ethyl)pyrimidin-2-amine (20(+));
(−)-5-(5-(difluoromethyl)-1,3,4-oxadiazol-2-yl)-N-(1-(4-fluorophenyl)ethyl)pyrimidin-2-amine (20(−));
5-(5-(difluoromethyl)-1,3,4-oxadiazol-2-yl)-N-(1-(4-fluorophenyl)-2-methoxyethyl)pyrimidin-2-amine (21);
5-(5-(difluoromethyl)-1,3,4-oxadiazol-2-yl)-N-(1-(4-fluorophenyl)propyl)pyrimidin-2-amine (22);
5-(5-(difluoromethyl)-1,3,4-oxadiazol-2-yl)-N-(1-(4-fluorophenyl)butyl)pyrimidin-2-amine (23);
5-(5-(difluoromethyl)-1,3,4-oxadiazol-2-yl)-N-(1-(4-fluorophenyl)-2-methylpropyl)pyrimidin-2-amine (24);
5-(1-((5-(5-(difluoromethyl)-1,3,4-oxadiazol-2-yl)pyrimidin-2-yl)amino)cyclopropyl)picolinonitrile (25);
1-(4-((5-(5-(difluoromethyl)-1,3,4-oxadiazol-2-yl)pyrimidin-2-yl)amino)-4-(4-fluorophenyl)piperidin-1-yl)ethanone (26);
N-(1-cyclohexylcyclopropyl)-5-(5-(difluoromethyl)-1,3,4-oxadiazol-2-yl)pyrimidin-2-amine (27);
5-(5-(difluoromethyl)-1,3,4-oxadiazol-2-yl)-N-(1-isopropylcyclopropyl)pyrimidin-2-amine (28);
5-(5-(difluoromethyl)-1,3,4-oxadiazol-2-yl)-N-(5-fluoro-2,3-dihydro-1H-inden-1-yl)pyrimidin-2-amine (29);
2-((5-(5-(difluoromethyl)-1,3,4-oxadiazol-2-yl)pyrimidin-2-yl)amino)-2-(4-fluorophenyl)-1-morpholinoethanone (30);
5-(5-(difluoromethyl)-1,3,4-oxadiazol-2-yl)-N-(1-(5-fluoropyridin-2-yl)ethyl)pyrimidin-2-amine (31);
N-(1-(4-(difluoromethoxy)phenyl)cyclopropyl)-5-(5-(difluoromethyl)-1,3,4-oxadiazol-2-yl)pyrimidin-2-amine (32);
N-(1-(4-(difluoromethoxy)-2-fluorophenyl)cyclopropyl)-5-(5-(difluoromethyl)-1,3,4-oxadiazol-2-yl)pyrimidin-2-amine (33);
5-(5-(difluoromethyl)-1,3,4-oxadiazol-2-yl)-N-(6-fluoro-1,2,3,4-tetrahydronaphthalen-1-yl)pyrimidin-2-amine (34);
2-((5-(5-(difluoromethyl)-1,3,4-oxadiazol-2-yl)pyrimidin-2-yl)amino)-2-(4-fluorophenyl)-N-phenylacetamide (35);
N-(cyclopropyl(4-fluorophenyl)methyl)-5-(5-(difluoromethyl)-1,3,4-oxadiazol-2-yl)pyrimidin-2-amine (36);
N-(4,4-difluoro-1-(4-fluorophenyl)cyclohexyl)-5-(5-(difluoromethyl)-1,3,4-oxadiazol-2-yl)pyrimidin-2-amine (37);
N-(2-((5-(5-(difluoromethyl)-1,3,4-oxadiazol-2-yl)pyrimidin-2-yl)amino)-2-(4-fluorophenyl)ethyl)methanesulfonamide (38);
(+)-N-(2-((5-(5-(difluoromethyl)-1,3,4-oxadiazol-2-yl)pyrimidin-2-yl)amino)-2-(4-fluorophenyl)ethyl)methanesulfonamide (38(+));
(−)-N-(2-((5-(5-(difluoromethyl)-1,3,4-oxadiazol-2-yl)pyrimidin-2-yl)amino)-2-(4-fluorophenyl)ethyl)methanesulfonamide (38(−));
N-(2-((5-(5-(difluoromethyl)-1,3,4-oxadiazol-2-yl)pyrimidin-2-yl)amino)-2-(4-fluorophenyl)ethyl)benzenesulfonamide (39);
N-(1-(2-methoxyphenyl)cyclopropyl)-5-(5-(trifluoromethyl)-1,3,4-oxadiazol-2-yl)pyrimidin-2-amine (40);
N-(1-(3-methoxyphenyl)cyclopropyl)-5-(5-(trifluoromethyl)-1,3,4-oxadiazol-2-yl)pyrimidin-2-amine (41);
N-(1-(4-methoxyphenyl)cyclopropyl)-5-(5-(trifluoromethyl)-1,3,4-oxadiazol-2-yl)pyrimidin-2-amine (42);
N-(1-(4-bromophenyl)cyclopropyl)-5-(5-(difluoromethyl)-1,3,4-oxadiazol-2-yl)pyrimidin-2-amine (47);
4-(1-((5-(5-(difluoromethyl)-1,3,4-oxadiazol-2-yl)pyrimidin-2-yl)amino)cyclopropyl)benzonitrile (48);
N-(1-(2-chlorophenyl)cyclopropyl)-5-(5-(difluoromethyl)-1,3,4-oxadiazol-2-yl)pyrimidin-2-amine (52);
5-(5-(difluoromethyl)-1,3,4-oxadiazol-2-yl)-N-(1-(3-(trifluoromethoxy)phenyl)cyclopropyl)pyrimidin-2-amine (53);
5-(5-(difluoromethyl)-1,3,4-oxadiazol-2-yl)-N-(1-(4-(trifluoromethoxy)phenyl)cyclopropyl)pyrimidin-2-amine (54);
5-(5-(difluoromethyl)-1,3,4-oxadiazol-2-yl)-N-(1-(2-(trifluoromethoxy)phenyl)cyclopropyl)pyrimidin-2-amine (55);
5-(5-(difluoromethyl)-1,3,4-oxadiazol-2-yl)-N-(1-(2-(trifluoromethyl)phenyl)cyclopropyl)pyrimidin-2-amine (58);
5-(5-(difluoromethyl)-1,3,4-oxadiazol-2-yl)-N-(1-(2,3-difluorophenyl)cyclopropyl)pyrimidin-2-amine (60);
5-(5-(difluoromethyl)-1,3,4-oxadiazol-2-yl)-N-(1-(2,5-difluorophenyl)cyclopropyl)pyrimidin-2-amine (61);
N-(1-(2-chloro-4-fluorophenyl)cyclopropyl)-5-(5-(difluoromethyl)-1,3,4-oxadiazol-2-yl)pyrimidin-2-amine (62);
5-(5-(difluoromethyl)-1,3,4-oxadiazol-2-yl)-N-(1-(4-fluoro-2-(trifluoromethyl)phenyl)cyclopropyl)pyrimidin-2-amine (63);
N-(1-(6-bromopyridin-3-yl)cyclopropyl)-5-(5-(difluoromethyl)-1,3,4-oxadiazol-2-yl)pyrimidin-2-amine (64);
5-(5-(difluoromethyl)-1,3,4-oxadiazol-2-yl)-N-(1-(pyridin-3-yl)cyclopropyl)pyrimidin-2-amine (65);
5-(5-(difluoromethyl)-1,3,4-oxadiazol-2-yl)-N-(1-(5-fluoropyridin-2-yl)cyclopropyl)pyrimidin-2-amine (67);
5-(5-(difluoromethyl)-1,3,4-oxadiazol-2-yl)-N-(1-(4-(2,2,2-trifluoroethoxy)phenyl)cyclopropyl)pyrimidin-2-amine (68);
N-(4-(1-((5-(5-(difluoromethyl)-1,3,4-oxadiazol-2-yl)pyrimidin-2-yl)amino)cyclopropyl)benzyl)methanesulfonamide (69);
5-(5-(difluoromethyl)-1,3,4-oxadiazol-2-yl)-N-(1-(2-fluoro-4-(trifluoromethoxy)phenyl)cyclopropyl)pyrimidin-2-amine (70);

5-(5-(difluoromethyl)-1,3,4-oxadiazol-2-yl)-N-(1-(2-fluoro-4-(trifluoromethyl)phenyl)cyclopropyl)pyrimidin-2-amine (71);

N-(1-(3-chloro-2-fluorophenyl)cyclopropyl)-5-(5-(difluoromethyl)-1,3,4-oxadiazol-2-yl)pyrimidin-2-amine (73);

5-(5-(difluoromethyl)-1,3,4-oxadiazol-2-yl)-N-(1-(2,4,6-trifluorophenyl)cyclopropyl)pyrimidin-2-amine (74);

5-(5-(difluoromethyl)-1,3,4-oxadiazol-2-yl)-N-(1-(2-fluoro-5-(trifluoromethoxy)phenyl)cyclopropyl)pyrimidin-2-amine (75);

N-(1-(5-chloro-2-fluorophenyl)cyclopropyl)-5-(5-(difluoromethyl)-1,3,4-oxadiazol-2-yl)pyrimidin-2-amine (76);

N-(1-(2-chloro-3-methylphenyl)cyclopropyl)-5-(5-(difluoromethyl)-1,3,4-oxadiazol-2-yl)pyrimidin-2-amine (77);

N-(2-((5-(5-(difluoromethyl)-1,3,4-oxadiazol-2-yl)pyrimidin-2-yl)amino)-2-(4-fluorophenyl)ethyl)acetamide (78);

(+)-N-(2-((5-(5-(difluoromethyl)-1,3,4-oxadiazol-2-yl)pyrimidin-2-yl)amino)-2-(4-fluorophenyl)ethyl)acetamide (78(+));

(−)-N-(2-((5-(5-(difluoromethyl)-1,3,4-oxadiazol-2-yl)pyrimidin-2-yl)amino)-2-(4-fluorophenyl)ethyl)acetamide (78(−));

N-(2-((5-(5-(difluoromethyl)-1,3,4-oxadiazol-2-yl)pyrimidin-2-yl)amino)-2-(4-fluorophenyl)ethyl)benzamide (79);

N-(1-(2-chloro-5-fluorophenyl)cyclopropyl)-5-(5-(difluoromethyl)-1,3,4-oxadiazol-2-yl)pyrimidin-2-amine (80);

N-(1-(2-chloro-5-(trifluoromethyl)phenyl)cyclopropyl)-5-(5-(difluoromethyl)-1,3,4-oxadiazol-2-yl)pyrimidin-2-amine (81);

N-(1-(2-bromopyridin-4-yl)cyclopropyl)-5-(5-(difluoromethyl)-1,3,4-oxadiazol-2-yl)pyrimidin-2-amine (82);

4-(1-((5-(5-(difluoromethyl)-1,3,4-oxadiazol-2-yl)pyrimidin-2-yl)amino)cyclopropyl)picolinonitrile (83);

5-(5-(difluoromethyl)-1,3,4-oxadiazol-2-yl)-N-(1-(2-fluoro-4-(2,2,2-trifluoroethoxy)phenyl)cyclopropyl)pyrimidin-2-amine (84);

N-(1-(2-chloro-3-(trifluoromethyl)phenyl)cyclopropyl)-5-(5-(difluoromethyl)-1,3,4-oxadiazol-2-yl)pyrimidin-2-amine (85);

N-(1-(2-chloro-3-(difluoromethoxy)phenyl)cyclopropyl)-5-(5-(difluoromethyl)-1,3,4-oxadiazol-2-yl)pyrimidin-2-amine (86);

N-(1-(2-chloro-3-(2,2,2-trifluoroethoxy)phenyl)cyclopropyl)-5-(5-(difluoromethyl)-1,3,4-oxadiazol-2-yl)pyrimidin-2-amine (87);

N-(1-(2-chloro-5-(2,2,2-trifluoroethoxy)phenyl)cyclopropyl)-5-(5-(difluoromethyl)-1,3,4-oxadiazol-2-yl)pyrimidin-2-amine (89);

N-(1-(2-chloro-5-methylphenyl)cyclopropyl)-5-(5-(difluoromethyl)-1,3,4-oxadiazol-2-yl)pyrimidin-2-amine (90);

N-(1-(2-chloro-3-fluorophenyl)cyclopropyl)-5-(5-(difluoromethyl)-1,3,4-oxadiazol-2-yl)pyrimidin-2-amine (91);

1-(4-((5-(5-(difluoromethyl)-1,3,4-oxadiazol-2-yl)pyrimidin-2-yl)amino)-4-isopropylpiperidin-1-yl)ethanone (92);

1-((5-(5-(difluoromethyl)-1,3,4-oxadiazol-2-yl)pyrimidin-2-yl)amino)-1-(2,4-difluorophenyl)propan-2-ol (93);

N1-(5-(5-(difluoromethyl)-1,3,4-oxadiazol-2-yl)pyrimidin-2-yl)-1-(4-fluorophenyl)-N2,N2-dimethylethane-1,2-diamine (94);

5-(5-(difluoromethyl)-1,3,4-oxadiazol-2-yl)-N-(4-(2,4-difluorophenyl)-1-methylpiperidin-4-yl)pyrimidin-2-amine (95);

N1-(5-(5-(difluoromethyl)-1,3,4-oxadiazol-2-yl)pyrimidin-2-yl)-1-(4-fluorophenyl)ethane-1,2-diamine (96);

5-(5-(difluoromethyl)-1,3,4-oxadiazol-2-yl)-N-(2-(2,4-difluorophenyl)propan-2-yl)pyrimidin-2-amine (97);

5-(5-(difluoromethyl)-1,3,4-oxadiazol-2-yl)-N-(2-(2,6-difluorophenyl)propan-2-yl)pyrimidin-2-amine (98);

5-(5-(difluoromethyl)-1,3,4-oxadiazol-2-yl)-N-(1-(2,4-difluorophenyl)ethyl)pyrimidin-2-amine (99);

5-[5-(difluoromethyl)-1,3,4-oxadiazol-2-yl]-N-[(1R)-1-(2,4-difluorophenyl)ethyl]pyrimidin-2-amine (99-R);

5-[5-(difluoromethyl)-1,3,4-oxadiazol-2-yl]-N-[(1S)-1-(2,4-difluorophenyl)ethyl]pyrimidin-2-amine (99-S);

5-(5-(difluoromethyl)-1,3,4-oxadiazol-2-yl)-N-(1-(2,6-difluorophenyl)ethyl)pyrimidin-2-amine (100);

(+)-5-(5-(difluoromethyl)-1,3,4-oxadiazol-2-yl)-N-(1-(2,6-difluorophenyl)ethyl)pyrimidin-2-amine (100(+));

(−)-5-(5-(difluoromethyl)-1,3,4-oxadiazol-2-yl)-N-(1-(2,6-difluorophenyl)ethyl)pyrimidin-2-amine (100(−));

5-(5-(difluoromethyl)-1,3,4-oxadiazol-2-yl)-N-(1-(2,4-difluorophenyl)-3,3,3-trifluoropropyl)pyrimidin-2-amine (101);

5-(5-(difluoromethyl)-1,3,4-oxadiazol-2-yl)-N-(1-(2,6-difluorophenyl)-3,3,3-trifluoropropyl)pyrimidin-2-amine (102);

N-(2-((5-(5-(difluoromethyl)-1,3,4-oxadiazol-2-yl)pyrimidin-2-yl)amino)-2-(2,4-difluorophenyl)ethyl)methanesulfonamide (103);

(+)-N-(2-((5-(5-(difluoromethyl)-1,3,4-oxadiazol-2-yl)pyrimidin-2-yl)amino)-2-(2,4-difluorophenyl)ethyl)methanesulfonamide (103(+));

(−)-N-(2-((5-(5-(difluoromethyl)-1,3,4-oxadiazol-2-yl)pyrimidin-2-yl)amino)-2-(2,4-difluorophenyl)ethyl)methanesulfonamide (103(−));

N-(2-((5-(5-(difluoromethyl)-1,3,4-oxadiazol-2-yl)pyrimidin-2-yl)amino)-2-(2,6-difluorophenyl)ethyl)methanesulfonamide (104);

N-(1-(2-(difluoromethoxy)-6-fluorophenyl)cyclopropyl)-5-(5-(difluoromethyl)-1,3,4-oxadiazol-2-yl)pyrimidin-2-amine (105);

N-(1-(2,6-difluoro-4-methoxyphenyl)cyclopropyl)-5-(5-(difluoromethyl)-1,3,4-oxadiazol-2-yl)pyrimidin-2-amine (106);

N-(1-(2,6-difluoro-4-methylphenyl)cyclopropyl)-5-(5-(difluoromethyl)-1,3,4-oxadiazol-2-yl)pyrimidin-2-amine (107);

N-(2-((5-(5-(difluoromethyl)-1,3,4-oxadiazol-2-yl)pyrimidin-2-yl)amino)-2-(4-fluorophenyl)ethyl)ethanesulfonamide (108);

N-(2-((5-(5-(difluoromethyl)-1,3,4-oxadiazol-2-yl)pyrimidin-2-yl)amino)-2-(4-fluorophenyl)ethyl)propane-2-sulfonamide (109);

N-(2-((5-(5-(difluoromethyl)-1,3,4-oxadiazol-2-yl)pyrimidin-2-yl)amino)-2-(4-fluorophenyl)ethyl)cyclopropanesulfonamide (110);

N-(2-((5-(5-(difluoromethyl)-1,3,4-oxadiazol-2-yl)pyrimidin-2-yl)amino)-2-(4-fluorophenyl)ethyl)propane-1-sulfonamide (111);

N-(2-((5-(5-(difluoromethyl)-1,3,4-oxadiazol-2-yl)pyrimidin-2-yl)amino)-2-(4-fluorophenyl)ethyl)-2-methylpropane-1-sulfonamide (112);

N-(2-((5-(5-(difluoromethyl)-1,3,4-oxadiazol-2-yl)pyrimidin-2-yl)amino)-2-(4-fluorophenyl)ethyl)-N-methylmethanesulfonamide (113);

(+)-N-(2-((5-(5-(difluoromethyl)-1,3,4-oxadiazol-2-yl)pyrimidin-2-yl)amino)-2-(4-fluorophenyl)ethyl)-N-methylmethanesulfonamide (113(+));

N-(2-((5-(5-(difluoromethyl)-1,3,4-oxadiazol-2-yl)pyrimidin-2-yl)amino)-2-(4-fluorophenyl)ethyl)-2,2,2-trifluoroacetamide (114);

N-(2-(4-(difluoromethoxy)phenyl)-2-((5-(5-(difluoromethyl)-1,3,4-oxadiazol-2-yl)pyrimidin-2-yl)amino)ethyl)methanesulfonamide (115)

(+)-N-(2-(4-(difluoromethoxy)phenyl)-2-((5-(5-(difluoromethyl)-1,3,4-oxadiazol-2-yl)pyrimidin-2-yl)amino)ethyl)methanesulfonamide (115(+));

(−)-N-(2-(4-(difluoromethoxy)phenyl)-2-((5-(5-(difluoromethyl)-1,3,4-oxadiazol-2-yl)pyrimidin-2-yl)amino)ethyl)methanesulfonamide (115(−));

N-(2-(4-(difluoromethoxy)-2-fluorophenyl)-2-((5-(5-(difluoromethyl)-1,3,4-oxadiazol-2-yl)pyrimidin-2-yl)amino)ethyl)methanesulfonamide (116);

(+)—N-(2-(4-(difluoromethoxy)-2-fluorophenyl)-2-((5-(5-(difluoromethyl)-1,3,4-oxadiazol-2-yl)pyrimidin-2-yl)amino)ethyl)methanesulfonamide (116(+));

(−)-N-(2-(4-(difluoromethoxy)-2-fluorophenyl)-2-((5-(5-(difluoromethyl)-1,3,4-oxadiazol-2-yl)pyrimidin-2-yl)amino)ethyl)methanesulfonamide (116(−));

N-(2-(4-(difluoromethoxy)-2,6-difluorophenyl)-2-((5-(5-(difluoromethyl)-1,3,4-oxadiazol-2-yl)pyrimidin-2-yl)amino)ethyl)methanesulfonamide (117);

N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)methanesulfonamide (118);

(+)—N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)methanesulfonamide (118(+));

N-(2-((5-(5-(difluoromethyl)-1,3,4-oxadiazol-2-yl)pyrimidin-2-yl)amino)-2-(4-fluorophenyl)ethyl)-2,2,2-trifluoroethanesulfonamide (119);

2-(2-((5-(5-(difluoromethyl)-1,3,4-oxadiazol-2-yl)pyrimidin-2-yl)amino)-2-(4-fluorophenyl)ethyl)isothiazolidine 1,1-dioxide (120);

(+)-2-(2-((5-(5-(difluoromethyl)-1,3,4-oxadiazol-2-yl)pyrimidin-2-yl)amino)-2-(4-fluorophenyl)ethyl)isothiazolidine 1,1-dioxide (120(+));

(−)-2-(2-((5-(5-(difluoromethyl)-1,3,4-oxadiazol-2-yl)pyrimidin-2-yl)amino)-2-(4-fluorophenyl)ethyl)isothiazolidine 1,1-dioxide (120(−));

N-(2-((5-(5-(difluoromethyl)-1,3,4-oxadiazol-2-yl)pyrimidin-2-yl)amino)-2-(2,4,6-trifluorophenyl)ethyl)methanesulfonamide (121);

N-(2-((5-(5-(difluoromethyl)-1,3,4-oxadiazol-2-yl)pyrimidin-2-yl)amino)-2-(4-(trifluoromethoxy)phenyl)ethyl)methanesulfonamide (122);

(+)—N-(2-((5-(5-(difluoromethyl)-1,3,4-oxadiazol-2-yl)pyrimidin-2-yl)amino)-2-(4-(trifluoromethoxy)phenyl)ethyl)methanesulfonamide (122(+));

(−)-N-(2-((5-(5-(difluoromethyl)-1,3,4-oxadiazol-2-yl)pyrimidin-2-yl)amino)-2-(4-(trifluoromethoxy)phenyl)ethyl)methanesulfonamide (122(−));

N-(2-cyclopropyl-2-((5-(5-(difluoromethyl)-1,3,4-oxadiazol-2-yl)pyrimidin-2-yl)amino)ethyl)methanesulfonamide (123);

(+)—N-(2-cyclopropyl-2-((5-(5-(difluoromethyl)-1,3,4-oxadiazol-2-yl)pyrimidin-2-yl)amino)ethyl)methanesulfonamide (123(+));

(−)-N-(2-cyclopropyl-2-((5-(5-(difluoromethyl)-1,3,4-oxadiazol-2-yl)pyrimidin-2-yl)amino)ethyl)methanesulfonamide (123(−));

N-(2-((5-(5-(difluoromethyl)-1,3,4-oxadiazol-2-yl)pyrimidin-2-yl)amino)-2-(tetrahydro-2H-pyran-4-yl)ethyl)methanesulfonamide (124);

N-(3-((5-(5-(difluoromethyl)-1,3,4-oxadiazol-2-yl)pyrimidin-2-yl)amino)-3-(4-fluorophenyl)propyl)methanesulfonamide (125);

5-(5-(difluoromethyl)-1,3,4-oxadiazol-2-yl)-N-((4-fluorophenyl)(1-(methylsulfonyl)azetidin-3-yl)methyl)pyrimidin-2-amine (126);

N-(1-((5-(5-(difluoromethyl)-1,3,4-oxadiazol-2-yl)pyrimidin-2-yl)amino)-1-(4-fluorophenyl)propan-2-yl)methanesulfonamide (127);

N-(3-(((5-(5-(difluoromethyl)-1,3,4-oxadiazol-2-yl)pyrimidin-2-yl)amino)(4-fluorophenyl)methyl)phenyl)methanesulfonamide (128);

N-(4-(((5-(5-(difluoromethyl)-1,3,4-oxadiazol-2-yl)pyrimidin-2-yl)amino)(4-fluorophenyl)methyl)phenyl)methanesulfonamide (129);

N-(2-(((5-(5-(difluoromethyl)-1,3,4-oxadiazol-2-yl)pyrimidin-2-yl)amino)(4-fluorophenyl)methyl)phenyl)methanesulfonamide (130);

N-(2-(2-((5-(5-(difluoromethyl)-1,3,4-oxadiazol-2-yl)pyrimidin-2-yl)amino)-2-(4-fluorophenyl)ethyl)phenyl)methanesulfonamide (131);

N-(3-(2-((5-(5-(difluoromethyl)-1,3,4-oxadiazol-2-yl)pyrimidin-2-yl)amino)-2-(4-fluorophenyl)ethyl)phenyl)methanesulfonamide (132);

N-(4-(2-((5-(5-(difluoromethyl)-1,3,4-oxadiazol-2-yl)pyrimidin-2-yl)amino)-2-(4-fluorophenyl)ethyl)phenyl)methanesulfonamide (133);

N-(2-cyclopropoxy-1-(2,4-difluorophenyl)ethyl)-5-(5-(difluoromethyl)-1,3,4-oxadiazol-2-yl)pyrimidin-2-amine (134);

N-(2-cyclopropoxy-1-(4-(difluoromethoxy)-2-fluorophenyl)ethyl)-5-(5-(difluoromethyl)-1,3,4-oxadiazol-2-yl)pyrimidin-2-amine (135);

(+)—N-(2-cyclopropoxy-1-(4-(difluoromethoxy)-2-fluorophenyl)ethyl)-5-(5-(difluoromethyl)-1,3,4-oxadiazol-2-yl)pyrimidin-2-amine (135(+));

(−)-N-(2-cyclopropoxy-1-(4-(difluoromethoxy)-2-fluorophenyl)ethyl)-5-(5-(difluoromethyl)-1,3,4-oxadiazol-2-yl)pyrimidin-2-amine (135(−));

N-(2-cyclopropoxy-1-(4-(trifluoromethoxy)phenyl)ethyl)-5-(5-(difluoromethyl)-1,3,4-oxadiazol-2-yl)pyrimidin-2-amine (136);

(+)—N-(2-cyclopropoxy-1-(4-(trifluoromethoxy)phenyl)ethyl)-5-(5-(difluoromethyl)-1,3,4-oxadiazol-2-yl)pyrimidin-2-amine (136(+));

(−)-N-(2-cyclopropoxy-1-(4-(trifluoromethoxy)phenyl)ethyl)-5-(5-(difluoromethyl)-1,3,4-oxadiazol-2-yl)pyrimidin-2-amine (136(−));

N-(2-((5-(5-(difluoromethyl)-1,3,4-oxadiazol-2-yl)pyrimidin-2-yl)amino)-2-(2,4-difluorophenyl)ethyl)-N-methylmethanesulfonamide (137);

(+)—N-(2-((5-(5-(difluoromethyl)-1,3,4-oxadiazol-2-yl)pyrimidin-2-yl)amino)-2-(2,4-difluorophenyl)ethyl)-N-methylmethanesulfonamide (137(+));

N-(2-((5-(5-(difluoromethyl)-1,3,4-oxadiazol-2-yl)pyrimidin-2-yl)amino)-2-(2,4-difluorophenyl)ethyl)-N-(2,2,2-trifluoroethyl)methanesulfonamide (138);

(+)—N-(2-((5-(5-(difluoromethyl)-1,3,4-oxadiazol-2-yl)pyrimidin-2-yl)amino)-2-(2,4-difluorophenyl)ethyl)-N-(2,2,2-trifluoroethyl)methanesulfonamide (138(+));

N-(2-((5-(5-(difluoromethyl)-1,3,4-oxadiazol-2-yl)pyrimidin-2-yl)amino)-2-(2,4-difluorophenyl)ethyl)ethanesulfonamide (139);

(+)—N-(2-((5-(5-(difluoromethyl)-1,3,4-oxadiazol-2-yl)pyrimidin-2-yl)amino)-2-(2,4-difluorophenyl)ethyl)ethanesulfonamide (139(+));

N-(2-((5-(5-(difluoromethyl)-1,3,4-oxadiazol-2-yl)pyrimidin-2-yl)amino)-2-(2,4-difluorophenyl)ethyl)-N-methylethanesulfonamide (140);

(+)—N-(2-((5-(5-(difluoromethyl)-1,3,4-oxadiazol-2-yl)pyrimidin-2-yl)amino)-2-(2,4-difluorophenyl)ethyl)-N-methylethanesulfonamide (140(+));

N-(2-((5-(5-(difluoromethyl)-1,3,4-oxadiazol-2-yl)pyrimidin-2-yl)amino)-2-(2,4-difluorophenyl)ethyl)-N-(2,2,2-trifluoroethyl)ethanesulfonamide (141);

(+)—N-(2-((5-(5-(difluoromethyl)-1,3,4-oxadiazol-2-yl)pyrimidin-2-yl)amino)-2-(2,4-difluorophenyl)ethyl)-N-(2,2,2-trifluoroethyl)ethanesulfonamide (141(+));

N-(2-((5-(5-(difluoromethyl)-1,3,4-oxadiazol-2-yl)pyrimidin-2-yl)amino)-2-(2,4-difluorophenyl)ethyl)cyclopropanesulfonamide (142);

(+)—N-(2-((5-(5-(difluoromethyl)-1,3,4-oxadiazol-2-yl)pyrimidin-2-yl)amino)-2-(2,4-difluorophenyl)ethyl)cyclopropanesulfonamide (142(+));

N-(2-((5-(5-(difluoromethyl)-1,3,4-oxadiazol-2-yl)pyrimidin-2-yl)amino)-2-(2,4-difluorophenyl)ethyl)-N-methylcyclopropanesulfonamide (143);

(+)—N-(2-((5-(5-(difluoromethyl)-1,3,4-oxadiazol-2-yl)pyrimidin-2-yl)amino)-2-(2,4-difluorophenyl)ethyl)-N-methylcyclopropanesulfonamide (143(+));

N-(2-((5-(5-(difluoromethyl)-1,3,4-oxadiazol-2-yl)pyrimidin-2-yl)amino)-2-(2,4-difluorophenyl)ethyl)-N-(2,2,2-trifluoroethyl)cyclopropanesulfonamide (144);

(+)—N-(2-((5-(5-(difluoromethyl)-1,3,4-oxadiazol-2-yl)pyrimidin-2-yl)amino)-2-(2,4-difluorophenyl)ethyl)-N-(2,2,2-trifluoroethyl)cyclopropanesulfonamide (144(+));

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-methylmethanesulfonamide (145);

(+)—N-(2-(4-(difluoromethoxy)-2-fluorophenyl)-2-((5-(5-(difluoromethyl)-1,3,4-oxadiazol-2-yl)pyrimidin-2-yl)amino)ethyl)-N-methylmethanesulfonamide (145(+));

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-(2,2,2-trifluoroethyl)methanesulfonamide (146);

(+)—N-(2-(4-(difluoromethoxy)-2-fluorophenyl)-2-((5-(5-(difluoromethyl)-1,3,4-oxadiazol-2-yl)pyrimidin-2-yl)amino)ethyl)-N-(2,2,2-trifluoroethyl)methanesulfonamide (146(+));

N-(2-(4-(difluoromethoxy)-2-fluorophenyl)-2-((5-(5-(difluoromethyl)-1,3,4-oxadiazol-2-yl)pyrimidin-2-yl)amino)ethyl)ethanesulfonamide (147);

(+)—N-(2-(4-(difluoromethoxy)-2-fluorophenyl)-2-((5-(5-(difluoromethyl)-1,3,4-oxadiazol-2-yl)pyrimidin-2-yl)amino)ethyl)ethanesulfonamide (147(+));

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-methylethanesulfonamide (148);

(+)—N-(2-(4-(difluoromethoxy)-2-fluorophenyl)-2-((5-(5-(difluoromethyl)-1,3,4-oxadiazol-2-yl)pyrimidin-2-yl)amino)ethyl)-N-methylethanesulfonamide (148(+));

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-(2,2,2-trifluoroethyl)ethanesulfonamide (149);

(+)—N-(2-(4-(difluoromethoxy)-2-fluorophenyl)-2-((5-(5-(difluoromethyl)-1,3,4-oxadiazol-2-yl)pyrimidin-2-yl)amino)ethyl)-N-(2,2,2-trifluoroethyl)ethanesulfonamide (149(+));

N-(2-(4-(difluoromethoxy)-2-fluorophenyl)-2-((5-(5-(difluoromethyl)-1,3,4-oxadiazol-2-yl)pyrimidin-2-yl)amino)ethyl)cyclopropanesulfonamide (150);

(+)—N-(2-(4-(difluoromethoxy)-2-fluorophenyl)-2-((5-(5-(difluoromethyl)-1,3,4-oxadiazol-2-yl)pyrimidin-2-yl)amino)ethyl)cyclopropanesulfonamide (150(+));

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-methylcyclopropanesulfonamide (151);

(+)—N-(2-(4-(difluoromethoxy)-2-fluorophenyl)-2-((5-(5-(difluoromethyl)-1,3,4-oxadiazol-2-yl)pyrimidin-2-yl)amino)ethyl)-N-methylcyclopropanesulfonamide (151(+));

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-(2,2,2-trifluoroethyl)cyclopropanesulfonamide (152);

(+)—N-(2-(4-(difluoromethoxy)-2-fluorophenyl)-2-((5-(5-(difluoromethyl)-1,3,4-oxadiazol-2-yl)pyrimidin-2-yl)amino)ethyl)-N-(2,2,2-trifluoroethyl)cyclopropanesulfonamide (152(+));

N-(2-((5-(5-(difluoromethyl)-1,3,4-oxadiazol-2-yl)pyrimidin-2-yl)amino)-2-(4-(trifluoromethoxy)phenyl)ethyl)-N-methylmethanesulfonamide (153);

(+)—N-(2-((5-(5-(difluoromethyl)-1,3,4-oxadiazol-2-yl)pyrimidin-2-yl)amino)-2-(4-(trifluoromethoxy)phenyl)ethyl)-N-methylmethanesulfonamide (153(+));

N-(2-((5-(5-(difluoromethyl)-1,3,4-oxadiazol-2-yl)pyrimidin-2-yl)amino)-2-(4-(trifluoromethoxy)phenyl)ethyl)-N-(2,2,2-trifluoroethyl)methanesulfonamide (154);

(+)—N-(2-((5-(5-(difluoromethyl)-1,3,4-oxadiazol-2-yl)pyrimidin-2-yl)amino)-2-(4-(trifluoromethoxy)phenyl)ethyl)-N-(2,2,2-trifluoroethyl)methanesulfonamide (154(+));

N-(2-((5-(5-(difluoromethyl)-1,3,4-oxadiazol-2-yl)pyrimidin-2-yl)amino)-2-(4-(trifluoromethoxy)phenyl)ethyl)ethanesulfonamide (155);

(+)—N-(2-((5-(5-(difluoromethyl)-1,3,4-oxadiazol-2-yl)pyrimidin-2-yl)amino)-2-(4-(trifluoromethoxy)phenyl)ethyl)ethanesulfonamide (155(+));

N-(2-((5-(5-(difluoromethyl)-1,3,4-oxadiazol-2-yl)pyrimidin-2-yl)amino)-2-(4-(trifluoromethoxy)phenyl)ethyl)-N-methylethanesulfonamide (156);

(+)—N-(2-((5-(5-(difluoromethyl)-1,3,4-oxadiazol-2-yl)pyrimidin-2-yl)amino)-2-(4-(trifluoromethoxy)phenyl)ethyl)-N-methylethanesulfonamide (156(+));

N-(2-((5-(5-(difluoromethyl)-1,3,4-oxadiazol-2-yl)pyrimidin-2-yl)amino)-2-(4-(trifluoromethoxy)phenyl)ethyl)-N-(2,2,2-trifluoroethyl)ethanesulfonamide (157);

(+)—N-(2-((5-(5-(difluoromethyl)-1,3,4-oxadiazol-2-yl)pyrimidin-2-yl)amino)-2-(4-(trifluoromethoxy)phenyl)ethyl)-N-(2,2,2-trifluoroethyl)ethanesulfonamide (157(+));

N-(2-((5-(5-(difluoromethyl)-1,3,4-oxadiazol-2-yl)pyrimidin-2-yl)amino)-2-(4-(trifluoromethoxy)phenyl)ethyl)cyclopropanesulfonamide (158);

(+)—N-(2-((5-(5-(difluoromethyl)-1,3,4-oxadiazol-2-yl)pyrimidin-2-yl)amino)-2-(4-(trifluoromethoxy)phenyl)ethyl)cyclopropanesulfonamide (158(+));

N-(2-((5-(5-(difluoromethyl)-1,3,4-oxadiazol-2-yl)pyrimidin-2-yl)amino)-2-(4-(trifluoromethoxy)phenyl)ethyl)-N-methylcyclopropanesulfonamide (159);

(+)—N-(2-((5-(5-(difluoromethyl)-1,3,4-oxadiazol-2-yl)pyrimidin-2-yl)amino)-2-(4-(trifluoromethoxy)phenyl)ethyl)-N-methylcyclopropanesulfonamide (159(+));

N-(2-((5-(5-(difluoromethyl)-1,3,4-oxadiazol-2-yl)pyrimidin-2-yl)amino)-2-(4-(trifluoromethoxy)phenyl)ethyl)-N-(2,2,2-trifluoroethyl)cyclopropanesulfonamide (160);

(+)—N-(2-((5-(5-(difluoromethyl)-1,3,4-oxadiazol-2-yl)pyrimidin-2-yl)amino)-2-(4-(trifluoromethoxy)phenyl)ethyl)-N-(2,2,2-trifluoroethyl)cyclopropanesulfonamide (160(+));

5-(5-(difluoromethyl)-1,3,4-oxadiazol-2-yl)-N-(1-(4-fluorophenyl)-2-(methylsulfonyl)ethyl)pyrimidin-2-amine (161);

(+)-5-(5-(difluoromethyl)-1,3,4-oxadiazol-2-yl)-N-(1-(4-fluorophenyl)-2-(methylsulfonyl)ethyl)pyrimidin-2-amine (161(+));

(−)-5-(5-(difluoromethyl)-1,3,4-oxadiazol-2-yl)-N-(1-(4-fluorophenyl)-2-(methylsulfonyl)ethyl)pyrimidin-2-amine (161(−));

5-(5-(difluoromethyl)-1,3,4-oxadiazol-2-yl)-N-(1-(4-fluorophenyl)-2-(2,2,2-trifluoroethoxy)ethyl)pyrimidin-2-amine (162);

(+)-5-(5-(difluoromethyl)-1,3,4-oxadiazol-2-yl)-N-(1-(4-fluorophenyl)-2-(2,2,2-trifluoroethoxy)ethyl)pyrimidin-2-amine (162(+));

(−)-5-(5-(difluoromethyl)-1,3,4-oxadiazol-2-yl)-N-(1-(4-fluorophenyl)-2-(2,2,2-trifluoroethoxy)ethyl)pyrimidin-2-amine (162(−));

5-(5-(difluoromethyl)-1,3,4-oxadiazol-2-yl)-N-(1-(2,4-difluorophenyl)-2-(2,2,2-trifluoroethoxy)ethyl)pyrimidin-2-amine (163);

(+)-5-(5-(difluoromethyl)-1,3,4-oxadiazol-2-yl)-N-(1-(2,4-difluorophenyl)-2-(2,2,2-trifluoroethoxy)ethyl)pyrimidin-2-amine (163(+));

(−)-5-(5-(difluoromethyl)-1,3,4-oxadiazol-2-yl)-N-(1-(2,4-difluorophenyl)-2-(2,2,2-trifluoroethoxy)ethyl)pyrimidin-2-amine (163(−));

N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)ethanesulfonamide (164);

(+)—N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)ethanesulfonamide (164(+));

(−)-N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)ethanesulfonamide (164(−));

N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)cyclopropanesulfonamide (165);

(+)—N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)cyclopropanesulfonamide (165(+));

(−)-N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)cyclopropanesulfonamide (165(−));

N-(2-((5-(5-(difluoromethyl)-1,3,4-oxadiazol-2-yl)pyrimidin-2-yl)amino)-2-(4-fluorophenyl)ethyl)-N-methylacetamide (166);

(+)—N-(2-((5-(5-(difluoromethyl)-1,3,4-oxadiazol-2-yl)pyrimidin-2-yl)amino)-2-(4-fluorophenyl)ethyl)-N-methylacetamide (166(+));

(−)-N-(2-((5-(5-(difluoromethyl)-1,3,4-oxadiazol-2-yl)pyrimidin-2-yl)amino)-2-(4-fluorophenyl)ethyl)-N-methylacetamide (166(−));

N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)acetamide (167);

(+)—N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)acetamide (167(+));

(−)-N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)acetamide (167(−));

N-(2-((5-(5-(difluoromethyl)-1,3,4-oxadiazol-2-yl)pyrimidin-2-yl)amino)-2-(4-fluorophenyl)ethyl)cyclopropanecarboxamide (168);

(+)—N-(2-((5-(5-(difluoromethyl)-1,3,4-oxadiazol-2-yl)pyrimidin-2-yl)amino)-2-(4-fluorophenyl)ethyl)cyclopropanecarboxamide (168(+));

(−)-N-(2-((5-(5-(difluoromethyl)-1,3,4-oxadiazol-2-yl)pyrimidin-2-yl)amino)-2-(4-fluorophenyl)ethyl)cyclopropanecarboxamide (168(−));

N-(2-((5-(5-(difluoromethyl)-1,3,4-oxadiazol-2-yl)pyrimidin-2-yl)amino)-2-(4-fluorophenyl)ethyl)-N-methylcyclopropanecarboxamide (169);

(+)—N-(2-((5-(5-(difluoromethyl)-1,3,4-oxadiazol-2-yl)pyrimidin-2-yl)amino)-2-(4-fluorophenyl)ethyl)-N-methylcyclopropanecarboxamide (169(+));

(−)-N-(2-((5-(5-(difluoromethyl)-1,3,4-oxadiazol-2-yl)pyrimidin-2-yl)amino)-2-(4-fluorophenyl)ethyl)-N-methylcyclopropanecarboxamide (169(−));

N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)cyclopropanecarboxamide (170);

(+)—N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)cyclopropanecarboxamide (170(+));

(−)-N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)cyclopropanecarboxamide (170(−));

N-(2-((5-(5-(difluoromethyl)-1,3,4-oxadiazol-2-yl)pyrimidin-2-yl)amino)-2-(3,4-difluorophenyl)ethyl)methanesulfonamide (171);

(+)—N-(2-((5-(5-(difluoromethyl)-1,3,4-oxadiazol-2-yl)pyrimidin-2-yl)amino)-2-(3,4-difluorophenyl)ethyl)methanesulfonamide (171(+));

(−)-N-(2-((5-(5-(difluoromethyl)-1,3,4-oxadiazol-2-yl)pyrimidin-2-yl)amino)-2-(3,4-difluorophenyl)ethyl)methanesulfonamide (171(−));

N-(2-((5-(5-(difluoromethyl)-1,3,4-oxadiazol-2-yl)pyrimidin-2-yl)amino)-2-(3,4-difluorophenyl)ethyl)-N-(2,2,2-trifluoroethyl)methanesulfonamide (172);

(+)—N-(2-((5-(5-(difluoromethyl)-1,3,4-oxadiazol-2-yl)pyrimidin-2-yl)amino)-2-(3,4-difluorophenyl)ethyl)-N-(2,2,2-trifluoroethyl)methanesulfonamide (172(+));

(−)-N-(2-((5-(5-(difluoromethyl)-1,3,4-oxadiazol-2-yl)pyrimidin-2-yl)amino)-2-(3,4-difluorophenyl)ethyl)-N-(2,2,2-trifluoroethyl)methanesulfonamide (172(−));

N-(2-(4-chlorophenyl)-2-((5-(5-(difluoromethyl)-1,3,4-oxadiazol-2-yl)pyrimidin-2-yl)amino)ethyl)methanesulfonamide (173);

(+)-N-(2-(4-chlorophenyl)-2-((5-(5-(difluoromethyl)-1,3,4-oxadiazol-2-yl)pyrimidin-2-yl)amino)ethyl)methanesulfonamide (173(+));

(−)-N-(2-(4-chlorophenyl)-2-((5-(5-(difluoromethyl)-1,3,4-oxadiazol-2-yl)pyrimidin-2-yl)amino)ethyl)methanesulfonamide (173(−));

N-(2-(4-chlorophenyl)-2-((5-(5-(difluoromethyl)-1,3,4-oxadiazol-2-yl)pyrimidin-2-yl)amino)ethyl)-N-(2,2,2-trifluoroethyl)methanesulfonamide (174);

(+)-N-(2-(4-chlorophenyl)-2-((5-(5-(difluoromethyl)-1,3,4-oxadiazol-2-yl)pyrimidin-2-yl)amino)ethyl)-N-(2,2,2-trifluoroethyl)methanesulfonamide (174(+));

(−)-N-(2-(4-chlorophenyl)-2-((5-(5-(difluoromethyl)-1,3,4-oxadiazol-2-yl)pyrimidin-2-yl)amino)ethyl)-N-(2,2,2-trifluoroethyl)methanesulfonamide (174(−));

5-(5-(difluoromethyl)-1,3,4-oxadiazol-2-yl)-N-(1-(4-fluorophenyl)-2-(4-(trifluoromethyl)-1H-imidazol-1-yl)ethyl)pyrimidin-2-amine (175);

(+)-5-(5-(difluoromethyl)-1,3,4-oxadiazol-2-yl)-N-(1-(4-fluorophenyl)-2-(4-(trifluoromethyl)-1H-imidazol-1-yl)ethyl)pyrimidin-2-amine (175(+));

(−)-5-(5-(difluoromethyl)-1,3,4-oxadiazol-2-yl)-N-(1-(4-fluorophenyl)-2-(4-(trifluoromethyl)-1H-imidazol-1-yl)ethyl)pyrimidin-2-amine (175(−));

5-(5-(difluoromethyl)-1,3,4-oxadiazol-2-yl)-N-(1-(4-fluorophenyl)-2-(4-(trifluoromethyl)-1H-pyrazol-1-yl)ethyl)pyrimidin-2-amine (176);

(+)-5-(5-(difluoromethyl)-1,3,4-oxadiazol-2-yl)-N-(1-(4-fluorophenyl)-2-(4-(trifluoromethyl)-1H-pyrazol-1-yl)ethyl)pyrimidin-2-amine (176(+));

(−)-5-(5-(difluoromethyl)-1,3,4-oxadiazol-2-yl)-N-(1-(4-fluorophenyl)-2-(4-(trifluoromethyl)-1H-pyrazol-1-yl)ethyl)pyrimidin-2-amine (176(−));

1-(2-((5-(5-(difluoromethyl)-1,3,4-oxadiazol-2-yl)pyrimidin-2-yl)amino)-2-(4-fluorophenyl)ethyl)pyrrolidin-2-one (177);

(+)-1-(2-((5-(5-(difluoromethyl)-1,3,4-oxadiazol-2-yl)pyrimidin-2-yl)amino)-2-(4-fluorophenyl)ethyl)pyrrolidin-2-one (177(+));

(−)-1-(2-((5-(5-(difluoromethyl)-1,3,4-oxadiazol-2-yl)pyrimidin-2-yl)amino)-2-(4-fluorophenyl)ethyl)pyrrolidin-2-one (177(−));

5-(5-(difluoromethyl)-1,3,4-oxadiazol-2-yl)-N-(1-(4-fluorophenyl)-2-(3-(trifluoromethyl)-1H-pyrrol-1-yl)ethyl)pyrimidin-2-amine (178);

(+)-5-(5-(difluoromethyl)-1,3,4-oxadiazol-2-yl)-N-(1-(4-fluorophenyl)-2-(3-(trifluoromethyl)-1H-pyrrol-1-yl)ethyl)pyrimidin-2-amine (178(+));

(−)-5-(5-(difluoromethyl)-1,3,4-oxadiazol-2-yl)-N-(1-(4-fluorophenyl)-2-(3-(trifluoromethyl)-1H-pyrrol-1-yl)ethyl)pyrimidin-2-amine (178(−));

2-((5-(5-(difluoromethyl)-1,3,4-oxadiazol-2-yl)pyrimidin-2-yl)(1-(4-fluorophenyl)cyclopropyl)amino)-N,N-dimethylacetamide (179);

2-((5-(5-(difluoromethyl)-1,3,4-oxadiazol-2-yl)pyrimidin-2-yl)(1-(4-fluorophenyl)cyclopropyl)amino)-N,N-diethylacetamide (180);

2-(dimethylamino)-2-oxoethyl (5-(5-(difluoromethyl)-1,3,4-oxadiazol-2-yl)pyrimidin-2-yl)(1-(4-fluorophenyl)cyclopropyl)carbamate (181);

2-(diethylamino)-2-oxoethyl (5-(5-(difluoromethyl)-1,3,4-oxadiazol-2-yl)pyrimidin-2-yl)(1-(4-fluorophenyl)cyclopropyl)carbamate (182);

2-amino-N-(5-(5-(difluoromethyl)-1,3,4-oxadiazol-2-yl)pyrimidin-2-yl)-N-(1-(4-fluorophenyl)cyclopropyl)acetamide (183); or ((5-(5-(difluoromethyl)-1,3,4-oxadiazol-2-yl)pyrimidin-2-yl)(1-(4-fluorophenyl)cyclopropyl)amino)methyl dihydrogen phosphate (184); and pharmaceutically acceptable salts, co-crystals, tautomers, stereoisomers, solvates, hydrates, polymorphs, isotopically enriched derivatives, and prodrugs thereof.

In one aspect, the compound of Formula I is that wherein the compound inhibits (or is identified to inhibit) histone deacetylase 6 (HDAC6).

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions. The compounds can also attain affinity through weaker interactions with the metal such as van der Waals interactions, pi cation interactions, pi-anion interactions, dipole-dipole interactions, ion-dipole interactions. In one aspect, the compound is identified as having a bonding interaction with the metal via the pyrimidine moiety.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In another aspect, provided are pharmaceutical compositions comprising the compound of any of the formula herein (e.g., Formula I) and a pharmaceutically acceptable carrier. In certain embodiments, the pharmaceutical composition comprises an additional therapeutic agent. In certain embodiments, the additional therapeutic agent is an anti-cancer agent (e.g., platinum-based chemotherapeutic agents, vinca alkaloids, Akt inhibitors, alkylating agents, androgen receptor antagonists, anti-estrogens, Bcl-2 inhibitors, BRAF kinase inhibitors, BTK inhibitors, CAR-T Cells, anti-CD38 antibodies, CDK inhibitors, anti-CTLA-4 antibodies, ERK/MAPK inhibitors, farnesyltransferase inhibitors, IL-6 inhibitors, immunomodulatory agents, immuno-oncology agents, JAK2/FLT3 inhibitors, kinesin spindle protein inhibitors, MEK inhibitors, anti-PD-1 antibodies, anti-PD-L1 antibodies, PI3K inhibitors, proteasome inhibitors, radiation (sensitizer), radioisotopes (sensitizer), synthetic retinoids (AM80), taxanes, tyrosine kinase inhibitors, VDR agonists, VEGF inhibitors, or oncolytic viruses). In certain embodiments, the pharmaceutical composition comprises two or more additional therapeutic agents selected from those listed above.

In another aspect, provided are methods of inhibiting metalloenzyme activity comprising contacting a compound of any of the formula herein (e.g., Formula I) with a metalloenzyme. In certain embodiments, the contacting is in vivo. In certain embodiments, the contacting is in vitro. In certain embodiments, the metalloenzyme comprises a metal atom that is iron, zinc, heme iron, manganese, magnesium, iron sulfide cluster, nickel, molybdenum, or copper. In certain embodiments, the metalloenzyme is a histone deacetylase (HDAC). In certain embodiments, the metalloenzyme is HDAC6.

In another aspect, provided are methods of modulating metalloenzyme activity in a subject, comprising contacting the subject with a compound of any of the formula herein (e.g., Formula I), in an amount and under conditions sufficient to modulate metalloenzyme activity.

In another aspect, provided are methods of treating a subject suffering from or susceptible to a disorder or disease, wherein the subject has been identified as in need of treatment for the disorder or disease, comprising administering to said subject in need thereof, an effective amount of a compound or pharmaceutical composition of any of the formula herein (e.g., Formula I), such that said subject is treated for said disorder.

In another aspect the subject is an animal other than a human.

In another aspect, provided are methods of treating a subject suffering from or susceptible to a metalloenzyme-related disorder or disease, comprising administering to the subject an effective amount of a compound or pharmaceutical composition of any of the formula herein (e.g., Formula I).

In another aspect, provided are methods of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of any of the formula herein (e.g., Formula I), such that said subject is treated for said disorder.

In another aspect, provided are methods of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any of the formula herein (e.g., Formula I), such that metalloenzyme activity in said subject is modulated (e.g., down regulated, inhibited).

The methods herein include those wherein the disease or disorder is mediated by a histone deacetylase (e.g., HDAC6).

The methods herein include those wherein the disease or disorder is cancer, a proliferative disease, a neurodegenerative disease, pain, an autoimmune or inflammatory disorder, an infection, a metabolic disorder, an hematologic disorder, or a cardiovascular disease, or a combination thereof.

The methods herein include those wherein the disease or disorder is cancer or a proliferative disease, wherein the cancer or proliferative disease includes a carcinoma, a sarcoma, a leukemia, a blastoma, a lymphoma, a myeloma, a melanoma, or a combination thereof.

The methods herein include those wherein the disease or disorder is multiple myeloma, melanoma, breast cancer, pancreatic cancer, ovarian cancer, prostate cancer, hepatocellular cancer, renal cancer, leukemia, T-cell lymphoma, cardiac cancer, bone cancer, glioblastoma, neuroblastoma, oral squamous cell carcinoma, urothelial cancer, lung cancer, cervical cancer, rectal cancer, liver cancer, pancreatic cancer, brain cancer, kidney cancer, stomach cancer, skin cancer, colon cancer, head and neck squamous cell carcinoma, Burkitt's Lymphoma, esophageal cancer, Hodgkin's lymphoma, bladder cancer, gastric cancer, or a combination thereof.

The methods herein include those wherein the disease or disorder is rheumatoid arthritis, spondylitis arthritis, psoriatic arthritis, multiple sclerosis, systemic lupus erythematosus, inflammatory bowel disease, graft versus host disease, transplant rejection, fibrotic disease, Crohn's Disease, type-1 diabetes, eczema, psoriasis, sepsis, airway hyperresponsiveness, ulcerative colitis, or a combination thereof.

The methods herein include those wherein the disease or disorder is peripheral neuropathy, chemotherapy induced peripheral neuropathy, diabetic peripheral neuropathy, neuropathy, neuralgia, trigeminal neuralgia, postherpetic neuralgia, autoimmune peripheral neuropathy, Leber's hereditary optic neuropathy, POEMS syndrome, Cattleman disease, pain due to tumor infiltration, HIV related peripheral neuropathy, post-amputation phantom pain syndrome, Charcot-Marie Tooth disease, medication induced peripheral neuropathy, or a combination thereof.

The methods herein include those wherein the disease or disorder is epilepsy, attention deficit disorder, depression, anxiety, Alzheimer's disease, Parkinson's Disease, Huntington's Disease, amyotrophic lateral sclerosis, spinal muscular atrophy, essential tremor, central nervous system trauma, multiple sclerosis, Charcot-Marie-Tooth (MCT), cerebral ischemia, stroke, Gulf War Illness, or a combination thereof.

The methods herein include those wherein the disease or disorder is an infection caused by virus, fungus, or bacteria, or a combination thereof.

The methods herein include those wherein the disease or disorder is metabolic syndrome, diabetes, obesity, high blood pressure, heart failure, cyst growth in autosomal dominant polycystic kidney disease (ADPKD), or a combination thereof.

The methods herein include those wherein the disease or disorder is cardiovascular stress, pressure overload, chronic ischemia, infarction-reperfusion injury, hypertension, atherosclerosis, peripheral artery disease, heart failure, hypertrophy, angina, arrhythmias, hypercholesterolemia, atherosclerosis, or stroke, or a combination thereof.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present disclosure "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the present disclosure.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 μg/kg to about 200 mg/kg, preferably about 0.01 mg/kg to about 200 mg/kg, more preferably about 0.015 mg/kg to about 30 mg/kg of body weight. In other embodiments, the therapeutically effect amount may range from about 1.0 pM to about 10 μM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 μg/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the present disclosure are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore, the compounds of the present disclosure include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a $C_1$-$C_6$ alkyl chain. Examples of alkyl groups include methyl, ethyl, n-propyl, isopropyl, tert-butyl, and n-pentyl. Alkyl groups may be optionally substituted with one or more substituents.

The term "haloalkyl" refers to an alkyl group that is substituted by one or more halo substituents. Examples of haloalkyl groups include fluoromethyl, difluoromethyl, trifluoromethyl, bromomethyl, chloromethyl, and 2,2,2-trifluoroethyl.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "arylalkenyl" refers to an unsaturated hydrocarbon chain that may be a straight chain or branched chain, containing 2 to 12 carbon atoms and at least one carbon-carbon double bond wherein one or more of the $sp^2$ hybridized carbons of the alkenyl unit attaches to an aryl moiety. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The term "arylalkynyl" refers to an unsaturated hydrocarbon chain that may be a straight chain or branched chain, containing 2 to 12 carbon atoms and at least one carbon-carbon triple bond wherein one or more of the sp hybridized carbons of the alkynyl unit attaches to an aryl moiety. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl substituent.

As used herein, the term "halogen", "hal" or "halo" means —F, —C$_1$, —Br or —I.

The term "alkylthio" refers to an —S-alkyl substituent.

The term "alkoxyalkyl" refers to an -alkyl-O-alkyl substituent.

The term "haloalkoxy" refers to an —O-alkyl that is substituted by one or more halo substituents. Examples of haloalkoxy groups include trifluoromethoxy, and 2,2,2-trifluoroethoxy.

The term "haloalkoxyalkyl" refers to an -alkyl-O-alkyl' where the alkyl' is substituted by one or more halo substituents.

The term "haloalkylaminocarbonyl" refers to a —C(O)-amino-alkyl where the alkyl is substituted by one or more halo substituents.

The term "haloalkylthio" refers to an —S-alkyl that is substituted by one or more halo substituents. Examples of haloalkylthio groups include trifluoromethylthio, and 2,2,2-trifluoroethylthio.

The term "haloalkylcarbonyl" refers to an —C(O)-alkyl that is substituted by one or more halo substituents. An example of a haloalkylcarbonyl group includes trifluoroacetyl.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "cycloalkoxy" refers to an —O-cycloalkyl substituent.

The term "cycloalkoxyalkyl" refers to an -alkyl-O-cycloalkyl substituent.

The term "cycloalkylalkoxy" refers to an —O-alkyl-cycloalkyl substituent.

The term "cycloalkylaminocarbonyl" refers to an —C(O)—NH-cycloalkyl substituent.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "aryloxy" refers to an —O-aryl substituent.

The term "arylalkoxy" refers to an —O-alkyl-aryl substituent.

The term "arylalkylthio" refers to an —S-alkyl-aryl substituent.

The term "arylthioalkyl" refers to an -alkyl-S-aryl substituent.

The term "arylalkylaminocarbonyl" refers to a —C(O)-amino-alkyl-aryl substituent.

The term "arylalkylsulfonyl" refers to an —S(O)$_2$-alkyl-aryl substituent.

The term "arylalkylsulfinyl" refers to an —S(O)-alkyl-aryl substituent.

The term "aryloxyalkyl" refers to an -alkyl-O-aryl substituent.

The term "alkylaryl" refers to an -aryl-alkyl substituent.

The term "arylalkyl" refers to an -alkyl-aryl substituent.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heteroarylalkyl" refers to an -alkyl-heteroaryl substituent.

The term "heteroaryloxy" refers to an —O-heteroaryl substituent.

The term "heteroarylalkoxy" refers to an —O-alkyl-heteroaryl substituent.

The term "heteroaryloxyalkyl" refers to an -alkyl-O-heteroaryl substituent.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "heterocycloalkylalkyl" refers to an -alkyl-heterocycloalkyl substituent.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxyalkyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carboxamido, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl. In certain embodiments, substituents on any group include alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, thiocarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, or amido. In certain embodiments, substituents on any group include alkyl, halogen, haloalkyl, cyano, nitro, alkoxy, hydroxyl, hydroxylalkyl, carboxyl, formyl, alkylcarbonyl, alkoxycarbonyl, alkylcarbonyloxy, thio, mercapto, mercaptoalkyl, amino, aminoalkyl, dialkylamino, alkylcarbonylamino, alkylaminocarbonyl, or alkylamino.

Compounds of the present disclosure can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. Design And Optimization in Organic Synthesis, 2$^{nd}$ Edition, Carlson R, Ed, 2005; Elsevier Science Ltd.; Jahnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

As can be appreciated by the skilled artisan, methods of synthesizing the compounds of the formulae herein will be evident to those of ordinary skill in the art, including in the schemes and examples herein. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present disclosure.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present disclosure. The compounds herein may also be represented in multiple tautomeric forms, in such instances, the present disclosure expressly includes all tautomeric forms of the compounds described herein, even though only a single tautomeric form may be represented. All such isomeric forms of such compounds herein are expressly included in the present disclosure. All crystal forms and polymorphs of the compounds described herein are expressly included in the present disclosure. Also embodied are extracts and fractions comprising compounds of the present disclosure. The term isomers is intended to include diastereoisomers, enantiomers, regioisomers, structural isomers, rotational isomers, tautomers, and the like. For compounds which contain one or more stereogenic centers, e.g., chiral compounds, the methods of the present disclosure may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the present disclosure is administered to cells or a subject.

Reference to compounds of Formula (I) herein include those compounds of Formulae I-a to I-i.

Methods of Treatment

In one aspect, provided are methods of treating a subject suffering from or susceptible to a disorder or disease, comprising administering to the subject an effective amount of a compound or pharmaceutical composition of any of the formula herein (e.g., Formula I).

In other aspects, provided are methods of treating a subject suffering from or susceptible to a disorder or disease, wherein the subject has been identified as in need of treatment for a metalloenzyme-mediated disorder or disease, comprising administering to said subject in need thereof, an effective amount of a compound or pharmaceutical composition of any of the formula herein (e.g., Formula I), such that said subject is treated for said disorder.

In one aspect, provided are methods of modulating the metalloenzyme activity of a cell in a subject, comprising contacting the subject with a compound of any of the formula herein (e.g., Formula I), in an amount and under conditions sufficient to modulate metalloenzyme activity.

In one embodiment, the modulation is inhibition.

In another aspect, provided are methods of treating a subject suffering from or susceptible to a metalloenzyme-mediated disorder or disease, comprising administering to the subject an effective amount of a compound or pharmaceutical composition of any of the formula herein (e.g., Formula I).

In other aspects, provided are methods of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of any of the formula herein (e.g., Formula I), such that said subject is treated for said disorder.

In certain embodiments, provided are methods of treating a disease, disorder or symptom thereof, wherein the disorder is cancer, a proliferative disease, a neurodegenerative disease, pain, an autoimmune or inflammatory disorder, an infection, a metabolic disorder, an hematologic disorder, or a cardiovascular disease.

In certain embodiments, the disorder or disease is cancer or a proliferative disease. In certain embodiments, the cancer or proliferative disease includes a carcinoma, a sarcoma, a leukemia, a blastoma, a lymphoma, a myeloma, or a melanoma, or a combination thereof. In certain embodiments, the disorder or disease is multiple myeloma, melanoma, breast cancer, pancreatic cancer, ovarian cancer, prostate cancer, hepatocellular cancer, renal cancer, leukemia, T-cell lymphoma, cardiac cancer, bone cancer, glioblastoma, neuroblastoma, oral squamous cell carcinoma, urothelial cancer, lung cancer, cervical cancer, rectal cancer, liver cancer, pancreatic cancer, brain cancer, kidney cancer, stomach cancer, skin cancer, colon cancer, head and neck squamous cell carcinoma, Burkitt's Lymphoma, esophageal cancer, Hodgkin's lymphoma, bladder cancer, or gastric cancer, or a combination thereof.

In certain embodiments, the disorder or disease is rheumatoid arthritis, spondylitis arthritis, psoriatic arthritis, multiple sclerosis, systemic lupus erythematosus, inflammatory bowel disease, graft versus host disease, transplant rejection, fibrotic disease, Crohn's Disease, type-1 diabetes, eczema, psoriasis, sepsis, airway hyperresponsiveness, ulcerative colitis, or a combination thereof.

In certain embodiments, the disorder or disease is peripheral neuropathy, chemotherapy induced peripheral neuropathy, diabetic peripheral neuropathy, neuropathy, neuralgia, trigeminal neuralgia, postherpetic neuralgia, autoimmune peripheral neuropathy, Leber's hereditary optic neuropathy, POEMS syndrome, Cattleman disease, pain due to tumor infiltration, HIV related peripheral neuropathy, post-amputation phantom pain syndrome, Charcot-Marie Tooth disease, medication induced peripheral neuropathy, or a combination thereof.

In certain embodiments, the disorder or disease is peripheral neuropathy, including drug induced peripheral neuropathy (e.g., chemotherapy induced peripheral neuropathy). In certain embodiments, the disorder or disease is peripheral neuropathy induced by treatment with an anti-cancer agent (e.g., alkylating agents, CAR-T Cells, anti-CD38 antibodies, anti-CTLA-4 antibodies, epothilones, immunomodulatory agents, immuno-oncology agents, anti-PD-1 antibodies, anti-PD-L1 antibodies, proteasome inhibitors, taxanes, platinum-based chemotherapeutic agents, and *vinca* alkaloids). In certain embodiments, the disorder or disease is peripheral neuropathy induced by treatment with arsenic trioxide, bortezomib, cabazitaxel, carboplatin, carfilzomib, cisplatin, carboplatin, oxaliplatin, cyclophosphamide, darzalex, docetaxel, elotuzumab, eribulin, fluorouracil (5-FU), gefitinib, gemcitabine hydrochloride, indatuximab, ixazomib, ravtansine, ipilimumab, ixabepilone, lenalidomide, nab-paclitaxel, nivolumab, oxaliplatin, paclitaxel, pomalidomide, temozolomide, thalidomide, vinblastine, vincristine, vindesine, or vinorelbine.

In certain embodiments, the disorder or disease is peripheral neuropathy induced by treatment with a drug other than an anti-cancer agent (e.g., cardiovascular agents, statins, antimicrobial agents, immunosuppressants, anti-alcohol drugs, anticonvulsants, TNF-α inhibitors, and nucleoside analog reverse transcriptase inhibitors (NRTIs)). In certain embodiments, the disorder or disease is peripheral neuropathy induced by treatment with atorvastatin, pitavastatin, lovastatin, simvastatin, pravastatin, fluvastatin, rosuvastatin, amiodarone, chloramphenicol, chloroquine, dapsone, fluoroquinolones, hydralazine, etanercept, ethambutol, isoniazid, linezolid, metronidazole, nitrofurantoin, leflunomide, phenytoin, didanosine, stavudine, or zalcitabine.

In certain embodiments, the disorder or disease is cancer and peripheral neuropathy (e.g., chemotherapy induced peripheral neuropathy).

In certain embodiments, the disorder or disease is epilepsy, attention deficit disorder, depression, anxiety, Alzheimer's disease, Parkinson's Disease, Huntington's Disease, amyotrophic lateral sclerosis, spinal muscular atrophy, essential tremor, central nervous system trauma, multiple sclerosis, Charcot-Marie-Tooth (MCT), cerebral ischemia, stroke, Gulf War Illness, or a combination thereof.

In certain embodiments, the disorder or disease is an infection caused by virus, fungus, or bacteria, or a combination thereof.

In certain embodiments, the disorder or disease is metabolic syndrome, diabetes, obesity, high blood pressure, heart failure, cyst growth in autosomal dominant polycystic kidney disease (ADPKD), or a combination thereof.

In certain embodiments, the disorder or disease is cardiovascular stress, pressure overload, chronic ischemia, infarction-reperfusion injury, hypertension, atherosclerosis, peripheral artery disease, heart failure, hypertrophy, angina, arrhythmias, hypercholesterolemia, atherosclerosis, or stroke, or a combination thereof.

In certain embodiments, the subject is a mammal, preferably a primate or human.

In another embodiment, provided are methods as described above, wherein the effective amount of the compound of any of the formula herein (e.g., Formula I) is as described above.

In another embodiment, provided are methods as described above, wherein the compound of any of the formula herein (e.g., Formula I) is administered intravenously, intramuscularly, subcutaneously, intracerebroventricularly, orally or topically.

In another embodiment, provided are methods as described herein wherein the compound of any of the formula herein (e.g., Formula I) demonstrates selectivity for an activity range against a target enzyme (e.g., HDAC6 $IC_{50}$<1.0 µM).

In certain embodiments, the compound of any of the formula herein (e.g., Formula I) selectively inhibits HDAC6 over another protein. In some embodiments, the compound of any of the formula herein (e.g., Formula I) selectively inhibits HDAC6 over another HDAC. In some embodiments, the compound of any of the formula herein (e.g., Formula I) selectively inhibits HDAC6 over a class I HDAC (e.g., HDAC1, HDAC2, HDAC3, HDAC8). In some embodiments, the compound of any of the formula herein (e.g., Formula I) selectively inhibits HDAC6 over a class IIA HDAC (e.g., HDAC4, HDAC5, HDAC7, HDAC9). In some embodiments, the compound of any of the formula herein (e.g., Formula I) selectively inhibits HDAC6 over a class IIB HDAC (e.g., HDAC10). In some embodiments, the compound of any of the formula herein (e.g., Formula I) selectively inhibits HDAC6 over a class III HDAC (e.g., SIRT1, SIRT2, SIRT3, SIRT4, SIRT5, SIRT6, SIRT7). In some embodiments, the compound of any of the formula herein (e.g., Formula I) selectively inhibits HDAC6 over a class IV HDAC (e.g., HDAC11). In some embodiments, the compound of any of the formula herein (e.g., Formula I) selectively inhibits HDAC6 over HDAC1, HDAC2, HDAC3, HDAC4, HDAC5, HDAC7, HDAC8, HDAC9, HDAC10, and HDAC11. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In other embodiments, provided are methods as described above, wherein the compound of any of the formula herein (e.g., Formula I) is administered alone or in combination with one or more other therapeutics. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

Another object of the present disclosure is the use of a compound as described herein (e.g., a compound of Formula I) in the manufacture of a medicament for use in the treatment of a metalloenzyme-mediated disorder or disease. Another object of the present disclosure is the use of a compound as described herein (e.g., a compound of Formula I) for use in the treatment of a metalloenzyme-mediated disorder or disease. Another object of the present disclosure is the use of a compound as described herein (e.g., a compound of Formula I) in the manufacture of an agricultural composition for use in the treatment or prevention of a metalloenzyme-mediated disorder or disease in agricultural or agrarian settings.

Pharmaceutical Compositions

In one aspect, provided are pharmaceutical compositions comprising the compound of any of the formula herein (e.g., Formula I) and a pharmaceutically acceptable carrier.

A compound or composition, as described herein, can be administered in combination with one or more additional therapeutic agents (e.g., therapeutically and/or prophylactically active agents). The compounds or compositions can be administered in combination with additional therapeutic agents that improve their activity (e.g., activity (e.g., potency and/or efficacy) in treating a disease in a subject in need thereof, in preventing a disease in a subject in need thereof, and/or in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional therapeutic agent to exhibit a synergistic effect that is absent in a pharmaceutical composition including one of the compound and the additional therapeutic agent, but not both.

The compound or composition can be administered concurrently with, prior to, or subsequent to one or more additional therapeutic agents, which may be useful as, e.g., combination therapies. Therapeutic agents include therapeutically active agents. Therapeutic agents also include prophylactically active agents. Therapeutic agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional therapeutic agent is a therapeutic agent useful for treating and/or preventing a disease (e.g., cancer, proliferative disease, neurodegenerative disease, autoimmune or inflammatory disorder, infection, metabolic disorder, hematologic disorder, cardiovascular disease). Each additional therapeutic agent may be administered at a dose and/or on a time schedule determined for that therapeutic agent. The additional therapeutic agents may also be administered together with each other and/or with the compound or composition described herein in a single dose or administered separately in different doses. The particular combination to employ in a regimen will take into account compatibility of the compound described herein with the additional therapeutic agent(s) and/or the desired therapeutic and/or prophylactic effect to be achieved. In general, it is expected that the additional therapeutic agent(s) in combination be utilized at levels that do not exceed the levels at which they are utilized individually. In some embodiments, the levels utilized in combination will be lower than those utilized individually.

In certain embodiments, the additional therapeutic agent (e.g., as part of a pharmaceutical composition or a combination therapy) may induce an undesired side effect (e.g., peripheral neuropathy). The compound of Formula I is useful for treatment of the undesired side effect when administered in combination with the additional therapeutic agent (e.g., as part of a pharmaceutical composition or a combination therapy).

The additional therapeutic agents include, but are not limited to, anti-proliferative agents, anti-cancer agents, anti-angiogenesis agents, anti-inflammatory agents, and immunosuppressants. In certain embodiments, the additional therapeutic agent is an immunotherapy. In certain embodiments, the additional therapeutic agent is an anti-proliferative agent. In certain embodiments, the additional therapeutic agent is an anti-cancer agent. In certain embodiments, the anti-cancer agents include, but are not limited to, epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), cell signaling pathway inhibitors (e.g., tyrosine protein kinase inhibitors), modulators of protein stability (e.g., proteasome inhibitors), Hsp90 inhibitors, glucocorticoids, all-trans retinoic acids, anti-estrogens (e.g., tamoxifen, raloxifene, and megestrol), LHRH agonists (e.g., goserelin and leuprolide), anti-androgens (e.g. flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g. dacarbazine, temozolomide), platinum-based chemotherapeutic agents (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g., thapsigargin), thalidomide, lenalidomide, pomalidomide, tyrosine kinase inhibitors (e.g., axitinib (AGO13736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE), ixazomib (NINLARO)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the additional therapeutic agent is an immunotherapy. In certain embodiments, the immunotherapy is useful in the treatment of a cancer. Exemplary immunotherapies include, but are not limited to, T-cell therapies, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies. In certain embodiments, the immunotherapy is a T-cell therapy. In certain embodiments, the T-cell therapy is chimeric antigen receptor T cells (CAR-T). In certain embodiments, the immunotherapy is an antibody. In certain embodiments, the antibody is an anti-PD-1 antibody, an anti-PD-L1 antibody, an anti-CTLA-4 antibody, an anti-TIM3 antibody, an anti-OX40 antibody, an anti-GITR antibody, an anti-LAG-3 antibody, an anti-CD137 antibody, an anti-CD27 antibody, an anti-CD28 antibody, an anti-CD28H antibody, an anti-CD30 antibody, an anti-CD39 antibody, an anti-CD40 antibody, an anti-CD47 antibody, an anti-CD48 antibody, an anti-CD70 antibody, an anti-CD73 antibody, an anti-CD96 antibody, an anti-CD160 antibody, an anti-CD200 antibody, an anti-CD244 antibody, an anti-ICOS antibody, an anti-TNFRSF25 antibody, an anti-TMIGD2 antibody, an anti-DNAM1 antibody, an anti-BTLA antibody, an anti-LIGHT antibody, an anti-TIGIT antibody, an anti-VISTA antibody, an anti-HVEM antibody, an anti-Siglec antibody, an anti-GAL1 antibody, an anti-GAL3 antibody, an anti-GAL9 antibody, an anti-BTNL2 (butrophylins) antibody, an anti-B7-H3 antibody, an anti-B7-H4 antibody, an anti-B7-H5 antibody, an anti-B7-H6 antibody, an anti-KIR antibody, an anti-LIR antibody, an anti-ILT antibody, an anti-MICA antibody, an anti-MICB antibody, an anti-NKG2D antibody, an anti-NKG2A antibody, an anti-TGFβ antibody, an anti-TGFβR antibody, an anti-CXCR4 antibody, an anti-CXCL12 antibody, an anti-CCL2 antibody, an anti-IL-10 antibody, an anti-IL-13 antibody, an anti-IL-23 antibody, an anti-phosphatidylserine antibody, an anti-neuropilin antibody, an anti-GalCer antibody, an anti-HER2 antibody, an anti-VEGFA antibody, an anti-VEGFR antibody, an anti-EGFR antibody, or an anti-Tie2 antibody. In certain embodiments, the antibody is pembrolizumab, nivolumab, pidilizumab, ipilimumab, tremelimumab, durvalumab, atezolizumab, avelumab, PF-06801591, utomilumab, PDR001, PBF-509, MGB453, LAG525, AMP-224, INCSHR1210, INCAGN1876, INCAGN1949, samalizumab, PF-05082566, urelumab, lirilumab, lulizumab, BMS-936559, BMS-936561, BMS-986004, BMS-986012, BMS-986016, BMS-986178, IMP321, IPH2101, IPH2201, varilumab, ulocuplumab, monalizumab, MEDI0562, MEDI0680, MEDI1873, MEDI6383, MEDI6469, MEDI9447, AMG228, AMG820, CC-90002, CDX-1127, CGEN15001T, CGEN15022, CGEN15029, CGEN15049, CGEN15027, CGEN15052, CGEN15092, CX-072, CX-2009, CP-870893, lucatumumab, dacetuzumab, Chi Lob 7/4, RG6058, RG7686, RG7876, RG7888, TRX518, MK-4166, MGA271, IMC-CS4, emactuzumab, trastuzumab, pertuzumab, obinutuzumab, cabiralizumab, margetuximab, enoblituzumab, mogamulizumab, panitumumab, carlumab, bevacizumab, rituximab, or cetuximab.

In certain embodiments, the compounds or pharmaceutical compositions described herein can be administered in combination with an anti-cancer therapy including, but not limited to, surgery, radiation therapy, and transplantation (e.g., stem cell transplantation, bone marrow transplantation).

In certain embodiments, the additional therapeutic agent is selected from the group consisting of platinum-based chemotherapeutic agents, vinca alkaloids, Akt inhibitors, alkylating agents, androgen receptor antagonists, anti-estrogens, Bcl-2 inhibitors, BRAF kinase inhibitors, BTK inhibitors, CAR-T Cells, anti-CD38 antibodies, CDK inhibitors, anti-CTLA-4 antibodies, ERK/MAPK inhibitors, farnesyltransferase inhibitors, IL-6 inhibitors, immunomodulatory agents, immuno-oncology agents, JAK2/FLT3 inhibitors, kinesin spindle protein inhibitors, MEK inhibitors, anti-PD-1 antibodies, anti-PD-L1 antibodies, PI3K inhibitors, proteasome inhibitors, radiation (sensitizer), radioisotopes (sensitizer), synthetic retinoids (AM80), taxanes, tyrosine kinase inhibitors, VDR agonists, VEGF inhibitors, oncolytic viruses, and a combination thereof. In certain embodiments, the additional therapeutic agent is selected from the group consisting of all trans tetinoic acid (ATRA), arsenic trioxide, berberine, bevacizumab, bortezomib, cabazitaxel, carfilzomib, cisplatin, carboplatin, oxaliplatin, clarithromycin, cyclophosphamide, cytarabine, darzalex, dexamethasone, docetaxel, elotuzumab, enzalutamide, epirubicin, fluorouracil (5-FU), gefitinib, gemcitabine hydrochloride, ibrutinib, idelalisib, indatuximab, ixazomib, ravtansine, ipilimumab, lenalidomide, lonafarnib, methotrexate, nab-paclitaxel, nivolumab, paclitaxel, pacritinib, pomalidomide, sorafenib, temozolomide, thalidomide, vemurafenib, vinblastine, vindesine, vinorelbine, and vincristine.

In certain embodiments, the additional therapeutic agent is selected from the group consisting of cardiovascular agents, statins, antimicrobial agents, immunosuppressants, anti-alcohol drugs, anticonvulsants, TNF-α inhibitors, and nucleoside analog reverse transcriptase inhibitors (NRTIs). In certain embodiments, the additional therapeutic agent is atorvastatin, pitavastatin, lovastatin, simvastatin, pravastatin, fluvastatin, rosuvastatin, amiodarone, chloramphenicol, chloroquine, dapsone, fluoroquinolones, hydralazine, etanercept, ethambutol, isoniazid, linezolid, metronidazole, nitrofurantoin, leflunomide, phenytoin, didanosine, stavudine, or zalcitabine.

In one aspect, provided are kits comprising an effective amount of a compound of Formula I, in unit dosage form, together with instructions for administering the compound to a subject suffering from or susceptible to a metalloenzyme-mediated disease or disorder, including cancer, proliferative disease, neurodegenerative disease, autoimmune or inflammatory disorder, infection, metabolic disorder, hematologic disorder, and cardiovascular disease. In other embodiments the disease, disorder or symptom thereof is a carcinoma, a leukemia, a blastoma, a lymphoma, a myeloma, or a melanoma. In other embodiments the disease, disorder or symptom thereof is multiple myeloma, melanoma, breast cancer, pancreatic cancer, ovarian cancer, prostate cancer, hepatocellular cancer, renal cancer, leukemia, T-cell lymphoma, bone cancer, glioblastoma, neuroblastoma, oral squamous cell carcinoma, urothelial cancer, lung cancer, cervical cancer, colon cancer, head and neck squamous cell carcinoma, Burkitt's Lymphoma, esophageal cancer, Hodgkin's lymphoma, bladder cancer, or gastric cancer. In other embodiments the disease, disorder or symptom thereof is rheumatoid arthritis, spondylitis arthritis, psoriatic arthritis, multiple sclerosis, systemic lupus erythematosus, inflammatory bowel disease, graft versus host disease, transplant rejection, fibrotic disease, Crohn's Disease, type-1 diabetes, eczema, psoriasis, sepsis, airway hyperresponsiveness, or ulcerative colitis. In other embodiments the disease, disorder or symptom thereof is epilepsy, attention deficit disorder, Alzheimer's disease, Parkinson's Disease, Huntington's Disease, amyotrophic lateral sclerosis, spinal muscular atrophy, essential tremor, central nervous system trauma, multiple sclerosis, Charcot-Marie-Tooth (MCT), peripheral neuropathy, or cerebral ischemia. In other embodiments the disease, disorder or symptom thereof is an infection caused by virus, fungus, or bacteria. In other embodiments the disease, disorder or symptom thereof is metabolic syndrome, diabetes, obesity, high blood pressure, heart failure, or cyst growth in autosomal dominant polycystic kidney disease (ADPKD). In other embodiments the disease, disorder or symptom thereof is cardiovascular stress, pressure overload, chronic ischemia, infarction-reperfusion injury, hypertension, atherosclerosis, peripheral artery disease, heart failure, hypertrophy, angina, arrhythmias, hypercholesterolemia, atherosclerosis, or stroke.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The present disclosure also provides a pharmaceutical composition, comprising an effective amount a compound described herein and a pharmaceutically acceptable carrier. In an embodiment, a compound of any of the formula herein (e.g., Formula I) is administered to a subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of the disclosure may be varied so as to obtain an amount of the active ingredient which is effective to achieve the desired therapeutic response for a particular patient, composition, and mode of administration, without being toxic (or unacceptably toxic) to the patient.

In use, at least one compound according to the present disclosure is administered in a pharmaceutically effective amount to a subject in need thereof in a pharmaceutical carrier by intravenous, intramuscular, subcutaneous, or intracerebroventricular injection or by oral administration or topical application. In accordance with the present disclosure, a compound of the disclosure may be administered alone or in conjunction with a second, different therapeutic. By "in conjunction with" is meant together, substantially simultaneously or sequentially. In one embodiment, a compound of the disclosure is administered acutely. The compound of the disclosure may therefore be administered for a short course of treatment, such as for about 1 day to about 1 week. In another embodiment, the compound of the disclosure may be administered over a longer period of time to ameliorate chronic disorders, such as, for example, for about one week to several months depending upon the condition to be treated.

By "pharmaceutically effective amount" as used herein is meant an amount of a compound of the disclosure, high enough to significantly positively modify the condition to be treated but low enough to avoid serious side effects (at a reasonable benefit/risk ratio), within the scope of sound medical judgment. A pharmaceutically effective amount of a compound of the disclosure will vary with the particular goal to be achieved, the age and physical condition of the patient being treated, the severity of the underlying disease, the duration of treatment, the nature of concurrent therapy and the specific compound employed. For example, a therapeutically effective amount of a compound of the disclosure administered to a child or a neonate will be reduced proportionately in accordance with sound medical judgment. The effective amount of a compound of the disclosure will thus be the minimum amount which will provide the desired effect.

A decided practical advantage of the present disclosure is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the disclosure may be required to be coated in a material to protect the compound from the action of enzymes, acids and other natural conditions which may inactivate the compound. In order to administer a compound of the disclosure by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of *Theobroma*; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and *Echinacea*, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the present disclosure (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the present disclosure subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521, 222; 5,403,841; 5,077,033; 4,882,150; and 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407, 713; 5,352,456; 5,332,213; 5,336,168; 5,290,561; 5,254, 346; 5,164,189; 5,163,899; 5,088,977; 5,087,240; 5,008, 110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the present disclosure, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the present disclosure could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an $IC_{50}$ of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

General Experimental Procedures

Definitions of variables in the structures in schemes herein are commensurate with those of corresponding positions in the formulae delineated herein. The example compounds listed in Table 2 were characterized by the HPLC and LCMS methods described in Table 1.

COMMON ABBREVIATIONS

ACN acetonitrile
br broad
d doublet
DCM dichloromethane
dd doublet of doublets
dba dibenzylideneacetone
DFAA difluoroacetic anhydride
DIPEA diisopropylethylamine
DMF dimethylformamide
DMSO dimethyl sulfoxide
dppf 1,1'-ferrocenediyl-bis(diphenylphosphine)
EtOAc ethyl acetate
h hour(s)
HRMS high resolution mass spectrometry
HPLC high performance liquid chromatography
LCMS liquid chromatography and mass spectrometry
MS mass spectrometry
MW microwave
m multiplet
MeOH methanol
min minutes
mL milliliter(s)
m/z mass to charge ratio
NMP N-methyl-2-pyrrolidone
NMR nuclear magnetic resonance
ppm parts per million
rt or RT room temperature
s singlet
t triplet
TFAA trifluoroacetic anhydride
TLC thin layer chromatography Example 1

N-(1-phenylcyclopropyl)-5-(5-(trifluoromethyl)-1,3,4-oxadiazol-2-yl) pyrimidin-2-amine (1)

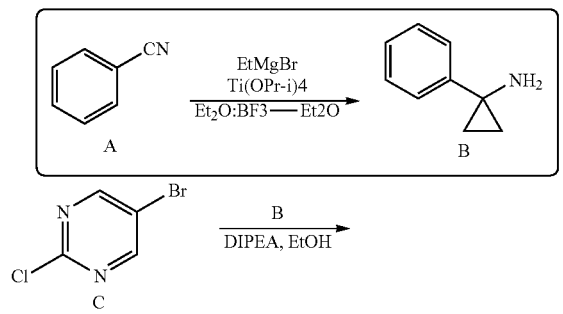

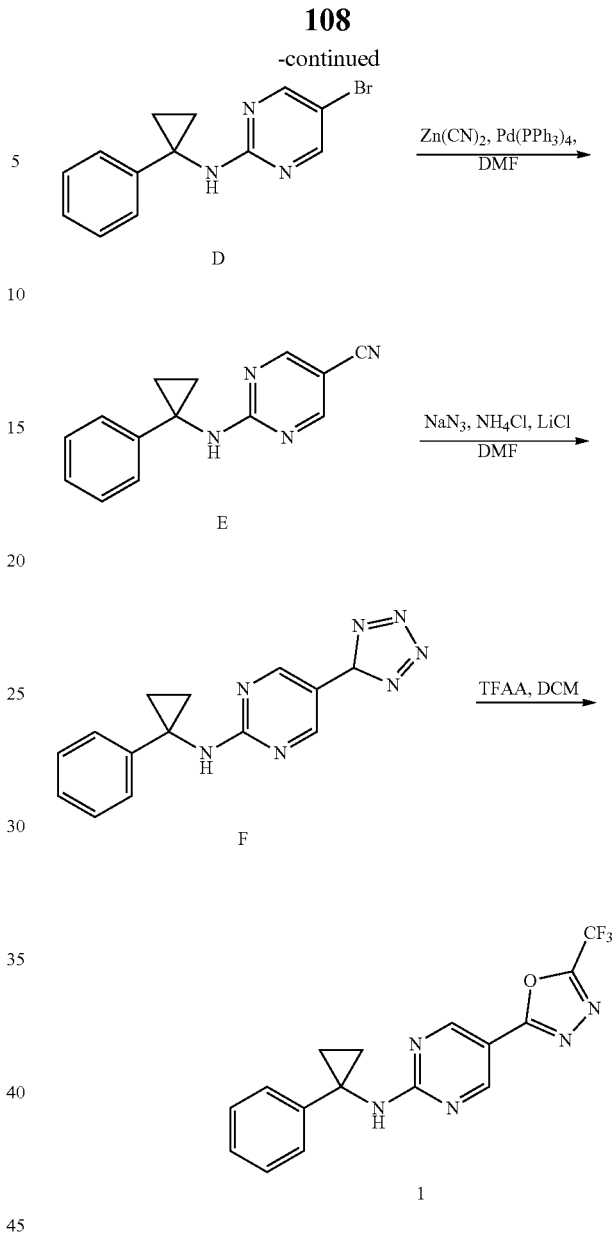

1-phenylcyclopropan-1-amine (B)

To a stirred solution of benzonitrile (A, 5.0 g, 48.54 mmol) in diethyl ether (50 mL), ethyl magnesium bromide (3M, 34.20 mL, 106.7 mmol) and titanium isopropoxide (15.16 g, 53.39 mmol) were added at −70° C. and the reaction was stirred at RT for 2 h. BF$_3$·OEt$_2$ (13.77 g, 97.08 mmol) was added at 0° C. and stirred at RT for 8 h. The progress of the reaction was monitored by thin layer chromatography (TLC). After completion of the reaction, the reaction mixture was quenched with NH$_4$Cl solution and basified with 10% NaOH solution, extracted with 10% (MeOH/DCM). The combined organic layer was washed with brine, dried over anhydrous Na$_2$SO$_4$ and concentrated under reduced pressure. The crude product was purified by silica gel column chromatography 50% EtOAc/hexane to afford compound B (5.0 g, 38.7%) as a pale-yellow liquid. $^1$H NMR (400 MHz, DMSO-d$_6$) δ 7.32 (m, 4H), 7.10 (m, 1H), 2.23 (s, 2H), 0.98-0.90 (m, 2H), 0.93-0.82 (m, 2H).

5-bromo-N-(1-phenylcyclopropyl) pyrimidin-2-amine (D)

To a stirred solution of 2-bromo-5-chloropyrimidine (C, 5.0 g, 25.8 mmol) and compound B (6.8 g, 51.6 mmol) in EtOH (50 mL), DIPEA (19 mL, 103 mmol) was added and stirred at 90° C. for 16 h. The progress of the reaction was monitored by TLC. After completion of the reaction, the reaction mixture was concentrated under reduced pressure. The crude product was purified by silica gel column chromatography 20% EtOAc/hexane to afford compound D (3.3 g, 44.6%) as a light yellow solid. $^1$H NMR (400 MHz, DMSO-$d_6$) δ 8.30 (br s, 1H), 8.32 (s, 2H), 7.22 (t, J=7.6 Hz, 2H), 7.13-7.08 (m, 3H), 1.26-1.19 (m, 4H); LC-MS: m/z 290.05 [M+H]$^+$.

2-((1-phenylcyclopropyl) amino) pyrimidine-5-carbonitrile (E)

To a stirred solution of compound D (2.2 g, 7.58 mmol) in DMF (15 mL), Zn(CN)$_2$ (1.77 g, 15.1 mmol) was added and degassed under argon atmosphere for 20 min. To the resulting reaction mixture Pd(PPh$_3$)$_4$ (0.86 g, 0.75 g) was added and degassed for 15 min. The reaction mixture was stirred at 100° C. for 16 h. After completion of the reaction, the reaction mixture was filtered through a pad of Celite, diluted with water and extracted with EtOAc. The combined organic layer was washed with brine, dried over anhydrous Na$_2$SO$_4$ and concentrated under reduced pressure. The residue was purified by silica gel column chromatography 30% EtOAc/hexane to afford E (1.2 g, 60%) as an off white solid. $^1$H NMR (400 MHz, DMSO-$d_6$) δ 9.11 (s, 1H), 8.69 (dd, J=4.4, 2.8 Hz, 2H), 7.24 (t, J=7.6 Hz, 2H), 7.13-7.11 (m, 3H), 1.31-1.22 (m, 4H); LC-MS: m/z 237.0 [M+H]$^+$.

N-(1-phenylcyclopropyl)-5-(5H-tetrazol-5-yl) pyrimidin-2-amine (F)

To a stirred solution of compound E (300 mg, 1.27 mmol) in DMF (5 mL), NaN3 (107 mg, 1.65 mmol), NH$_4$Cl (89 mg, 1.65 mmol) and LiCl (20 mg) were added and stirred at 100° C. for 14 h. After completion of the reaction, the reaction mixture was quenched with ice water and acidified with 2N HCl solution to pH=2. Precipitated solid was filtered and solid washed with cold water to afford F (0.25 g, 70.6%) as an off white solid. LC-MS: m/z 280.20 [M+H]$^+$.

N-(1-phenylcyclopropyl)-5-(5-(trifluoromethyl)-1,3,4-oxadiazol-2-yl) pyrimidin-2-amine (1)

To a stirred solution of compound F (250 mg, 896 mmol) in DCM (5 mL), trifluoroacetic anhydride (TFAA, 225 mg, 1.07 mmol) was added at 0° C. and the reaction was allowed to stir at RT for 4 h. The progress of the reaction was monitored by TLC. After completion of the reaction, the reaction mixture was evaporated to dryness. The residue was dissolved in saturated solution of NaHCO$_3$ and extracted with 5% MeOH in DCM. The combined organic layer was washed with brine, dried over anhydrous Na$_2$SO$_4$ and concentrated under reduced pressure. The crude product was purified by silica gel column chromatography 20% EtOAc/hexane to afford compound 1 (45 mg, 14.51%). $^1$H NMR (400 MHz, DMSO-$d_6$) δ 9.10 (s, 1H), 8.95-8.85 (m, 2H), 7.25 (dd, J=8.4, 6.9 Hz, 2H), 7.22-7.07 (m, 3H), 1.43-1.21 (m, 4H); LC-MS: m/z 348.05 [M+H]$^+$; HPLC: 99.9%.

Example 2

N-(1-phenylethyl)-5-(5-(trifluoromethyl)-1,3,4-oxadiazol-2-yl)pyrimidin-2-amine (2)

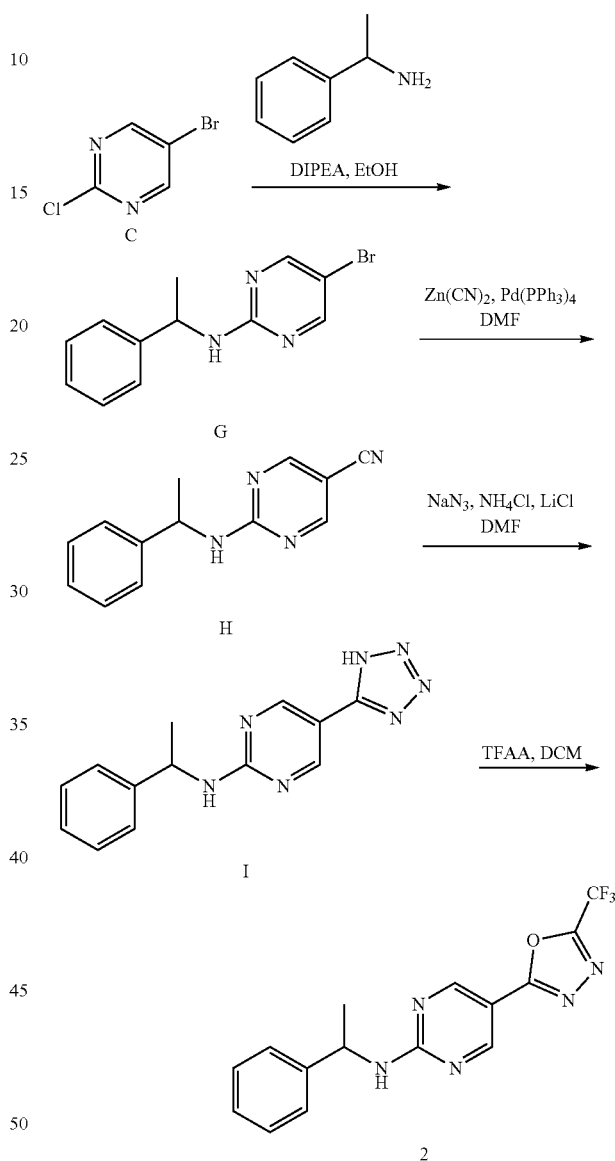

5-bromo-N-(1-phenylethyl) pyrimidin-2-amine (G)

To a stirred solution of 5-bromo-2-chloropyrimidine (C, 5 g, 26 mmol) in EtOH (20 mL), 1-phenylethan-1-amine (6.26 g, 52 mmol) in DIPEA (30 mL) was added at 90° C. and the reaction mixture was stirred at 90° C. for 14 h. The progress of the reaction was monitored by TLC. After completion of the reaction, the reaction mixture was cooled to RT and concentrated under reduced pressure. The crude product was purified by silica gel column chromatography using 10% EtOAc/hexane to afford compound G (6 g, 83.68%) as a white solid. LC-MS: m/z 277.9 [M+H]$^+$.

2-((1-phenylethyl)amino)pyrimidine-5-carbonitrile (H)

To a stirred solution of compound G (4 g, 14 mmol) in DMF, $Zn(CN)_2$ (2.52 g, 21 mmol) was added and purged with argon for 20 min. $Pd(PPh_3)_4$ (1.61 g, 1.4 mmol) was added and again purged with argon for 20 min and then stirred at 120° C. for 14 h. The progress of the reaction was monitored by TLC. After completion of the reaction, the reaction mixture was quenched with saturated aqueous $NH_4Cl$ solution and extracted with EtOAc. The combined organic layer was washed with brine, dried over anhydrous $Na_2SO_4$ and concentrated under reduced pressure. The crude product was purified by silica gel column chromatography using 10% EtOAc/hexane to afford compound H (3 g, 92%) as an off white solid. $^1H$ NMR (400 MHz, $CDCl_3$) δ 8.51 (s, 1H), 8.42 (s, 1H), 7.37-7.31 (m, 4H), 7.30-7.27 (m, 1H), 6.02 (d, J=7.2 Hz, 1H), 5.28-5.20 (m, 1H), 1.61-1.56 (m, 3H).

N-(1-phenylethyl)-5-(1H-tetrazol-5-yl)pyrimidin-2-amine (I)

To a stirred solution of compound H (0.7 g, 3.1 mmol) in DMF (10 mL), NaN3 (0.6 g, 9.3 mmol), $NH_4Cl$ (0.5 g, 9.3 mmol) and LiCl (50 mg) were added and the reaction mixture was stirred at 100° C. for 16 h. The progress of the reaction was monitored by TLC. After completion of the reaction, the reaction mixture was evaporated to dryness. The residue was basified with 10% NaOH solution and extracted with EtOAc. Aqueous layer was acidified with HCl solution to pH=2 and concentrated under reduced pressure. The residue was dissolved in 20% MeOH in DCM and stirred for 10 min, then the solution was dried over anhydrous $Na_2SO_4$ and concentrated under reduced pressure to afford compound I (600 mg, crude) as an off white solid. LC-MS: m/z 268.10 $[M+H]^+$.

N-(1-phenylethyl)-5-(5-(trifluoromethyl)-1,3,4-oxadiazol-2-yl)pyrimidin-2-amine (2)

To a stirred solution of compound I (0.4 g, 1.4 mmol) in DCM (5 mL), TFAA (0.3 mL, 2.2 mmol) was added and the reaction mixture was stirred at RT for 3 h. The progress of the reaction was monitored by TLC. After completion of the reaction, the reaction mixture was quenched with ice water and extracted with DCM. The combined organic layer was washed with brine, dried over anhydrous $Na_2SO_4$ and concentrated under reduced pressure. The crude product was purified by silica gel column chromatography using 3% MeOH/DCM to afford compound 2 (0.1 g, 20%) as a white solid. $^1H$ NMR (400 MHz, DMSO-$d_6$) δ 8.85 (dd, J=17.0, 9.7 Hz, 3H), 7.40 (d, J=7.6 Hz, 2H), 7.31 (t, J=7.5 Hz, 2H), 7.21 (t, J=7.3 Hz, 1H), 5.24-5.18 (m, 1H), 1.49 (d, J=7.0 Hz, 3H); LC-MS: m/z 336.05 $[M+H]^+$; HPLC Purity: 99.35%.

Example 3

N-((6-methylpyridin-2-yl) methyl)-5-(5-(trifluoromethyl)-1, 3, 4-oxadiazol-2-yl) pyrimidin-2-amine (3)

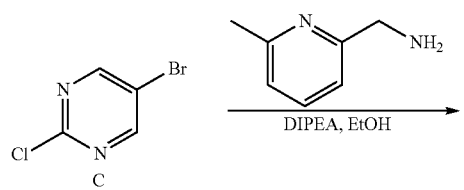

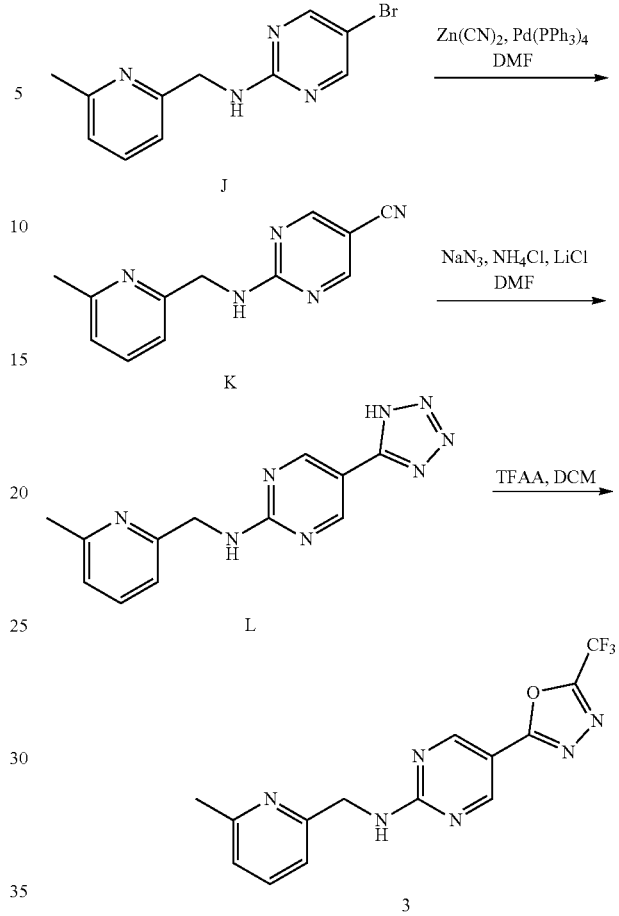

5-bromo-N-((6-methylpyridin-2-yl)methyl)pyrimidin-2-amine (J)

To a stirred solution of (6-methylpyridin-2-yl)methanamine (0.2 g, 1.63 mmol) in ethanol (5 mL), 5-bromo-2-chloropyrimidine (C, 0.4 g, 2.07 mmol) and DIPEA (0.9 mL, 4.91 mmol) were added and the reaction mixture was heated to 90° C. for 4 h. The progress of the reaction was monitored by TLC. After completion of the reaction, the reaction mixture was concentrated under reduced pressure. The crude product was purified by silica gel column chromatography using 10% EtOAc/hexane to afford compound J (0.15 g, 32%) as an off white solid. LC-MS: m/z 278.95 $[M+H]^+$.

2-(((6-methylpyridin-2-yl) methyl) amino) pyrimidine-5-carbonitrile (K)

A stirred solution of compound J (0.15 g, 0.53 mmol) and $Zn(CN)_2$ (0.28 g, 2.42 mmol) in DMF (2 mL) was purged with argon for 20 min and then $Pd(PPh_3)_4$ (0.093 g, 0.08 mmol) was added. The reaction mixture was further purged with argon for 20 min and then stirred at 110° C. for 12 h. After completion of the reaction, the reaction mixture was quenched with ice water and filtered through Celite and washed with EtOAc. The filtrate was concentrated under reduced pressure. The residue was suspended in water and the obtained solid was filtered and dried to afford compound K (0.15 g, crude) as a white powder. LC-MS: m/z 226.05 $[M+H]^+$.

113

N-((6-methylpyridin-2-yl) methyl)-5-(1H-tetrazol-5-yl) pyrimidin-2-amine (L)

To a stirred solution of compound K (0.15 g, 0.66 mmol) in DMF (3 mL), NaN3 (0.13 g, 2 mmol), NH$_4$Cl (0.1 g, 2 mmol) and LiCl (20 mg) were added and the reaction mixture was stirred at 100° C. for 14 h. The progress of the reaction was monitored by TLC. After completion of the reaction, the reaction mixture was quenched with ice water and acidified with 2N HCl solution to pH=2, extracted with 10% MeOH/DCM. The combined organic layer was washed with brine, dried over anhydrous Na$_2$SO$_4$ and concentrated under reduced pressure to afford compound L (0.14 g, crude) as a white solid. LC-MS: m/z 269.05 [M+H]$^+$.

N-((6-methylpyridin-2-yl) methyl)-5-(5-(trifluoromethyl)-1, 3, 4-oxadiazol-2-yl) pyrimidin-2-amine (3)

To a stirred solution of compound L (0.14 g, 0.52 mmol) in DCM (2 mL), TFAA (0.4 mL, 2.64 mmol) was added and the reaction mixture was stirred at RT for 12 h. The progress of the reaction was monitored by TLC. After completion of the reaction, the reaction mixture was concentrated under reduced pressure. The residue was dissolved in water and extracted with EtOAc. The combined organic layer was washed with brine, dried over anhydrous Na$_2$SO$_4$ and concentrated under reduced pressure. The crude product was purified by silica gel column chromatography using 80% EtOAc/hexane to afford compound 3 (0.05 g, 28%) as an off white solid. $^1$H NMR (400 MHz, DMSO-d$_6$) δ 8.96-8.83 (m, 2H), 8.77 (t, J=6.3 Hz, 1H), 7.62 (t, J=7.7 Hz, 1H), 7.10 (dd, J=13.2, 7.7 Hz, 2H), 4.65 (d, J=6.3 Hz, 2H), 2.45 (s, 3H). LC-MS: m/z 337.05 [M+H]$^+$; HPLC Purity: 95.69%.

Example 4

5-(5-(difluoromethyl)-1,3,4-oxadiazol-2-yl)-N-(1-phenylcyclopropyl)pyrimidin-2-amine (4)

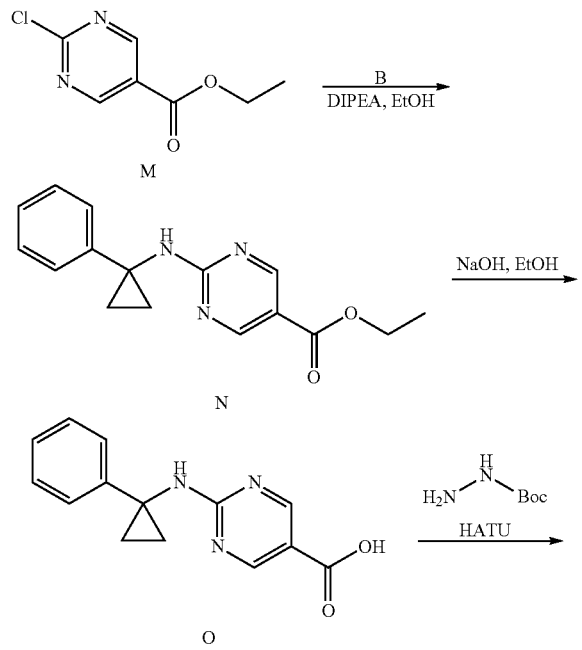

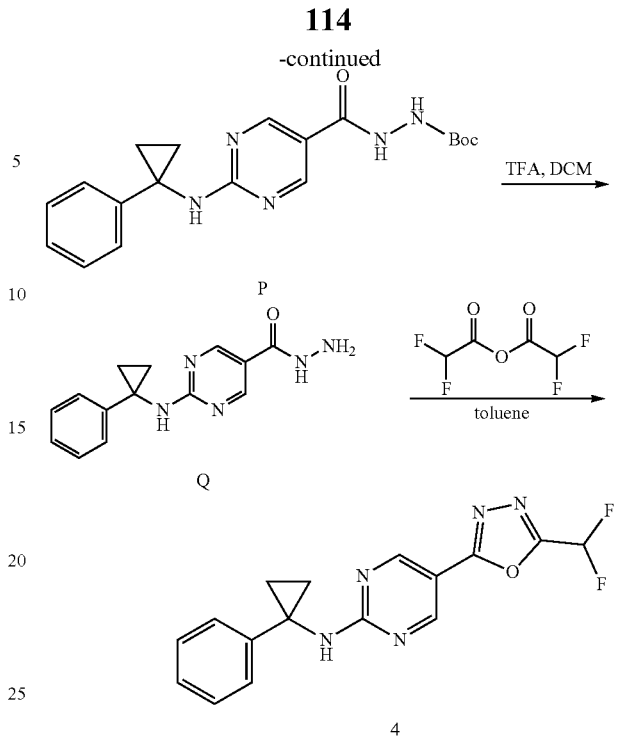

ethyl 2-((1-phenylcyclopropyl)amino)pyrimidine-5-carboxylate (N)

To a stirred solution of compound B (2 g, 10.7 mmol) in ethanol (20 mL), DIPEA (9 mL, 53 mmol) and compound M (1.42 g, 10.7 mmol) were added and the reaction mixture was stirred at 90° C. for 8 h. The progress of the reaction was monitored by TLC. After completion of the reaction, the reaction mixture was concentrated under reduced pressure. The crude product was purified by silica gel column chromatography using 30% EtOAc/hexane to afford compound N (2.7 g, 88.8%) as an off white solid. $^1$H NMR (400 MHz, CDCl$_3$) δ 8.91 (s, 1H), 8.85 (s, 1H), 7.24-7.14 (m, 5H), 6.35 (s, 1H), 4.35 (q, J=7.1 Hz, 2H), 1.48-1.32 (m, 7H).

2-((1-phenylcyclopropyl)amino)pyrimidine-5-carboxylic acid (O)

To a stirred solution of compound N (2.77 g, 9.5 mmol) in ethanol:water (20 mL:20 mL), NaOH (0.76 g, 19 mmol) was added and the reaction mixture was stirred at 60° C. for 2 h. The progress of the reaction was monitored by TLC. After completion of the reaction, the reaction mixture was neutralized with 2N HCl solution and extracted with EtOAc. The organic layer was separated and washed with brine, dried over anhydrous Na$_2$SO$_4$ and concentrated under reduced pressure. The crude product was purified by trituration using ether and pentane to afford of compound O (2.2 g, 90.16%) as a white solid. $^1$H NMR (400 MHz, DMSO-d$_6$) δ 12.76 (s, 1H), 8.83 (s, 1H), 8.70 (d, J=17.2 Hz, 2H), 7.24 (t, J=7.6 Hz, 2H), 7.14 (d, J=8.1 Hz, 3H), 1.34-1.21 (m, 4H).

Tert-butyl 2-(2-((1-phenylcyclopropyl) amino) pyrimidine-5-carbonyl) hydrazine-1-carboxylate (P)

To a stirred solution of compound O (1.0 g, 3.90 mmol) in DCM (10 mL), tert-butyl hydrazinecarboxylate (0.56 g, 4.29 mmol), HATU (1.78 g, 4.68 mmol) and DIPEA (0.75 g, 5.85 mmol) were added at 0° C. under nitrogen atmosphere and stirred at room temperature for 12 h. After consumption of the starting material (by TLC), the reaction mixture was quenched with water and extracted with EtOAc. The combined organic layer was washed with brine, dried over Na$_2$SO$_4$ and concentrated under reduced pressure. The residue was purified by column chromatography to afford compound P (0.9 g, 62.5%) as a pale yellow oil. LC-MS: m/z 370.1 [M+H]$^+$.

2-((1-phenylcyclopropyl)amino)pyrimidine-5-carbohydrazide (Q)

To a stirred solution of compound P (0.9 g, 2.43 mmol) in DCM (12 mL), TFA (0.8 mL) was added and stirred at room temperature for 2 h. After complete consumption of the starting material (by TLC), the reaction mixture was concentrated under reduced pressure to obtain the product as a TFA salt. The salt was basified with NaHCO$_3$ solution and extracted with 15% MeOH/DCM. The combined organic layer was washed with brine, dried over anhydrous Na$_2$SO$_4$ and concentrated under reduced pressure. The crude product was purified by silica gel column chromatography using 5% MeOH/DCM to afford Q (0.6 g, 91.4%) as an off white solid. LC-MS: m/z 270.15 [M+H]$^+$.

5-(5-(difluoromethyl)-1,3,4-oxadiazol-2-yl)-N-(1-phenylcyclopropyl)pyrimidin-2-amine (4)

To a stirred solution of compound Q (0.3 g, 1.11 mmol) in toluene (5 mL), 2,2-difluoroacetic anhydride (0.13 mL, 1.11 mmol) was added. The reaction mixture was stirred at RT for 30 min and then stirred at 70° C. for 17 h. The progress of the reaction was monitored by TLC. After completion of the reaction, the reaction mixture was concentrated under reduced pressure. The crude product was purified by silica gel column chromatography using 20% EtOAc/hexane to afford 4 (80 mg, 21.8%) as an off white solid. $^1$H NMR (400 MHz, DMSO-d$_6$) δ 9.02 (s, 1H), 8.93-8.82 (m, 2H), 7.52 (s, 1H), 7.25 (t, J=7.6 Hz, 2H), 7.15 (dd, J=16.9, 7.8 Hz, 3H), 1.37-1.24 (m, 4H); LC-MS: m/z 330.1 [M+H]$^+$; HPLC Purity: 99.7%.

Example 5

5-(5-(difluoromethyl)-1,3,4-oxadiazol-2-yl)-N-(1-(4-fluorophenyl)cyclopropyl)pyrimidin-2-amine (5)

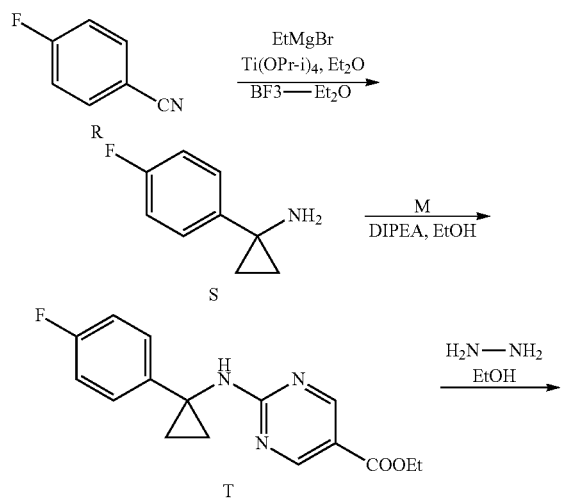

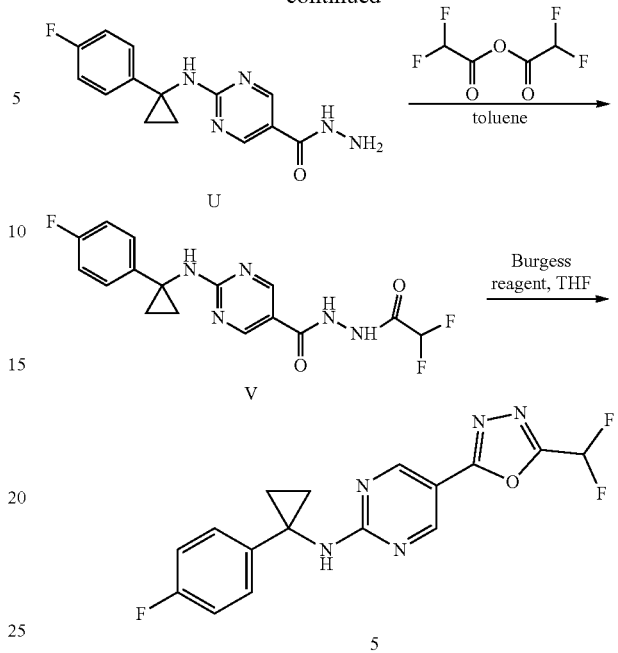

1-(4-fluorophenyl)cyclopropan-1-amine (S)

To a stirred solution of 4-fluorobenzonitrile (R, 10 g, 82.64 mmol) in diethyl ether (200 mL), ethyl magnesium bromide (3M in THF, 60.6 mL, 181.81 mmol) and titanium isopropoxide (25.81 g, 90.9 mmol) were added at −70° C. and the reaction mixture was stirred at RT for 2 h. BF$_3$·OEt$_2$ (23.47 g, 165.28 mmol) was added at 0° C. and stirred at RT for 8 h. The progress of the reaction was monitored by TLC. After completion of the reaction, the reaction mixture was quenched with NH$_4$Cl solution, basified with 10% NaOH solution, and extracted with 10% MeOH/DCM. The combined organic layer was washed with brine, dried over anhydrous Na$_2$SO$_4$ and concentrated under reduced pressure. The crude product was purified by silica gel column chromatography using 70% EtOAc/hexane to afford compound S (4.5 g, 36.08%) as a thick oil. $^1$H NMR (400 MHz, DMSO-d$_6$) δ 7.37-7.30 (m, 2H), 7.09-7.04 (m, 2H), 2.92 (bs, 2H), 0.95-0.82 (m, 4H); LC-MS: m/z 151.95 [M+H]$^+$.

ethyl 2-((1-(4-fluorophenyl)cyclopropyl)amino)pyrimidine-5-carboxylate (T)

To a stirred solution of 1-(4-fluorophenyl)cyclopropan-1-amine (S, 0.7 g, 4.63 mmol) in EtOH (10 mL), ethyl 2-chloropyrimidine-5-carboxylate (M, 1.03 g, 5.56 mmol) and DIPEA (2.5 mL, 13.9 mmol) were added at RT and the reaction mixture was stirred at 90° C. for 12 h. The progress of the reaction was monitored by TLC. After completion, the reaction mixture was concentrated under reduced pressure. The crude product was purified by silica gel column chromatography using 10% EtOAc/hexane to afford compound T (0.7 g, 50.1%) as a white solid. LC-MS: m/z 302.1 [M+H]$^+$.

2-((1-(4-fluorophenyl)cyclopropyl)amino)pyrimidine-5-carbohydrazide (U)

To a stirred solution of compound T (0.4 g, 1.32 mmol) in EtOH (10 mL), hydrazine hydrate (2 mL) was added and the reaction mixture was stirred at 90° C. for 12 h. The progress of the reaction was monitored by TLC. After completion of the reaction, the reaction mixture was concentrated under reduced pressure. The crude product was purified by silica gel column chromatography using 5% MeOH/DCM to afford compound U (0.3 g, 78.7%) as a white solid. $^1$H NMR (400 MHz, DMSO-$d_6$) δ 0.95 (s, 1H), 8.65-8.61 (m, 2H), 8.57 (s, 1H), 7.19 (t, J=8.8 Hz, 2H), 7.04 (t, J=8.8 Hz, 2H), 4.39 (s, 2H), 1.27-1.18 (m, 4H); LC-MS: m/z 288.05 [M+H]$^+$.

N'-(2,2-difluoroacetyl)-2-((1-(4-fluorophenyl)cyclopropyl)amino)pyrimidine-5-carbohydrazide (V)

To a stirred solution of compound U (0.3 g, 1.14 mmol) in toluene (10 mL), 2,2-difluoroacetic anhydride (0.18 mL, 1.56 mmol) was added. Reaction mixture was stirred at RT for 30 min and then stirred at 90° C. for 16 h. The progress of the reaction was monitored by TLC. After completion of the reaction, the reaction mixture was concentrated under reduced pressure. The crude product was purified by silica gel column chromatography using 5% MeOH/DCM to afford compound V (0.2 g, 55.2%) as a thick oil. LC-MS: m/z 365.85 [M+H]$^+$.

5-(5-(difluoromethyl)-1,3,4-oxadiazol-2-yl)-N-(1-(4-fluorophenyl)cyclopropyl)pyrimidin-2-amine (5)

To a stirred solution of compound V (0.1 g, 0.27 mmol) in THF (2 mL), Burgess reagent (0.13 g, 0.54 mmol) was added and the reaction mixture was stirred at 80° C. for 30 min in microwave. The progress of the reaction was monitored by TLC. After completion of the reaction, the reaction mixture was concentrated under reduced pressure. The reaction mixture was diluted with water and extracted with EtOAc. The combined organic layer was washed with brine, dried over Na$_2$SO$_4$ and concentrated under reduced pressure. The crude product was purified by silica gel column chromatography using 20% EtOAc/hexane to afford compound 5 (0.035 g, 36.8%) as an off white solid. $^1$H NMR (400 MHz, DMSO-$d_6$) δ 9.02 (s, 1H), 8.88 (d, J=8.2 Hz, 2H), 7.45 (t, J=51.4 Hz, 1H), 7.23 (dd, J=8.6, 5.4 Hz, 2H), 7.07 (t, J=8.7 Hz, 2H), 1.35-1.21 (m, 4H); LC-MS: m/z 348.10 [M+H]$^+$; HPLC Purity: 99.7%.

Example 6

5-(5-(difluoromethyl)-1,3,4-oxadiazol-2-yl)-N-(1-phenylethyl)pyrimidin-2-amine (6)

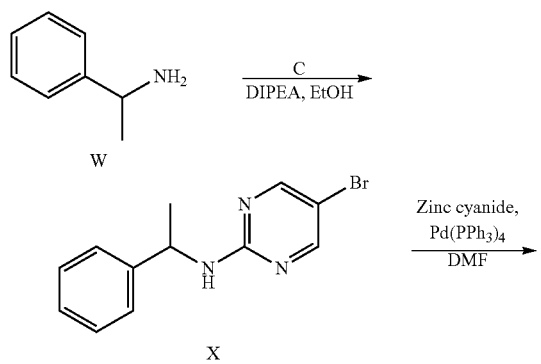

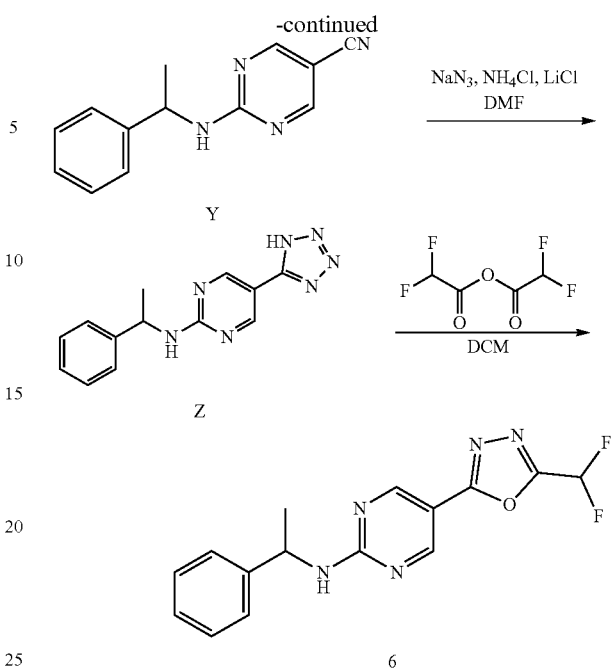

5-bromo-N-(1-phenylethyl)pyrimidin-2-amine (X)

To a stirred solution of 1-phenylethan-1-amine (W, 5.0 g, 26.0 mmol) in EtOH (20 mL), 5-bromo-2-chloropyrimidine (C, 6.26 g, 52.0 mmol) and DIPEA (30 mL, 156 mmol) were added and the reaction mixture was heated to 90° C. for 16 h. The progress of the reaction was monitored by TLC. After completion of the reaction, the reaction mixture was concentrated under reduced pressure. The crude product was purified by silica gel column chromatography using 5% EtOAc/hexane to afford compound X (6.0 g, 83.6%) as a brown oil. LC-MS: m/z 278.20 [M+H]$^+$.

2-((1-phenylethyl)amino)pyrimidine-5-carbonitrile (Y)

To a stirred solution of compound X (4.0 g, 14.0 mmol) in dry DMF (20 mL), zinc cyanide (2.52 g, 21.0 mmol) was added and the suspension was purged with nitrogen gas for 20 min. Pd(PPh$_3$)$_4$ (1.61 g, 1.40 mmol) was added and the suspension was again purged with nitrogen for 20 min. The reaction mixture was stirred at 120° C. for 14 h. The progress of the reaction was monitored by TLC. After completion of the reaction, the reaction mixture was filtered through a pad of Celite and washed with EtOAc. The combined organic layer was washed with cold water, dried over anhydrous Na$_2$SO$_4$ and concentrated under reduced pressure. The crude product was purified by silica gel column chromatography using 10% EtOAc/hexane to afford compound Y (3 g, 92.8%) as a thick oil. LC-MS: m/z 225.15 (M+H)+. $^1$H NMR (400 MHz, DMSO-$d_6$) δ 8.51 (s, 1H), 8.42 (s, 1H), 7.39-7.27 (m, 5H), 6.03 (d, J=7.2 Hz, 1H), 5.28-5.20 (m, 1H), 1.60 (d, J=6.8 Hz, 3H).

N-(1-phenylethyl)-5-(1H-tetrazol-5-yl)pyrimidin-2-amine (Z)

To a stirred solution of compound Y (0.7 g, 3.10 mmol) in DMF (10 mL), NaN3 (0.60 g, 9.30 mmol), NH$_4$Cl (0.5 g, 9.30 mmol) and LiCl (50 mg) were added and the reaction mixture was stirred at 100° C. for 16 h. The progress of the reaction was monitored by TLC. After completion of the reaction, the reaction mixture was concentrated under reduced pressure. The residue was dissolved in cold water and adjust to pH=4-5 by using HCl solution. The obtained solid was filtered, washed with water, dried to afford compound Z (0.7 g, crude) as a thick oil. LC-MS: m/z 268.05 [M+H]$^+$.

5-(5-(difluoromethyl)-1,3,4-oxadiazol-2-yl)-N-(1-phenylethyl)pyrimidin-2-amine (6)

To a stirred solution of compound Z (0.7 g, 2.60 mmol) in DCM (15 mL), 2,2-difluoroacetic anhydride (0.4 mL, 3.90 mmol) was added at 0° C. and the reaction mixture was stirred at RT for 16 h. The progress of the reaction was monitored by TLC. After completion of the reaction, the reaction mixture was concentrated under reduced pressure. The crude product was purified by silica gel column chromatography using 20% EtOAc/hexane to afford compound 6 (0.2 g, 24%) as an off white solid. $^1$H NMR (400 MHz, DMSO-d$_6$) δ 8.84 (d, J=12.4 Hz, 2H), 8.76 (d, J=8.3 Hz, 1H), 7.51 (t, J=51.2 Hz, 1H), 7.40 (d, J=7.8 Hz, 2H), 7.31 (t, J=7.5 Hz, 2H), 7.21 (t, J=7.3 Hz, 1H), 5.25-5.18 (m, 1H), 1.49 (d, J=7.0 Hz, 3H); LC-MS: m/z 317.95 [M+H]$^+$; HPLC Purity: 99.1%.

Example 7

N-benzhydryl-5-(5-(difluoromethyl)-1,3,4-oxadiazol-2-yl)pyrimidin-2-amine (7)

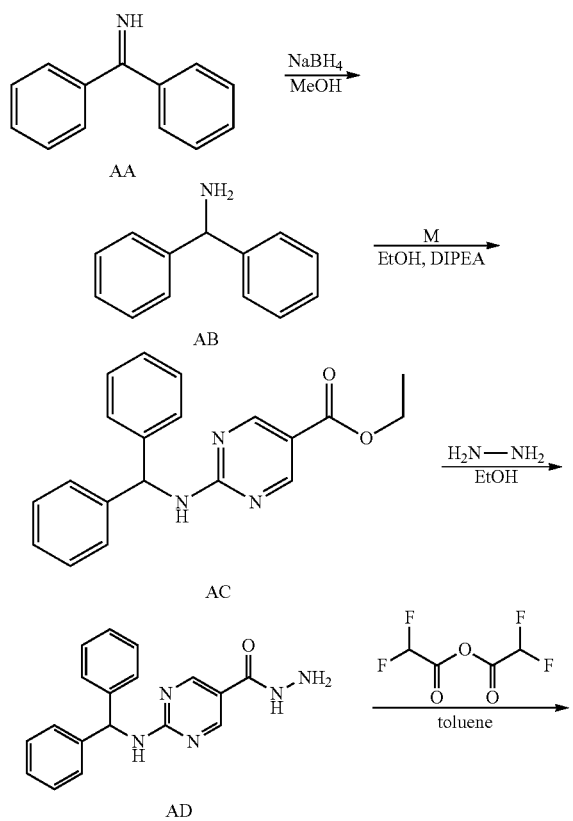

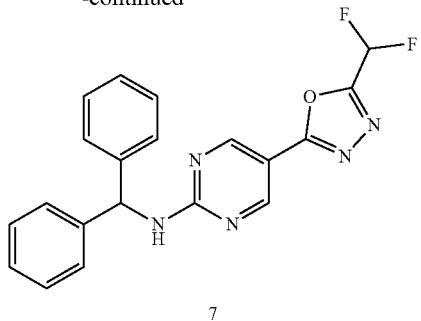

7

Diphenylmethanamine (AB)

To a stirred solution of diphenylmethanimine (AA, 1.5 g, 8.28 mmol) in MeOH (20 mL), NaBH$_4$ (0.47 g, 12.4 mmol) was added and the reaction mixture was stirred at RT for 3 h. The progress of the reaction was monitored by TLC. After completion of the reaction, the reaction mixture was concentrated under reduced pressure. The reaction mixture was diluted with water and extracted with 10% MeOH/DCM. The combined organic layer was washed with brine, dried over Na$_2$SO$_4$ and concentrated under reduced pressure to afford compound AB (0.8 g, 53%) as a thick oil. $^1$H NMR (400 MHz, DMSO-d$_6$) δ 7.82-7.78 (m, 4H), 7.36-7.29 (m, 4H), 7.25-7.16 (m, 2H), 5.08 (s, 1H), 2.23 (s, 2H).

ethyl 2-(benzhydrylamino)pyrimidine-5-carboxylate (AC)

To a stirred solution of compound AB (0.7 g, 3.76 mmol) in ethanol (10 mL), ethyl 2-chloropyrimidine-5-carboxylate (0.68 g, 3.76 mmol) and DIPEA (1.45 g, 11.9 mmol) were added at 80° C. and the reaction mixture was stirred at 90° C. for 12 h. The progress of the reaction was monitored by TLC. After completion of the reaction, the reaction mixture was concentrated under reduced pressure. The crude product was purified by silica gel column chromatography using 20% EtOAc/hexane to afford compound AC (0.5 g, 40%) as a white solid. LC-MS: m/z 334.05 [M+H]$^+$.

2-(benzhydrylamino)pyrimidine-5-carbohydrazide (AD)

To a stirred solution of compound AC (0.5 g, 1.50 mmol) in ethanol (10 mL), hydrazine hydrate (3 mL) was added and the reaction mixture was stirred at 90° C. for 12 h. The progress of the reaction was monitored by TLC. After completion of the reaction, the reaction mixture was concentrated under reduced pressure. The crude product was purified by silica gel column chromatography using 5% MeOH/DCM to afford compound AD (0.3 g, 62.7%) as a white solid. LC-MS: m/z 320.05 [M+H]$^+$.

N-benzhydryl-5-(5-(difluoromethyl)-1,3,4-oxadiazol-2-yl)pyrimidin-2-amine (7)

To a stirred solution of compound AD (0.3 g, 0.94 mmol) in toluene (5 mL), 2,2-difluoroacetic anhydride (0.19 g, 1.12 mmol) was added. The reaction mixture was stirred at RT for 30 min and then stirred at 80° C. for 16 h. The progress of the reaction was monitored by TLC. After completion of the reaction, the reaction mixture was concentrated under reduced pressure. The crude product was purified by silica gel column chromatography using 20% EtOAc/hexane to afford compound 7 (0.085 g, 23.8%) as a thick oil. $^1$H NMR (400 MHz, DMSO-$d_6$) δ 9.24 (d, J=9.3 Hz, 1H), 8.91 (d, J=5.4 Hz, 2H), 7.52 (s, 1H), 7.45-7.37 (m, 4H), 7.33 (dd, J=8.5, 6.8 Hz, 4H), 7.29-7.20 (m, 2H), 6.52 (d, J=9.2 Hz, 1H); LC-MS: m/z 380.10 [M+H]$^+$; HPLC Purity: 95.2%.

Example 8

5-(5-(difluoromethyl)-1,3,4-oxadiazol-2-yl)-N-(1-(4-fluorophenyl)cyclopropyl)-N-methylpyrimidin-2-amine (8)

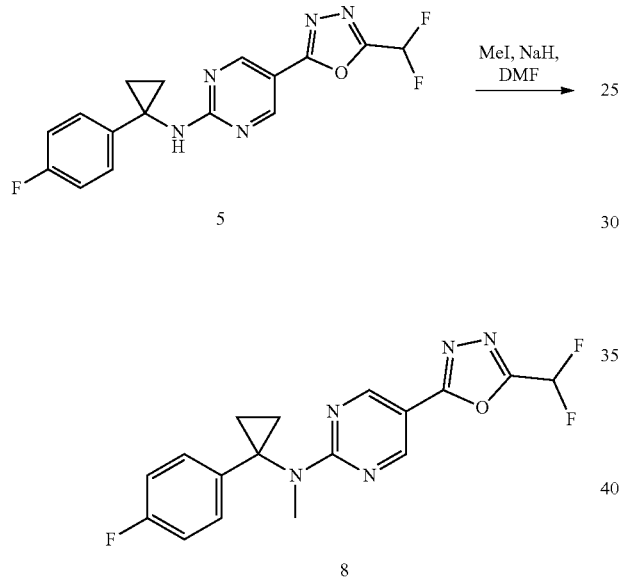

5-(5-(difluoromethyl)-1, 3, 4-oxadiazol-2-yl)-N-(1-(4-fluorophenyl) cyclopropyl)-N-methylpyrimidin-2-amine (8)

To a stirred solution of compound 5 (0.18 g, 5.2 mmol) in THF (2 mL), NaH (60%, 12 mg, 5.2 mmol) was added and the reaction mixture was stirred at 0° C. for 20 min. MeI (0.032 mL, 5.2 mmol) was added at 0° C. and the reaction mixture was stirred at RT for 1 h. The progress of the reaction was monitored by TLC. After completion of the reaction, the reaction mixture was quenched with water and extracted with EtOAc. The combined organic layer was washed with brine, dried over Na$_2$SO$_4$ and concentrated under reduced pressure. The crude product was purified by silica gel column chromatography using 10% EtOAc/hexane to afford compound 8 (70 mg, 37.4%) as an off white solid; $^1$H NMR (400 MHz, DMSO-$d_6$) δ 8.96 (d, J=19.8 Hz, 2H), 7.52 (t, J=51.6 Hz, 1H), 7.12-7.05 (m, 4H), 3.29 (s, 3H), 1.44 (s, 4H); LC-MS: m/z 362 [M+H]$^+$; HPLC Purity: 99.3%.

Example 9

5-(5-(difluoromethyl)-1,3,4-oxadiazol-2-yl)-N-(2-(4-fluorophenyl)propan-2-yl)pyrimidin-2-amine (9)

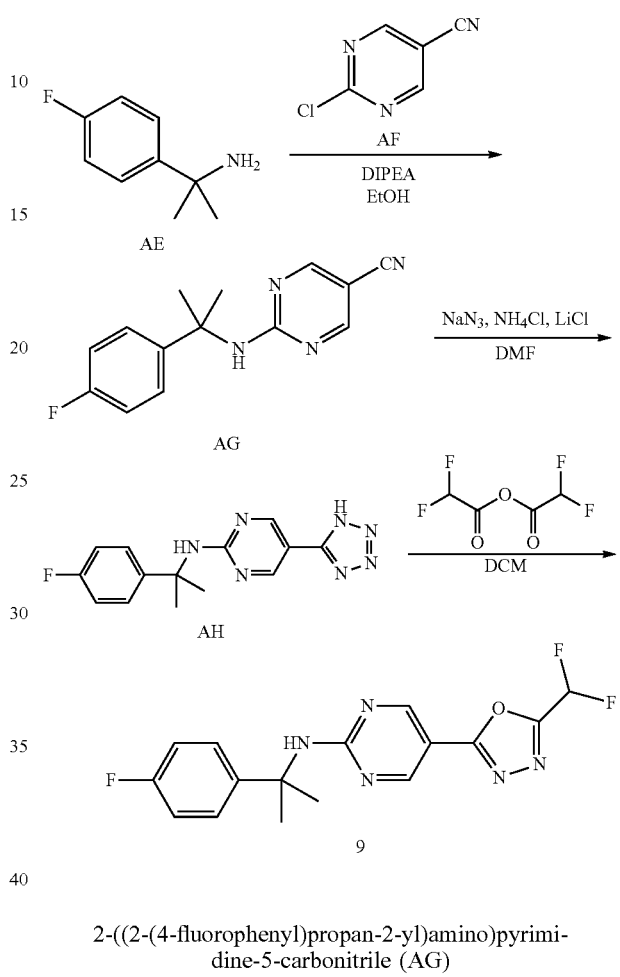

2-((2-(4-fluorophenyl)propan-2-yl)amino)pyrimidine-5-carbonitrile (AG)

To a stirred solution of 2-(4-fluorophenyl)propan-2-amine (AE, 0.5 g, 32.0 mmol) in ethanol (15 mL), 2-chloropyrimidine-5-carbonitrile (AF, 0.6 g, 4.20 mmol) and DIPEA (2.7 mL, 16.0 mmol) were added and the reaction mixture was stirred at 90° C. for 14 h. The progress of the reaction was monitored by TLC. After completion of the reaction, the reaction mixture was concentrated under reduced pressure. The crude product was purified by silica gel column chromatography using 10% EtOAc/hexane to afford compound AG (0.58 g, 69.3%) as a white solid. LC-MS: m/z 257.05 [M+H]$^+$.

N-(2-(4-fluorophenyl)propan-2-yl)-5-(1H-tetrazol-5-yl)pyrimidin-2-amine (AH)

To a stirred solution of compound AG (0.58 g, 2.20 mmol) in DMF (10 mL), NaN$_3$ (0.44 g, 6.70 mmol), NH$_4$Cl (0.35 g, 6.70 mmol) and LiCl (90 mg) were added and the reaction mixture was stirred at 100° C. for 16 h. The progress of the reaction was monitored by TLC. After completion of the reaction, the reaction mixture was concentrated under reduced pressure. The residue was dissolved in cold water and adjust to pH=4-5 by using aqueous HCl solution. The obtained solid was filtered, washed with water, dried to afford compound AH (0.6 g, crude) as an off white solid. LC-MS: m/z 300.05 [M+H]⁺.

5-(5-(difluoromethyl)-1,3,4-oxadiazol-2-yl)-N-(2-(4-fluorophenyl)propan-2-yl)pyrimidin-2-amine (9)

To a stirred solution of compound AH (0.6 g, 2.0 mmol) in DCM (15 mL), 2,2-difluoroacetic anhydride (0.32 mL, 3.0 mmol) was added and the reaction mixture was stirred at RT for 16 h. The progress of the reaction was monitored by TLC. After completion of the reaction, the reaction mixture was quenched with water and extracted with DCM. The combined organic layer was washed with brine, dried over anhydrous Na$_2$SO$_4$ and concentrated under reduced pressure. The crude product was purified by silica gel column chromatography using 20% EtOAc/hexane to afford compound 9 (0.06 g, 8.5%) as an off white solid. $^1$H NMR (400 MHz, DMSO-d$_6$) δ 8.86 (s, 1H), 8.62 (s, 1H), 8.48 (s, 1H), 7.38-7.35 (m, 2H), 7.48 (s, 1H), 7.07 (t, J=7.2 Hz, 2H), 1.70 (s, 6H). LC-MS: m/z 350.0 [M+H]⁺; HPLC Purity: 98.3%.

Example 10

5-(5-(difluoromethyl)-1,3,4-oxadiazol-2-yl)-N-(1-(2,4-difluorophenyl)cyclopropyl)pyrimidin-2-amine (10)

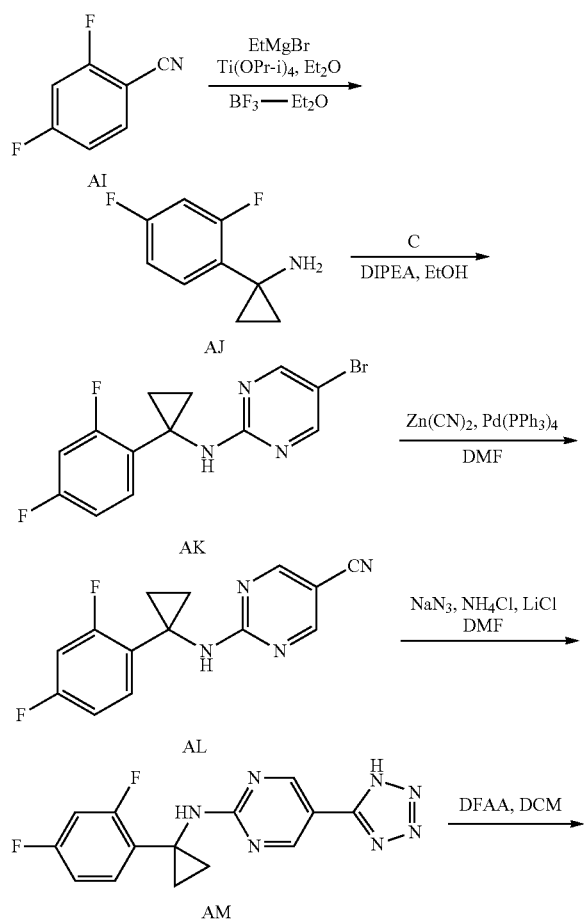

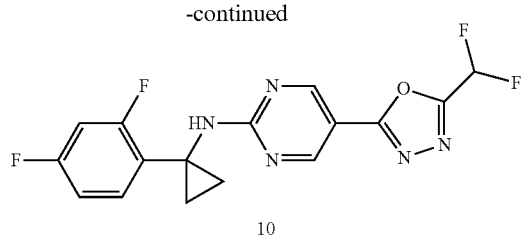

1-(2,4-difluorophenyl)cyclopropan-1-amine (AJ)

To a stirred solution of 2,4-difluorobenzonitrile (AI, 2.0 g, 28.7 mmol) in dry diethyl ether (250 mL), EtMgBr (10.5 mL, 3M solution in THF, 63.3 mmol) and Ti(O-iPr)$_4$ (4.5 g, 31.5 mmol) were added at −78° C. BF$_3$·Et$_2$O (10.7 mL, 57.4 mmol) was added and the reaction mixture was allowed to stirred at RT for 12 h. The progress of the reaction was monitored by TLC. After completion of the reaction, the reaction mixture was quenched with NH$_4$Cl solution and extracted with EtOAc. The combined organic layer was washed with brine, dried over anhydrous Na$_2$SO$_4$ and concentrated under reduced pressure. The crude product was purified by silica gel column chromatography using 30% EtOAc/hexane to afford compound AJ (1.0 g, 20%) as a pale yellow oil. LC-MS: m/z 170 [M+1]⁺.

5-bromo-N-(1-(2,4-difluorophenyl)cyclopropyl)pyrimidin-2-amine (AK)

To a stirred solution of compound AJ (0.5 g, 2.95 mmol) in ethanol (10 mL), DIPEA (1.5 mL, 8.85 mmol) and 5-bromo-2-chloropyrimidine (C, 0.85 g, 4.43 mmol) were added and the reaction mixture was stirred at 90° C. for 8 h. The progress of the reaction was monitored by TLC. After completion of the reaction, the reaction mixture was concentrated under reduced pressure. The crude product was purified by silica gel column chromatography 10% EtOAc/hexane to afford compound AK (0.65 g, 67%) as a thick oil; LC-MS: m/z 327.89 [M+1]⁺.

2-((1-(2,4-difluorophenyl)cyclopropyl)amino)pyrimidine-5-carbonitrile (AL)

A stirred solution of compound 4 (0.64 g, 1.96 mmol) and Zn(CN)$_2$ (0.91 g, 7.84 mmol) in DMF (10 mL) was purged for 20 min and then Pd(PPh$_3$)$_4$ (0.34 g, 0.29 mmol) was added. The reaction mixture was further purged with argon for 20 min. The reaction mixture was stirred at 110° C. for 12 h. After completion of the reaction, the reaction mixture was quenched with ice water, filtered through Celite bed, and washed with EtOAc. The filtrate was concentrated under reduced pressure. The residue was dissolved in water and obtained solid was filtered, dried to afford compound AL (0.5 g, crude) as a white powder. LC-MS: m/z 272.96 [M+H]⁺.

N-(1-(2,4-difluorophenyl)cyclopropyl)-5-(1H-tetrazol-5-yl)pyrimidin-2-amine (AM)

To a stirred solution of compound AL (0.5 g, 1.80 mmol) in DMF (10 mL), NaN$_3$ (0.5 g, 9.19 mmol), NH$_4$Cl (0.6 g, 9.19 mmol) and LiCl (150 mg) were added and the reaction mixture was stirred at 100° C. for 16 h. The progress of the reaction was monitored by TLC. After completion of the reaction, the reaction mixture was quenched with ice water and acidified with 2N HCl solution to pH=2. The precipitated solid was filtered and washed with cold water to afford compound AM (0.4 g, 69%) as a white solid. LC-MS: m/z 316 [M+H]⁺.

5-(5-(difluoromethyl)-1,3,4-oxadiazol-2-yl)-N-(1-(2,4-difluorophenyl)cyclopropyl)pyrimidin-2-amine (10)

To a stirred solution of compound AM (0.25 g, 0.79 mmol) in DCM (10 mL), 2,2-difluoroacetic anhydride (0.46 mL, 3.96 mmol) was added at 0° C. and the reaction mixture was stirred at RT for 16 h. The progress of the reaction was monitored by TLC. After completion of the reaction, the reaction mixture was quenched with water and extracted with DCM. The combined organic layer was washed with brine, dried over anhydrous Na₂SO₄ and concentrated under reduced pressure. The crude product was purified by silica gel column chromatography using 10% MeOH/DCM to afford compound 10 (0.08 g, 27.6%) as a white solid. ¹H NMR (400 MHz, DMSO-d₆) δ 9.04 (s, 1H), 8.82 (d, J=7.2 Hz, 2H), 7.69-7.64 (m, 1H), 7.18 (t, J=8.0 Hz, 1H), 6.99 (t, J=8.2 Hz, 2H), 1.30-1.27 (m, 2H), 1.23-1.20 (m, 2H), LC-MS: m/z 366.03 [M+H]⁺; HPLC Purity: 99%.

Example 11

5-(5-(difluoromethyl)-1,3,4-oxadiazol-2-yl)-N-(1-(2,6-difluorophenyl)cyclopropyl)pyrimidin-2-amine (11)

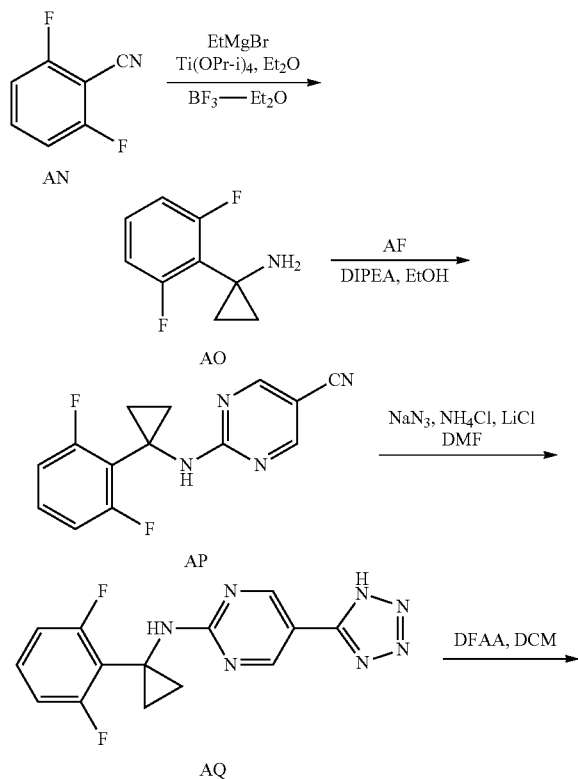

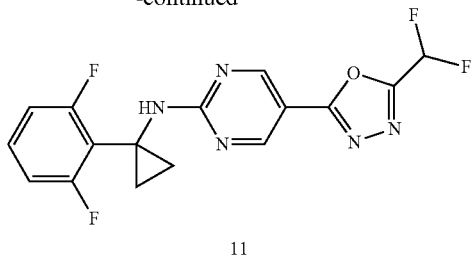

1-(2,6-difluorophenyl)cyclopropan-1-amine (AO)

To a stirred solution of 2,6-difluorobenzonitrile (AN, 2.0 g, 14.3 mmol) in dry THF (50 mL), EtMgBr (10.5 mL, 3M solution in THF, 31.6 mmol) and Ti(O-iPr)₄ (4.67 mL, 15.8 mmol) were added at 0° C. BF₃·Et₂O (4.08 g, 28.7 mmol) was added and the reaction mixture was stirred at RT for 12 h. The progress of the reaction was monitored by TLC. After completion of the reaction, the reaction mixture was quenched with NH₄Cl solution and extracted with EtOAc. The combined organic layer was washed with brine, dried over anhydrous Na₂SO₄ and concentrated under reduced pressure. The crude product was purified by silica gel column chromatography using 60% EtOAc/hexane to afford compound AO (1.2 g, 50%) as a pale yellow oil. LC-MS: m/z 170 [M+1]⁺. ¹H NMR (400 MHz, DMSO-d₆) δ 7.32-7.25 (m, 1H), 7.04-6.97 (m, 2H), 2.26 (s, 2H), 0.90-0.75 (m, 4H).

2-((1-(2,6-difluorophenyl)cyclopropyl)amino)pyrimidine-5-carbonitrile (AP)

To a stirred solution of compound AO (0.8 g, 4.73 mmol) in Ethanol (10 mL), DIPEA (40 mL, 23.6 mmol) and 2-chloropyrimidine-5-carbonitrile (AF, 0.85 g, 6.15 mmol) were added and the reaction mixture was stirred at 90° C. for 8 h. The progress of the reaction was monitored by TLC. After completion of the reaction, the reaction mixture was concentrated under reduced pressure. The crude product was purified by silica gel column chromatography using 10% EtOAc/hexane to afford compound AP (1.1 g, 85%) as a thick oil. LC-MS: m/z 273.05 [M+1]⁺.

N-(1-(2,6-difluorophenyl)cyclopropyl)-5-(1H-tetrazol-5-yl)pyrimidin-2-amine (AQ)

To a stirred solution of compound AP (0.7 g, 2.57 mmol) in DMF (10 mL), NaN₃ (0.7 g, 12.8 mmol), NH₄Cl (0.83 g, 12.8 mmol) and LiCl (210 mg) were added and the reaction mixture was stirred at 100° C. for 16 h. The progress of the reaction was monitored by TLC. After completion of the reaction, the reaction mixture was quenched with ice water and acidified with 2N HCl solution to pH=2. The precipitated solid was filtered and solid washed with cold water to afford compound AQ (0.52 g, 64%) as a white solid. LC-MS: m/z 316.05 [M+H]⁺.

5-(5-(difluoromethyl)-1,3,4-oxadiazol-2-yl)-N-(1-(2,6-difluorophenyl)cyclopropyl)pyrimidin-2-amine (11)

To a stirred solution of compound AP (0.5 g, 1.58 mmol) in DCM (15 mL), 2,2-difluoroacetic anhydride (0.24 mL, 2.38 mmol) was added at 0° C. and the reaction mixture was stirred at RT for 16 h. The progress of the reaction was monitored by TLC. After completion of the reaction, the reaction mixture was quenched with water and extracted with DCM. The combined organic layer was washed with brine, dried over anhydrous Na$_2$SO$_4$ and concentrated under reduced pressure.

The crude product was purified by silica gel column chromatography using 12% EtOAc/hexane to afford compound 11 (0.35 g, 61.3%) as a white solid. $^1$H NMR (400 MHz, DMSO-d$_6$) δ 8.99 (s, 1H), 8.82 (s, 2H), 7.51 (t, J=51 Hz, 1H), 7.32-7.28 (m, 1H), 6.99 (t, J=8.2 Hz, 2H), 1.30-1.27 (m, 2H), 1.23-1.20 (m, 2H), LC-MS: m/z 366 [M+H]$^+$; HPLC Purity: 99.7%.

Example 12

2-(difluoromethyl)-5-(2-(1-phenylcyclopropoxy)pyrimidin-5-yl)-1,3,4-oxadiazole (12)

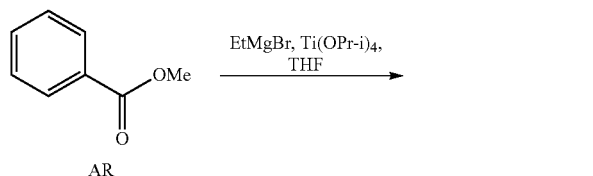

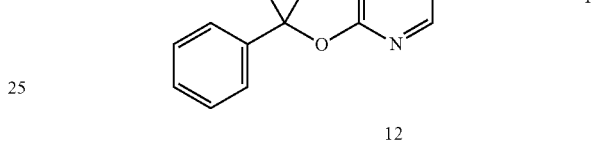

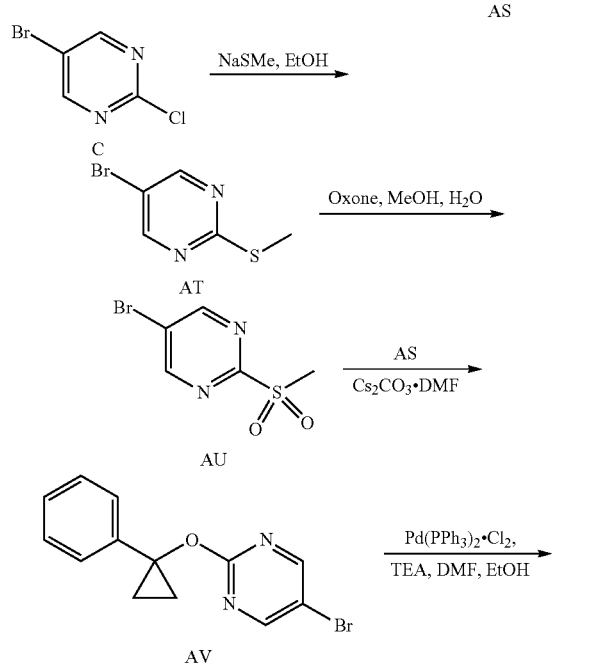

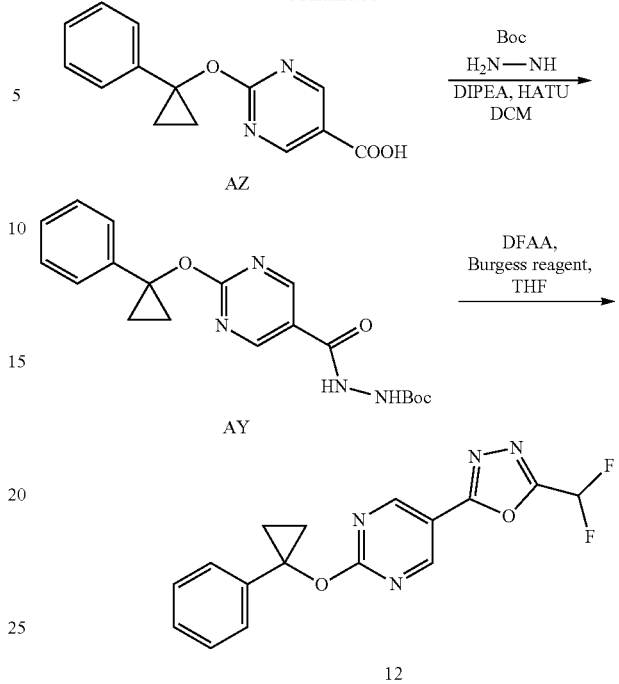

1-phenylcyclopropan-1-ol (AS)

To a stirred solution of ethyl benzoate (AR, 10 g, 73.4 mmol) in THF (120 mL), EtMgBr (3M in THF, 68.5 mL, 205.6 mmol) and Ti(OPr-i)$_4$ (29.2 g, 102.76 mmol) were added and the reaction mixture was stirred at RT for 16 h. The progress of the reaction was monitored by TLC. After completion of the reaction, the reaction mixture was quenched with saturated aqueous NH$_4$Cl solution and extracted with EtOAc. The combined organic layer was washed with brine, dried over anhydrous Na$_2$SO$_4$ and concentrated under reduced pressure. The crude product was purified by silica gel column chromatography using 20% EtOAc/hexane to afford compound AS (2.5 g, 25.5%) as a colorless liquid. LC-MS: m/z 134.86 [M+H]$^+$.

5-bromo-2-(methylthio)pyrimidine (AT)

To a stirred solution of 5-bromo-2-chloropyrimidine (C, 9 g, 46.5 mmol) in EtOH (50 mL), sodium thiomethoxide (3.25 g, 46.5 mmol) was added and the reaction mixture was stirred at RT for 16 h. The progress of the reaction was monitored by TLC. After completion of the reaction, the reaction mixture was quenched with water and extracted with EtOAc. The combined organic layer was washed with brine, dried over anhydrous Na$_2$SO$_4$ and concentrated under reduced pressure to afford compound AT (8.7 g, crude) as an off white solid. LC-MS: m/z 204.85 [M+H]$^+$.

5-bromo-2-(methylsulfonyl)pyrimidine (AU)

To a stirred solution of compound AT (8.7 g, 42.4 mmol) in MeOH:H$_2$O (1:1, 70 mL), oxone (12.9 g, 84.8 mmol) was added and the reaction mixture was stirred at RT for 4 h. The progress of the reaction was monitored by TLC. After completion of the reaction, the reaction mixture was diluted with DCM and aqueous layer was extracted with DCM. The combined organic layer was washed with brine, dried over anhydrous Na₂SO₄ and concentrated under reduced pressure to afford compound AU (9.6 g, crude) as an off white solid. LC-MS: m/z 237.00 [M+H]⁺.

5-bromo-2-(1-phenylcyclopropoxy)pyrimidine (AV)

To a stirred solution of compound AS (3 g, 22.3 mmol) in DMF (25 mL), Cs₂CO₃ (14.5 g, 44.6 mmol) and compound AU (4.75 g, 20.0 mmol) were added at 0° C. and the reaction mixture was stirred at 0° C. for 3 h. The progress of the reaction was monitored by TLC. After completion of the reaction, the reaction mixture was diluted with water and extracted with EtOAc. The combined organic layer was washed with brine, dried over anhydrous Na₂SO₄ and concentrated under reduced pressure. The crude product was purified by silica gel column chromatography using 10% EtOAc/hexane to afford compound AV (3 g, 46%) as an off white solid. LC-MS: m/z 292.87 [M+H]⁺; ¹H NMR (400 MHz, DMSO-d₆) δ 8.54-8.45 (m, 2H), 7.42-7.19 (m, 5H), 1.56-1.26 (m, 4H).

ethyl 2-(1-phenylcyclopropoxy)pyrimidine-5-carboxylate (AW)

To a stirred solution of compound AV (3 g, 10.3 mmol) in DMF:EtOH (1:1, 30 mL), Pd(PPh₃)ₙCl₂ (1.51 g, 2.16 mmol) was added. The suspension was purged with argon for 30 min and then triethyl amine (3.58 mL, 25.7 mmol) was added. The reaction mixture was stirred at 100° C. for 4 h under carbon monoxide pressure. The progress of the reaction was monitored by TLC. After completion of the reaction, the reaction mixture was diluted with EtOAc and washed with water. The combined organic layer was washed with brine, dried over anhydrous Na₂SO₄ and concentrated under reduced pressure. The crude product was purified by silica gel column chromatography using 20% EtOAC/hexane to afford compound AW (1 g, 34.2%) as an off white solid. LC-MS: m/z 285.08 [M+H]⁺.

2-(1-phenylcyclopropoxy)pyrimidine-5-carboxylic acid (AX)

To a stirred solution of compound AW (1 g, 3.51 mmol) in EtOH (20 mL), NaOH (0.28 g, 7.0 mmol) in water was added at 0° C. and the reaction mixture was at RT for 1 h. The progress of the reaction was monitored by TLC. After completion of the reaction, the reaction mixture was concentrated under reduced pressure. The reaction mixture was diluted with water and acidified with HCl to pH=5. The solid obtained was filtered and dried to afford compound AX (0.54 g, crude) as an off white solid. LC-MS: m/z 257.00 [M+H]⁺.

tert-butyl 2-(2-(1-phenylcyclopropoxy)pyrimidine-5-carbonyl)hydrazine-1-carboxylate (AY)

To a stirred solution of compound AX (0.52 g, 2.02 mmol) in DCM (25 mL), tert-butyl hydrazinecarboxylate (0.32 g, 2.43 mmol), HATU (0.92 g, 2.43 mmol), DIPEA (1 mL, 6.06 mmol) were added at 0° C. and the reaction mixture was stirred at RT for 16 h. The progress of the reaction was monitored by TLC. After completion of the reaction, the reaction mixture was diluted with water and extracted with DCM. The combined organic layer was washed with brine, dried over anhydrous Na₂SO₄ and concentrated under reduced pressure. The crude product was purified by silica gel column chromatography using 50% EtOAC/hexane to afford compound AY (0.3 g, 39.9%) as an off white solid. LC-MS: m/z 371.05 [M+H]⁺.

2-(difluoromethyl)-5-(2-(1-phenylcyclopropoxy)pyrimidin-5-yl)-1,3,4-oxadiazole (12)

To a stirred solution of compound AY (0.27 g, 0.72 mmol) in THF (10 mL), Burgess reagent (0.43 g, 1.82 mmol) and DFAA (0.5 mL) were added at 0° C. The reaction mixture was stirred at RT for 12 h. The progress of the reaction was monitored by TLC. After completion of the reaction, the reaction mixture was concentrated under reduced pressure. The crude product was purified by silica gel column chromatography using 30% EtOAc/hexane to afford compound 12 (0.07 g, 31%) as an off white solid. ¹H NMR (400 MHz, DMSO-d₆) δ 9.18 (s, 2H), 7.56 (t, J=51.2 Hz, 1H), 7.29-7.27 (m, 2H), 7.23-7.21 (m, 3H), 1.49-1.44 (m, 4H), LC-MS: m/z 331.08 [M+H]⁺; HPLC Purity: 98.8%.

Example 13

5-(5-(difluoromethyl)-1,3,4-oxadiazol-2-yl)-N-(3,3,3-trifluoro-1-(4-fluorophenyl)propyl) pyrimidin-2-amine (13)

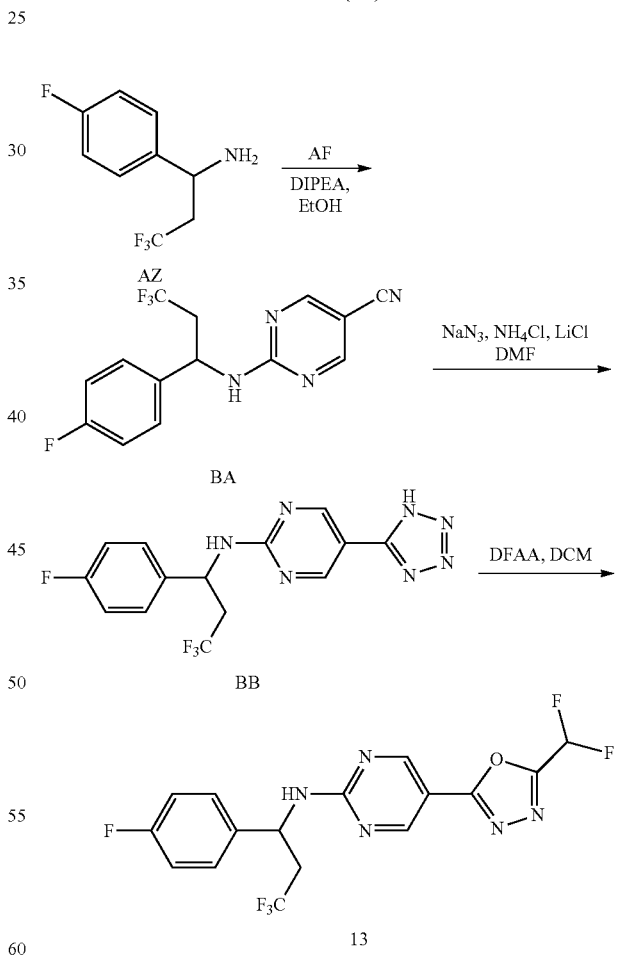

2-((3,3,3-trifluoro-1-(4-fluorophenyl)propyl)amino)pyrimidine-5-carbonitrile (BA)

To a stirred solution of 3,3,3-trifluoro-1-(4-fluorophenyl)propan-1-amine (AZ, 0.4 g, 1.90 mmol) in EtOH (10 mL), 2-chloropyrimidine-5-carbonitrile (AF, 0.35 g, 2.50 mmol) and DIPEA (1.6 mL, 9.50 mmol) were added and the reaction mixture was stirred at 90° C. for 14 h. The progress of the reaction was monitored by TLC. After completion of the reaction, the reaction mixture was concentrated under reduced pressure. The crude product was purified by silica gel column chromatography using 10% EtOAc/hexane to afford compound BA (0.55 g, 91.6%) as a white solid. LC-MS: m/z 311 [M+H]+.

5-(1H-tetrazol-5-yl)-N-(3,3,3-trifluoro-1-(4-fluoro-phenyl)propyl)pyrimidin-2-amine (BB)

To a stirred solution of compound BA (0.55 g, 1.70 mmol) in DMF (7 mL), NaN3 (0.35 g, 5.30 mmol), NH4Cl (0.27 g, 5.30 mmol) and LiCl (50 mg) were added and the reaction mixture was stirred at 100° C. for 16 h. The progress of the reaction was monitored by TLC. After completion of the reaction, the reaction mixture was concentrated under reduced pressure. The residue was dissolved in cold water and adjust to pH=4-5 by using HCl solution. The obtained solid was filtered, washed with water, and dried to afford compound BB (0.5 g, crude) as an off white solid. LC-MS: m/z 354.05 [M+H]+.

5-(5-(difluoromethyl)-1,3,4-oxadiazol-2-yl)-N-(3,3,3-trifluoro-1-(4-fluorophenyl)propyl)pyrimidin-2-amine (13)

To a stirred solution of compound BB (0.5 g, 1.40 mmol) in DCM (15 mL), 2,2-difluoroacetic anhydride (0.22 mL, 2.10 mmol) was added and the reaction mixture was stirred at RT for 16 h. The progress of the reaction was monitored by TLC. After completion of the reaction, the reaction mixture was quenched with water and extracted with DCM. The combined organic layer was washed with brine, dried over anhydrous Na2SO4 and concentrated under reduced pressure. The crude product was purified by silica gel column chromatography using 20% EtOAc/hexane to afford compound 13 (0.06 g, 8.5%) as colorless sticky liquid. 1H NMR (400 MHz, DMSO-d6) δ 8.92 (d, J=9.2 Hz, 1H), 8.88 (s, 2H), 7.52 (t, J=7 Hz, 3H), 7.19 (d, J=8.6 Hz, 2H), 5.57-5.51 (m, 1H), 3.02-2.96 (m, 1H), 2.85-2.79 (m, 1H). LC-MS: m/z 403.97 [M+H]+; HPLC Purity: 99.7%.

Example 14

5-(5-(difluoromethyl)-1,3,4-oxadiazol-2-yl)-N-(1-(4'-fluoro-[1,1'-biphenyl]-2-yl)cyclopropyl)pyrimidin-2-amine (14)

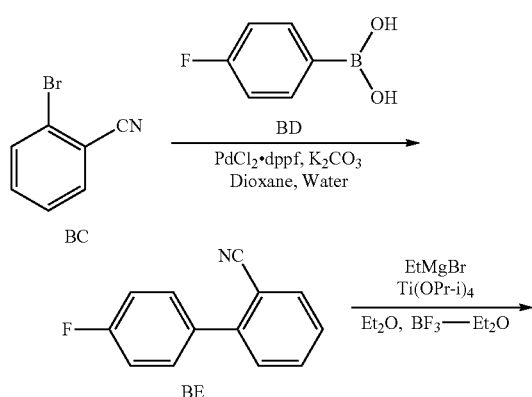

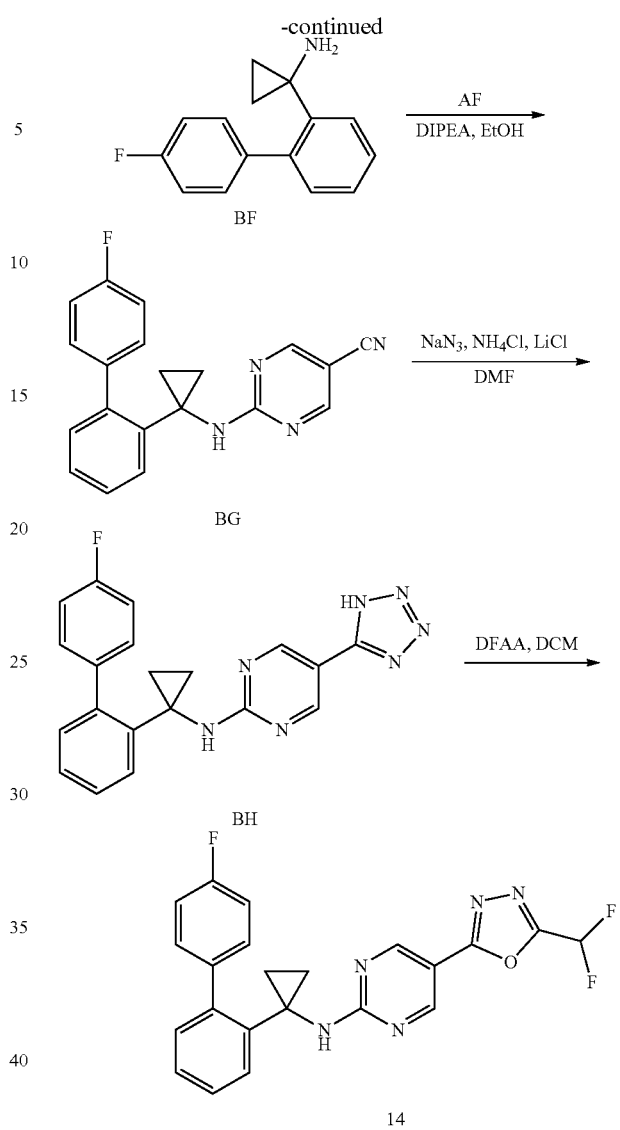

4'-fluoro-[1,1'-biphenyl]-2-carbonitrile (BE)

To a stirred solution of 2-bromobenzonitrile (BC, 4 g, 10.9 mmol) in dioxane:water (13 mL), K2CO3 (3.03 g, 21.9 mmol) and (4-fluorophenyl)boronic acid (BD, 1.84 g, 13.1 mmol) were added and purged under argon atmosphere for 10 min. Pd(dppf)Cl2 (0.89 g, 1.09 mmol) was added and the reaction mixture was stirred at 90° C. for 12 h. The progress of the reaction was monitored by TLC. After completion of the reaction, the reaction mixture was quenched with water and extracted with EtOAc. The combined organic layer was washed with brine, dried over anhydrous Na2SO4 and concentrated under reduced pressure. The crude product was purified by column chromatography using 10% EtOAc/hexane to afford compound BE (2.0 g, 92.5%) as an off white solid. 1H NMR (400 MHz, DMSO-d6) δ 7.95-7.93 (m, 1H), 7.80-7.76 (m, 1H), 7.65-7.56 (m, 4H), 7.40-7.35 (m, 2H).

1-(4'-fluoro-[1,1'-biphenyl]-2-yl)cyclopropan-1-amine (BF)

To a stirred solution of compound BE (0.5 g, 2.53 mmol) in dry Et2O (10 mL), EtMgBr (1.86 mL, 3M solution in THF, 5.58 mmol) and Ti(O-iPr)$_4$ (0.79 g, 2.79 mmol) were added at 0° C. and the reaction mixture was stirred at RT for 1 h. BF$_3$·OEt$_2$ (0.72 g, 2.79 mmol) was added and the reaction mixture was stirred at RT for 2 h. The progress of the reaction was monitored by TLC.

After completion of the reaction, the reaction mixture was quenched with saturated aqueous NH$_4$Cl solution and extracted with EtOAc. The combined organic layer was washed with brine, dried over anhydrous Na$_2$SO$_4$ and concentrated under reduced pressure. The crude product was purified by silica gel column chromatography using 20% EtOAc/hexane to afford compound BF (0.9 g, 39%) as a pale yellow oil. LC-MS: m/z 227.90 [M+H]$^+$.

2-((1-(4'-fluoro-[1,1'-biphenyl]-2-yl)cyclopropyl) amino)pyrimidine-5-carbonitrile (BG)

To a stirred solution of compound BF (0.55 g, 3.96 mmol) in EtOH (10 mL), 2-chloropyrimidine-5-carbonitrile (AF, 0.9 g, 3.96 mmol) and DIPEA (1.53 g, 11.9 mmol) were added at 80° C. and the reaction mixture was stirred at 90° C. for 12 h. The progress of the reaction was monitored by TLC. After completion of the reaction, the reaction mixture was concentrated under reduced pressure. The crude product was purified by silica gel column chromatography using 20% EtOAc/hexane to afford compound BG (0.5 g, 38.4%) as a yellow oil. LC-MS: m/z 331.08 [M+H]$^+$.

N-(1-(4'-fluoro-[1,1'-biphenyl]-2-yl)cyclopropyl)-5-(1H-tetrazol-5-yl)pyrimidin-2-amine (BH)

To a stirred solution of compound BG (0.5 g, 1.51 mmol) in DMF (10 mL), NaN$_3$ (0.29 g, 4.54 mmol), NH$_4$Cl (0.24 g, 4.54 mmol) and LiCl (70 mg) were added and the reaction mixture was stirred at 90° C. for 16 h. The progress of the reaction was monitored by TLC. After completion of the reaction, the reaction mixture was quenched with ice water and acidified with 2N HCl solution to pH=2, extracted with 10% MeOH/DCM. The combined organic layer was washed with brine, dried over anhydrous Na$_2$SO$_4$ and concentrated under reduced pressure to afford compound BH (0.3 g, 53%) as a white solid. LC-MS: m/z 374.05 [M+H]$^+$.

5-(5-(difluoromethyl)-1,3,4-oxadiazol-2-yl)-N-(1-(4'-fluoro-[1,1'-biphenyl]-2-yl)cyclopropyl) pyrimidin-2-amine (14)

To a stirred solution of compound BH (0.3 g, 0.8 mmol) in DCM (10 mL), DFAA (0.29 g, 1.20 mmol) was added at 0° C. and the reaction mixture was stirred at RT for 16 h. The progress of the reaction was monitored by TLC. After completion of the reaction, the reaction mixture was quenched with water and extracted with DCM. The combined organic layer was washed with brine, dried over anhydrous Na$_2$SO$_4$ and concentrated under reduced pressure. The crude product was purified by silica gel column chromatography using 10% EtOAc/hexane to afford compound 14 (55 mg, 16%) as a thick oil. $^1$H NMR (400 MHz, DMSO-d$_6$) δ 8.89 (s, 1H), 8.80 (s, 1H), 7.95 (d, J=7.2 Hz, 1H), 7.91 (s, 1H), 7.51 (d, J=53.7 Hz, 1H), 7.41-7.37 (m, 2H), 7.32-7.23 (m, 4H), 7.09-7.07 (m, 1H), 1.07-1.04 (m, 2H), 1.01-0.98 (m, 2H), LC-MS: m/z 424.07 [M+H]$^+$; HPLC Purity: 99.8%.

Example 15

5-(5-(difluoromethyl)-1,3,4-oxadiazol-2-yl)-N-(2,2,2-trifluoro-1-(4-fluorophenyl)ethyl)pyrimidin-2-amine (15)

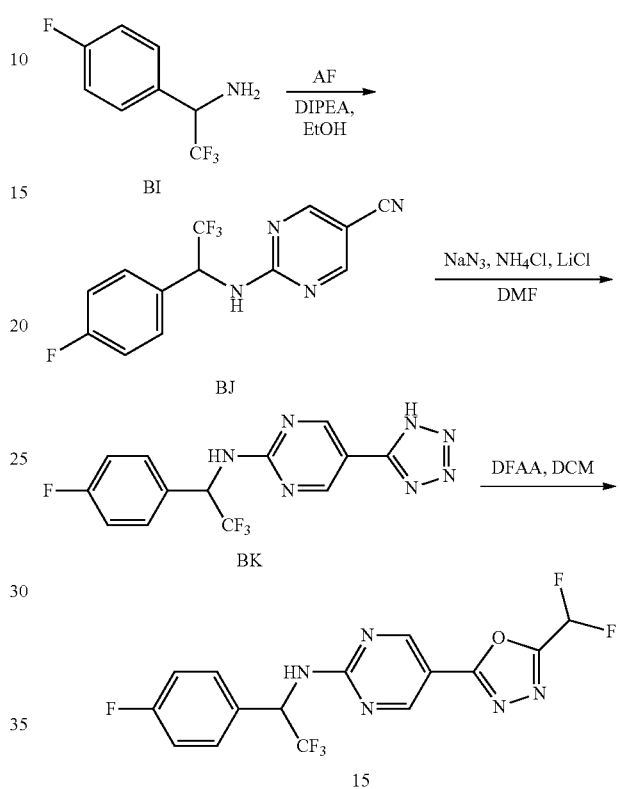

2-((2,2,2-trifluoro-1-(4-fluorophenyl)ethyl)amino) pyrimidine-5-carbonitrile (BJ)

To a stirred solution of 2,2,2-trifluoro-1-(4-fluorophenyl)ethan-1-amine (1BI 0.5 g, 2.59 mmol) in EtOH (10 mL), 2-chloropyrimidine-5-carbonitrile (AF, 0.47 g, 3.36 mmol) and DIPEA (2.19 mL, 12.9 mmol) were added and the reaction mixture was stirred at 90° C. for 14 h. The progress of the reaction was monitored by TLC. After completion of the reaction, the reaction mixture was concentrated under reduced pressure. The crude product was purified by silica gel column chromatography using 10% EtOAc/hexane to afford compound BJ (0.17 g, 22.1%) as a white solid.

5-(1H-tetrazol-5-yl)-N-(2,2,2-trifluoro-1-(4-fluorophenyl)ethyl)pyrimidin-2-amine (BK)

To a stirred solution of compound BJ (0.17 g, 0.57 mmol) in DMF (10 mL), NaN$_3$ (0.18 g, 2.87 mmol), NH$_4$Cl (0.15 g, 2.87 mmol) and LiCl (50 mg) were added and the reaction mixture was stirred at 100° C. for 16 h. The progress of the reaction was monitored by TLC. After completion of the reaction, the reaction mixture was concentrated under reduced pressure. The residue was dissolved in cold water and adjust to pH=4-5 by using HCl solution. The obtained solid was filtered and washed with water, dried to afford compound BK (0.18 g, crude) as an off white solid. LC-MS: m/z 340.05 [M+H]$^+$.

5-(5-(difluoromethyl)-1,3,4-oxadiazol-2-yl)-N-(2,2,2-trifluoro-1-(4-fluorophenyl)ethyl)pyrimidin-2-amine (15)

To a stirred solution of compound BK (0.17 g, 4.40 mmol) in DCM (20 mL), 2,2-difluoroacetic anhydride (0.12 mL, 8.90 mmol) was added and the reaction mixture was stirred at RT for 16 h.

The progress of the reaction was monitored by TLC. After completion, the reaction mixture was quenched with water and extracted with DCM. The combined organic layer was washed with brine, dried over anhydrous $Na_2SO_4$ and concentrated under reduced pressure. The crude product was purified by silica gel column chromatography using 20% EtOAc/hexane to afford compound (0.027 g, 3.5%) as an off white solid. $^1H$ NMR (400 MHz, DMSO-$d_6$) δ 9.57 (d, J=10.4 Hz, 1H), 8.99 (d, J=10.4 Hz, 2H), 7.80-7.78 (m, 2H), 7.54 (t, J=51 Hz, 1H), 7.28 (t, J=8.8 Hz, 2H), 6.27-6.20 (m, 1H); LC-MS: m/z 390 [M+H]$^+$; HPLC Purity: 99.7%.

Example 16

5-(5-(difluoromethyl)-1,3,4-oxadiazol-2-yl)-N-(1-(4'-fluoro-[1,1'-biphenyl]-4-yl)cyclopropyl) pyrimidin-2-amine (16)

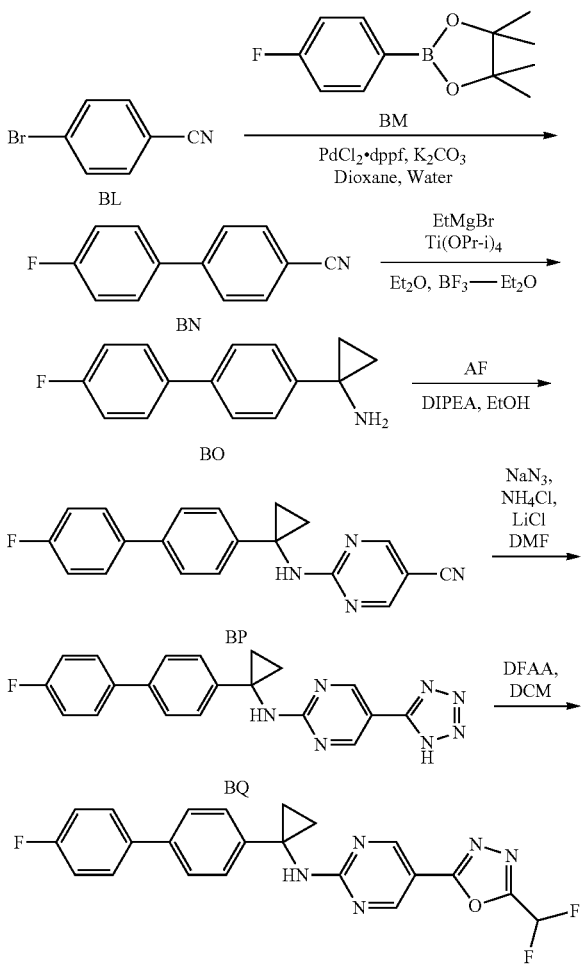

4'-fluoro-[1,1'-biphenyl]-4-carbonitrile (BN)

To a stirred solution of 4-bromobenzonitrile (BL, 2.0 g, 10.9 mmol) in dioxane:Water (13 mL), $K_2CO_3$ (3.03 g, 21.9 mmol) and 2-(4-fluorophenyl)-4,4,5,5-tetramethyl-1,3,2-dioxaborolane (BM, 2.92 g, 13.1 mmol) was added and the suspension was purged with argon for 10 min. Pd(dppf)$C_{12}$. (0.89 g, 1.09 mmol) was added and the reaction mixture was stirred at 90° C. for 12 h. The progress of the reaction was monitored by TLC. After completion of the reaction, the reaction mixture was quenched with water and extracted with EtOAc. The combined organic layer was washed with brine, dried over anhydrous $Na_2SO_4$ and concentrated under reduced pressure. The crude product was purified by column chromatography using 10% EtOAc/hexane to afford compound BN (2.0 g, 92.5%) as an off white solid. LC-MS: m/z 198 [M+H]$^+$. 1-(4'-fluoro-[1,1'-biphenyl]-4-yl)cyclopropan-1-amine (BO)

To a stirred solution of compound BN (2.0 g, 10.1 mmol) in dry $Et_2O$ (30 mL), EtMgBr (7.44 mL, 3M solution, 22.3 mmol) and Ti(O-iPr)$_4$ (3.17 g, 11.1 mmol) were added at 0° C. and the reaction mixture was stirred at RT for 1 h. $BF_3 \cdot OEt_2$ (2.88 g, 20.3 mmol) was added and the reaction mixture was stirred at RT for 2 h. The progress of the reaction was monitored by TLC.

After completion of the reaction, the reaction mixture was quenched with $NH_4Cl$ solution and extracted with EtOAc. The combined organic layer was washed with brine, dried over anhydrous $Na_2SO_4$ and concentrated under reduced pressure. The crude product was purified by silica gel column chromatography using 20% EtOAc/hexane to afford compound BO (0.9 g, 39.1%) as a pale yellow oil. LC-MS: m/z 228.05 [M+H]$^+$.

2-((1-(4'-fluoro-[1,1'-biphenyl]-4-yl)cyclopropyl)amino)pyrimidine-5-carbonitrile (BP)

To a stirred solution of compound BO (0.55 g, 3.96 mmol) in EtOH (10 mL), 2-chloropyrimidine-5-carbonitrile (AF, 0.9 g, 3.96 mmol) and DIPEA (1.53 g, 11.9 mmol) were added at 80° C. and the reaction mixture was stirred at 90° C. for 12 h. The progress of the reaction was monitored by TLC. After completion of the reaction, the reaction mixture was concentrated under reduced pressure. The crude product was purified by silica gel column chromatography using 20% EtOAc/hexane to afford compound BP (0.5 g, 38.4%) as a yellow oil; LC-MS: m/z 331.08 [M+H]$^+$

N-(1-(4'-fluoro-[1,1'-biphenyl]-4-yl)cyclopropyl)-5-(1H-tetrazol-5-yl)pyrimidin-2-amine (BQ)

To a stirred solution of compound BP (0.5 g, 1.51 mmol) in DMF (10 mL), $NaN_3$ (0.29 g, 4.54 mmol), $NH_4Cl$ (0.24 g, 4.54 mmol) and LiCl (70 mg) were added and the reaction mixture was stirred at 100° C. for 16 h. The progress of the reaction was monitored by TLC. After completion of the reaction, the reaction mixture was quenched with ice water and acidified with 2N HCl solution to pH=2. The precipitated solid was filtered and washed with cold water to afford compound BQ (0.3 g, 53%) as a white solid. LC-MS: m/z 374.05 [M+H]$^+$.

5-(5-(difluoromethyl)-1,3,4-oxadiazol-2-yl)-N-(1-(4'-fluoro-[1,1'-biphenyl]-4-yl)cyclopropyl) pyrimidin-2-amine (16)

To a stirred solution of compound BQ (0.5 g, 1.34 mmol) in pyridine (10 mL), DFAA (0.21 mL, 2.01 mmol) was added at 0° C. and the reaction mixture was stirred at 80° C. for 14 h. The progress of the reaction was monitored by TLC. After completion of the reaction, the reaction mixture was quenched with water and extracted with EtOAc. The combined organic layer was washed with brine, dried over anhydrous $Na_2SO_4$ and concentrated under reduced pressure. The crude product was purified by silica gel column chromatography using 5% MeOH/DCM to afford compound 16 (40 mg, 7%) as a thick oil. $^1$H NMR (400 MHz, DMSO-$d_6$) δ 9.06 (s, 1H), 8.89 (d, J=2.8 Hz, 1H), 8.85 (d, J=2.8 Hz, 1H), 7.65-7.62 (m, 2H), 7.52-7.50 (m, 3H), 7.38 (t, J=51.4 Hz, 1H), 7.26-7.21 (m, 3H), 1.38-1.30 (m, 4H), LC-MS: m/z 424.05 [M+H]$^+$; HPLC Purity: 97.8%.

Example 17

5-(5-(difluoromethyl)-1,3,4-oxadiazol-2-yl)-N-(4-(4-fluorophenyl)-1-phenylpiperidin-4-yl)pyrimidin-2-amine (17)

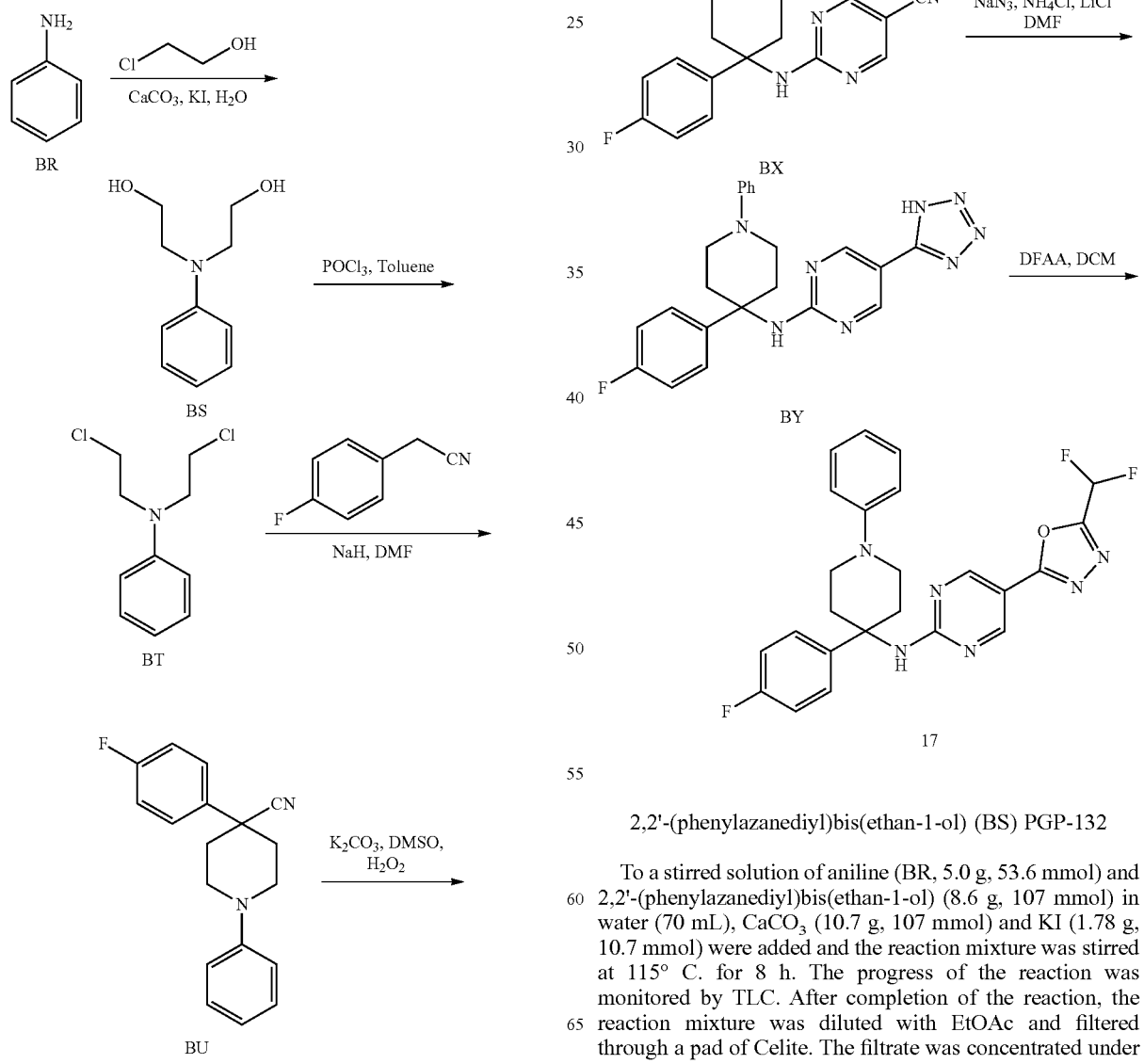

2,2'-(phenylazanediyl)bis(ethan-1-ol) (BS) PGP-132

To a stirred solution of aniline (BR, 5.0 g, 53.6 mmol) and 2,2'-(phenylazanediyl)bis(ethan-1-ol) (8.6 g, 107 mmol) in water (70 mL), CaCO$_3$ (10.7 g, 107 mmol) and KI (1.78 g, 10.7 mmol) were added and the reaction mixture was stirred at 115° C. for 8 h. The progress of the reaction was monitored by TLC. After completion of the reaction, the reaction mixture was diluted with EtOAc and filtered through a pad of Celite. The filtrate was concentrated under reduced pressure and the crude product was purified by column chromatography using 30% EtOAc/hexane to afford compound BS (16.4 g, crude) as a white solid. LC-MS: m/z 181.9 [M+H]+.

N,N-bis(2-chloroethyl)aniline (BT)

A stirred solution of compound BS (9.0 g, 49.4 mmol) in POCl3 (50 mL) was refluxed for 2 h. After completion of the reaction, the reaction mixture was concentrated under reduced pressure. The residue was dissolved in water and extracted with EtOAc. The combined organic layer was washed with brine, dried over anhydrous Na2SO4 and concentrated under reduced pressure. The crude product was purified by silica gel column chromatography using 15% EtOAc/hexane to afford compound BT (6.1 g, 57%) as a thick oil. $^1$H NMR (400 MHz, CDCl3) δ 7.29-7.25 (m, 2H), 6.80-6.69 (m, 3H), 3.79-3.49 (m, 8H).

4-(4-fluorophenyl)-1-phenylpiperidine-4-carbonitrile (BU)

To a stirred solution of compound BT (6.1 g, 27.9 mmol) in DMF (70 mL), NaH (60% 3.35 g, 83.9 mmol) was added at 0° C. and the reaction mixture was stirred for 10 min. To the resulting reaction mixture 2-(4-fluorophenyl)acetonitrile (3.8 g, 27.9 mmol) was added and the reaction mixture was stirred at 60° C. for 16 h. The progress of the reaction was monitored by TLC. After completion of the reaction, the reaction mixture was quenched with water and extracted with EtOAc. The combined organic layer was washed with brine, dried over anhydrous Na2SO4 and concentrated under reduced pressure. The crude product was purified by silica gel column chromatography using 20% EtOAc/hexane to afford compound BU (6.0 g, 77%) as a sticky solid.

4-(4-fluorophenyl)-1-phenylpiperidine-4-carboxamide (BV)

To a stirred solution of compound BU (6.0 g, 21.3 mmol) in DMSO (60 mL), K2CO3 (11.8 g, 85.4 mmol) and H2O2 (30%, 9.6 mL, 85.4 mmol) were added and the reaction mixture was stirred at 115° C. for 8 h. The progress of the reaction was monitored by TLC. After completion of the reaction, the reaction mixture was quenched with ice water and obtained solid was filtered, dried.

The crude product was purified by column chromatography using 5% MeOH/DCM to afford compound BV (4 g, 63%) as a white solid.

4-(4-fluorophenyl)-1-phenylpiperidin-4-amine (BW)

To a stirred solution of compound BV (2.5 g, 8.36 mmol) in t-BuOH (30 mL), NaOCl (1.74 g, 23.4 mmol) and 3N NaOH (15.5 mL) were added and the reaction mixture was stirred at RT for 14 h. The progress of the reaction was monitored by TLC. After completion of the reaction, the reaction mixture was quenched with water and the obtained solid was filtered and dried to afford compound BW (0.35 g, 86%). LC-MS: m/z 280 [M+H]+.

2-((4-(4-fluorophenyl)-1-phenylpiperidin-4-yl)amino)pyrimidine-5-carbonitrile (BX)

To a stirred solution of compound BW (0.4 g, 2.86 mmol) in ethanol (10 mL), 2-chloropyrimidine-5-carbonitrile (AF, 0.77 g, 5.0 mmol) and DIPEA (2.6 mL, 14.3 mmol) were added and the reaction mixture was heated to 90° C. for 4 h. The progress of the reaction was monitored by TLC. After completion of the reaction, the reaction mixture was concentrated under reduced pressure. The crude product was purified by silica gel column chromatography using 50% EtOAc/hexane to afford compound BX (0.5 g, 50%) as an off white solid. LC-MS: m/z 374.05 [M+H]+.

N-(4-(4-fluorophenyl)-1-phenylpiperidin-4-yl)-5-(1H-tetrazol-5-yl)pyrimidin-2-amine (BY)

To a stirred solution of compound BX (0.5 g, 1.33 mmol) in DMF (10 mL), NaN3 (0.43 g, 6.68 mmol), NH4Cl (0.36 g, 6.68 mmol) and LiCl (90 mg) were added and the reaction mixture was stirred at 100° C. for 14 h. The progress of the reaction was monitored by TLC. After completion of the reaction, the reaction mixture was quenched with ice water, acidified with 2N HCl solution to pH=2, and extracted with 10% MeOH/DCM. The combined organic layer was washed with brine, dried over anhydrous Na2SO4 and concentrated under reduced pressure to afford compound BY (0.53 g, 96%) as an off white solid. LC-MS: m/z 417.05 [M+H]+.

5-(5-(difluoromethyl)-1,3,4-oxadiazol-2-yl)-N-(4-(4-fluorophenyl)-1-phenylpiperidin-4-yl)pyrimidin-2-amine (17)

To a stirred solution of compound BY (0.53 g, 1.27 mmol) in pyridine (10 mL), DFAA (0.21 mL, 1.91 mmol) was added dropwise at 0° C. The reaction was stirred at RT for 16 h. The progress of the reaction was monitored by TLC. After completion of the reaction, the reaction mixture was quenched with water and extracted with DCM. The combined organic layer was washed with brine, dried over anhydrous Na2SO4 and concentrated under reduced pressure. The crude product was purified by silica gel column chromatography using 12% EtOAc/hexane to afford compound 17 (31 mg, 5.2%) as an off white solid. $^1$H NMR (400 MHz, DMSO) δ 8.81 (br s, 1H), 8.62 (br s, 1H), 8.56 (s, 1H), 7.43 (t, J=52 Hz, 1H), 7.42-7.40 (m, 1H), 7.15 (t, J=8.0 Hz, 2H), 7.13 (t, J=8.4 Hz, 2H), 6.88 (d, J=8.0 Hz, 2H), 6.70 (t, J=4.0 Hz, 1H), 3.35 (d, J=12.4 Hz, 2H), 2.94 (t, J=11.6 Hz, 2H), 2.71 (d, J=12.4 Hz, 2H), 2.10-2.06 (m, 2H), 1.10 (s, 1H); LC-MS: m/z 467.14 [M+H]+; HPLC Purity: 99.7%.

Example 18

5-(5-(difluoromethyl)-1,3,4-oxadiazol-2-yl)-N-(1-(4'-fluoro-[1,1'-biphenyl]-3-yl)cyclopropyl)pyrimidin-2-amine (18)

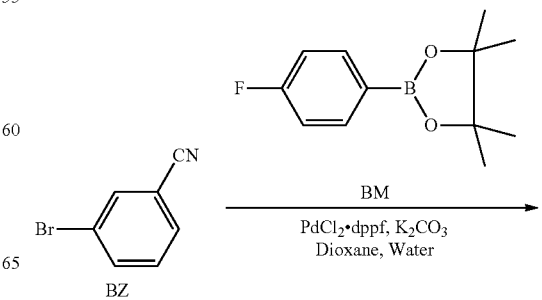

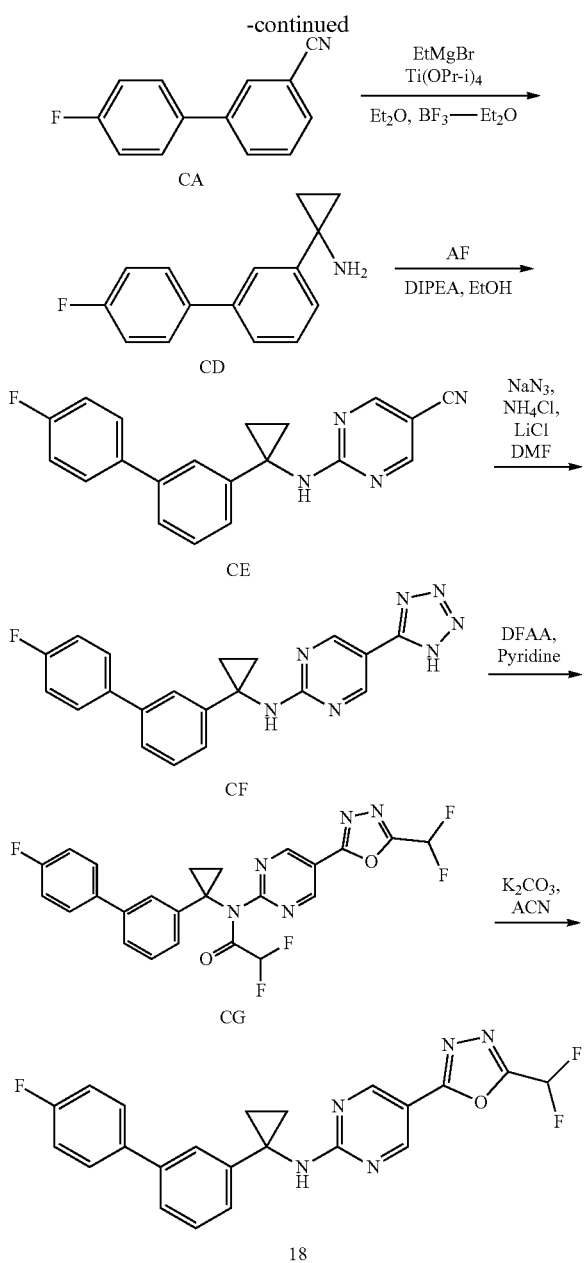

4'-fluoro-[1,1'-biphenyl]-3-carbonitrile (CA)

To a stirred solution of 3-bromobenzonitrile (BZ, 2.0 g, 10.9 mmol) in dioxane:water (13 mL), $K_2CO_3$ (3.03 g, 21.9 mmol) and 2-(4-fluorophenyl)-4,4,5,5-tetramethyl-1,3,2-dioxaborolane (BM, 2.92 g, 13.1 mmol) were added and the suspension was purged with argon for 10 min.

Pd(dppf)Cl$_2$ (0.89 g, 1.09 mmol) was added and the reaction mixture was stirred at 90° C. for 12 h.

The progress of the reaction was monitored by TLC. After completion of the reaction, the reaction mixture was quenched with water and extracted with EtOAc. The combined organic layer was washed with brine, dried over anhydrous $Na_2SO_4$ and concentrated under reduced pressure. The crude product was purified by column chromatography using 10% EtOAc/hexane to afford compound CA (2.0 g, 92.6%) as an off white solid LC-MS: m/z 198.1[M+1]$^+$.

1-(4'-fluoro-[1,1'-biphenyl]-3-yl)cyclopropan-1-amine (CD)

To a stirred solution of compound CA (2.0 g, 10.1 mmol) in dry Et$_2$O (30 mL), EtMgBr (3M in THF 7.44 mL, 3M solution, 22.3 mmol) and Ti(O-iPr)$_4$ (3.17 g, 11.1 mmol) were added at 0° C. and the reaction mixture was stirred at RT for 1 h. BF$_3$·OEt$_2$ (2.88 g, 20.3 mmol) was added and the reaction mixture was stirred at RT for 2 h. The progress of the reaction was monitored by TLC. After completion of the reaction, the reaction mixture was quenched with NH$_4$Cl solution and extracted with EtOAc. The combined organic layer was washed with brine, dried over anhydrous Na$_2$SO$_4$ and concentrated under reduced pressure. The crude product was purified by silica gel column chromatography using 20% EtOAc/hexane to afford compound CD (0.9 g, 39.1%) as a pale yellow oil. LC-MS: m/z 228.05 [M+1]$^+$.

2-((1-(4'-fluoro-[1,1'-biphenyl]-3-yl)cyclopropyl)amino)pyrimidine-5-carbonitrile (CE)

To a stirred solution of compound CD (0.55 g, 3.96 mmol) in EtOH (10 mL), 2-chloropyrimidine-5-carbonitrile (AF, 0.9 g, 3.96 mmol) and DIPEA (1.53 g, 11.9 mmol) were added at 80° C. and the reaction mixture was stirred at 90° C. for 12 h. The progress of the reaction was monitored by TLC. After completion of the reaction, the reaction mixture was concentrated under reduced pressure. The crude product was purified by silica gel column chromatography using 20% EtOAc/hexane to afford compound CE (0.6 g, 46%) as a yellow oil. LC-MS: m/z 331.10 [M+H]$^+$. $^1$H NMR (400 MHz, DMSO-d$_6$) δ 9.17 (s, 1H), 8.72-8.69 (m, 2H), 7.66-7.62 (m, 2H), 7.52 (d, J=8.0 Hz, 2H), 7.28-7.20 (m, 4H), 1.36-1.28 (m, 4H).

N-(1-(4'-fluoro-[1,1'-biphenyl]-3-yl)cyclopropyl)-5-(1H-tetrazol-5-yl)pyrimidin-2-amine (CF)

To a stirred solution of compound CE (0.6 g, 1.81 mmol) in DMF (70 mL), NaN$_3$ (0.35 g, 5.45 mmol), NH$_4$Cl (0.29 g, 5.45 mmol) and LiCl (70 mg) were added and the reaction mixture was stirred at 90° C. for 16 h. The progress of the reaction was monitored by TLC. After completion of the reaction, the reaction mixture was quenched with ice water, acidified with 2N HCl solution to pH=2, and extracted with 10% MeOH/DCM. The combined organic layer was washed with brine, dried over anhydrous Na$_2$SO$_4$ and concentrated under reduced pressure to afford compound CF (0.5 g, 73%) as a white solid. LC-MS: m/z 374.05 [M+H]$^+$.

N-(5-(5-(difluoromethyl)-1,3,4-oxadiazol-2-yl)pyrimidin-2-yl)-2,2-difluoro-N-(1-(4'-fluoro-[1,1'-biphenyl]-3-yl)cyclopropyl)acetamide (CG)

To a stirred solution of compound CF (0.5 g, 1.34 mmol) in pyridine (5 mL), DFAA (0.34 g, 2.01 mmol) was added at 0° C. and the reaction mixture was stirred at 80° C. for 4 h. The progress of the reaction was monitored by TLC. After completion of the reaction, the reaction mixture was quenched with water and extracted with DCM. The combined organic layer was washed with brine, dried over anhydrous Na$_2$SO$_4$ and concentrated under reduced pressure. The crude product was purified by silica gel column chromatography using 10% EtOAc/hexane to afford compound CG (0.3 g, 44%) as a thick oil LC-MS: m/z 424.07 [M+H]$^+$.

5-(5-(difluoromethyl)-1,3,4-oxadiazol-2-yl)-N-(1-(4'-fluoro-[1,1'-biphenyl]-3-yl)cyclopropyl)pyrimidin-2-amine (18)

To a stirred solution of compound CG (0.3 g, 0.59 mmol) in ACN (5 mL), K$_2$CO$_3$ (0.2 g, 1.49 mmol) was added at 0° C. and the reaction mixture was stirred at 80° C. for 16 h. The progress of the reaction was monitored by TLC. After completion of the reaction, the reaction mixture was quenched with water and extracted with EtOAc. The combined organic layer was washed with brine, dried over anhydrous Na$_2$SO$_4$ and concentrated under reduced pressure. The crude product was purified by silica gel column chromatography using 20% EtOAc/hexane to afford compound 18 (0.11 g, 43.4%) as a thick colorless oil. $^1$H NMR (400 MHz, DMSO-d$_6$) δ 9.06 (s, 1H), 8.87 (dd, J=2.8, 2.4 Hz, 2H), 7.64-7.51 (m, 2H), 7.44 (s, 1H), 7.39-7.32 (m, 3H), 7.29-7.19 (m, 3H), 1.49-1.42 (m, 2H), 1.32-1.30 (m, 2H), LC-MS: m/z 424.07 [M+H]$^+$; HPLC Purity: 98.1%.

Example 19

5-(5-(difluoromethyl)-1,3,4-oxadiazol-2-yl)-N-(1-(4-fluorophenyl)-2-phenoxyethyl)pyrimidin-2-amine (19)

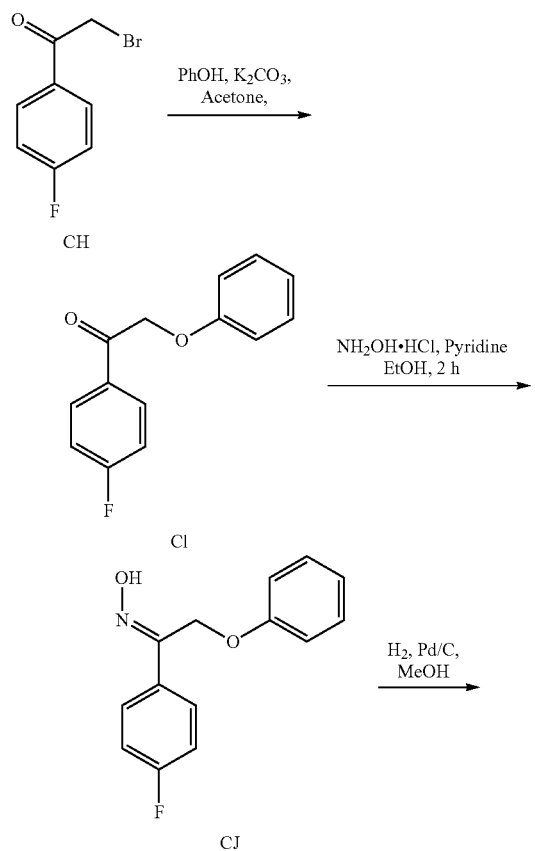

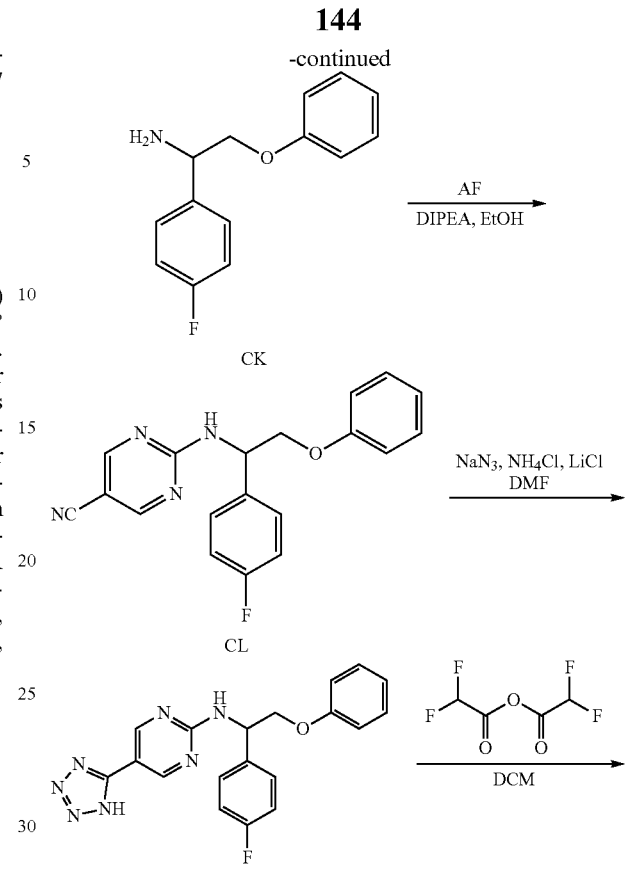

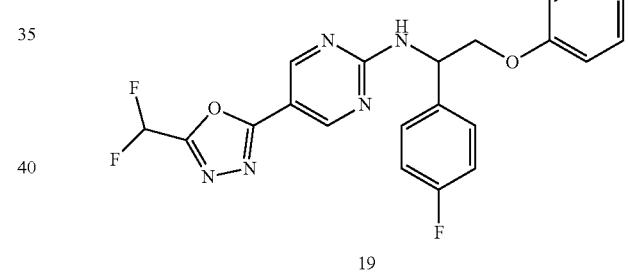

1-(4-fluorophenyl)-2-phenoxyethan-1-one (CI)

To a stirred solution of 2-bromo-1-(4-fluorophenyl)ethan-1-one (CH, 3.0 g, 13.8 mmol) in acetone (200 mL), K$_2$CO$_3$ (2.86 g, 20.7 mmol) and phenol (1.62 g, 17.2 mmol) were added and the reaction mixture was stirred at 80° C. for 4 h. The progress of the reaction was monitored by TLC. After completion of the reaction, the reaction mixture was quenched with water and extracted with EtOAc. The combined organic layer was washed with brine, dried over anhydrous Na$_2$SO$_4$ and concentrated under reduced pressure. The crude product was purified by silica gel column chromatography using 5% EtOAc/hexane to afford compound CI (1.5 g, 47.3%) as an off white solid. LC-MS: m/z 231.01 [M+H]$^+$.

(Z)-1-(4-fluorophenyl)-2-phenoxyethan-1-one oxime (CJ)

To a stirred solution of compound CI (1.28 g, 5.56 mmol) in EtOH (55 mL), NH$_2$OH·HCl (0.96 g, 13.9 mmol) was added followed by addition of pyridine (94 mL) and the reaction mixture was stirred at RT for 16 h. The progress of the reaction was monitored by TLC. After completion of the reaction, the reaction mixture was diluted with 1N HCl solution to pH=4 and extracted with EtOAc. The combined organic layer was washed with brine, dried over anhydrous Na$_2$SO$_4$ and concentrated under reduced pressure to afford compound CJ (1.21 g, 88.2%) as an off white solid LC-MS: m/z 246 [M+H]$^+$.

1-(4-fluorophenyl)-2-phenoxyethan-1-amine (CK)

To a stirred solution of CJ (1.2 g, 4.89 mmol) in MeOH (25 mL), Pd/C (150 mg) was added at RT and stirred for 16 h under H$_2$ atmosphere. After consumption of the starting material (by TLC), the reaction mixture was filtered through celite bed and washed with MeOH. The filtrate was concentrated under reduced pressure afford compound CK (1.0 g, 77%) as a thick oil. LC-MS: m/z 232 [M+H]$^+$.

2-((1-(4-fluorophenyl)-2-phenoxyethyl)amino)pyrimidine-5-carbonitrile (CL)

To a stirred solution of compound CK (0.5 g, 2.16 mmol) in ethanol (10 mL), 2-chloropyrimidine-5-carbonitrile (AF, 0.33 g, 2.38 mmol) and DIPEA (1.8 mL, 10.8 mmol) were added and the reaction mixture was heated to 90° C. for 16 h. The progress of the reaction was monitored by TLC. After completion of the reaction, the reaction mixture was concentrated under reduced pressure. The crude product was purified by silica gel column chromatography using 20% EtOAc/hexane to afford compound CL (0.62 g, 86.8%) as a white solid. LC-MS: m/z 334.05 [M+H]$^+$.

N-(1-(4-fluorophenyl)-2-phenoxyethyl)-5-(1H-tetrazol-5-yl)pyrimidin-2-amine (CM)

To a stirred solution of compound CL (0.61 g, 1.80 mmol) in DMF (10 mL), NaN$_3$ (0.6 g, 9.2 mmol), NH$_4$Cl (0.5 g, 9.2 mmol) and LiCl (90 mg) were added and the reaction mixture was stirred at 100° C. for 16 h. The progress of the reaction was monitored by TLC. After completion of the reaction, the reaction mixture was quenched with ice water, acidified with 2N HCl solution to pH=2, and extracted with 10% MeOH/DCM. The combined organic layer was washed with brine, dried over anhydrous Na$_2$SO$_4$ and concentrated under reduced pressure to afford compound CM (0.62 g, crude) as a thick oil. LC-MS: m/z 377.10 [M+H]$^+$.

5-(5-(difluoromethyl)-1,3,4-oxadiazol-2-yl)-N-(1-(4-fluorophenyl)-2-phenoxyethyl)pyrimidin-2-amine (19)

To a stirred solution of compound CM (0.5 g, 1.32 mmol) in DCM (10 mL), 2,2-difluoroacetic anhydride (0.22 mL, 1.99 mmol) was added at 0° C. Reaction mixture was stirred at RT for 30 min and then stirred at 90° C. for 16 h. The progress of the reaction was monitored by TLC. After completion of the reaction, the reaction mixture was concentrated under reduced pressure. The crude product was purified by silica gel column chromatography using 20% EtOAc/hexane to afford compound 19 (0.05 g, 8.81%) as an off white solid. $^1$H NMR (400 MHz, DMSO-d$_6$) δ 9.01 (d, J=8.0 Hz, 1H), 8.82 (d, J=8.4 Hz, 2H), 7.56-7.52 (m, 2H), 7.52 (t, J=51.2 Hz, 1H), 7.27-7.20 (m, 4H), 6.94 (d, J=7.6 Hz, 3H), 5.58 (s, 1H), 4.42 (t, J=7.6 Hz, 1H), 4.25-4.22 (m, 1H); LC-MS: m/z 428.07 [M+H]$^+$; HPLC Purity: 97.7%.

Example 20

5-(5-(difluoromethyl)-1,3,4-oxadiazol-2-yl)-N-(1-(4-fluorophenyl)ethyl)pyrimidin-2-amine (20)

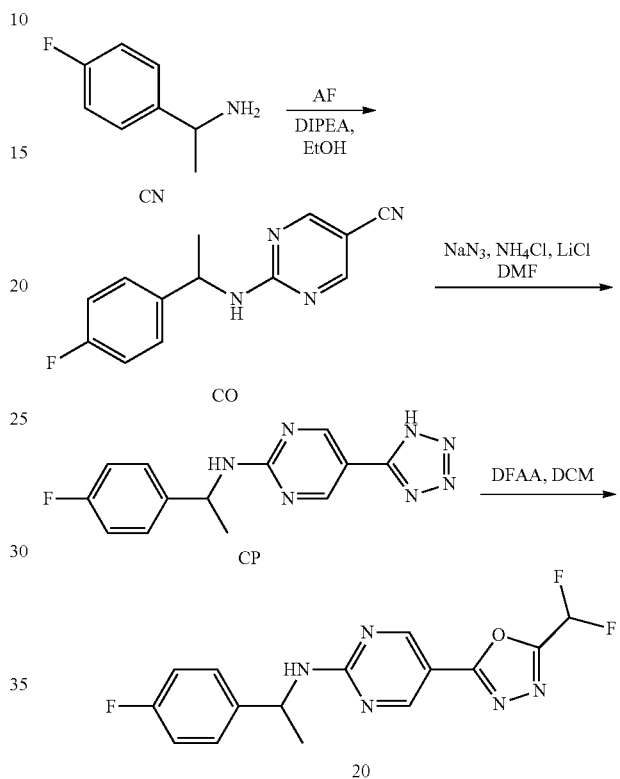

2-((1-(4-fluorophenyl)ethyl)amino)pyrimidine-5-carbonitrile (CO)

To a stirred solution of 1-(4-fluorophenyl)ethan-1-amine (CN, 0.5 g, 3.59 mmol) in ethanol (10 mL), 2-chloropyrimidine-5-carbonitrile (AF, 0.55 g, 3.95 mmol) and DIPEA (3.0 mL, 17.9 mmol) were added and the reaction mixture was heated to 90° C. for 12 h. The progress of the reaction was monitored by TLC. After completion of the reaction, the reaction mixture was concentrated under reduced pressure. The crude product was purified by silica gel column chromatography using 20% EtOAc/hexane to afford compound CO (0.8 g, 91%) as a white solid.
LC-MS: m/z 243.1 [M+H]$^+$.

N-(1-(4-fluorophenyl)ethyl)-5-(1H-tetrazol-5-yl)pyrimidin-2-amine (CP)

To a stirred solution of compound CO (0.8 g, 3.30 mmol) in DMF (10 mL), NaN$_3$ (0.89 g, 16.5 mmol), NH$_4$Cl (1.0 g, 16.5 mmol) and LiCl (240 mg) were added and the reaction mixture was stirred at 95° C. for 12 h. The progress of the reaction was monitored by TLC. After completion of the reaction, the reaction mixture was concentrated under reduced pressure. The residue was dissolved in cold water and adjusted to pH=4-5 by using aqueous HCl solution. The obtained solid was filtered, washed with water, dried to afford compound CP (0.8 g, crude) as a thick oil.
LC-MS: m/z 286.05 [M+H]+.

5-(5-(difluoromethyl)-1,3,4-oxadiazol-2-yl)-N-(1-(4-fluorophenyl)ethyl)pyrimidin-2-amine (20)

To a stirred solution of compound CP (0.4 g, 1.4 mmol) in DCM (10 mL), 2,2-difluoroacetic anhydride (1.5 mL, 6.78 mmol) was added at 0° C. The reaction mixture was stirred at RT for 30 min and then stirred at 90° C. for 16 h. The progress of the reaction was monitored by TLC. After completion of the reaction, the reaction mixture was concentrated under reduced pressure. The crude product was purified by silica gel column chromatography using 80% EtOAc/hexane to afford compound 20 (0.1 g, 21%) as an off white solid. $^1$H NMR (400 MHz, DMSO-$d_6$) δ 8.83 (dd, J=11.0, 8.0 Hz, 3H), 7.50 (t, J=51.4 Hz, 1H), 7.40-7.39 (m, 2H), 7.12 (t, J=8.8 Hz, 2H), 5.20 (t, J=7.6 Hz, 1H), 1.45 (d, J=6.8 Hz, 3H); LC-MS: m/z 336 [M+H]+; HPLC Purity: 99.8%.

Example 21

5-(5-(difluoromethyl)-1,3,4-oxadiazol-2-yl)-N-(1-(4-fluorophenyl)-2-methoxyethyl)pyrimidin-2-amine (21)

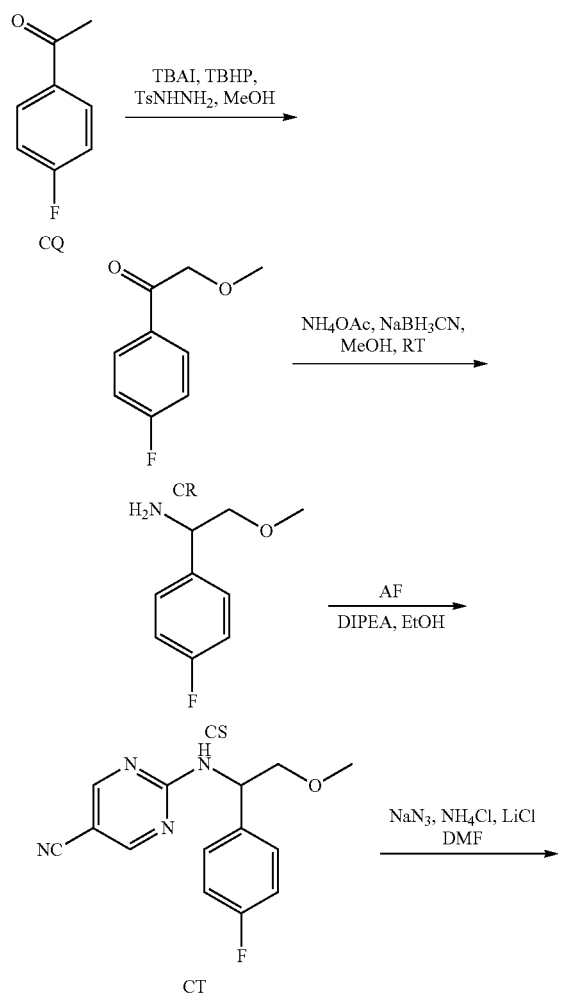

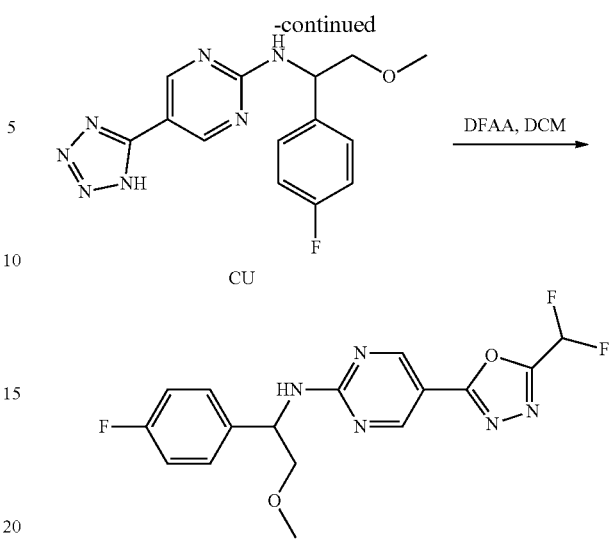

1-(4-fluorophenyl)-2-methoxyethan-1-one (CR)

To a stirred solution of 1-(4-fluorophenyl)ethan-1-one (CQ, 4.0 g, 28.0 mmol) and tetrabutyl ammonium iodide (TBAI, 2.14 g, 5.79 mmol) in MeOH (75 mL), TsNHNH$_2$ (5.2 g, 28.0 mmol) and tert-butyl hydroperoxide (TBHP, 70%, 21.6 mL, 168 mmol) were added and the reaction mixture was stirred at RT for 16 h. The progress of the reaction was monitored by TLC. After completion of the reaction, the reaction mixture was quenched using saturated aqueous Na$_2$S2O3 solution and extracted with EtOAc. The combined organic layer was washed with brine, dried over anhydrous Na$_2$SO$_4$ and concentrated under reduced pressure. The crude product was purified by silica gel column chromatography using 8% EtOAc/hexane to afford compound CR (2.5 g, 52%) as a thick oil. LC-MS: m/z 169 [M+H]+.

1-(4-fluorophenyl)-2-methoxyethan-1-amine (CS)

To a stirred solution of compound CR (1.2 g, 7.14 mmol) in MeOH (15 mL), NH$_4$OAc (5.5 g, 71.4 mmol) was added and the reaction mixture was stirred at RT for 2 h. NaCNBH$_3$ (0.9 g, 74.2 mmol) was added and the reaction mixture was stirred at RT for 16 h. The progress of the reaction was monitored by TLC. After completion of the reaction, the reaction mixture was concentrated under reduced pressure. The residue was diluted with 1N HCl solution to pH=1 and extracted with EtOAc. The aqueous layer was basified with 10% NaOH solution to pH=10 and extracted with EtOAc. The combined organic layer was washed with brine, dried over anhydrous Na$_2$SO$_4$ and concentrated under reduced pressure to afford compound CS (0.68 g, 56.6%) as a thick oil.
LC-MS: m/z 170.1 [M+H]+.

2-((1-(4-fluorophenyl)-2-methoxyethyl)amino)pyrimidine-5-carbonitrile (CT)

To a stirred solution of compound CS (0.5 g, 2.95 mmol) in ethanol (10 mL), 2-chloropyrimidine-5-carbonitrile (AF, 0.45 g, 3.25 mmol) and DIPEA (2.52 mL, 14.7 mmol) were added and the reaction mixture was heated to 90° C. for 16 h. The progress of the reaction was monitored by TLC. After completion of the reaction, the reaction mixture was concentrated under reduced pressure. The crude product was purified by silica gel column chromatography using 20% EtOAc/hexane to afford compound CT (0.61 g, 76%) as a white solid. LC-MS: m/z 272.05 [M+H]+.

N-(1-(4-fluorophenyl)-2-methoxyethyl)-5-(1H-tetrazol-5-yl)pyrimidin-2-amine (CU)

To a stirred solution of compound CT (0.6 g, 2.20 mmol) in DMF (10 mL), NaN₃ (0.71 g, 11.0 mmol), NH₄Cl (0.6 g, 11.0 mmol) and LiCl (90 mg) were added and the reaction mixture was stirred at 100° C. for 16 h. The progress of the reaction was monitored by TLC. After completion of the reaction, the reaction mixture was concentrated under reduced pressure. The residue was dissolved in cold water and adjust to pH=4-5 by using HCl solution. The obtained solid was filtered and washed with water, dried to afford compound CU (0.65 g, crude) as an off white solid. LC-MS: m/z 316.2 [M+H]+.

5-(5-(difluoromethyl)-1,3,4-oxadiazol-2-yl)-N-(1-(4-fluorophenyl)-2-methoxyethyl)pyrimidin-2-amine (21)

To a stirred solution of compound CU6 (0.31 g, 2.06 mmol) in DCM (10 mL), 2,2-difluoroacetic anhydride (0.34 mL, 3.90 mmol) was added. The reaction mixture was stirred at RT for 16 h. The progress of the reaction was monitored by TLC. After completion of the reaction, the reaction mixture was concentrated under reduced pressure. The crude product was purified by silica gel column chromatography using 50% EtOAc/hexane to afford compound 21 (0.1 g, 13.5%) as a colorless sticky solid. ¹H NMR (400 MHz, DMSO-d₆) δ 8.85 (d, J=12.8 Hz, 2H), 8.80 (d, J=8.8 Hz, 1H), 7.51 (t, J=51.2 Hz, 1H), 7.47-7.45 (m, 2H), 7.16 (t, J=8.8 Hz, 2H), 5.36-5.33 (m, 1H), 3.65 (t, J=9.4 Hz, 1H), 3.54-3.51 (m, 1H), 3.28 (s, 3H); LC-MS: m/z 366.1 [M−H]; HPLC Purity: 99.6%.

Example 22

5-(5-(difluoromethyl)-1,3,4-oxadiazol-2-yl)-N-(1-(4-fluorophenyl)propyl)pyrimidin-2-amine (22)

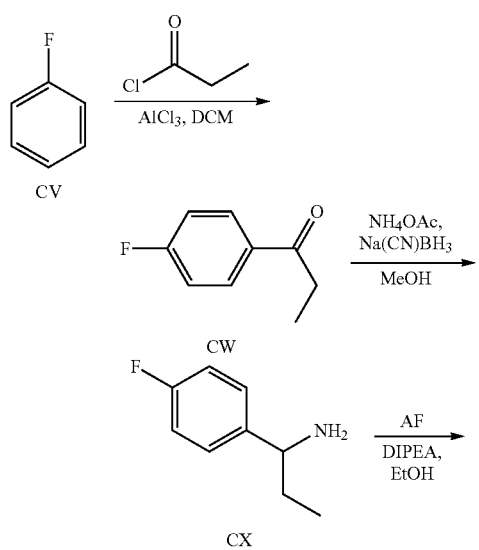

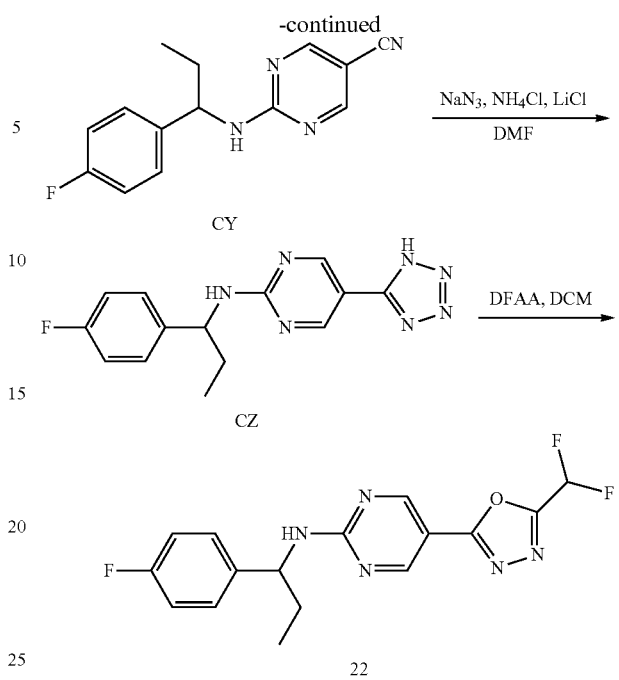

1-(4-fluorophenyl)propan-1-one (CW)

To a solution of anhydrous AlCl₃ (13.8 g, 104 mmol) in DCM (10 mL) at 0° C., a solution of propionyl chloride (6.8 mL, 78.1 mmol) in DCM (25 mL) was added drop wise and the reaction mixture was stirred at RT for 1 h. To this a solution, fluorobenzene (CV, 5.0 g, 52.0 mmol) in DCM (15 mL) was added drop wise and the reaction mixture was stirred at RT for 12 h. The progress of the reaction was monitored by TLC. After completion of the reaction, the reaction mixture was quenched with water and extracted with EtOAc. The combined organic layer was washed with brine, dried over anhydrous Na₂SO₄ and concentrated under reduced pressure. The crude product was purified by column chromatography using 5% EtOAc/hexane to afford compound CW (4.0 g, 50%) as an off white solid LC-MS: m/z 153.05 [M+H]+.

1-(4-fluorophenyl)propan-1-amine (CX)

To a stirred solution of compound CW (4.0 g, 26.3 mmol) in MeOH (50 mL), ammonium acetate (20.2 g, 263 mmol) was added and the reaction mixture was stirred at RT for 30 min. NaCNBH₃ (3.30 g, 52.6 mmol) was added and the reaction mixture was stirred at RT for 12 h. The progress of the reaction was monitored by TLC. After completion of the reaction, the reaction mixture was diluted with 1N HCl solution and extracted with EtOAc. The aqueous layer basified with 10% NaOH solution and extracted with 10% MeOH/DCM. The combined organic layer was washed with brine, dried over anhydrous Na₂SO₄ and concentrated under reduced pressure to afford compound CX (2.0 g, 49.7%) as a thick oil. LC-MS: m/z 154 [M+H]+.

2-((1-(4-fluorophenyl) propyl) amino) pyrimidine-5-carbonitrile (CY)

To a stirred solution of compound CX (0.55 g, 3.59 mmol) in ethanol (10 mL), 2-chloropyrimidine-5-carbonitrile (AF, 0.50 g, 3.59 mmol) and DIPEA (1.94 mL, 10.7 mmol) were added and the reaction mixture was heated to 90° C. for 12 h. The progress of the reaction was monitored by TLC. After completion of the reaction, the reaction mixture was concentrated under reduced pressure. The crude product was purified by silica gel column chromatography using 5% MeOH/DCM to afford compound CY (0.8 g, 87%) as an off white solid. LC-MS: m/z 257.1 [M+H]$^+$; $^1$H NMR (400 MHz, DMSO-d$_6$) δ 8.81 (d, J=7.6 Hz, 1H), 8.61 (s, 2H), 7.38-7.34 (m, 2H), 7.14-7.04 (m, 2H), 4.90-4.85 (m, 1H), 2.29-1.46 (m, 2H), 0.83-0.78 (m, 3H).

N-(1-(4-fluorophenyl)propyl)-5-(1H-tetrazol-5-yl)pyrimidin-2-amine (CZ)

To a stirred solution of compound CY (0.5 g, 1.95 mmol) in DMF (10 mL), NaN$_3$ (0.38 g, 5.85 mmol), NH$_4$Cl (0.31 g, 5.85 mmol) and LiCl (82 mg) were added and the reaction mixture was stirred at 95° C. for 12 h. The progress of the reaction was monitored by TLC. After completion of the reaction, the reaction mixture was concentrated under reduced pressure. The residue was dissolved in cold water and adjust to pH=4-5 by using HCl solution. The obtained solid was filtered, washed with water, dried to afford compound CZ (0.3 g, crude) as a thick oil. LC-MS: m/z 300.1 [M+H]$^+$.

5-(5-(difluoromethyl)-1,3,4-oxadiazol-2-yl)-N-(1-(4-fluorophenyl)propyl)pyrimidin-2-amine (22)

To a stirred solution of compound CZ (0.3 g, 1.0 mmol) in DCM (10 mL), 2,2-difluoroacetic anhydride (0.16 mL) was added at 0° C. The reaction mixture was stirred at RT for 6 h. The progress of the reaction was monitored by TLC. After completion of the reaction, the reaction mixture was concentrated under reduced pressure. The crude product was purified by silica gel column chromatography using 5% MeOH/DCM to afford compound 22 (0.11 g, 31.4%) as an off white solid. $^1$H NMR (400 MHz, DMSO-d$_6$) δ 8.83 (d, J=12.4 Hz, 2H), 8.77 (d, J=8.8 Hz, 1H), 7.51 (t, J=51.4 Hz, 1H), 7.44-7.38 (m, 2H), 7.13 (t, J=8.8 Hz, 2H), 5.01-4.95 (m, 1H), 1.88-1.72 (m, 2H), 0.88 (t, J=7.2 Hz, 3H); LC-MS: m/z 350.06 [M+H]$^+$; HPLC Purity: 99.8%.

Example 23

5-(5-(difluoromethyl)-1,3,4-oxadiazol-2-yl)-N-(1-(4-fluorophenyl)butyl)pyrimidin-2-amine (23)

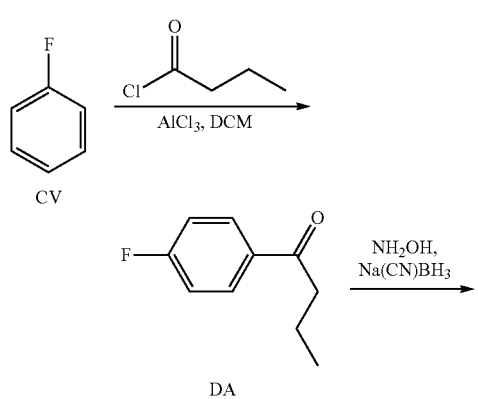

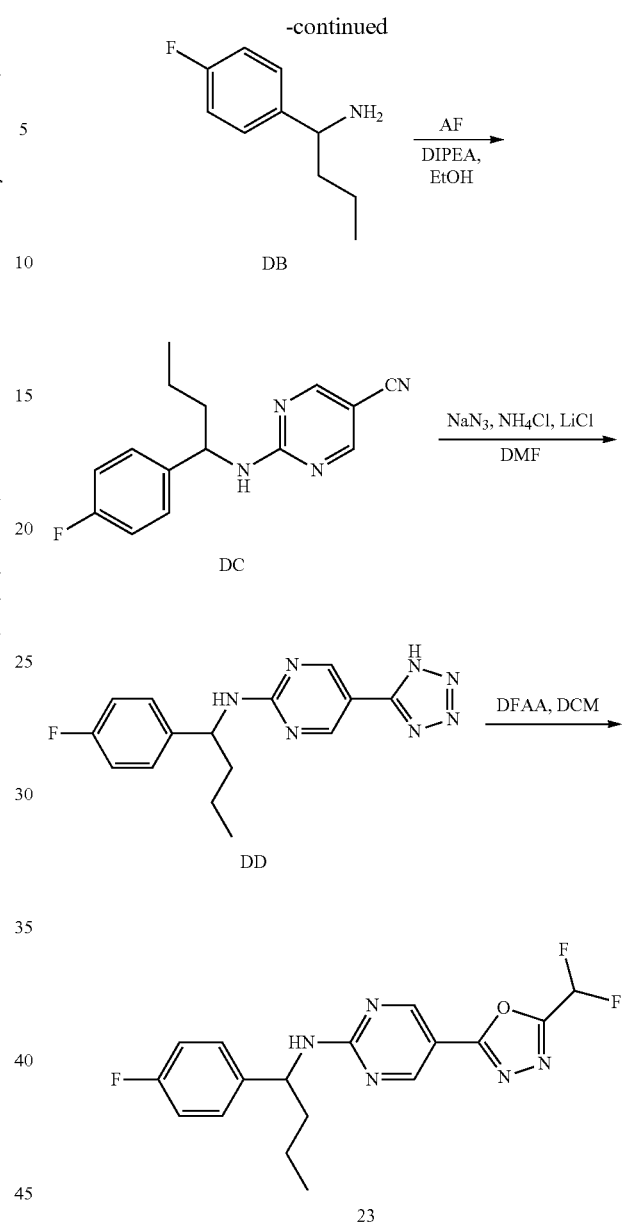

1-(4-fluorophenyl)butan-1-one (DA)

To a solution of anhydrous AlCl$_3$ (13.8 g, 104 mmol) in DCM (10 mL) at 0° C. was added solution of butyryl chloride (7.0 mL, 78.1 mmol) in DCM (25 mL) and the reaction mixture was stirred at RT for 1 h. To this a solution of fluorobenzene (CV, 5.0 g, 52.0 mmol) in DCM (15 mL) was added drop wise and the reaction mixture was stirred at RT for 12 h. The progress of the reaction was monitored by TLC. After completion of the reaction, the reaction mixture was quenched with water and extracted with EtOAc. The combined organic layer was washed with brine, dried over anhydrous Na$_2$SO$_4$ and concentrated under reduced pressure. The crude product was purified by column chromatography using 5% EtOAc/hexane to afford compound DA (3.5 g, 40.6%) as an off white solid LC-MS: m/z 167.01 [M+H]$^+$.

1-(4-fluorophenyl)butan-1-amine (DB)

To a stirred solution of compound DA (3.0 g, 18.0 mmol) in MeOH (30 mL), ammonium acetate (13.9 g, 180 mmol) was added and the reaction mixture was stirred at RT for 30 min. NaCNBH$_3$ (2.26 g, 36.1 mmol) was added and the reaction mixture was stirred at RT for 12 h. The progress of the reaction was monitored by TLC. After completion of the reaction, the reaction mixture was diluted with 1N HCl solution and extracted with EtOAc. The aqueous layer was basified with 10% NaOH solution and extracted with 10% MeOH/DCM. The combined organic layer was washed with brine, dried over anhydrous Na$_2$SO$_4$ and concentrated under reduced pressure to afford compound DB (1.5 g, 50%) as a thick oil. LC-MS: m/z 168.15 [M+H]$^+$.

2-((1-(4-fluorophenyl)butyl)amino)pyrimidine-5-carbonitrile (DC)

To a stirred solution of compound DB (0.5 g, 3.0 mmol) in ethanol (10 mL), 2-chloropyrimidine-5-carbonitrile (AF, 0.46 g, 3.31 mmol) and DIPEA (2.5 mL, 15.0 mmol) were added and the reaction mixture was heated to 90° C. for 12 h. The progress of the reaction was monitored by TLC. After completion of the reaction, the reaction mixture was concentrated under reduced pressure. The crude product was purified by silica gel column chromatography using 20% EtOAc/hexane to afford compound DC (0.8 g, 98%) as an off white solid. LC-MS: m/z 271.05 [M+H]$^+$.

N-(1-(4-fluorophenyl)butyl)-5-(1H-tetrazol-5-yl)pyrimidin-2-amine (DD)

To a stirred solution of compound DC (0.8 g, 2.96 mmol) in DMF (10 mL), NaN$_3$ (0.8 g, 14.8 mmol), NH$_4$Cl (0.95 g, 14.8 mmol) and LiCl (240 mg) were added and the reaction mixture was stirred at 95° C. for 12 h. The progress of the reaction was monitored by TLC. After completion of the reaction, the reaction mixture was concentrated under reduced pressure. The residue was dissolved in cold water and adjust to pH=4-5 by using HCl solution. The obtained solid was filtered, washed with water, dried to afford compound DD (0.51 g, crude) as a thick oil. LC-MS: m/z 314.05 [M+H]$^+$.

5-(5-(difluoromethyl)-1,3,4-oxadiazol-2-yl)-N-(1-(4-fluorophenyl)butyl)pyrimidin-2-amine (23)

To a stirred solution of compound DD (0.5 g, 1.59 mmol) in DCM (10 mL), 2,2-difluoroacetic anhydride (2.0 mL) was added at 0° C. The reaction mixture was stirred at RT for 6 h. The progress of the reaction was monitored by TLC. After completion of the reaction, the reaction mixture was concentrated under reduced pressure. The crude product was purified by silica gel column chromatography using 60% EtOAc/hexane to afford compound 23 (0.085 g, 14%) as an off white solid. $^1$H NMR (400 MHz, DMSO-d$_6$) δ 8.83 (d, J=9.2 Hz, 2H), 8.87 (d, J=8.8 Hz, 1H), 7.51 (t, J=51.4 Hz, 1H), 7.44-7.39 (m, 2H), 7.13 (t, J=8.8 Hz, 2H), 5.11-5.05 (m, 1H), 1.87-1.79 (m, 1H), 1.71-1.64 (m, 1H), 1.41-1.23 (m, 2H), 0.89-0.86 (m, 3H), LC-MS: m/z 364.17 [M+H]$^+$; HPLC Purity: 98.3%.

Example 24

5-(5-(difluoromethyl)-1,3,4-oxadiazol-2-yl)-N-(1-(4-fluorophenyl)-2-methylpropyl)pyrimidin-2-amine (24)

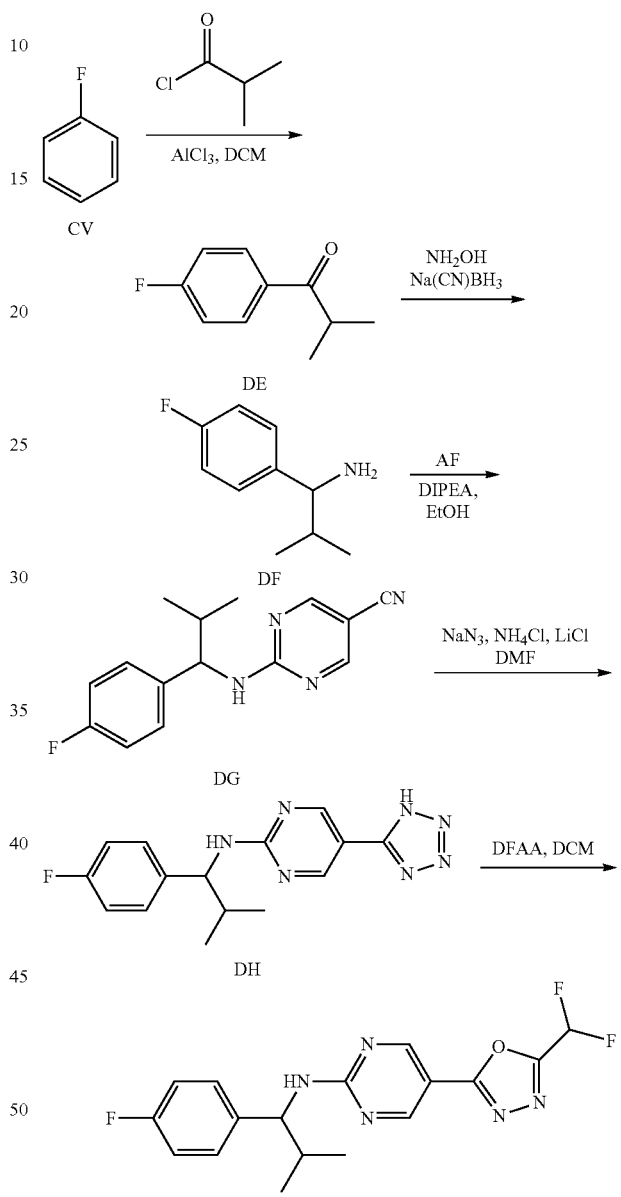

1-(4-fluorophenyl)butan-1-one (DE)

To the solution of anhydrous AlCl$_3$ (13.8 g, 104 mmol) in DCM (10 mL) at 0° C., was added drop wise a solution of isobutyryl chloride (8.5 mL, 78.1 mmol) in DCM (25 mL) and the reaction mixture was stirred at RT for 1 h. To this a reaction mixture, a solution of fluorobenzene (CV, 5.0 g, 52.0 mmol) in DCM (15 mL) was added drop wise and stirred at RT for 12 h. The progress of the reaction was monitored by TLC. After completion of the reaction, the reaction mixture was quenched with water and extracted with EtOAc. The combined organic layer was washed with brine, dried over anhydrous Na$_2$SO$_4$ and concentrated under reduced pressure. The crude product was purified by column chromatography using 5% EtOAc/hexane to afford compound DE (3.5 g, 40%) as an off white solid. LC-MS: m/z 166.96 [M+H]$^+$.

1-(4-fluorophenyl)-2-methylpropan-1-amine (DF)

To a stirred solution of compound DE (3.0 g, 18.0 mmol) in MeOH (30 mL), ammonium acetate (14.0 g, 180 mmol) was added and the reaction mixture was stirred at RT for 30 min. Sodium cyano borohydride (2.26 g, 36.1 mmol) was added and the reaction mixture was stirred at RT for 12 h. The progress of the reaction was monitored by TLC. After completion of the reaction, the reaction mixture was diluted with 1N HCl solution and extracted with EtOAc. The aqueous layer basified with 10% NaOH solution and extracted with 10% MeOH/DCM. The combined organic layer was washed with brine, dried over anhydrous Na$_2$SO$_4$ and concentrated under reduced pressure to afford compound DF (1.0 g, 33%) as a thick oil. LC-MS: m/z 168.05 [M+H]$^+$.

2-((1-(4-fluorophenyl)-2-methylpropyl)amino)pyrimidine-5-carbonitrile (DG)

To a stirred solution of compound DF (0.5 g, 3.0 mmol) in ethanol (10 mL), 2-chloropyrimidine-5-carbonitrile (AF, 0.46 g, 3.31 mmol) and DIPEA (2.5 mL, 15.0 mmol) were added and the reaction mixture was heated to 90° C. for 12 h. The progress of the reaction was monitored by TLC. After completion of the reaction, the reaction mixture was concentrated under reduced pressure. The crude product was purified by silica gel column chromatography using 20% EtOAc/hexane to afford compound DG (0.8 g, 98%) as an off white solid. LC-MS: m/z 270.95 [M+H]$^+$.

N-(1-(4-fluorophenyl)-2-methylpropyl)-5-(1H-tetrazol-5-yl)pyrimidin-2-amine (DH)

To a stirred solution of compound DG (0.8 g, 2.96 mmol) in DMF (10 mL), NaN$_3$ (0.8 g, 14.8 mmol), NH$_4$Cl (0.95 g, 14.8 mmol) and LiCl (240 mg) were added and the reaction mixture was stirred at 95° C. for 12 h. The progress of the reaction was monitored by TLC. After completion of the reaction, the reaction mixture was concentrated under reduced pressure. The residue was dissolved in cold water and adjust to pH=4-5 by using HCl solution. The obtain solid was filtered, washed with water, and dried to afford compound DH (0.5 g, crude) as a thick oil. LC-MS: m/z 314.11 [M+H]$^+$.

5-(5-(difluoromethyl)-1,3,4-oxadiazol-2-yl)-N-(1-(4-fluorophenyl)-2-methylpropyl)pyrimidin-2-amine (24)

To a stirred solution of compound DH (0.5 g, 1.59 mmol) in DCM (10 mL), 2,2-difluoroacetic anhydride (2.0 mL) was added at 0° C. Reaction mixture was stirred at RT for 6 h. The progress of the reaction was monitored by TLC. After completion of the reaction, the reaction mixture was concentrated under reduced pressure. The crude product was purified by silica gel column chromatography using 60% EtOAc/hexane to afford compound 24 (0.33 g, 57%) as an off white solid. $^1$H NMR (400 MHz, DMSO-d$_6$) δ 8.84-8.79 (m, 3H), 7.51 (t, J=51.4 Hz, 1H), 7.45-7.41 (m, 2H), 7.13 (t, J=8.8 Hz, 2H), 4.79 (t, J=9.2 Hz, 1H), 2.11-2.05 (m, 1H), 1.0 (d, J=6.4 Hz, 3H), 0.71 (d, J=6.8 Hz, 3H) LC-MS: m/z 364 [M+H]$^+$; HPLC Purity: 99.4%.

Example 25

5-(1-((5-(5-(difluoromethyl)-1,3,4-oxadiazol-2-yl)pyrimidin-2-yl)amino) cyclopropyl) picolinonitrile (25)

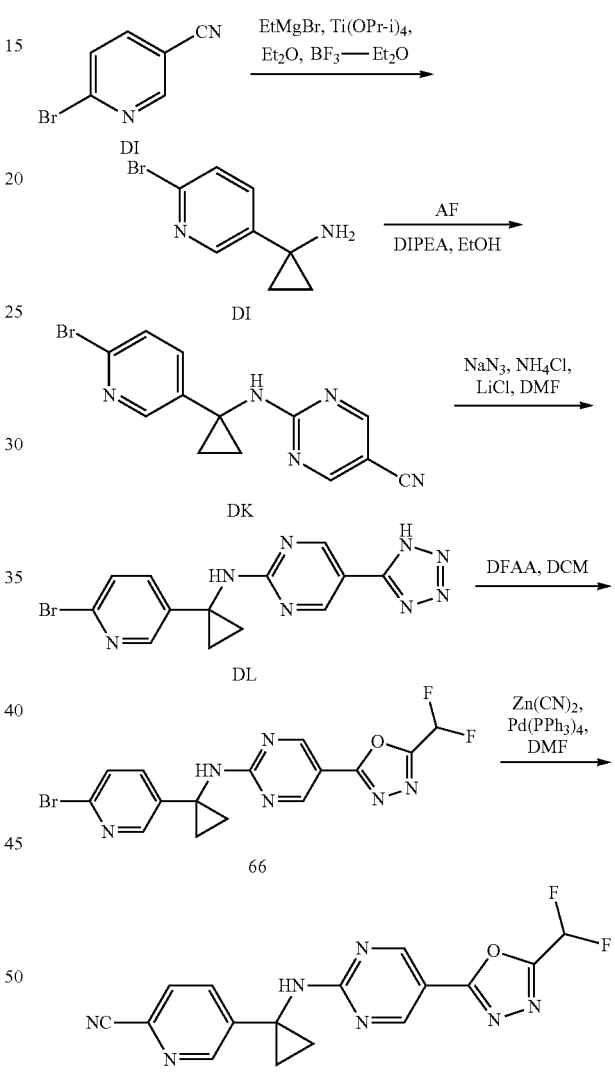

1-(6-bromopyridin-3-yl)cyclopropan-1-amine (DJ)

To a stirred solution of 6-bromonicotinonitrile (DI, 1 g, 5.46 mmol) in diethyl ether (30 mL), ethyl magnesium bromide (3M in THF, 4 mL, 12.02 mmol) and titanium isopropoxide (1.70 g, 6.00 mmol) were added at −78° C. and the reaction mixture was stirred at RT for 2 h. BF$_3$·OEt$_2$ (1.53 g, 10.92 mmol) was added at 0° C. and stirred at RT for 14 h. The progress of the reaction was monitored by TLC. After completion of the reaction, the reaction mixture was quenched with aqueous saturated NH₄Cl solution, basified with 10% NaOH solution and extracted with 10% MeOH/DCM. The combined organic layer was washed with brine, dried over anhydrous Na₂SO₄ and concentrated under reduced pressure. The crude product was purified by silica gel column chromatography using 5% MeOH/DCM to afford compound DJ (0.6 g, 51.7%) as a brown liquid. LC-MS: m/z 215.09 [M+H+2]⁺.

2-((1-(6-bromopyridin-3-yl)cyclopropyl)amino)pyrimidine-5-carbonitrile (DK)

To a stirred solution of compound DJ (0.6 g, 2.81 mmol) in ethanol (20 mL), 2-chloropyrimidine-5-carbonitrile (AF, 0.51 g, 3.66 mmol) and DIPEA (2.45 mL, 14.05 mmol) were added and the reaction mixture was heated to 90° C. for 14 h. The progress of the reaction was monitored by TLC. After completion of the reaction, the reaction mixture was concentrated under reduced pressure. The crude product was purified by silica gel column chromatography using 20% EtOAc/hexane to afford compound DK (0.4 g, 44.9%) as a brown liquid. LC-MS: m/z 315.95 [M+H]⁺.

N-(1-(6-bromopyridin-3-yl)cyclopropyl)-5-(1H-tetrazol-5-yl)pyrimidin-2-amine (DL)

To a stirred solution of compound DK (0.3 g, 0.948 mmol) in DMF (5 mL), NaN₃ (0.185 g, 2.84 mmol), NH₄Cl (0.152 g, 2.84 mmol) and LiCl (30 mg) were added and the reaction mixture was stirred at 100° C. for 14 h. The progress of the reaction was monitored by TLC. After completion of the reaction, the reaction mixture was quenched with ice water, acidified with 2N HCl solution to pH=2, and extracted with 10% MeOH/DCM. The combined organic layer was washed with brine, dried over anhydrous Na₂SO₄ and concentrated under reduced pressure to afford compound DL (0.3 g, crude) as an off white solid. LC-MS: m/z 358.98 [M+H]⁺.

N-(1-(6-bromopyridin-3-yl)cyclopropyl)-5-(5-(difluoromethyl)-1,3,4-oxadiazol-2-yl)pyrimidin-2-amine (66)

To a stirred solution of compound DL (0.3 g, 0.835 mmol) in DCM (10 mL), DFAA (1 mL) was added and the reaction mixture was stirred at RT for 12 h. The progress of the reaction was monitored by TLC. After completion of the reaction, the reaction mixture was concentrated under reduced pressure. The residue was dissolved in saturated solution of NaHCO₃ and extracted with EtOAc. The combined organic layer was washed with brine, dried over anhydrous Na₂SO₄ and concentrated under reduced pressure. The crude product was purified by silica gel column chromatography using 20% EtOAc/hexane to afford compound 66 (0.09 g, 26.3%) as an off white solid. LC-MS: m/z 409.05 [M+H]⁺.

5-(1-((5-(5-(difluoromethyl)-1,3,4-oxadiazol-2-yl)pyrimidin-2-yl)amino)cyclopropyl)picolinonitrile (25)

A stirred solution of compound 66 (0.08 g, 0.195 mmol) and Zn(CN)₂ (0.034 g, 0.293 mmol) in DMF (2 mL) was purged with argon for 20 min and then Pd(PPh₃)₄ (0.022 g, 0.019 mmol) was added. The reaction mixture was further purged with argon for 20 min and stirred at 150° C. for 5 h. After completion of the reaction, the reaction mixture was quenched with ice water, filtered through Celite and washed with EtOAc. The filtrate was washed with brine, dried over anhydrous Na₂SO₄ and concentrated under reduced pressure. The crude product was purified by silica gel column chromatography using 40% EtOAc/hexane to afford 25 (0.04 g, 51.7%) as an off white solid. ¹H NMR (400 MHz, DMSO-d₆) δ 9.12 (s, 1H), 8.94 (s, 1H), 8.87 (s, 1H), 8.51 (d, J=2.0 Hz, 1H), 7.92 (d, J=8.4 Hz, 1H), 7.76-7.74 (m, 1H), 7.53 (t, J=51.4 Hz, 1H), 1.56-1.55 (m, 2H), 1.45-1.42 (m, 2H), LC-MS: m/z 356.05 [M+H]⁺; HPLC Purity: 99.2%.

Example 26

1-(4-((5-(5-(difluoromethyl)-1,3,4-oxadiazol-2-yl)pyrimidin-2-yl)amino)-4-(4-fluorophenyl) piperidin-1-yl) ethan-1-one (26)

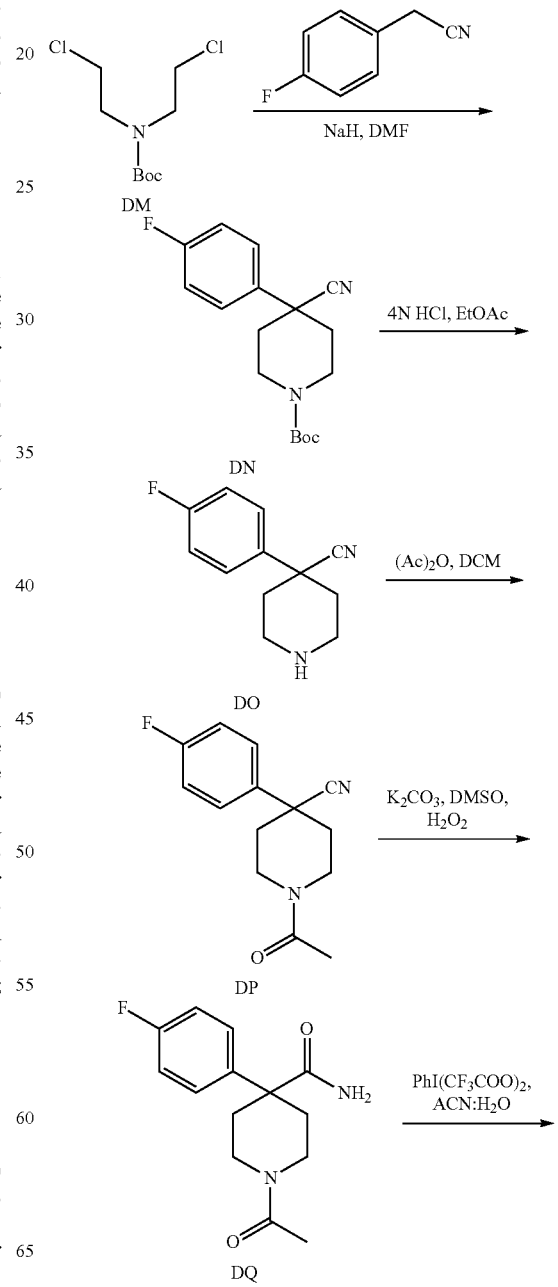

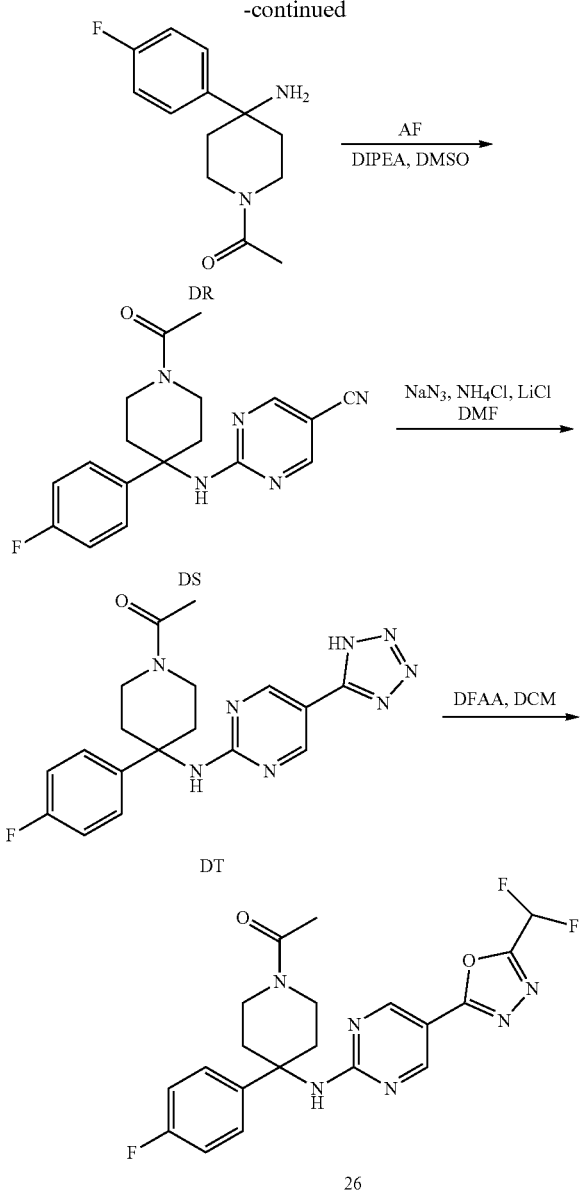

tert-butyl 4-cyano-4-(4-fluorophenyl)piperidine-1-carboxylate (DN)

To a stirred solution of 2-(4-fluorophenyl)acetonitrile (3.2 g, 23.7 mmol) and tert-butyl bis(2-chloroethyl)carbamate (DM, 6.69 g, 23.7 mmol) in DMF (40 mL), NaH (60%, 2.8 g, 71.1 mmol) was added and the reaction mixture was stirred at 60° C. for 16 h. The progress of the reaction was monitored by TLC. After completion of the reaction, the reaction mixture was quenched using water and extracted with EtOAc. The combined organic layer was washed with brine, dried over anhydrous $Na_2SO_4$ and concentrated under reduced pressure. The crude product was purified by silica gel column chromatography using 10% EtOAc/hexane to afford compound DN (4.2 g, 58%) as a thick oil.

4-(4-fluorophenyl)piperidine-4-carbonitrile (DO)

To a stirred solution of compound DN (4.2 g, 5.50 mmol) in EtOAc (5 mL), 4M HCl in EtOAc (10 mL) was added at 0° C. and stirred at RT for 2 h The progress of the reaction was monitored by TLC. After completion of the reaction, the reaction mixture was concentrated under reduced pressure to afford compound DO (30 g, crude) as a white solid. LC-MS: m/z 204.95 $[M+H]^+$.

1-acetyl-4-(4-fluorophenyl)piperidine-4-carbonitrile (DP)

To a stirred solution of compound DO (3.0 g, 14.6 mmol) in DCM (30 mL), acetic acid (2.9 mL, 29.3 mmol) was added at 0° C. and the reaction mixture was stirred at RT for 16 h. The progress of the reaction was monitored by TLC. After completion of the reaction, the reaction mixture was concentrated under reduced pressure. The crude product was purified by column chromatography using 5% MeOH/DCM to afford compound DP (2.8 g, 77%) as a white solid. LC-MS: m/z 247 $[M+H]^+$. $^1$H NMR (400 MHz, DMSO-$d_6$) δ 11.9 (s, 1H), 7.62-7.57 (m, 2H), 7.31-7.25 (m, 2H), 4.59-4.56 (m, 1H), 4.02-3.98 (m, 1H), 3.33-3.26 (m, 1H), 2.81-2.74 (m, 1H), 2.16-2.01 (m, 4H), 1.90-1.81 (m, 2H).

1-acetyl-4-(4-fluorophenyl)piperidine-4-carboxamide (DQ)

To a stirred solution of compound DP (2.8 g, 11.3 mmol) in DMSO (30 mL), $K_2CO_3$ (6.3 g, 45.5 mmol) and $H_2O_2$ (30%, 5.1 mL, 45.5 mmol) were added and the reaction mixture was stirred at RT for 16 h. The progress of the reaction was monitored by TLC. After completion of the reaction, the reaction mixture was quenched with ice-water and the obtained solid was filtered and dried. The crude product was purified by column chromatography using 5% MeOH/DCM to afford compound DQ (2.8 g, 93%) as a white solid. LC-MS: m/z 265.04 $[M+H]^+$.

1-(4-amino-4-(4-fluorophenyl)piperidin-1-yl)ethan-1-one (DR)

To a stirred solution of compound DQ (2.6 g, 9.84 mmol) in ACN:Water (1:1, 30 mL), PhI(CF$_3$COO)$_2$ (5.0 g, 11.8 mmol) was added and the reaction mixture was stirred at 60° C. for 7 h. The progress of the reaction was monitored by TLC. After completion of the reaction, the reaction mixture was quenched with water and extracted with 10% MeOH/DCM. The combined organic layer was washed with brine, dried over anhydrous $Na_2SO_4$ and concentrated under reduced pressure. The crude product was purified by silica gel column chromatography using 5% MeOH/DCM to afford compound DR (0.67 g, 29%) as a thick oil. LC-MS: m/z 220.1 $[M+H]^+$.

2-((1-acetyl-4-(4-fluorophenyl)piperidin-4-yl)amino) pyrimidine-5-carbonitrile (DS)

To a stirred solution of compound DR (0.4 g, 2.86 mmol) in ethanol (10 mL), 2-chloropyrimidine-5-carbonitrile (AF, 0.67 g, 2.86 mmol) and DIPEA (2.6 mL, 14.3 mmol) were added and the reaction mixture was heated to 90° C. for 16 h. The progress of the reaction was monitored by TLC. After completion of the reaction, the reaction mixture was concentrated under reduced pressure. The crude product was purified by silica gel column chromatography using 50% EtOAc/hexane to afford compound DS (0.4 g, 41%) as a white solid. LC-MS: m/z 341.1 $[M+H]^+$.

1-(4-((5-(1H-tetrazol-5-yl)pyrimidin-2-yl)amino)-4-(4-fluorophenyl)piperidin-1-yl)ethan-1-one (DT)

To a stirred solution of compound DS (0.4 g, 1.17 mmol) in DMF (10 mL), NaN₃ (0.31 g, 5.8 mmol), NH₄Cl (0.37 g, 5.88 mmol) and LiCl (120 mg) were added and the reaction mixture was stirred at 100° C. for 16 h. The progress of the reaction was monitored by TLC. After completion of the reaction, the reaction mixture was quenched with ice water, acidified with 2N HCl solution to pH=2, and extracted with 10% MeOH/DCM. The combined organic layer was washed with brine, dried over anhydrous Na₂SO₄ and concentrated under reduced pressure to afford compound DT (0.27 g, crude) as a thick oil. LC-MS: m/z 383.10 [M+H]⁺.

1-(4-((5-(5-(difluoromethyl)-1,3,4-oxadiazol-2-yl)pyrimidin-2-yl)amino)-4-(4-fluorophenyl) piperidin-1-yl)ethan-1-one (26)

To a stirred solution of compound DT (0.26 g, 0.69 mmol) in DCM (15 mL), 2,2-difluoroacetic anhydride (0.12 mL, 1.04 mmol) was added at 0° C. and the reaction mixture was stirred at RT for 16 h. The progress of the reaction was monitored by TLC. After completion of the reaction, the reaction mixture was concentrated under reduced pressure. The crude product was purified by silica gel column chromatography using 6% MeOH/DCM to afford compound 26 (0.04 g, 13%) as a white solid. ¹H NMR (400 MHz, DMSO-d₆) δ 8.86 (s, 1H), 8.63 (s, 2H), 7.47 (t, J=51.2 Hz, 1H), 7.41-7.38 (m, 2H), 7.07 (t, J=9.2 Hz, 2H), 4.25 (d, J=13.2 Hz, 1H), 2.83 (t, J=12.4 Hz, 1H), 2.63-2.59 (m, 3H), 1.98 (s, 3H), 1.93-1.90 (m, 1H), 1.80-1.74 (m, 1H); LC-MS: m/z 431 [M−H]; HPLC Purity: 95.1%.

Example 27

N-(1-cyclohexylcyclopropyl)-5-(5-(difluoromethyl)-1,3,4-oxadiazol-2-yl)pyrimidin-2-amine (27)

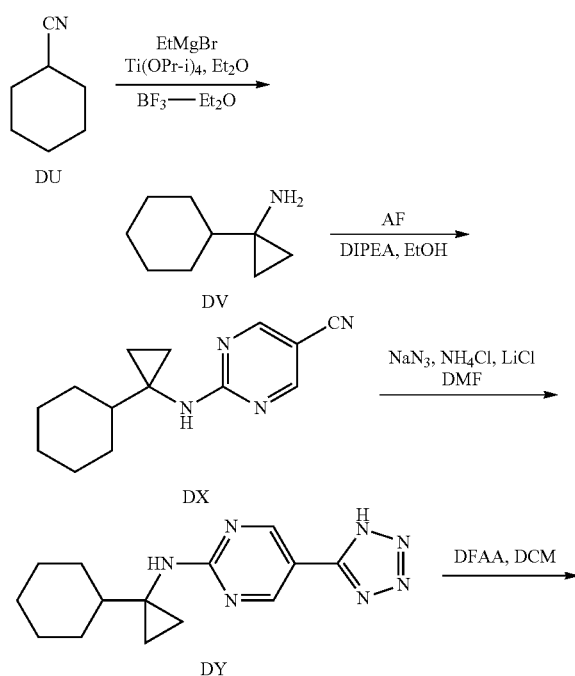

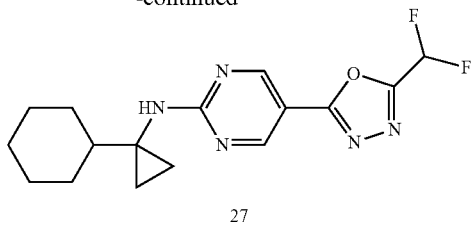

27

1-cyclohexylcyclopropan-1-amine (DV)

To a stirred solution of cyclohexanecarbonitrile (DU, 1.50 g, 13.74 mmol) in diethyl ether (80 mL), ethyl magnesium bromide (3M in THF, 11.45 mL, 34.35 mmol) and titanium isopropoxide (4.29 g, 15.11 mmol) were added at −78° C. and the reaction mixture was stirred at RT for 2 h. BF₃·OEt₂ (3.89 g, 27.48 mmol) was added at 0° C. and stirred at RT for 14 h. The progress of the reaction was monitored by TLC. After completion of the reaction, the reaction mixture was quenched with NH₄Cl solution, basified with 10% NaOH solution, and extracted with 10% MeOH/DCM. The combined organic layer was washed with brine, dried over anhydrous Na₂SO₄ and concentrated under reduced pressure. The crude product was purified by silica gel column chromatography using 30% EtOAc/hexane to afford compound DV (0.6 g, 31.4%) as a brown liquid. LC-MS: m/z 140.0 [M+H]⁺.

2-((1-cyclohexylcyclopropyl)amino)pyrimidine-5-carbonitrile (DX)

To a stirred solution of compound DV (0.4 g, 2.87 mmol) in ethanol (10 mL), 2-chloropyrimidine-5-carbonitrile (AF, 0.44 g, 3.16 mmol) and DIPEA (2.50 mL, 14.35 mmol) were added and the reaction mixture was heated to 90° C. for 14 h. The progress of the reaction was monitored by TLC. After completion of the reaction, the reaction mixture was concentrated under reduced pressure. The crude product was purified by silica gel column chromatography using 10% EtOAc/hexane to afford compound DX (0.55 g, 79%) as a white solid. LC-MS: m/z 243.0 [M+H]⁺.

N-(1-cyclohexylcyclopropyl)-5-(1H-tetrazol-5-yl)pyrimidin-2-amine (DY)

To a stirred solution of compound DX (0.5 g, 2.06 mmol) in DMF (10 mL), NaN₃ (0.66 g, 10.3 mmol), NH₄Cl (0.55 g, 10.3 mmol) and LiCl (100 mg) were added and the reaction mixture was stirred at 100° C. for 14 h. The progress of the reaction was monitored by TLC. After completion of the reaction, the reaction mixture was concentrated under reduced pressure. The residue was suspended in water and the obtained solid was filtered, washed with water, and dried to afford compound DY (0.43 g, crude) as a yellow solid. LC-MS: m/z 286.08 [M+H]⁺.

N-(1-cyclohexylcyclopropyl)-5-(5-(difluoromethyl)-1,3,4-oxadiazol-2-yl)pyrimidin-2-amine (27)

To a stirred solution of compound DY (0.4 g, 1.40 mmol) in DCM (10 mL), DFAA (2 mL) was added and the reaction mixture was stirred at RT for 12 h. The progress of the reaction was monitored by TLC. After completion of the reaction, the reaction mixture was concentrated under reduced pressure. The residue was dissolved in a saturated solution of NaHCO₃ and extracted with EtOAc. The combined organic layer was washed with brine, dried over anhydrous Na₂SO₄ and concentrated under reduced pressure. The crude product was purified by silica gel column chromatography using 50% EtOAc/hexane to afford compound 27 (0.024 g, 5%) as an off white solid. $^1$H NMR (400 MHz, DMSO-d₆) δ 8.88 (d, J=3.2 Hz, 2H), 8.78 (d, J=2.8 Hz, 1H), 8.50 (s, 1H), 7.51 (t, J=51.4 Hz, 1H), 1.75 (d, J=11.6 Hz, 2H), 1.65 (d, J=12.0 Hz, 2H), 1.56 (d, J=11.6 Hz, 1H), 1.43 (t, J=12.0 Hz, 1H), 1.16-0.99 (m, 3H), 0.93-0.85 (m, 2H), 0.76-0.73 (m, 1H), 0.64-0.61 (m, 2H), LC-MS: m/z 336.16 [M+H]⁺; HPLC Purity: 99.3%.

Example 28

5-(5-(difluoromethyl)-1,3,4-oxadiazol-2-yl)-N-(1-isopropylcyclopropyl)pyrimidin-2-amine (28)

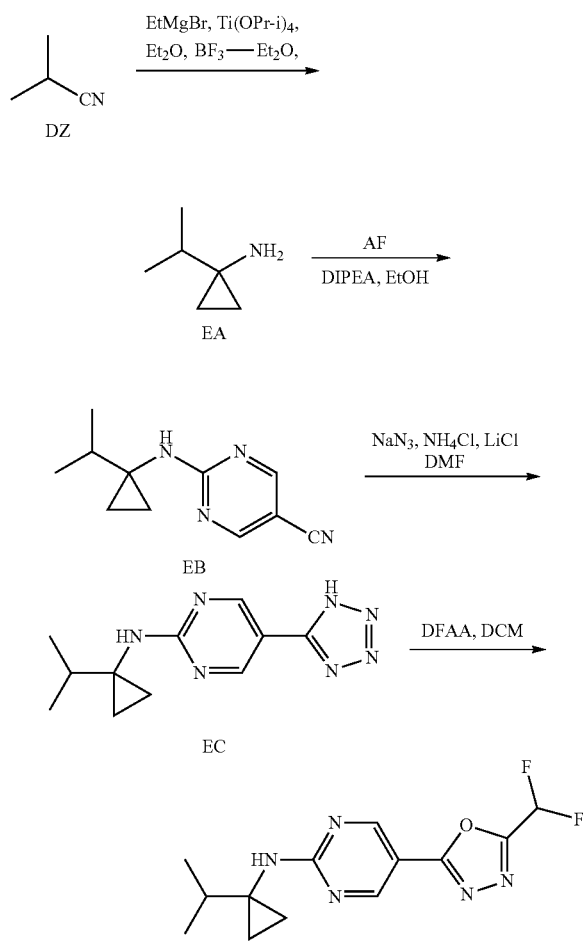

1-isopropylcyclopropan-1-amine (EA)

To a stirred solution of isobutyronitrile (DZ, 2 g, 28.9 mmol) in diethyl ether (40 mL), ethyl magnesium bromide (3M in THF, 21.25 mL, 63.6 mmol) and titanium isopropoxide (9.04 g, 31.8 mmol) were added at −78° C. and the reaction mixture was stirred at RT for 2 h. BF₃·OEt₂ (8.23 g, 57.8 mmol) was added at 0° C. and stirred at RT for 14 h. The progress of the reaction was monitored by TLC. After completion of the reaction, the reaction mixture was quenched with NH₄Cl solution, basified with 10% NaOH solution, and extracted with 10% MeOH/DCM. The combined organic layer was washed with brine, dried over anhydrous Na₂SO₄ and concentrated under reduced pressure. The crude product was purified by silica gel column chromatography using 30% EtOAc/hexane to afford compound EA (0.8 g, 27.8%) as a brown liquid. $^1$H NMR (400 MHz, DMSO-d₆) δ 8.12 (br s, 2H), 1.58-1.45 (m, 2H), 0.95-0.88 (m, 4H), 0.72-0.63 (m, 5H).

2-((1-isopropylcyclopropyl)amino)pyrimidine-5-carbonitrile (EB)

To a stirred solution of compound EA (0.35 g, 3.52 mmol) in ethanol (10 mL), 2-chloropyrimidine-5-carbonitrile (AF, 0.49 g, 3.16 mmol) and DIPEA (1.84 mL, 10.5 mmol) were added and the reaction mixture was heated to 90° C. for 14 h. The progress of the reaction was monitored by TLC. After completion of the reaction, the reaction mixture was concentrated under reduced pressure. The crude product was purified by silica gel column chromatography using 20% EtOAc/hexane to afford compound EB (0.3 g, 42%) as an off white solid. LC-MS: m/z 203.05 [M+H]⁺.

N-(1-isopropylcyclopropyl)-5-(1H-tetrazol-5-yl)pyrimidin-2-amine (EC)

To a stirred solution of compound EB (0.3 g, 1.48 mmol) in DMF (5 mL), NaN₃ (0.28 g, 4.44 mmol), NH₄Cl (0.24 g, 4.44 mmol) and LiCl (50 mg) were added and the reaction mixture was stirred at 100° C. for 14 h. The progress of the reaction was monitored by TLC. After completion of the reaction, the reaction mixture was quenched with ice water, acidified with 2N HCl solution to pH=2, and extracted with 10% MeOH/DCM. The combined organic layer was washed with brine, dried over anhydrous Na₂SO₄ and concentrated under reduced pressure to afford compound EC (0.3 g, crude) as a light yellow solid. LC-MS: m/z 245.95 [M+H]⁺.

5-(5-(difluoromethyl)-1,3,4-oxadiazol-2-yl)-N-(1-isopropylcyclopropyl)pyrimidin-2-amine (28)

To a stirred solution of compound EC (0.3 g, 1.22 mmol) in DCM (5 mL), DFAA (0.5 mL) was added and the reaction mixture was stirred at RT for 12 h. The progress of the reaction was monitored by TLC. After completion of the reaction, the reaction mixture was concentrated under reduced pressure. The residue was dissolved in saturated solution of NaHCO₃ and extracted with EtOAc. The combined organic layer was washed with brine, dried over anhydrous Na₂SO₄ and concentrated under reduced pressure. The crude product was purified by silica gel column chromatography using 30% EtOAc/hexane to afford compound 28 (0.06 g, 16.6%) as an off white solid. $^1$H NMR (400 MHz, DMSO-d₆) δ 8.89 (s, 1H), 8.81 (s, 1H), 8.50 (s, 1H), 7.51 (t, J=51.4 Hz, 1H), 1.89-1.83 (m, 1H), 0.86 (d, J=6.8 Hz, 6H), 0.76-0.67 (m, 2H), 0.66-0.64 (m, 2H); LC-MS: m/z 296 [M+H]⁺; HPLC Purity: 99.8%.

Example 29

5-(5-(difluoromethyl)-1,3,4-oxadiazol-2-yl)-N-(5-fluoro-2,3-dihydro-1H-inden-1-yl)pyrimidin-2-amine (29)

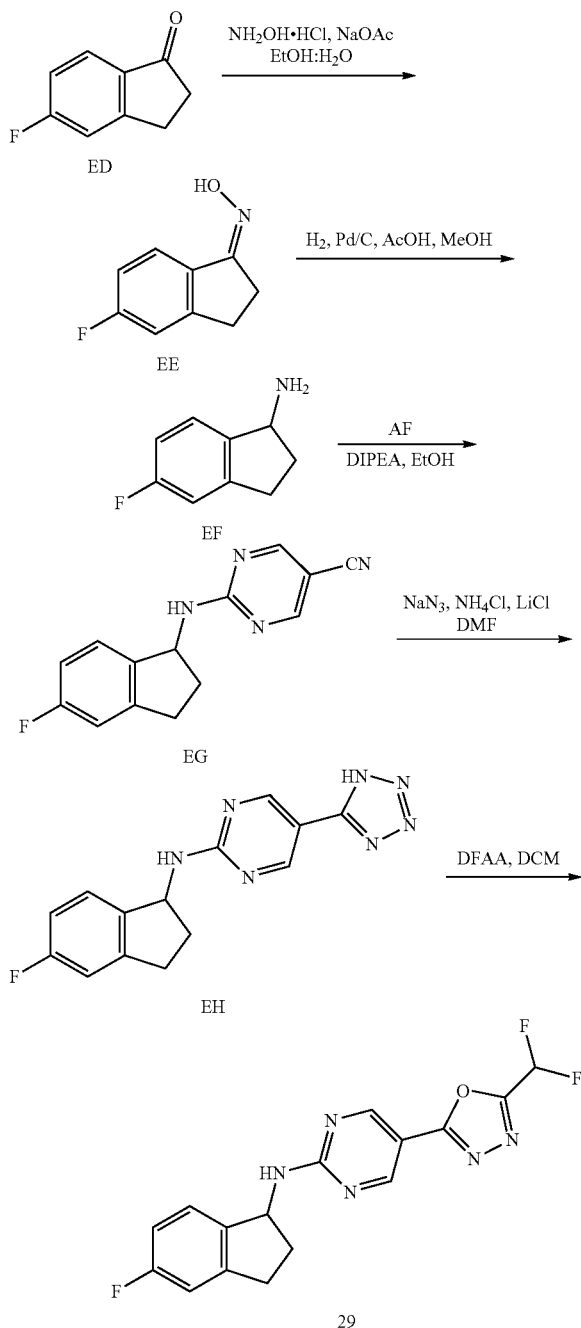

(Z)-5-fluoro-2,3-dihydro-1H-inden-1-one oxime (EE)

To a stirred solution of 5-fluoro-2,3-dihydro-1H-inden-1-one (ED, 2 g, 13.32 mmol) in EtOH (50 mL), aqueous NaOAc (2.73 g, 33.3 mmol) and NH$_2$OH·HCl (2.31 g, 33.3 mmol) were added and the reaction mixture was stirred at 90° C. for 12 h. The progress of the reaction was monitored by TLC. After completion of the reaction, the reaction mixture was concentrated under reduced pressure. The residue was washed with water and dried to afford compound EE (2 g, 90.9%) as a white solid. LC-MS: m/z 166 [M+H]$^+$.

5-fluoro-2,3-dihydro-1H-inden-1-amine (EF)

To a stirred solution of compound EE (2 g, 11.1 mmol) in MeOH (50 mL), acetic acid (10 mL) and palladium on carbon (200 mg) were added and stirred under hydrogen balloon pressure at RT for 12 h. The progress of the reaction was monitored by TLC. After completion of the reaction, the reaction mixture was filtered through pad of celite and washed with MeOH. The filtrate was concentrated under reduced pressure. The crude product was purified by silica gel column chromatography using 10% MeOH/DCM to afford compound EF (1.2 g, 65.5%) as a brown liquid. LC-MS: m/z 135.00 [M-16]$^+$.

2-((5-fluoro-2,3-dihydro-1H-inden-1-yl)amino)pyrimidine-5-carbonitrile (EG)

To a stirred solution of compound EF (0.5 g, 3.30 mmol) in ethanol (10 mL), 2-chloropyrimidine-5-carbonitrile (AF, 0.69 g, 4.96 mmol) and DIPEA (2.72 mL, 9.90 mmol) were added and the reaction mixture was heated to 90° C. for 14 h. The progress of the reaction was monitored by TLC. After completion of the reaction, the reaction mixture was concentrated under reduced pressure. The crude product was purified by silica gel column chromatography using 15% EtOAc/hexane to afford compound EG (0.70 g, 83.3%) as a white solid. LC-MS: m/z 254.95 [M+H]$^+$.

N-(5-fluoro-2,3-dihydro-1H-inden-1-yl)-5-(1H-tetrazol-5-yl)pyrimidin-2-amine (EH)

To a stirred solution of compound EG (0.6 g, 2.35 mmol) in DMF (10 mL), NaN$_3$ (0.76 g, 11.7 mmol), NH$_4$Cl (0.62 g, 11.5 mmol) and LiCl (180 mg) were added and the reaction mixture was stirred at 100° C. for 14 h. The progress of the reaction was monitored by TLC. After completion of the reaction, the reaction mixture was quenched with ice water, acidified with 2N HCl solution to pH=2, and extracted with 10% MeOH/DCM. The combined organic layer was washed with brine, dried over anhydrous Na$_2$SO$_4$ and concentrated under reduced pressure to afford compound EH (0.30 g, crude) as a yellow solid. LC-MS: m/z 297.95 [M+H]$^+$.

5-(5-(difluoromethyl)-1,3,4-oxadiazol-2-yl)-N-(5-fluoro-2,3-dihydro-1H-inden-1-yl)pyrimidin-2-amine (29)

To a stirred solution of compound EH (0.3 g, 1.00 mmol) in DCM (10 mL), DFAA (1 mL) was added and the reaction mixture was stirred at RT for 12 h. The progress of the reaction was monitored by TLC. After completion of the reaction, the reaction mixture was concentrated under reduced pressure. The residue was dissolved in saturated solution of NaHCO$_3$ and extracted with EtOAc. The combined organic layer was washed with brine, dried over anhydrous Na$_2$SO$_4$ and concentrated under reduced pressure. The crude product was purified by silica gel column chromatography using 30% EtOAc/hexane to afford compound 29 (0.03 g, 8.5%) as an off white solid. $^1$H NMR (400 MHz, DMSO-d$_6$) δ 8.91 (d, J=21.2 Hz, 2H), 8.61 (d, J=8.4

Hz, 1H), 7.53 (t, J=51.4 Hz, 1H), 7.24-7.21 (m, 1H), 7.10-7.08 (m, 1H), 6.98-6.94 (m, 1H), 5.63-5.57 (m, 1H), 3.04-3.0 (m, 1H), 2.97-2.86 (m, 1H), 2.07-1.99 (m, 1H); LC-MS: m/z 347.95 [M+H]$^+$; HPLC Purity: 99.7%.

Example 30

2-((5-(5-(difluoromethyl)-1,3,4-oxadiazol-2-yl)pyrimidin-2-yl)amino)-2-(4-fluorophenyl)-1-morpholinoethan-1-one (30)

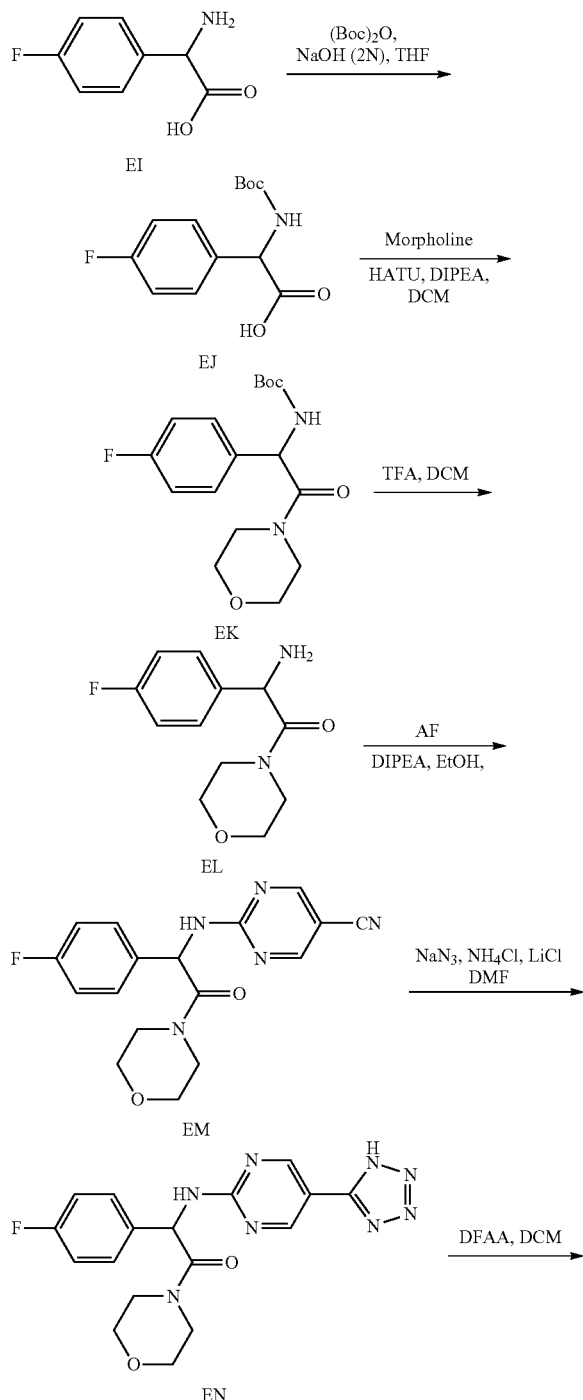

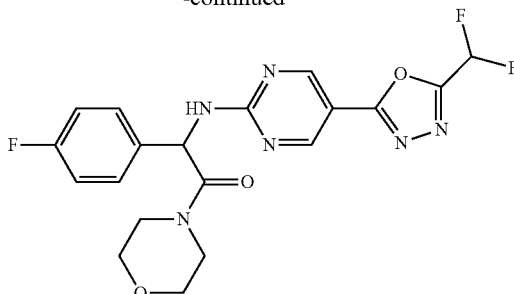

2-((tert-butoxycarbonyl)amino)-2-(4-fluorophenyl)acetic acid (EJ)

To a stirred solution of 2-amino-2-(4-fluorophenyl)acetic acid (EI, 2.5 g, 14.77 mmol) in THF (25 mL), boc anhydride (3.54 g, 16.25 mmol) and NaOH (3N, 20 mL) were added and stirred at room temperature for 12 h. The progress of the reaction was monitored by TLC. After completion of the reaction, reaction mixture was quenched with 6N HCl solution and extracted with EtOAc. The combined organic layer was washed with brine, dried over Na$_2$SO$_4$ and concentrated under reduced pressure to afford compound EJ (2.2 g, crude) as a brown oil. LC-MS: m/z 269.23 [M+H]$^+$.

tert-butyl (1-(4-fluorophenyl)-2-morpholino-2-oxoethyl)carbamate (EK)

To a stirred solution of compound EJ (1 g, 3.71 mmol) in DCM (15 mL), morpholine (0.35 g, 4.08 mmol), HATU (1.69 g, 4.45 mmol) and DIPEA (1.90 mL, 11.13 mmol) were added at 0° C. under nitrogen atmosphere and stirred at room temperature for 12 h. The progress of the reaction was monitored by TLC. After completion of the reaction, the reaction mixture was quenched with water and extracted with EtOAc. The combined organic layer was washed with brine, dried over Na$_2$SO$_4$ and concentrated under reduced pressure. The crude product was purified by silica gel column chromatography using 5% MeOH/DCM to afford compound EK (1.1 g, 88%) as an off white solid. LC-MS: m/z 239.07 [M+H-100]$^+$.

2-amino-2-(4-fluorophenyl)-1-morpholinoethan-1-one (EL)

To a stirred solution of compound EK (1.1 g, 3.25 mmol) in DCM (12 mL), TFA (1 mL) was added and the reaction mixture was stirred at room temperature for 2 h. The progress of the reaction was monitored by TLC. After completion of the reaction, the reaction mixture was concentrated under reduced pressure to obtain compound as a TFA salt. The salt was basified with NaHCO$_3$ solution and extracted with 15% MeOH/DCM. The combined organic layer was washed with brine, dried over anhydrous Na$_2$SO$_4$ and concentrated under reduced pressure. The crude product was purified by silica gel column chromatography using 5% MeOH/DCM to afford compound EL (0.6 g, 77.9%) as an off white solid. LC-MS: m/z 238.94 [M+H]$^+$.

2-((1-(4-fluorophenyl)-2-morpholino-2-oxoethyl)amino)pyrimidine-5-carbonitrile (EM)

To a stirred solution of compound EL (0.6 g, 2.51 mmol) in ethanol (10 mL), 2-chloropyrimidine-5-carbonitrile (AF, 0.45 g, 3.26 mmol) and DIPEA (2.19 mL, 12.55 mmol) were added and the reaction mixture was heated to 90° C. for 14 h. The progress of the reaction was monitored by TLC. After completion of the reaction, the reaction mixture was concentrated under reduced pressure. The crude product was purified by silica gel column chromatography using 5% MeOH/DCM to afford compound EM (0.55 g, 64%) as a brown liquid. LC-MS: m/z 342.0 [M+H]$^+$.

2-((5-(1H-tetrazol-5-yl)pyrimidin-2-yl)amino)-2-(4-fluorophenyl)-1-morpholinoethan-1-one (EN)

To a stirred solution of compound EM (0.55 g, 1.61 mmol) in DMF (10 mL), NaN$_3$ (0.314 g, 4.83 mmol), NH$_4$Cl (0.258 g, 4.83 mmol) and LiCl (50 mg) were added and the reaction mixture was stirred at 100° C. for 14 h. The progress of the reaction was monitored by TLC. After completion of the reaction, the reaction mixture was concentrated under reduced pressure. The residue was washed with water and dried to afford compound EN (0.30 g, crude) as an off white solid. LC-MS: m/z 385.0 [M+H]$^+$.

2-((5-(5-(difluoromethyl)-1,3,4-oxadiazol-2-yl)pyrimidin-2-yl)amino)-2-(4-fluorophenyl)-1-morpholinoethan-1-one (30)

To a stirred solution of compound EN (0.3 g, 0.780 mmol) in DCM (10 mL), DFAA (0.20 g, 1.15 mmol) was added and the reaction mixture was stirred at RT for 12 h. The progress of the reaction was monitored by TLC. After completion of the reaction, the reaction mixture was concentrated under reduced pressure. The residue was dissolved in saturated solution of NaHCO$_3$ and extracted with EtOAc. The combined organic layer was washed with brine, dried over anhydrous Na$_2$SO$_4$ and concentrated under reduced pressure. The crude product was purified by silica gel column chromatography using 50% EtOAc/hexane to afford compound 30 (0.107 g, 31.5%) as an off white solid. $^1$H NMR (400 MHz, DMSO-d$_6$) δ 8.91 (d, J=2.0 Hz, 2H), 8.55 (d, J=7.2 Hz, 1H), 7.58-7.53 (m, 2H), 7.55 (t, J=51.2 Hz, 1H), 7.21 (t, J=8.8 Hz, 2H), 6.10 (d, J=7.2 Hz, 1H), 3.54-3.47 (m, 7H), 3.21-3.19 (m, 1H); LC-MS: m/z 435.05 [M+H]$^+$; HPLC Purity: 99.1%.

Example 31

5-(5-(difluoromethyl)-1,3,4-oxadiazol-2-yl)-N-(1-(5-fluoropyridin-2-yl)ethyl)pyrimidin-2-amine (31)

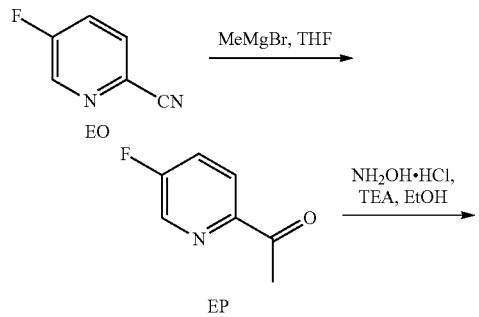

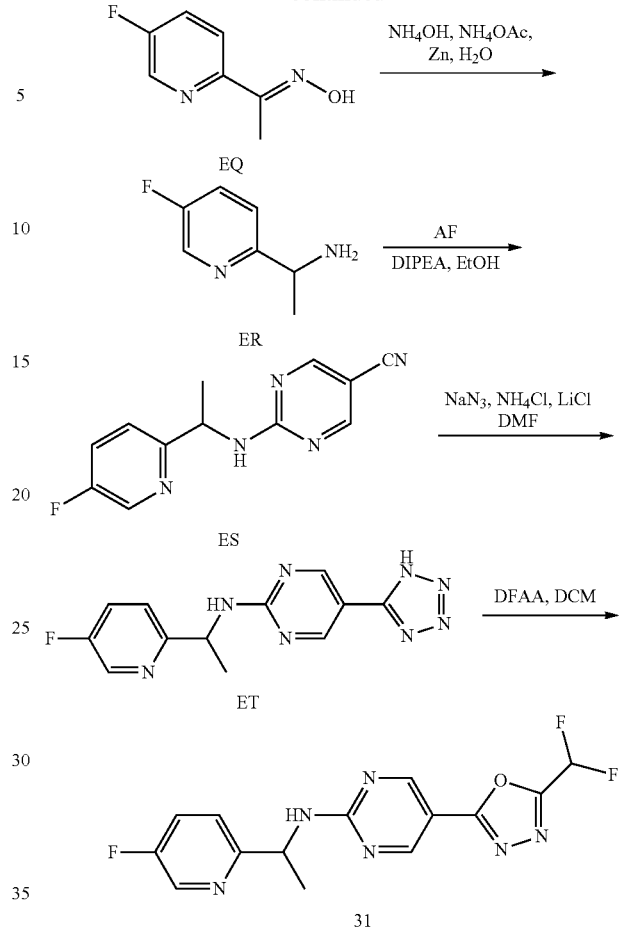

1-(5-fluoropyridin-2-yl)ethan-1-one (EP)

To a stirred solution of 5-fluoropicolinonitrile (EO, 2.9 g, 23.75 mmol) in THF (20 mL), methyl magnesium bromide (3M in THF, 10.2 mL, 30.87 mmol) was added at −65° C. and stirred for 1.5 h. The reaction mixture was further stirred at RT for 3 h. 2M HCl (10 mL) was added and the reaction mixture was further stirred at RT for 14 h. The progress of the reaction was monitored by TLC. After completion of the reaction, the reaction mixture was quenched with saturated aqueous NaHCO$_3$ solution and extracted with DCM. The combined organic layer was washed with brine, dried over anhydrous Na$_2$SO$_4$ and concentrated under reduced pressure. The crude product was purified by silica gel column chromatography using 15% EtOAc/hexane to afford compound EP (1.8 g, 54.5%) as a colorless liquid. LC-MS: m/z 140.00 [M+H]$^+$.

(E)-1-(5-fluoropyridin-2-yl)ethan-1-one oxime (EQ)

To a stirred solution of compound EP (1.8 g, 12.9 mmol) in EtOH (20 mL), triethyl amine (3.38 mL, 19.4 mmol) and NH$_2$OH·HCl (1.3 g, 19.4 mmol) were added and the reaction mixture was stirred at RT for 12 h. The progress of the reaction was monitored by TLC. After completion of the reaction, the reaction mixture was concentrated under reduced pressure. The residue was dissolved in water and extracted with EtOAc. The combined organic layer was washed with brine, dried over anhydrous Na₂SO₄ and concentrated under reduced pressure. The crude product was purified by silica gel column chromatography using 25% EtOAc/hexane to afford EQ (1.8 g, 94.7%) as an off white solid. LC-MS: m/z 154.84 [M+H]⁺.

1-(5-fluoropyridin-2-yl)ethan-1-amine (ER)

To a stirred solution of compound EQ (1.8 g, 11.6 mmol) in H₂O (25 mL), NH₄OH (4 g, 116 mmol), NH₄OAc (1.07 g, 13.9 mmol) and zinc dust (3.08 g, 46.4 mmol) were added and the reaction mixture was heated to 50° C. for 3 h. The progress of the reaction was monitored by TLC. After completion of the reaction, the reaction mixture was quenched with aqueous NaCl solution and EtOAc and the resulting solution was stirred for 1 h at room temperature. The resulting mixture was filtered through pad of celite and washed with EtOAc. The combined filtrate was washed with 2.5% NaOH solution, brine, dried over anhydrous Na₂SO₄ and concentrated under reduced pressure. The crude product was purified by silica gel column chromatography using 5% MeOH/DCM to afford ER (1 g, 62.5%) as a brown liquid. LC-MS: m/z 140.99 [M+H]⁺.

2-((1-(5-fluoropyridin-2-yl)ethyl)amino)pyrimidine-5-carbonitrile (ES)

To a stirred solution of compound ER (0.5 g, 3.56 mmol) in ethanol (10 mL), 2-chloropyrimidine-5-carbonitrile (AF, 0.74 g, 5.35 mmol) and DIPEA (1.86 mL, 10.7 mmol) were added and the reaction mixture was heated to 90° C. for 14 h. The progress of the reaction was monitored by TLC. After completion of the reaction, the reaction mixture was concentrated under reduced pressure. The crude product was purified by silica gel column chromatography using 15% EtOAc/hexane to afford compound ES (0.70 g, 80.7%) as an off white solid. LC-MS: m/z 243.90 [M+H]⁺.

N-(1-(5-fluoropyridin-2-yl)ethyl)-5-(1H-tetrazol-5-yl)pyrimidin-2-amine (ET)

To a stirred solution of compound ES (0.7 g, 2.87 mmol) in DMF (10 mL), NaN₃ (0.92 g, 14.3 mmol), NH₄Cl (0.767 g, 14.3 mmol) and LiCl (210 mg) were added and the reaction mixture was stirred at 100° C. for 14 h. The progress of the reaction was monitored by TLC. After completion of the reaction, the reaction mixture was concentrated under reduced pressure. The residue was suspended in water and the obtained solid was filtered, washed with water and dried to afford compound ET (0.6 g, crude) as an off white solid. LC-MS: m/z 287.00 [M+H]⁺.

5-(5-(difluoromethyl)-1,3,4-oxadiazol-2-yl)-N-(1-(5-fluoropyridin-2-yl)ethyl)pyrimidin-2-amine (31)

To a stirred solution of compound ET (0.6 g, 2.09 mmol) in DCM (10 mL), DFAA (0.79 g, 4.19 mmol) was added and the reaction mixture was stirred at RT for 12 h. The progress of the reaction was monitored by TLC. After completion of the reaction, the reaction mixture was concentrated under reduced pressure. The residue was dissolved in aqueous saturated solution of NaHCO₃ and extracted with EtOAc. The combined organic layer was washed with brine, dried over anhydrous Na₂SO₄ and concentrated under reduced pressure. The crude product was purified by silica gel column chromatography using 50% EtOAc/hexane to afford compound 31 (0.1 g, 14%) as an off white solid. ¹H NMR (400 MHz, DMSO-d₆) δ 8.85 (d, J=4.0 Hz, 2H), 8.71 (d, J=7.2 Hz, 1H), 8.50 (d, J=8.8 Hz, 1H), 7.71-7.62 (m, 1H), 7.51 (t, J=51.4 Hz, 1H), 7.48-7.43 (m, 1H), 5.30-5.25 (m, 1H), 1.38 (d, J=6.8 Hz, 3H); LC-MS: m/z 337 [M+H]⁺; HPLC Purity: 99.7%.

Example 32

N-(1-(4-(difluoromethoxy)phenyl)cyclopropyl)-5-(5-(difluoromethyl)-1,3,4-oxadiazol-2-yl)pyrimidin-2-amine (32)

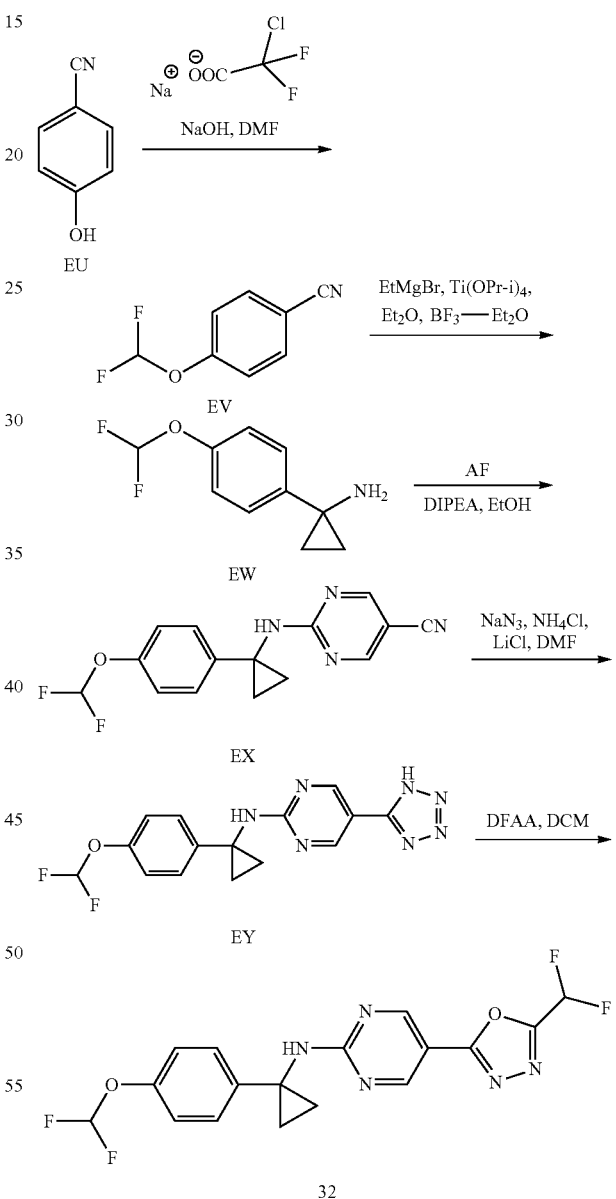

4-(difluoromethoxy)benzonitrile (EV)

To a stirred solution of 4-hydroxybenzonitrile (EU, 5 g, 41.97 mmol) in DMF (50 mL), NaOH (2.01 g, 50.36 mmol) and sodium chlorodifluoro acetate (7.67 g, 50.36 mmol)

were added and the reaction mixture was stirred at 125° C. for 8 h. The progress of the reaction was monitored by TLC.

After completion of the reaction, the reaction mixture was quenched with water and extracted with EtOAc. The combined organic layer was washed with brine, dried over anhydrous Na$_2$SO$_4$ and concentrated under reduced pressure. The crude product was purified by silica gel column chromatography using 5% MeOH/DCM to afford compound EV (3.8 g, 53.5%) as an off white solid. $^1$H NMR (400 MHz, DMSO-d$_6$) δ 7.88 (d, J=7.5 Hz, 2H), 7.42 (t, J=52.4 Hz, 1H), 7.18-7.15 (m, 2H).

1-(4-(difluoromethoxy)phenyl)cyclopropan-1-amine (EW)

To a stirred solution of compound EV (4 g, 23.66 mmol) in diethyl ether (100 mL), ethyl magnesium bromide (3M in THF, 17.3 mL, 52.03 mmol) and titanium isopropoxide (7.39 g, 26.02 mmol) were added at −78° C. and the reaction mixture was stirred at RT for 2 h. BF$_3$·OEt$_2$ (6.72 g, 47.32 mmol) was added at 0° C. and the reaction mixture was stirred at RT for 14 h. The progress of the reaction was monitored by TLC. After completion of the reaction, the reaction mixture was quenched with NH$_4$Cl solution, basified with 10% NaOH solution, and extracted with 10% MeOH/DCM. The combined organic layer was washed with brine, dried over anhydrous Na$_2$SO$_4$ and concentrated under reduced pressure. The crude product was purified by silica gel column chromatography using 5% MeOH/DCM to afford compound EW (1.5 g, 31.84%) as a brown liquid.

2-((1-(4-(difluoromethoxy)phenyl)cyclopropyl)amino)pyrimidine-5-carbonitrile (EX)

To a stirred solution of compound EW (0.71 g, 3.57 mmol) in ethanol (15 mL), 2-chloropyrimidine-5-carbonitrile (AF, 0.5 g, 3.57 mmol) and DIPEA (1.86 mL, 10.71 mmol) were added and the reaction mixture was heated to 90° C. for 14 h. The progress of the reaction was monitored by TLC. After completion of the reaction, the reaction mixture was concentrated under reduced pressure. The crude product was purified by silica gel column chromatography using 5% MeOH/DCM to afford compound EX (0.5 g, 46.3%) as an off white solid. LC-MS: m/z 302.99 [M+H]$^+$.

N-(1-(4-(difluoromethoxy)phenyl)cyclopropyl)-5-(1H-tetrazol-5-yl)pyrimidin-2-amine (EY)

To a stirred solution of compound EX (0.3 g, 0.992 mmol) in DMF (10 mL), NaN$_3$ (0.193 g, 2.97 mmol), NH$_4$Cl (0.159 g, 2.97 mmol) and LiCl (0.041 g, 0.992 mmol) were added and the reaction mixture was stirred at 100° C. for 14 h. The progress of the reaction was monitored by TLC. After completion of the reaction, the reaction mixture was concentrated under reduced pressure. The residue was dissolved in water and the obtain solid was filtered. The solid was washed with water and dried to afford compound EY (0.250 g, crude) as an off white solid. LC-MS: m/z 346.06 [M+H]$^+$.

N-(1-(4-(difluoromethoxy)phenyl)cyclopropyl)-5-(5-(difluoromethyl)-1,3,4-oxadiazol-2-yl)pyrimidin-2-amine (32)

To a stirred solution of compound EY (0.25 g, 0.723 mmol) in DCM (10 mL), DFAA (0.25 g, 1.44 mmol) was added and the reaction mixture was stirred at RT for 12 h. The progress of the reaction was monitored by TLC. After completion of the reaction, the reaction mixture was concentrated under reduced pressure. The residue was dissolved in saturated solution of NaHCO$_3$ and extracted with EtOAc. The combined organic layer was washed with brine, dried over anhydrous Na$_2$SO$_4$ and concentrated under reduced pressure. The crude product was purified by silica gel column chromatography using 5% MeOH/DCM to afford compound 32 (0.06 g, 21%) as an off white solid. $^1$H NMR (400 MHz, DMSO-d$_6$) δ 9.04 (s, 1H), 8.87 (d, J=10.8 Hz, 2H), 7.51 (t, J=51.1 Hz, 1H), 7.24 (d, J=8.4 Hz, 2H), 7.14 (t, J=74.4 Hz, 1H), 7.07 (d, J=8.8 Hz, 2H), 1.33-1.25 (m, 4H); LC-MS: m/z 395.95 [M+H]$^+$; HPLC Purity: 99.6%.

Example 33

N-(1-(4-(difluoromethoxy)-2-fluorophenyl)cyclopropyl)-5-(5-(difluoromethyl)-1,3,4-oxadiazol-2-yl)pyrimidin-2-amine (33)

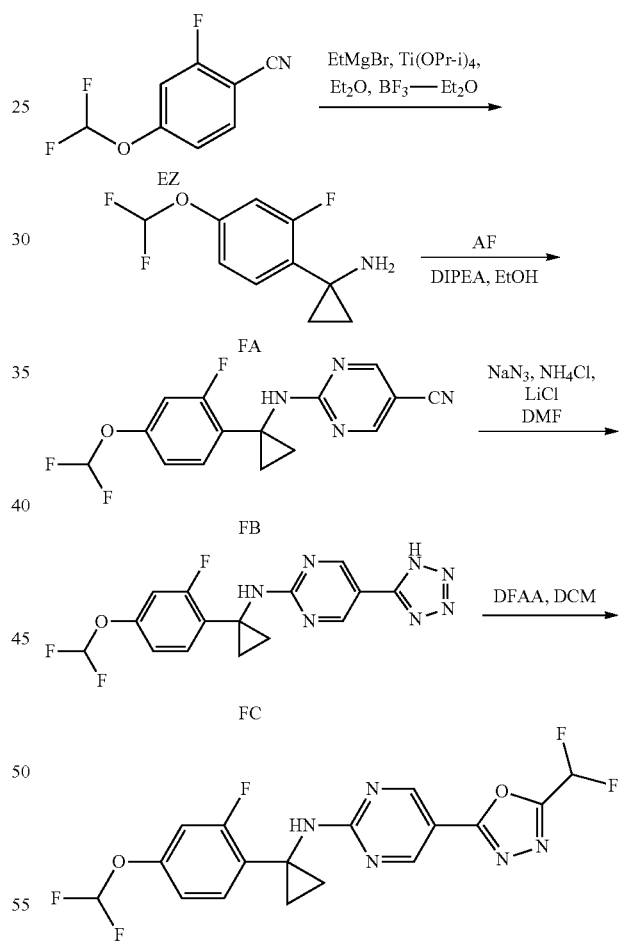

1-(4-(difluoromethoxy)-2-fluorophenyl)cyclopropan-1-amine (FA)

To a stirred solution of 4-(difluoromethoxy)-2-fluorobenzonitrile (EZ, 1 g, 5.34 mmol) in diethyl ether (30 mL), ethyl magnesium bromide (3M in THF, 3.91 mL, 11.75 mmol) and titanium isopropoxide (1.67 g, 5.87 mmol) were added at −78° C. and the reaction mixture was stirred at RT for 2 h. BF$_3$·OEt$_2$ (1.51 g, 10.68 mmol) was added at 0° C. and stirred at RT for 14 h. The progress of the reaction was monitored by TLC. After completion of the reaction, the reaction mixture was quenched with NH$_4$Cl solution, basified with 10% NaOH solution, and extracted with 10% MeOH/DCM. The combined organic layer was washed with brine, dried over anhydrous Na$_2$SO$_4$ and concentrated under reduced pressure. The crude product was purified by silica gel column chromatography using 5% MeOH/DCM to afford compound FA (0.458 g, 39.4%) as a brown liquid. LC-MS: m/z 218.00 [M+H]$^+$.

2-((1-(4-(difluoromethoxy)-2-fluorophenyl)cyclopropyl)amino)pyrimidine-5-carbonitrile (FB)

To a stirred solution of compound FA (0.45 g, 2.07 mmol) in ethanol (10 mL), 2-chloropyrimidine-5-carbonitrile (AF, 0.34 g, 2.48 mmol) and DIPEA (1.44 mL, 8.28 mmol) were added and the reaction mixture was heated to 90° C. for 14 h. The progress of the reaction was monitored by TLC. After completion of the reaction, the reaction mixture was concentrated under reduced pressure. The crude product was purified by silica gel column chromatography using 5% MeOH/DCM to afford compound FB (0.5 g, 76.3%) as a white solid. LC-MS: m/z 320.95 [M+H]$^+$.

N-(1-(4-(difluoromethoxy)-2-fluorophenyl)cyclopropyl)-5-(1H-tetrazol-5-yl)pyrimidin-2-amine (FC)

To a stirred solution of compound FB (0.5 g, 1.56 mmol) in DMF (10 mL), NaN$_3$ (0.304 g, 4.68 mmol), NH$_4$Cl (0.252 g, 4.68 mmol) and LiCl (100 mg) were added and the reaction mixture was stirred at 100° C. for 14 h. The progress of the reaction was monitored by TLC. After completion of the reaction, the reaction mixture was concentrated under reduced pressure. The residue was dissolved in water and the obtained solid was filtered, washed with water, and dried to afford compound FC (0.4 g, crude) as a brown liquid. LC-MS: m/z 364.03 [M+H]$^+$.

N-(1-(4-(difluoromethoxy)-2-fluorophenyl)cyclopropyl)-5-(5-(difluoromethyl)-1,3,4-oxadiazol-2-yl)pyrimidin-2-amine (33)

To a stirred solution of compound FC (0.4 g, 1.10 mmol) in DCM (15 mL), DFAA (0.383 g, 2.20 mmol) was added and the reaction mixture was stirred at RT for 12 h. The progress of the reaction was monitored by TLC. After completion of the reaction, the reaction mixture was concentrated under reduced pressure. The residue was dissolved in aqueous saturated solution of NaHCO$_3$ and extracted with EtOAc. The combined organic layer was washed with brine, dried over anhydrous Na$_2$SO$_4$ and concentrated under reduced pressure. The crude product was purified by silica gel column chromatography using 50% EtOAc/hexane to afford compound 33 (0.08 g, 17.5%) as an off white solid. $^1$H NMR (400 MHz, DMSO-d$_6$) δ 9.05 (s, 1H), 8.85 (d, J=17.6 Hz, 2H), 7.15-7.67 (m, 1H), 7.51 (t, J=51.2 Hz, 1H), 7.23 (t, J=67.4 Hz, 1H), 7.02-7.01 (m, 1H), 6.95-6.93 (m, 1H), 1.28-1.25 (m, 2H), 1.20-1.19 (m, 2H); LC-MS: m/z 413.95 [M+H]$^+$; HPLC Purity: 99.5%.

Example 34

5-(5-(difluoromethyl)-1,3,4-oxadiazol-2-yl)-N-(6-fluoro-1,2,3,4-tetrahydronaphthalen-1-yl)pyrimidin-2-amine (34)

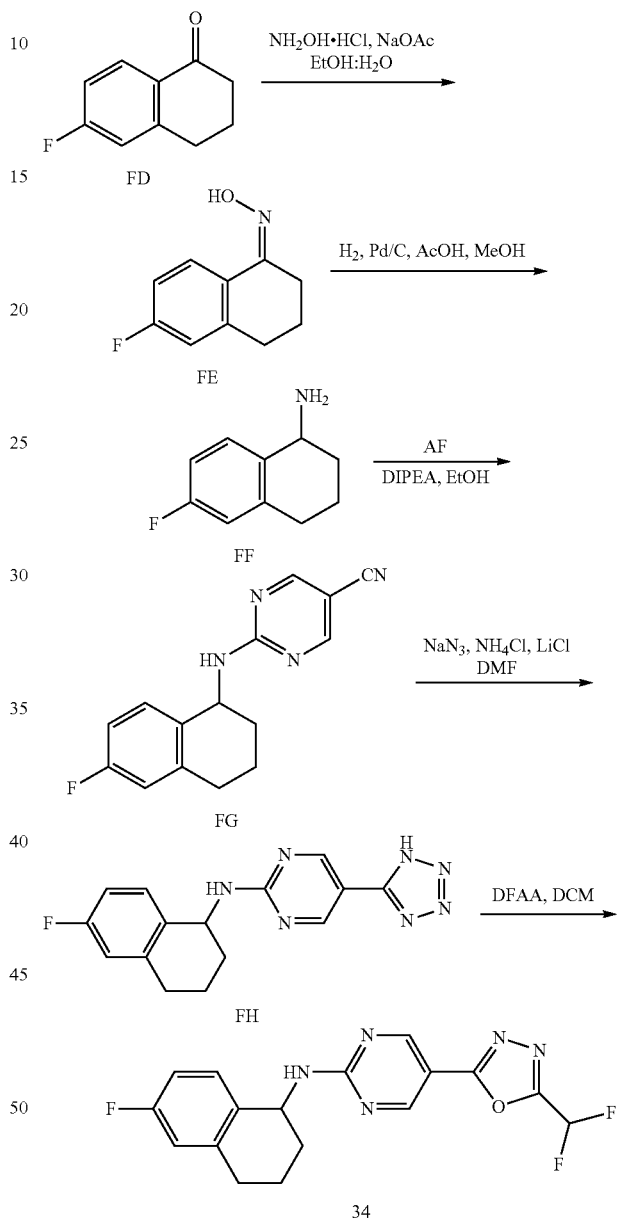

(Z)-6-fluoro-3,4-dihydronaphthalen-1(2H)-one oxime (FE)

To a stirred solution of 6-fluoro-3,4-dihydronaphthalen-1(2H)-one (FD, 2 g, 12.18 mmol) in ethanol (50 mL), aqueous NaOAc (2.49 g, 30.4 mmol) and NH$_2$OH·HCl (2.11 g, 30.4 mmol) were added and the reaction mixture was stirred at 90° C. for 12 h. The progress of the reaction was monitored by TLC. After completion of the reaction, the reaction mixture was concentrated under reduced pressure.

The residue was washed with water and dried to afford compound FE (2 g, 95%) as a white solid. LC-MS: m/z 179.90 [M+H]⁺.

6-fluoro-1,2,3,4-tetrahydronaphthalen-1-amine (FF)

To a stirred solution of compound FE (2 g, 11.1 mmol) in methanol (50 mL), acetic acid (10 mL) and palladium on carbon (200 mg) were added and stirred under hydrogen balloon pressure at RT for 12 h. The progress of the reaction was monitored by TLC. After completion of the reaction, the reaction mixture was filtered through pad of celite and washed with methanol. The filtrate was concentrated under reduced pressure. The crude product was purified by silica gel column chromatography using 10% MeOH/DCM to afford compound FF (1.2 g, 65%) as a brown liquid. LC-MS: m/z 148.85 [M-16]⁺.

2-((6-fluoro-1,2,3,4-tetrahydronaphthalen-1-yl)amino)pyrimidine-5-carbonitrile (FG)

To a stirred solution of compound FF (0.5 g, 3.02 mmol) in ethanol (10 mL), 2-chloropyrimidine-5-carbonitrile (AF, 0.46 g, 3.32 mmol) and DIPEA (1.58 mL, 9.06 mmol) were added and the reaction mixture was heated to 90° C. for 14 h. The progress of the reaction was monitored by TLC. After completion of the reaction, the reaction mixture was concentrated under reduced pressure. The crude product was purified by silica gel column chromatography using 20% EtOAc/hexane to afford compound FG (0.7 g, 86%) as an off white solid. LC-MS: m/z 269.00 [M+H]⁺.

N-(6-fluoro-1,2,3,4-tetrahydronaphthalen-1-yl)-5-(1H-tetrazol-5-yl)pyrimidin-2-amine (FH)

To a stirred solution of compound FG (0.6 g, 2.23 mmol) in DMF (10 mL), NaN₃ (0.72 g, 11.1 mmol), NH₄Cl (0.59 g, 11.1 mmol) and LiCl (180 mg) were added and the reaction mixture was stirred at 100° C. for 14 h. The progress of the reaction was monitored by TLC. After completion of the reaction, the reaction mixture was quenched with ice water, acidified with 2N HCl solution to pH=2, and extracted with 10% MeOH/DCM. The combined organic layer was washed with brine, dried over anhydrous Na₂SO₄ and concentrated under reduced pressure to afford compound FH (0.5 g, crude) as an off white solid. LC-MS: m/z 312.0 [M+H]⁺.

5-(5-(difluoromethyl)-1,3,4-oxadiazol-2-yl)-N-(6-fluoro-1,2,3,4-tetrahydronaphthalen-1-yl)pyrimidin-2-amine (34)

To a stirred solution of compound FH (0.3 g, 0.96 mmol) in DCM (15 mL), DFAA (1 mL) was added and the reaction mixture was stirred at RT for 12 h. The progress of the reaction was monitored by TLC. After completion of the reaction, the reaction mixture was concentrated under reduced pressure. The residue was dissolved in a saturated solution of NaHCO₃ and extracted with EtOAc. The combined organic layer was washed with brine, dried over anhydrous Na₂SO₄ and concentrated under reduced pressure. The crude product was purified by silica gel column chromatography using 20% EtOAc/hexane to afford compound 34 (0.06 g, 17%) as an off white solid. ¹H NMR (400 MHz, DMSO-d₆) δ 8.93 (d, J=2.8 Hz, 1H), 8.87 (d, J=3.2 Hz, 1H), 8.57 (d, J=8.8 Hz, 1H), 7.53 (t, J=51.4 Hz, 1H), 7.23-7.19 (m, 1H), 6.97-6.92 (m, 2H), 5.32-5.28 (m, 1H), 2.82-2.72 (m, 2H), 2.02-1.92 (m, 2H), 1.87-1.74 (m, 2H); LC-MS: m/z 362 [M+H]⁺; HPLC Purity: 99.0%.

Example 35

2-((5-(5-(difluoromethyl)-1,3,4-oxadiazol-2-yl)pyrimidin-2-yl)amino)-2-(4-fluorophenyl)-N-phenylacetamide (35)

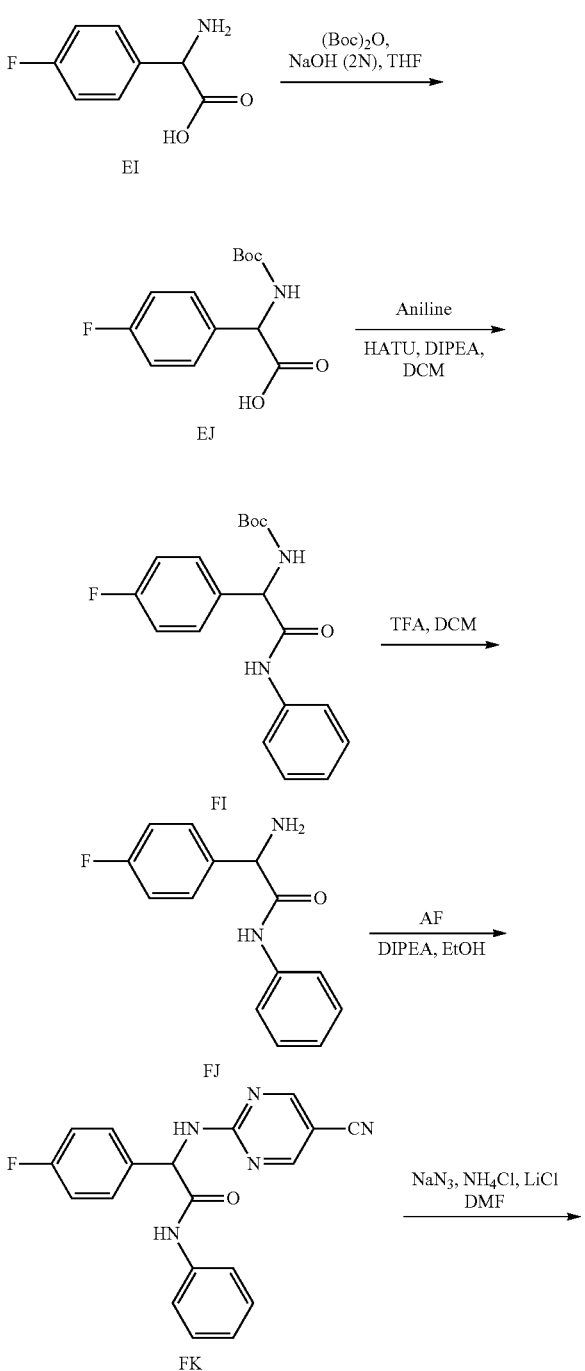

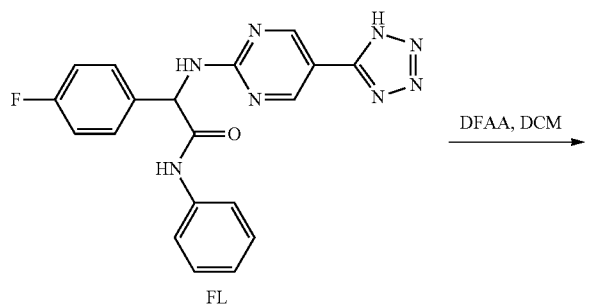

FL

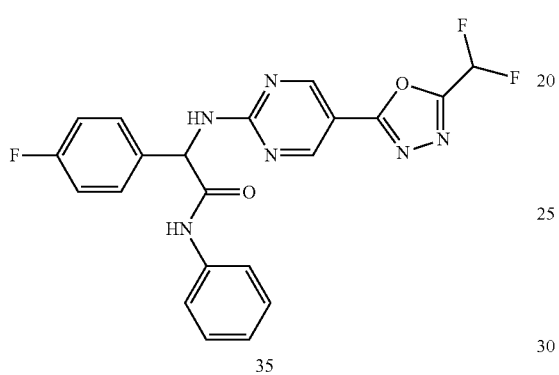

35

2-((tert-butoxycarbonyl)amino)-2-(4-fluorophenyl) acetic acid (EJ)

To a stirred solution of 2-amino-2-(4-fluorophenyl)acetic acid (EI, 2.5 g, 14.77 mmol) in THF (25 mL), boc anhydride (3.54 g, 16.25 mmol) and NaOH (3N, 20 mL) were added and stirred at room temperature for 12 h. The progress of the reaction was monitored by TLC. After completion of the reaction, reaction mixture was quenched with 6N HCl solution and extracted using EtOAc. The combined organic layer was washed with brine, dried over Na$_2$SO$_4$ and concentrated under reduced pressure to afford compound EJ (2.2 g, crude) as a brown oil. LC-MS: m/z 170 [M+H–100]$^+$.

tert-butyl (1-(4-fluorophenyl)-2-oxo-2-(phenylamino)ethyl)carbamate (FI)

To a stirred solution of compound EJ (1.1 g, 4.08 mmol) in DCM (25 mL), aniline (0.41 g, 4.49 mmol), HATU (1.86 g, 4.89 mmol) and DIPEA (2.13 mL, 12.24 mmol) were added at 0° C. under nitrogen atmosphere and the reaction mixture was stirred at room temperature for 12 h. The progress of the reaction was monitored by TLC After completion, the reaction mixture was quenched with water and extracted with EtOAc. The combined organic layer was washed with brine, dried over Na$_2$SO$_4$ and concentrated under reduced pressure. The crude product was purified by silica gel column chromatography using 5% MeOH/DCM to afford compound FI (1 g, 71.42%) as an off white solid. LC-MS: m/z 289.07 [M–56]+.

2-amino-2-(4-fluorophenyl)-N-phenylacetamide (FJ)

To a stirred solution of compound FI (1 g, 2.90 mmol) in DCM (12 mL), TFA (0.8 mL) was added and the reaction mixture was stirred at room temperature for 2 h. The progress of the reaction was monitored by TLC. After completion of the reaction, the reaction mixture was concentrated under reduced pressure to obtain the product as a TFA salt. The salt was basified with NaHCO$_3$ solution and extracted with 15% MeOH/DCM. The combined organic layer was washed with brine, dried over anhydrous Na$_2$SO$_4$ and concentrated under reduced pressure. The crude amine product was purified by silica gel column chromatography using 5% MeOH/DCM to afford compound FJ (0.6 g, 84.6%) as an off white solid. LC-MS: m/z 244.93 [M+H]$^+$.

2-((5-cyanopyrimidin-2-yl)amino)-2-(4-fluorophenyl)-N-phenylacetamide (FK)

To a stirred solution of compound FJ (0.5 g, 2.04 mmol) in ethanol (10 mL), 2-chloropyrimidine-5-carbonitrile (AF, 0.42 g, 3.07 mmol) and DIPEA (1.78 mL, 10.2 mmol) were added and the reaction mixture was heated to 90° C. for 14 h. The progress of the reaction was monitored by TLC. After completion of the reaction, the reaction mixture was concentrated under reduced pressure. The crude product was purified by silica gel column chromatography using 5% MeOH/DCM to afford compound FK (0.6 g, 84.5%) as a brown liquid. LC-MS: m/z 347.95 [M+H]$^+$.

2-((5-(1H-tetrazol-5-yl)pyrimidin-2-yl)amino)-2-(4-fluorophenyl)-N-phenylacetamide (FL)

To a stirred solution of compound FK (0.6 g, 1.72 mmol) in DMF (10 mL), NaN$_3$ (0.336 g, 5.18 mmol), NH$_4$Cl (0.277 g, 5.18 mmol) and LiCl (60 mg) were added and the reaction mixture was stirred at 100° C. for 14 h. The progress of the reaction was monitored by TLC. After completion of the reaction, the reaction mixture was quenched with ice water and acidified with 2N HCl solution to pH=2. The precipitated solid was filtered and washed with cold water to afford compound FL (0.3 g, crude) as an off white solid. LC-MS: m/z 391.05 [M+H]$^+$.

2-((5-(5-(difluoromethyl)-1,3,4-oxadiazol-2-yl)pyrimidin-2-yl)amino)-2-(4-fluorophenyl)-N-phenylacetamide (35)

To a stirred solution of compound FL (0.3 g, 0.768 mmol) in DCM (10 mL), DFAA (0.20 g, 1.15 mmol) was added and the reaction mixture was stirred at RT for 12 h. The progress of the reaction was monitored by TLC. After completion of the reaction, the reaction mixture was concentrated under reduced pressure. The residue was dissolved in saturated solution of NaHCO$_3$ and extracted with EtOAc. The combined organic layer was washed with brine, dried over anhydrous Na$_2$SO$_4$ and concentrated under reduced pressure. The crude product was purified by silica gel column chromatography using 50% EtOAc/hexane to afford compound 35 (0.007 g, 2%) as an off white solid. $^1$H NMR (400 MHz, DMSO-d$_6$) δ 10.4 (s, 1H), 8.94 (d, J=8.0 Hz, 1H), 8.76 (d, J=7.6 Hz, 1H), 7.66-7.63 (m, 2H), 7.59-7.57 (m, 2H), 7.40 (t, J=51.2 Hz, 1H), 7.31-7.22 (m, 4H), 7.04 (t, J=7.6 Hz, 1H), 5.90 (d, J=7.2 Hz, 1H), 1.23 (s, 1H). LC-MS: m/z 441.1 [M+H]$^+$; HPLC Purity: 92.2%.

Example 36

N-(cyclopropyl(4-fluorophenyl)methyl)-5-(5-(difluoromethyl)-1,3,4-oxadiazol-2-yl)pyrimidin-2-amine (36)

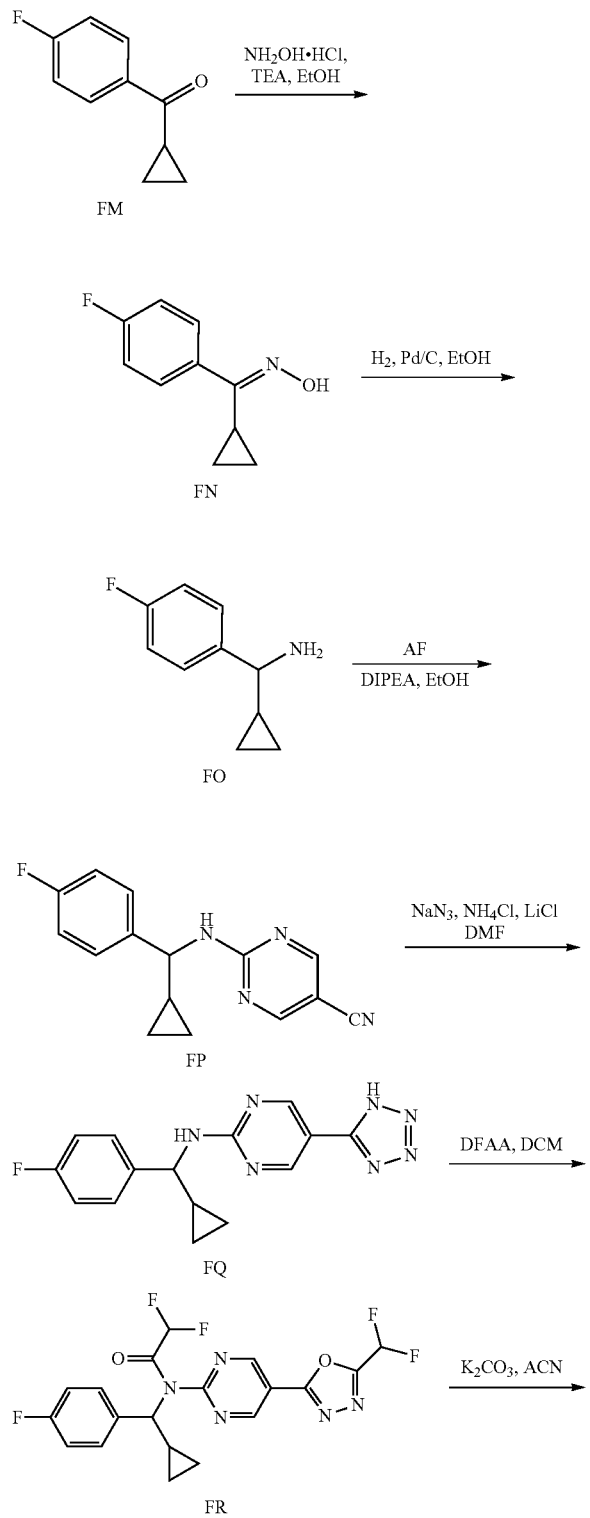

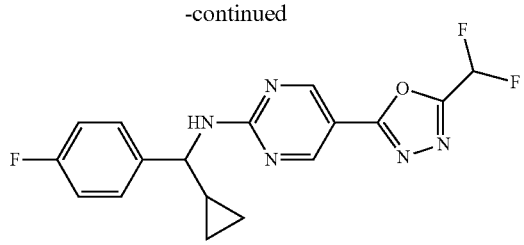

(E)-cyclopropyl(4-fluorophenyl)methanone oxime (FN)

To a stirred solution of cyclopropyl(4-fluorophenyl)methanone (FM, 5 g, 30.4 mmol) in EtOH (50 mL), triethyl amine (10.5 mL, 76.1 mmol) and NH$_2$OH·HCl (5.2 g, 76.1 mmol) were added and the reaction mixture was stirred at 90° C. for 12 h. The progress of the reaction was monitored by TLC. After completion of the reaction, the reaction mixture was concentrated under reduced pressure. The residue was washed with water and the solid dried to afford compound FN (5 g, 91.7%) as an off white solid. $^1$H NMR (400 MHz, DMSO-d$_6$) δ 11.0 (s, 1H), 7.43-7.40 (m, 2H), 7.25-7.16 (m, 2H), 0.89-0.85 (m, 2H), 0.76-0.73 (m, 1H), 0.51-0.47 (m, 2H).

cyclopropyl(4-fluorophenyl)methanamine (FO)

To a stirred solution of compound FN (5 g, 27.9 mmol) in EtOH (50 mL), acetic acid (10 mL) and palladium on carbon (500 mg) were added and stirred under hydrogen balloon pressure at RT for 12 h. The progress of the reaction was monitored by TLC. After completion of the reaction, the reaction mixture was filtered through a pad of celite and washed with MeOH. The filtrate was concentrated under reduced pressure. The crude product was purified by silica gel column chromatography using 10% MeOH/DCM to afford compound FO (4 g, 86.9%) as a brown liquid. LC-MS: m/z 166.05 [M+H]$^+$.

2-((cyclopropyl(4-fluorophenyl)methyl)amino)pyrimidine-5-carbonitrile (FP)

To a stirred solution of compound FO (0.5 g, 3.02 mmol) in ethanol (10 mL), 2-chloropyrimidine-5-carbonitrile (AF, 0.5 g, 3.63 mmol) and DIPEA (2.63 mL, 15.1 mmol) were added and the reaction mixture was heated to 90° C. for 12 h. The progress of the reaction was monitored by TLC. After completion of the reaction, the reaction mixture was concentrated under reduced pressure. The crude product was purified by silica gel column chromatography using 30% EtOAc/hexane to afford compound FP (0.2 g, 24.6%) as a pale yellow solid. LC-MS: m/z 269.03 [M+H]$^+$.

N-(cyclopropyl(4-fluorophenyl)methyl)-5-(1H-tetrazol-5-yl)pyrimidin-2-amine (FQ)

To a stirred solution of compound FP (0.2 g, 0.74 mmol) in DMF (20 mL), NaN$_3$ (0.24 g, 3.72 mmol), NH$_4$Cl (0.19 g, 3.72 mmol) and LiCl (60 mg) were added and the reaction mixture was stirred at 95° C. for 12 h. The progress of the reaction was monitored by TLC. After completion of the reaction, the reaction mixture was concentrated under reduced pressure. The residue was dissolved in cold water and adjust to pH=4-5 by using aqueous HCl solution. The obtained solid was filtered and dried to afford compound FQ (0.25 g, crude) as an off white solid. LC-MS: m/z 312.0 [M+H]⁺.

N-(cyclopropyl(4-fluorophenyl)methyl)-N-(5-(5-(difluoromethyl)-1,3,4-oxadiazol-2-yl)pyrimidin-2-yl)-2,2-difluoroacetamide (FR)

To a stirred solution of compound FQ (0.25 g, 0.80 mmol) in DCM (10 mL), DFAA (0.5 mL) was added at 0° C. The reaction mixture was stirred at RT for 12 h. The progress of the reaction was monitored by TLC. After completion of the reaction, the reaction mixture was concentrated under reduced pressure. The crude product was purified by silica gel column chromatography using 10% MeOH/DCM to afford compound FR (0.1 g, 28.4%) as an off white solid. ¹H NMR (400 MHz, DMSO-$d_6$) δ 9.30 (s, 2H), 7.56-7.51 (m, 2H), 7.49 (t, J=51.2 Hz, 1H), 7.14-7.10 (m, 1H), 6.92 (t, J=52.4 Hz, 1H), 5.30 (d, J=10 Hz, 1H), 1.96 (br s, 1H), 0.80 (s, 1H), 0.46-0.45 (m, 2H), 0.22-0.21 (m, 2H).

N-(cyclopropyl(4-fluorophenyl)methyl)-5-(5-(difluoromethyl)-1,3,4-oxadiazol-2-yl)pyrimidin-2-amine (36)

To a stirred solution of compound FR (0.1 g, 0.22 mmol) in ACN (2 mL), $K_2CO_3$ (0.09 g, 0.68 mmol) was added and the reaction mixture was heated to 80° C. for 12 h. The progress of the reaction was monitored by TLC. After completion of the reaction, the reaction mixture was filtered through a pad of celite and washed with EtOAC. The filtrate was concentrated under reduced pressure. The crude product was diluted with EtOAC and washed with water. The combined organic layer was washed with brine, dried over anhydrous $Na_2SO_4$ and concentrated under reduced pressure. The crude product was purified by silica gel column chromatography using 20% EtOAc/hexane to afford 36 (0.03 g, 36%) as an off white solid. ¹H NMR (400 MHz, DMSO-$d_6$) δ 8.93 (d, J=8.8 Hz, 1H), 8.56 (br s, 1H), 8.76 (br s, 1H), 7.51 (t, J=51.2 Hz, 1H), 7.49-7.47 (m, 2H), 7.14 (t, J=8.8 Hz, 2H), 4.40 (t, J=8.8 Hz, 1H), 1.32-1.28 (m, 1H), 0.55-0.51 (m, 2H), 0.42-0.40 (m, 2H). LC-MS: m/z 362.1 [M+H]⁺; HPLC Purity: 95.9%.

Example 37

N-(4,4-difluoro-1-(4-fluorophenyl)cyclohexyl)-5-(5-(difluoromethyl)-1,3,4-oxadiazol-2-yl)pyrimidin-2-amine (37)

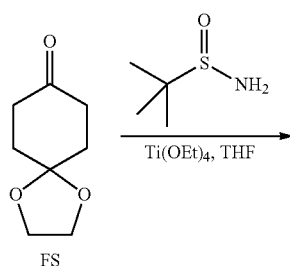

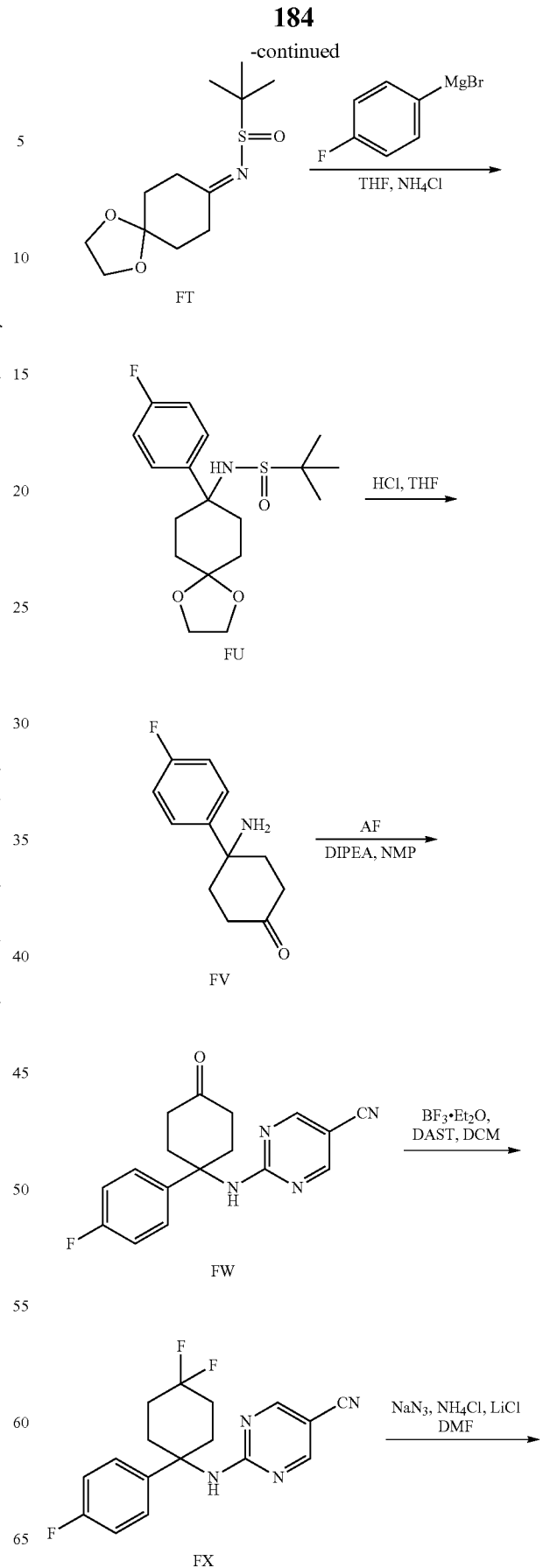

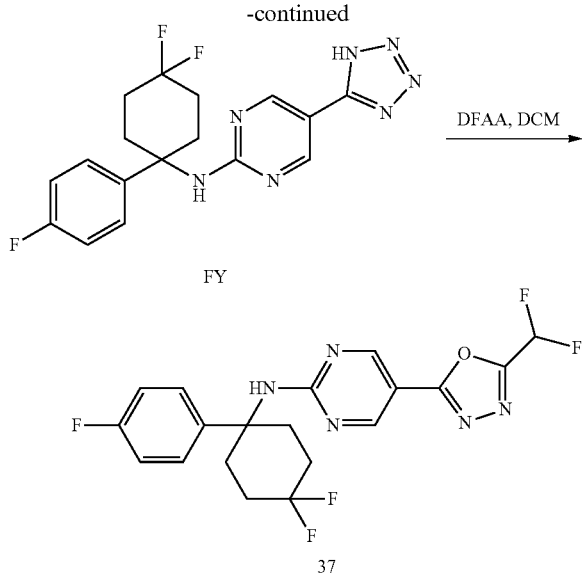

2-methyl-N-(1,4-dioxaspiro[4.5]decan-8-ylidene)
propane-2-sulfinamide (FT)

To a stirred solution of 1,4-dioxaspiro[4.5]decan-8-one (FS, 9 g, 57.62 mmol) in DCE (150 mL), Ti(OEt)$_4$ (39.4 g, 172.8 mmol) and 2-methylpropane-2-sulfinamide (15.3 g, 126.7 mmol) were added at 0° C. and the reaction mixture stirred at RT for 16 h. The progress of the reaction was monitored by TLC. After completion of the reaction, the reaction mixture was quenched with saturated aqueous NaHCO$_3$ solution. The obtained solid was filtered and filtrate was extracted with EtOAc. The combined organic layer was washed with brine, dried over anhydrous Na$_2$SO$_4$ and concentrated under reduced pressure. The crude product was purified by silica gel column chromatography using 50% EtOAc/hexane to afford compound FT (10 g, 67%) as an off white solid. $^1$H NMR (400 MHz, DMSO-d$_6$) δ 3.94 (s, 1H), 3.02 (s, 4H)), 2.98-2.91 (m, 1H), 2.79-2.72 (m, 1H), 2.35 (t, J=6.8 Hz, 1H), 1.94-1.78 (m, 4H), 1.12 (s, 9H), 1.07 (s, 1H).

N-(8-(4-fluorophenyl)-1,4-dioxaspiro[4.5]decan-8-yl)-2-methylpropane-2-sulfinamide (FU)

To a stirred solution of compound FT (6 g, 23.13 mmol) in THF (60 mL) was added 1 M solution of (4-fluorophenyl) magnesium bromide in THF (60 mL) and the reaction was stirred at 0° C. for 3 h. The progress of the reaction was monitored by TLC. After completion of the reaction, the reaction mixture was quenched with aqueous NH$_4$Cl solution and extracted with EtOAc. The combined organic layer was washed with brine, dried over anhydrous Na$_2$SO$_4$ and concentrated under reduced pressure. The crude product was purified by silica gel column chromatography using 70% EtOAc/hexane to afford compound FU (5.9 g, 71.95%) as an off white solid. $^1$H NMR (400 MHz, DMSO-d$_6$) δ 7.56-7.52 (m, 2H), 7.11 (t, J=8.8 Hz, 2H), 5.21 (s, 1H), 3.86-3.83 (m, 4H), 2.22-2.08 (m, 4H), 1.19-1.80 (m, 2H), 1.49-1.45 (m, 2H), 1.12-1.08 (s, 9H).

4-amino-4-(4-fluorophenyl)cyclohexan-1-one (FV)

To a stirred solution of compound FU (5.9 g, 16.59 mmol) in THF (30 mL), 2M HCl (30 mL) was added and stirred reaction mixture at 50° C. for 16 h. The progress of the reaction was monitored by TLC. After completion of the reaction, the reaction mixture was concentrated under reduced pressure. The reaction residue was quenched with aqueous NaOH solution and extracted with EtOAc. The combined organic layer was washed with brine, dried over anhydrous Na$_2$SO$_4$ and concentrated under reduced pressure. The residue was dissolved in EtOAc, filtered, concentrated and dried to afford compound FV (2.4 g, crude) as an off white solid. $^1$H NMR (400 MHz, DMSO-d$_6$) δ 8.86 (s, 2H), 7.80-7.76 (m, 2H), 7.32 (t, J=8.8 Hz, 2H), 2.69-2.54 (m, 4H), 2.41-2.35 (m, 2H), 2.24-2.18 (m, 2H).

2-((1-(4-fluorophenyl)-4-oxocyclohexyl)amino)pyrimidine-5-carbonitrile (FW)

To a stirred solution of compound FV (1.5 g, 7.23 mmol) in NMP (15 mL), 2-chloropyrimidine-5-carbonitrile (AF, 1 g, 7.23 mmol) and DIPEA (6.3 mL, 36.1 mmol) were added and the reaction mixture was heated to 130° C. for 5 h. The progress of the reaction was monitored by TLC. After completion of the reaction, the reaction mixture was concentrated under reduced pressure. The crude product was purified by silica gel column chromatography using 50% EtOAc/hexane to afford compound FW (1 g, 44.6%) as an off white solid. LC-MS: m/z 311.05 [M+H]$^+$.

2-((4,4-difluoro-1-(4-fluorophenyl)cyclohexyl)amino)pyrimidine-5-carbonitrile (FX)

To a stirred solution of compound FW (0.5 g, 1.61 mmol) in DCM (10 mL), BF$_3$·Et$_2$O (0.38 g, 2.73 mmol) and DAST (1.27 g, 7.88 mmol) were added and the reaction mixture stirred at RT for 16 h. The progress of the reaction was monitored by TLC. After completion of the reaction, the reaction mixture was quenched with saturated aqueous NaHCO$_3$ solution and extracted with DCM. The combined organic layer was washed with brine, dried over anhydrous Na$_2$SO$_4$ and concentrated under reduced pressure. The crude product was purified by silica gel column chromatography using 80% EtOAC/hexane to afford compound FX (0.35 g, 65.4%) as an off white solid. LC-MS: m/z 333.10 [M+H]$^+$.

N-(4,4-difluoro-1-(4-fluorophenyl)cyclohexyl)-5-(1H-tetrazol-5-yl)pyrimidin-2-amine (FY)

To a stirred solution of compound FX (0.35 g, 1.05 mmol) in DMF (10 mL), NaN$_3$ (0.34 g, 5.26 mmol), NH$_4$Cl (0.28 g, 5.26 mmol) and LiCl (50 mg) were added and the reaction mixture was stirred at 95° C. for 12 h. The progress of the reaction was monitored by TLC. After completion of the reaction, the reaction mixture was concentrated under reduced pressure. The residue was dissolved in cold water and adjust to pH=4-5 by using HCl solution. The obtained solid was filtered, washed with water, dried to afford compound FY (0.18 g, crude) as an off white solid. LC-MS: m/z 376.10 [M+H]$^+$.

N-(4,4-difluoro-1-(4-fluorophenyl)cyclohexyl)-5-(5-(difluoromethyl)-1,3,4-oxadiazol-2-yl)pyrimidin-2-amine (37)

To a stirred solution of compound FY (0.18 g, 0.47 mmol) in DCM (5 mL), DFAA (0.5 mL) was added at 0° C. The reaction mixture was stirred at RT for 12 h. The progress of the reaction was monitored by TLC. After completion of the reaction, the reaction mixture was concentrated under reduced pressure. The crude product was purified by silica gel column chromatography using 10% MeOH/DCM to afford compound 37 (0.05 g, 24.6%) as an off white solid. ¹H NMR (400 MHz, DMSO-d₆) δ 8.90 (br s, 1H), 8.69 (br s, 1H), 7.50 (t, J=51.4 Hz, 1H), 7.46-7.42 (m, 2H), 7.10 (t, J=8.8 Hz, 2H), 2.75-2.72 (m, 2H), 2.16-2.13 (m, 1H), 2.01-1.98 (m, 4H); LC-MS: m/z 426.1 [M+H]⁺; HPLC Purity: 99.7%.

Example 38

N-(2-((5-(5-(difluoromethyl)-1,3,4-oxadiazol-2-yl)pyrimidin-2-yl)amino)-2-(4-fluorophenyl)ethyl)methanesulfonamide (38)

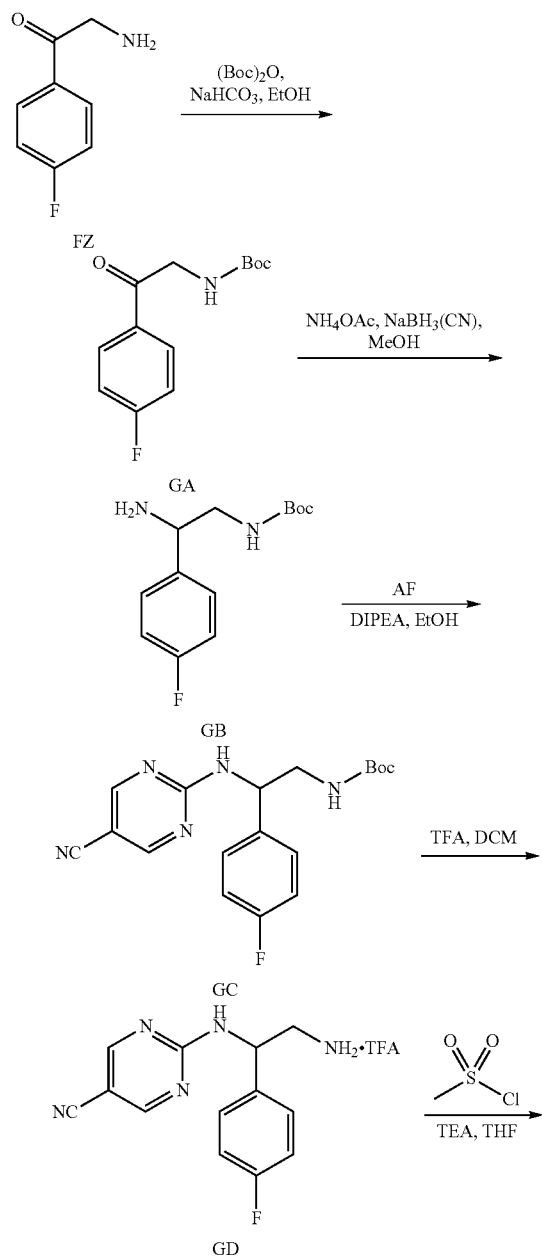

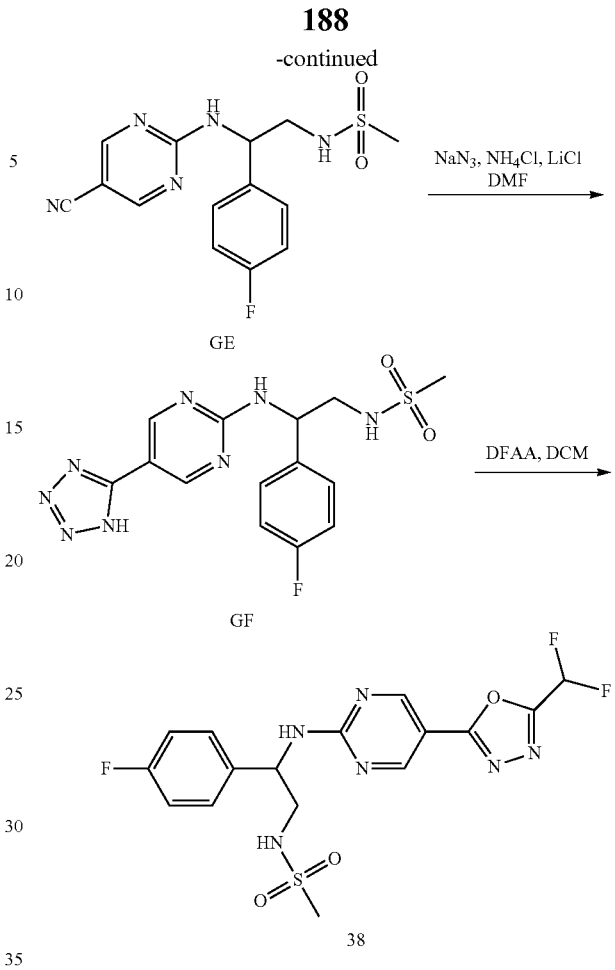

tert-butyl (2-(4-fluorophenyl)-2-oxoethyl)carbamate (GA)

To a stirred solution of 2-amino-1-(4-fluorophenyl)ethan-1-one (FZ, 5 g, 26.7 mmol) in EtOH (250 mL), NaHCO₃ (6.6 g, 79.1 mmol) and Boc anhydride (6.11 g, 28.0 mmol) were added and stirred at room temperature for 12 h. The progress of the reaction was monitored by TLC. After completion of the reaction, the reaction mixture was concentrated under reduced pressure. The residue was suspended in diethyl ether and the solid obtained was filtered, washed with pentane and dried to afford GA (6.1 g, crude) as a white solid LC-MS: m/z 153.90 [M+H−100]+.

tert-butyl (2-amino-2-(4-fluorophenyl)ethyl)carbamate (GB)

To a stirred solution of compound GA (4 g, 15.7 mmol) in MeOH (125 mL), ammonium acetate (24.3 g, 315.8 mmol) was added and the reaction mixture was stirred at RT for 30 min. NaCNBH₃ (2.67 g, 42.6 mmol) was added and the reaction mixture was stirred at 60° C. for 3 h. The progress of the reaction was monitored by TLC. After completion of the reaction, the reaction mixture was concentrated under reduced pressure. The residue was diluted with EtOAC, basified with 10% NaOH solution and extracted with EtOAC. The combined organic layer was washed with brine, dried over anhydrous Na₂SO₄ and concentrated under reduced pressure to afford compound GB (3.8 g, crude) as a brown oil. LC-MS: m/z 255.10 [M+H]⁺.

tert-butyl (2-((5-cyanopyrimidin-2-yl)amino)-2-(4-fluorophenyl)ethyl)carbamate (GC)

To a stirred solution of compound GB (3.5 g, 13.7 mmol) in ethanol (50 mL), 2-chloropyrimidine-5-carbonitrile (AF, 2.11 g, 15.1 mmol) and DIPEA (7.17 mL, 41.1 mmol) were added and the reaction mixture was heated to 90° C. for 12 h. The progress of the reaction was monitored by TLC. After completion of the reaction, the reaction mixture was concentrated under reduced pressure. The crude product was purified by silica gel column chromatography using 30% EtOAc/hexane to afford compound GC (4.6 g, 93.8%) as a pale yellow solid. LC-MS: m/z 358.05 [M+H]$^+$.

2-((2-amino-1-(4-fluorophenyl)ethyl)amino)pyrimidine-5-carbonitrile (GD)

To a stirred solution of compound GC (4.6 g, 12.87 mmol) in DCM (100 mL), TFA (10 mL) was added at 0° C. and stirred at room temperature for 4 h. The progress of the reaction was monitored by TLC. After completion of the reaction, the reaction mixture was concentrated under reduced pressure to obtain compound GD as a TFA salt. The crude product was triturated with diethyl ether and dried to afford compound GD (3 g, crude) as a white solid. LC-MS: m/z 258.0 [M+H]$^+$.

N-(2-((5-cyanopyrimidin-2-yl)amino)-2-(4-fluorophenyl)ethyl)methanesulfonamide (GE)

To a stirred solution of compound GD (1 g, 2.69 mmol) in DCM (20 mL), triethyl amine (1.12 mL 8.08 mmol) and mesyl chloride (0.31 mL, 4.04 mmol) were added at 0° C. and the reaction mixture was stirred at RT for 1 h. The progress of the reaction was monitored by TLC. After completion of the reaction, the reaction mixture was quenched with saturated NaHCO$_3$ solution and extracted with DCM. The combined organic layer was washed with brine, dried over anhydrous Na$_2$SO$_4$ and concentrated under reduced pressure. The crude product was triturated with n-pentane and dried to afford compound GE (0.8 g, crude) as an off white solid. LC-MS: m/z 336.0 [M+H]$^+$.

N-(2-((5-(1H-tetrazol-5-yl)pyrimidin-2-yl)amino)-2-(4-fluorophenyl)ethyl)methanesulfonamide (GF)

To a stirred solution of compound GD (0.8 g, 2.38 mmol) in DMF (10 mL), NaN$_3$ (0.77 g, 11.9 mmol), NH$_4$Cl (0.63 g, 11.9 mmol) and LiCl (250 mg) were added and the reaction mixture was stirred at 95° C. for 12 h. The progress of the reaction was monitored by TLC. After completion of the reaction, the reaction mixture was quenched with ice water, acidified with 2N HCl solution to pH=2, and extracted with 10% MeOH/DCM. The combined organic layer was washed with brine, dried over anhydrous Na$_2$SO$_4$ and concentrated under reduced pressure to afford compound GF (0.7 g, crude) as an off white solid. LC-MS: m/z 379.10 [M+H]$^+$.

N-(2-((5-(5-(difluoromethyl)-1,3,4-oxadiazol-2-yl)pyrimidin-2-yl)amino)-2-(4-fluorophenyl)ethyl)methanesulfonamide (38)

To a stirred solution of compound GF (0.33 g, 0.873 mmol) in DCM (10 mL), DFAA (0.5 mL) was added at 0° C. Reaction mixture was stirred at RT for 12 h. The progress of the reaction was monitored by TLC. After completion of the reaction, the reaction mixture was concentrated under reduced pressure. The crude product was purified by silica gel column chromatography using 90% EtOAc/hexane to afford compound 38 (0.06 g, 16%) as an off white solid. $^1$H NMR (400 MHz, DMSO-d$_6$) δ 8.87 (d, J=10.8 Hz, 1H), 8.69 (d, J=8.8 Hz, 1H), 7.51 (t, J=51.2 Hz, 1H), 7.49-7.45 (m, 3H), 7.25 (t, J=6.0 Hz, 1H), 7.17 (t, J=8.8 Hz, 2H), 5.30-5.24 (m, 1H), 3.41-3.30 (m, 2H), 2.83 (s, 3H). LC-MS: m/z 429.05 [M+H]$^+$; HPLC Purity: 99.3%.

Chiral Preparative HPLC Details for 38 (+) and 38(−)

The enantiomers were separated by normal-phase preparative high performance liquid chromatography (YMC CHIRALART CELLULOSE-SC®, 250×4.6 mm, 5; Mobile Phase: A; 1% TFA in MTBE/B; IPA; Inj. Vol: 10.0 μL, Col. Temp.: 30° C.; Flow rate: 1.0 mL/min) to obtain 38(+) (65 mg) and 38(−) (60 mg).

38(+): $^1$H NMR (400 MHz, DMSO-d$_6$) δ 8.88 (s, 1H), 8.86 (s, 1H), 8.69 (d, J=8.4 HZ, 1H), 7.64-7.38 (m, 3H), 7.25 (t, J=5.4 Hz, 1H), 7.17 (t, J=8.8 Hz, 2H), 5.30-5.24 (m, 1H), 3.43-3.38 (m, 1H), 2.83 (s, 3H). LC-MS: m/z 429.30 [M+H]$^+$; HPLC Purity: 99.3%.

38(−): $^1$H NMR (400 MHz, DMSO-d$_6$) δ 8.88 (s, 1H), 8.86 (s, 1H), 8.69 (d, J=8.8 HZ, 1H), 7.64-7.38 (m, 3H), 7.25 (t, J=5.6 Hz, 1H), 7.17 (t, J=8.8 Hz, 2H), 5.30-5.24 (m, 1H), 3.43-3.34 (m, 1H), 2.83 (s, 3H). LC-MS: m/z 429.10 [M+H]$^+$; HPLC Purity: 99.1%.

Example 39

N-(2-((5-(5-(difluoromethyl)-1,3,4-oxadiazol-2-yl)pyrimidin-2-yl)amino)-2-(4-fluorophenyl)ethyl)benzenesulfonamide (39)

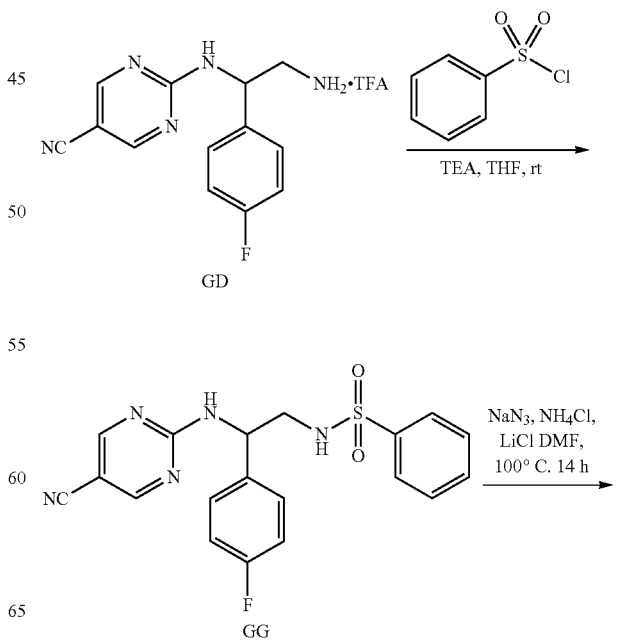

191
-continued

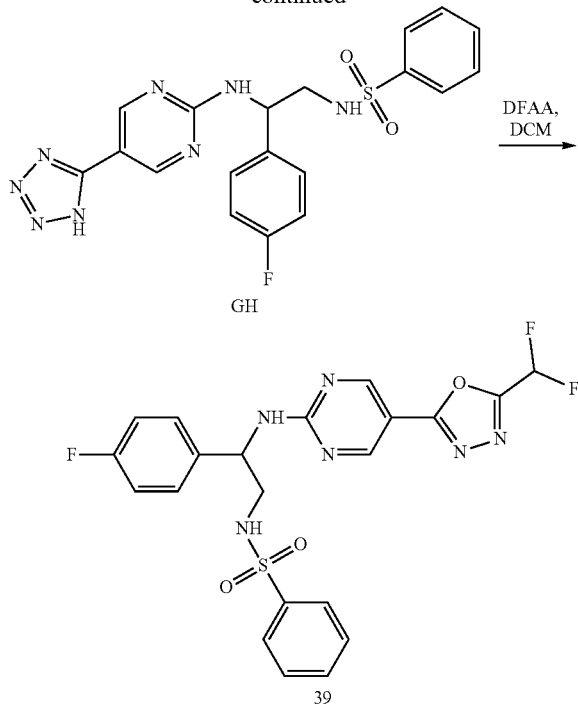

N-(2-((5-cyanopyrimidin-2-yl)amino)-2-(4-fluorophenyl)ethyl)benzenesulfonamide (GG)

To a stirred solution of compound GD (1 g, 2.69 mmol) in DCM (20 mL), triethyl amine (1.12 mL 8.08 mmol) and benzene sulphonyl chloride (0.71 g, 4.04 mmol) were added at 0° C. and the reaction mixture was stirred at RT for 1 h. The progress of the reaction was monitored by TLC. After completion of the reaction, the reaction mixture was quenched with aqueous saturated NaHCO₃ solution and extracted with DCM. The combined organic layer was washed with brine, dried over anhydrous Na₂SO₄ and concentrated under reduced pressure. The crude product was triturated with n-pentane and dried to afford compound GG (0.7 g, crude) as a white solid. LC-MS: m/z 398.05 [M+H]⁺.

N-(2-((5-(1H-tetrazol-5-yl)pyrimidin-2-yl)amino)-2-(4-fluorophenyl)ethyl)benzenesulfonamide (GH)

To a stirred solution of compound GG (0.7 g, 1.76 mmol) in DMF (20 mL), NaN₃ (0.57 g, 8.80 mmol), NH₄Cl (0.47 g, 8.80 mmol) and LiCl (185 mg) were added and the reaction mixture was stirred at 95° C. for 12 h. The progress of the reaction was monitored by TLC. After completion of the reaction, the reaction mixture was quenched with ice water, acidified with 2N HCl solution to pH=2, and extracted with 10% MeOH/DCM. The combined organic layer was washed with brine, dried over anhydrous Na₂SO₄ and concentrated under reduced pressure to afford compound GH (0.6 g, crude) as an off white solid. LC-MS: m/z 441.05 [M+H]⁺.

N-(2-((5-(5-(difluoromethyl)-1,3,4-oxadiazol-2-yl)pyrimidin-2-yl)amino)-2-(4-fluorophenyl)ethyl)benzenesulfonamide (39)

To a stirred solution of compound GH (0.3 g, 0.681 mmol) in DCM (10 mL), DFAA (0.5 mL) was added at 0°

192

C. and the reaction mixture was stirred at RT for 12 h. The progress of the reaction was monitored by TLC. After completion of the reaction, the reaction mixture was concentrated under reduced pressure. The crude product was purified by silica gel column chromatography using 70% EtOAc/hexane to afford compound 39 (0.11 g, 32.9%) as an off white solid. ¹H NMR (400 MHz, DMSO-d₆) δ 8.86 (br s, 1H), 8.16 (br s, 1H), 8.63 (d, J=8.8 Hz, 1H), 7.92-7.90 (m, 1H), 7.76-7.74 (m, 2H), 7.64-7.56 (m, 2H), 7.54 (t, J=51.2 Hz, 1H), 7.52-7.51 (m, 1H), 7.40-7.36 (m, 2H), 7.13 (t, J=8.8 Hz, 2H), 5.23-5.17 (m, 1H), 3.23-3.17 (m, 1H), 3.12-3.06 (m, 1H). LC-MS: m/z 491.05 [M+H]⁺; HPLC Purity: 98.9%.

Example 40

N-(1-(2-methoxyphenyl)cyclopropyl)-5-(5-(trifluoromethyl)-1,3,4-oxadiazol-2-yl)pyrimidin-2-amine (40)

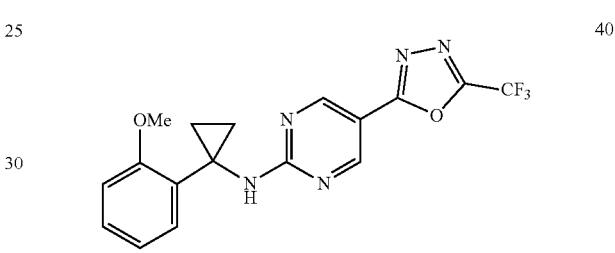

Example 40 was prepared in a manner analogous to the synthetic process used for the preparation of Example 1. ¹H NMR (400 MHz, DMSO-d₆) δ 8.88 (s, 1H), 8.81 (s, 1H), 8.64 (s, 1H), 7.54 (dd, J=7.6, 1.8 Hz, 1H), 7.23-7.14 (m, 1H), 6.92 (d, J=8.1 Hz, 1H), 6.88-6.79 (m, 1H), 3.84 (s, 3H), 1.14-1.08 (m, 4H).

Example 41

N-(1-(3-methoxyphenyl)cyclopropyl)-5-(5-(trifluoromethyl)-1,3,4-oxadiazol-2-yl)pyrimidin-2-amine (41)

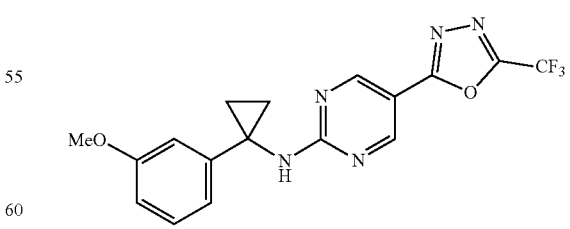

Example 41 was prepared in a manner analogous to the synthetic process used for the preparation of Example 1. ¹H NMR (400 MHz, DMSO-d₆) δ 9.05 (s, 1H), 8.95-8.86 (m, 2H), 7.16 (t, J=7.8 Hz, 1H), 6.78-6.68 (m, 3H), 3.69 (s, 3H), 1.38-1.23 (m, 4H).

Example 42

N-(1-(4-methoxyphenyl)cyclopropyl)-5-(5-(trifluoromethyl)-1,3,4-oxadiazol-2-yl)pyrimidin-2-amine (42)

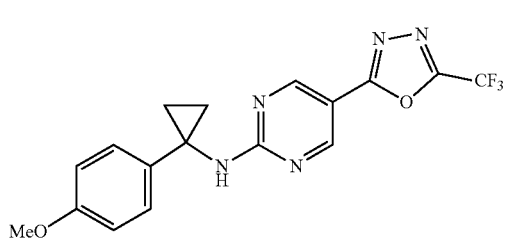

Example 42 was prepared in a manner analogous to the synthetic process used for the preparation of Example 1. $^1$H NMR (400 MHz, DMSO-d$_6$) δ 9.06 (s, 1H), 8.89 (d, J=2.3 Hz, 2H), 7.19-7.10 (m, 2H), 6.86-6.77 (m, 2H), 3.69 (s, 3H), 1.29-1.17 (m, 4H).

Example 43

5-(5-(difluoromethyl)-1,3,4-oxadiazol-2-yl)-N-(1-(3-methoxyphenyl)cyclopropyl)pyrimidin-2-amine (43)

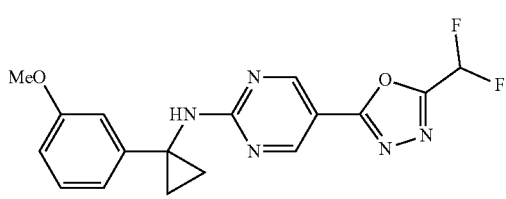

Example 43 was prepared in a manner analogous to the synthetic process used for the preparation of Example 4. $^1$H NMR (400 MHz, DMSO-d$_6$) δ 8.99 (s, 1H), 8.92-8.83 (m, 2H), 7.51 (t, J=7.8 Hz, 1H), 7.16 (t, J=7.8 Hz, 1H), 6.78-6.68 (m, 3H), 3.69 (s, 3H), 1.37-1.22 (m, 4H).

Example 44

5-(5-(difluoromethyl)-1,3,4-oxadiazol-2-yl)-N-(1-(4-methoxyphenyl)cyclopropyl)pyrimidin-2-amine (44)

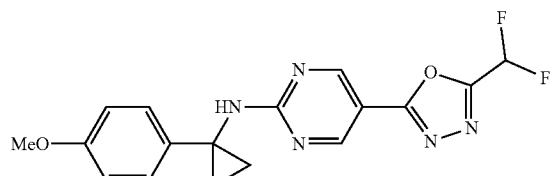

Example 44 was prepared in a manner analogous to the synthetic process used for the preparation of Example 10. $^1$H NMR (400 MHz, DMSO-d$_6$) δ 8.99 (s, 1H), 8.86 (d, J=3.5 Hz, 2H), 7.52 (t, J=52.2 Hz, 1H), 7.19-7.10 (m, 2H), 6.85-6.75 (m, 2H), 3.69 (s, 3H), 1.28-1.11 (m, 4H).

Example 45

5-(5-(difluoromethyl)-1,3,4-oxadiazol-2-yl)-N-(1-(4-(trifluoromethyl) phenyl)cyclopropyl) pyrimidin-2-amine (45)

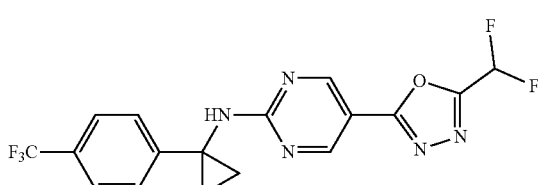

Example 45 was prepared in a manner analogous to the synthetic process used for the preparation of Example 5. $^1$H NMR (400 MHz, DMSO-d$_6$) δ 9.09 (s, 1H), 8.93 (d, J=2.9 Hz, 1H), 8.85 (d, J=3.0 Hz, 1H), 7.67-7.57 (m, 2H), 7.52 (s, 1H), 7.37 (t, J=9.2 Hz, 2H), 1.49-1.33 (m, 4H).

Example 46

5-(5-(difluoromethyl)-1,3,4-oxadiazol-2-yl)-N-(1-(2-methoxyphenyl)cyclopropyl)pyrimidin-2-amine (46)

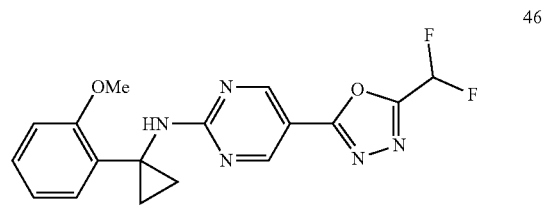

Example 46 was prepared in a manner analogous to the synthetic process used for the preparation of Example 10. $^1$H NMR (400 MHz, DMSO-d$_6$) δ 8.85 (s, 1H), 8.78 (s, 1H), 8.57 (s, 1H), 7.62 (t, J=52.0 Hz, 1H), 7.57-7.47 (m, 1H), 7.21-7.16 (m, 1H), 6.92 (dd, J=8.3, 1.1 Hz, 1H), 6.82-6.78 (m, 1H), 3.83 (s, 3H), 1.16-1.12 (m, 4H).

Example 47

N-(1-(4-bromophenyl)cyclopropyl)-5-(5-(difluoromethyl)-1,3,4-oxadiazol-2-yl)pyrimidin-2-amine (47)

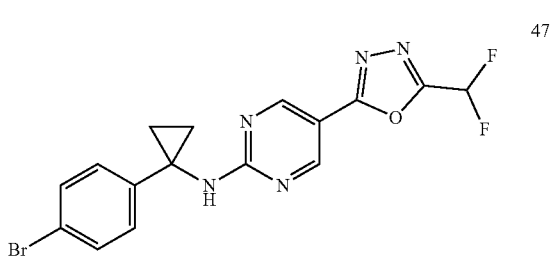 [SMILES: FC(F)c1nnc(-c2cnc(NC3(c4ccc(Br)cc4)CC3)nc2)o1]

Example 47 was prepared in a manner analogous to the synthetic process used for the preparation of Example 5. $^1$H NMR (400 MHz, DMSO-d$_6$) δ 9.03 (s, 1H), 8.89 (brs, 1H), 8.85 (brs, 1H), 7.51 (t, J=52.0 Hz, 1H), 7.44-7.42 (m, 2H), 7.12 (d, J=8.8 Hz, 2H), 1.35-1.27 (m, 4H).

Example 48

4-(1-((5-(5-(difluoromethyl)-1,3,4-oxadiazol-2-yl)pyrimidin-2-yl)amino) cyclopropyl) benzonitrile (48)

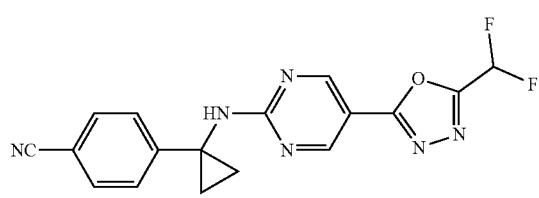

48

Example 48 was prepared in a manner analogous to the synthetic process used for the preparation of Example 5. $^1$H NMR (400 MHz, DMSO-d$_6$) δ 9.08 (s, 1H), 8.93 (d, J=3.0 Hz, 1H), 8.85 (d, J=3.1 Hz, 1H), 7.75-7.67 (m, 2H), 7.52 (t, J=52.1 Hz, 1H), 7.35-7.27 (m, 2H), 1.51-1.44 (m, 2H), 1.44-1.36 (m, 2H).

Example 49

5-(5-(difluoromethyl)-1,3,4-oxadiazol-2-yl)-N-(1-(3-(trifluoromethyl)phenyl) cyclopropyl) pyrimidin-2-amine (49)

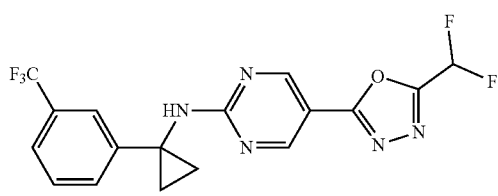

49

Example 49 was prepared in a manner analogous to the synthetic process used for the preparation of Example 5. $^1$H NMR (400 MHz, DMSO-d$_6$) δ 9.10 (s, 1H), 8.95-8.84 (m, 2H), 7.65 (t, J=52.1 Hz, 1H), 7.55-7.45 (m, 4H), 1.48-1.39 (m, 2H), 1.35 (t, J=3.5 Hz, 2H).

Example 50

N-(1-(4-chlorophenyl)cyclopropyl)-5-(5-(difluoromethyl)-1,3,4-oxadiazol-2-yl)pyrimidin-2-amine (50)

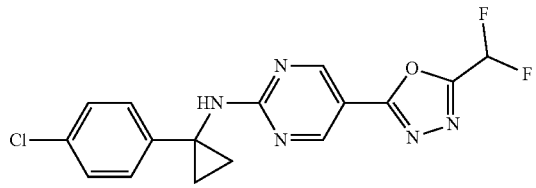

50

Example 50 was prepared in a manner analogous to the synthetic process used for the preparation of Example 11. $^1$H NMR (400 MHz, DMSO-d$_6$) δ 9.10 (s, 1H), 8.95-8.84 (m, 2H), 7.65 (t, J=51.2 Hz, 1H), 7.55-7.45 (m, 4H), 1.48-1.39 (m, 2H), 1.35 (t, J=3.5 Hz, 2H).

Example 51

N-(1-(3-chlorophenyl)cyclopropyl)-5-(5-(difluoromethyl)-1,3,4-oxadiazol-2-yl)pyrimidin-2-amine (51)

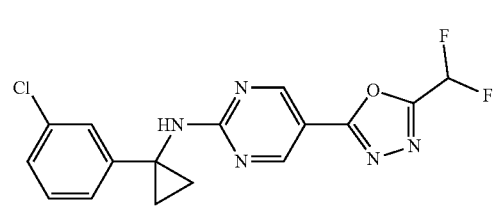

51

Example 51 was prepared in a manner analogous to the synthetic process used for the preparation of Example 11. $^1$H NMR (400 MHz, DMSO-d$_6$) δ 9.05 (s, 1H), 8.94-8.84 (m, 2H), 7.52 (t, J=51.1 Hz, 1H), 7.29 (t, J=7.8 Hz, 1H), 7.20 (d, J=9.0 Hz, 2H), 7.13 (d, J=7.9 Hz, 1H), 1.41-1.28 (m, 4H).

Example 52

N-(1-(2-chlorophenyl)cyclopropyl)-5-(5-(difluoromethyl)-1,3,4-oxadiazol-2-yl)pyrimidin-2-amine (52)

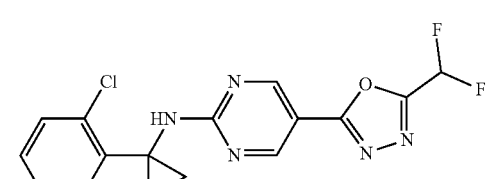

52

Example 52 was prepared in a manner analogous to the synthetic process used for the preparation of Example 11. $^1$H NMR (400 MHz, DMSO-d$_6$) δ 8.89 (d, J=5.8 Hz, 2H), 8.82 (s, 1H), 7.83 (dd, J=7.0, 2.3 Hz, 1H), 7.51 (t, J=51.0 Hz, 1H), 7.41-7.34 (m, 1H), 7.26-7.22 (m, 2H), 1.30-1.16 (m, 4H).

Example 53

5-(5-(difluoromethyl)-1,3,4-oxadiazol-2-yl)-N-(1-(3-(trifluoromethoxy)phenyl)cyclopropyl) pyrimidin-2-amine (53)

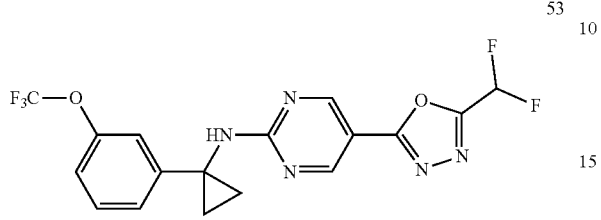

Example 53 was prepared in a manner analogous to the synthetic process used for the preparation of Example 11. $^1$H NMR (400 MHz, DMSO-$d_6$) δ 9.06 (s, 1H), 8.95-8.84 (m, 2H), 7.52 (t, J=51.2 Hz, 1H), 7.44-7.35 (m, 1H), 7.22-7.07 (m, 3H), 1.42-1.31 (m, 4H).

Example 54

5-(5-(difluoromethyl)-1,3,4-oxadiazol-2-yl)-N-(1-(4-(trifluoromethoxy)phenyl)cyclopropyl) pyrimidin-2-amine (54)

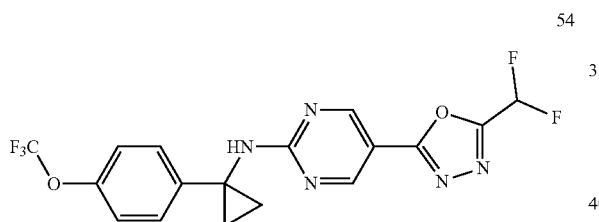

Example 54 was prepared in a manner analogous to the synthetic process used for the preparation of Example 11. $^1$H NMR (400 MHz, DMSO-$d_6$) δ 9.06 (s, 1H), 8.94-8.84 (m, 2H), 7.52 (t, J=51.2 Hz, 1H), 7.27 (t, J=8.3 Hz, 4H), 1.41-1.27 (m, 4H).

Example 55

5-(5-(difluoromethyl)-1,3,4-oxadiazol-2-yl)-N-(1-(2-(trifluoromethoxy)phenyl) cyclopropyl) pyrimidin-2-amine (55)

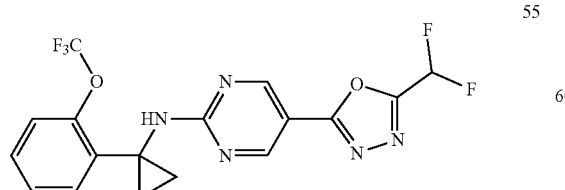

Example 55 was prepared in a manner analogous to the synthetic process used for the preparation of Example 11. $^1$H NMR (400 MHz, DMSO-$d_6$) δ 8.91 (s, 1H), 8.90-8.80 (m, 2H), 7.82 (dd, J=7.4, 1.9 Hz, 1H), 7.51 (t, J=51.4 Hz, 1H), 7.40-7.24 (m, 3H), 1.27-1.17 (m, 4H).

Example 56

5-(5-(difluoromethyl)-1,3,4-oxadiazol-2-yl)-N-(1-(2-fluorophenyl)cyclopropyl)pyrimidin-2-amine (56)

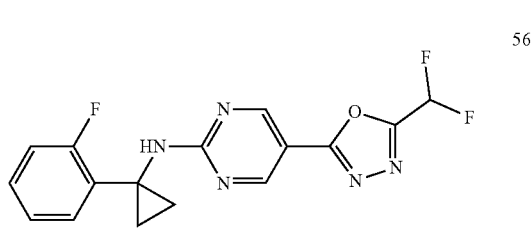 [SMILES: Fc1ccccc1C1(Nc2ncc(-c3nnc(C(F)F)o3)cn2)CC1]

Example 56 was prepared in a manner analogous to the synthetic process used for the preparation of Example 11. $^1$H NMR (400 MHz, DMSO-$d_6$) δ 9.01 (s, 1H), 8.85 (d, J=16.3 Hz, 2H), 7.67-7.57 (m, 1H), 7.37 (t, J=51.2 Hz, 1H), 7.24-7.20 (m, 1H), 7.14-7.04 (m, 2H), 1.33-1.12 (m, 4H).

Example 57

5-(5-(difluoromethyl)-1,3,4-oxadiazol-2-yl)-N-(1-(3-fluorophenyl)cyclopropyl)pyrimidin-2-amine (57)

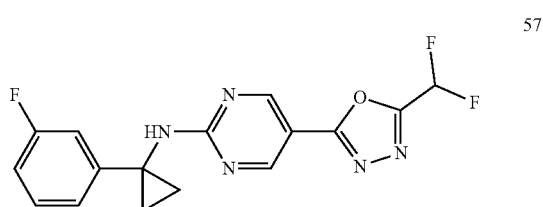

Example 57 was prepared in a manner analogous to the synthetic process used for the preparation of Example 11. $^1$H NMR (400 MHz, DMSO-$d_6$) δ 9.03 (s, 1H), 8.93-8.83 (m, 2H), 7.51 (t, J=51.2 Hz, 1H), 7.28-7.25 (m, 1H), 7.03-6.88 (m, 3H), 1.42-1.26 (m, 4H).

Example 58

5-(5-(difluoromethyl)-1,3,4-oxadiazol-2-yl)-N-(1-(2-(trifluoromethyl)phenyl) cyclopropyl) pyrimidin-2-amine (58)

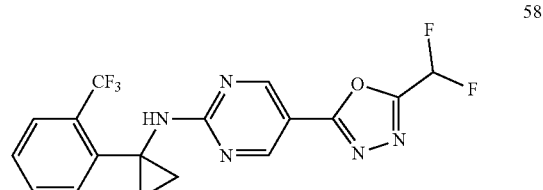

Example 58 was prepared in a manner analogous to the synthetic process used for the preparation of Example 11. $^1$H NMR (400 MHz, DMSO-d$_6$) δ 8.84 (s, 1H), 8.79 (s, 1H), 8.53 (s, 1H), 8.09 (d, J=7.8 Hz, 1H), 7.66-7.53 (m, 1H), 7.50-7.43 (m, 1H), 7.42 (t, J=51.2 Hz, 1H), 7.40-7.38 (m, 1H), 1.27 (s, 4H).

Example 59

5-(5-(difluoromethyl)-1,3,4-oxadiazol-2-yl)-N-(1-(3,4-difluorophenyl)cyclopropyl) pyrimidin-2-amine (59)

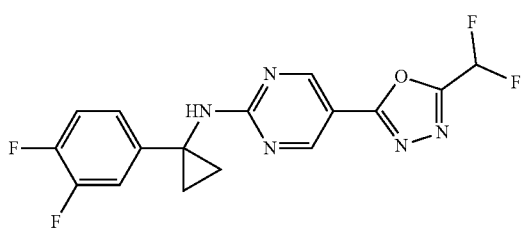

Example 59 was prepared in a manner analogous to the synthetic process used for the preparation of Example 11. $^1$H NMR (400 MHz, DMSO-d$_6$) δ 9.02 (s, 1H), 8.91-8.83 (m, 2H), 7.51 (t, J=51.4 Hz, 1H), 7.28-7.23 (m, 1H), 7.22-7.11 (m, 1H), 7.06-6.98 (m, 1H), 1.39-1.23 (m, 4H).

Example 60

5-(5-(difluoromethyl)-1,3,4-oxadiazol-2-yl)-N-(1-(2,3-difluorophenyl)cyclopropyl) pyrimidin-2-amine (60)

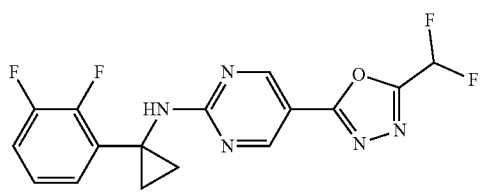

Example 60 was prepared in a manner analogous to the synthetic process used for the preparation of Example 11. $^1$H NMR (400 MHz, DMSO-d$_6$) δ 9.10 (s, 1H), 8.87 (d, J=9.8 Hz, 2H), 7.52 (t, J=51.4 Hz, 1H), 7.42 (dd, J=14.8, 7.5 Hz, 1H), 7.27 (q, J=8.4 Hz, 1H), 7.16-7.06 (m, 1H), 1.39-1.19 (m, 4H).

Example 61

5-(5-(difluoromethyl)-1,3,4-oxadiazol-2-yl)-N-(1-(2,5-difluorophenyl)cyclopropyl) pyrimidin-2-amine (61)

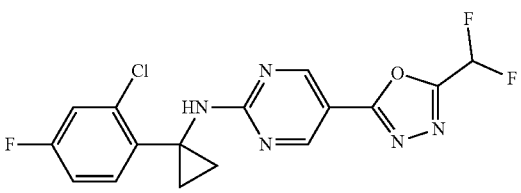

Example 61 was prepared in a manner analogous to the synthetic process used for the preparation of Example 11. $^1$H NMR (400 MHz, DMSO-d$_6$) δ 9.06 (s, 1H), 8.91 (s, 1H), 8.85 (s, 1H), 7.52 (t, J=51.4 Hz, 1H), 7.44-7.34 (m, 1H), 7.22-7.04 (m, 2H), 1.38-1.28 (m, 2H), 1.28-1.16 (m, 2H).

Example 62

N-(1-(2-chloro-4-fluorophenyl)cyclopropyl)-5-(5-(difluoromethyl)-1,3,4-oxadiazol-2-yl)pyrimidin-2-amine (62)

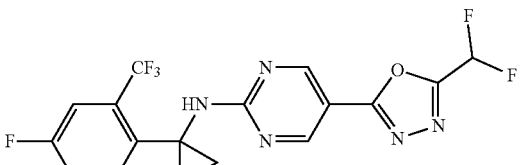

Example 62 was prepared in a manner analogous to the synthetic process used for the preparation of Example 11. $^1$H NMR (400 MHz, DMSO-d$_6$) δ 8.91 (s, 1H), 8.85 (s, 1H), 8.79 (s, 1H), 7.85 (dd, J=8.7, 6.4 Hz, 1H), 7.49 (t, J=51.4 Hz, 1H), 7.38-7.28 (m, 1H), 7.18-7.12 (m, 1H), 1.27-1.09 (m, 4H).

Example 63

5-(5-(difluoromethyl)-1,3,4-oxadiazol-2-yl)-N-(1-(4-fluoro-2-(trifluoromethyl) phenyl)cyclopropyl) pyrimidin-2-amine (63)

Example 63 was prepared in a manner analogous to the synthetic process used for the preparation of Example 11. $^1$H NMR (400 MHz, DMSO-$d_6$) δ 8.85 (d, J=19.1 Hz, 2H), 8.65 (s, 1H), 8.18 (dd, J=8.7, 5.9 Hz, 1H), 7.65 (t, J=51.2 Hz, 1H), 7.57-7.42 (m, 2H), 1.30 (s, 4H).

Example 64

N-(1-(6-bromopyridin-3-yl)cyclopropyl)-5-(5-(difluoromethyl)-1,3,4-oxadiazol-2-yl)pyrimidin-2-amine (64)

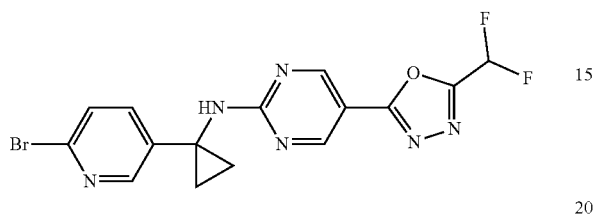

64

Example 64 was prepared in a manner analogous to the synthetic process used for the preparation of Example 11. $^1$H NMR (400 MHz, DMSO-$d_6$) δ 9.07 (s, 1H), 8.95-8.85 (m, 2H), 8.21 (d, J=1.7 Hz, 1H), 7.53 (t, J=51.2 Hz, 1H), 7.40 (d, J=1.3 Hz, 2H), 1.41 (d, J=5.5 Hz, 2H), 1.32 (q, J=5.1 Hz, 2H).

Example 65

5-(5-(difluoromethyl)-1,3,4-oxadiazol-2-yl)-N-(1-(pyridin-3-yl)cyclopropyl)pyrimidin-2-amine (65)

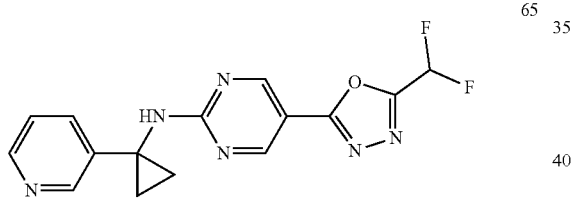

65

Example 65 was prepared in a manner analogous to the synthetic process used for the preparation of Example 18. $^1$H NMR (400 MHz, DMSO-$d_6$) δ 9.09 (s, 1H), 8.96-8.86 (m, 2H), 8.45-8.34 (m, 2H), 7.66 (t, J=51.4 Hz, 1H), 7.61-7.51 (m, 1H), 7.31 (d, J=6.3 Hz, 1H), 1.46-1.38 (m, 2H), 1.37-1.29 (m, 2H).

Example 66

N-(1-(4-chloro-2-fluorophenyl)cyclopropyl)-5-(5-(difluoromethyl)-1,3,4-oxadiazol-2-yl)pyrimidin-2-amine (66)

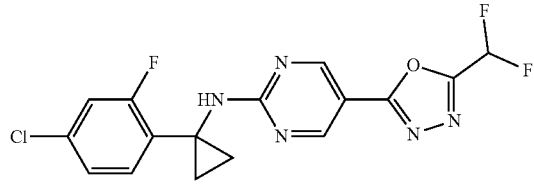

66

Example 66 was prepared in a manner analogous to the synthetic process used for the preparation of Example 11. $^1$H NMR (400 MHz, DMSO-$d_6$) δ 9.05 (s, 1H), 8.90-8.82 (m, 2H), 7.65 (t, J=8.5 Hz, 1H), 7.51 (t, J=51.4 Hz, 1H), 7.41-7.28 (m, 1H), 7.24-7.16 (m, 1H), 1.33-1.16 (m, 4H).

Example 67

5-(5-(difluoromethyl)-1,3,4-oxadiazol-2-yl)-N-(1-(5-fluoropyridin-2-yl)cyclopropyl) pyrimidin-2-amine (67)

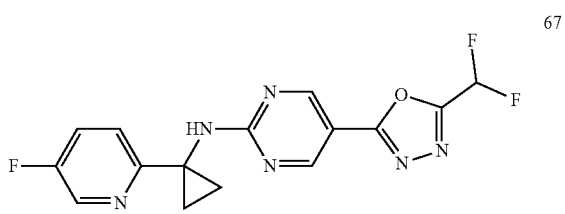 [SMILES: Fc1ccc(C2(Nc3ncc(-c4nnc(C(F)F)o4)cn3)CC2)nc1]

67

Example 67 was prepared in a manner analogous to the synthetic process used for the preparation of Example 18. $^1$H NMR (400 MHz, DMSO-$d_6$) δ 9.08 (s, 1H), 8.94 (d, J=3.1 Hz, 1H), 8.87 (d, J=3.1 Hz, 1H), 8.43 (d, J=2.9 Hz, 1H), 7.66 (t, J=51.4 Hz, 1H), 7.61-7.50 (m, 1H), 7.29 (dd, J=8.9, 4.3 Hz, 1H), 1.57 (q, J=4.3 Hz, 2H), 1.28 (q, J=4.3 Hz, 2H).

Example 68

5-(5-(difluoromethyl)-1,3,4-oxadiazol-2-yl)-N-(1-(4-(2,2,2-trifluoroethoxy)phenyl) cyclopropyl) pyrimidin-2-amine (68)

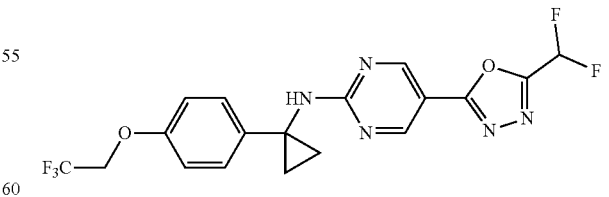

68

Example 68 was prepared in a manner analogous to the synthetic process used for the preparation of Example 11. $^1$H NMR (400 MHz, DMSO-$d_6$) δ 9.01 (s, 1H), 8.91-8.83 (m, 2H), 7.52 (t, J=51.4 Hz, 1H), 7.20-7.13 (m, 2H), 6.94 (dd, J=8.8, 1.6 Hz, 2H), 4.74-4.62 (m, 2H), 1.25 (dd, J=12.2, 2.8 Hz, 4H).

Example 69

N-(4-(1-((5-(5-(difluoromethyl)-1,3,4-oxadiazol-2-yl)pyrimidin-2-yl)amino)cyclopropyl) benzyl) methanesulfonamide (69)

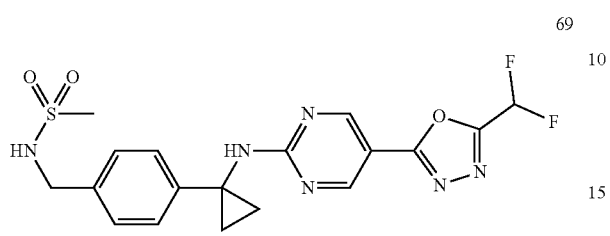

69

Example 69 was prepared in a manner analogous to the synthetic process used for the preparation of Example 11. $^1$H NMR (400 MHz, DMSO-$d_6$) δ 9.02 (s, 1H), 8.92-8.81 (m, 2H), 7.65 (t, J=51.2 Hz, 1H), 7.54-7.42 (m, 1H), 7.22 (d, J=8.1 Hz, 2H), 7.15 (d, J=8.3 Hz, 2H), 4.08 (d, J=6.1 Hz, 2H), 2.84 (s, 3H), 1.28 (dd, J=13.2, 10.3 Hz, 4H).

Example 70

5-(5-(difluoromethyl)-1,3,4-oxadiazol-2-yl)-N-(1-(2-fluoro-4-(trifluoromethoxy) phenyl) cyclopropyl) pyrimidin-2-amine (70)

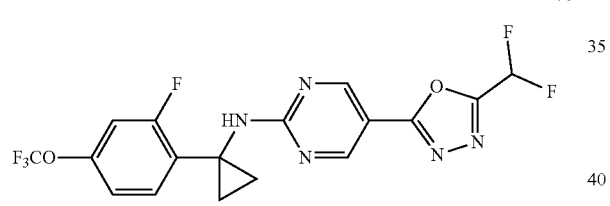

70

Example 70 was prepared in a manner analogous to the synthetic process used for the preparation of Example 11. $^1$H NMR (400 MHz, DMSO-$d_6$) δ 9.08 (s, 1H), 8.87 (d, J=14.2 Hz, 2H), 7.77 (t, J=8.7 Hz, 1H), 7.52 (t, J=51.0 Hz, 1H), 7.29 (dd, J=11.0, 2.4 Hz, 1H), 7.19-7.12 (m, 1H), 1.36-1.25 (m, 2H), 1.22 (t, J=3.4 Hz, 2H).

Example 71

5-(5-(difluoromethyl)-1,3,4-oxadiazol-2-yl)-N-(1-(2-fluoro-4-(trifluoromethyl)phenyl) cyclopropyl)pyrimidin-2-amine (71)

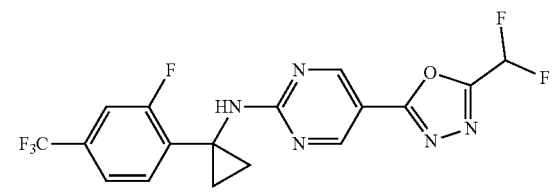

71

Example 71 was prepared in a manner analogous to the synthetic process used for the preparation of Example 11. $^1$H NMR (400 MHz, DMSO-$d_6$) δ 9.13 (s, 1H), 8.86 (d, J=2.9 Hz, 2H), 7.82 (t, J=7.9 Hz, 1H), 7.64 (t, J=51.1 Hz, 1H), 7.62-7.47 (m, 2H), 1.44-1.32 (m, 2H), 1.32-1.22 (m, 2H).

Example 72

5-(5-(difluoromethyl)-1,3,4-oxadiazol-2-yl)-N-(1-(3,5-difluorophenyl)cyclopropyl) pyrimidin-2-amine (72)

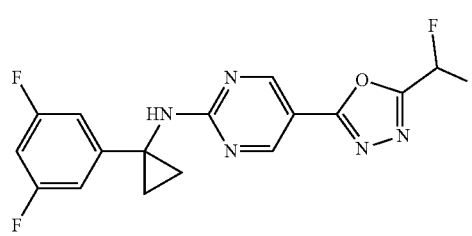

72

Example 72 was prepared in a manner analogous to the synthetic process used for the preparation of Example 11. $^1$H NMR (400 MHz, DMSO-$d_6$) δ 9.03 (s, 1H), 8.96-8.85 (m, 2H), 7.52 (t, J=51.2 Hz, 1H), 7.02-6.98 (m, 1H), 6.84-6.72 (m, 2H), 1.48-1.41 (m, 2H), 1.33 (q, J=5.6, 5.0 Hz, 2H).

Example 73

N-(1-(3-chloro-2-fluorophenyl)cyclopropyl)-5-(5-(difluoromethyl)-1,3,4-oxadiazol-2-yl)pyrimidin-2-amine (73)

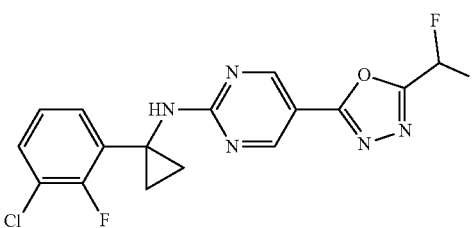

73

Example 73 was prepared in a manner analogous to the synthetic process used for the preparation of Example 11. $^1$H NMR (400 MHz, DMSO-$d_6$) δ 9.09 (s, 1H), 8.85 (d, J=11.2 Hz, 2H), 7.64-7.59 (m, 1H), 7.51 (t, J=51.2 Hz, 1H), 7.44-7.38 (m, 1H), 7.13 (t, J=7.6 Hz, 1H), 1.33-1.30 (m, 2H), 1.23-1.20 (m, 2H).

Example 74

5-(5-(difluoromethyl)-1,3,4-oxadiazol-2-yl)-N-(1-(2,4,6-trifluorophenyl)cyclopropyl) pyrimidin-2-amine (74)

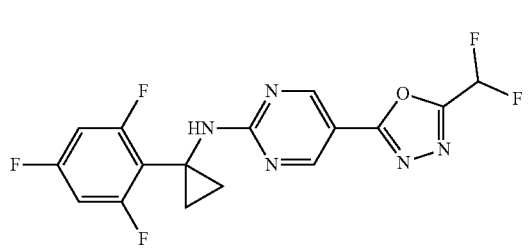

Example 74 was prepared in a manner analogous to the synthetic process used for the preparation of Example 11. $^1$H NMR (400 MHz, DMSO-d$_6$) δ 8.99 (s, 1H), 8.83 (s, 2H), 7.51 (t, J=51.4 Hz, 1H), 7.07 (t, J=8.9 Hz, 2H), 1.28-1.16 (m, 4H).

Example 75

5-(5-(difluoromethyl)-1,3,4-oxadiazol-2-yl)-N-(1-(2-fluoro-5-(trifluoromethoxy)phenyl) cyclopropyl) pyrimidin-2-amine (75)

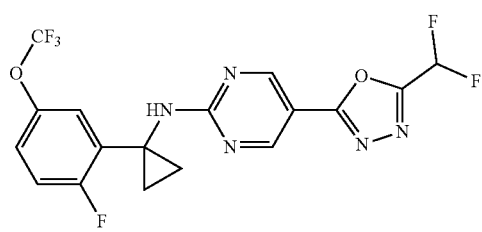

Example 75 was prepared in a manner analogous to the synthetic process used for the preparation of Example 11. $^1$H NMR (400 MHz, DMSO-d$_6$) δ 9.10 (s, 1H), 8.86 (d, JJ=2.6 Hz, 2H), 7.67-7.56 (m, 1H), 7.52 (t, J=51.0 Hz, 1H), 7.33-7.22 (m, 2H), 1.39-1.29 (m, 2H), 1.29-1.18 (m, 2H).

Example 76

N-(1-(5-chloro-2-fluorophenyl)cyclopropyl)-5-(5-(difluoromethyl)-1,3,4-oxadiazol-2-yl)pyrimidin-2-amine (76)

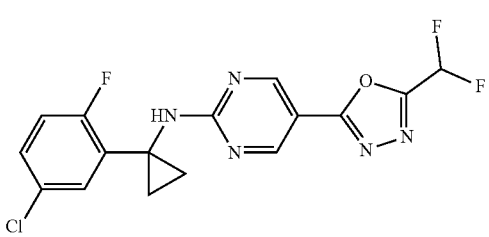

Example 76 was prepared in a manner analogous to the synthetic process used for the preparation of Example 11. $^1$H NMR (400 MHz, DMSO-d$_6$) δ 9.07 (s, 1H), 8.91 (s, 1H), 8.85 (s, 1H), 7.67-7.59 (m, 1H), 7.52 (t, J=51.2 Hz, 1H), 7.35-7.31 (m, 1H), 7.18 (dd, J=10.4, 8.7 Hz, 1H), 1.38-1.26 (m, 2H), 1.26-1.15 (m, 2H).

Example 77

N-(1-(2-chloro-3-methylphenyl)cyclopropyl)-5-(5-(difluoromethyl)-1,3,4-oxadiazol-2-yl)pyrimidin-2-amine (77)

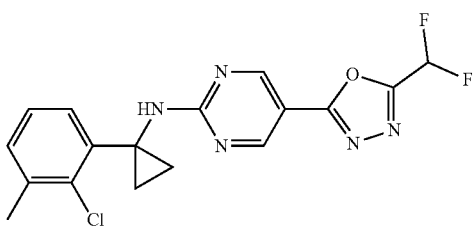

Example 77 was prepared in a manner analogous to the synthetic process used for the preparation of Example 11. $^1$H NMR (400 MHz, DMSO-d$_6$) δ 8.90-8.78 (m, 3H), 7.71-7.61 (m, 1H), 7.51 (t, J=51.4 Hz, 1H), 7.25-7.11 (m, 2H), 2.31 (s, 3H), 1.30-1.14 (m, 4H).

Examples 78(+) and 78(−)

N-(2-((5-(5-(difluoromethyl)-1,3,4-oxadiazol-2-yl)pyrimidin-2-yl)amino)-2-(4-fluorophenyl)ethyl)acetamide (78(+) and 78(−))

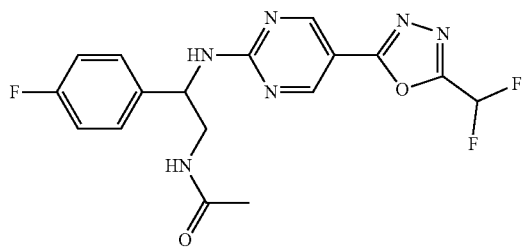

Example 78 was prepared in a manner analogous to the synthetic processes (and respective appropriate reagents and intermediates) used for the preparation of other compounds exemplified herein.

Chiral Preparative SFC Details for 78(+) and 78(−)

The enantiomers were separated by supercritical fluid chromatography (Chiralpak IG, 250×30 mm, 5; Mobile Phase: A—CO$_2$; B—0.1% NH$_3$ in Methanol; Gradient Elution 25-30% B, 1 min, 30-35% B, 2 min, 35% hold 8 min, 35-50% in 4 min; Flow rate: 80.0 mL/min) to obtain 78(+) (60 mg) and 78(−) (60 mg).

78(+): $^1$H NMR (400 MHz, DMSO-d6): δ 8.85 (d, J=17.2 Hz, 2H), 8.68 (d, J=8.8 Hz, 1H), 8.03 (t, J=5.6 Hz, 1H), 7.64-7.39 (m, 3H), 7.15 (t, J=8.8 Hz, 2H), 5.26-5.20 (m, 1H), 3.50-3.35 (m, 2H), 1.77 (s, 3H); LC-MS: m/z 393.10 [M+H]⁺; HPLC: 99.08%; C-HPLC: 100.00% (RT: 4.03); SOR: +88.72, Solvent: Methanol, Path length: 10 mm, Concentration: 0.25 w/v %.

78(−): ¹H NMR (400 MHz, DMSO-d6): δ 8.85 (d, J=17.2 Hz, 2H), 8.67 (d, J=8.4 Hz, 1H), 8.02 (t, J=5.6 Hz, 1H), 7.64-7.38 (m, 3H), 7.15 (t, J=8.8 Hz, 2H), 5.25-5.20 (m, 1H), 3.50-3.35 (m, 2H), 1.76 (s, 3H); LC-MS: m/z 393.15 [M+H]⁺; HPLC: 97.81%; C-HPLC: 99.40% (RT: 5.09); SOR: −62.00, Solvent: Methanol, Path length: 10 mm, Concentration: 0.5 w/v %.

Examples 103(+) and 103(−)

N-(2-((5-(5-(difluoromethyl)-1,3,4-oxadiazol-2-yl)pyrimidin-2-yl)amino)-2-(2,4-difluorophenyl)ethyl)methanesulfonamide (103)

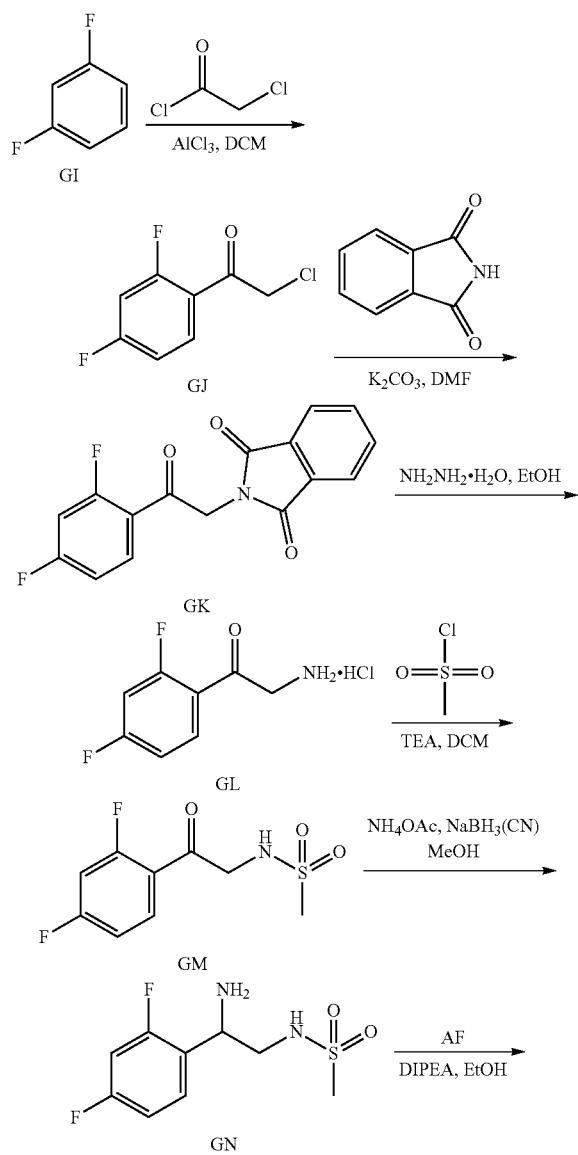

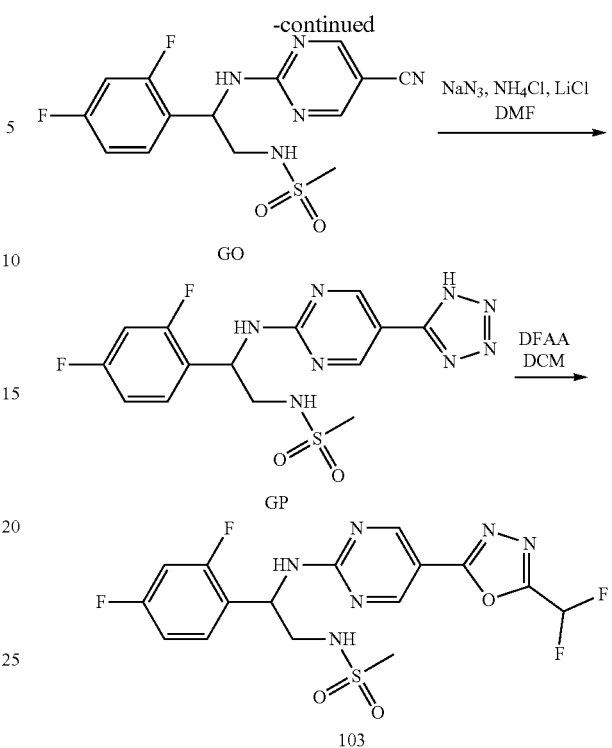

2-chloro-1-(2,4-difluorophenyl)ethan-1-one (GJ)

To a stirred solution of AlCl₃ (14.8 g, 131.4 mmol) in DCM (100 mL) was added 2-chloroacetyl chloride (23.3 g, 175.2 mmol) at 0° C. and stirred at RT for 1 h. To the resulting reaction mixture, a solution of 1,3-difluorobenzene (GI, 10.0 g, 87.6 mmol) in DCM (20 mL) was added dropwise at 0° C. and stirred at RT for 2 h. The progress of the reaction was monitored by TLC. After completion of the reaction, the reaction mixture was quenched with 1N HCl solution, neutralized with 2N NaOH solution and extracted with DCM. The combined organic layer was washed with brine, dried over anhydrous Na₂SO₄ and concentrated under reduced pressure. The crude product was purified by silica gel column chromatography using 10% EtOAc/hexane to afford compound GJ (14.1 g, 84.5%) as an off-white solid. ¹H NMR (400 MHz, CDCl₃): δ 8.08-8.02 (m, 1H), 7.06-7.01 (m, 1H), 6.96-6.91 (m, 1H), 4.71 (s, 2H).

2-(2-(2,4-difluorophenyl)-2-oxoethyl)isoindoline-1,3-dione (GK)

To a stirred solution of phthalimide (12.0 g, 81.0 mmol) in DMF (30 mL) was added K₂CO₃ (20.3 g, 147.2 mmol) and the reaction mixture was stirred at RT for 15 min. To the resulting reaction mixture, a solution of compound GJ (14.0 g, 73.6 mmol) in DMF (20 mL) was added and the reaction mixture was stirred at RT for 16 h. The progress of reaction was monitored by TLC. After completion of the reaction, the reaction mixture was poured into crushed ice. The solid precipitate was filtered and then washed with water followed by hexane. The solid was dried under high vacuum to yield compound GK (9.5 g, 43.0%) as an off-white solid. ¹H NMR (400 MHz, DMSO-d6): δ 8.07-8.01 (m, 1H), 7.97-7.89 (m, 4H), 7.57-7.51 (m, 1H), 7.33-7.28 (m, 1H), 5.06 (s, 2H); LC-MS: m/z 302.0 [M+H]⁺.

2-amino-1-(2,4-difluorophenyl)ethan-1-one hydrochloride (GL)

To a stirred solution of compound GK (9.5 g, 31.56 mmol) in EtOH (250 mL) was added hydrazine hydrate (41.0 g, 63.12 mmol) and the reaction mixture was stirred at 90° C. for 1 h. The reaction mixture was concentrated under reduced pressure. To the crude residue was added 2N HCl and the resulting solution was heated to 50° C. for 15 min and then stirred at RT for 30 min. The resulting precipitate was filtered and the filtrate was concentrated under reduced pressure to yield crude compound which was washed with diethyl ether and pentane and dried under vacuum to afford compound GL (6.1 g, 94.0%) as a brown solid. $^1$H NMR (400 MHz, DMSO-d6): δ 11.18 (s, 1H), 8.51 (brs, 2H), 8.11-8.05 (m, 1H), 7.57-7.51 (m, 1H), 7.35-7.29 (m, 1H), 4.39 (s, 2H); LC-MS: m/z 171.95 [M+H]$^+$.

N-(2-(2,4-difluorophenyl)-2-oxoethyl)methanesulfonamide (GM)

To a stirred solution of compound GL (6.0 g, 29.13 mmol) in DCM (100 mL) was added triethylamine (12.7 mL, 87.38 mmol) and mesyl chloride (5.0 g, 43.69 mmol) at 0° C. and the reaction mixture was stirred at 0° C. for 30 min. The progress of the reaction was monitored by TLC. After completion of the reaction, the reaction mixture was quenched with saturated NaHCO$_3$ solution. The organic layer was separated, dried over anhydrous Na$_2$SO$_4$ and concentrated under reduced pressure. The crude product was purified by silica gel column chromatography using 18-20% EtOAc/hexane to afford compound GM (1.1 g, 15.0%) as an off-white solid. $^1$H NMR (400 MHz, CDCl$_3$): δ 8.12-8.06 (m, 1H), 7.08-7.01 (m, 1H), 6.99-6.97 (m, 1H), 5.32 (brs, 1H), 4.60-4.58 (m, 2H), 3.03 (s, 3H).

N-(2-amino-2-(2,4-difluorophenyl)ethyl)methanesulfonamide (GN)

To a stirred solution of compound GM (1.1 g, 4.41 mmol) in MeOH (50 mL) was added ammonium acetate (6.81 g, 8.83 mmol) and the reaction mixture was stirred at RT for 30 min. To the resulting reaction mixture, NaBH$_3$CN (0.75 g, 11.9 mmol) was added and the reaction mixture was stirred at 80° C. for 16 h. After completion of the reaction, the reaction mixture was concentrated under reduced pressure. The residue was dissolved with EtOAc and washed with a saturated NaHCO$_3$ solution. The organic layer was separated, dried over anhydrous Na$_2$SO$_4$, and concentrated under reduced pressure to afford compound GN (1.0 g, 90.0%) as a light brown semi solid. LC-MS: m/z 251.0 [M+H]$^+$.

N-(2-((5-cyanopyrimidin-2-yl)amino)-2-(2,4-difluorophenyl)ethyl)methanesulfonamide (GO)

To a stirred solution of compound GN (1.0 g, 4.00 mmol) and 2-chloropyrimidine-5-carbonitrile (AF, 0.56 g, 4.00 mmol) in EtOH (40 mL) was added DIPEA (2.0 mL, 12.0 mmol) and the reaction mixture was stirred at 90° C. for 16 h. The progress of reaction was monitored by TLC. After completion of the reaction, the reaction mixture was concentrated under reduced pressure. The crude residue was dissolved in EtOAc and washed with water and brine. The organic layer was dried over anhydrous Na$_2$SO$_4$ and concentrated under reduced pressure. The crude product was purified by silica gel column chromatography using 7.5-8% EtOAc/hexane to afford compound GO (0.4 g, 29.0%) as an off-white solid. $^1$H NMR (400 MHz, CDCl$_3$): δ 8.52 (brs, 2H), 7.38-7.32 (m, 1H), 6.90-6.86 (m, 2H), 6.68-6.66 (m, 1H), 5.51-5.46 (m, 1H), 4.59-4.56 (m, 1H), 3.62 (t, J=6.4 Hz, 2H), 2.98 (s, 3H); LC-MS: m/z 354.05 [M+H]$^+$.

N-(2-((5-(1H-tetrazol-5-yl)pyrimidin-2-yl)amino)-2-(2,4-difluorophenyl)ethyl)methanesulfonamide (GP)

To a stirred solution of compound GO (0.4 g, 1.13 mmol) in DMF (15 mL) was added NaN$_3$ (0.37 g, 5.66 mmol), NH$_4$Cl (0.31 g, 5.66 mmol) followed by LiCl (0.095 g) and the reaction mixture was stirred at 100° C. for 16 h. The progress of the reaction was monitored by TLC. After completion of the reaction, the reaction mixture was concentrated under reduced pressure. The residue was quenched with ice water and acidified with 6N HCl solution to pH 4 and extracted with EtOAc. The combined organic layer was washed with brine, dried over anhydrous Na$_2$SO$_4$ and concentrated under reduced pressure to afford compound GP (0.41 g, crude) as an off-white solid. LC-MS: m/z 397.05 [M+H]$^+$.

N-(2-((5-(5-(difluoromethyl)-1,3,4-oxadiazol-2-yl)pyrimidin-2-yl)amino)-2-(2,4-difluorophenyl)ethyl)methanesulfonamide (103)

To a stirred solution of compound GP (0.4 g, 1.01 mmol) in DCM (15 mL) was added DFAA (0.17 mL, 1.5 mmol) at 0° C. and the reaction was stirred at RT for 16 h. The progress of reaction was monitored by TLC. After completion of the reaction, the reaction mixture was quenched with water and the product was extracted with DCM. The combined organic layer was washed with brine, dried over anhydrous Na$_2$SO$_4$ and concentrated under reduced pressure. The crude compound was purified by silica gel column chromatography using 8-10% EtOAc/hexane to afford racemic 103 (0.25 g, 55.5%) as an off-white solid.

Chiral Preparative HPLC Details for 103(+) and 103(−)

The enantiomers were separated by normal-phase preparative high performance liquid chromatography (Chiralpak IA, 250×30 mm, 5; Mobile Phase: A; n-Hexane+0.1% DEA/B; DCM:MeOH (1:1); Isocratic Elution 28% B; Flow rate: 30.0 mL/min) to obtain 103(+) (50 mg) and 103(−) (50 mg).

103(+): $^1$H NMR (400 MHz, DMSO-d6): δ 8.89 (d, J=11.2 Hz, 2H), 8.70 (d, J=8.8 Hz, 1H), 7.65-7.39 (m, 2H), 7.34 (brs, 1H), 7.26-7.20 (m, 1H), 7.12-7.08 (m, 1H), 5.56-5.50 (m, 1H), 3.37-3.30 (m, 2H), 2.86 (s, 3H); LC-MS: m/z 447.15 [M+H]$^+$; C-HPLC: 98.13%; SOR: +21.04, Solvent: Methanol, Path length: 10 mm, Concentration: 0.5 w/v %.

103(−): $^1$H NMR (400 MHz, DMSO-d6): δ 8.89 (d, J=11.6 Hz, 2H), 8.69 (brs, 1H), 7.65-7.39 (m, 2H), 7.34 (brs, 1H), 7.26-7.20 (m, 1H), 7.12-7.07 (m, 1H), 5.52 (brs, 1H), 3.40-3.30 (m, 2H), 2.86 (s, 3H); LC-MS: m/z 447.15 [M+H]$^+$; C-HPLC: 100%; SOR: −63.88, Solvent: Methanol, Path length: 10 mm, Concentration: 0.5 w/v %.

Example 108

N-(2-((5-(5-(difluoromethyl)-1,3,4-oxadiazol-2-yl)pyrimidin-2-yl)amino)-2-(4-fluorophenyl)ethyl)ethanesulfonamide (108)

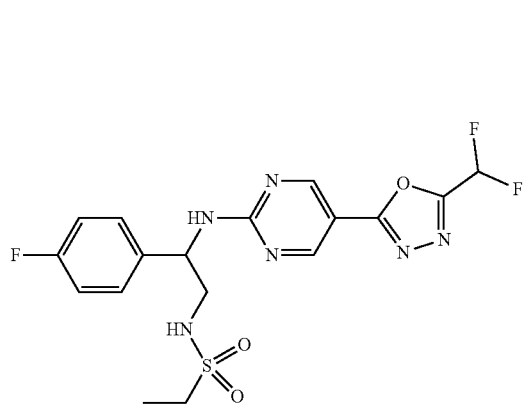

Example 108 was prepared in a manner analogous to the synthetic process used for the preparation of Example 38. $^1$H NMR (400 MHz, DMSO-d$_6$) δ 8.88 (s, 1H), 8.86 (s, 1H), 8.67 (d, J=8.4 HZ, 1H), 7.64-7.38 (m, 3H), 7.28 (s, 1H), 7.17 (t, J=8.8 Hz, 2H), 5.27-5.25 (m, 1H), 3.36 (br, 1H), 2.95-2.92 (m, 2H), 1.08 (t, J=7.4 Hz, 3H).

Example 109

N-(2-((5-(5-(difluoromethyl)-1,3,4-oxadiazol-2-yl)pyrimidin-2-yl)amino)-2-(4-fluorophenyl)ethyl)propane-2-sulfonamide (109)

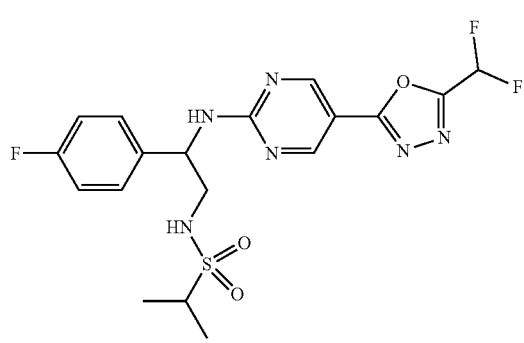

Example 109 was prepared in a manner analogous to the synthetic process used for the preparation of Example 38: $^1$H NMR (400 MHz, DMSO-d$_6$) δ 8.88 (s, 1H), 8.86 (s, 1H), 8.66 (d, J=8.8 HZ, 1H), 7.64-7.38 (m, 3H), 7.27-7.25 (m, 1H), 7.16 (t, J=8.6 Hz, 2H), 5.26-5.22 (m, 1H), 3.42-3.37 (m, 1H), 3.12-3.09 (m, 1H), 1.14-1.12 (m, 6H).

Example 110

N-(2-((5-(5-(difluoromethyl)-1,3,4-oxadiazol-2-yl)pyrimidin-2-yl)amino)-2-(4-fluorophenyl)ethyl)cyclopropanesulfonamide (110)

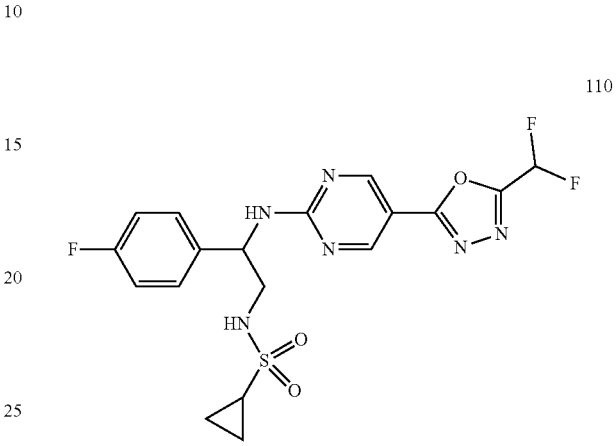

Example 110 was prepared in a manner analogous to the synthetic process used for the preparation of Example 38: $^1$H NMR (400 MHz, DMSO-d$_6$) δ 8.88 (s, 1H), 8.86 (s, 1H), 8.68 (d, J=8.8 HZ, 1H), 7.64-7.30 (m, 4H), 7.17 (t, J=8.8 Hz, 2H), 5.32-5.27 (m, 1H), 3.45-3.40 (m, 1H), 3.36 (t, J=6.6 Hz, 1H), 0.89-0.87 (m, 4H).

Example 111

N-(2-((5-(5-(difluoromethyl)-1,3,4-oxadiazol-2-yl)pyrimidin-2-yl)amino)-2-(4-fluorophenyl)ethyl)propane-1-sulfonamide (111)

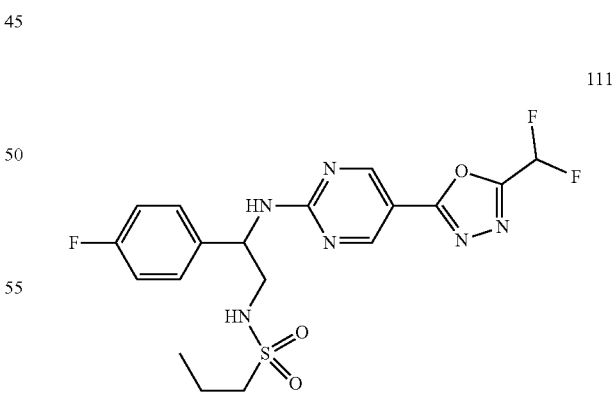

Example 111 was prepared in a manner analogous to the synthetic process used for the preparation of Example 38: $^1$H NMR (400 MHz, DMSO-d$_6$) δ 8.88 (s, 1H), 8.86 (s, 1H), 8.68 (d, J=8.8 HZ, 1H), 7.64-7.39 (m, 3H), 7.28 (br, 1H), 7.17 (t, J=8.6 Hz, 2H), 5.28-5.22 (m, 1H), 3.38-3.36 (m, 1H), 2.93-2.782 (m, 2H), 1.59-1.52 (m, 2H), 0.88 (t, J=7.4 Hz, 3H).

Example 112

N-(2-((5-(5-(difluoromethyl)-1,3,4-oxadiazol-2-yl)pyrimidin-2-yl)amino)-2-(4-fluorophenyl)ethyl)-2-methylpropane-1-sulfonamide (112)

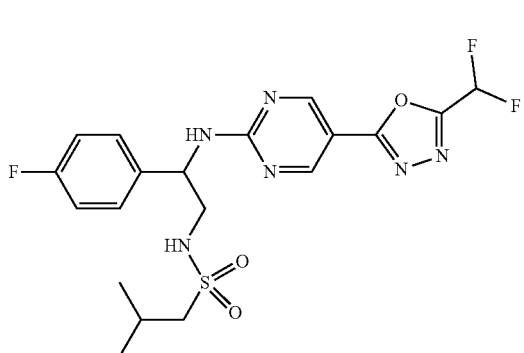

112

Example 112 was prepared in a manner analogous to the synthetic process used for the preparation of Example 38: $^1$H NMR (400 MHz, DMSO-$d_6$) δ 8.88 (s, 1H), 8.86 (s, 1H), 8.67 (d, J=8.8 HZ, 1H), 7.64-7.38 (m, 3H), 7.27 (t, J=5.8 Hz, 1H), 7.17 (t, J=9.0 Hz, 2H), 5.26-5.24 (m, 1H), 3.39-3.35 (m, 1H), 2.80-2.78 (m, 2H), 2.01-1.98 (m, 1H), 0.94 (dd, J=6.6, 1.0 HZ, 6H).

Example 113(+)

N-(2-((5-(5-(difluoromethyl)-1,3,4-oxadiazol-2-yl)pyrimidin-2-yl)amino)-2-(4-fluorophenyl)ethyl)-N-methylmethanesulfonamide (113(+))

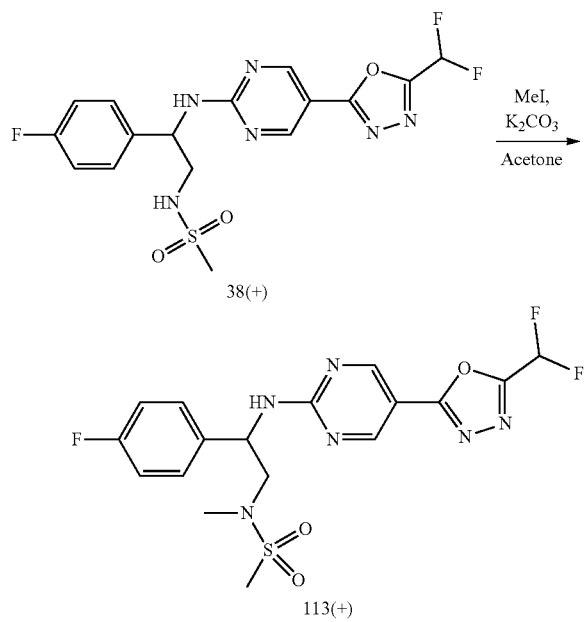

N-(2-((5-(5-(difluoromethyl)-1,3,4-oxadiazol-2-yl)pyrimidin-2-yl)amino)-2-(4-fluorophenyl)ethyl)-N-methylmethanesulfonamide (113(+))

To a stirred solution of 38(+) (0.1 g, 0.23 mmol) in acetone (10 mL) was added dry $K_2CO_3$ (0.096 g, 0.70 mmol) and the reaction was stirred at RT for 10 min. The reaction mixture was cooled to 0° C. and methyl iodide (0.132 g, 0.93 mmol) was added. The reaction mixture was allowed to stir at RT for 6 h and the reaction progress was monitored by TLC. After completion of the reaction, the reaction mixture was filtered through celite and washed with acetone. The filtrate was evaporated under reduced pressure. The crude compound was purified by silica gel column chromatography using 35% EtOAc/hexane to afford 113(+) (0.056 g, 54.0%) as an off white solid. $^1$H NMR (400 MHz, DMSO-d6): δ 8.88 (d, J=6.8 Hz, 2H), 8.73 (d, J=8.8 Hz, 1H), 7.65-7.39 (m, 3H), 7.19 (t, J=9.2 Hz, 2H), 5.46-5.40 (m, 1H), 3.50-3.44 (m, 2H), 2.84 (s, 3H), 2.79 (s, 3H); LC-MS: m/z 443.15 [M+H]$^+$; C-HPLC: 99.61% (RT: 7.22); SOR: +90.21, Solvent: Methanol, Path length: 10 mm, Concentration: 0.605 w/v %

Examples 115(+) and 115(−)

N-(2-(4-(difluoromethoxy)phenyl)-2-((5-(5-(difluoromethyl)-1,3,4-oxadiazol-2-yl)pyrimidin-2-yl)amino)ethyl)methanesulfonamide (115)

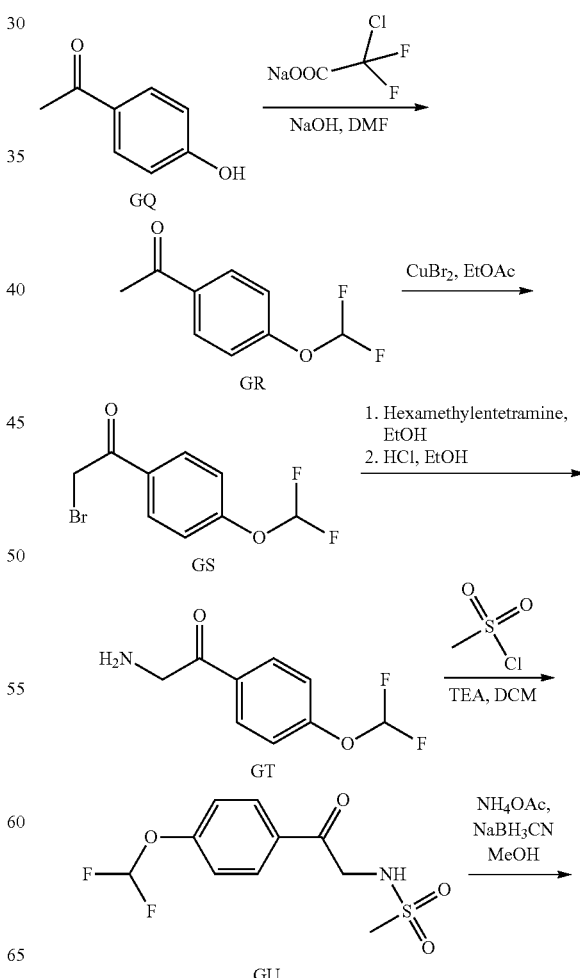

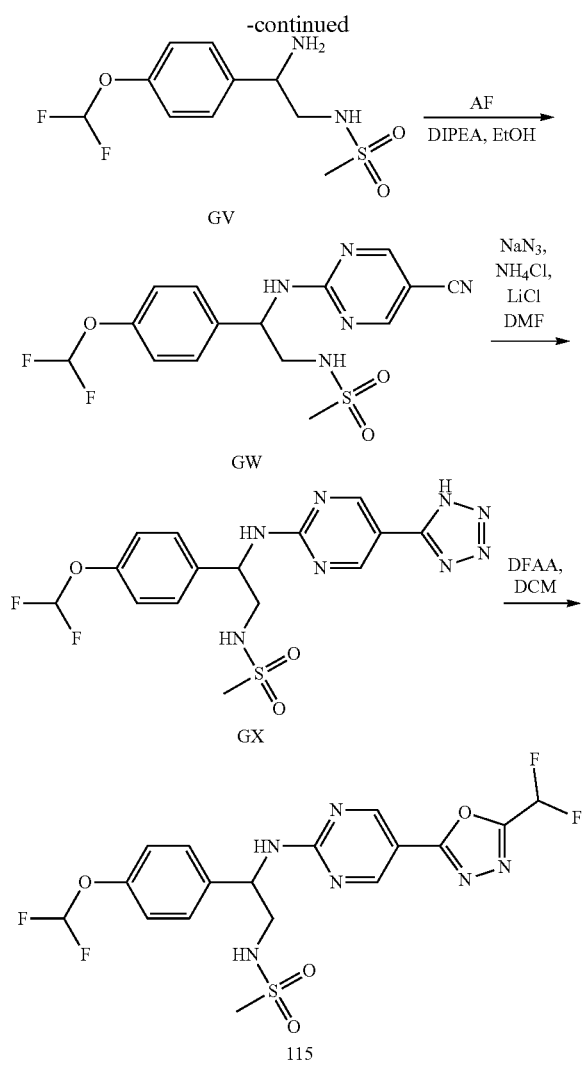

1-(4-(difluoromethoxy)phenyl)ethan-1-one (3)

To a stirred solution of 4-hydroxyacetophenone (GQ, 5.0 g, 36.76 mmol) in DMF (50 mL) was added sodium 2-chloro-2,2-difluoroacetate (6.2 g, 40.44 mmol) followed by NaOH (1.76 g, 44.11 mmol) and the reaction mixture was stirred at 100° C. for 14 h. After completion of the reaction, the reaction mixture was diluted with cold water and the product was extracted with EtOAc. The combined organic layer was dried over anhydrous $Na_2SO_4$ and concentrated under reduced pressure. The crude product was purified by silica gel column chromatography using 20-30% EtOAc/hexane to afford compound GR (3.5 g, 51.0%) as a colorless liquid. $^1H$ NMR (400 MHz, DMSO-d6): δ 8.05-8.01 (m, 2H), 7.59-7.22 (m, 3H), 2.50 (s, 3H); LC-MS: m/z 187.0 $[M+H]^+$.

2-bromo-1-(4-(difluoromethoxy)phenyl)ethan-1-one (GS)

To a stirred solution of compound GR (3.5 g, 18.81 mmol) in ethyl acetate (100 mL) was added copper(II) bromide (4.6 g, 20.69 mmol) and the reaction mixture was stirred at RT for 24 h under $N_2$ atmosphere. The progress of the reaction was monitored by TLC. After completion of the reaction, the reaction mixture was filtered through celite. The filtrate was concentrated under reduced pressure. The crude compound was purified by silica gel column chromatography using 10-20% DCM/hexane to afford compound GS (3.0 g, 61.0%) as a white solid. $^1H$ NMR (400 MHz, DMSO-d6): δ 8.08 (d, J=8.8 Hz, 2H), 7.62-7.25 (m, 3H), 4.92 (s, 2H).

2-amino-1-(4-(difluoromethoxy)phenyl)ethan-1-one (GT)

To a stirred solution of compound GS (4.0 g, 15.15 mmol) in EtOH (100 mL) was added hexamethylenetetramine (3.2 g, 22.72 mmol) and the reaction mixture was stirred at RT for 2 h. The reaction mixture was cooled to 0° C., concentrated HCl (4 mL) was added and the reaction was stirred at RT for 24 h. After completion of the reaction, the reaction mixture was concentrated under reduced pressure to afford compound GT (6 g) as an off white solid which was used as such for the next step. LC-MS: m/z 201.95 $[M+H]^+$.

N-(2-(4-(difluoromethoxy)phenyl)-2-oxoethyl)methanesulfonamide (GU)

To a stirred solution of compound GT (6.0 g, 29.85 mmol) in DCM (100 mL) was added triethylamine (8.4 mL, 59.70 mmol) and the reaction mixture was stirred at RT for 30 min. To the reaction mixture, mesyl chloride (3.6 mL, 44.71 mmol) was added at 0° C. and the reaction mixture was stirred at RT for 4 h. The progress of the reaction was monitored by TLC. After completion of the reaction, the reaction mixture was quenched with water and the product was extracted with DCM. The combined organic layer was dried over anhydrous $Na_2SO_4$ and concentrated under reduced pressure. The crude product was purified by silica gel column chromatography using 2% MeOH/DCM to afford compound GU (0.8 g, 9.5%) as an off white solid which was used for the next step without further purification.

N-(2-amino-2-(4-(difluoromethoxy)phenyl)ethyl)methanesulfonamide (GV)

To a stirred solution of compound GU (0.8 g, 2.86 mmol) in MeOH (100 mL) was added ammonium acetate (4.4 g, 57.34 mmol) and the reaction mixture was stirred at RT for 30 min. To the resulting reaction mixture, $NaBH_3CN$ (0.49 g, 7.74 mmol) was added and the reaction mixture was stirred at 80° C. for 12 h. After completion of the reaction, the reaction mixture was concentrated under reduced pressure. The residue was diluted with water and the product was extracted with 10% MeOH-DCM. The combined organic layer was dried over anhydrous $Na_2SO_4$ and concentrated under reduced pressure to afford compound GV (0.5 g, 62.5%) as a colorless semi solid which was used for the next reaction without further purification.

N-(2-((5-cyanopyrimidin-2-yl)amino)-2-(4-(difluoromethoxy)phenyl)ethyl)methanesulfonamide (GW)

To a stirred solution of compound GV (0.5 g, 1.78 mmol) and 2-chloropyrimidine-5-carbonitrile (AF, 0.37 g, 2.67 mmol) in EtOH (20 mL) was added DIPEA (0.96 mL, 5.35 mmol) and the reaction mixture was stirred at 90° C. for 14 h. The progress of the reaction was monitored by TLC. After completion of the reaction, the reaction mixture was concentrated under reduced pressure. The crude product was purified by silica gel column chromatography using 2%

MeOH/DCM to afford compound GW (0.35 g, 51.0%) as an off white solid. ¹H NMR (400 MHz, DMSO-d6): δ 8.80 (d, J=8.4 Hz, 1H), 8.69 (s, 2H), 7.46-7.39 (m, 2H), 7.38-7.14 (m, 4H), 5.23-5.18 (m, 1H), 3.41-3.37 (m, 1H), 3.30-3.25 (m, 1H), 2.83 (s, 3H); LC-MS: m/z 384.05 [M+H]⁺.

N-(2-((5-(1H-tetrazol-5-yl)pyrimidin-2-yl)amino)-2-(2,4-difluorophenyl)ethyl)methanesulfonamide (GX)

To a stirred solution of compound GW (0.35 g, 0.91 mmol) in DMF (15 mL) was added NaN₃ (0.18 g, 2.74 mmol), NH₄Cl (0.15 g, 2.74 mmol) followed by LiCl (0.038 g, 0.91 mmol) and the reaction mixture was stirred at 100° C. for 14 h. The progress of the reaction was monitored by TLC. After completion of the reaction, the reaction mixture was concentrated under reduced pressure. The residue was quenched with ice water and acidified with 6N HCl solution to pH 4. The precipitate was filtered and dried under vacuum to afford compound GX (0.32 g, 82.0%) as a light brown sticky solid. ¹H NMR (400 MHz, DMSO-d6): δ 8.85 (brs, 2H), 8.37 (d, J=8.4 Hz, 1H), 7.49-7.01 (m, 7H), 5.32-5.18 (m, 1H), 3.39-3.32 (m, 2H), 2.83 (s, 3H); LC-MS: m/z 427.05 [M+H]⁺.

N-(2-(4-(difluoromethoxy)phenyl)-2-((5-(5-(difluoromethyl)-1,3,4-oxadiazol-2-yl)pyrimidin-2-yl)amino)ethyl)methanesulfonamide (115)

To a stirred solution of compound GX (0.32 g, 0.75 mmol) in DCM (30 mL) was added DFAA (0.17 mL, 1.5 mmol) at 0° C. and the reaction was stirred at RT for 8 h. The progress of the reaction was monitored by TLC. After completion of the reaction, the reaction mixture was quenched with water and the product was extracted with DCM. The combined organic layer was washed with brine, dried over anhydrous Na₂SO₄ and concentrated under reduced pressure. The crude compound which was purified by silica gel column chromatography using 1-2% MeOH/DCM to afford racemic 115 (0.2 g, 56.0%).

Chiral Preparative HPLC Details for 115(+) and 115(−)

The enantiomers were separated by normal-phase preparative high performance liquid chromatography (Chiralpak IA, 250×30 mm, 5; Mobile Phase: A; n-Hexane+0.1% DEA/B; DCM:MeOH (1:1); Isocratic Elution 35% B; Flow rate: 30.0 mL/min) to obtain 115(+) (40 mg) and 115(−) (25 mg).

115(+): ¹H NMR (400 MHz, DMSO-d6): δ 8.87 (d, J=11.2 Hz, 2H), 8.70 (d, J=8.8 Hz, 1H), 7.64-7.39 (m, 3H), 7.38-7.01 (m, 4H), 5.30-5.24 (m, 1H), 3.43-3.37 (m, 1H), 2.84 (s, 3H), one proton merged in solvent peak; LC-MS: m/z 477.20 [M+H]⁺. C-HPLC: 99.56% (RT: 9.47); SOR: +98.06, Solvent: Methanol, Path length: 10 mm, Concentration: 0.537 w/v %.

115(−): ¹H NMR (400 MHz, DMSO-d6): δ 8.86 (d, J=12 Hz, 2H), 8.70 (d, J=9.2 Hz, 1H), 7.63-7.00 (m, 7H), 5.28-5.23 (m, 1H), 3.38-3.36 (m, 1H), 2.83 (s, 3H), one proton merged in solvent peak; LC-MS: m/z 477.10 [M+H]⁺. C-HPLC: 97.18% (RT: 10.90), SOR: −78.50, Solvent: Methanol, Path length: 10 mm, Concentration: 0.534 w/v %.

Examples 116(+) and 116(−)

N-(2-(4-(difluoromethoxy)-2-fluorophenyl)-2-((5-(5-(difluoromethyl)-1,3,4-oxadiazol-2-yl)pyrimidin-2-yl)amino)ethyl)methanesulfonamide (116(+) and 116(−))

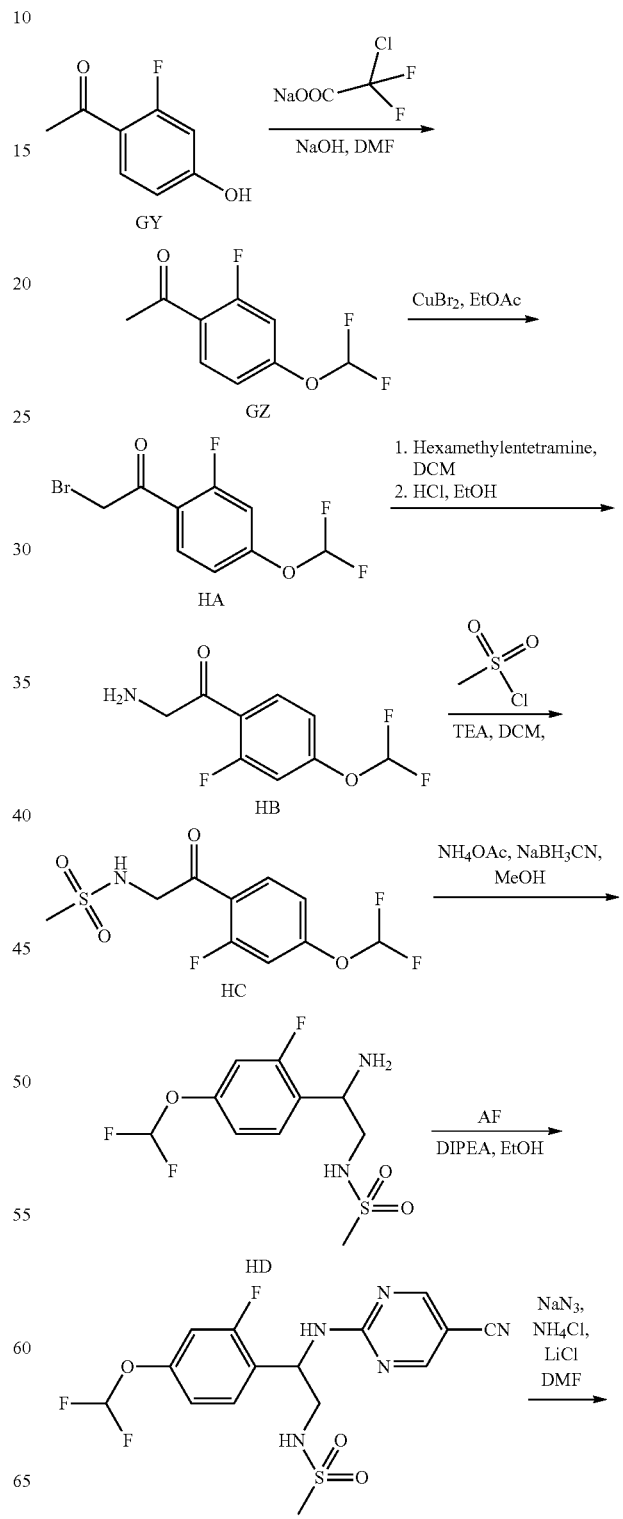

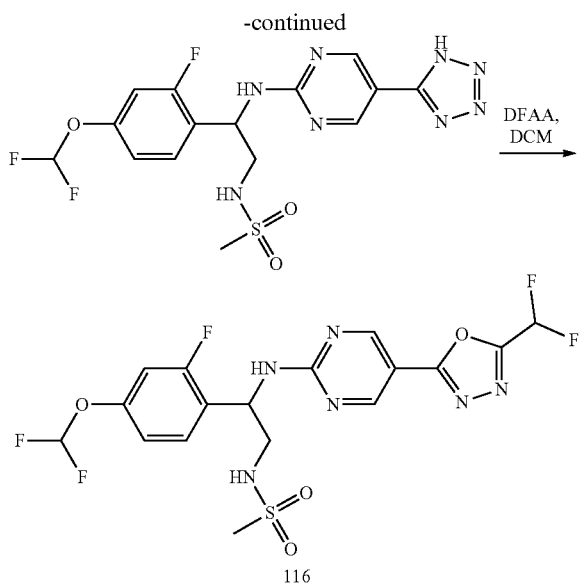

1-(4-(difluoromethoxy)-2-fluorophenyl)ethan-1-one (GZ)

To a stirred solution of 2'-fluoro-4'-hydroxyacetophenone (GY, 5.0 g, 32.46 mmol) in DMF (50 mL) was added sodium 2-chloro-2,2-difluoroacetate (5.94 g, 38.96 mmol) followed by NaOH (1.55 g, 38.96 mmol) and the reaction mixture was stirred at 110° C. for 12 h. After completion of the reaction, the reaction mixture was diluted with cold water and the product was extracted with EtOAc. The combined organic layer was dried over anhydrous $Na_2SO_4$ and concentrated under reduced pressure. The crude product was purified by silica gel column chromatography using 20-30% EtOAc/hexane to afford compound GZ (3.0 g, 45.0%) as a colorless liquid. $^1$H NMR (400 MHz, DMSO-d6): δ 7.91 (t, J=8.6 Hz, 1H), 7.62-7.25 (m, 2H), 7.14 (dd, J=2.4 Hz, 8.8 Hz, 1H), 2.56 (d, J=4.4 Hz, 3H); LC-MS: m/z 204.85 [M+H]$^+$.

2-bromo-1-(4-(difluoromethoxy)-2-fluorophenyl)ethan-1-one (HA)

To a stirred solution of GZ (3.0 g, 14.70 mmol) in ethyl acetate (60 mL) was added copper(II) bromide (3.93 g, 17.64 mmol) and the reaction mixture was stirred at RT for 24 h under $N_2$ atmosphere. The progress of the reaction was monitored by TLC. After completion of the reaction, the reaction mixture was filtered through celite. The filtrate was concentrated under reduced pressure. The crude compound was purified by silica gel column chromatography using 20-30% EtOAc/hexane to afford compound HA (2.3 g, 55.0%) as a colorless liquid. $^1$H NMR (400 MHz, DMSO-d6): δ 8.00 (t, J=8.8 Hz, 1H), 7.65-7.29 (m, 2H), 7.18 (dd, J=2.4 Hz, 8.8 Hz, 1H), 4.82 (d, J=1.6 Hz, 2H).

2-amino-1-(4-(difluoromethoxy)-2-fluorophenyl)ethan-1-one (HB)

To a stirred solution of compound HA (3.6 g, 12.7 mmol) in EtOH (50 mL) was added hexamethylenetetramine (2.7 g, 19.08 mmol) and the reaction mixture was stirred at RT for 2 h. To the resulting reaction mixture, concentrated HCl (3 mL) was added at 0° C. and stirred at RT for 24 h. After completion of the reaction, the reaction mixture was concentrated under reduced pressure to afford compound HB (4.0 g, crude) as an off-white solid which was used as such for the next reaction. LC-MS: m/z 220.05 [M+H]$^+$.

N-(2-(4-(difluoromethoxy)-2-fluorophenyl)-2-oxoethyl)methanesulfonamide (HC)

To a stirred solution of compound HB (4.0 g, 14.13 mmol) in DCM (100 mL) was added triethylamine (5.9 mL, 42.40 mmol) and the reaction mixture was stirred at RT for 30 min. To the resulting reaction mixture, mesyl chloride (2.4 g, 21.20 mmol) was added at 0° C. and the reaction mixture was stirred at RT for 4 h. The progress of the reaction was monitored by TLC. After completion of the reaction, the reaction mixture was quenched with water and the product was extracted with DCM. The combined organic layer was dried over anhydrous $Na_2SO_4$ and concentrated under reduced pressure. The crude product was purified by silica gel column chromatography using 30% EtOAc/hexane to afford compound HC (2.0 g, 47.5%) as an off white solid. $^1$H NMR (400 MHz, DMSO-d6): δ 7.98 (d, J=8.6 Hz, 1H), 7.65-7.28 (m, 3H), 7.18 (d, J=8.8 Hz, 1H), 4.46 (brs, 2H), 2.96 (s, 3H); LC-MS: m/z 297.90 [M+H]$^+$.

N-(2-amino-2-(4-(difluoromethoxy)-2-fluorophenyl)ethyl)methanesulfonamide (HD)

To a stirred solution of compound HC (1.0 g, 3.36 mmol) in MeOH (50 mL) was added ammonium acetate (5.2 g, 67.34 mmol) and the reaction mixture was stirred at RT for 30 min. Then $NaBH_3CN$ (0.58 g, 9.10 mmol) was added and the reaction mixture was stirred at 80° C. for 12 h. After completion of the reaction, the reaction mixture was concentrated under reduced pressure. The residue was diluted with water and the product was extracted with 10% MeOH/DCM. The combined organic layer was dried over anhydrous $Na_2SO_4$ and concentrated under reduced pressure to afford compound HD (1.0 g, crude) as a colorless sticky solid. LC-MS: m/z 299.00 [M+H]$^+$.

N-(2-((5-cyanopyrimidin-2-yl)amino)-2-(4-(difluoromethoxy)-2-fluorophenyl)ethyl)methanesulfonamide (HE)

To a stirred solution of compound HD (1.0 g, 3.35 mmol) and 2-chloropyrimidine-5-carbonitrile (AF, 0.46 g, 3.35 mmol) in EtOH (25 mL) was added DIPEA (1.8 mL, 10.06 mmol) and the reaction mixture was stirred at 90° C. for 14 h. The progress of the reaction was monitored by TLC. After completion of the reaction, the reaction mixture was concentrated under reduced pressure to yield crude product which was purified by silica gel column chromatography using 40-50% EtOAc/hexane to afford compound HE (0.55 g, 41.0%) as an off-white solid. $^1$H NMR (400 MHz, DMSO-d6): δ 8.79 (d, J=8.8 Hz, 1H), 8.71 (s, 2H), 7.56-6.81 (m, 7H), 5.49-5.44 (m, 1H), 2.86 (s, 3H); LC-MS: m/z 402.10 [M+H]$^+$.

N-(2-((5-(1H-tetrazol-5-yl)pyrimidin-2-yl)amino)-2-(4-(difluoromethoxy)-2-fluorophenyl)ethyl)methanesulfonamide (HF)

To a stirred solution of compound HE (0.55 g, 1.37 mmol) in DMF (20 mL) was added $NaN_3$ (0.27 g, 4.11 mmol) and $NH_4Cl$ (0.22 g, 4.11 mmol) followed by LiCl (0.057 g, 1.37 mmol) and the reaction mixture was stirred at 100° C. for 14 h. Progress of the reaction was monitored by TLC. After completion of the reaction, the reaction mixture was concentrated under reduced pressure. The residue was quenched with ice water and acidified with 6N HCl solution to pH 4. The precipitate was filtered and dried under vacuum to afford compound HF (0.6 g, crude) as a light brown semi solid. $^1$H NMR (400 MHz, DMSO-d6): δ 8.86-8.83 (m, 2H), 8.40 (d, J=8.8 Hz, 1H), 7.95 (s, 1H), 7.60-7.51 (m, 1H), 7.46-7.03 (m, 6H), 5.52-5.47 (m, 1H), 2.873 (s, 3H); LC-MS: m/z 445.15 [M+H]$^+$.

N-(2-(4-(difluoromethoxy)-2-fluorophenyl)-2-((5-(5-(difluoromethyl)-1,3,4-oxadiazol-2-yl)pyrimidin-2-yl)amino)ethyl)methanesulfonamide (116)

To a stirred solution of compound HF (0.6 g, 1.35 mmol) in DCM (20 mL) was added DFAA (0.29 mL, 2.70 mmol) at 0° C. and the reaction was stirred at RT for 8 h. The progress of reaction was monitored by TLC. After completion of the reaction, the reaction mixture was quenched with water and the product was extracted with DCM. The combined organic layer was washed with brine, dried over anhydrous Na$_2$SO$_4$ and concentrated under reduced pressure. The crude compound was purified by silica gel column chromatography using 5% MeOH/DCM to afford racemic 116 (0.08 g, 12.0%).

Chiral Preparative HPLC Details for 116(+) and 116(−)

The enantiomers were separated by normal-phase preparative high performance liquid chromatography (Chiralpak IA, 250×30 mm, 5; Mobile Phase: A; n-Hexane+0.1% DEA/B; DCM:MeOH (6:4); Isocratic Elution 27% B; Flow rate: 30.0 mL/min) to obtain 116(+) (40 mg) and 116(−) (40 mg).

116(+): (0.04 g, 6.0%); $^1$H NMR (400 MHz, DMSO-d6): δ 8.89 (d, J=12.0 Hz, 2H), 8.69 (d, J=8.4 Hz, 1H), 7.65-7.27 (m, 4H), 7.14-7.04 (m, 2H), 5.56-5.50 (m, 1H), 3.38-3.35 (m, 2H), 2.87 (s, 3H); LC-MS: m/z 495.15 [M+H]$^+$. C-HPLC: 98.41% (RT: 13.70), SOR: +65.99, Solvent: Methanol, Path length: 10 mm, Concentration: 0.527 w/v %.

116(−): (0.04 g, 6.0%); $^1$H NMR (400 MHz, DMSO-d6): δ 8.89 (d, J=12.8 Hz, 2H), 8.69 (d, J=8.4 Hz, 1H), 7.65-7.27 (m, 4H), 7.15-7.03 (m, 2H), 5.56-5.50 (m, 1H), 3.40-3.36 (m, 2H), 2.87 (s, 3H); LC-MS: m/z 495.15 [M+H]$^+$. HPLC: 99.47% (RT: 11.37), SOR: −93.09, Solvent: Methanol, Path length: 10 mm, Concentration: 0.518 w/v %.

Example 118(+)

N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)methanesulfonamide (118(+))

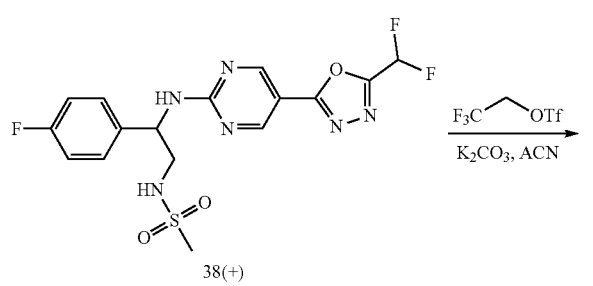

38(+)

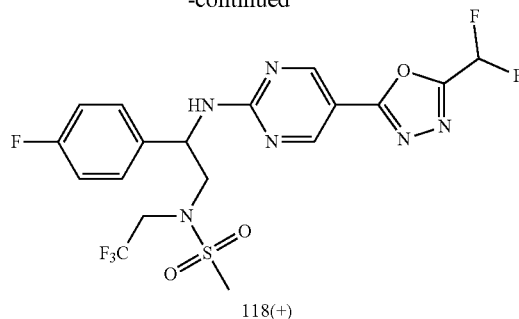

118(+)

To a stirred solution of compound 38(+) (0.1 g, 0.23 mmol) in ACN (10 mL), dry K$_2$CO$_3$ (0.1 g, 0.69 mmol) was added followed by 2,2,2-trifluoroethyl trifluoromethanesulfonate (0.11 g, 0.47 mmol) and the reaction mixture was stirred at 90° C. for 12 h. After 12 h, 2,2,2-trifluoroethyl trifluoromethanesulfonate (0.11 g, 0.47 mmol) was again added and the reaction mixture was stirred at 90° C. for another 12 h. The progress of the reaction was monitored by TLC. After completion of the reaction, the reaction mixture was filtered through celite and the filtrate was concentrated under reduced pressure. The residue was dissolved in EtOAc and washed with water. The organic layer was dried over anhydrous Na$_2$SO$_4$ and concentrated under reduced pressure to obtain crude compound as semi solid which was purified by silica gel column chromatography using 35% EtOAc/hexane to afford compound 118(+) (0.06 g, 50.0%) as an off-white solid. $^1$H NMR (400 MHz, DMSO-d6): δ 8.89 (d, J=12 Hz, 2H), 8.68 (d, J=9.6 Hz, 1H), 7.64-7.39 (m, 3H), 7.20 (t, J=8.8 Hz, 2H), 5.56-5.54 (m, 1H), 4.22-4.09 (m, 2H), 3.71-3.61 (m, 2H), 3.01 (s, 3H); LCMS: 511.15 (M+H); C-HPLC: 99.41% (RT: 19.55); SOR: +72.36, Solvent: Methanol, Path length: 10 mm, Concentration: 0.563 w/v %.

Examples 122(+) and 122(−)

N-(2-((5-(5-(difluoromethyl)-1,3,4-oxadiazol-2-yl)pyrimidin-2-yl)amino)-2-(4-(trifluoromethoxy)phenyl)ethyl)methanesulfonamide (122(+) and 122(−))

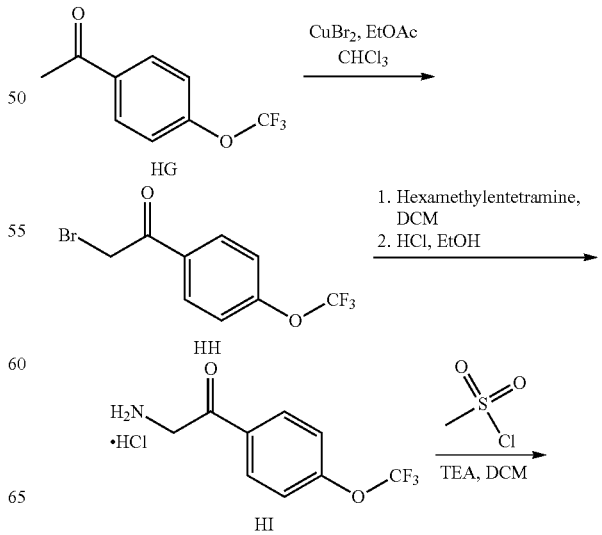

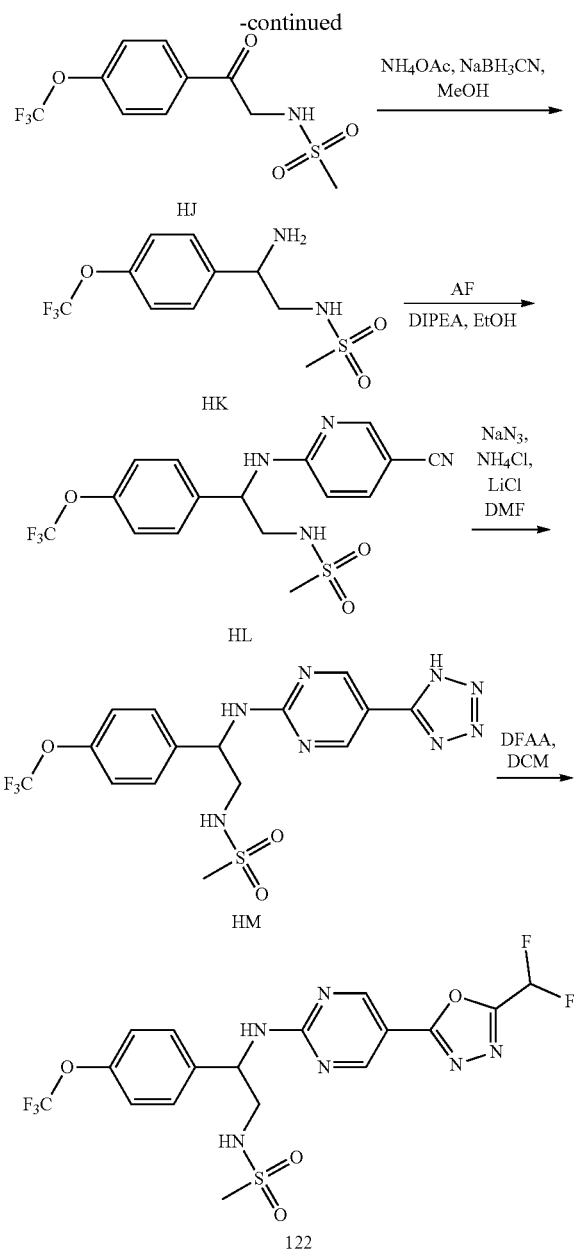

2-bromo-1-(4-(trifluoromethoxy)phenyl)ethan-1-one (HH)

To a preheated (80° C.) stirred solution of copper(II) bromide (17.2 g, 77.2 mmol) in EtOAc (20 mL) was added 4′-(trifluoromethoxy)acetophenone (HG, 8.7 g, 42.89 mmol) in chloroform (10 mL) and the reaction mixture was stirred at 80° C. for 4 h. The progress of the reaction was monitored by TLC. After completion of the reaction, the reaction mixture was filtered through celite. The filtrate was concentrated under reduced pressure to yield crude compound which was purified by silica gel column chromatography using 2-2.5% DCM/hexane to afford compound HH (7 g, 58.0%) as an off white solid. $^1$H NMR (400 MHz, CDCl3): δ 8.05 (d, J=8.0 Hz, 2H), 7.32 (d, J=8.8 Hz, 2H), 4.41 (s, 2H).

2-amino-1-(4-(trifluoromethoxy)phenyl)ethan-1-one hydrochloride (HI)

To a stirred solution of compound HH (5.5 g, 19.5 mmol) in DCM (180 mL) was added hexamethylenetetramine (4.0 g, 29.2 mmol) and the reaction mixture was stirred at RT for 2 h. A white precipitate was obtained which was filtered, washed with DCM and dried under high vacuum to get an off white solid. This solid was dissolved in EtOH (180 mL), concentrated HCl (10 mL) was added and the reaction mixture was stirred at RT for 12 h. After completion of the reaction, the reaction mixture was concentrated under reduced pressure. The residue was washed with EtOAc and hexane and dried under high vacuum to afford compound HI (7.85 g, crude) as an off white solid which was used as such for the next reaction. $^1$H NMR (400 MHz, DMSO-d6): δ 8.49 (brs, 3H), 8.16 (d, J=8.8 Hz, 2H), 7.58 (d, J=8.4 Hz, 2H), 4.62 (brs, 2H).

N-(2-oxo-2-(4-(trifluoromethoxy)phenyl)ethyl)methanesulfonamide (HJ)

To a stirred solution of compound HI (2.7 g, 10.58 mmol) in DCM (100 mL) was added triethylamine (4.4 mL, 31.76 mmol) at 0° C. and the reaction mixture was stirred for 15 min. Then mesyl chloride (1.4 g, 12.70 mmol) was added dropwise and the reaction mixture was stirred at 0° C. for 30 min. The progress of the reaction was monitored by TLC. After completion of the reaction, the reaction mixture was quenched with saturated NaHCO$_3$ solution and the aqueous layer was extracted with DCM. The combined organic layer was dried over anhydrous Na$_2$SO$_4$ and concentrated under reduced pressure. The crude product was purified by silica gel column chromatography using 20-22% EtOAc/hexane to afford compound HJ (0.66 g, 21.0%) as an off white solid. $^1$H NMR (400 MHz, DMSO-d6): δ 8.12 (d, J=8.4 Hz, 2H), 7.54 (d, J=8.4 Hz, 2H), 7.45-7.43 (m, 1H), 4.65 (d, J=5.6 Hz, 2H), 2.98 (s, 3H).

N-(2-amino-2-(4-(trifluoromethoxy)phenyl)ethyl) methanesulfonamide (HK)

To a stirred solution of compound HJ (0.2 g, 0.67 mmol) in MeOH (5 mL) was added ammonium acetate (1.03 g, 13.46 mmol) and the reaction mixture was stirred at RT for 30 min. Then NaBH$_3$CN (0.12 g, 1.81 mmol) was added and the reaction mixture was stirred at 80° C. for 4 h. The progress of the reaction was monitored by TLC. After completion of the reaction, the reaction mixture was concentrated under reduced pressure. The residue was diluted with water and basified with 10% NaOH solution to pH 10. The aqueous layer was extracted with EtOAc. The combined organic layer was dried over anhydrous Na$_2$SO$_4$ and concentrated under reduced pressure to afford compound HK (0.8 g, 67.0%) as a colorless sticky solid which was used as such for the next reaction. $^1$H NMR (400 MHz, DMSO-d6): δ 7.50 (d, J=8.8 Hz, 2H), 7.32 (d, J=8.4 Hz, 2H), 4.09 (brs, 1H), 3.40-3.95 (m, 1H), 3.17 (s, 2H), 3.13-2.99 (m, 2H), 2.88-2.81 (m, 3H); LC-MS: m/z 299.25 [M+H]$^+$.

N-(2-((5-cyanopyrimidin-2-yl)amino)-2-(4-(trifluoromethoxy)phenyl)ethyl)methanesulfonamide (HL)

To a stirred solution of compound HK (0.2 g, 0.67 mmol) in EtOH (5 mL) was added DIPEA (0.25 g, 2.01 mmol) followed by 2-chloropyrimidine-5-carbonitrile (AF, 0.09 g, 0.67 mmol) and the reaction mixture was stirred at 90° C. for 16 h. The progress of reaction was monitored by TLC. After completion of the reaction, the reaction mixture was concentrated under reduced pressure to yield crude compound which was purified by silica gel column chromatography using 50% EtOAc/hexane to afford compound HL (0.7 g, 65.5%) as an off white solid. $^1$H NMR (400 MHz, DMSO-d6): δ 8.83 (d, J=8.4 Hz, 1H), 8.71 (d, J=2.8 Hz, 2H), 7.53 (d, J=8.0 Hz, 2H), 7.35 (d, J=8.4 Hz, 2H), 7.27 (t, J=5.8 Hz, 1H), 5.27-5.21 (m, 1H), 3.46-3.34 (m, 2H), 2.84 (s, 3H); LC-MS: m/z 402.10 [M+H]$^+$.

N-(2-((5-(1H-tetrazol-5-yl)pyrimidin-2-yl)amino)-2-(4-(trifluoromethoxy)phenyl)ethyl)methanesulfonamide (HM)

To a stirred solution of compound HL (0.7 g, 1.74 mmol) in DMF (10 mL) was added NaN$_3$ (0.34 g, 5.23 mmol) and NH$_4$Cl (0.28 g, 5.23 mmol) followed by LiCl (0.073 g, 1.74 mmol) and the reaction mixture was stirred at 100° C. for 14 h. Progress of the reaction was monitored by TLC. After completion of the reaction, the reaction mixture was concentrated under reduced pressure. The residue was quenched with ice water and acidified with 6N HCl solution to pH 3. The aqueous phase was extracted with ethyl acetate. The combined organic layer was dried over anhydrous Na$_2$SO$_4$ and concentrated under reduced pressure to afford compound HM (0.7 g, 90.5%) as an off white solid which was used as such for the next reaction. LC-MS: m/z 445.15 [M+H]$^+$.

N-(2-((5-(5-(difluoromethyl)-1,3,4-oxadiazol-2-yl)pyrimidin-2-yl)amino)-2-(4-(trifluoromethoxy)phenyl)ethyl)methanesulfonamide (122)

To a stirred solution of compound HM (0.7 g, 1.57 mmol) in DCM (10 mL) was added DFAA (0.4 g, 2.36 mmol) at 0° C. and the reaction was stirred at RT for 5 h. The progress of reaction was monitored by TLC. After completion of the reaction, the reaction mixture was quenched with water and the product was extracted with DCM. The combined organic layer was washed with brine, dried over anhydrous Na$_2$SO$_4$ and concentrated under reduced pressure to afford crude compound which was purified by silica gel column chromatography using 20-30% EtOAc/hexane to afford racemic 122 (0.4 g, 51.5%).

Chiral Preparative HPLC Details for 122(+) and 122(−

The enantiomers were separated by normal-phase preparative high performance liquid chromatography (Chiralpak IA, 250×30 mm, 5; Mobile Phase: A; n-Hexane+0.1% DEA/B; DCM:MeOH (6:4); Isocratic Elution 27% B; Flow rate: 30.0 mL/min) to obtain 122(+) (85 mg) and 122(−) (85 mg).

122(+): $^1$H NMR (400 MHz, DMSO-d6): δ 8.88 (d, J=14.4 Hz, 2H), 8.74 (d, J=8.4 Hz, 1H), 7.65-7.35 (m, 5H), 7.29 (t, J=6.0 Hz, 1H), 5.33-5.28 (m, 1H), 3.43-3.36 (m, 2H), 2.84 (s, 3H); LC-MS: m/z 495.15 [M+H]$^+$. C-HPLC: 96.03% (RT: 13.25), SOR: +70.02, Solvent: Methanol, Path length: 10 mm, Concentration: 0.539 w/v % 122(−): $^1$H NMR (400 MHz, DMSO-d6): δ 8.88 (d, J=13.6 Hz, 2H), 8.74 (d, J=8.8 Hz, 1H), 7.65-7.35 (m, 5H), 7.29 (t, J=6.0 Hz, 1H), 5.34-5.28 (m, 1H), 3.45-3.34 (m, 2H), 2.84 (s, 3H); LC-MS: m/z 495.15 [M+H]$^+$. C-HPLC: 99.65% (RT: 11.27), SOR: −105.59, Solvent: Methanol, Path length: 10 mm, Concentration: 0.543 w/v %.

Examples 123(+) and 123(−)

N-(2-cyclopropyl-2-((5-(5-(difluoromethyl)-1,3,4-oxadiazol-2-yl)pyrimidin-2-yl)amino)ethyl)methanesulfonamide (123(+) and 123(−))

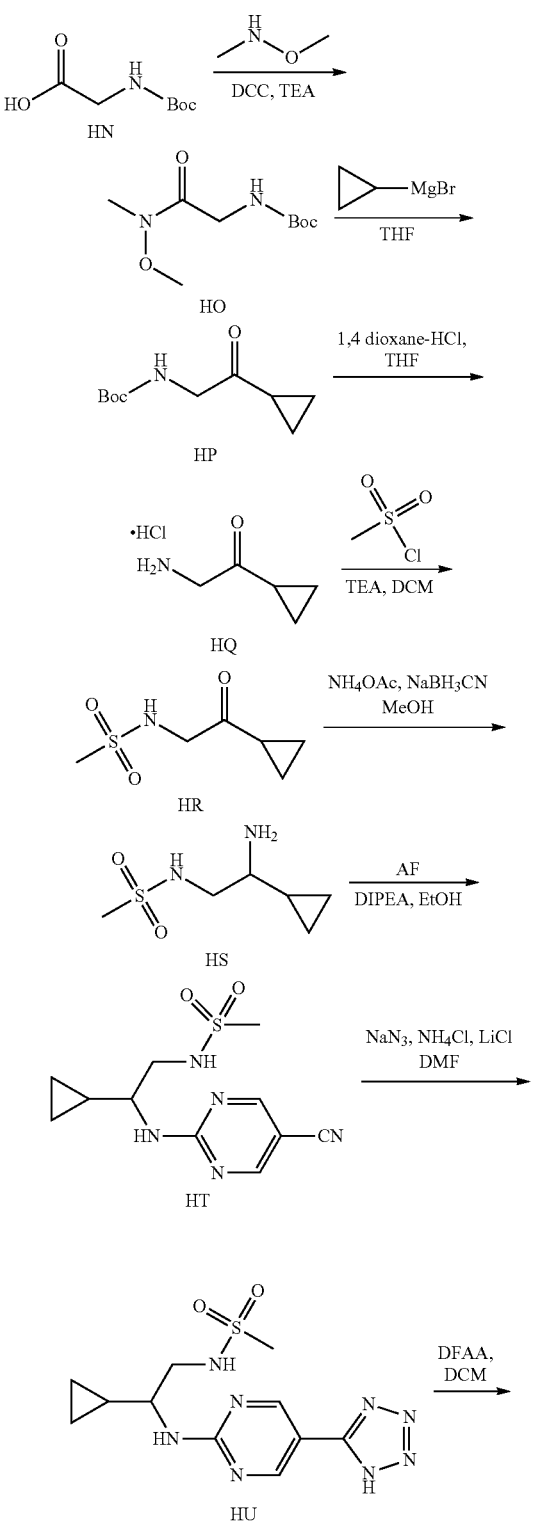

-continued

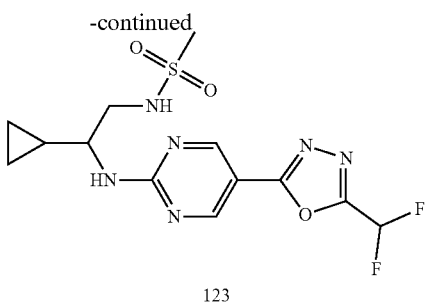

123 tert-butyl (2-(methoxy(methyl)amino)-2-oxoethyl)
carbamate (HO)

To a stirred solution of (tert-butoxycarbonyl)glycine (HN, 5.0 g, 28.57 mmol) and triethylamine (4.1 mL, 31.42 mmol) in DCM (80 mL) was added N,O-dimethylhydroxylamine (3.0 g, 31.42 mmol) followed by DCC (6.5 g, 31.42 mmol) in DCM (20 mL) and the reaction mixture was stirred at RT for 12 h. The progress of the reaction was monitored by TLC. After completion of the reaction, the reaction mixture was filtered through celite and washed with DCM. The filtrate was concentrated under reduced pressure to yield the crude compound which was purified by silica gel column chromatography using 10% EtOAc/hexane to afford compound HO (6.0 g, 97.0%) as an off-white solid. $^1$H NMR (400 MHz, CDCl$_3$): δ 5.27 (brs, 1H), 4.08 (brs, 2H), 3.72 (s, 3H), 3.21 (s, 3H), 1.46 (s, 9H).

tert-butyl (2-cyclopropyl-2-oxoethyl)carbamate
(HP)

To a stirred solution of compound HO (1.0 g, 4.59 mmol) in THF (20 mL) was added cyclopropylmagnesium bromide (0.5 M in THF) (45 mL, 22.93 mmol) at 0° C. and the reaction mixture was stirred at RT for 12 h. The progress of the reaction was monitored by TLC. After completion of the reaction, the reaction mixture was quenched with saturated NH$_4$Cl solution and the aqueous layer was extracted with EtOAc. The combined organic layer was dried over anhydrous Na$_2$SO$_4$ and concentrated under reduced pressure. The crude product was purified by silica gel column chromatography using 40% EtOAc/hexane to afford compound HP (0.66 g, 73.0%) as an off white solid. $^1$H NMR (400 MHz, CDCl3): δ 5.25 (brs, 1H), 4.17 (d, J=4.4 Hz, 2H), 1.92-1.86 (m, 1H), 1.42 (s, 9H), 1.09-1.06 (m, 2H), 0.96-0.91 (m, 2H).

2-amino-1-cyclopropylethan-1-one hydrochloride
(HQ)

To a stirred solution of compound HP (3.1 g, 15.57 mmol) in THF (15 mL) was added 1,4 dioxane·HCl (15.7 mL) at 0° C. and the reaction mixture was stirred at RT for 4 h. The progress of reaction was monitored by TLC. The reaction mixture was concentrated under reduced pressure. The obtained HCl salt was triturated with DCM and diethyl ether and dried under vacuum to afford compound HQ (2.0 g, 95.0%) as an off white solid. $^1$H NMR (400 MHz, DMSO-d6): δ 8.17 (brs, 3H), 4.07 (s, 2H), 2.16-2.13 (m, 1H), 1.06-0.99 (m, 2H), 0.98-0.94 (m, 2H).

N-(2-cyclopropyl-2-oxoethyl)methanesulfonamide
(HR)

To a stirred solution of compound HQ (1.8 g, 13.33 mmol) in DCM (20 mL) was added triethylamine (5.3 mL, 39.99 mmol) at 0° C. and the reaction mixture was stirred for 30 min. To the resulting reaction mixture, mesyl chloride (1.0 mL, 13.33 mmol) was added at 0° C. and the reaction mixture was stirred for 30 min. The progress of reaction was monitored by TLC. After completion of the reaction, the reaction mixture was quenched with water and the product was extracted with DCM. The combined organic layer was dried over anhydrous Na$_2$SO$_4$ and concentrated under reduced pressure. The solid compound was triturated with diethyl ether to afford compound HR (2.2 g, 94.0%) as an off white solid. $^1$H NMR (400 MHz, CDCl$_3$): δ 5.12 (brs, 1H), 4.24 (d, J=5.2 Hz, 2H), 2.97 (s, 3H), 1.96-1.90 (m, 1H), 1.19-1.15 (m, 2H), 1.08-1.03 (m, 2H).

N-(2-amino-2-cyclopropylethyl)methanesulfonamide
(HS)

To a stirred solution of compound HR (2.7 g, 15.25 mmol) in MeOH (27 mL) was added ammonium acetate (23.5 g, 305.08 mmol) and the reaction mixture was stirred at RT for 30 min. Then NaBH$_3$CN (2.3 g, 38.0 mmol) was added portion wise at 0° C. and the reaction mixture was stirred at 65° C. for 12 h. After completion of the reaction, the reaction mixture was concentrated under reduced pressure. The residue was quenched with water and basified with 10% NaOH solution to pH 9-10. The aqueous phase was extracted with DCM. The combined organic layer was dried over anhydrous Na$_2$SO$_4$ and concentrated under reduced pressure to afford compound HS (1.5 g, 55.0%) as a light brown semi solid which was used as such for the next step. $^1$H NMR (400 MHz, DMSO-d6): δ 3.05-3.03 (m, 1H), 2.90 (s, 3H), 2.88-2.82 (m, 1H), 2.17-2.12 (m, 1H), 0.74-0.66 (m, 1H), 0.40-0.30 (m, 2H), 0.25-0.16 (m, 2H).

N-(2-((5-cyanopyrimidin-2-yl)amino)-2-cyclopropylethyl)methanesulfonamide (HT)

To a stirred solution of compound HS (1.5 g, 8.43 mmol) in EtOH (20 mL) was added DIPEA (4.3 g, 25.28 mmol) followed by 2-chloropyrimidine-5-carbonitrile (AF, 1.2 g, 8.43 mmol) and the reaction mixture was stirred at 90° C. for 6 h. The progress of reaction was monitored by TLC. After completion of the reaction, the reaction mixture was concentrated under reduced pressure. The crude product was purified by silica gel column chromatography using 50% EtOAc/hexane. The product was further triturated with diethyl ether and pentane to afford compound HT (1.01 g, 42.0%) as an off white solid. $^1$H NMR (400 MHz, DMSO-d6): δ 8.67-8.65 (m, 2H), 8.21 (d, J=8.8 Hz, 1H), 7.07 (t, J=6.2 Hz, 1H), 3.64-3.56 (m, 1H), 3.32-3.13 (m, 2H), 2.87 (s, 3H), 1.06-0.85 (m, 1H), 0.52-0.46 (m, 1H), 0.40-0.34 (m, 1H), 0.32-0.19 (m, 2H); LC-MS: m/z 282.05 [M+H]$^+$.

N-(2-((5-(1H-tetrazol-5-yl)pyrimidin-2-yl)amino)-2-cyclopropylethyl)methanesulfonamide (HU)

To a stirred solution of compound HT (1.0 g, 3.59 mmol) in DMF (10 mL) was added NaN$_3$ (1.15 g, 17.79 mmol), NH$_4$Cl (0.96 g, 17.79 mmol) followed by LiCl (0.3 g) and the reaction mixture was stirred at 100° C. for 6 h. Progress of the reaction was monitored by TLC. After completion of the reaction, DMF was removed under reduced pressure. The residue was quenched with ice water and acidified with 6N HCl solution to pH 4. The aqueous layer was extracted with 10% MeOH/DCM. The combined organic layer was dried over anhydrous Na$_2$SO$_4$ and concentrated under reduced pressure to afford compound HU (1.12 g, 97.0%) as a light brown solid which was used as such for the next step. ¹H NMR (400 MHz, DMSO-d6): δ 8.83 (s, 2H), 7.80 (d, J=8.8 Hz, 1H), 7.07 (t, J=6.2 Hz, 1H), 3.68-3.63 (m, 1H), 3.23-3.16 (m, 3H), 2.89 (s, 3H), 1.06-1.02 (m, 1H), 0.50-0.46 (m, 1H), 0.41-0.32 (m, 2H), 0.27-0.23 (m, 1H); LC-MS: m/z 325.05 [M+H]⁺.

N-(2-cyclopropyl-2-((5-(5-(difluoromethyl)-1,3,4-oxadiazol-2-yl)pyrimidin-2-yl)amino)ethyl)methanesulfonamide (123)

To a stirred solution of compound HU (1.1 g, 3.39 mmol) in DCM (40 mL) was added DFAA (0.6 mL, 6.70 mmol) at 0° C. and the reaction was stirred at RT for 12 h. The progress of reaction was monitored by TLC. After completion of the reaction, the reaction mixture was quenched with water and basified to pH 7-8 using aq. NaHCO₃. The aqueous phase was extracted with DCM. The combined organic layer was dried over anhydrous Na₂SO₄ and concentrated under reduced pressure. The crude compound was purified by silica gel column chromatography using 25% EtOAc/hexane. The compound was further triturated with diethyl ether and pentane to afford racemic 123 (0.5 g, 41.0%) as an off white solid.

Chiral Preparative SFC Details for 123(+) and 123(−)

The enantiomers were separated by supercritical fluid chromatography (Chiralpak IA, 250×30 mm, 5; Mobile Phase: A; CO₂/B; 0.1% NH₃ in Methanol; Gradient Elution 20% B, 5 min, 20-25% in 4 min, 25-30% in 3 min, 30% B hold 13 min; Flow rate: 80.0 mL/min) to obtain 123(+) (61 mg) and 123(−) (44 mg).

123(+): (0.061 g, 4.8%); ¹H NMR (400 MHz, DMSO-d6): δ 8.85 (s, 2H), 8.12 (d, J=8.8 Hz, 1H), 7.65-7.39 (m, 1H), 7.09 (t, J=6.2 Hz, 1H), 3.69-3.66 (m, 1H), 3.27-3.18 (m, 2H), 2.88 (s, 3H), 1.05-1.02 (m, 1H), 0.51-0.47 (m, 1H), 0.40-0.32 (m, 2H), 0.26-0.23 (m, 1H); LC-MS: m/z 375.10 [M+H]⁺; C-HPLC: 100% (RT: 3.94); SOR: +31.56, Solvent: Methanol, Path length: 10 mm, Concentration: 0.64 w/v %.

123(−): (0.044 g, 3.5%); ¹H NMR (400 MHz, DMSO-d6): δ 8.85 (s, 2H), 8.12 (d, J=8.8 Hz, 1H), 7.65-7.39 (m, 1H), 7.09 (t, J=6.2 Hz, 1H), 3.69-3.66 (m, 1H), 3.25-3.18 (m, 2H), 2.88 (s, 3H), 1.07-1.02 (m, 1H), 0.51-0.48 (m, 1H), 0.40-0.32 (m, 2H), 0.28-0.23 (m, 1H); LC-MS: m/z 375.10 [M+H]⁺; C-HPLC: 100% (RT: 4.82); SOR: −14.83, Solvent: Methanol, Path length: 10 mm, Concentration: 0.53 w/v %.

Example 125

N-(3-((5-(5-(difluoromethyl)-1,3,4-oxadiazol-2-yl)pyrimidin-2-yl)amino)-3-(4-fluorophenyl)propyl)methanesulfonamide (125)

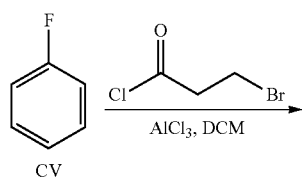

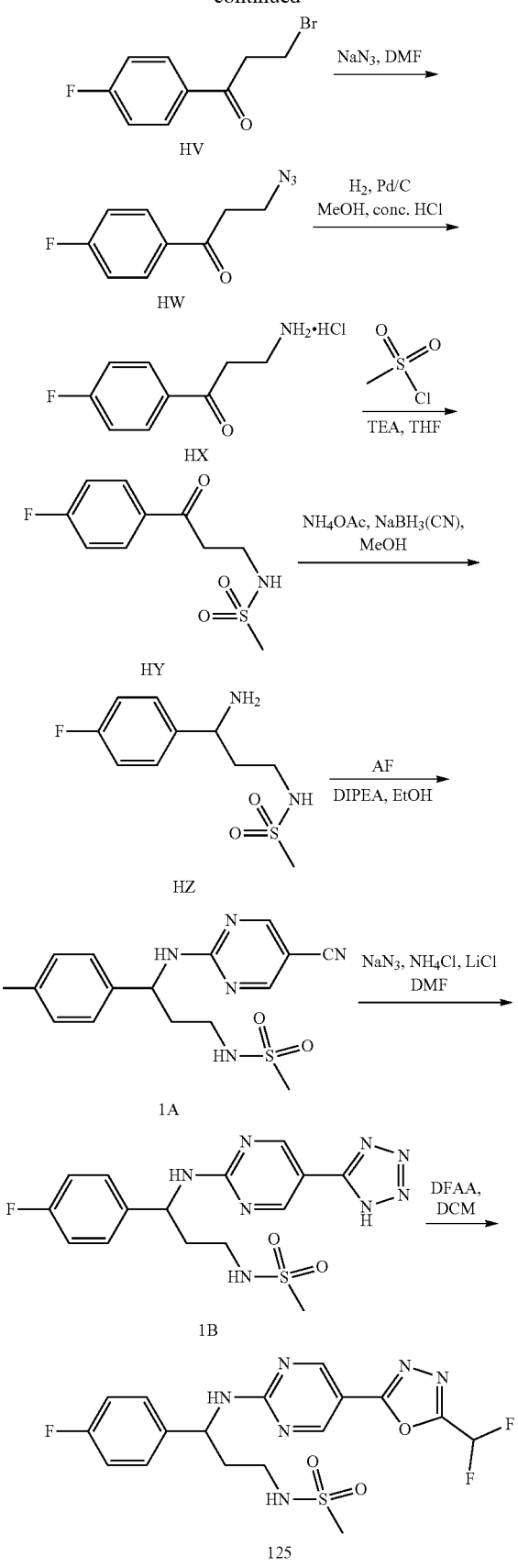

3-bromo-1-(4-fluorophenyl)propan-1-one (HV)

To a stirred solution of AlCl₃ (6.9 g, 52 mmol) in DCM (50 mL) was added 3-bromopropanoyl chloride (5.2 mL, 52 mmol) at 0° C. and the reaction mixture was stirred at RT for 1 h. Fluorobenzene (CV, 5.0 g, 52 mmol) dissolved in DCM (10 mL) was added dropwise at 0° C. and the reaction mixture was stirred at RT for 2 h. The progress of the reaction was monitored by TLC. After completion of the reaction, the reaction mixture was quenched with water, neutralized with 2N NaOH solution and extracted with DCM. The combined organic layer was washed with brine, dried over anhydrous Na₂SO₄ and concentrated under reduced pressure to afford compound HV (11.0 g, 92.0%) as a black solid. ¹H NMR (400 MHz, CDCl3): δ 8.03-7.98 (m, 2H), 7.17 (t, J=8.6 Hz, 2H), 3.75 (t, J=7.0 Hz, 2H), 3.56 (t, J=6.8 Hz, 2H).

3-azido-1-(4-fluorophenyl)propan-1-one (HW)

To a stirred solution of compound HV (5.0 g, 21.7 mmol) in MeOH (200 mL) was added NaN₃ (4.2 g, 65.1 mmol) followed by KI (35 mg) in water (30 mL) and the reaction mixture was stirred at 60° C. for 2.5 h. The progress of reaction was monitored by TLC. After completion of the reaction, the reaction mixture was concentrated under reduced pressure. The crude residue was dissolved in EtOAc and washed with water. The organic layer was dried over anhydrous Na₂SO₄ and concentrated under reduced pressure to afford compound HW (3.5 g, 86.0%) as a brown sticky semi solid. ¹H NMR (400 MHz, DMSO-d6): δ 8.09-8.06 (m, 2H), 7.37 (t, J=8.6 Hz, 2H), 3.65 (t, J=6.2 Hz, 2H), 3.36 (t, J=6.2 Hz, 2H).

3-amino-1-(4-fluorophenyl)propan-1-one hydrochloride (HX)

To a stirred solution of compound HW (3.5 g, 18.13 mmol) in MeOH (100 mL) and conc. HCl (12 mL) was added Pd/C (0.35 g, 10% w/w) under N₂ atmosphere. The reaction mixture was stirred under H₂ balloon pressure at RT for 2 h. After completion of the reaction, the reaction mixture was filtered through celite and washed thoroughly with MeOH. The filtrate was concentrated under reduced pressure to afford compound HX (2.4 g, 92.0%) as a brown sticky semi solid. LC-MS: m/z 168.00 [M+H]⁺.

N-(3-(4-fluorophenyl)-3-oxopropyl)methanesulfonamide (HY)

To a stirred solution of compound HX (2.4 g, 11.8 mmol) in DCM (100 mL) was added triethyl amine (4.9 mL, 35.4 mmol) at 0° C. and the reaction mixture was stirred for 15 min. Then mesyl chloride (2.0 g, 17.82 mmol) dissolved in DCM (25 mL) was added dropwise at 0° C. and the reaction mixture was stirred for 45 min. The progress of the reaction was monitored by TLC. After completion of the reaction, the reaction mixture was quenched with saturated NaHCO₃ solution. The organic layer was separated, dried over anhydrous Na₂SO₄ and concentrated under reduced pressure. The crude product was purified by silica gel column chromatography using 2-5% MeOH/DCM to afford compound HY (2.1 g, 73.0%) as an off white solid. LC-MS: m/z 246.00 [M+H]⁺.

N-(3-amino-3-(4-fluorophenyl)propyl)methanesulfonamide (HZ)

To a stirred solution of compound HY (2.1 g, 8.5 mmol) in MeOH (20 mL) was added ammonium acetate (13.0 g, 171.4 mmol) and the reaction mixture was stirred at RT for 30 min. To the resulting reaction mixture, NaBH₃CN (1.4 g, 23.1 mmol) was added and the reaction mixture was stirred at 75° C. for 16 h. After completion of the reaction, the reaction mixture was concentrated under reduced pressure. The residue was diluted with EtOAc and washed with saturated NaHCO₃ solution. The organic layer was dried over anhydrous Na₂SO₄ and concentrated under reduced pressure to afford compound HZ (1.75 g, 83.0%) as a brown sticky semi solid. ¹H NMR (400 MHz, DMSO-d6): δ 7.43-7.39 (m, 2H), 7.16 (t, J=8.8 Hz, 2H), 4.05-3.95 (m, 2H), 2.92-2.89 (m, 1H), 2.88-2.79 (m, 4H), 1.99 (s, 1H), 1.83-1.73 (m, 2H), 1.18 (t, J=7.0 Hz, 1H); LC-MS: m/z 247.05 [M+H]⁺.

N-(3-((5-cyanopyrimidin-2-yl)amino)-3-(4-fluorophenyl)propyl)methanesulfonamide (IA)

To a stirred solution of compound HZ (0.6 g, 2.4 mmol) and 2-chloropyrimidine-5-carbonitrile (AF, 0.34 g, 2.4 mmol) in EtOH (15 mL) was added DIPEA (1.2 mL, 7.2 mmol) and the reaction mixture was stirred at 90° C. for 16 h. The progress of reaction was monitored by TLC. After completion of the reaction, the reaction mixture was concentrated under reduced pressure. The crude residue was dissolved in EtOAc and washed with water and brine. The organic layer was dried over anhydrous Na₂SO₄ and concentrated under reduced pressure. The crude product was purified by silica gel column chromatography using 50% EtOAc/hexane to afford compound IA (0.4 g, 47.5%) as an off white solid. ¹H NMR (400 MHz, CDCl3): δ 8.51 (d, J=22.4 Hz, 2H), 7.35-7.32 (m, 2H), 7.08 (t, J=8.4 Hz, 2H), 5.98 (d, J=8.8 Hz, 1H), 5.27-5.22 (m, 1H), 4.93-4.90 (m, 1H), 3.30-3.23 (m, 1H), 3.19-3.12 (m, 1H), 2.95 (s, 3H), 2.21-2.16 (m, 2H); LC-MS: m/z 350.20 [M+H]⁺.

N-(3-((5-(1H-tetrazol-5-yl)pyrimidin-2-yl)amino)-3-(4-fluorophenyl)propyl)methanesulfonamide (IB)

To a stirred solution of compound IA (0.4 g, 1.14 mmol) in DMF (15 mL) was added NaN₃ (0.31 g, 5.7 mmol) and NH₄Cl (0.37 g, 5.7 mmol) followed by LiCl (0.09 g) and the reaction mixture was stirred at 100° C. for 16 h. Progress of the reaction was monitored by TLC. After completion of the reaction, the reaction mixture was concentrated under reduced pressure. The residue was quenched with ice water and acidified with 6N HCl solution to pH 4. The product was extracted with EtOAc. The combined organic layer was washed with brine, dried over anhydrous Na₂SO₄ and concentrated under reduced pressure to afford compound IB (0.33 g, 73.5%) as a sticky mass. LC-MS: m/z 393.45 [M+H]⁺.

N-(3-((5-(5-(difluoromethyl)-1,3,4-oxadiazol-2-yl)pyrimidin-2-yl)amino)-3-(4-fluorophenyl)propyl)methanesulfonamide (125)

To a stirred solution of compound IB (0.32 g, 0.83 mmol) in DCM (15 mL) was added DFAA (0.22 mL, 1.24 mmol) at 0° C. and the reaction was stirred at RT for 16 h. The progress of the reaction was monitored by TLC. After completion of the reaction, the reaction mixture was quenched with water and the product was extracted with DCM. The combined organic layer was washed with brine, dried over anhydrous Na₂SO₄ and concentrated under reduced pressure to afford crude compound which was purified by silica gel column chromatography using 5% MeOH/DCM to afford 125 (0.065 g, 17.5%) as an off-white solid.

$^1$H NMR (400 MHz, DMSO-d6): δ 8.86-8.83 (m, 3H), 7.64-7.38 (m, 3H), 7.15 (t, J=9.2 Hz, 2H), 7.07 (t, J=5.6 Hz, 1H), 5.23-5.17 (m, 1H), 3.08-2.93 (m, 2H), 2.85 (s, 3H), 2.11-2.02 (m, 1H), 1.99-1.87 (m, 1H); LC-MS: m/z 443.15 [M+H]$^+$, HPLC: 95.64%.

Example 127

N-(1-((5-(5-(difluoromethyl)-1,3,4-oxadiazol-2-yl)pyrimidin-2-yl)amino)-1-(4-fluorophenyl)propan-2-yl)methanesulfonamide (127)

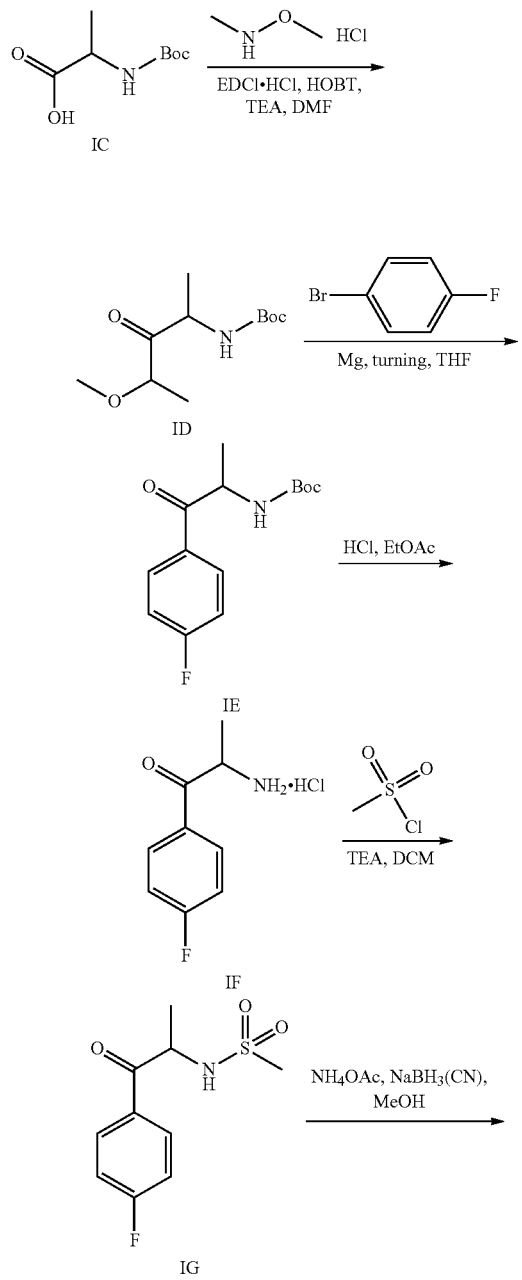

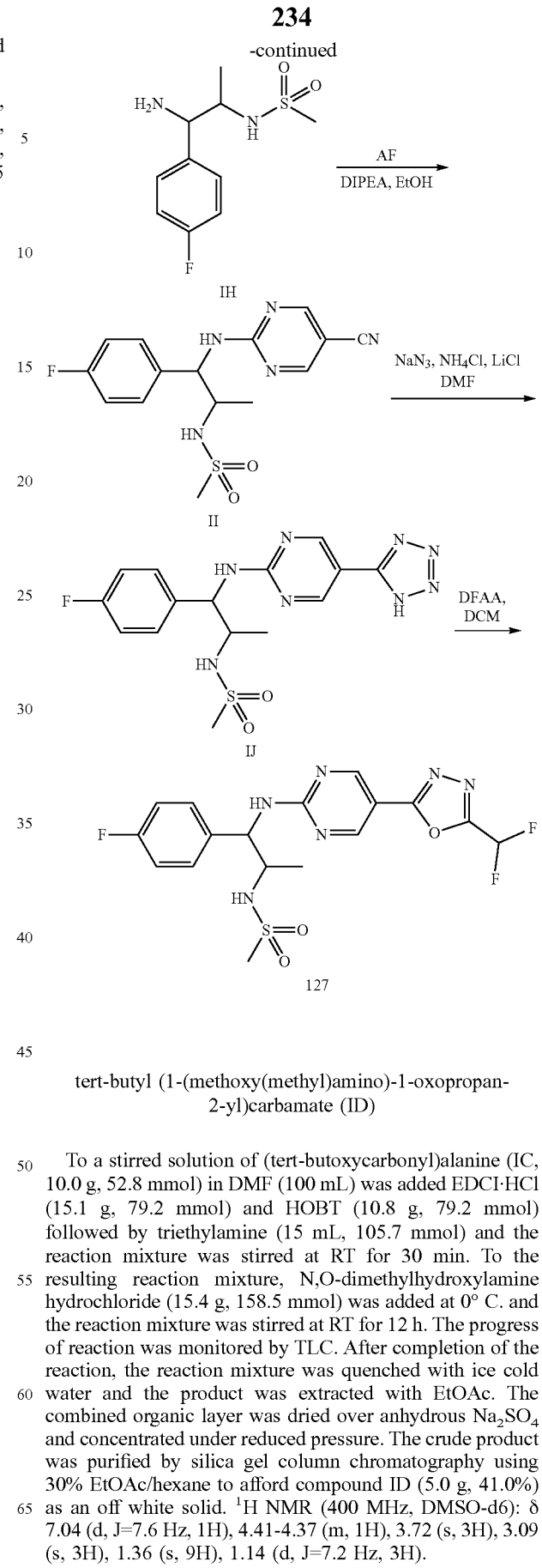

tert-butyl (1-(methoxy(methyl)amino)-1-oxopropan-2-yl)carbamate (ID)

To a stirred solution of (tert-butoxycarbonyl)alanine (IC, 10.0 g, 52.8 mmol) in DMF (100 mL) was added EDCI·HCl (15.1 g, 79.2 mmol) and HOBT (10.8 g, 79.2 mmol) followed by triethylamine (15 mL, 105.7 mmol) and the reaction mixture was stirred at RT for 30 min. To the resulting reaction mixture, N,O-dimethylhydroxylamine hydrochloride (15.4 g, 158.5 mmol) was added at 0° C. and the reaction mixture was stirred at RT for 12 h. The progress of reaction was monitored by TLC. After completion of the reaction, the reaction mixture was quenched with ice cold water and the product was extracted with EtOAc. The combined organic layer was dried over anhydrous Na$_2$SO$_4$ and concentrated under reduced pressure. The crude product was purified by silica gel column chromatography using 30% EtOAc/hexane to afford compound ID (5.0 g, 41.0%) as an off white solid. $^1$H NMR (400 MHz, DMSO-d6): δ 7.04 (d, J=7.6 Hz, 1H), 4.41-4.37 (m, 1H), 3.72 (s, 3H), 3.09 (s, 3H), 1.36 (s, 9H), 1.14 (d, J=7.2 Hz, 3H).

tert-butyl (1-(4-fluorophenyl)-1-oxopropan-2-yl) carbamate (IE)

To magnesium turnings (3.3 g, 137.93 mmol) in dry THF (40 mL) under $N_2$ atmosphere, 1-bromo-4-fluorobenzene (24.1 g, 137.93 mmol) was added and the mixture was stirred at RT for 30 min. Compound ID (4.0 g, 17.24 mmol) in THF (20 mL) was added and the reaction mixture was stirred at RT for 12 h. The progress of reaction was monitored by TLC. After completion of the reaction, the reaction mixture was quenched with saturated $NH_4Cl$ solution and the product was extracted with EtOAc. The combined organic layer was dried over anhydrous $Na_2SO_4$ and concentrated under reduced pressure. The crude product was purified by silica gel column chromatography using 40% EtOAc/hexane to afford compound IE (3.0 g, 65%) as an off white solid. LC-MS: m/z 168 [M−Boc+H]$^+$.

2-amino-1-(4-fluorophenyl)propan-1-one hydrochloride (IF)

To a stirred solution of compound IE (3.0 g, 11.23 mmol) in EtOAc (30 mL) was added HCl in EtOAc (15 mL) at 0° C. and the reaction mixture was stirred at RT for 12 h. The reaction mixture was diluted with EtOAc and the solid was filtered off and dried under vacuum to afford compound IF (2.1 g, 92%) as a white solid. $^1$H NMR (400 MHz, DMSO-d6): δ 8.55 (brs, 3H), 8.18-8.15 (m, 2H), 7.43 (t, J=8.8 Hz, 2H), 5.12 (q, J=7.0 Hz, 1H), 1.42 (d, J=7.6 Hz, 3H); LC-MS: m/z 168 [M+H]$^+$.

N-(1-(4-fluorophenyl)-1-oxopropan-2-yl)methanesulfonamide (IG)

To a stirred solution of compound IF (2.0 g, 9.85 mmol) and mesyl chloride (1.13 mL, 14.77 mmol) in DCM (30 mL) was added triethyl amine (4.15 mL, 29.55 mmol) at 0° C. and the reaction mixture was stirred at RT for 8 h. The progress of reaction was monitored by TLC. After completion of the reaction, the reaction mixture was quenched with water and the product was extracted with DCM. The combined organic layer was dried over anhydrous $Na_2SO_4$ and concentrated under reduced pressure. The crude product was purified by silica gel column chromatography using 30% EtOAc/hexane to afford compound IG (1.5 g, 62.0%) as a white solid. $^1$H NMR (400 MHz, DMSO-d6): δ 8.14-8.10 (m, 2H), 7.39 (t, J=8.8 Hz, 2H), 5.13-5.09 (m, 1H), 2.94 (s, 3H), 1.30 (d, J=6.8 Hz, 3H); LC-MS: m/z 246.2 [M+H]$^+$.

N-(1-amino-1-(4-fluorophenyl)propan-2-yl)methanesulfonamide (IH)

To a stirred solution of compound IG (1.5 g, 6.12 mmol) in MeOH (20 mL) was added ammonium acetate (9.4 g, 122.24 mmol) and the reaction mixture was stirred at RT for 30 min. Then $NaBH_3CN$ (1.0 g, 16.53 mmol) was added portion wise at 0° C. and the reaction mixture was stirred at 80° C. for 12 h. After completion of the reaction, the reaction mixture was concentrated under reduced pressure. The residue was quenched with water and basified with 10% NaOH solution to pH 9-10. The aqueous phase was extracted with DCM. The combined organic layer was dried over anhydrous $Na_2SO_4$ and concentrated under reduced pressure to afford compound IH (1.5 g, crude) as a sticky solid which was used as such for the next reaction. LC-MS: m/z 246.95 [M+H]$^+$.

N-(1-((5-cyanopyrimidin-2-yl)amino)-1-(4-fluorophenyl)propan-2-yl)methanesulfonamide (II)

To a stirred solution of compound IH (1.5 g, 6.09 mmol) in EtOH (30 mL) was added DIPEA (3.3 mL, 18.29 mmol) followed by 2-chloropyrimidine-5-carbonitrile (AF, 0.94 g, 6.70 mmol) and the reaction mixture was stirred at 90° C. for 12 h. The progress of reaction was monitored by TLC. After completion of the reaction, the reaction mixture was concentrated under reduced pressure. The crude product was purified by silica gel column chromatography using 2-5% MeOH/DCM to afford compound 11 (1.2 g, 57.0%) as an off white solid. LC-MS: m/z 350.05 [M+H]$^+$.

N-(1-((5-(1H-tetrazol-5-yl)pyrimidin-2-yl)amino)-1-(4-fluorophenyl)propan-2-yl)methanesulfonamide (IJ)

To a stirred solution of compound 11 (0.5 g, 1.43 mmol) in DMF (15 mL) was added $NaN_3$ (0.28 g, 4.29 mmol) and $NH_4Cl$ (0.23 g, 4.29 mmol) followed by LiCl (0.06 g, 1.43 mmol) and the reaction mixture was stirred at 100° C. for 14 h. The progress of the reaction was monitored by TLC. After completion of the reaction, it was concentrated under reduced pressure. The residue was quenched with ice water and acidified with 1N HCl solution. The aqueous layer was extracted with EtOAc. The combined organic layer was dried over anhydrous $Na_2SO_4$ and concentrated under reduced pressure to afford compound JJ (0.35 g, 62.5%) as a white solid which was used as such for the next reaction. LC-MS: m/z 393.45 [M+H]$^+$.

N-(1-((5-(5-(difluoromethyl)-1,3,4-oxadiazol-2-yl)pyrimidin-2-yl)amino)-1-(4-fluorophenyl)propan-2-yl)methanesulfonamide (127)

To a stirred solution of compound IJ (0.35 g, 0.89 mmol) in DCM (10 mL) was added DFAA (0.19 mL, 1.78 mmol) at 0° C. and the reaction was stirred at RT for 4 h. The progress of reaction was monitored by TLC. After completion of the reaction, the reaction mixture was diluted with DCM, washed with saturated $NaHCO_3$ solution. Organic layer was dried over anhydrous $Na_2SO_4$ and concentrated under reduced pressure. The crude compound was purified by silica gel column chromatography using 2-5% MeOH/DCM to afford a mixture of diastereomers 127A (0.06 g, 15.0%) and 127B (0.01 g, 2.5%) as an off-white solid.

127A: $^1$H NMR (400 MHz, DMSO-d6): δ 8.85 (d, J=10.8 Hz, 2H), 8.68 (d, J=9.2 Hz, 1H), 7.64-7.38 (m, 3H), 7.24 (d, J=8.8 Hz, 1H), 7.16 (t, J=8.8 Hz, 2H), 5.08 (t, J=8.8 Hz, 1H), 3.77-3.69 (m, 1H), 2.38 (s, 3H), 1.22 (d, J=6.8 Hz, 3H); LC-MS: m/z 443.10 [M+H]$^+$; HPLC: 94.78%.

127B: $^1$H NMR (400 MHz, DMSO-d6): δ 8.87 (d, J=21.6 Hz, 2H), 8.49 (d, J=9.2 Hz, 1H), 7.64-7.39 (m, 3H), 7.18 (t, J=7.7 Hz, 3H), 5.21 (t, J=7.6 Hz, 1H), 3.79-3.74 (m, 1H), 2.58 (s, 3H), 1.11 (d, J=6.4 Hz, 3H); LC-MS: m/z 443.10 [M+H]$^+$; HPLC: 73.71%.

Example 128

N-(3-(((5-(5-(difluoromethyl)-1,3,4-oxadiazol-2-yl)pyrimidin-2-yl)amino)(4-fluorophenyl)methyl)phenyl)methanesulfonamide (128)

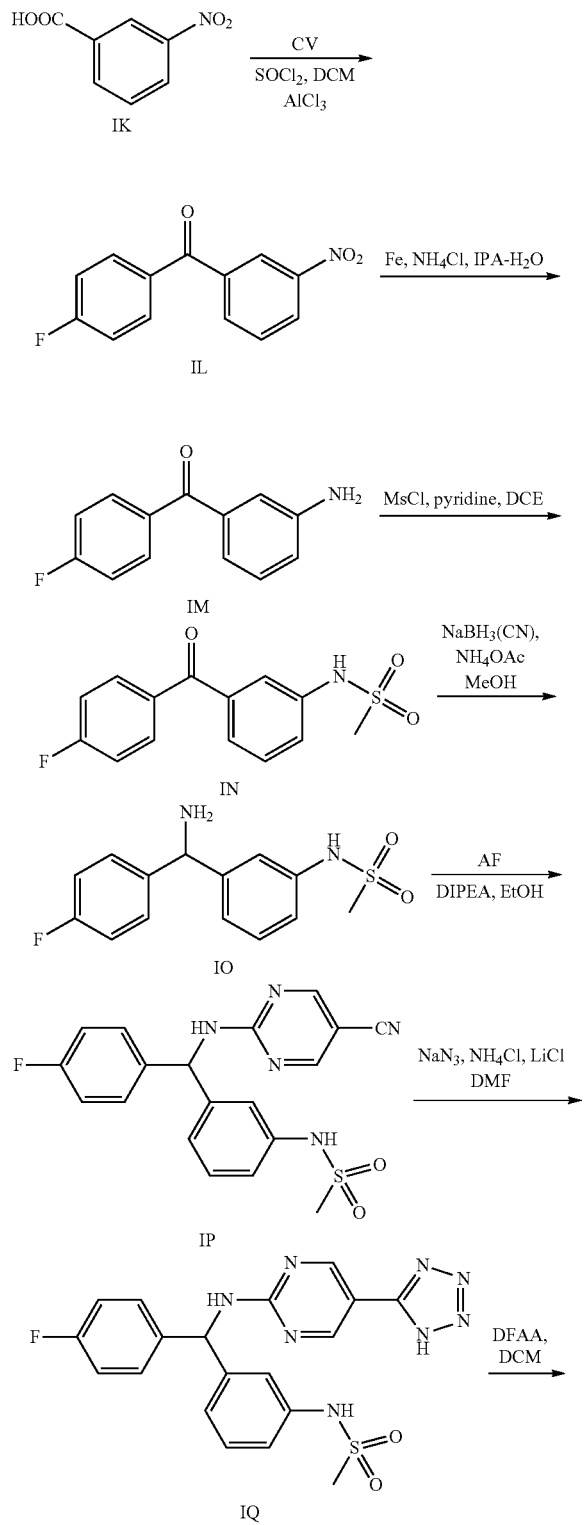

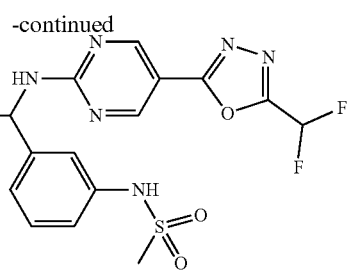

128

(4-fluorophenyl)(3-nitrophenyl)methanone (IL)

To a stirred solution of 3-nitrobenzoic acid (IK, 5.0 g, 29.94 mmol) in DCE (50 mL), thionyl chloride (2.5 mL, 38.92 mmol) was added at 0° C. and the reaction was stirred at 50° C. for 2 h. The progress of the reaction was monitored by TLC. After completion of the reaction, the reaction was cooled to 0° C., fluorobenzene (CV, 13.9 mL, 149.2 mmol) and AlCl$_3$ (4.36 g, 32.82 mmol) were added and the reaction was stirred at RT for 6 h. The progress of the reaction was monitored by TLC. After completion of the reaction, the reaction mixture was quenched with 1N HCl solution and the product was extracted with DCM. The combined organic layer was washed with brine, dried over anhydrous Na$_2$SO$_4$ and concentrated under reduced pressure. The crude product was triturated with diethyl ether to afford IL (6.0 g, 82.0%) as a pale yellow solid. $^1$H NMR (400 MHz, DMSO-d6): δ 8.52-8.49 (m, 1H), 8.43 (s, 1H), 8.15 (d, J=8.0 Hz, 1H), 7.91-7.84 (m, 3H), 7.46-7.41 (m, 2H).

(3-aminophenyl)(4-fluorophenyl)methanone (IM)

To a stirred solution of compound IL (2.0 g, 8.16 mmol) in IPA (20 mL), iron powder (2.28 g, 40.81 mmol) and NH$_4$Cl (2.20 g, 40.81 mmol) in (20 mL) water were added and the reaction was stirred at 80° C. for 3 h. The progress of the reaction was monitored by TLC. After completion of the reaction, the reaction mixture was filtered, washed with MeOH and the filtrate was concentrated under reduced pressure. The residue was quenched with water and the product was extracted with EtOAc. The combined organic layer was washed with brine, dried over anhydrous Na$_2$SO$_4$ and concentrated under reduced pressure. The crude product was triturated with diethyl ether to afford IM (1.7 g, 96.0%) as a light yellow solid. $^1$H NMR (400 MHz, DMSO-d6): δ 7.80-7.77 (m, 2H), 7.39-7.35 (m, 2H), 7.19-7.15 (m, 1H), 6.92 (s, 1H), 6.84-6.79 (m, 2H), 5.40 (s, 2H).

N-(3-(4-fluorobenzoyl)phenyl)methanesulfonamide (IN)

To a stirred solution of compound IM (1.7 g, 7.90 mmol) in DCE (20 mL), pyridine (1.3 mL, 15.8 mmol) and mesyl chloride (0.9 mL, 11.86 mmol) were added at 0° C. and stirred for 2 h. The progress of the reaction was monitored by TLC. After completion of the reaction, the reaction mixture was quenched with water and the product was extracted with DCM. The combined organic layer was washed with brine, dried over anhydrous Na$_2$SO$_4$ and concentrated under reduced pressure. The crude product was purified by silica gel column chromatography using 30% EtOAc/hexane to afford IN (1.5 g, 65.0%) as an off-white semisolid. LC-MS: m/z 294.25 [M+H]$^+$.

N-(3-(amino(4-fluorophenyl)methyl)phenyl)methanesulfonamide (IO)

To a stirred solution of compound IN (1.5 g, 5.11 mmol) in MeOH (20 mL), ammonium acetate (7.8 g, 102.3 mmol) and NaBH$_3$CN (0.98 g, 15.35 mmol) were added and the reaction was stirred at 80° C. for 2 h. After completion of the reaction, the reaction mixture was concentrated under reduced pressure. The residue was diluted with water and the product was extracted with DCM.

The combined organic layer was washed with brine, dried over anhydrous Na$_2$SO$_4$ and concentrated under reduced pressure to afford IO (0.95 g, 63%) as a light brown semisolid. $^1$H NMR (400 MHz, DMSO-d6): δ 7.42-7.38 (m, 2H), 7.25-7.21 (m, 2H), 7.14-7.08 (m, 3H), 7.04-7.01 (m, 1H), 5.09-5.08 (m, 1H), 2.95 (s, 3H).

N-(3-(((5-cyanopyrimidin-2-yl)amino)(4-fluorophenyl)methyl)phenyl)methanesulfonamide (IP)

To a stirred solution of compound IO (0.91 g, 3.29 mmol) and 2-chloropyrimidine-5-carbonitrile (AF, 0.55 g, 3.95 mmol) in EtOH (10 mL), DIPEA (1.6 mL, 9.87 mmol) was added and the reaction was stirred at 90° C. for 12 h. The progress of the reaction was monitored by TLC. After completion of the reaction, the reaction mixture was concentrated under reduced pressure. The crude product was purified by silica gel column chromatography using 15% EtOAc/hexane to afford compound IP (0.7 g, 53.0%) as an off white semisolid. LC-MS: m/z 397.80 [M+H]$^+$.

N-(3-(((5-(1H-tetrazol-5-yl)pyrimidin-2-yl)amino)(4-fluorophenyl)methyl)phenyl)methanesulfonamide (IQ)

To a stirred solution of compound IP (600 mg, 1.51 mmol) in DMF (10 mL), NaN$_3$ (491 mg, 7.55 mmol), NH$_4$Cl (408 mg, 7.55 mmol) and LiCl (180 mg) were added and the reaction was stirred at 100° C. for 12 h. After completion of the reaction, the reaction mixture was concentrated under reduced pressure. The residue was quenched with ice water and acidified with 2N HCl solution to pH=4. The product was extracted with 10% MeOH in DCM. The combined organic layer was washed with brine, dried over anhydrous Na$_2$SO$_4$ and concentrated under reduced pressure to afford IQ (500 mg, 75.0%) as an off white solid. LC-MS: m/z 441.10 [M+H]$^+$.

N-(3-(((5-(5-(difluoromethyl)-1,3,4-oxadiazol-2-yl)pyrimidin-2-yl)amino)(4-fluorophenyl)methyl)phenyl)methanesulfonamide (128)

To a stirred solution of compound IQ (500 mg, 1.13 mmol) in DCM (10 mL), DFAA (1 mL) was added at 0° C. and the reaction was stirred at RT for 12 h. The progress of the reaction was monitored by TLC. After completion of the reaction, the reaction mixture was quenched with 10% NaHCO$_3$ solution and the product was extracted with DCM. The combined organic layer was washed with brine, dried over anhydrous Na$_2$SO$_4$ and concentrated under reduced pressure. The crude product was purified by silica gel column chromatography using 35% EtOAc/hexane to afford compound 128 (60 mg, 10.0%) as an off-white solid. $^1$H NMR (400 MHz, DMSO-d6): δ 9.72 (s, 1H), 9.23 (d, J=8.8 Hz, 1H), 8.90 (d, J=6.8 Hz, 2H), 7.64-7.38 (m, 3H), 7.29-7.25 (m, 1H), 7.18-7.14 (m, 3H), 7.08-7.05 (m, 2H), 6.44 (d, J=8.8 Hz, 1H), 2.95 (s, 3H); LC-MS: 491.15 [M+H]$^+$, HPLC: 97.13%.

Example 129

N-(4-(((5-(5-(difluoromethyl)-1,3,4-oxadiazol-2-yl)pyrimidin-2-yl)amino)(4-fluorophenyl)methyl)phenyl)methanesulfonamide (129)

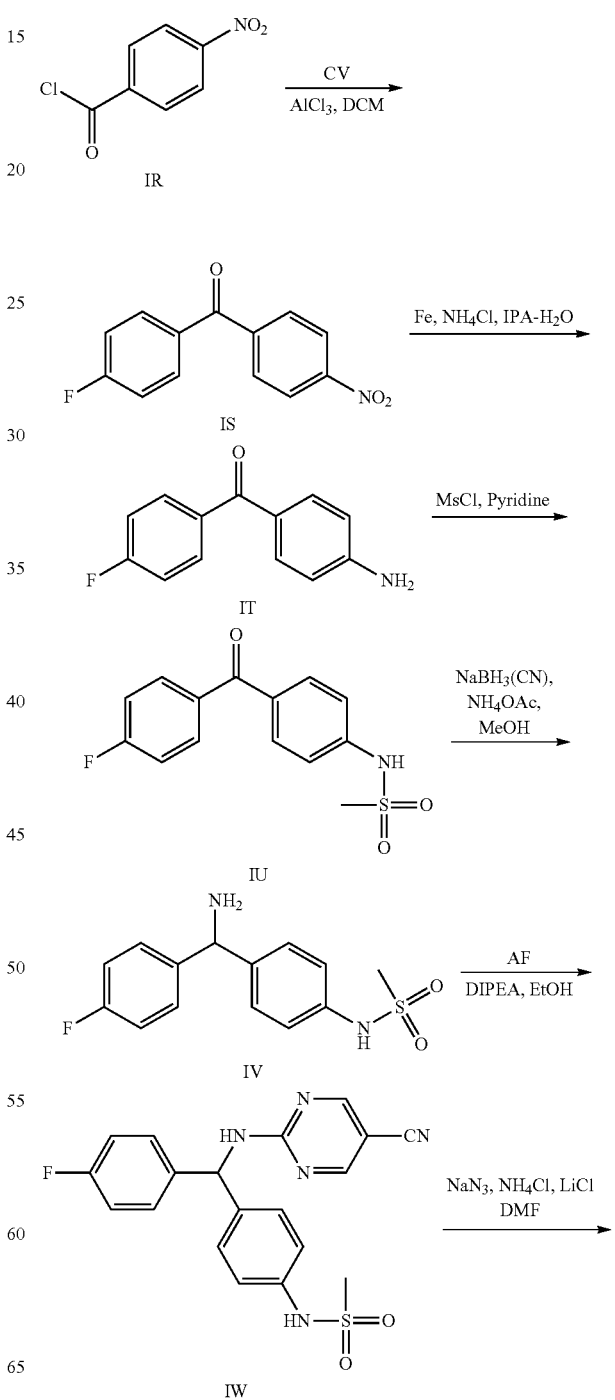

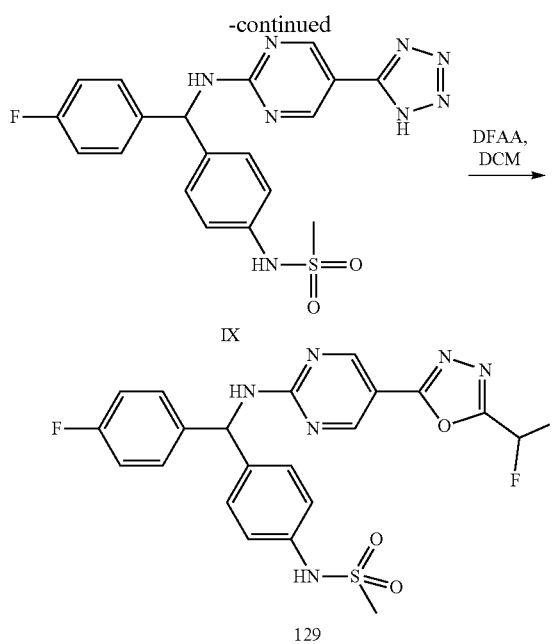

(4-fluorophenyl)(4-nitrophenyl)methanone (IS)

To a stirred solution of AlCl$_3$ (13.9 g, 104.1 mmol) in DCM (150 mL), 4-nitrobenzoyl chloride (IR, 14.5 g, 78.1 mmol) was added at 0° C. and stirred at RT for 1 h. To the resulting reaction mixture, fluorobenzene (CV, 5.0 g, 52.0 mmol) was added and the reaction was stirred at RT for 2 h. The progress of the reaction was monitored by TLC. After completion of the reaction, the reaction mixture was quenched with 1N HCl solution, neutralized with 2N NaOH solution and the product was extracted with EtOAc. The combined organic layer was washed with brine, dried over anhydrous Na$_2$SO$_4$ and concentrated under reduced pressure. The crude product was purified by silica gel column chromatography using 10% EtOAc/hexane to afford IS (5.0 g, 40.0%) as an off-white solid. $^1$H NMR (400 MHz, DMSO-d6): δ 8.38 (d, J=8.8 Hz, 2H), 7.96 (d, J=8.8 Hz, 2H), 7.89-7.86 (m, 2H), 7.46-7.41 (m, 2H).

(4-aminophenyl)(4-fluorophenyl)methanone (IT)

To a stirred solution of compound IS (5.0 g, 20.0 mmol) in IPA (30 mL), iron powder (5.7 g, 102.0 mmol) and NH$_4$Cl (5.5 g, 102.0 mmol) in water (30 mL) were added and the reaction was stirred at 80° C. for 3 h. The progress of the reaction was monitored by TLC. After completion of the reaction, the reaction mixture was filtered and the filtrate was concentrated under reduced pressure. The residue was diluted with water and the product was extracted with EtOAc. The combined organic layer was washed with brine, dried over anhydrous Na$_2$SO$_4$ and concentrated under reduced pressure. The crude product was purified by silica gel column chromatography using 10% EtOAc/hexane to afford IT (4.0 g, 92.0%) as a light yellow semisolid. $^1$H NMR (400 MHz, DMSO-d6): δ 7.69-7.65 (m, 2H), 7.51 (d, J=8.8 Hz, 2H), 7.34-7.30 (m, 2H), 6.60 (d, J=8.8 Hz, 2H), 6.17 (s, 2H).

N-(4-(4-fluorobenzoyl)phenyl)methanesulfonamide (IU)

To a stirred solution of compound IT (4.6 g, 21.39 mmol) in pyridine (60 mL), mesyl chloride (1.7 mL, 32.0 mmol) was added at 0° C. and stirred at RT for 4 h. The progress of the reaction was monitored by TLC. After completion of the reaction, the reaction mixture was quenched with water and the product was extracted with EtOAc. The combined organic layer was washed with brine, dried over anhydrous Na$_2$SO$_4$ and concentrated under reduced pressure. The crude product was purified by silica gel column chromatography using 10% EtOAc/hexane to afford IU (4.4 g, 71.0%) as an off-white solid. $^1$H NMR (400 MHz, DMSO-d6): δ 10.38 (s, 1H), 7.81-7.73 (m, 4H), 7.40-7.32 (m, 4H), 3.13 (s, 3H); LC-MS: m/z 294.05 [M+H]$^+$.

N-(4-(amino(4-fluorophenyl)methyl)phenyl)methanesulfonamide (IV)

To a stirred solution of compound IU (1.0 g, 3.4 mmol) in MeOH (10 mL), ammonium acetate (5.25 g, 68.0 mmol), NaBH$_3$CN (0.59 g, 9.2 mmol) were added and the reaction was stirred at 80° C. for 16 h. After completion of the reaction, the reaction mixture was concentrated under reduced pressure. The residue was quenched with 1N NaOH solution and extracted with EtOAc. The combined organic layer was washed with brine, dried over anhydrous Na$_2$SO$_4$ and concentrated under reduced pressure. The crude product was purified by silica gel column chromatography using 5% MeOH/DCM to afford IV (0.8 g, 80%) as a light brown semisolid. $^1$H NMR (400 MHz, DMSO-d6): δ 7.44-7.34 (m, 4H), 7.17-7.13 (m, 4H), 5.24 (s, 1H), 2.95 (s, 3H).

N-(4-(((5-cyanopyrimidin-2-yl)amino)(4-fluorophenyl)methyl)phenyl)methanesulfonamide (IW)

To a stirred solution of compound IV (0.8 g, 2.70 mmol) and 2-chloropyrimidine-5-carbonitrile (AF, 0.38 g, 2.70 mmol) in EtOH (15 mL), DIPEA (1.5 mL, 8.10 mmol) was added and the reaction was stirred at 90° C. for 16 h. The progress of the reaction was monitored by TLC. After completion of the reaction, the reaction mixture was concentrated under reduced pressure. The crude product was purified by silica gel column chromatography using 5% MeOH/DCM to afford compound IW (0.6 g, 56.0%) as an off-white semisolid. LC-MS: m/z 398.15 [M+H]$^+$.

N-(4-(((5-(1H-tetrazol-5-yl)pyrimidin-2-yl)amino)(4-fluorophenyl)methyl)phenyl)methanesulfonamide (IX)

To a stirred solution of compound IW (600 mg, 1.51 mmol) in DMF (15 mL), NaN$_3$ (491 mg, 7.55 mmol), NH$_4$Cl (408 mg, 7.55 mmol) and LiCl (80 mg) were added and the reaction was stirred at 100° C. for 16 h. After completion of the reaction, the reaction mixture was concentrated under reduced pressure. The residue was quenched with ice water and acidified with 2N HCl solution to pH=2. The precipitated solid was filtered, washed with cold water and dried to afford IX (600 mg, 90.0%) as an off-white solid. LC-MS: m/z 441.15 [M+H]$^+$.

N-(4-(((5-(5-(difluoromethyl)-1,3,4-oxadiazol-2-yl)pyrimidin-2-yl)amino)(4-fluorophenyl)methyl)phenyl)methanesulfonamide (129)

To a stirred solution of compound IX (650 mg, 1.5 mmol) in DCM (15 mL), DFAA (385 mg, 2.2 mmol) was added at 0° C. and the reaction was stirred at RT for 16 h. The progress of the reaction was monitored by TLC. After completion of the reaction, the reaction mixture was quenched with 10% NaHCO₃ solution and the product was extracted with DCM. The combined organic layer was washed with brine, dried over anhydrous Na₂SO₄ and concentrated under reduced pressure. The crude product was purified by silica gel column chromatography using 50% EtOAc/hexane to afford compound 129 (200 mg, 28.0%) as an off-white solid. ¹H NMR (400 MHz, DMSO-d6): δ 9.69 (s, 1H), 9.16 (d, J=8.8 Hz, 1H), 8.87 (d, J=6.0 Hz, 2H), 7.62-7.36 (m, 3H), 7.33-7.31 (m, 2H), 7.15-7.11 (m, 4H), 6.44 (d, J=8.8 Hz, 1H), 2.93 (s, 3H); LC-MS: 491.15 [M+H]⁺. HPLC: 98.91%.

Example 130

N-(2-(((5-(5-(difluoromethyl)-1,3,4-oxadiazol-2-yl)pyrimidin-2-yl)amino)(4-fluorophenyl)methyl)phenyl)methanesulfonamide (130)

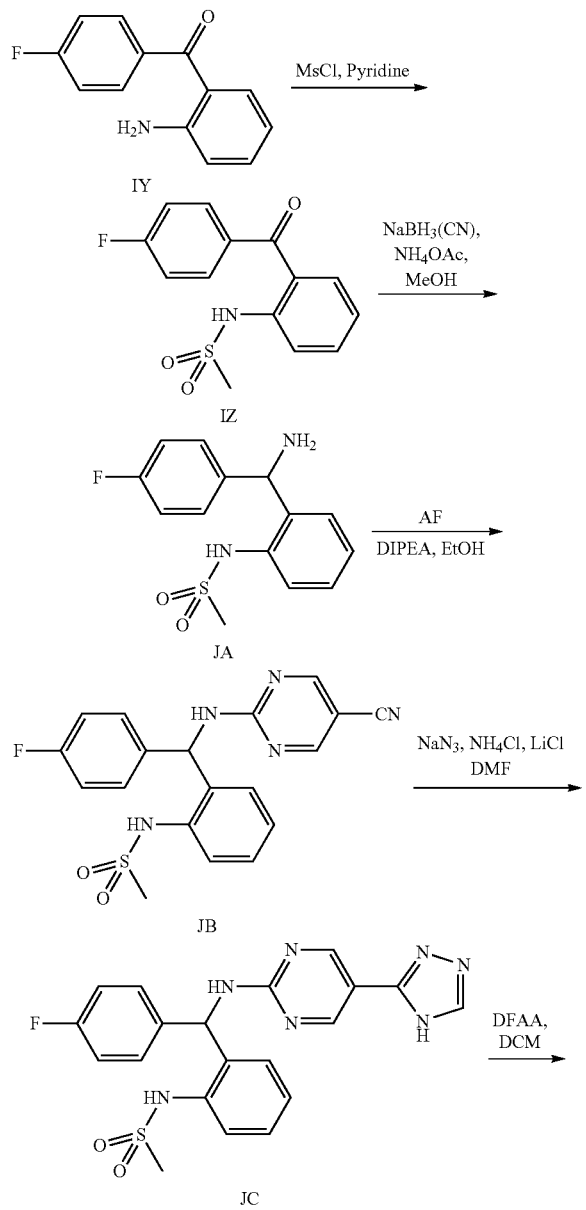

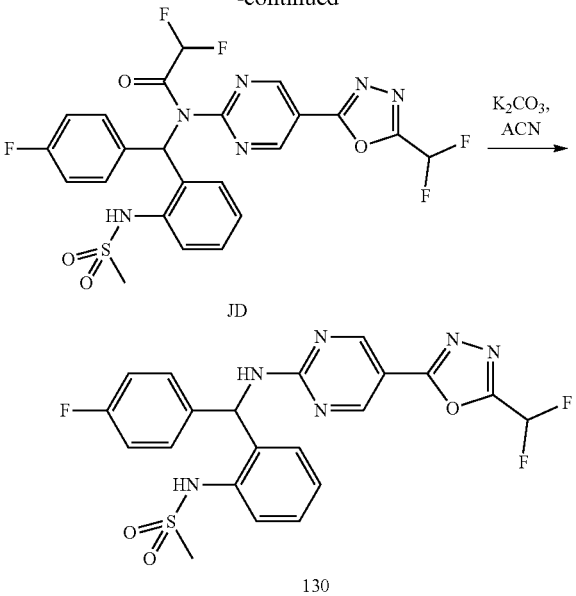

N-(2-(4-fluorobenzoyl)phenyl)methanesulfonamide (IZ)

To a stirred solution of (2-aminophenyl)(4-fluorophenyl)methanone (IY, 5.0 g, 23.25 mmol) in pyridine (25 mL), mesyl chloride (1.8 mL, 23.25 mmol) was added at 0° C. and the reaction was stirred at RT for 4 h. The progress of the reaction was monitored by TLC. After completion of the reaction, the reaction mixture was quenched with water and the product was extracted with EtOAc. The combined organic layer was washed with brine, dried over anhydrous Na₂SO₄ and concentrated under reduced pressure. The crude product was purified by silica gel column chromatography using 20% EtOAc/hexane to afford IZ (3.0 g, 22.0%) as a light brown thick oil. ¹H NMR (400 MHz, DMSO-d6): δ 9.63 (s, 1H), 7.78-7.73 (m, 2H), 7.65-7.61 (m, 1H), 7.54-7.52 (m, 1H), 7.46-7.43 (m, 1H), 7.39-7.30 (m, 3H), 3.00 (s, 3H).

N-(2-(amino(4-fluorophenyl)methyl)phenyl)methanesulfonamide (JA)

To a stirred solution of compound IZ (1.5 g, 5.11 mmol) in MeOH (15 mL), ammonium acetate (7.88 g, 102.3 mmol) and NaBH₃CN (0.82 g, 12.8 mmol) were added and the reaction was stirred at 80° C. for 16 h. After completion of the reaction, the reaction mixture was concentrated under reduced pressure. The residue was quenched with 1N NaOH solution and the product was extracted with EtOAc. The combined organic layer was washed with brine, dried over anhydrous Na₂SO₄ and concentrated under reduced pressure to afford JA (1.0 g, crude) as a light yellow sticky solid. ¹H NMR (400 MHz, DMSO-d6): δ 7.48-7.21 (m, 4H), 7.19-6.97 (m, 4H), 5.55 (s, 1H), 2.80 (s, 3H).

N-(2-(((5-cyanopyrimidin-2-yl)amino)(4-fluorophenyl)methyl)phenyl)methanesulfonamide (JB)

To a stirred solution of compound JA (0.5 g, 1.70 mmol) and 2-chloropyrimidine-5-carbonitrile (AF, 0.23 g, 1.70 mmol) in EtOH (10 mL), DIPEA (0.89 mL, 8.10 mmol) was added and the reaction was stirred at 90° C. for 8 h. The progress of the reaction was monitored by TLC. After completion of the reaction, the reaction mixture was concentrated under reduced pressure. The crude product was purified by silica gel column chromatography using 50% EtOAc/hexane to afford compound JB (0.35 g, 52.0%) as a light yellow semisolid. LC-MS: m/z 398.10 [M+H]+.

N-(2-(((5-(1H-tetrazol-5-yl)pyrimidin-2-yl)amino)(4-fluorophenyl)methyl)phenyl)methanesulfonamide (JC)

To a stirred solution of compound JB (350 mg, 0.88 mmol) in DMF (7 mL), NaN$_3$ (171 mg, 2.64 mmol), NH$_4$Cl (142 mg, 2.64 mmol) and LiCl (37 mg) were added and the reaction was stirred at 100° C. for 16 h. After completion of the reaction, the reaction mixture was concentrated under reduced pressure. The residue was quenched with ice water and acidified with 2N HCl solution till pH=2. The precipitated solid was filtered, washed with cold water and dried to afford JC (350 mg, 91.0%) as an off-white solid. LC-MS: m/z 441.10 [M+H]+.

N-(5-(5-(difluoromethyl)-1,3,4-oxadiazol-2-yl)pyrimidin-2-yl)-2,2-difluoro-N-((4-fluorophenyl)(2-(methylsulfonamido)phenyl)methyl)acetamide (JD)

To a stirred solution of compound JC (350 mg, 0.79 mmol) in DCM (5 mL), DFAA (207 mg, 1.19 mmol) was added at 0° C. and the reaction was stirred at RT for 8 h. The progress of the reaction was monitored by TLC. After completion of the reaction, the reaction mixture was quenched with water and the product was extracted with 10% MeOH/DCM. The combined organic layer was washed with brine, dried over anhydrous Na$_2$SO$_4$ and concentrated under reduced pressure. The crude product was purified by silica gel column chromatography using 40% EtOAc/hexane to afford compound JD (300 mg, 67.0%) as an off-white solid. LC-MS: 569.10 [M+H]+.

N-(2-(((5-(5-(difluoromethyl)-1,3,4-oxadiazol-2-yl)pyrimidin-2-yl)amino)(4-fluorophenyl)methyl)phenyl)methanesulfonamide (130)

To a stirred solution of compound JD (300 mg, 0.52 mmol) in ACN (5 mL), K$_2$CO$_3$ (145 mg, 1.05 mmol) was added at 0° C. and the reaction was stirred at 80° C. for 16 h. The progress of the reaction was monitored by TLC. After completion of the reaction, the reaction mixture was filtered. The filtrate was diluted with water and the product extracted with EtOAc. The combined organic layer was washed with brine, dried over anhydrous Na$_2$SO$_4$ and concentrated under reduced pressure. The crude product was purified by silica gel column chromatography using 30% EtOAc/hexane to afford 130 (50 mg, 20.0%) as an off-white solid. $^1$H NMR (400 MHz, DMSO-d6): δ 9.32 (s, 1H), 9.00 (d, J=8.4 Hz, 1H), 8.89 (m, 2H), 7.65-7.25 (m, 7H), 7.17-7.13 (m, 2H), 6.98 (d, J=8.8 Hz, 1H), 2.90 (s, 3H); LC-MS: 491.15 [M+H]+; HPLC: 96.94%.

Example 131

N-(2-(2-((5-(5-(difluoromethyl)-1,3,4-oxadiazol-2-yl)pyrimidin-2-yl)amino)-2-(4-fluorophenyl)ethyl)phenyl)methanesulfonamide (131)

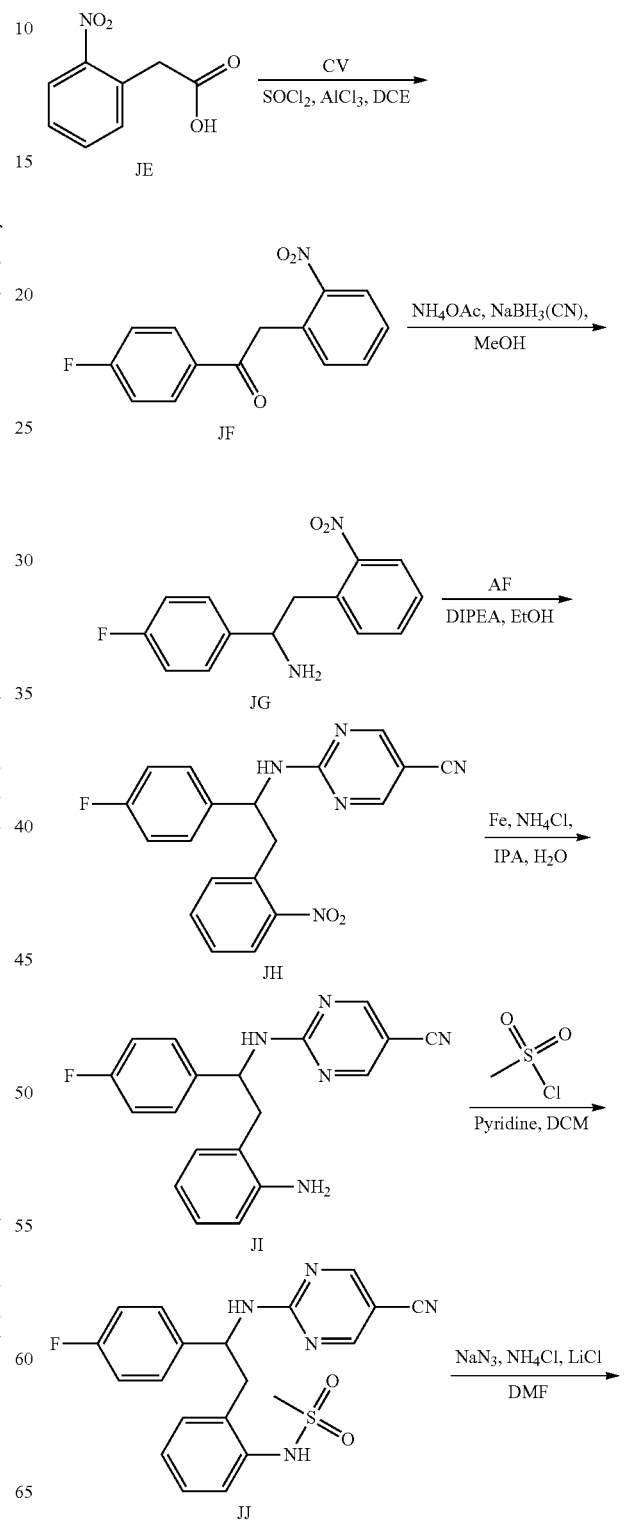

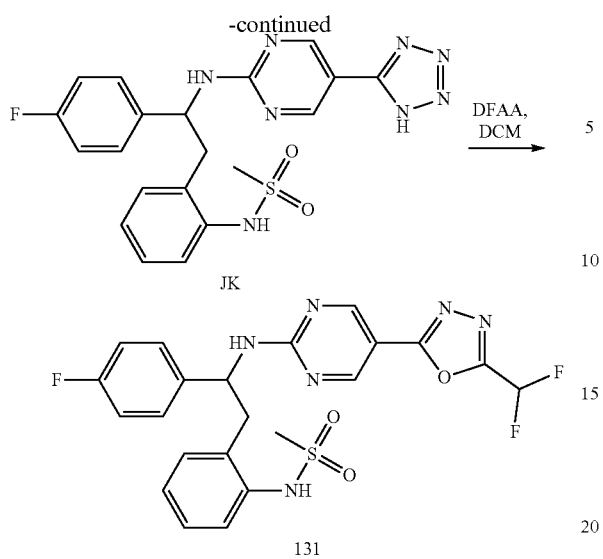

1-(4-fluorophenyl)-2-(2-nitrophenyl)ethan-1-one (JF)

To a stirred solution of 2-(2-nitrophenyl)acetic acid (JE, 2.0 g, 11.04 mmol) in DCE (10 mL) was added thionyl chloride (1.56 g, 13.25 mmol) at 0° C. and the reaction mixture was stirred at 70° C. for 4 h. To the resulting reaction mixture, AlCl$_3$ (1.5 g, 11.04 mmol) was added followed by fluorobenzene (CV, 10 mL) at 0° C. and the reaction mixture was stirred at 40° C. for 1 h. The progress of the reaction was monitored by TLC. After completion of the reaction, the reaction mixture was quenched with ice cold water and the product was extracted with DCM. The combined organic layer was washed with brine, dried over anhydrous Na$_2$SO$_4$ and concentrated under reduced pressure. The crude product was purified by silica gel column chromatography using 10% EtOAc/hexane to afford compound JF (0.5 g, 20.0%) as a light brown solid. $^1$H NMR (400 MHz, DMSO-d6): δ 8.16-8.10 (m, 3H), 7.74 (t, J=7.4 Hz, 1H), 7.60-7.54 (m, 2H), 7.40 (t, J=8.8 Hz, 2H) 4.87 (s, 2H); LC-MS: m/z 260.00 [M+H]$^+$.

1-(4-fluorophenyl)-2-(2-nitrophenyl)ethan-1-amine (JG)

To a stirred solution of compound JF (1.3 g, 5.01 mmol) in MeOH (20 mL) was added ammonium acetate (7.7 g, 100.38 mmol) and the reaction mixture was stirred at RT for 30 min. Then NaBH$_3$CN (0.8 g, 12.54 mmol) was added and the reaction mixture was stirred at 80° C. for 16 h. After completion of the reaction, the reaction mixture was concentrated under reduced pressure. The residue was diluted with EtOAc and washed with saturated NaHCO$_3$ solution. The organic layer was dried over anhydrous Na$_2$SO$_4$ and concentrated under reduced pressure to afford JG (0.8 g, 61.5%) as a light yellow sticky solid. $^1$H NMR (400 MHz, DMSO-d6): δ 7.88 (d, J=8.0 Hz, 1H), 7.57 (t, J=7.6 Hz, 1H), 7.44 (t, J=7.6 Hz, 1H), 7.31 (t, J=7.2 Hz, 3H), 7.11 (t, J=8.8 Hz, 2H), 4.20 (t, J=7.0 Hz, 1H), 3.25-3.15 (m, 2H); LC-MS: m/z 260.80 [M+H]$^+$.

2-((1-(4-fluorophenyl)-2-(2-nitrophenyl)ethyl)amino)pyrimidine-5-carbonitrile (JH)

To a stirred solution of compound JG (0.8 g, 3.07 mmol) in EtOH (15 mL) was added DIPEA (1.6 mL, 9.23 mmol) followed by 2-chloropyrimidine-5-carbonitrile (5, 0.51 g, 3.69 mmol) and the reaction mixture was stirred at 90° C. for 8 h. The progress of reaction was monitored by TLC. After completion of the reaction, the reaction mixture was concentrated under reduced pressure. The crude product was purified by silica gel column chromatography using 30% EtOAc/hexane to afford compound JH (0.7 g, 63.0%) as an off white solid. $^1$H NMR (400 MHz, DMSO-d6): δ 8.53 (brs, 1H), 8.47 (brs, 1H), 7.90 (d, J=8.0 Hz, 1H), 7.55 (t, J=7.4 Hz, 1H), 7.48-7.37 (m, 4H), 7.12 (t, J=8.8 Hz, 2H), 5.44-5.40 (m, 1H), 3.41-3.35 (m, 1H), 3.28-3.22 (m, 1H); LC-MS: m/z 364.10 [M+H]$^+$.

2-((2-(2-aminophenyl)-1-(4-fluorophenyl)ethyl)amino)pyrimidine-5-carbonitrile (JI)

To a stirred solution of compound JH (0.7 g, 1.92 mmol) in IPA (10 mL) was added NH$_4$Cl (0.52 g, 9.64 mmol) dissolved in water (10 mL) followed by iron powder (0.54 g, 9.64 mmol) at RT and the reaction mixture was stirred at 80° C. for 8 h. The progress of the reaction was monitored by TLC. After completion of the reaction, the reaction mixture was filtered. The filtrate was concentrated under reduced pressure. The residue was suspended in water and the product was extracted with EtOAc. The combined organic layer was dried over anhydrous Na$_2$SO$_4$ and concentrated under reduced pressure to afford compound JI (0.5 g, 78.0%) as a light brown solid which was used as such for the next step. $^1$H NMR (400 MHz, DMSO-d6): δ 8.81 (d, J=8.4 Hz, 1H), 8.58 (d, J=2.8 Hz, 2H), 7.45-7.42 (m, 2H), 7.13-7.08 (m, 2H), 6.87-6.82 (m, 2H), 6.59 (d, J=8.0 Hz, 1H), 6.40-6.37 (m, 1H), 5.32-5.28 (m, 1H), 4.94 (s, 2H), 3.03-2.97 (m, 1H), 2.86-2.81 (m, 1H); LC-MS: m/z 334.40 [M+H]$^+$.

N-(2-(2-((5-cyanopyrimidin-2-yl)amino)-2-(4-fluorophenyl)ethyl)phenyl)methanesulfonamide (JJ)

To a stirred solution of compound JI (0.05 g, 0.15 mmol) in DCM (2 mL) was added pyridine (0.035 g, 0.45 mmol) followed by mesyl chloride (0.02 g, 0.18 mmol) at 0° C. and the reaction mixture was stirred at 0° C. for 2 h. The progress of the reaction was monitored by TLC. After completion of the reaction, the reaction mixture was quenched with water and the product was extracted with EtOAc. The combined organic layer was dried over anhydrous Na$_2$SO$_4$ and concentrated under reduced pressure. The crude product was purified by silica gel column chromatography using 30-50% EtOAc/hexane to afford compound JJ (0.03 g, 48.5%) as an off white solid. $^1$H NMR (400 MHz, DMSO-d6): δ 9.18 (s, 1H), 8.83 (d, J=8.8 Hz, 1H), 8.60-8.55 (m, 2H), 7.44-7.41 (m, 2H), 7.28-7.23 (m, 2H), 7.18-7.06 (m, 4H), 5.39-5.33 (s, 1H), 3.24-3.10 (m, 2H), 2.99 (s, 3H).

N-(2-((5-(1H-tetrazol-5-yl)pyrimidin-2-yl)amino)-2-(2,4-difluorophenyl)ethyl)methanesulfonamide (JK)

To a stirred solution of compound JJ (0.3 g, 0.73 mmol) in DMF (5 mL) was added NaN$_3$ (0.14 g, 2.18 mmol), NH$_4$Cl (0.12 g, 2.18 mmol) followed by LiCl (0.03 g, 0.73 mmol) and the reaction mixture was stirred at 100° C. for 16 h. Progress of the reaction was monitored by TLC. After completion of the reaction, the reaction mixture was concentrated under reduced pressure. The residue was quenched with ice water and acidified with 1N HCl solution. The precipitated solid was filtered and dried under vacuum to yield compound JK (0.3 g, 90.6%) as an off white solid. $^1$H NMR (400 MHz, DMSO-d6): δ 9.29 (s, 1H), 8.79 (s, 1H), 8.40 (d, J=8.4 Hz, 1H), 7.51-7.48 (m, 2H), 7.33-7.28 (m, 2H), 7.21-7.09 (m, 4H), 5.40-5.38 (m, 1H), 3.42-3.31 (brs, 2H), 3.21 (d, J=6.8 Hz, 2H), 3.04 (s, 3H); LC-MS: m/z 455.50 [M+H]$^+$.

N-(2-(2-((5-(5-(difluoromethyl)-1,3,4-oxadiazol-2-yl)pyrimidin-2-yl)amino)-2-(4-fluorophenyl)ethyl)phenyl)methanesulfonamide (131)

To a stirred solution of compound JK (0.3 g, 0.66 mmol) in DCM (5 mL) was added DFAA (0.17 g, 0.99 mmol) at 0° C. and the reaction was stirred at RT for 8 h. The progress of reaction was monitored by TLC. After completion of the reaction, the reaction mixture was quenched with water and the product was extracted with 10% MeOH-DCM. The combined organic layer was dried over anhydrous Na$_2$SO$_4$ and concentrated under reduced pressure. The crude compound was purified by silica gel column chromatography using 40-50% EtOAc/hexane to afford 131 (0.1 g, 30.0%) as an off white solid. $^1$H NMR (400 MHz, DMSO-d6): δ 9.25 (s, 1H), 8.81-8.77 (m, 3H), 7.62-7.37 (m, 3H), 7.32-7.25 (m, 2H), 7.20-7.08 (m, 4H), 5.45-5.39 (m, 1H), 3.33-3.16 (m, 2H), 3.04 (s, 3H); LC-MS: m/z 505.10 [M+H]$^+$, HPLC: 99.60%.

Example 132

N-(3-(2-((5-(5-(difluoromethyl)-1,3,4-oxadiazol-2-yl)pyrimidin-2-yl)amino)-2-(4-fluorophenyl)ethyl)phenyl)methanesulfonamide (132)

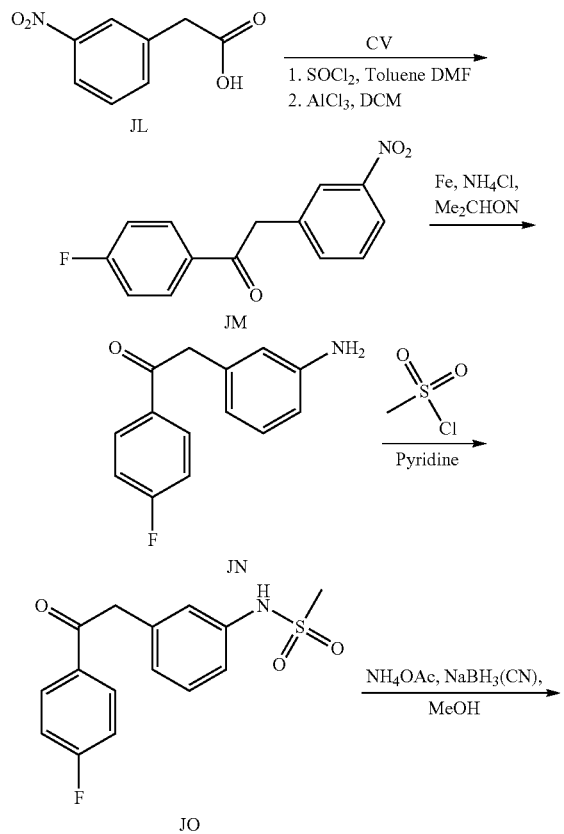

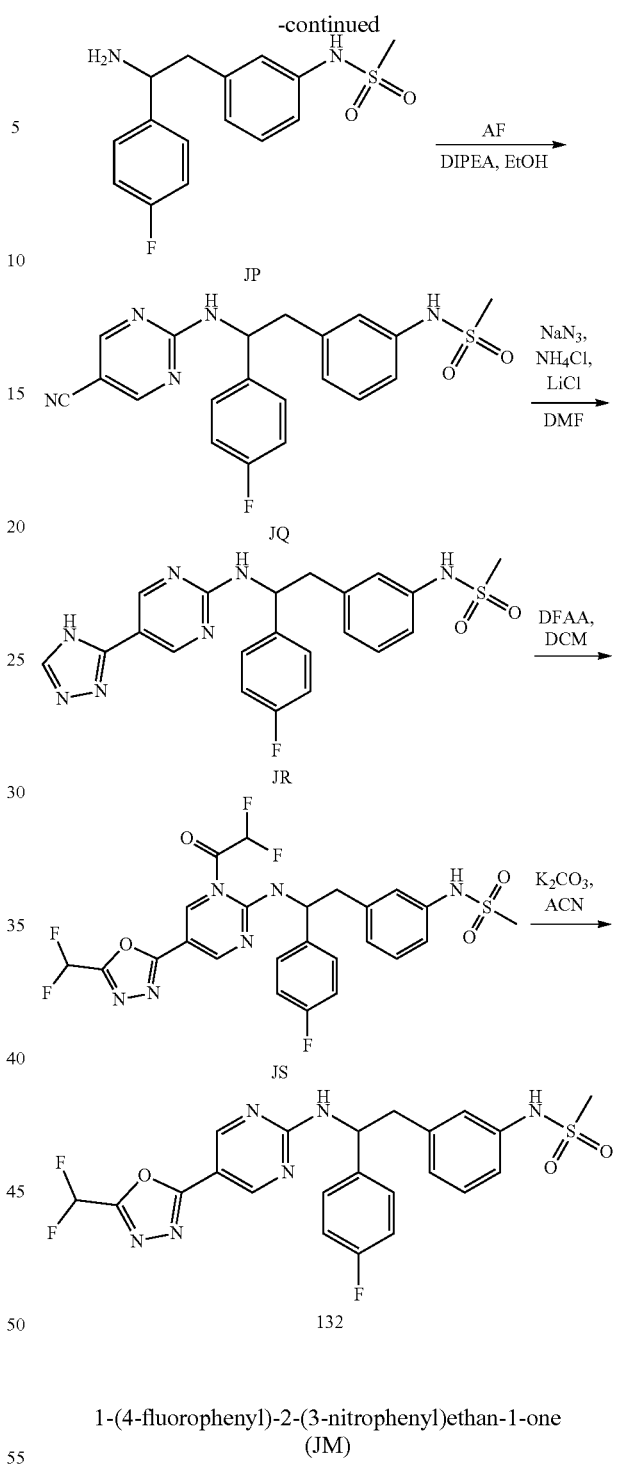

1-(4-fluorophenyl)-2-(3-nitrophenyl)ethan-1-one (JM)

To a stirred solution of 2-(3-nitrophenyl)acetic acid (JL, 5.0 g, 27.60 mmol) in DCE (20 mL) was added thionyl chloride (5.01 g, 42.51 mmol) at 0° C. and the reaction mixture was stirred at 80° C. for 1 h. To the resulting reaction mixture, AlCl$_3$ (4.0 g, 30.36 mmol) was added at 0° C. followed by fluorobenzene (CV, 3.9 g, 41.41 mmol) and the reaction mixture was stirred at 60° C. for 2 h. The progress of the reaction was monitored by TLC. After completion of the reaction, the reaction mixture was concentrated under reduced pressure. The residue was quenched with ice cold water and the product was extracted with DCM. The combined organic layer was dried over anhydrous $Na_2SO_4$ and concentrated under reduced pressure. The crude product was purified by silica gel column chromatography using 12% EtOAc/hexane to afford compound JM (4.0 g, 56.0%) as a white solid.

2-(3-aminophenyl)-1-(4-fluorophenyl)ethan-1-one (JN)

To a stirred solution of compound JM (3.0 g, 11.58 mmol) in IPA:water (1:1, 30 mL) was added $NH_4Cl$ (3.1 g, 57.91 mmol) followed by iron powder (3.2 g, 57.91 mmol) at RT and the reaction mixture was stirred at 80° C. for 3 h. The progress of the reaction was monitored by TLC. After completion of the reaction, the reaction mixture was filtered and the filtrate was concentrated under reduced pressure. The residue was suspended in water and the product was extracted with EtOAc. The combined organic layer was dried over anhydrous $Na_2SO_4$ and concentrated under reduced pressure. The crude compound was purified by silica gel column chromatography using 50-60% EtOAc/hexane to afford compound JN (1.8 g, 68.0%) as a light brown liquid. $^1H$ NMR (400 MHz, DMSO-d6): δ 8.10-8.07 (m, 2H), 7.33 (t, J=9.0 Hz, 2H), 6.93 (t, J=7.4 Hz, 1H), 6.45-6.36 (m, 3H), 5.02 (s, 2H), 4.15 (s, 2H); LC-MS: m/z 230.20 $[M+H]^+$.

N-(3-(2-(4-fluorophenyl)-2-oxoethyl)phenyl)methanesulfonamide (JO)

To a stirred solution of compound JN (2.3 g, 10.04 mmol) in pyridine (30 mL) was added mesyl chloride (2.3 g, 20.08 mmol) at 0° C. and the reaction mixture was stirred at 0° C. for 1 h. The progress of the reaction was monitored by TLC. After completion of the reaction, the reaction mixture was concentrated under reduced pressure. The residue was quenched with water and the product was extracted with EtOAc. The combined organic layer was dried over anhydrous $Na_2SO_4$ and concentrated under reduced pressure. The crude product was purified by silica gel column chromatography using 15% EtOAc/hexane to afford compound JO (3.2 g, 95.5%) as a brown liquid. $^1H$ NMR (400 MHz, DMSO-d6): δ 9.71 (brs, 1H), 8.14-8.10 (m, 2H), 7.36 (t, J=8.8 Hz, 2H), 7.27 (t, J=7.6 Hz, 1H), 7.10-7.07 (m, 2H), 7.00 (d, J=7.2 Hz, 1H), 4.38 (s, 2H), 2.96 (s, 3H); LC-MS: m/z 308.05 $[M+H]^+$.

N-(3-(2-amino-2-(4-fluorophenyl)ethyl)phenyl)methanesulfonamide (JP)

To a stirred solution of compound JO (1.0 g, 3.25 mmol) in MeOH (20 mL) was added ammonium acetate (5.0 g, 65.14 mmol) at 0° C. and the reaction mixture was stirred 0° C. for 1 h. To the resulting reaction mixture, $NaBH_3CN$ (0.55 g, 8.79 mmol) was added and the reaction mixture was stirred at 80° C. for 8 h. After completion of the reaction, the reaction mixture was concentrated under reduced pressure. The residue was quenched with 10% NaOH solution and the product was extracted with EtOAc. The combined organic layer was dried over anhydrous $Na_2SO_4$ and concentrated under reduced pressure. The crude product was purified by silica gel column chromatography using 60-100% EtOAc/hexane to afford compound JP (0.75 g, 75.0%) as a brown liquid. LC-MS: m/z 309.00 $[M+H]^+$.

N-(3-(2-((5-cyanopyrimidin-2-yl)amino)-2-(4-fluorophenyl)ethyl)phenyl)methanesulfonamide (JQ)

To a stirred solution of compound JP (0.75 g, 2.43 mmol) in EtOH (20 mL) was added DIPEA (1.8 mL, 9.74 mmol) followed by 2-chloropyrimidine-5-carbonitrile (AF, 0.41 g, 2.92 mmol) and the reaction mixture was stirred at 90° C. for 16 h. The progress of the reaction was monitored by TLC. After completion of the reaction, the reaction mixture was concentrated under reduced pressure. The crude product was purified by silica gel column chromatography using 30% EtOAc/hexane to afford compound JQ (0.5 g, 50.0%) as a yellow liquid. $^1H$ NMR (400 MHz, DMSO-d6): δ 9.61 (s, 1H), 8.96 (d, J=8.8 Hz, 1H), 8.59 (s, 2H), 7.45-7.42 (m, 2H), 7.21-7.09 (m, 4H), 7.03-6.96 (m, 2H), 5.31-5.25 (m, 1H), 3.14-3.08 (m, 1H), 3.02-3.01 (m, 1H), 2.87 (s, 3H); LC-MS: m/z 412.15 $[M+H]^+$.

N-(3-(2-((5-(1H-tetrazol-5-yl)pyrimidin-2-yl)amino)-2-(4-fluorophenyl)ethyl)phenyl)methanesulfonamide (JR)

To a stirred solution of compound JQ (0.45 g, 1.09 mmol) in DMF (12 mL) was added $NaN_3$ (0.36 g, 5.47 mmol), $NH_4Cl$ (0.30 g, 5.47 mmol) followed by LiCl (0.1 g) and the reaction mixture was stirred at 100° C. for 16 h. Progress of the reaction was monitored by TLC. After completion of the reaction, the reaction mixture was concentrated under reduced pressure. The residue was quenched with ice water and acidified with 1N HCl solution. The precipitated solid was filtered and dried under vacuum to yield compound JR (0.4 g, 80.5%) as a brown liquid. LC-MS: m/z 455.15 $[M+H]^+$.

N-(5-(5-(difluoromethyl)-1,3,4-oxadiazol-2-yl)pyrimidin-2-yl)-2,2-difluoro-N-(1-(4-fluorophenyl)-2-(3-(methylsulfonamido)phenyl)ethyl)acetamide (JS)

To a stirred solution of compound JR (0.4 g, 0.88 mmol) in DCM (15 mL) was added DFAA (0.31 g, 1.76 mmol) at 0° C. and the reaction was stirred at RT for 16 h. The progress of reaction was monitored by TLC. After completion of the reaction, the reaction mixture was quenched with water and the product was extracted with DCM. The organic layer was dried over anhydrous $Na_2SO_4$ and concentrated under reduced pressure. The crude compound was purified by silica gel column chromatography using 36% EtOAc/hexane to afford compound JS (0.185 g, 42.0%) as a light brown solid. LC-MS: m/z 583.35 $[M+H]^+$.

N-(3-(2-((5-(5-(difluoromethyl)-1,3,4-oxadiazol-2-yl)pyrimidin-2-yl)amino)-2-(4-fluorophenyl)ethyl)phenyl)methanesulfonamide (132)

To a stirred solution of compound JS (0.18 g, 0.31 mmol) in ACN (10 mL) was added $K_2CO_3$ (0.43 g, 3.09 mmol) and the reaction was stirred at 80° C. for 5 h. The progress of reaction was monitored by TLC. After completion of the reaction, the reaction mixture was cooled to RT and the solids were filtered. The filtrate was concentrated under reduced pressure. The residue was diluted with water and the product was extracted with EtOAc. The combined organic layer was dried over anhydrous $Na_2SO_4$ and concentrated under reduced pressure. The crude product was purified by silica gel column chromatography using 25-30% EtOAc/hexane to afford 132 (0.06 g, 38.5%) as an off white solid. $^1H$ NMR (400 MHz, DMSO-d6): δ 9.61 (s, 1H), 8.89 (d, J=8.8 Hz, 1H), 8.78 (d, J=11.6 Hz, 2H), 7.63-7.37 (m, 3H), 7.22-7.12 (m, 4H), 7.05 (d, J=7.6 Hz, 1H), 6.98 (d, J=8.0 Hz, 1H), 5.38-5.32 (m, 1H), 3.16-3.11 (m, 1H), 3.04-2.99 (m, 1H), 2.87 (s, 3H); LC-MS: m/z 505.20 $[M+H]^+$; HPLC: 95.24%.

Example 133

N-(4-(2-((5-(5-(difluoromethyl)-1,3,4-oxadiazol-2-yl)pyrimidin-2-yl)amino)-2-(4-fluorophenyl)ethyl)phenyl)methanesulfonamide (133)

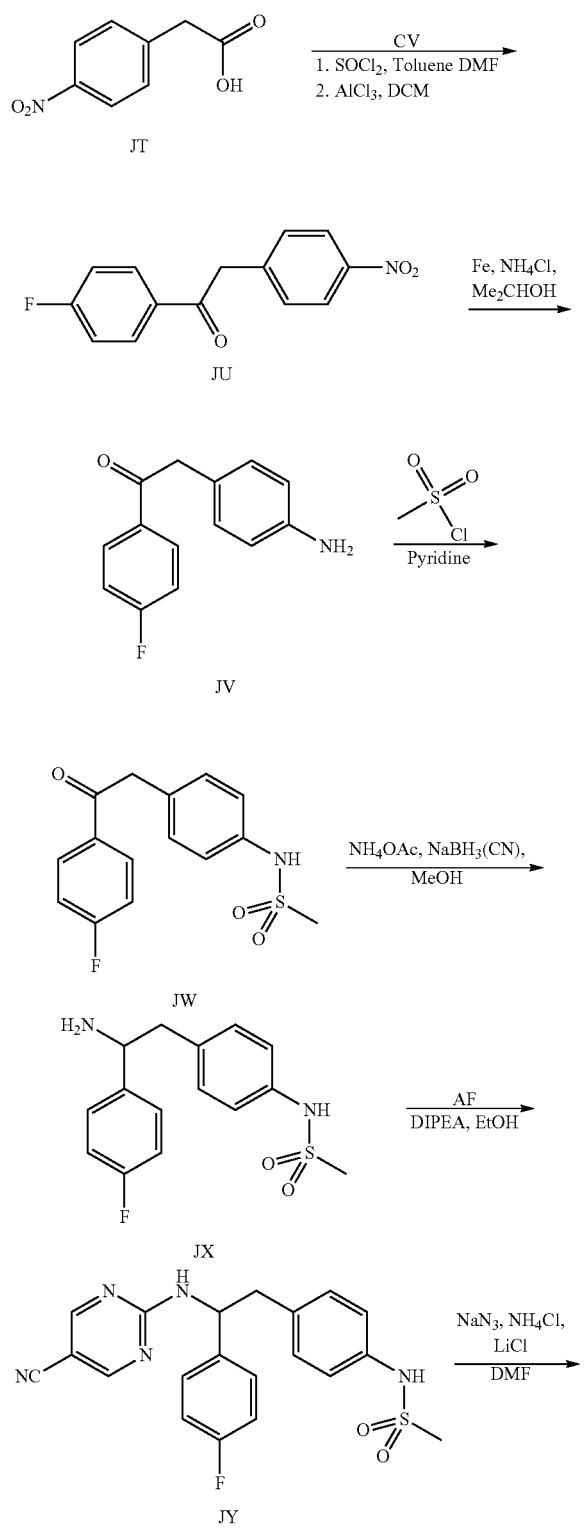

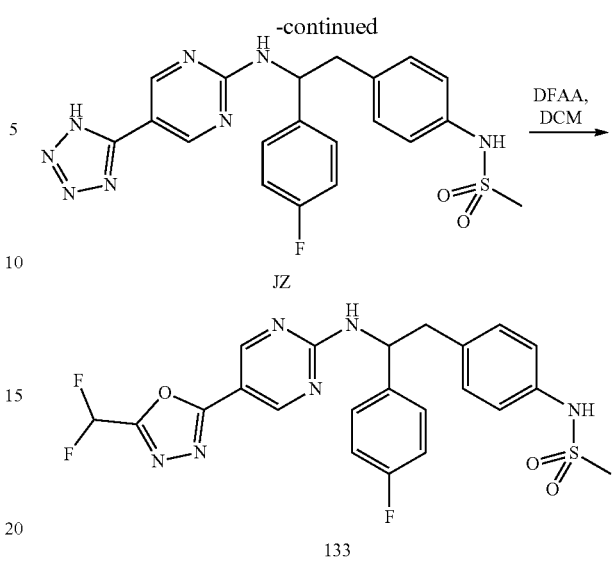

1-(4-fluorophenyl)-2-(4-nitrophenyl)ethan-1-one (JU)

To a stirred solution of 2-(4-nitrophenyl)acetic acid (JT, 5.0 g, 27.60 mmol) in DCE (30 mL) was added thionyl chloride (5.01 g, 42.51 mmol) at 0° C. and the reaction mixture was stirred at 80° C. for 3 h. To the resulting reaction mixture, fluorobenzene (CV, 3.9 g, 41.41 mmol) was added at 0° C. followed by AlCl$_3$ (4.0 g, 30.36 mmol) portion wise and the reaction mixture was stirred at 60° C. for 3 h. The progress of the reaction was monitored by TLC. After completion of the reaction, the reaction mixture was cooled to RT, quenched with dilute HCl and washed with EtOAc. The aqueous layer was basified with 10% NaOH solution and the product was extracted with EtOAc. The combined organic layer was dried over anhydrous Na$_2$SO$_4$ and concentrated under reduced pressure. The crude product was purified by silica gel column chromatography using 8% EtOAc/hexane to afford compound JU (3.6 g, 24.0%) as a white solid. $^1$H NMR (400 MHz, DMSO-d6): δ 8.19 (d, J=8.8 Hz, 2H), 8.16-8.13 (m, 2H), 7.54 (d, J=8.0 Hz, 2H), 7.39 (t, J=8.8 Hz, 2H), 4.62 (s, 2H); LC-MS: m/z 257.95 [M−H]$^+$.

2-(4-aminophenyl)-1-(4-fluorophenyl)ethan-1-one (JV)

To a stirred solution of compound JU (3.4 g, 13.12 mmol) in IPA:water (1:1, 40 mL) was added NH$_4$Cl (3.5 g, 65.63 mmol) followed by iron powder (3.7 g, 65.63 mmol) at RT and the reaction mixture was stirred at 80° C. for 3 h. The progress of the reaction was monitored by TLC. After completion of the reaction, the reaction mixture was filtered and the filtrate was concentrated under reduced pressure. Water was added to the residue and the product was extracted with EtOAc. The combined organic layer was dried over anhydrous Na$_2$SO$_4$ and concentrated under reduced pressure. The crude compound was purified by silica gel column chromatography using 40% EtOAc/hexane to afford compound JV (3.0 g, 99.8%) as a yellow liquid. $^1$H NMR (400 MHz, DMSO-d6): δ 8.09-8.06 (m, 2H), 7.32 (t, J=8.8 Hz, 2H), 6.89 (d, J=7.6 Hz, 2H), 6.47 (d, J=8.0 Hz, 2H), 4.95 (brs, 2H), 4.12 (s, 2H); LC-MS: m/z 230.00 [M+H]$^+$.

N-(4-(2-(4-fluorophenyl)-2-oxoethyl)phenyl)methanesulfonamide (JW)

To a stirred solution of compound JV (3.0 g, 13.10 mmol) in pyridine (20 mL) was added mesyl chloride (2.0 mL, 26.20 mmol) at −10° C. and the reaction mixture was stirred at 0° C. for 1 h. The progress of the reaction was monitored by TLC. After completion of the reaction, the reaction mixture was concentrated under reduced pressure. The residue was quenched with water and the product was extracted with EtOAc. The combined organic layer was dried over anhydrous $Na_2SO_4$ and concentrated under reduced pressure. The crude product was purified by silica gel column chromatography using 28% EtOAc/hexane to afford compound JW (3.2 g, 80.0%) as a brown semi solid. $^1$H NMR (400 MHz, DMSO-d6): δ 9.67 (brs, 1H), 8.14-8.10 (m, 2H), 7.36 (t, J=8.8 Hz, 2H), 7.21 (d, J=8.4 Hz, 2H), 7.14 (d, J=8.4 Hz, 2H), 4.34 (s, 2H), 2.96 (s, 3H); LC-MS: m/z 307.75 $[M+H]^+$.

N-(4-(2-amino-2-(4-fluorophenyl)ethyl)phenyl)methanesulfonamide (JX)

To a stirred solution of compound JW (1.0 g, 3.25 mmol) in MeOH (20 mL) was added ammonium acetate (5.0 g, 65.14 mmol) at 0° C. and the reaction mixture was stirred at 0° C. for 1 h. To the resulting reaction mixture, $NaBH_3CN$ (0.55 g, 8.79 mmol) was added and the reaction mixture was stirred at 80° C. for 8 h. After completion of the reaction, the reaction mixture was concentrated under reduced pressure. The residue was quenched with 10% NaOH solution and the product was extracted with EtOAc. The combined organic layer was dried over anhydrous $Na_2SO_4$ and concentrated under reduced pressure. The crude product was purified by silica gel column chromatography using 70% EtOAc/hexane to afford compound JX (0.3 g, 22.5%) as a brown liquid. LC-MS: m/z 292.15 $[M-16]^+$.

N-(4-(2-((5-cyanopyrimidin-2-yl)amino)-2-(4-fluorophenyl)ethyl)phenyl)methanesulfonamide (JY)

To a stirred solution of compound JX (0.3 g, 0.97 mmol) in EtOH (8 mL) was added DIPEA (0.7 mL, 3.89 mmol) followed by 2-chloropyrimidine-5-carbonitrile (AF, 0.16 g, 1.16 mmol) and the reaction mixture was stirred at 90° C. for 16 h. The progress of the reaction was monitored by TLC. After completion of the reaction, the reaction mixture was concentrated under reduced pressure. The crude product was purified by silica gel column chromatography using 30% EtOAc/hexane to afford compound JY (0.22 g, 55.0%) as a yellow solid. $^1$H NMR (400 MHz, DMSO-d6): δ 9.58 (s, 1H), 8.93 (d, J=8.8 Hz, 1H), 8.59-8.57 (m, 2H), 7.46-7.43 (m, 2H), 7.22 (d, J=8.8 Hz, 2H), 7.13 (t, J=8.8 Hz, 2H), 7.06 (d, J=8.0 Hz, 2H), 5.31-5.25 (m, 1H), 3.09-2.94 (m, 2H), 2.91 (s, 3H); LC-MS: m/z 412.10 $[M+H]^+$.

N-(4-(2-((5-(1H-tetrazol-5-yl)pyrimidin-2-yl)amino)-2-(4-fluorophenyl)ethyl)phenyl)methanesulfonamide (JZ)

To a stirred solution of compound JY (0.2 g, 0.48 mmol) in DMF (10 mL) was added $NaN_3$ (0.16 g, 2.43 mmol) and $NH_4Cl$ (0.13 g, 2.43 mmol) followed by LiCl (0.06 g) and the reaction mixture was stirred at 100° C. for 16 h. Progress of the reaction was monitored by TLC. After completion of the reaction, the reaction mixture was concentrated under reduced pressure. The residue was quenched with ice water and acidified with 1N HCl solution. The precipitated solid was filtered off and dried under vacuum to yield compound JZ (0.13 g, 59.0%) as a light brown solid. $^1$H NMR (400 MHz, DMSO-d6): δ 9.56 (s, 1H), 8.77-8.72 (m, 2H), 8.56 (d, J=8.8 Hz, 1H), 7.49-7.45 (m, 2H), 7.25 (d, J=8.4 Hz, 2H), 7.12 (t, J=8.8 Hz, 3H), 7.06 (d, J=8.4 Hz, 2H), 5.28-5.27 (m, 1H), 3.11-3.05 (m, 1H), 2.99-2.94 (m, 1H), 2.88 (s, 3H); LC-MS: m/z 455.10 $[M+H]^+$.

N-(4-(2-((5-(5-(difluoromethyl)-1,3,4-oxadiazol-2-yl)pyrimidin-2-yl)amino)-2-(4-fluorophenyl)ethyl)phenyl)methanesulfonamide (133)

To a stirred solution of compound JZ (0.13 g, 0.28 mmol) in DCM (10 mL) was added DFAA (0.15 g, 0.85 mmol) at 0° C. and the reaction was stirred at RT for 16 h. The progress of reaction was monitored by TLC. After completion of the reaction, the reaction mixture cooled to 0° C., quenched with water and the product was extracted with DCM. The combined organic layer was dried over anhydrous $Na_2SO_4$ and concentrated under reduced pressure to afford crude compound which was purified by silica gel column chromatography using 48% EtOAc/hexane to afford 133 (0.05 g, 35.0%) as an off white solid. $^1$H NMR (400 MHz, DMSO-d6): δ 9.56 (s, 1H), 8.85-8.74 (m, 3H), 7.62-7.36 (m, 3H), 7.25 (d, J=8.4 Hz, 2H), 7.14 (t, J=8.8 Hz, 2H), 7.06 (d, J=8.0 Hz, 2H), 5.34-5.28 (m, 1H), 3.11-3.05 (m, 1H), 3.01-2.96 (m, 1H), 2.89 (s, 3H); LC-MS: m/z 505.20 $[M+H]^+$; HPLC: 88.78%.

Example 134

N-(2-cyclopropoxy-1-(2,4-difluorophenyl)ethyl)-5-(5-(difluoromethyl)-1,3,4-oxadiazol-2-yl)pyrimidin-2-amine (134A and 134B)

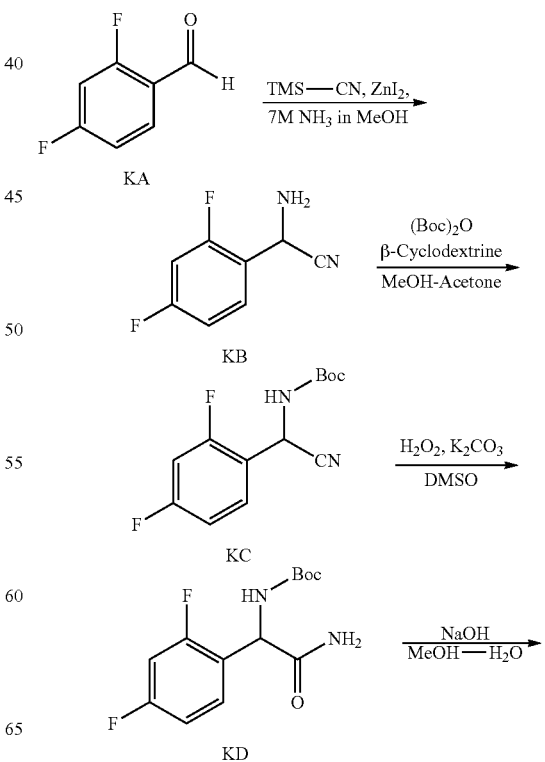

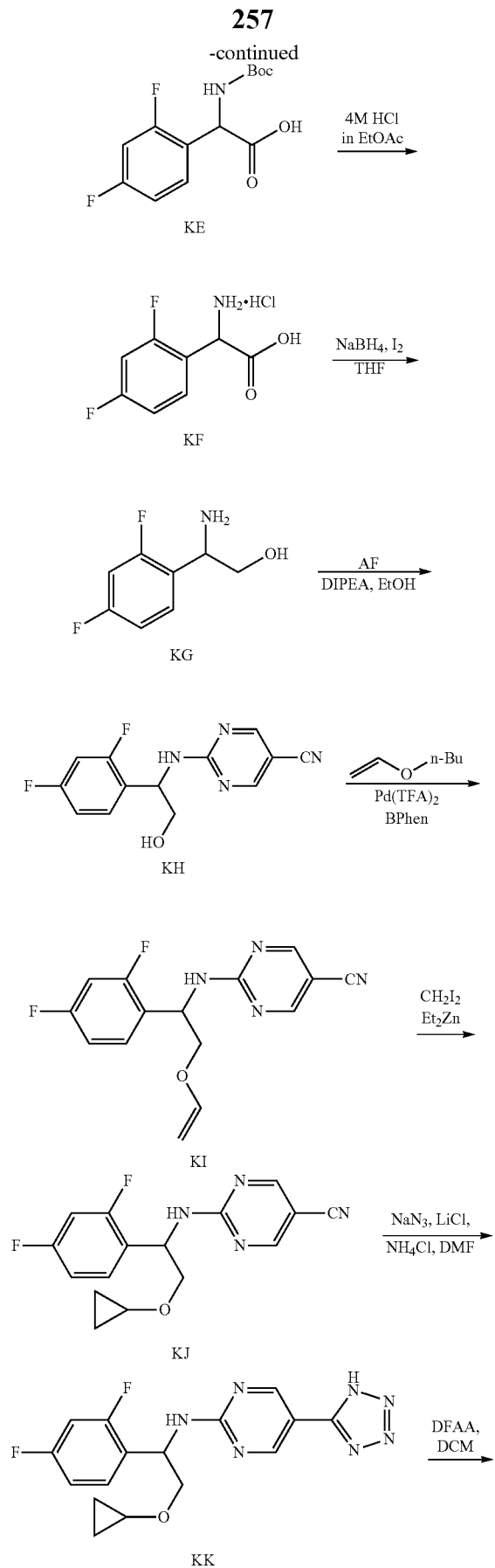

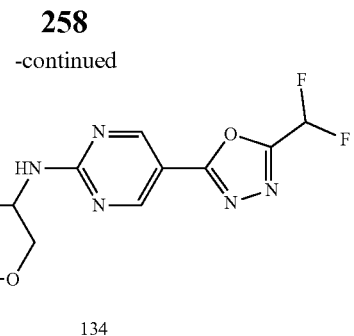

134

2-amino-2-(2,4-difluorophenyl)acetonitrile (KB)

A mixture of 2,4-difluorobenzaldehyde (KA, 15.0 g, 105.63 mmol), TMS-CN (13.1 g, 132.04 mmol) and catalytic $ZnI_2$ (0.15 g) was stirred at RT for 2 h. Then 7M $NH_3$ in MeOH (200 mL) was added and the reaction mixture was stirred at 50° C. for 3 h. The progress of the reaction was monitored by TLC. After completion of the reaction, the reaction mixture was cooled to RT and concentrated under reduced pressure to yield compound KB (17.0 g, crude) as a brown solid, which was used as such for the next reaction.

tert-butyl (cyano(2,4-difluorophenyl)methyl)carbamate (KC)

To a stirred solution of compound KB (17.0 g, 101.19 mmol) in MeOH:Acetone (1:1, 200 mL) was added β-Cyclodextrine (11.5 g, 10.12 mmol) followed by di-tert-butyl dicarbonate (24.2 g, 111.31 mmol) at RT and the reaction mixture was stirred at RT for 12 h. After completion of the reaction, the reaction mixture was filtered and the filtrate was concentrated under reduced pressure. Water was added to the residue and the product was extracted with EtOAc. The combined organic layer was washed with water and brine, dried over anhydrous $Na_2SO_4$ and concentrated under reduced pressure to yield the crude compound which was purified by silica gel column chromatography eluting with 5% EtOAc/hexane to afford compound KC (13.0 g, 48.1%) as a pale yellow solid. $^1$H NMR (400 MHz, DMSO-d6): δ 8.36 (brs, 1H), 7.64-7.58 (m, 1H), 7.40-7.34 (m, 1H), 7.22-7.18 (m, 1H), 5.98 (d, J=7.6 Hz, 1H), 1.40 (s, 9H).

tert-butyl (2-amino-1-(2,4-difluorophenyl)-2-oxo-ethyl)carbamate (KD)

To a stirred solution of compound KC (13.0 g, 48.51 mmol) in DMSO (100 mL) was added $K_2CO_3$ (26.1 g, 194.04 mmol) followed by $H_2O_2$ (22 mL, 194.04 mmol, 30% in water) at 10° C. and the reaction mixture was stirred at RT for 7 h. The progress of the reaction was monitored by TLC. After completion of the reaction, the reaction mixture was quenched with ice water and the white precipitate was filtered. The solid was washed with water and hexane and dried under high vacuum to afford compound KD (11.0 g, crude) which was used as such for the next step. $^1$H NMR (400 MHz, DMSO-d6): δ 7.46-7.37 (m, 3H), 7.23-7.18 (m, 2H), 7.07 (t, J=8.6 Hz, 1H), 5.28 (d, J=8.0 Hz, 1H), 1.37 (s, 9H).

2-((tert-butoxycarbonyl)amino)-2-(2,4-difluorophenyl)acetic acid (KE)

To a stirred solution of compound KD (11.0 g, 38.46 mmol) in MeOH (100 mL) was added NaOH (3.1 g, 76.92 mmol) in water (50 mL) at RT and the reaction mixture was stirred at 75° C. for 12 h. After completion of the reaction, the reaction mixture was concentrated under reduced pressure. The residue was quenched with water and washed with EtOAc. The aqueous layer was treated with 2N HCl to pH 3 and the product was extracted with EtOAc. The combined organic layer was washed with water and brine, dried over anhydrous $Na_2SO_4$ and concentrated under reduced pressure to afford compound KE (10.5 g, 95.1%) as an off white solid. LC-MS: m/z 188.0 $[M+1-boc]^+$.

2-amino-2-(2,4-difluorophenyl)acetic acid hydrochloride (KF)

To a stirred solution of compound KE (10.0 g, 34.84 mmol) in EtOAc (100 mL) was added 4M HCl in EtOAc (50 mL) at RT and the reaction mixture was stirred at RT for 4 h. After completion of the reaction, the reaction mixture was concentrated under reduced pressure and the residue was triturated with diethyl ether to afford compound KF (9.0 g, crude) as a white sticky solid. LC-MS: m/z 187.95 $[M+H]^+$.

2-amino-2-(2,4-difluorophenyl)ethan-1-ol (KG)

To a stirred solution of compound KF (9.0 g, 40.36 mmol) in THF (250 mL) was added $NaBH_4$ (5.9 g, 161.44 mmol) at 0° C. followed by dropwise addition of 12 (10.2 g, 40.36 mmol) in THF (50 mL) and the reaction mixture was stirred at 70° C. for 15 h. After completion of the reaction, the reaction mixture was quenched with MeOH and concentrated under reduced pressure. Then 2N KOH solution was added to the residue and the mixture was stirred at RT for 2 h. The product was extracted with DCM. The combined organic layer was washed with water and brine, dried over anhydrous $Na_2SO_4$ and concentrated under reduced pressure to yield compound KG (5.0 g, crude) as a colorless sticky liquid which was used as such for the next step. LC-MS: m/z 174.00 $[M+H]^+$.

2-((1-(2,4-difluorophenyl)-2-hydroxyethyl)amino) pyrimidine-5-carbonitrile (KH)

To a stirred solution of compound KG (5.0 g, 28.90 mmol) in EtOH (50 mL) was added 2-chloropyrimidine-5-carbonitrile (AF, 4.0 g, 28.90 mmol) and DIPEA (20.0 mL, 115.6 mmol) in a sealed tube and the reaction mixture was stirred at 90° C. for 8 h. The progress of the reaction was monitored by TLC. After completion of the reaction, the reaction mixture was concentrated under reduced pressure to yield the crude compound which was purified by silica gel column chromatography using 30% EtOAc/hexane to afford compound KH (2.5 g, 38.5%) as an off white solid. $^1$H NMR (400 MHz, DMSO-d6): δ 8.75 (d, J=8.4 Hz, 1H), 8.68 (d, J=3.2 Hz, 2H), 7.50-7.44 (m, 1H), 7.21-7.15 (m, 1H), 7.07-7.02 (m, 1H), 5.38-5.32 (m, 1H), 5.07 (t, J=5.8 Hz, 1H), 3.66-3.58 (m, 2H); LC-MS: m/z 277.00 $[M+H]^+$.

2-((1-(2,4-difluorophenyl)-2-(vinyloxy)ethyl)amino) pyrimidine-5-carbonitrile (KI)

To a stirred solution of compound KH (1.5 g, 6.64 mmol) in n-butyl vinyl ether (40 mL), BPhen (0.22 g, 0.66 mmol) was added and argon was purged through 30 min. Then Pd $(TFA)_2$ (0.22 g, 0.66 mmol) was added and argon was purged for further 10 min. The reaction mixture was stirred at 70° C. for 7 h in a sealed tube. After completion of the reaction, the reaction mixture was quenched with water and the product was extracted with EtOAc. The combined organic layer was washed with water and brine, dried over anhydrous $Na_2SO_4$ and concentrated under reduced pressure to yield the crude compound which was purified by silica gel column chromatography using 10% EtOAc/hexane to afford compound KI (1.2 g, 35.6%) as a pale yellow thick liquid. $^1$H NMR (400 MHz, DMSO-d6): δ 9.08 (d, J=8.4 Hz, 1H), 8.71 (s, 2H), 7.57-7.51 (m, 1H), 7.27-7.22 (m, 1H), 7.13-7.08 (m, 1H), 6.53-6.47 (m, 1H), 5.67-5.61 (m, 1H), 4.25-4.21 (m, 1H), 4.03-4.00 (m, 2H), 3.90-3.86 (m, 1H); LC-MS: m/z 303.05 $[M+H]^+$.

2-((2-cyclopropoxy-1-(2,4-difluorophenyl)ethyl) amino)pyrimidine-5-carbonitrile (KJ)

To a stirred solution of compound KI (0.3 g, 0.95 mmol) in diethyl ether (10 mL) was added $Et_2Zn$ (5.2 mL, 5.23 mmol, 15% in toluene) at RT followed by dropwise addition of diiodomethane (1.2 g, 4.75 mmol) and the reaction mixture was allowed to reflux for 5 h. The progress of the reaction was monitored by TLC and LCMS. After completion of the reaction, the reaction mixture was quenched with 1N HCl and the product was extracted with DCM. The combined organic layer was washed with water and brine, dried over anhydrous $Na_2SO_4$ and concentrated under reduced pressure to yield the crude compound which was purified by silica gel column chromatography using 10% EtOAc/hexane to afford compound KJ (0.023 g, 8.0%) as a yellow sticky solid. LC-MS: m/z 317.15 $[M+H]^+$.

N-(2-cyclopropoxy-1-(2,4-difluorophenyl)ethyl)-5-(1H-tetrazol-5-yl)pyrimidin-2-amine (KK)

To a stirred solution of compound KJ (0.07 g, 0.23 mmol) in DMF (3 mL) was added $NaN_3$ (0.075 g, 1.16 mmol) and $NH_4Cl$ (0.061 g, 1.16 mmol) followed by LiCl (0.01 g, 0.23 mmol) and the reaction mixture was stirred at 100° C. for 12 h. Progress of the reaction was monitored by TLC. After completion of the reaction, the reaction mixture was concentrated under reduced pressure. The residue was quenched with ice water and acidified with 1N HCl solution and the product was extracted with 15% MeOH-DCM. The combined organic layer was dried over anhydrous $Na_2SO_4$ and concentrated under reduced pressure to yield compound KK (0.07 g, crude) as a brown sticky liquid which was used as such for the next reaction. LC-MS: m/z 360.15 $[M+H]^+$.

N-(2-cyclopropoxy-1-(2,4-difluorophenyl)ethyl)-5-(5-(difluoromethyl)-1,3,4-oxadiazol-2-yl)pyrimidin-2-amine (134)

To a stirred solution of compound KK (0.06 g, 0.17 mmol) in DCM (5 mL) was added DFAA (0.1 mL) at 0° C. and the reaction was stirred at RT for 24 h. The progress of reaction was monitored by TLC. After completion of the reaction, the reaction mixture was quenched with aqueous $NaHCO_3$ solution and extracted with DCM. Organic layer was dried over anhydrous $Na_2SO_4$ and concentrated under reduced pressure to afford crude compound which was purified by silica gel column chromatography using 10% EtOAc/hexane to afford racemic 134 (0.022 g, 32.5%) as a yellow sticky solid.

Chiral Preparative HPLC Details for 134A and 134B

The enantiomers were separated by normal-phase preparative high performance liquid chromatography (YMC Chiralart Cellulose-SC, 250×20 mm, 5; Mobile Phase: n-Hexane: Isopropyl alcohol (95:5)+0.1% NH₃; Flow rate: 20.0 mL/min) to obtain 134A (2.9 mg) and 134B (3.0 mg).

134A: ¹H NMR (400 MHz, CD3OD): δ 8.89 (s, 2H), 7.49-7.43 (m, 1H), 7.30-7.04 (m, 1H), 6.98-6.89 (m, 2H), 5.65 (t, J=6.2 Hz, 1H), 3.81 (d, J=6.4 Hz, 2H), 3.40-3.36 (m, 1H), 1.32-1.28 (m, 1H), 0.54-0.43 (m, 4H); LC-MS: m/z 410.25 [M+H]⁺; HPLC: 99.22%: C-HPLC: 99.47% (RT: 12.99).

134B: ¹H NMR (400 MHz, CD3OD): δ 8.89 (s, 2H), 7.49-7.43 (m, 1H), 7.30-7.04 (m, 1H), 6.98-6.89 (m, 2H), 5.65 (t, J=6.4 Hz, 1H), 3.81 (d, J=6.4 Hz, 2H), 3.40-3.38 (m, 1H), 1.31-1.27 (m, 1H), 0.54-0.43 (m, 4H); LC-MS: m/z 410.25 [M+H]⁺; HPLC: 98.62%: C-HPLC: 96.36% (RT: 14.64).

Example 137(+)

N-(2-((5-(5-(difluoromethyl)-1,3,4-oxadiazol-2-yl)pyrimidin-2-yl)amino)-2-(2,4-difluorophenyl)ethyl)-N-methylmethanesulfonamide (137(+))

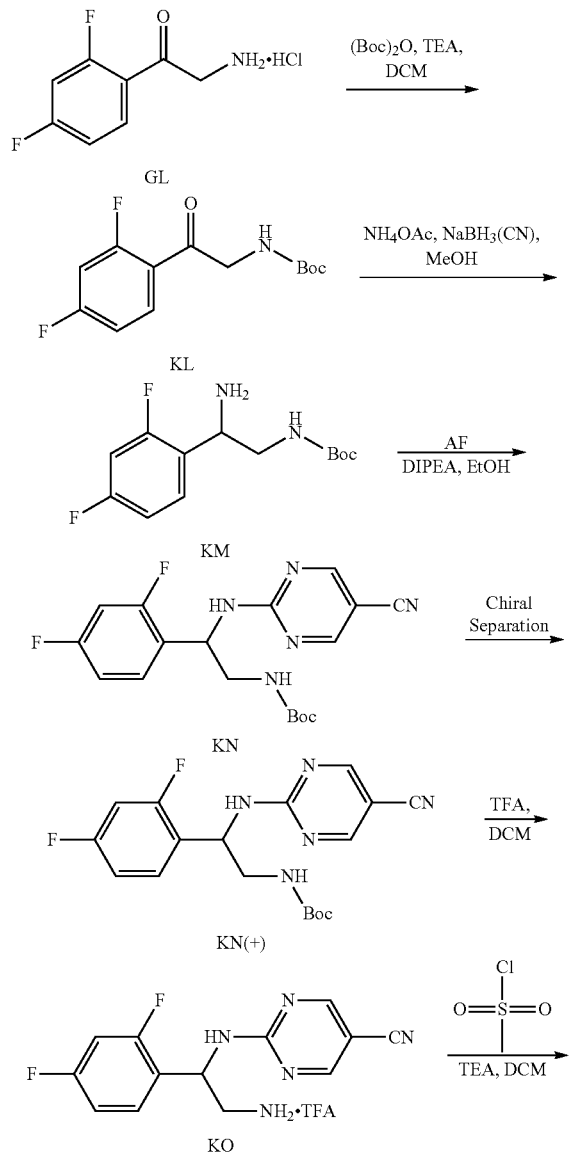

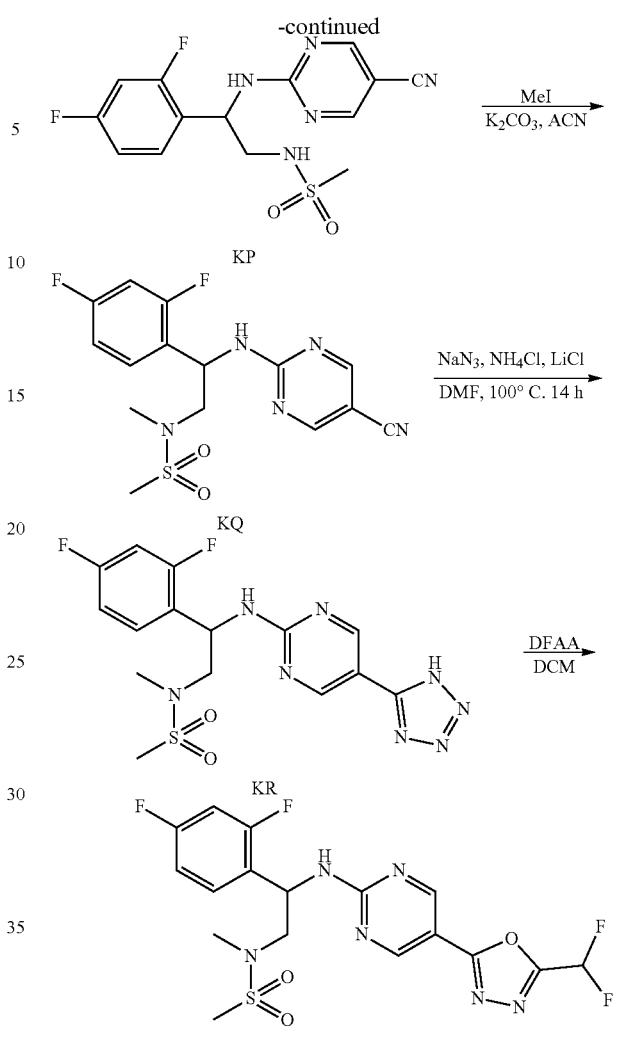

tert-butyl (2-(2,4-difluorophenyl)-2-oxoethyl)carbamate (KL)

To a stirred solution of compound GL (60.0 g, 0.29 mol) in DCM (1 L) was added triethylamine (162 mL, 1.16 mol) at 0° C. and the reaction mixture was stirred for 15 min. To the resulting reaction mixture, di-tert-butyl dicarbonate (94.8 g, 0.43 mol) was added and the reaction mixture was stirred at RT for 6 h. The progress of the reaction was monitored by TLC. After completion of the reaction, the reaction mixture was quenched with water and the product was extracted with DCM. The combined organic layer was dried over anhydrous Na₂SO₄ and concentrated under reduced pressure. The crude compound was purified by silica gel column chromatography using 10-20% EtOAc/hexane to afford compound KL (40.0 g, 51.0%) as an off white solid. ¹H NMR (400 MHz, CDCl₃): δ 8.07-8.01 (m, 1H), 7.00 (t, J=7.8 Hz, 1H), 6.91 (t, J=8.8 Hz, 1H), 5.48 (brs, 1H), 4.56 (s, 2H), 1.47 (s, 9H). LC-MS: m/z 171.90 [M+1-boc]⁺.

tert-butyl (2-amino-2-(2,4-difluorophenyl)ethyl)carbamate (KM)

To a stirred solution of compound KL (40.0 g, 0.15 mol) in MeOH (500 mL) was added ammonium acetate (227.3 g, 2.95 mol) and the reaction mixture was stirred at RT for 30 min. To the resulting reaction mixture, NaBH$_3$CN (23.1 g, 0.37 mol) was added and the reaction mixture was stirred at 80° C. for 16 h. After completion of the reaction, the reaction mixture was concentrated under reduced pressure. The residue was quenched with saturated NaHCO$_3$ solution and the product was extracted with EtOAc. The combined organic layer was dried over anhydrous Na$_2$SO$_4$ and concentrated under reduced pressure to afford compound KM (20.0 g, 50.0%) as a light brown thick liquid. $^1$H NMR (400 MHz, DMSO-d6): δ 7.56-7.51 (m, 1H), 7.13-7.08 (m, 1H), 7.06-7.01 (m, 1H), 6.82 (t, J=5.6 Hz, 1H), 4.13 (t, J=6.4 Hz, 1H), 3.11-2.99 (m, 2H), 1.92 (s, 2H), 1.32 (s, 9H). LC-MS: m/z 273.05 [M+H]$^+$.

tert-butyl (2-((5-cyanopyrimidin-2-yl)amino)-2-(2,4-difluorophenyl)ethyl)carbamate (KN)

To a stirred solution of compound KM (10.0 g, 0.04 mol) and 2-chloropyrimidine-5-carbonitrile (7, 5.6 g, 0.04 mol) in EtOH (150 mL) was added DIPEA (20.3 mL, 0.11 mol) and the reaction mixture was stirred at 90° C. for 15 h. The progress of reaction was monitored by TLC. After completion of the reaction, the reaction mixture was concentrated under reduced pressure. The crude residue was dissolved in EtOAc and washed with water and brine. The organic layer was dried over anhydrous Na$_2$SO$_4$ and concentrated under reduced pressure. The crude product was purified by silica gel column chromatography using 0-2% MeOH/DCM to afford compound KN (10.0 g, 72.5%) as an off-white solid. $^1$H NMR (400 MHz, DMSO-d6): δ 8.72-8.67 (m, 3H), 7.49-7.43 (m, 1H), 7.19-7.14 (m, 1H), 7.04-6.97 (m, 2H), 5.45-5.41 (m, 1H), 3.35-3.26 (m, 2H), 1.30 (s, 9H); LC-MS: m/z 376.20 [M+H]$^+$; HPLC: 99.43%.

Chiral Preparative HPLC Details for KN(+)

The enantiomers were separated by chiral preparative high performance liquid chromatography (Chiralpak IA, 250×30 mm, 5; Mobile Phase: n-Hexane: Isopropyl alcohol (85:15)+0.1% NH$_3$; Flow rate: 30.0 mL/min) to obtain KN(+) (3.047 g) as an off-white solid. $^1$H NMR (400 MHz, DMSO-d6): δ 8.75-8.68 (m, 3H), 7.50-7.44 (m, 1H), 7.17 (t, J=9.8 Hz, 1H), 7.06-6.99 (m, 2H), 5.45-5.41 (m, 1H), 3.39-3.25 (m, 2H), 1.30 (s, 9H); LC-MS: m/z 376.10 [M+H]$^+$; HPLC: 97.74%; C-HPLC: 99.64% (RT-6.58).

2-((2-amino-1-(2,4-difluorophenyl)ethyl)amino)pyrimidine-5-carbonitrile·TFAsalt (KO)

To a stirred solution of compound KN(+) (0.6 g, 1.6 mmol) in DCM (10 mL) was added TFA (3 mL) at 0° C. and the reaction mixture was stirred at RT for 2 h. The progress of the reaction was monitored by TLC. After completion of the reaction, the reaction mixture was concentrated under reduced pressure to yield solid compound which was washed with diethyl ether and dried under vacuum to afford compound KO (TFA salt, 0.6 g, crude) as an off white solid which was used as such for the next reaction. LC-MS: m/z 275.95 [M+H]$^+$.

N-(2-((5-cyanopyrimidin-2-yl)amino)-2-(2,4-difluorophenyl)ethyl)methanesulfonamide (KP)

To a stirred solution of compound KO (0.6 g, 1.54 mmol) in DCM (10 mL) was added triethyl amine (0.54 mL, 3.85 mmol) followed by mesyl chloride (0.15 mL, 1.85 mmol) at 0° C. and the reaction mixture was stirred at 0° C. for 2 h. The progress of the reaction was monitored by TLC. After completion of the reaction, the reaction mixture was quenched with water and the product was extracted with DCM. The combined organic layer was dried over anhydrous Na$_2$SO$_4$ and concentrated under reduced pressure. The crude product was purified by silica gel column chromatography using 15-20% EtOAc/hexane to afford compound KP (0.3 g, 53.0%) as a brown thick liquid. $^1$H NMR (400 MHz, DMSO-d6): δ 8.77 (d, J=8.4 Hz, 1H), 8.71 (s, 2H), 7.57-7.51 (m, 1H), 7.31 (t, J=6.0 Hz, 1H), 7.24-7.19 (m, 1H), 7.11-7.07 (m, 1H), 5.49-5.44 (m, 1H), 3.37-3.29 (m, 2H), 2.85 (s, 3H); LC-MS: m/z 354.20 [M+H]$^+$.

N-(2-((5-cyanopyrimidin-2-yl)amino)-2-(2,4-difluorophenyl)ethyl)-N-methylmethanesulfonamide (KQ)

To a stirred solution of compound KP (0.3 g, 0.85 mmol) in ACN (5 mL) was added dry K$_2$CO$_3$ (0.17 g, 1.27 mmol) followed by methyl iodide (0.14 g, 1.02 mmol) in a sealed tube and the reaction mixture was stirred at 90° C. for 16 h. The progress of the reaction was monitored by TLC.

After completion of the reaction, the reaction mixture was quenched with water and the product was extracted with DCM. The combined organic layer was dried over anhydrous Na$_2$SO$_4$ and concentrated under reduced pressure. The crude product was purified by silica gel column chromatography eluting with 15-20% EtOAc/hexane to afford compound KQ (0.27 g, 86.8%) as an off white solid. $^1$H NMR (400 MHz, DMSO-d6): δ 8.86 (d, J=8.8 Hz, 1H), 8.72 (s, 2H), 7.65-7.60 (m, 1H), 7.23 (t, J=10.0 Hz, 1H), 7.12 (t, J=8.2 Hz, 1H), 5.68-5.62 (m, 1H), 3.48-3.42 (m, 2H), 2.83 (s, 3H), 2.79 (s, 3H); LC-MS: m/z 368.20 [M+H]$^+$.

N-(2-((5-(1H-tetrazol-5-yl)pyrimidin-2-yl)amino)-2-(2,4-difluorophenyl)ethyl)-N-methylmethanesulfonamide (KR)

To a stirred solution of compound KQ (0.27 g, 0.74 mmol) in DMF (5 mL) was added NaN$_3$ (0.19 g, 2.94 mmol) and NH$_4$Cl (0.16 g, 2.94 mmol) followed by LiCl (0.03 g, 0.074 mmol) and the reaction mixture was stirred at 100° C. for 14 h. Progress of the reaction was monitored by TLC. After completion of the reaction, the reaction mixture was concentrated under reduced pressure. The residue was quenched with ice water and acidified with 6N HCl solution to pH 4. The resulting white precipitate was filtered and dried under vacuum to afford compound KR (0.25 g, crude). LC-MS: m/z 411.25 [M+H]$^+$.

N-(2-((5-(5-(difluoromethyl)-1,3,4-oxadiazol-2-yl)pyrimidin-2-yl)amino)-2-(2,4-difluorophenyl)ethyl)-N-methylmethanesulfonamide (137(+))

To a stirred solution of compound KR (0.25 g, 0.61 mmol) in DCM (10 mL) was added DFAA (0.14 mL, 1.2 mmol) at 0° C. and the reaction was stirred at RT for 16 h. The progress of reaction was monitored by TLC. After completion of the reaction, the reaction mixture was quenched with water and the product was extracted with DCM. The combined organic layer was washed with brine, dried over anhydrous Na$_2$SO$_4$ and concentrated under reduced pressure. The crude compound which was purified by silica gel column chromatography using 10-20% EtOAc/hexane to afford 137(+) (0.11 g, 39.3%) as an off white solid. $^1$H NMR (400 MHz, DMSO-d6): δ 8.90 (brs, 2H), 8.77 (d, J=9.2 Hz, 1H), 7.69-7.39 (m, 2H), 7.26-7.21 (m, 1H), 7.14-7.10 (m, 1H), 5.75-5.68 (m, 1H), 3.45 (d, J=7.6 Hz, 2H), 2.84 (s, 3H), 2.81 (s, 3H); LC-MS: m/z 461.15 [M+H]⁺; HPLC: 95.11%; C-HPLC: 95.82% (RT: 8.98); SOR: +24.4, Solvent: Methanol, Path length: 100 mm, Concentration: 100 w/v %.

Example 138(+)

N-(2-((5-(5-(difluoromethyl)-1,3,4-oxadiazol-2-yl)pyrimidin-2-yl)amino)-2-(2,4-difluorophenyl)ethyl)-N-(2,2,2-trifluoroethyl)methanesulfonamide (138(+))

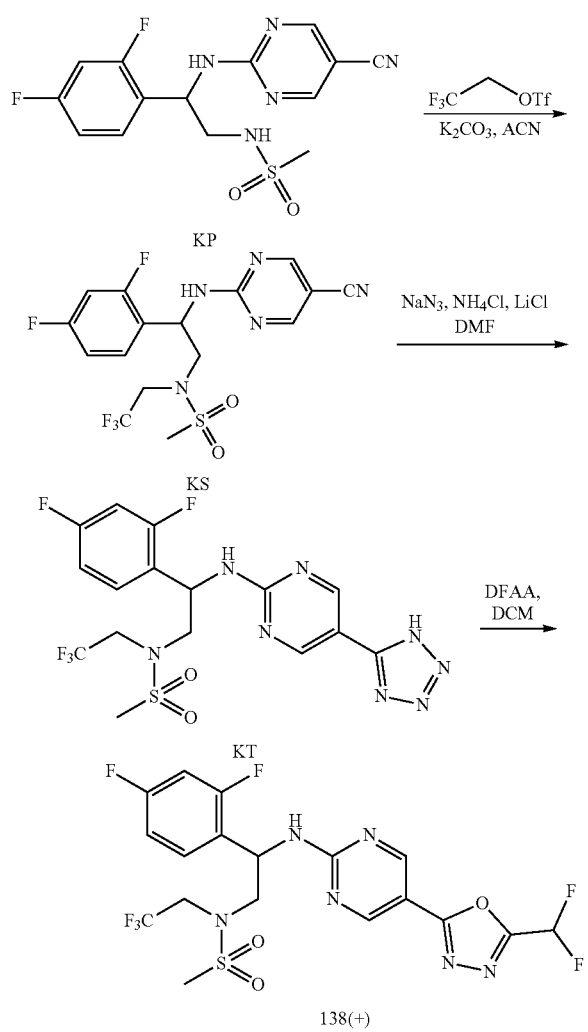

N-(2-((5-cyanopyrimidin-2-yl)amino)-2-(2,4-difluorophenyl)ethyl)-N-(2,2,2-trifluoroethyl)methanesulfonamide (KS)

To a stirred solution of compound KP (0.34 g, 0.96 mmol) in ACN (10 mL), K₂CO₃ (0.397 g, 2.88 mmol) was added at 0° C. and stirred for 10 min. To the resulting reaction mixture 2,2,2-trifluoroethyl trifluoromethanesulfonate (0.35 mL, 2.41 mmol) was added and the reaction was stirred at 60° C. for 6 h. The progress of the reaction was monitored by TLC. After completion of the reaction, the reaction mixture was diluted with EtOAc and washed with water. The organic layer was washed with brine, dried over anhydrous Na₂SO₄ and concentrated under reduced pressure. The crude product was purified by silica gel column chromatography using 30-32% EtOAc/hexane to afford KS (0.315 g, 75.0%) as an off white solid. ¹H NMR (400 MHz, DMSO-d6): δ 8.78 (d, J=8.8 Hz, 1H), 8.73 (s, 2H), 7.59-7.57 (m, 1H), 7.26-7.21 (m, 1H), 7.14-7.11 (m, 1H), 5.76-5.75 (m, 1H), 4.17-4.11 (m, 2H), 3.68-3.63 (m, 2H), 3.02 (s, 3H); LC-MS: 436.55 [M+H]⁺.

N-(2-((5-(1H-tetrazol-5-yl)pyrimidin-2-yl)amino)-2-(2,4-difluorophenyl)ethyl)-N-(2,2,2-trifluoroethyl)methanesulfonamide (KT)

To a stirred solution of compound KS (0.31 g, 0.71 mmol) in DMF (10 mL), NaN₃ (0.23 g, 3.57 mmol), NH₄Cl (0.2 g, 3.57 mmol) and LiCl (0.09 g) were added and the reaction was stirred at 100° C. for 16 h. After completion of the reaction, the reaction mixture was quenched with ice water and acidified with 2N HCl solution to pH=2. The precipitated solid was filtered, washed with cold water and dried to afford KT (0.3 g, 88.0%) as an off white solid. LC-MS: m/z 479.55 [M+H]⁺.

N-(2-((5-(5-(difluoromethyl)-1,3,4-oxadiazol-2-yl)pyrimidin-2-yl)amino)-2-(2,4-difluorophenyl)ethyl)-N-(2,2,2-trifluoroethyl)methanesulfonamide (138(+))

To a stirred solution of compound KT (0.30 g, 0.62 mmol) in DCM (25 mL), DFAA (0.15 mL, 1.21 mmol) was added at 0° C. and the reaction was stirred at RT for 16 h. The progress of the reaction was monitored by TLC. After completion of the reaction, the reaction mixture was diluted with DCM and washed with saturated NaHCO₃ solution. The organic layer was washed with brine, dried over anhydrous Na₂SO₄ and concentrated under reduced pressure. The crude product was purified by silica gel column chromatography using 20-22% EtOAc/hexane to afford 138(+) (0.12 g, 44.0%) as an off white solid. ¹H NMR (400 MHz, DMSO-d6): δ 8.90 (d, J=7.2 Hz, 2H), 8.69 (d, J=8.8 Hz, 1H), 7.64-7.09 (m, 4H), 5.83-5.77 (m, 1H), 4.24-4.10 (m, 2H), 3.72-3.61 (m, 2H), 3.02 (s, 3H); LC-MS: 529.60 [M+H]⁺; HPLC: 99.86%, C-HPLC: 97.46% (RT: 7.13); SOR: +66.80, Solvent: Methanol, Path length: 100 mm, Concentration: 0.28 w/v %.

Example 139(+)

N-(2-((5-(5-(difluoromethyl)-1,3,4-oxadiazol-2-yl)pyrimidin-2-yl)amino)-2-(2,4-difluorophenyl)ethyl)ethanesulfonamide (139(+))

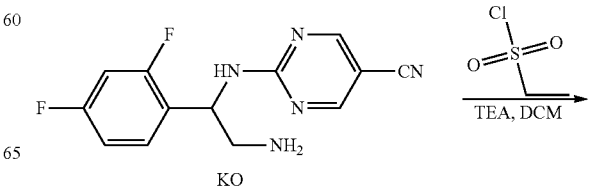

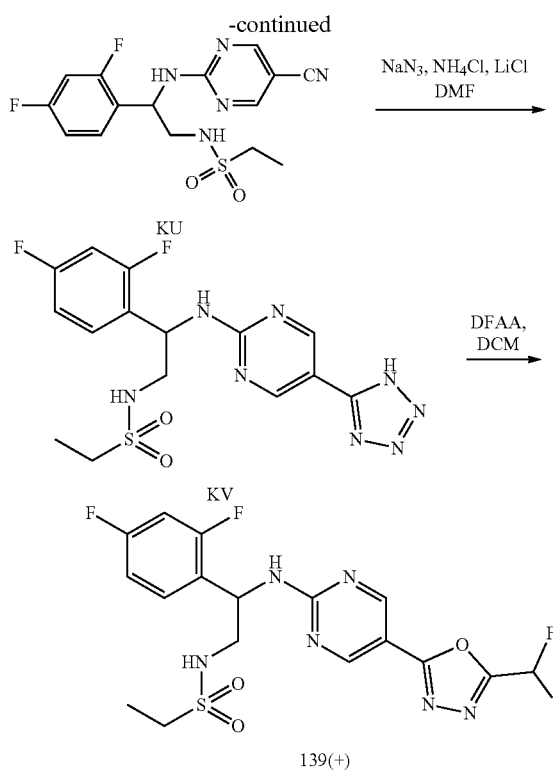

N-(2-((5-cyanopyrimidin-2-yl)amino)-2-(2,4-difluorophenyl)ethyl)ethanesulfonamide (KU)

To a stirred solution of compound KO (0.60 g, 1.54 mmol) in DCM (10 mL), Triethyl amine (0.54 mL, 3.85 mmol) and ethanesulfonyl chloride (0.18 g, 1.85 mmol) were added at 0° C. and stirred at RT for 2 h. The progress of the reaction was monitored by TLC. After completion of the reaction, the reaction mixture was diluted with water and the product was extracted with DCM. The combined organic layer was washed with brine, dried over anhydrous Na$_2$SO$_4$ and concentrated under reduced pressure. The crude product was purified by silica gel column chromatography using 30% EtOAc/hexane to afford KU (0.3 g, 52.0%) as an off white solid. $^1$H NMR (400 MHz, DMSO-d6): δ 8.75 (d, J=8.4 Hz, 1H), 8.71 (s, 2H), 7.56-7.06 (m, 4H), 5.48-5.42 (m, 1H), 3.35-3.26 (m, 2H), 2.99-2.89 (m, 2H), 1.10 (t, J=7.2 Hz, 3H); LC-MS: 368.20 [M+H]$^+$.

N-(2-((5-(1H-tetrazol-5-yl)pyrimidin-2-yl)amino)-2-(2,4-difluorophenyl)ethyl)ethanesulfonamide (KV)

To a stirred solution of compound KU (0.30 g, 0.80 mmol) in DMF (4 mL), NaN$_3$ (0.21 g, 3.20 mmol), NH$_4$Cl (0.18 g, 3.20 mmol) and LiCl (0.004 g) were added and the reaction was stirred at 100° C. for 16 h. After completion of the reaction, the reaction mixture was concentrated under reduced pressure. The residue was quenched with ice water and acidified with 6N HCl solution to pH=4. The precipitated solid was filtered, washed with cold water, and dried to afford KV (0.29 g, 86.5%) as an off white solid. LC-MS: m/z 411.25 [M+H]$^+$.

N-(2-((5-(5-(difluoromethyl)-1,3,4-oxadiazol-2-yl)pyrimidin-2-yl)amino)-2-(2,4-difluorophenyl)ethyl)ethanesulfonamide (139(+))

To a stirred solution of compound 3 (0.29 g, 0.70 mmol) in DCM (5 mL), DFAA (0.17 mL, 1.40 mmol) was added at 0° C. and the reaction was stirred at RT for 16 h. The progress of the reaction was monitored by TLC. After completion of the reaction, the reaction mixture was diluted with water and the product was extracted with DCM. The combined organic layer was washed with brine, dried over anhydrous Na$_2$SO$_4$ and concentrated under reduced pressure. The crude product was purified by silica gel column chromatography using 50% EtOAc/hexane to afford 139(+) (0.12 g, 43.0%) as an off white solid. $^1$H NMR (400 MHz, DMSO-d6): δ 8.89 (d, J=12.0 Hz, 2H), 8.67 (d, J=8.4 Hz, 1H), 7.64-7.07 (m, 5H), 5.54-5.48 (m, 1H), 3.40-3.36 (m, 2H), 3.02-2.88 (m, 2H), 1.10 (t, J=7.2 Hz, 3H); LC-MS: 461.20 [M+H]$^+$; HPLC: 98.57%, C-HPLC: 99.74% (RT: 12.47); SOR: +82.57, Solvent: methanol, Path length: 100 mm, Concentration: 0.2005 w/v %.

Example 140 (+)

N-(2-((5-(5-(difluoromethyl)-1,3,4-oxadiazol-2-yl)pyrimidin-2-yl)amino)-2-(2,4-difluorophenyl)ethyl)-N-methylethanesulfonamide (140(+))

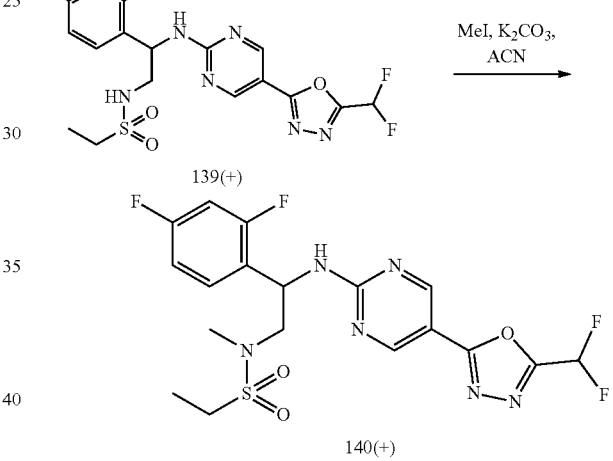

N-(2-((5-(5-(difluoromethyl)-1,3,4-oxadiazol-2-yl)pyrimidin-2-yl)amino)-2-(2,4-difluorophenyl)ethyl)-N-methylethanesulfonamide (140(+))

To a stirred solution of 139(+) (0.20 g, 0.43 mmol) in ACN (10 mL), K$_2$CO$_3$ (0.18 g, 1.30 mmol), was added at 0° C. and stirred for 15 min. To the resulting reaction mixture methyl iodide (0.19 mL, 3.0 mmol) was added and the reaction was stirred at RT for 16 h. The progress of the reaction was monitored by TLC. After completion of the reaction, the reaction mixture was diluted with EtOAc and washed with water. The organic layer was washed with brine, dried over anhydrous Na$_2$SO$_4$ and concentrated under reduced pressure. The crude product was purified by silica gel column chromatography using 50% EtOAc/hexane to afford 140(+) (0.125 g, 61.0%) as an off white solid. $^1$H NMR (400 MHz, DMSO-d6): δ 8.88 (d, J=3.6 Hz, 2H), 8.75 (d, J=9.2 Hz, 1H), 7.67-7.08 (m, 4H), 5.74-5.66 (m, 1H), 3.50 (d, J=7.6 Hz, 2H), 3.01 (q, J=7.4 Hz, 2H), 2.83 (s, 3H), 1.09 (t, J=7.4 Hz, 3H); LC-MS: 475.05 [M+H]$^+$; HPLC: 99.25%, C-HPLC: 99.37% (RT: 7.53); SOR: +60.56, Solvent: Methanol, Path length: 100 mm, Concentration: 0.275 w/v %.

Example 141(+)

N-(2-((5-(5-(difluoromethyl)-1,3,4-oxadiazol-2-yl)pyrimidin-2-yl)amino)-2-(2,4-difluorophenyl)ethyl)-N-(2,2,2-trifluoroethyl)ethanesulfonamide (141(+))

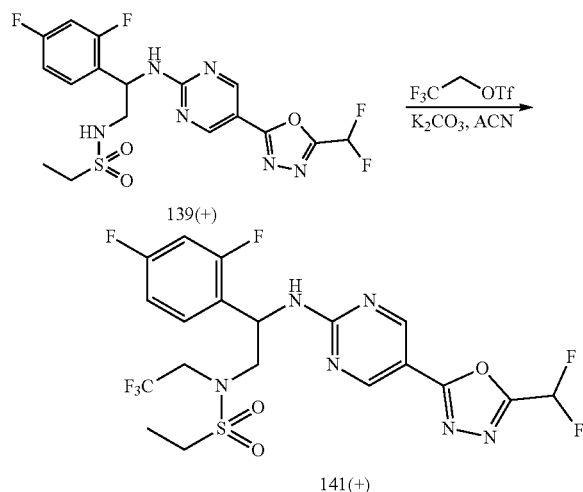

N-(2-((5-(5-(difluoromethyl)-1,3,4-oxadiazol-2-yl)pyrimidin-2-yl)amino)-2-(2,4-difluorophenyl)ethyl)-N-(2,2,2-trifluoroethyl)ethanesulfonamide (141(+))

To a stirred solution of 139(+) (0.20 g, 0.43 mmol) in ACN (10 mL), $K_2CO_3$ (0.18 g, 1.30 mmol) was added at 0° C. and stirred for 10 min. To the resulting reaction mixture 2,2,2-trifluoroethyl trifluoromethanesulfonate (0.19 mL, 1.30 mmol) was added and the reaction was stirred at 60° C. for 16 h. The progress of the reaction was monitored by TLC. After completion of the reaction, the reaction mixture was diluted with EtOAc and washed with water. The combined organic layer was washed with brine, dried over anhydrous $Na_2SO_4$ and concentrated under reduced pressure. The crude product was purified by silica gel column chromatography using 50% EtOAc/hexane to afford 141(+) (0.065 g, 27.5%) as an off white solid. $^1$H NMR (400 MHz, DMSO-d6): δ 8.90 (d, J=7.2 Hz, 2H), 8.70 (d, J=9.2 Hz, 1H), 7.64-7.10 (m, 4H), 5.83-5.77 (m, 1H), 4.24-4.12 (m, 2H), 3.74-3.58 (m, 2H), 3.24-3.15 (m, 2H), 1.12 (t, J=7.4 Hz, 3H); LC-MS: 543.15 [M+H]$^+$; HPLC: 99.33%, C-HPLC: 98.88% (RT: 6.19); SOR: +78.18, Solvent: methanol, Path length: 100 mm, Concentration: 0.33 w/v %.

Example 142(+)

N-(2-((5-(5-(difluoromethyl)-1,3,4-oxadiazol-2-yl)pyrimidin-2-yl)amino)-2-(2,4-difluorophenyl)ethyl)cyclopropanesulfonamide (142(+))

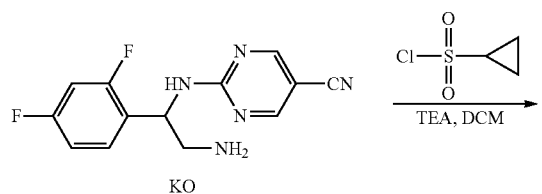

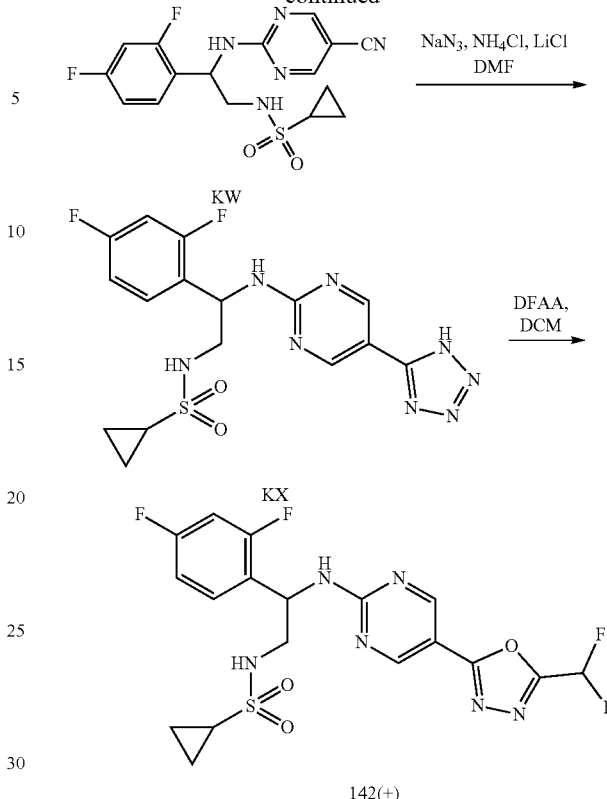

N-(2-((5-cyanopyrimidin-2-yl)amino)-2-(2,4-difluorophenyl)ethyl)cyclopropanesulfonamide (2)

To a stirred solution of compound KO (0.80 g, 2.90 mmol) in DCM (10 mL), triethyl amine (1.21 mL, 8.72 mmol) was added at 0° C. and stirred for 30 min. To the resulting reaction mixture, cyclopropanesulfonyl chloride (0.36 g, 2.61 mmol) was added and the reaction was stirred at RT for 1 h. The progress of the reaction was monitored by TLC. After completion of the reaction, the reaction mixture was diluted with water and the product was extracted with DCM. The combined organic layer was washed with brine, dried over anhydrous $Na_2SO_4$ and concentrated under reduced pressure. The crude product was purified by silica gel column chromatography using 40% EtOAc/hexane to afford KW (0.4 g, 36.0%) as a light yellow solid. $^1$H NMR (400 MHz, DMSO-d6): δ 8.76 (d, J=9.6 Hz, 1H), 8.70 (s, 2H), 7.56-7.50 (m, 1H), 7.40-7.37 (m, 1H), 7.23-7.17 (m, 1H), 7.10-7.05 (m, 1H), 5.50-5.45 (m, 1H), 3.41-3.36 (m, 2H), 0.90-0.86 (m, 4H), 1 Proton merged in solvent; LC-MS: 380.10 [M+H]$^+$.

N-(2-((5-(1H-tetrazol-5-yl)pyrimidin-2-yl)amino)-2-(2,4-difluorophenyl)ethyl)cyclopropanesulfonamide (KX)

To a stirred solution of compound KW (0.40 g, 1.05 mmol) in DMF (10 mL), NaN$_3$ (0.20 g, 3.16 mmol), NH$_4$Cl (0.17 g, 3.16 mmol) and LiCl (0.044 g) were added and the reaction was stirred at 100° C. for 16 h. After completion of the reaction, the reaction mixture was concentrated under reduced pressure. The residue was quenched with ice water and acidified with 6N HCl solution to pH=2. The precipi- N-(2-((5-(5-(difluoromethyl)-1,3,4-oxadiazol-2-yl)
pyrimidin-2-yl)amino)-2-(2,4-difluorophenyl)ethyl)
cyclopropanesulfonamide (142(+))

To a stirred solution of compound KX (0.40 g, 0.94 mmol) in DCM (5 mL), DFAA (0.32 g, 1.89 mmol) was added at 0° C. and the reaction was stirred at RT for 8 h. The progress of the reaction was monitored by TLC. After completion of the reaction, the reaction mixture was diluted with water and the product was extracted with 10% MeOH/DCM. The combined organic layer was washed with brine, dried over anhydrous Na$_2$SO$_4$ and concentrated under reduced pressure. The crude product was purified by silica gel column chromatography using 50% EtOAc/hexane to afford 142(+) (0.25 g, 56.0%) as an off white solid. $^1$H NMR (400 MHz, DMSO-d6): δ 8.87 (d, J=12.4 Hz, 2H), 8.67 (d, J=8.4 Hz, 1H), 7.63-7.06 (m, 5H), 5.57-5.51 (m, 1H), 3.43-3.35 (m, 2H), 0.91-0.86 (m, 4H), 1H merged in solvent peak; LC-MS: 473.15 [M+H]$^+$; HPLC: 98.94%, C-HPLC: 99.39% (RT: 12.37); SOR: +86.25, Solvent: methanol, Path length: 100 mm, Concentration: 0.25 w/v %.

Example 143(+)

N-(2-((5-(5-(difluoromethyl)-1,3,4-oxadiazol-2-yl)
pyrimidin-2-yl)amino)-2-(2,4-difluorophenyl)ethyl)-
N-methylcyclopropanesulfonamide (143(+))

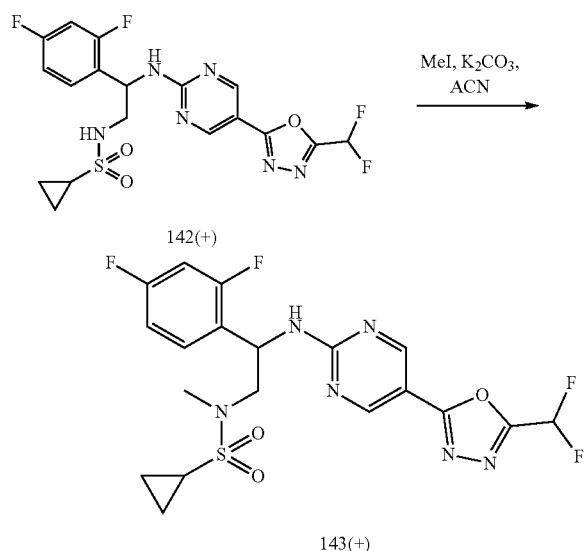

N-(2-((5-(5-(difluoromethyl)-1,3,4-oxadiazol-2-yl)
pyrimidin-2-yl)amino)-2-(2,4-difluorophenyl)ethyl)-
N-methylcyclopropanesulfonamide (143(+))

To a stirred solution of compound 142(+) (0.18 g, 0.38 mmol) in ACN (5 mL), K$_2$CO$_3$ (0.16 g, 1.14 mmol) and methyl iodide (0.16 mL, 2.66 mmol) were added at 0° C. and stirred at RT for 16 h. The progress of the reaction was monitored by TLC. After completion of the reaction, the reaction mixture was filtered and the filtrate was concentrated under reduced pressure. The residue was diluted with water and the product was extracted with EtOAc. The combined organic layer was washed with brine, dried over anhydrous Na$_2$SO$_4$ and concentrated under reduced pressure. The crude product was purified by silica gel column chromatography using 40% EtOAc/hexane to afford compound 143(+) (0.09 g, 49.0%) as an off white solid. $^1$H NMR (400 MHz, DMSO-d6): δ 8.88 (d, J=3.6 Hz, 2H), 8.78 (d, J=8.8 Hz, 1H), 7.67-7.09 (m, 4H), 5.74-5.69 (m, 1H), 3.51 (d, J=8.0 Hz, 2H), 2.85 (s, 3H), 2.55-2.54 (m, 1H), 0.92-0.85 (m, 4H); LC-MS: 487.15 [M+H]$^+$; HPLC: 98.99%; C-HPLC: 99.24% (RT: 6.97); SOR: +61.71, Solvent: methanol, Path length: 50 mm, Concentration: 0.275 w/v %.

Example 144(+)

N-(2-((5-(5-(difluoromethyl)-1,3,4-oxadiazol-2-yl)
pyrimidin-2-yl)amino)-2-(2,4-difluorophenyl)ethyl)-
N-(2,2,2-trifluoroethyl)cyclopropanesulfonamide
(144(+))

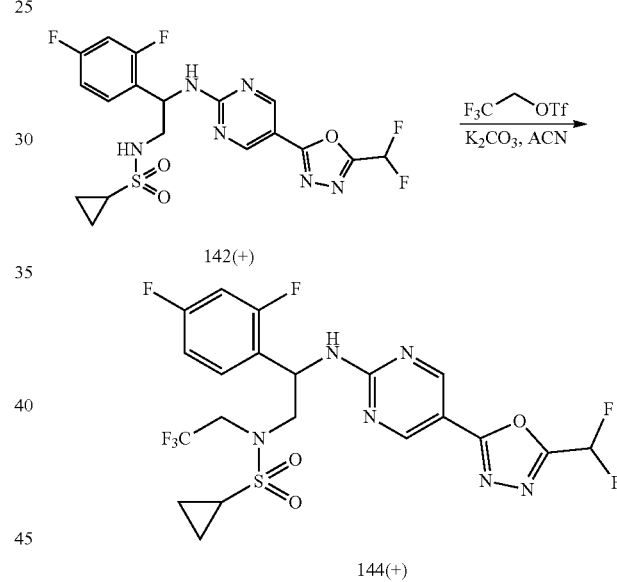

To a stirred solution of compound 142(+) (0.15 g, 0.30 mmol) in ACN (5 mL), K$_2$CO$_3$ (0.13 g, 0.90 mmol) and 2,2,2-trifluoroethyl trifluoromethanesulfonate (0.15 g, 0.60 mmol) were added at RT and stirred at 90° C. for 5 h. The progress of the reaction was monitored by TLC. After completion of the reaction, the reaction mixture was diluted with water and the product was extracted with EtOAc. The combined organic layer was washed with brine, dried over anhydrous Na$_2$SO$_4$ and concentrated under reduced pressure. The crude product was purified by silica gel column chromatography using 30% EtOAc/hexane to afford compound 144(+) (0.053 g, 31.0%) as an off white solid. $^1$H NMR (400 MHz, DMSO-d6): δ 8.90 (d, J=8.4 Hz, 2H), 8.74 (d, J=9.6 Hz, 1H), 7.65-7.11 (m, 4H), 5.89-5.83 (m, 1H), 4.28-4.10 (m, 2H), 3.76-3.65 (m, 2H), 2.72-2.65 (m, 1H), 1.05-0.64 (s, 4H); LC-MS: 555.20 [M+H]$^+$; HPLC: 97.90%; C-HPLC: 99.78% (RT: 6.41); SOR: +86.34 Solvent: methanol, Path length: 100 mm, Concentration: 0.2005 w/v %.

Example 145(+)

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-methylmethanesulfonamide (145(+))

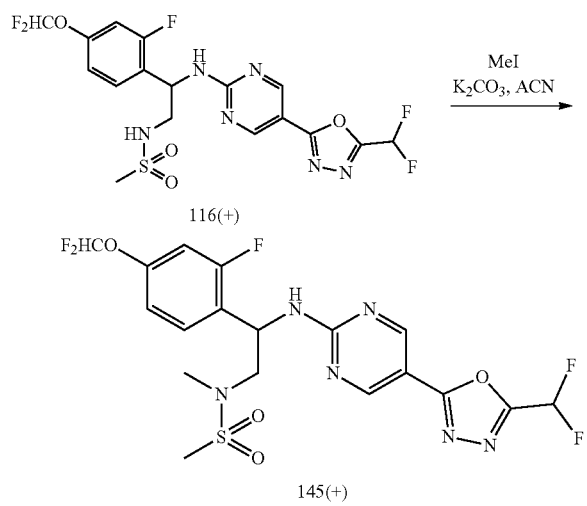

To a stirred solution of compound 116(+) (0.17 g, 0.34 mmol) in ACN (10 mL), K$_2$CO$_3$ (0.14 g, 1.03 mmol) and methyl iodide (0.14 g, 1.03 mmol) were added at 0° C. and stirred at RT for 16 h. The progress of the reaction was monitored by TLC. After completion of the reaction, the reaction mixture was concentrated under reduced pressure. The crude product was purified by silica gel column chromatography using 5% MeOH/DCM to afford compound 145(+) (0.168 g, 96.5%) as an off white solid. $^1$H NMR (400 MHz, DMSO-d6): δ 8.89 (d, J=5.2 Hz, 2H), 8.77 (d, J=9.2 Hz, 1H), 7.67-7.05 (m, 5H), 5.74-5.68 (m, 1H), 3.45 (d, J=7.2 Hz, 2H), 2.84 (s, 3H), 2.82 (s, 3H); LC-MS: 509.10 [M+H]$^+$; HPLC: 99.05%; C-HPLC: 99.15% (RT: 9.11); SOR: +69.87, Solvent: methanol, Path length: 100 mm, Concentration: 0.23 w/v %.

Example 146(+)

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-(2,2,2-trifluoroethyl)methanesulfonamide (146(+))

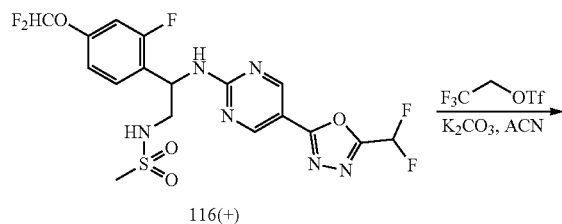

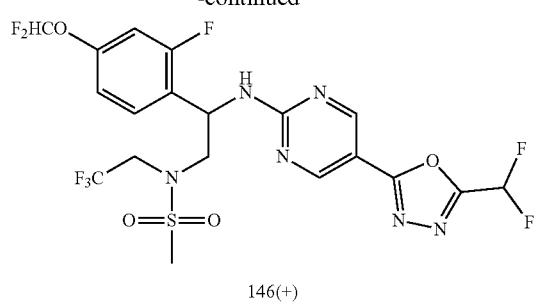

To a stirred solution of compound 116(+) (0.23 g, 0.46 mmol) in ACN (10 mL), K$_2$CO$_3$ (0.19 g, 1.39 mmol) and 2,2,2-trifluoroethyl trifluoromethanesulfonate (0.16 g, 0.69 mmol) were added at RT and stirred at 60° C. for 16 h. The progress of the reaction was monitored by TLC. After completion of the reaction, the reaction mixture was diluted with EtOAc and washed with water. The organic layer was washed with brine, dried over anhydrous Na$_2$SO$_4$ and concentrated under reduced pressure. The crude product was purified by silica gel column chromatography using 5% MeOH/DCM to afford compound 146(+) (0.185 g, 69.0%) as a light yellow solid. $^1$H NMR (400 MHz, DMSO-d6): δ 8.90 (d, J=8.8 Hz, 2H), 8.70 (d, J=8.8 Hz, 1H), 7.64-7.06 (m, 5H), 5.84-5.78 (m, 1H), 4.25-4.12 (m, 2H), 3.73-3.62 (m, 2H), 3.03 (s, 3H); LC-MS: 577.15 [M+H]$^+$; HPLC: 97.74%; C-HPLC: 99.44% (RT: 9.20); SOR: +90.86, Solvent: methanol, Path length: 100 mm, Concentration: 0.23 w/v %.

Example 147(+)

N-(2-(4-(difluoromethoxy)-2-fluorophenyl)-2-((5-(5-(difluoromethyl)-1,3,4-oxadiazol-2-yl)pyrimidin-2-yl)amino)ethyl)ethanesulfonamide (147(+))

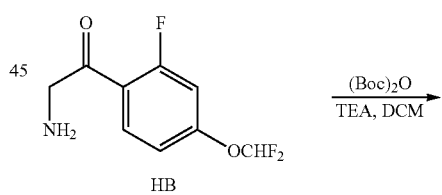

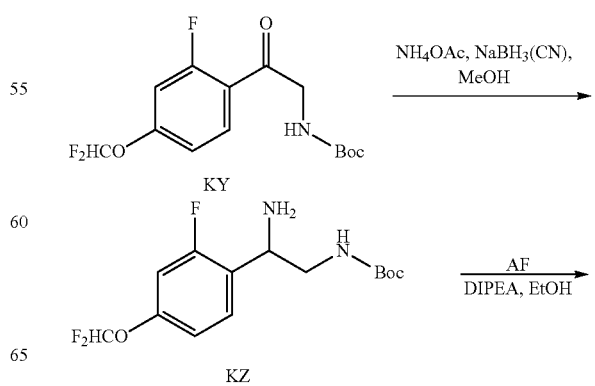

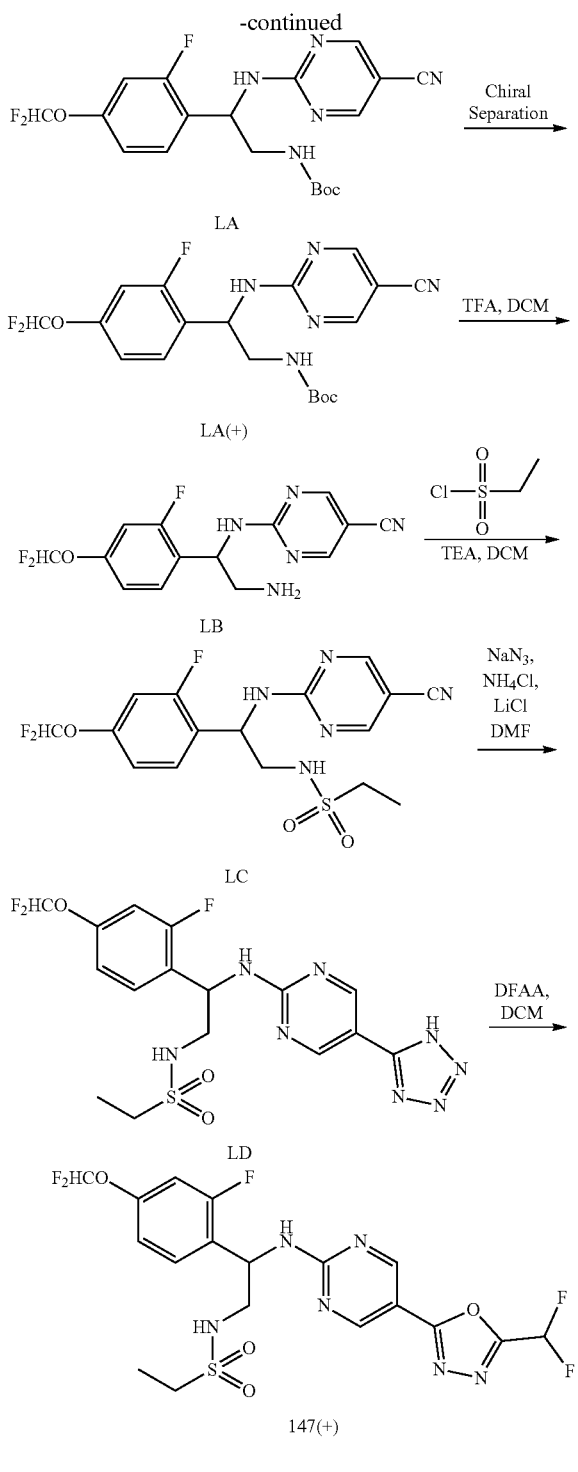

tert-butyl (2-(4-(difluoromethoxy)-2-fluorophenyl)-
2-oxoethyl)carbamate (KY)

To a stirred solution of compound HB (6.3 g, 24.6 mmol) in DCM (100 mL), triethyl amine (10.2 mL, 73.9 mmol) and (Boc)$_2$O (6.90 mL, 29.5 mmol) were added at 0° C. and stirred at RT for 2 h. The progress of the reaction was monitored by TLC. After completion of the reaction, the reaction mixture was diluted with DCM and washed with water. The combined organic layer was washed with brine, dried over anhydrous Na$_2$SO$_4$ and concentrated under reduced pressure. The crude product was purified by silica gel column chromatography using 20% EtOAc/hexane to afford KY (4.8 g, 61.0%) as a white solid. $^1$H NMR (400 MHz, CDCl$_3$): δ 8.01 (t, J=8.4 Hz, 1H), 7.00 (d, J=8.8 Hz, 1H), 6.92 (d, J=12.0 Hz, 1H), 6.76-6.40 (m, 1H), 5.44 (s, 1H), 4.55 (s, 2H), 1.45 (s, 9H); LC-MS: m/z 220.0 [M−Boc+H]$^+$.

tert-butyl (2-amino-2-(4-(difluoromethoxy)-2-fluorophenyl)ethyl)carbamate (KZ)

To a stirred solution of compound KY (4.80 g, 15.0 mmol) in MeOH (50 mL), ammonium acetate (23.0 g, 300 mmol) and Na(BH$_3$)CN (2.50 g, 40.5 mmol) were added and the reaction was stirred at 60° C. for 6 h. The progress of the reaction was monitored by TLC. After completion of the reaction, the reaction mixture was concentrated under reduced pressure. The residue was diluted with 10% NaOH solution and the product was extracted with 10% MeOH/DCM. The combined organic layer was washed with brine, dried over anhydrous Na$_2$SO$_4$ and concentrated under reduced pressure. The crude product was purified by silica gel column chromatography using 2-5% MeOH/DCM to afford KZ (3.48 g, 72.0%) as a colorless oil. $^1$H NMR (400 MHz, CD$_3$OD): δ 7.48-7.44 (m, 1H), 7.04-6.67 (m, 4H), 4.24 (t, J=6.6 Hz, 1H), 3.29-3.27 (m, 2H), 1.39 (s, 9H).

tert-butyl(2-((5-cyanopyrimidin-2-yl)amino)-2-(4-(difluoromethoxy)-2-fluorophenyl)ethyl)carbamate (LA)

To a stirred solution of 2-chloropyrimidine-5-carbonitrile (AF, 1.82 g, 13.0 mmol) and compound KZ (3.48 g, 10.8 mmol) in EtOH (50 mL), DIPEA (3.70 mL, 21.7 mmol) was added and the reaction was stirred at 85° C. for 6 h. The progress of the reaction was monitored by TLC. After completion of the reaction, the reaction mixture was concentrated under reduced pressure. The residue was diluted with EtOAc and washed with water. The organic layer was washed with brine, dried over anhydrous Na$_2$SO$_4$ and concentrated under reduced pressure. The crude product was purified by silica gel column chromatography using 20% EtOAc/hexane to afford compound LA (3.8 g, 83.0%) as an off white solid. $^1$H NMR (400 MHz, DMSO-d6): δ 8.72-8.67 (m, 2H), 7.49-7.43 (m, 1H), 7.24-6.98 (m, 5H), 5.43-5.41 (m, 1H), 3.35-3.26 (m, 2H), 1.30 (s, 9H). LC-MS: m/z 424.15 [M+H]$^+$; HPLC: 99.80%.

Chiral Preparative HPLC Details for LA(+)

The enantiomers were separated by chiral preparative high performance liquid chromatography (Chiralpak IA, 250×30 mm, 5; Mobile Phase: n-Hexane: Isopropyl alcohol (85:15)+0.1% NH$_3$; Flow rate: 30.0 mL/min) to afford LA(+) (1.7 g) as an off-white solid. $^1$H NMR (400 MHz, DMSO-d6): δ 8.72-8.67 (m, 2H), 7.49-6.87 (m, 6H), 5.44-5.41 (m, 1H), 3.35-3.26 (m, 2H), 1.30 (s, 9H). LC-MS: m/z 424.20 [M+H]$^+$; HPLC: 98.59%; C-HPLC: 99.41% (RT: 7.39); SOR: +65.67, Solvent: methanol, Path length: 10 mm, Concentration: 0.529 w/v %

2-((2-amino-1-(4-(difluoromethoxy)-2-fluorophenyl)
ethyl)amino)pyrimidine-5-carbonitrile (LB)

To a stirred solution of compound LA(+) (1.0 g, 2.36 mmol) in DCM (50 mL), 30% TFA in DCM (5 mL) was added and the reaction was stirred at RT for 1 h. The progress of the reaction was monitored by TLC. After completion of the reaction, the reaction mixture was evaporated to dryness to afford compound LB (TFA salt, 1.25 g, crude) as a light brown sticky solid. LC-MS: 324.05 [M+H]$^+$.

N-(2-((5-cyanopyrimidin-2-yl)amino)-2-(4-(difluoromethoxy)-2-fluorophenyl)ethyl)ethanesulfonamide (LC)

To a stirred solution of compound LB (1.25 g, 3.86 mmol) in DCM (100 mL), Triethyl amine (1.08 mL, 7.73 mmol) and ethanesulfonyl chloride (0.59 g, 4.64 mmol) were added at 0° C. and stirred at RT for 30 min. The progress of the reaction was monitored by TLC. After completion of the reaction, the reaction mixture was diluted with DCM and washed with water. The organic layer was washed with brine, dried over anhydrous Na$_2$SO$_4$ and concentrated under reduced pressure. The crude product was purified by silica gel column chromatography using 5% MeOH/DCM to afford LC (0.9 g, 56.0%) as a light yellow solid. LC-MS: m/z 416.15 [M+H]$^+$.

N-(2-((5-(1H-tetrazol-5-yl)pyrimidin-2-yl)amino)-2-(4-(difluoromethoxy)-2-fluorophenyl)ethyl)ethanesulfonamide (LD)

To a stirred solution of compound LC (0.9 g, 2.16 mmol) in DMF (15 mL), NaN$_3$ (0.42 g, 6.50 mmol), NH$_4$Cl (0.36 g, 6.50 mmol) and LiCl (0.091 g) were added and the reaction was stirred at 100° C. for 16 h. The progress of the reaction was monitored by TLC. After completion of the reaction, the reaction mixture was concentrated under reduced pressure. The residue was diluted with EtOAc and washed with water. The organic layer was washed with brine, dried over anhydrous Na$_2$SO$_4$ and concentrated under reduced pressure. The crude product was purified by silica gel column chromatography using 2-5% MeOH/DCM to afford compound LD (0.85 g, 86.0%) as an off white solid. LC-MS: m/z 459.15 [M+H]$^+$.

N-(2-(4-(difluoromethoxy)-2-fluorophenyl)-2-((5-(5-(difluoromethyl)-1,3,4-oxadiazol-2-yl)pyrimidin-2-yl)amino)ethyl)ethanesulfonamide (147(+))

To a stirred solution of compound LD (0.85 g, 1.85 mmol) in DCM (10 mL), DFAA (0.64 mL, 5.56 mmol) was added and the reaction was stirred at RT for 16 h. The progress of the reaction was monitored by TLC. After completion of the reaction, the reaction mixture was diluted with DCM and washed with saturated NaHCO$_3$ solution. The organic layer was washed with brine, dried over anhydrous Na$_2$SO$_4$ and concentrated under reduced pressure. The crude product was purified by silica gel column chromatography using 2-5% MeOH/DCM to afford compound 147(+) (0.7 g, 74.0%) as an off white solid. $^1$H NMR (400 MHz, DMSO-d6): δ 8.88 (d, J=13.2 Hz, 2H), 8.66 (d, J=8.8 Hz, 1H), 7.70-7.00 (m, 6H), 5.12-4.98 (m, 1H), 3.35-3.33 (m, 2H), 2.97-2.93 (m, 2H), 1.10 (t, J=7.2 Hz, 3H); LC-MS: 509.15 [M+H]$^+$, HPLC: 98.53%; C-HPLC: 99.53% (RT: 10.15); SOR: +80.02, Solvent: methanol, Path length: 100 mm, Concentration: 100 w/v %

Example 148(+)

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-methylethanesulfonamide (148(+))

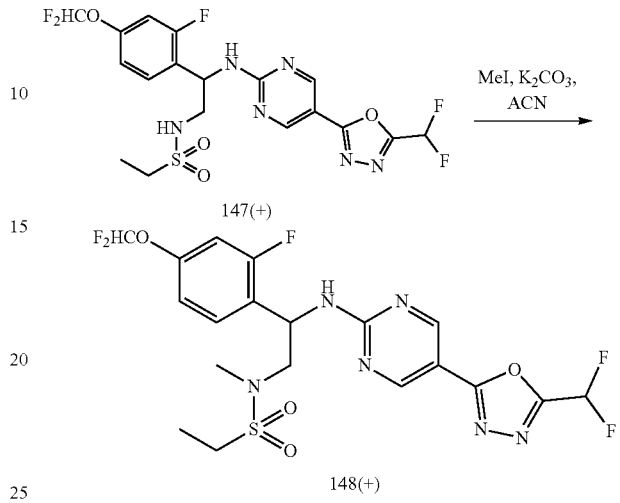

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-methylethanesulfonamide (148(+))

To a stirred solution of compound 147(+) (0.2 g, 0.39 mmol) in ACN (15 mL), K$_2$CO$_3$ (0.16 g, 1.18 mmol) and methyl iodide (0.22 g, 1.57 mmol) were added at 0° C. and stirred at RT for 16 h. The progress of the reaction was monitored by TLC. After completion of the reaction, the reaction mixture was filtered and the solids were washed with DCM. The filtrate was concentrated under reduced pressure. The crude product was purified by silica gel column chromatography using 5% MeOH/DCM to afford compound 148(+) (0.09 g, 44.0%) as an off white solid. $^1$H NMR (400 MHz, DMSO-d6): δ 8.89 (d, J=4.4 Hz, 2H), 8.75 (d, J=8.8 Hz, 1H), 7.67-7.05 (m, 5H), 5.75-5.67 (m, 1H), 3.52 (d, J=7.2 Hz, 2H), 3.01 (q, J=7.2 Hz, 2H), 2.85 (s, 3H), 1.10 (t, J=7.2 Hz, 3H); LC-MS: 523.20 [M+H]$^+$; HPLC: 96.92%; C-HPLC: 96.93% (RT: 7.42); SOR: +86.11, Solvent: methanol, Path length: 100 mm, Concentration: 100 w/v %.

Example 149(+)

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-(2,2,2-trifluoroethyl)ethanesulfonamide (149(+))

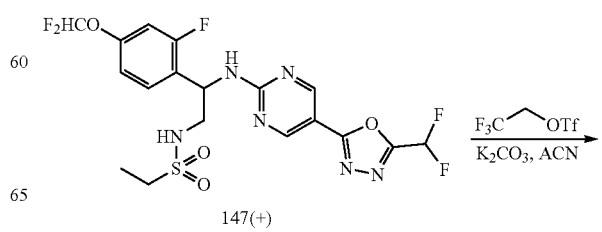

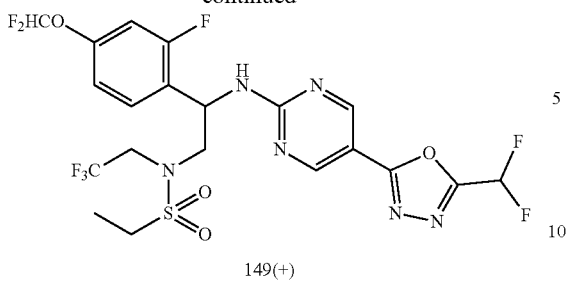

149(+)

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-(2,2,2-trifluoroethyl)ethanesulfonamide (149(+))

To a stirred solution of compound 147(+) (0.25 g, 0.49 mmol) in ACN (10 mL), K$_2$CO$_3$ (0.20 g, 1.47 mmol) and 2,2,2-trifluoroethyl trifluoromethanesulfonate (0.17 g, 0.73 mmol) were added at 0° C. and stirred at 60° C. for 16 h. The progress of the reaction was monitored by TLC. After completion of the reaction, the reaction mixture was diluted with EtOAc and washed with water. The organic layer was washed with brine, dried over anhydrous Na$_2$SO$_4$ and concentrated under reduced pressure. The crude product was purified by silica gel column chromatography using 5% MeOH/DCM to afford compound 149(+) (0.11 g, 38.0%) as sticky colorless solid. $^1$H NMR (400 MHz, DMSO-d6): δ 8.91 (d, J=7.6 Hz, 2H), 8.70 (d, J=9.2 Hz, 1H), 7.64-7.06 (m, 5H), 5.84-5.75 (m, 1H), 4.27-4.16 (m, 2H), 3.75-3.60 (m, 2H), 3.25-3.14 (m, 2H), 1.13 (t, J=7.2 Hz, 3H); LC-MS: 591.10 [M+H]$^+$; HPLC: 98.95%; C-HPLC: 98.69% (RT: 6.44); SOR: +77.47, Solvent: methanol, Path length: 100 mm, Concentration: 100 w/v %.

Example 150(+)

N-(2-(4-(difluoromethoxy)-2-fluorophenyl)-2-((5-(5-(difluoromethyl)-1,3,4-oxadiazol-2-yl)pyrimidin-2-yl)amino)ethyl)cyclopropanesulfonamide (150(+))

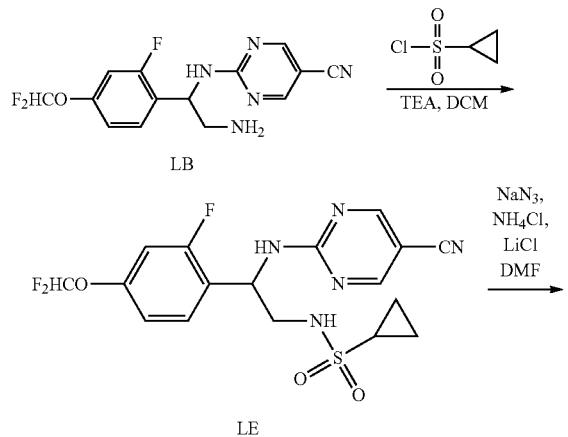

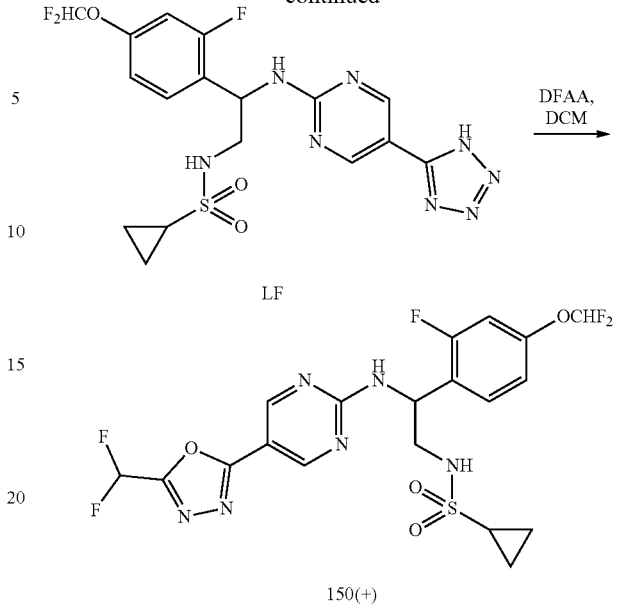

150(+)

N-(2-((5-cyanopyrimidin-2-yl)amino)-2-(4-(difluoromethoxy)-2-fluorophenyl)ethyl)cyclopropanesulfonamide (LE)

To a stirred solution of compound LB (0.55 g, 1.70 mmol) in DCM (50 mL), triethyl amine (0.47 mL, 3.40 mmol) and cyclopropanesulfonyl chloride (0.36 g, 2.55 mmol) were added at 0° C. and stirred at RT for 30 min. The progress of the reaction was monitored by TLC. After completion of the reaction, the reaction mixture was diluted with DCM and washed with water. The combined organic layer was washed with brine, dried over anhydrous Na$_2$SO$_4$ and concentrated under reduced pressure. The crude product was purified by silica gel column chromatography using 5% MeOH/DCM to afford LE (0.45 g, 62.0%) as a light yellow solid. $^1$H NMR (400 MHz, DMSO-d6): δ 8.76 (d, J=8.4 Hz, 1H), 8.71 (d, J=1.6 Hz, 2H), 7.56-7.02 (m, 5H), 5.51-5.46 (m, 1H), 3.41-3.34 (m, 2H), 0.89-0.86 (m, 4H), (1H merged in solvent peak); LC-MS: m/z 428.15 [M+H]$^+$.

N-(2-((5-(1H-tetrazol-5-yl)pyrimidin-2-yl)amino)-2-(4-(difluoromethoxy)-2-fluorophenyl)ethyl)cyclopropanesulfonamide (LF)

To a stirred solution of compound LE (0.45 g, 1.05 mmol) in DMF (10 mL), NaN$_3$ (0.205 g, 3.16 mmol), NH$_4$Cl (0.177 g, 3.16 mmol) and LiCl (0.044 g) were added and the reaction was stirred at 100° C. for 16 h. The progress of the reaction was monitored by TLC. After completion of the reaction, the reaction mixture was concentrated under reduced pressure. The residue was diluted with EtOAc and washed with water. The organic layer was washed with brine, dried over anhydrous Na$_2$SO$_4$ and concentrated under reduced pressure to afford compound LF (0.45 g, Crude) as a brown sticky solid. LC-MS: m/z 471.20 [M+H]$^+$.

N-(2-(4-(difluoromethoxy)-2-fluorophenyl)-2-((5-(5-(difluoromethyl)-1,3,4-oxadiazol-2-yl)pyrimidin-2-yl)amino)ethyl)cyclopropanesulfonamide (150(+))

To a stirred solution of compound LF (0.45 g, 0.95 mmol) in DCM (25 mL), DFAA (0.33 g, 1.91 mmol) was added and the reaction was stirred at RT for 16 h. The progress of the reaction was monitored by TLC. After completion of the reaction, the reaction mixture was diluted with DCM and washed with saturated NaHCO₃ solution. The organic layer was washed with brine, dried over anhydrous Na₂SO₄ and concentrated under reduced pressure. The crude product was purified by silica gel column chromatography using 2-5% MeOH/DCM to afford compound 150(+) (0.35 g, 70.5%) as an off white solid. ¹H NMR (400 MHz, DMSO-d6): δ 8.88 (d, J=13.2 Hz, 2H), 8.67 (d, J=8.8 Hz, 1H), 7.64-7.03 (m, 6H), 5.58-5.52 (m, 1H), 3.41-3.39 (m, 2H), 0.90-0.88 (m, 4H), (1H merged in solvent); LC-MS: 521.10 [M+H]⁺, HPLC: 98.59%; C-HPLC: 99.17% (RT: 11.19); SOR: +68.59, Solvent: methanol, Path length: 100 mm, Concentration: 100 w/v %

Example 151(+)

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-methylcyclopropanesulfonamide (151(+))

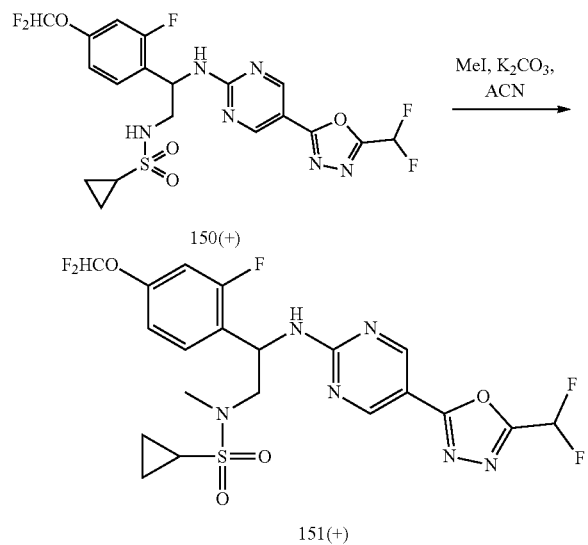

To a stirred solution of compound 150(+) (0.15 g, 0.28 mmol) in ACN (15 mL), K₂CO₃ (0.16 g, 1.15 mmol) and methyl iodide (0.28 g, 2.01 mmol) were added and the reaction was stirred at RT for 16 h. The progress of the reaction was monitored by TLC. After completion of the reaction, the reaction mixture was filtered through pad of celite and washed with DCM. The filtrate was concentrated under reduced pressure. The crude product was purified by silica gel column chromatography using 5% MeOH/DCM to afford compound 151(+) (0.09 g, 58.5%) as an off white solid. ¹H NMR (400 MHz, DMSO-d6): δ 8.90 (d, J=3.6 Hz, 2H), 8.78 (d, J=9.2 Hz, 1H), 7.67-7.05 (m, 5H), 5.75-5.69 (m, 1H), 3.54-3.52 (m, 2H), 2.86 (s, 3H), 2.56-2.54 (m, 1H), 0.92-0.86 (m, 4H); LC-MS: 535.15 [M+H]⁺; HPLC: 98.74%; C-HPLC: 98.84% (RT: 8.45); SOR: +69.86, Solvent: methanol, Path length: 100 mm, Concentration: 0.23 w/v %.

Example 152(+)

N-(2-(4-(difluoromethoxy)-2-fluorophenyl)-2-((5-(5-(difluoromethyl)-1,3,4-oxadiazol-2-yl)pyrimidin-2-yl)amino)ethyl)-N-(2,2,2-trifluoroethyl)cyclopropanesulfonamide (152(+))

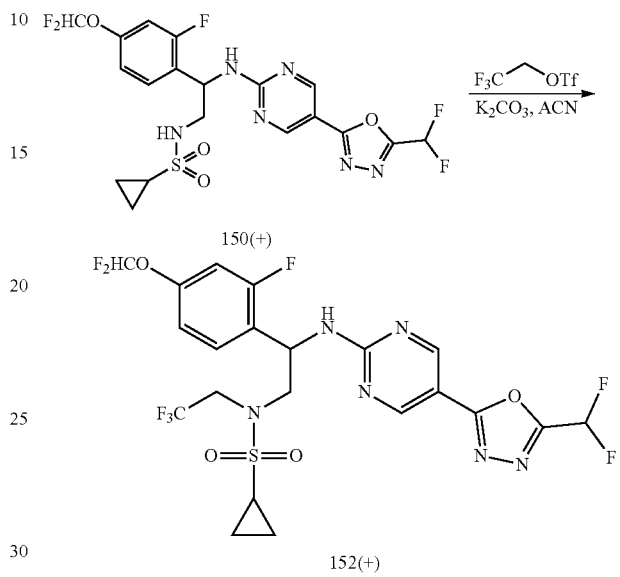

To a stirred solution of compound 150(+) (0.15 g, 0.28 mmol) in ACN (15 mL), K₂CO₃ (0.12 g, 0.86 mmol) and 2,2,2-trifluoroethyl trifluoromethanesulfonate (0.10 g, 0.43 mmol) were added at 0° C. and stirred at RT for 16 h. The progress of the reaction was monitored by TLC. After completion of the reaction, the reaction mixture was filtered through pad of celite and washed with DCM. The organic layer was concentrated under reduced pressure. The crude product was purified by silica gel column chromatography using 5% MeOH/DCM to afford compound to afford compound 152(+) (0.090 g, 52.0%) as an off white solid. ¹H NMR (400 MHz, DMSO-d6): δ 8.90 (d, J=9.2 Hz, 2H), 8.74 (d, J=9.2 Hz, 1H), 7.65-7.06 (m, 5H), 5.89-5.83 (m, 1H), 4.29-4.14 (m, 2H), 3.76-3.67 (m, 2H), 2.70-2.65 (m, 1H), 1.05-0.92 (m, 4H); LC-MS: 603.10 [M+H]⁺; HPLC: 99.25%; C-HPLC: 99.84% (RT: 7.20); SOR: +85.99, Solvent: methanol, Path length: 100 mm, Concentration: 0.23 w/v %.

Example 153(+)

N-(2-((5-(5-(difluoromethyl)-1,3,4-oxadiazol-2-yl)pyrimidin-2-yl)amino)-2-(4-(trifluoromethoxy)phenyl)ethyl)-N-methylmethanesulfonamide (153(+))

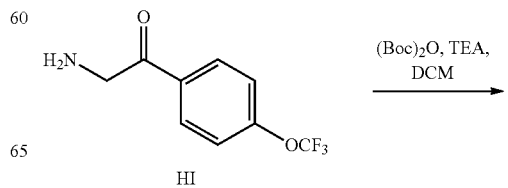

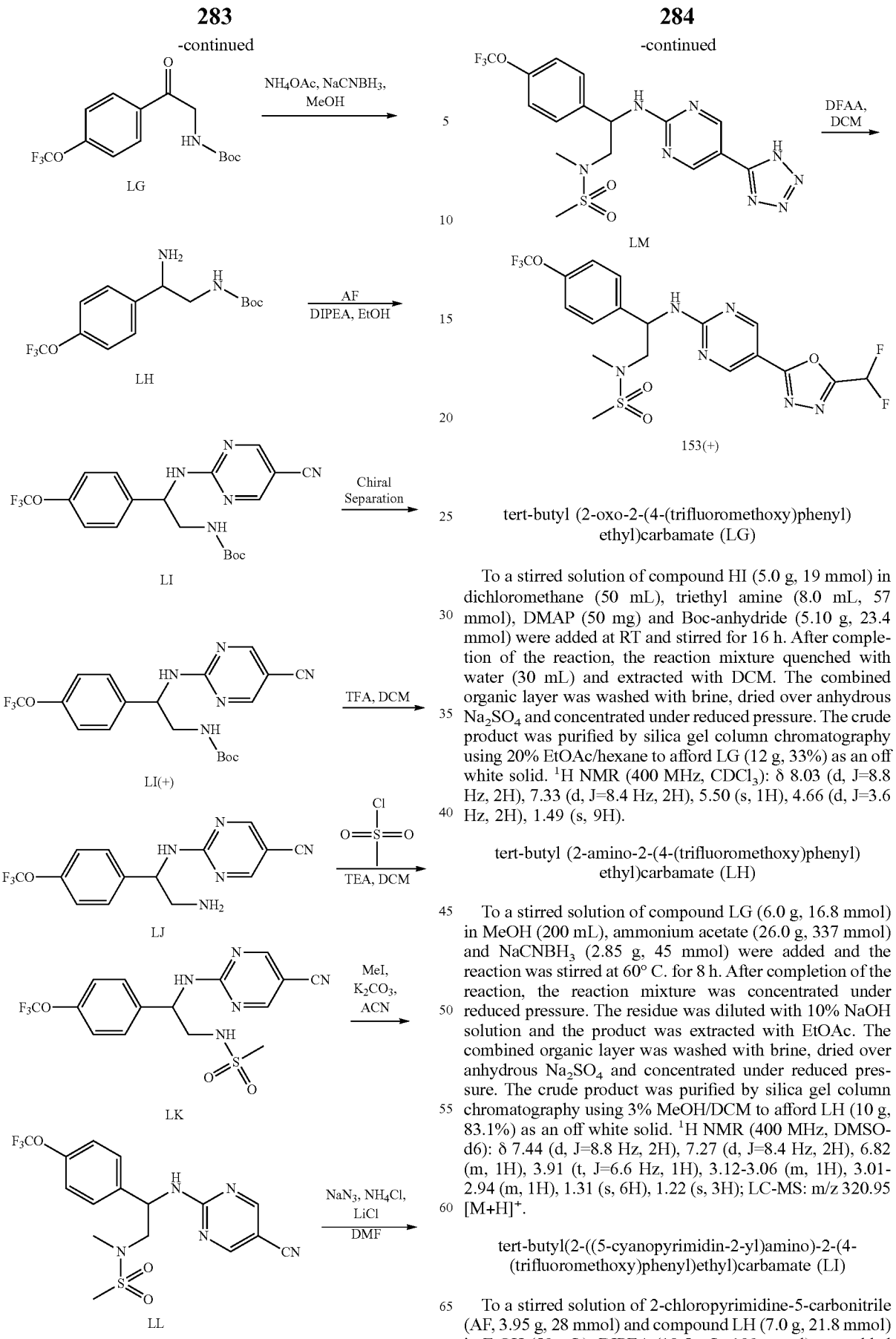

tert-butyl (2-oxo-2-(4-(trifluoromethoxy)phenyl)ethyl)carbamate (LG)

To a stirred solution of compound HI (5.0 g, 19 mmol) in dichloromethane (50 mL), triethyl amine (8.0 mL, 57 mmol), DMAP (50 mg) and Boc-anhydride (5.10 g, 23.4 mmol) were added at RT and stirred for 16 h. After completion of the reaction, the reaction mixture quenched with water (30 mL) and extracted with DCM. The combined organic layer was washed with brine, dried over anhydrous $Na_2SO_4$ and concentrated under reduced pressure. The crude product was purified by silica gel column chromatography using 20% EtOAc/hexane to afford LG (12 g, 33%) as an off white solid. $^1$H NMR (400 MHz, $CDCl_3$): δ 8.03 (d, J=8.8 Hz, 2H), 7.33 (d, J=8.4 Hz, 2H), 5.50 (s, 1H), 4.66 (d, J=3.6 Hz, 2H), 1.49 (s, 9H).

tert-butyl (2-amino-2-(4-(trifluoromethoxy)phenyl)ethyl)carbamate (LH)

To a stirred solution of compound LG (6.0 g, 16.8 mmol) in MeOH (200 mL), ammonium acetate (26.0 g, 337 mmol) and $NaCNBH_3$ (2.85 g, 45 mmol) were added and the reaction was stirred at 60° C. for 8 h. After completion of the reaction, the reaction mixture was concentrated under reduced pressure. The residue was diluted with 10% NaOH solution and the product was extracted with EtOAc. The combined organic layer was washed with brine, dried over anhydrous $Na_2SO_4$ and concentrated under reduced pressure. The crude product was purified by silica gel column chromatography using 3% MeOH/DCM to afford LH (10 g, 83.1%) as an off white solid. $^1$H NMR (400 MHz, DMSO-d6): δ 7.44 (d, J=8.8 Hz, 2H), 7.27 (d, J=8.4 Hz, 2H), 6.82 (m, 1H), 3.91 (t, J=6.6 Hz, 1H), 3.12-3.06 (m, 1H), 3.01-2.94 (m, 1H), 1.31 (s, 6H), 1.22 (s, 3H); LC-MS: m/z 320.95 $[M+H]^+$.

tert-butyl(2-((5-cyanopyrimidin-2-yl)amino)-2-(4-(trifluoromethoxy)phenyl)ethyl)carbamate (LI)

To a stirred solution of 2-chloropyrimidine-5-carbonitrile (AF, 3.95 g, 28 mmol) and compound LH (7.0 g, 21.8 mmol) in EtOH (50 mL), DIPEA (18.5 mL, 109 mmol) was added and the reaction was stirred at 90° C. for 16 h. The progress of the reaction was monitored by TLC. After completion of the reaction, the reaction mixture was concentrated under reduced pressure. The crude product was purified by silica gel column chromatography using 20% EtOAc/hexane to afford racemic compound LI (8.5 g, 91.9%) as an off white solid. $^1$H NMR (400 MHz, DMSO-d6): δ 8.79 (d, J=8.4 Hz, 1H), 8.67 (d, J=9.6 Hz, 2H), 7.46 (d, J=8.4 Hz, 2H), 7.30 (d, J=7.6 Hz, 2H), 6.99 (m, 1H), 5.22-5.17 (m, 1H), 3.36-3.29 (m, 2H), 1.29 (s, 9H). LC-MS: m/z 424.10 [M+H]$^+$; HPLC Purity: 98.60%.

Chiral Preparative HPLC Details for LI(+)

The enantiomers were separated by chiral preparative high performance liquid chromatography (Chiralpak IA, 250×30 mm, 5; Mobile Phase: n-Hexane: Isopropyl alcohol (85:15)+0.1% NH$_3$; Flow rate: 30.0 mL/min) to afford LI(+) (4.0 g, 43.0%) as an off-white solid. $^1$H NMR (400 MHz, DMSO-d6): δ 8.78 (d, J=8.0 Hz, 1H), 8.69-8.65 (m, 2H), 7.47-7.45 (m, 2H), 7.31-7.29 (m, 2H), 6.99-6.96 (m, 1H), 5.22-5.17 (m, 1H), 3.36-3.29 (m, 2H), 1.29 (s, 9H); LC-MS: m/z 424.10 [M+H]$^+$; C-HPLC: 99.74% (RT: 6.10); SOR: +61.8, Solvent: methanol, Path length: 10 mm, Concentration: 0.5 w/v %

2-((2-amino-1-(4-(trifluoromethoxy)phenyl)ethyl) amino)pyrimidine-5-carbonitrile (LJ)

To a stirred solution of compound LI(+) (2.3 g, 5.4 mmol) in DCM (10 mL), 30% TFA in DCM (20 mL) was added and the reaction was stirred at RT for 16 h. The progress of the reaction was monitored by TLC. After completion of the reaction, the reaction mixture was concentrated to afford compound L (2 g, crude) as a light brown thick oil. LCMS: 324.05 (M+H).

N-(2-((5-cyanopyrimidin-2-yl)amino)-2-(4-(trifluoromethoxy)phenyl)ethyl)methanesulfonamide (LK)

To a stirred solution of compound L (0.65 g, 2.0 mmol) in DCM (10 mL), triethyl amine (0.60 mL, 6.0 mmol) and methanesulfonyl chloride (0.25 g, 2.2 mmol) were added at 0° C. and stirred for 45 min. The progress of the reaction was monitored by TLC. After completion of the reaction, the reaction mixture was diluted with water and the product was extracted with DCM. The combined organic layer was washed with brine, dried over anhydrous Na$_2$SO$_4$ and concentrated under reduced pressure. The crude product was purified by silica gel column chromatography using 5% MeOH/DCM to afford LK (0.35 g, 43.0%) as an off white solid. LC-MS: m/z 402.15 [M+H]$^+$.

N-(2-((5-cyanopyrimidin-2-yl)amino)-2-(4-(trifluoromethoxy)phenyl)ethyl)-N-methylmethanesulfonamide (LL)

To a stirred solution of compound LK (0.3 g, 0.75 mmol) in ACN (5 mL), K$_2$CO$_3$ (0.31 g, 2.2 mmol) and methyl iodide (0.3 mL, 5.2 mmol) were added and the reaction was stirred at RT for 16 h. The progress of the reaction was monitored by TLC. After completion of the reaction, the reaction mixture was diluted with EtOAc and washed with water. The organic layer was concentrated under reduced pressure. The crude product was purified by silica gel column chromatography using 50% EtOAc/hexane to afford compound LL (0.25 g, 81.0%) as an off white solid. $^1$H NMR (400 MHz, DMSO-d6): δ 8.84 (m, 1H), 8.69 (s, 2H), 7.56 (d, J=8.8 Hz, 2H), 7.35 (d, J=8.4 Hz, 2H), 5.39 (m, 1H), 3.44-3.41 (m, 2H), 2.82 (s, 3H), 2.76 (s, 3H); LC-MS: 416.10 [M+H]$^+$.

N-(2-((5-(1H-tetrazol-5-yl)pyrimidin-2-yl)amino)-2-(4-(trifluoromethoxy)phenyl)ethyl)-N-methylmethanesulfonamide (LM)

To a stirred solution of compound LL (0.25 g, 0.6 mmol) in DMF (7 mL), NaN$_3$ (0.19 g, 3.0 mmol), NH$_4$Cl (0.16 g, 3.0 mmol) and LiCl (0.08 g) were added and the reaction was stirred at 100° C. for 16 h. After completion of the reaction, the reaction mixture was concentrated under reduced pressure. The residue was quenched with ice water and acidified with 6N HCl solution to pH=2. The precipitated solid was filtered, washed with cold water and dried to afford LM (0.25 g, 91.0%) as a brown solid. LC-MS: m/z 459.20 [M+H]$^+$.

N-(2-((5-(5-(difluoromethyl)-1,3,4-oxadiazol-2-yl) pyrimidin-2-yl)amino)-2-(4-(trifluoromethoxy)phenyl)ethyl)-N-methylmethanesulfonamide (153(+))

To a stirred solution of compound LM (0.25 g, 0.55 mmol) in DCM (10 mL), DFAA (0.19 g, 1.1 mmol) was added and the reaction was stirred at RT for 16 h. The progress of the reaction was monitored by TLC. After completion of the reaction, the reaction mixture was quenched with NaHCO$_3$ solution and the product was extracted with DCM. The combined organic layer was washed with brine, dried over anhydrous Na$_2$SO$_4$ and concentrated under reduced pressure. The crude product was purified by silica gel column chromatography using 50% EtOAc/hexane to afford compound 153(+) (0.065 g, 23.5%) as an off white solid. $^1$H NMR (400 MHz, DMSO-d6): δ 8.88 (d, J=10.8 Hz, 2H), 8.76 (d, J=8.8 Hz, 1H), 7.64-7.35 (m, 5H), 5.49-5.45 (m, 1H), 3.51-3.46 (m, 2H), 2.84 (s, 3H), 2.80 (s, 3H); LC-MS: 509.10 [M+H]$^+$, HPLC: 99.11%; C-HPLC: 99.31% (RT: 8.91); SOR: +76.10, Solvent: methanol, Path length: 100 mm, Concentration: 100 w/v %.

Example 154(+)

N-(2-((5-(5-(difluoromethyl)-1,3,4-oxadiazol-2-yl) pyrimidin-2-yl)amino)-2-(4-(trifluoromethoxy)phenyl)ethyl)-N-(2,2,2-trifluoroethyl)methanesulfonamide (154(+))

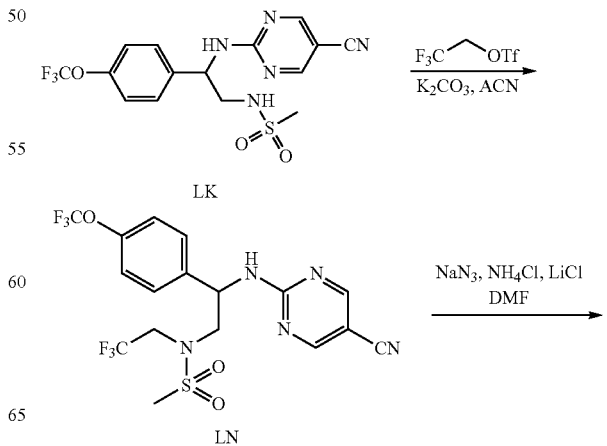

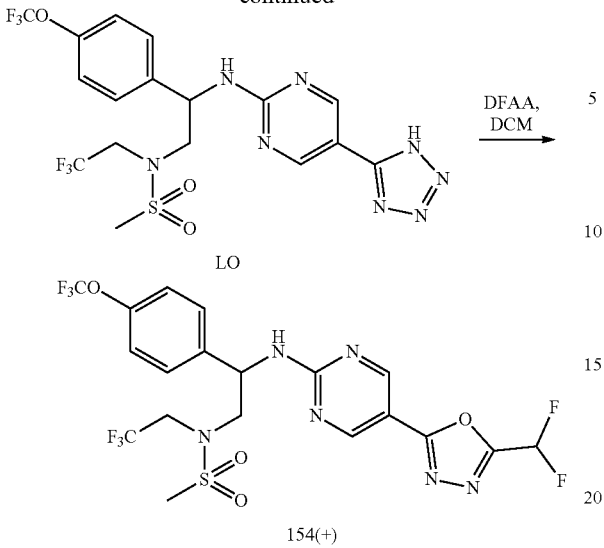

N-(2-((5-cyanopyrimidin-2-yl)amino)-2-(4-(trifluoromethoxy)phenyl)ethyl)-N-(2,2,2-trifluoroethyl)methanesulfonamide (LN)

To a stirred solution of compound LK (0.3 g, 0.74 mmol) in ACN (10 mL), $K_2CO_3$ (0.31 g, 2.24 mmol) and 2,2,2-trifluoroethyl trifluoromethanesulfonate (0.3 mL, 1.9 mmol) were added at 0° C. and stirred at RT for 16 h. The progress of the reaction was monitored by TLC. After completion of the reaction, the reaction mixture was diluted with EtOAc and washed with water. The combined organic layer was dried over anhydrous $Na_2SO_4$ and concentrated under reduced pressure. The crude product was purified by silica gel column chromatography using 50% EtOAc/hexane to afford compound LN (0.32 g, 89.0%) as an off white solid. $^1$H NMR (400 MHz, DMSO-d6): δ 8.78 (d, J=8.8 Hz, 1H), 8.72 (d, J=2.8 Hz, 2H), 7.55 (d, J=8.4 Hz, 2H), 7.37 (d, J=8.0 Hz, 2H), 5.53-5.51 (m, 1H), 4.18-4.10 (m, 2H), 3.69-3.64 (m, 2H), 3.01 (s, 3H); LC-MS: 484.10 [M+H]$^+$.

N-(2-((5-(1H-tetrazol-5-yl)pyrimidin-2-yl)amino)-2-(4-(trifluoromethoxy)phenyl)ethyl)-N-(2,2,2-trifluoroethyl)methanesulfonamide (LO)

To a stirred solution of compound LN (0.32 g, 0.6 mmol) in DMF (10 mL), $NaN_3$ (0.21 g, 3.3 mmol), $NH_4Cl$ (0.18 g, 3.3 mmol) and LiCl (0.08 g) were added and the reaction was stirred at 100° C. for 16 h. After completion of the reaction, the reaction mixture was concentrated under reduced pressure. The residue was quenched with ice water and acidified with 6N HCl solution to pH=2. The precipitated solid was filtered, washed with cold water and dried to afford LN (0.25 g, 72.0%) as a brown solid. LC-MS: m/z 527.10 [M+H]$^+$.

N-(2-((5-(5-(difluoromethyl)-1,3,4-oxadiazol-2-yl)pyrimidin-2-yl)amino)-2-(4-(trifluoromethoxy)phenyl)ethyl)-N-(2,2,2-trifluoroethyl)methanesulfonamide (154(+))

To a stirred solution of compound LO (0.25 g, 0.48 mmol) in DCM (10 mL), DFAA (0.16 g, 0.95 mmol) was added and the reaction was stirred at RT for 16 h. The progress of the reaction was monitored by TLC. After completion of the reaction, the reaction mixture was quenched with $NaHCO_3$ solution and extracted with DCM. The combined organic layer was washed with brine, dried over anhydrous $Na_2SO_4$ and concentrated under reduced pressure. The crude product was purified by silica gel column chromatography using 50% EtOAc/hexane to afford compound 154(+) (0.15 g, 55.0%) as an off white solid. $^1$H NMR (400 MHz, DMSO-d6): δ 8.89 (d, J=16.0 Hz, 2H), 8.70 (d, J=8.8 Hz, 1H), 7.64-7.37 (m, 5H), 5.60-5.55 (m, 1H), 4.25-4.10 (m, 2H), 3.74-3.62 (m, 2H), 3.03 (s, 3H); LC-MS: 577.05 [M+H]$^+$, HPLC: 98.89%; C-HPLC: 99.87% (RT: 5.88); SOR: +97.36, Solvent: methanol, Path length: 100 mm, Concentration: 0.23 w/v %.

Example 155(+)

N-(2-((5-(5-(difluoromethyl)-1,3,4-oxadiazol-2-yl)pyrimidin-2-yl)amino)-2-(4-(trifluoromethoxy)phenyl)ethyl)ethanesulfonamide (155(+))

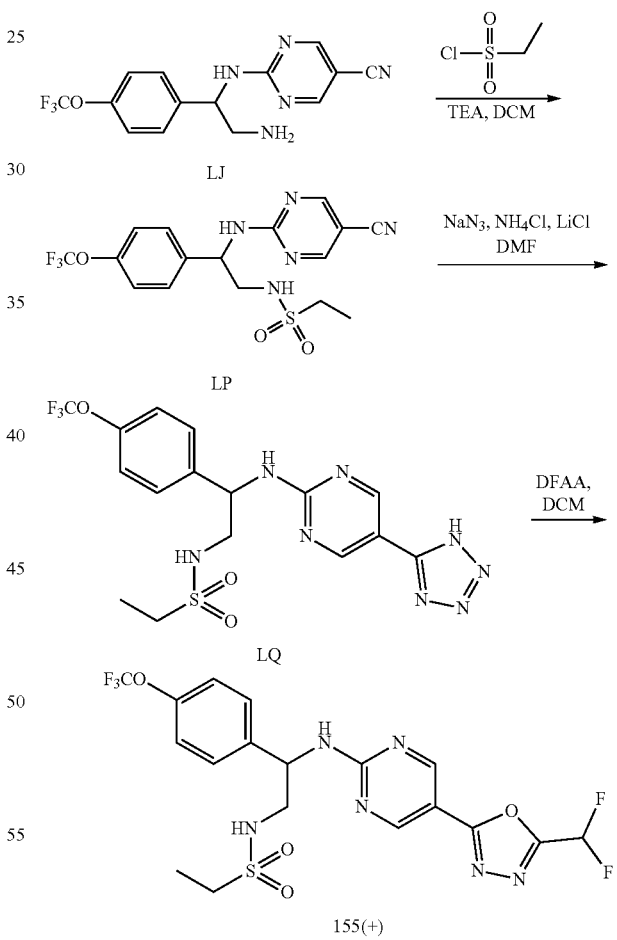

N-(2-((5-cyanopyrimidin-2-yl)amino)-2-(4-(trifluoromethoxy)phenyl)ethyl)ethanesulfonamide (LP)

To a stirred solution of compound L (0.65 g, 2.0 mmol) in DCM (10 mL), triethyl amine (0.83 mL, 6.0 mmol) and ethanesulfonyl chloride (0.23 g, 1.8 mmol) were added at 0°

C. and stirred for 45 min. The progress of the reaction was monitored by TLC. After completion of the reaction, the reaction mixture was quenched with water and the product was extracted with DCM. The combined organic layer was washed with brine, dried over anhydrous Na₂SO₄ and concentrated under reduced pressure. The crude product was purified by silica gel column chromatography using 50% EtOAc/hexane to afford LP (0.45 g, 54.0%) as an off white solid. ¹H NMR (400 MHz, DMSO-d6): δ 8.80 (d, J=8.8 Hz, 1H), 8.69 (d, J=2.4 Hz, 2H), 7.51 (d, J=8.0 Hz, 2H), 7.35-7.27 (m, 3H), 5.24-5.19 (m, 1H), 3.38-3.33 (m, 1H), 3.27-3.25 (m, 1H), 2.94-2.88 (m, 2H), 1.06 (t, J=7.2 Hz, 3H), LC-MS: m/z 416.15 [M+H]⁺.

N-(2-((5-(1H-tetrazol-5-yl)pyrimidin-2-yl)amino)-2-(4-(trifluoromethoxy)phenyl)ethyl)ethanesulfonamide (LQ)

To a stirred solution of compound LP (0.45 g, 1.0 mmol) in DMF (10 mL), NaN₃ (0.35 g, 5.4 mmol), NH₄Cl (0.27 g, 5.4 mmol) and LiCl (0.05 g) were added and the reaction was stirred at 100° C. for 16 h. After completion of the reaction, the reaction mixture was concentrated under reduced pressure. The residue was quenched with ice water and acidified with 1N HCl solution to pH=2. The precipitated solid was filtered, washed with cold water and dried to afford LQ (0.4 g, 81.0%) as an off white solid. LC-MS: m/z 459.0 [M+H]⁺.

N-(2-((5-(5-(difluoromethyl)-1,3,4-oxadiazol-2-yl)pyrimidin-2-yl)amino)-2-(4-(trifluoromethoxy)phenyl)ethyl)ethanesulfonamide (155(+))

To a stirred solution of compound LQ (0.4 g, 0.87 mmol) in DCM (10 mL), DFAA (0.30 g, 1.7 mmol) was added and the reaction was stirred at RT for 16 h. The progress of the reaction was monitored by TLC. After completion of the reaction, the reaction mixture was quenched with water and the product was extracted with DCM. The combined organic layer was washed with brine, dried over anhydrous Na₂SO₄ and concentrated under reduced pressure. The crude product was purified by silica gel column chromatography using 40% EtOAc/hexane to afford compound 155(+) (0.15 g, 34.0%) as an off white solid. ¹H NMR (400 MHz, DMSO-d6): δ 8.88 (d, J=14.0 Hz, 2H), 8.71 (d, J=8.8 Hz, 1H), 7.64-7.29 (m, 6H), 5.35-5.26 (m, 1H), 3.43-3.29 (m, 2H), 2.96-2.89 (m, 2H), 1.07 (t, J=7.4 Hz, 3H); LC-MS: 509.15 [M+H]⁺, HPLC: 97.71%; C-HPLC: 99.47% (RT: 11.94); SOR: +120.51, Solvent: methanol, Path length: 100 mm, Concentration: 100 w/v %

Example 156(+)

N-(2-((5-(5-(difluoromethyl)-1,3,4-oxadiazol-2-yl)pyrimidin-2-yl)amino)-2-(4-(trifluoromethoxy)phenyl)ethyl)-N-methylethanesulfonamide (156(+))

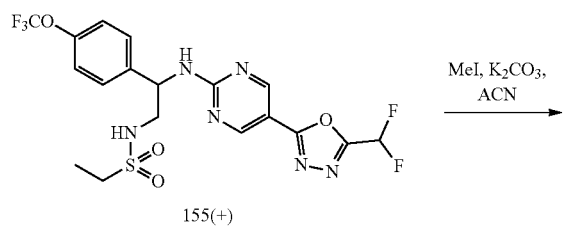

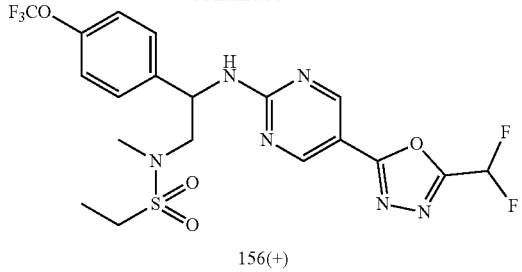

N-(2-((5-(5-(difluoromethyl)-1,3,4-oxadiazol-2-yl)pyrimidin-2-yl)amino)-2-(4-(trifluoromethoxy)phenyl)ethyl)-N-methylethanesulfonamide (156(+))

To a stirred solution of compound 155(+) (0.1 g, 0.19 mmol) in ACN (2 mL), K₂CO₃ (0.08 g, 0.58 mmol) and methyl iodide (0.027 g, 0.19 mmol) were added at 0° C. and stirred at RT for 16 h. The progress of the reaction was monitored by TLC. After completion of the reaction, the reaction mixture was filtered and the filtrate was concentrated under reduced pressure. The residue was diluted with water and the product was extracted with EtOAc. The combined organic layer was washed with brine, dried over anhydrous Na₂SO₄ and concentrated under reduced pressure. The crude product was purified by silica gel column chromatography using 40% EtOAc/hexane to afford compound 156(+) (0.055 g, 54.0%) as an off white solid. ¹H NMR (400 MHz, DMSO-d6): δ 8.88 (d, J=10.4 Hz, 2H), 8.74 (d, J=8.8 Hz, 1H), 7.64-7.35 (m, 5H), 5.49-5.43 (m, 1H), 3.53-3.49 (m, 2H), 3.01 (q, J=7.2 Hz, 2H), 2.83 (s, 3H), 1.10 (t, J=7.4 Hz, 3H); LC-MS: 523.15 [M+H]⁺; HPLC: 95.57%; C-HPLC: 95.86% (RT: 7.79); SOR: +73.63, Solvent-methanol, Path length: 100 mm, Concentration: 100 w/v %

Example 157(+)

N-(2-((5-(5-(difluoromethyl)-1,3,4-oxadiazol-2-yl)pyrimidin-2-yl)amino)-2-(4-(trifluoromethoxy)phenyl)ethyl)-N-(2,2,2-trifluoroethyl)ethanesulfonamide (157(+))

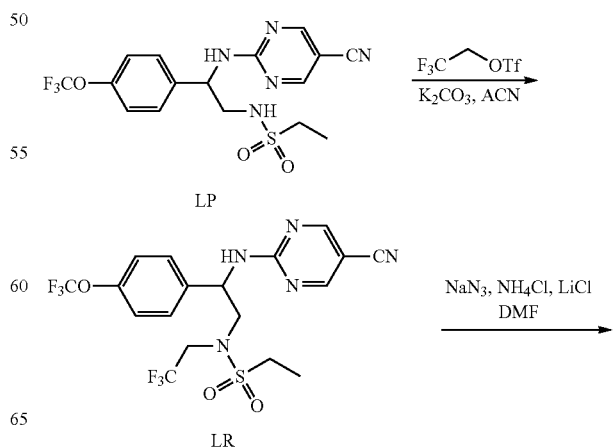

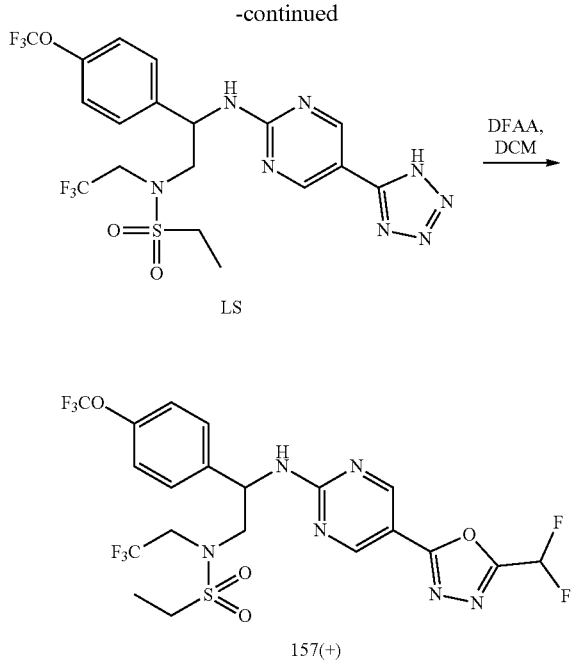

LS

157(+)

N-(2-((5-cyanopyrimidin-2-yl)amino)-2-(4-(trifluoromethoxy)phenyl)ethyl)-N-(2,2,2-trifluoroethyl)ethanesulfonamide (LR)

To a stirred solution of compound LP (0.4 g, 0.96 mmol) in ACN (10 mL), $K_2CO_3$ (0.4 g, 2.89 mmol) and 2,2,2-trifluoroethyl trifluoromethanesulfonate (0.56 g, 2.40 mmol) were added at 0° C. and stirred at 60° C. for 16 h. The progress of the reaction was monitored by TLC. After completion of the reaction, the reaction mixture was diluted with water and the product was extracted with EtOAc. The combined organic layer was washed with brine, dried over anhydrous $Na_2SO_4$ and concentrated under reduced pressure. The crude product was purified by silica gel column chromatography using 40% EtOAc/hexane to afford compound LR (0.25 g, 52.0%) as an off white solid. $^1$H NMR (400 MHz, DMSO-d6): δ 8.78 (d, J=8.8 Hz, 1H), 8.71 (d, J=1.3 Hz, 2H), 7.56 (d, J=8.4 Hz, 2H), 7.36 (d, J=8.0 Hz, 2H), 5.54-5.48 (m, 1H), 4.25-4.07 (m, 2H), 3.73-3.58 (m, 2H), 3.21-3.07 (m, 2H), 1.10 (t, J=7.2 Hz, 3H); LC-MS: m/z 498.15 [M+H]$^+$.

N-(2-((5-(1H-tetrazol-5-yl)pyrimidin-2-yl)amino)-2-(4-(trifluoromethoxy)phenyl)ethyl)-N-(2,2,2-trifluoroethyl)ethanesulfonamide (LS)

To a stirred solution of compound LR (0.25 g, 0.50 mmol) in DMF (5 mL), $NaN_3$ (0.10 g, 1.50 mmol), $NH_4Cl$ (0.08 g, 1.50 mmol) and LiCl (0.021 g) were added and the reaction was stirred at 100° C. for 16 h. After completion of the reaction, the reaction mixture was concentrated under reduced pressure. The residue was quenched with ice water and acidified with 1N HCl solution to pH=2. The precipitated solid was filtered, washed with cold water and dried to afford LS (0.2 g, 74.0%) as an off white solid. LC-MS: m/z 541.20 [M+H]$^+$.

N-(2-((5-(5-(difluoromethyl)-1,3,4-oxadiazol-2-yl)pyrimidin-2-yl)amino)-2-(4-(trifluoromethoxy)phenyl)ethyl)-N-(2,2,2-trifluoroethyl)ethanesulfonamide (157(+))

To a stirred solution of compound LS (0.2 g, 0.37 mmol) in DCM (2 mL), DFAA (0.10 g, 0.56 mmol) was added and the reaction was stirred at RT for 8 h. The progress of the reaction was monitored by TLC. After completion of the reaction, the reaction mixture was quenched with water and the product was extracted with 10% MeOH/DCM. The combined organic layer was washed with brine, dried over anhydrous $Na_2SO_4$ and concentrated under reduced pressure. The crude product was purified by silica gel column chromatography using 50% EtOAc/hexane to afford compound 157(+) (0.08 g, 37.0%) as an off white solid. $^1$H NMR (400 MHz, DMSO-d6): δ 8.90 (d, J=15.2 Hz, 2H), 8.71 (d, J=8.8 Hz, 1H), 7.61-7.37 (m, 5H), 5.58 (m, 1H), 4.30-4.10 (m, 2H), 3.72-3.64 (m, 2H), 3.20-3.14 (m, 2H), 1.12 (t, J=7.4 Hz, 3H); LC-MS: 591.05 [M+H]*, HPLC: 95.49%; C-HPLC: 99.85% (RT: 7.11); SOR: +71.49, Solvent: methanol, Path length: 100 mm, Concentration: 0.23 w/v %

Example 158(+)

N-(2-((5-(5-(difluoromethyl)-1,3,4-oxadiazol-2-yl)pyrimidin-2-yl)amino)-2-(4-(trifluoromethoxy)phenyl)ethyl)cyclopropanesulfonamide (158(+))

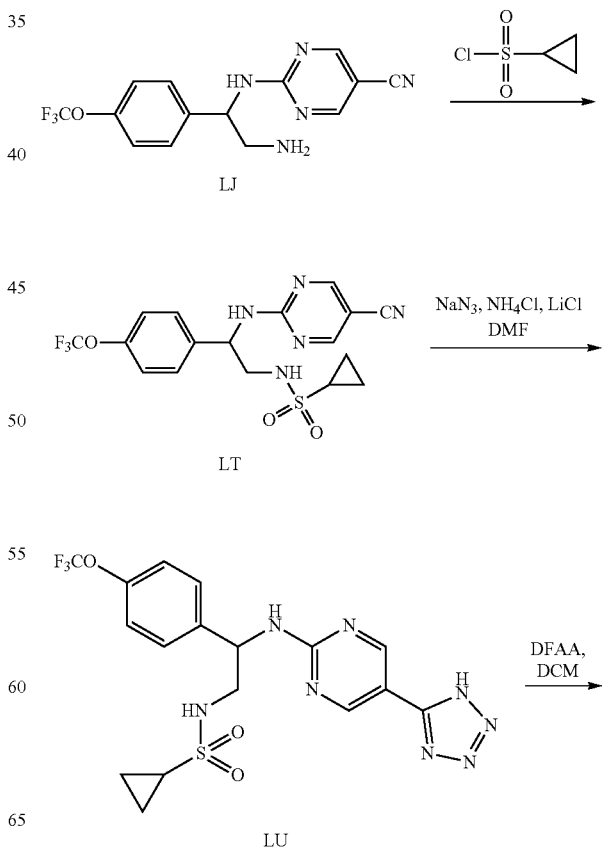

LJ

LT

LU

-continued

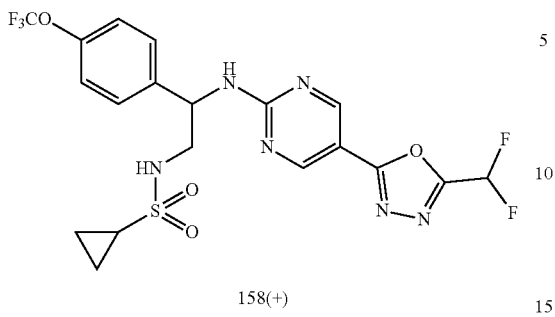

158(+)

N-(2-((5-cyanopyrimidin-2-yl)amino)-2-(4-(trifluoromethoxy)phenyl)ethyl)cyclopropanesulfonamide (LT)

To a stirred solution of compound L (0.7 g, 2.1 mmol) in DCM (10 mL), Et₃N (0.87 mL, 6.3 mmol) and cyclopropanesulfonyl chloride (0.27 g, 1.9 mmol) were added at 0° C. and stirred for 45 min. The progress of the reaction was monitored by TLC. After completion of the reaction, the reaction mixture was quenched with water and the product was extracted with DCM. The combined organic layer was washed with brine, dried over anhydrous Na₂SO₄ and concentrated under reduced pressure. The crude product was purified by silica gel column chromatography using 20% EtOAc/hexane to afford LT (0.45 g, 48.5%) as an off-white solid. ¹H NMR (400 MHz, DMSO-d6): δ 8.79 (d, J=8.8 Hz, 1H), 8.70 (s, 2H), 7.52 (d, J=8.4 Hz, 2H), 7.35-7.30 (m, 3H), 5.28-5.23 (m, 1H), 3.47-3.34 (m, 2H), 1.23 (s, 1H), 0.87-0.81 (m, 4H). LC-MS: m/z 428.15 [M+H]⁺.

N-(2-((5-(1H-tetrazol-5-yl)pyrimidin-2-yl)amino)-2-(4-(trifluoromethoxy)phenyl)ethyl)cyclopropanesulfonamide (LU)

To a stirred solution of compound LT (0.45 g, 1.0 mmol) in DMF (10 mL), NaN₃ (0.35 g, 5.4 mmol), NH₄Cl (0.27 g, 5.4 mmol) and LiCl (50 mg) were added and the reaction was stirred at 100° C. for 16 h. After completion of the reaction, the reaction mixture was quenched with ice water and acidified with 2N HCl solution to pH=2. The precipitated solid was filtered, washed with cold water and dried to afford LU (0.4 g, 80.8%) as an off white solid. LC-MS: m/z 471.15 [M+H]⁺.

N-(2-((5-(5-(difluoromethyl)-1,3,4-oxadiazol-2-yl) pyrimidin-2-yl)amino)-2-(4-(trifluoromethoxy)phenyl)ethyl)cyclopropanesulfonamide (158(+))

To a stirred solution of compound LU (0.4 g, 0.85 mmol) in DCM (10 mL), DFAA (0.29 g, 1.7 mmol) was added and the reaction was stirred at RT for 16 h. The progress of the reaction was monitored by TLC. After completion of the reaction, the reaction mixture was concentrated under reduced pressure. The residue was quenched with water and the product was extracted with DCM. The combined organic layer was washed with brine, dried over anhydrous Na₂SO₄ and concentrated under reduced pressure. The crude product was purified by silica gel column chromatography using 40% EtOAc/hexane to afford compound 158(+) (0.4 g, 90.9%) as an off white solid. ¹H NMR (400 MHz, DMSO-d6): δ 8.87 (d, J=13.2 Hz, 2H), 8.71 (d, J=8.8 Hz, 1H), 7.64-7.32 (m, 7H), 5.35-5.29 (m, 1H), 3.49-3.34 (m, 2H), 0.88-0.86 (m, 4H); LCMS: 521.15 (M+H); HPLC: 94.95%; C-HPLC: 99.47% (RT: 12.01).

Example 159(+)

N-(2-((5-(5-(difluoromethyl)-1,3,4-oxadiazol-2-yl) pyrimidin-2-yl)amino)-2-(4-(trifluoromethoxy)phenyl)ethyl)-N-methylcyclopropanesulfonamide (159(+))

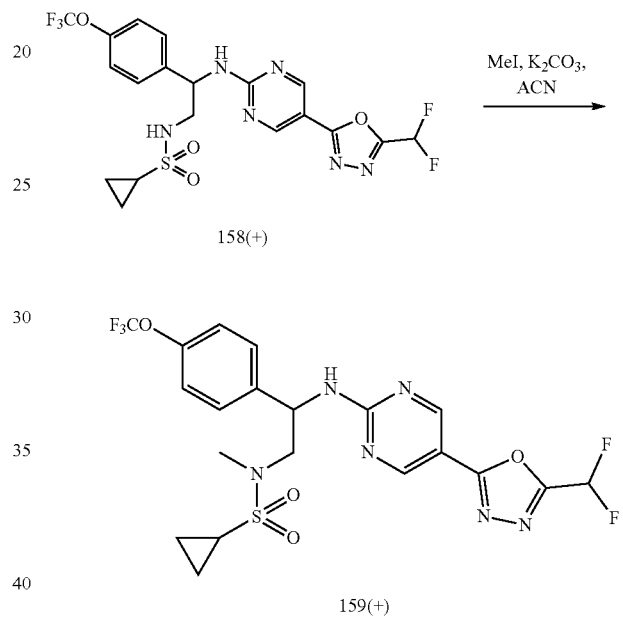

N-(2-((5-(5-(difluoromethyl)-1,3,4-oxadiazol-2-yl) pyrimidin-2-yl)amino)-2-(4-(trifluoromethoxy)phenyl)ethyl)-N-methylcyclopropanesulfonamide (159(+))

To a stirred solution of compound 158(+) (0.15 g, 0.28 mmol) in ACN (3 mL), K₂CO₃ (0.12 g, 0.84 mmol) was added at 0° C. stirred for 15 min, methyl iodide (0.28 g, 2.0 mmol) was added and the reaction was stirred at RT for 16 h. The progress of the reaction was monitored by TLC. After completion of the reaction, the reaction mixture was quenched with water and the product was extracted with EtOAc. The combined organic layer was washed with brine, dried over anhydrous Na₂SO₄ and concentrated under reduced pressure. The crude product was purified by silica gel column chromatography 30% EtOAc/hexane to afford compound 159(+) (0.08 g, 52.0%) as an off white solid. ¹H NMR (400 MHz, DMSO-d6): δ 8.88 (d, J=9.2 Hz, 1H), 8.78 (d, J=8.8 Hz, 1H), 7.64-7.35 (m, 5H), 5.48 (q, J=8.4 Hz, 1H), 3.59-3.51 (m, 2H), 2.84 (s, 3H), 2.60-2.53 (m, 1H), 1.23-1.22 (m, 1H), 0.93-0.84 (m, 4H); LCMS: 535.15 (M+H); HPLC: 98.82%; C-HPLC: 99.08% (RT: 7.61).

Example 160(+)

N-(2-((5-(5-(difluoromethyl)-1,3,4-oxadiazol-2-yl)pyrimidin-2-yl)amino)-2-(4-(trifluoromethoxy)phenyl)ethyl)-N-(2,2,2-trifluoroethyl)cyclopropanesulfonamide (160(+))

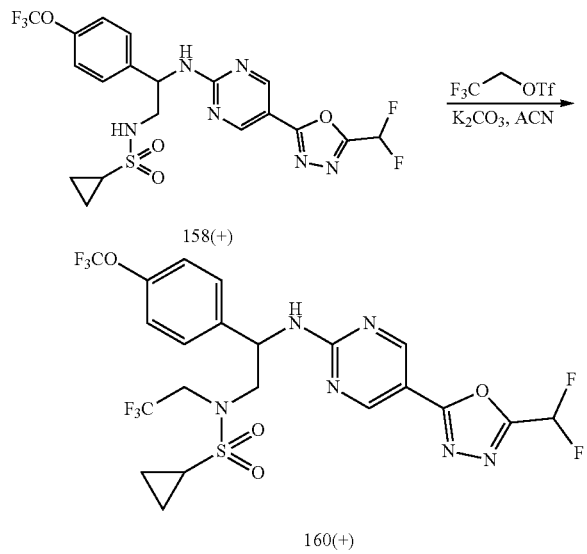

To a stirred solution of compound 158(+) (0.15 g, 0.3 mmol) in ACN (5 mL), K₂CO₃ (0.12 g, 0.8 mmol) was added at 0° C. stirred for 15 min, 2,2,2-trifluoroethyl trifluoromethanesulfonate (0.2 g, 0.8 mmol) was added and the reaction was stirred at RT for 16 h. The progress of the reaction was monitored by TLC. After completion of the reaction, the reaction mixture was quenched with water and the product was extracted with EtOAc. The combined organic layer was washed with brine, dried over anhydrous Na₂SO₄ and concentrated under reduced pressure. The crude product was purified by silica gel column chromatography 30% EtOAc/hexane to afford compound 160(+) (0.06 g, 34.2%) as an off white solid. ¹H NMR (400 MHz, DMSO-d6): δ 8.91 (d, J=14 Hz, 1H), 8.71 (d, J=9.2 Hz, 1H), 7.64-7.37 (m, 5H), 5.65-5.59 (m, 1H), 4.27-4.09 (m, 2H), 3.80-3.31 (m, 2H), 2.72-2.66 (m, 1H), 1.23 (m, 1H), 1.06-0.99 (m, 2H), 0.94-0.91 (m, 2H); LCMS: 603.25 (M+H); HPLC: 98.17%; C-HPLC: 98.55% (RT: 7.20).

Examples 161(+) and 161(−)

5-(5-(difluoromethyl)-1,3,4-oxadiazol-2-yl)-N-(1-(4-fluorophenyl)-2-(methylsulfonyl)ethyl)pyrimidin-2-amine (161(+) and 161(−))

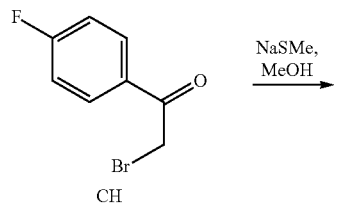

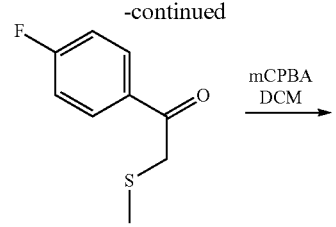

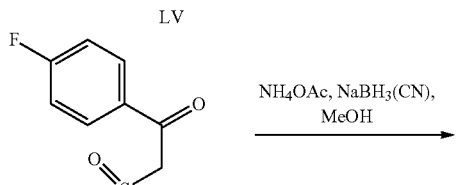

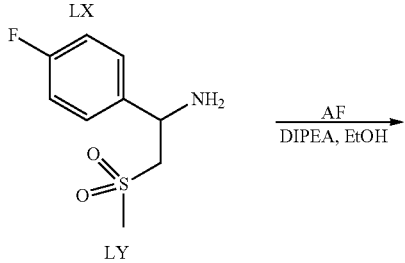

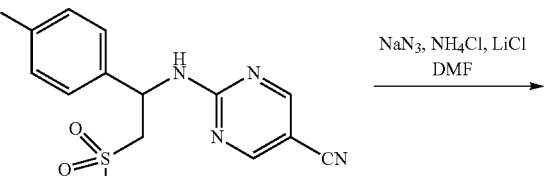

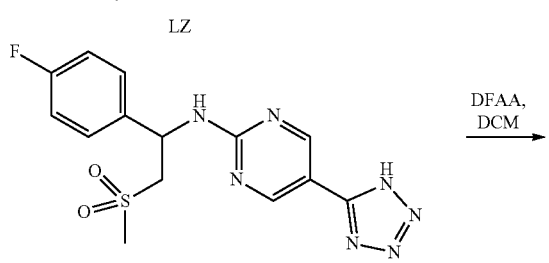

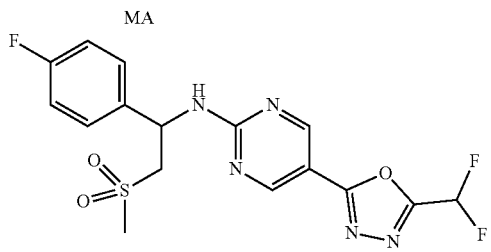

1-(4-fluorophenyl)-2-(methylthio)ethan-1-one (LV)

To a stirred solution of 2-bromo-1-(4-fluorophenyl)ethan-1-one (CH, 4.0 g, 18.43 mmol) in MeOH (70 mL), NaSMe (2.6 g, 36.86 mmol) was added at 0° C. and the reaction mixture was stirred at RT for 3 h. The progress of the reaction was monitored by TLC. After completion of the reaction, the reaction mixture was filtered through celite.

The filtrate was concentrated under reduced pressure. The residue was dissolved in EtOAc and washed with saturated NaHCO₃ solution. The organic layer was dried over anhydrous Na$_2$SO$_4$ and concentrated under reduced pressure to afford compound LV (3.0 g, 85.0%) as a yellow oil which was used as such for the next reaction. ¹H NMR (400 MHz, CDCl₃): δ 8.04-8.01 (m, 2H), 7.15 (t, J=8.4 Hz, 2H), 3.74 (s, 2H), 2.15 (s, 3H).

1-(4-fluorophenyl)-2-(methylsulfonyl)ethan-1-one (LX)

To a stirred solution of compound LV (3.4 g, 18.48 mmol) in DCM (50 mL), mCPBA (12.7 g, 73.91 mmol) was added at 0° C. and the reaction mixture was stirred at RT for 16 h. The progress of the reaction was monitored by TLC. After completion of the reaction, the reaction mixture was filtered through celite. The organic layer was separated, washed with NaHCO₃ solution, water and brine, dried over anhydrous Na$_2$SO$_4$ and concentrated under reduced pressure to afford compound LX (2.5 g, 64.0%) as an off-white solid which was used as such for the next reaction. ¹H NMR (400 MHz, CDCl₃): δ 8.08-8.05 (m, 2H), 7.21 (t, J=8.6 Hz, 2H), 4.59 (s, 2H), 3.16 (s, 3H); LC-MS: m/z 215.00 [M−H]⁺.

1-(4-fluorophenyl)-2-(methylsulfonyl)ethan-1-amine (LY)

To a stirred solution of compound LX (0.5 g, 2.31 mmol) in MeOH (10 mL), ammonium acetate (3.6 g, 46.29 mmol) was added at 0° C. and the reaction mixture was stirred at the same temperature for 30 min. To the resulting reaction mixture NaBH₃CN (0.29 g, 4.62 mmol) was added and stirred at RT for 16 h. The progress of the reaction was monitored by TLC. After completion of the reaction, the reaction mixture was concentrated under reduced pressure. The residue was diluted with water and basified with 10% NaOH solution. The aqueous layer was extracted with EtOAc. The combined organic layer was dried over anhydrous Na$_2$SO$_4$ and concentrated under reduced pressure to yield the pale yellow solid, which was dissolved in 4M HCl in EtOAc and stirred for 30 min. The reaction mixture was concentrated under reduced pressure and the residue was triturated with n-pentane to afford compound LY (0.3 g, 60.0%) as an off white solid. ¹H NMR (400 MHz, DMSO-d6): δ 8.85 (brs, 3H), 7.71-7.67 (m, 2H), 7.30 (t, J=8.8 Hz, 2H), 4.82 (brs, 1H), 3.99-3.84 (m, 2H), 2.86 (s, 3H); LC-MS: m/z 218.20 [M+H]⁺.

2-((1-(4-fluorophenyl)-2-(methylsulfonyl)ethyl) amino)pyrimidine-5-carbonitrile (LZ)

To a stirred solution of compound LY (0.30 g, 1.38 mmol) and 2-chloropyrimidine-5-carbonitrile (AF, 0.19 g, 1.38 mmol) in EtOH (5 mL), DIPEA (1.5 mL, 8.29 mmol) was added and the reaction mixture was stirred at 70° C. for 16 h. The progress of the reaction was monitored by TLC. After completion of the reaction, the reaction mixture was concentrated under reduced pressure. The residue was dissolved in EtOAc and then washed with water and brine. The organic layer was dried over anhydrous Na$_2$SO$_4$ and concentrated under reduced pressure. The crude product was purified by silica gel column chromatography (45% EtOAc/hexane) to afford compound LZ (0.3 g, 68.0%) as an off-white solid. ¹H NMR (400 MHz, DMSO-d6): δ 9.01 (d, J=8.8 Hz, 1H), 8.71 (d, J=6.8 Hz, 2H), 7.51-7.47 (m, 2H), 7.19 (t, J=8.8 Hz, 2H), 5.71-5.65 (m, 1H), 3.82-3.78 (m, 1H), 3.62-3.52 (m, 1H), 2.96 (s, 3H); LC-MS: m/z 320.95 [M+H]⁺.

N-(1-(4-fluorophenyl)-2-(methylsulfonyl)ethyl)-5-(1H-tetrazol-5-yl)pyrimidin-2-amine (MA)

To a stirred solution of compound LZ (0.3 g, 0.94 mmol) in DMF (10 mL) was added NaN₃ (0.3 g, 4.69 mmol) and NH₄Cl (0.25 g, 4.69 mmol) followed by LiCl (0.06 g) and the reaction mixture was stirred at 100° C. for 16 h. The progress of the reaction was monitored by TLC. After completion of the reaction, the reaction mixture was concentrated under reduced pressure. The residue was quenched with ice cold water and the product was extracted with EtOAc. The combined organic layer was dried over anhydrous Na$_2$SO$_4$ and concentrated under reduced pressure to afford compound MA (0.31 g, 91%) as an off white solid which was used as such for the next reaction. ¹H NMR (400 MHz, DMSO-d6): δ 16.65 (brs, 1H), 8.86 (s, 2H), 8.64 (d, J=8.8 Hz, 1H), 7.54-7.51 (m, 2H), 7.19 (t, J=8.8 Hz, 2H), 5.76-5.68 (m, 1H), 3.84-3.78 (m, 1H), 3.62-3.57 (m, 1H), 2.98 (s, 3H); LC-MS: m/z 364.10 [M+H]⁺.

5-(5-(difluoromethyl)-1,3,4-oxadiazol-2-yl)-N-(1-(4-fluorophenyl)-2-(methylsulfonyl)ethyl)pyrimidin-2-amine (161)

To a stirred solution of compound MA (0.3 g, 0.83 mmol) in DCM (10 mL), DFAA (0.29 g, 1.65 mmol) was added at 0° C. and the reaction was stirred at RT for 16 h. The progress of the reaction was monitored by TLC. After completion of the reaction, the reaction mixture was quenched with water, aqueous layer was extracted with DCM. The combined organic layer was dried over anhydrous Na$_2$SO$_4$ and concentrated under reduced pressure. The crude compound was purified by silica gel column chromatography (40% EtOAc/hexane) to afford racemic 161 (0.2 g, 59%) as an off white solid.

Chiral Preparative HPLC Details for 161(+) and 161(−)

The enantiomers were separated by normal-phase preparative high performance liquid chromatography (Chiralpak IA, 250×30 mm, 5; Mobile Phase: A; n-Hexane+0.1% DEA/B; DCM:MeOH (1:1); Isocratic Elution 45% B; Flow rate: 30.0 mL/min) to obtain 161(+) (65 mg) and 161(−) (70 mg).

161(+): ¹H NMR (400 MHz, DMSO-d6): δ 8.92 (d, J=8.8 Hz, 1H), 8.89 (s, 2H), 7.65-7.39 (m, 3H), 7.20 (t, J=8.8 Hz, 2H), 5.77-5.71 (m, 1H), 3.84-3.78 (m, 1H), 3.64-3.60 (m, 1H), 2.98 (s, 3H); LC-MS: m/z 414.10 [M+H]⁺; HPLC: 97.12%; C-HPLC: 99.83% (RT: 6.10); SOR: +158.90, Solvent: Methanol, Path length: 10 mm, Concentration: 0.255 w/v %.

161(−): ¹H NMR (400 MHz, DMSO-d6): δ 8.92 (d, J=8.8 Hz, 1H), 8.89 (s, 2H), 7.65-7.39 (m, 3H), 7.20 (t, J=8.8 Hz, 2H), 5.77-5.71 (m, 1H), 3.84-3.78 (m, 1H), 3.64-3.60 (m, 1H), 2.98 (s, 3H); LC-MS: m/z 414.10 [M+H]⁺; HPLC: 96.71%; C-HPLC: 99.25% (RT: 8.01); SOR: −155.76, Solvent: Methanol, Path length: 10 mm, Concentration: 0.25 w/v %.

Examples 162(+) and 162(−)

5-(5-(difluoromethyl)-1,3,4-oxadiazol-2-yl)-N-(1-(4-fluorophenyl)-2-(2,2,2-trifluoroethoxy)ethyl)pyrimidin-2-amine (162(+) and 162(Neg))

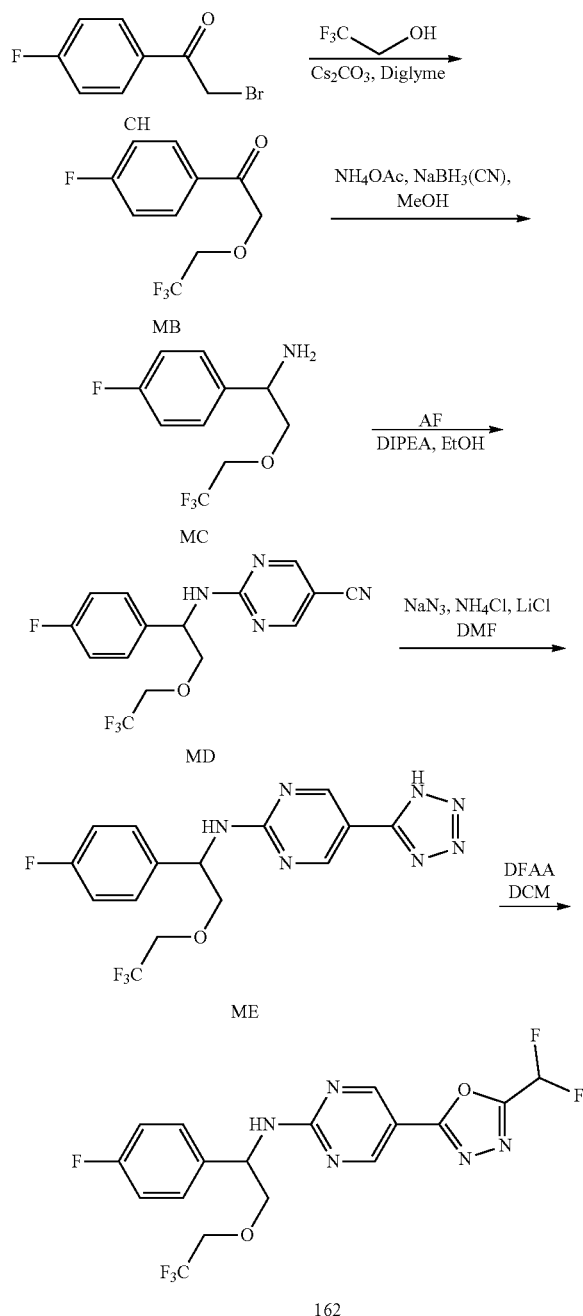

1-(4-fluorophenyl)-2-(2,2,2-trifluoroethoxy)ethan-1-one (MB)

To a stirred solution of 2,2,2-trifluoroethan-1-ol (6.4 g, 64.51 mmol) in diglyme (70 mL), $Cs_2CO_3$ (10.5 g, 32.25 mmol) was added and the reaction mixture was stirred at RT for 10 min. To the resulting reaction mixture 2-bromo-1-(4-fluorophenyl)ethan-1-one (CH, 7.0 g, 32.25 mmol) was added and stirred at RT for 4 h. The progress of the reaction was monitored by TLC. After completion of the reaction, the reaction mixture was filtered through celite and washed with diethyl ether. The filtrate was washed with water, then the organic layer was dried over anhydrous $Na_2SO_4$ and concentrated under reduced pressure. The crude product was purified by silica gel column chromatography (30% DCM/hexane) to afford compound MB (4.8 g, 63.0%) as an off-white solid. $^1$H NMR (400 MHz, $CDCl_3$): δ 7.99-7.95 (m, 2H), 7.18 (t, J=8.6 Hz, 2H), 4.92 (s, 2H), 4.05 (q, J=8.66 Hz, 2H); LC-MS: m/z 196.00 $[M+H]^+$.

1-(4-fluorophenyl)-2-(2,2,2-trifluoroethoxy)ethan-1-amine (MC)

To a stirred solution of compound MB (2.0 g, 8.47 mmol) in MeOH (30 mL), ammonium acetate (13.0 g, 169.49 mmol) was added followed by portion wise addition of $NaBH_3CN$ (1.4 g, 22.87 mmol) and the reaction mixture was stirred at 70° C. for 16 h. The progress of the reaction was monitored by TLC. After completion of the reaction, the reaction mixture was concentrated under reduced pressure. The residue was diluted with water and basified with 10% NaOH solution. The aqueous layer was extracted with EtOAc. The combined organic layer was dried over anhydrous $Na_2SO_4$ and concentrated under reduced pressure. To a stirred solution of crude compound in EtOAc (5 mL) was added 4M HCl in EtOAc at 0° C. The reaction mixture was concentrated under reduced pressure to yield solid compound which was triturated with diethyl ether to afford compound MC (1.7 g, 85.0%) as an off white solid. $^1$H NMR (400 MHz, DMSO-d6): δ 8.78 (brs, 3H), 7.64-7.60 (m, 2H), 7.29 (t, J=8.8 Hz, 2H), 4.57 (t, J=6.0 Hz, 1H), 4.19 (q, J=9.6 Hz, 2H), 4.03-3.98 (m, 1H), 3.92-3.88 (m, 1H); LC-MS: m/z 238.10 $[M+H]^+$.

2-((1-(4-fluorophenyl)-2-(2,2,2-trifluoroethoxy)ethyl)amino)pyrimidine-5-carbonitrile (MD)

To a stirred solution of compound MC (1.0 g, 4.21 mmol) and 2-chloropyrimidine-5-carbonitrile (5, 0.59 g, 4.21 mmol) in EtOH (10 mL), DIPEA (3.9 mL, 21.09 mmol) was added and the reaction mixture was stirred at 70° C. for 14 h. The progress of the reaction was monitored by TLC. After completion of the reaction, the reaction mixture was concentrated under reduced pressure. The crude product was purified by silica gel column chromatography (17% EtOAc/hexane) to afford compound MD (1.1 g, 78.5%) as a colorless thick oil. $^1$H NMR (400 MHz, DMSO-d6): δ 8.93 (d, J=8.8 Hz, 1H), 8.69-8.63 (m, 2H), 7.48-7.44 (m, 2H), 7.16 (t, J=9.2 Hz, 2H), 5.36-5.31 (m, 1H), 4.18-4.07 (m, 2H), 3.90-3.85 (m, 1H), 3.80-3.76 (m, 1H); LC-MS: m/z 341.00 $[M+H]^+$.

N-(1-(4-fluorophenyl)-2-(2,2,2-trifluoroethoxy)ethyl)-5-(1H-tetrazol-5-yl)pyrimidin-2-amine (ME)

To a stirred solution of compound MD (1.1 g, 3.23 mmol) in DMF (10 mL), $NaN_3$ (1.0 g, 16.17 mmol), $NH_4Cl$ (0.87 g, 16.17 mmol), LiCl (0.013 g, 0.323 mmol) were added and the reaction mixture was stirred at 90° C. for 14 h. The progress of the reaction was monitored by TLC. After completion of the reaction, the reaction mixture was concentrated under reduced pressure. The residue was quenched with ice-water, acidified with 1N HCl solution and extracted with EtOAc. The combined organic layer was dried over anhydrous Na$_2$SO$_4$ and concentrated under reduced pressure to afford compound ME (1.0 g, crude) as a brown thick oil which was used as such for the next reaction. LC-MS: m/z 384.15 [M+H]$^+$.

5-(5-(difluoromethyl)-1,3,4-oxadiazol-2-yl)-N-(1-(4-fluorophenyl)-2-(2,2,2-trifluoroethoxy)ethyl)pyrimidin-2-amine (162)

To a stirred solution of compound ME (1.0 g, 2.61 mmol) in DCM (10 mL), DFAA (2.2 g, 13.05 mmol) was added at 0° C. and the reaction was stirred at RT for 16 h. The progress of the reaction was monitored by TLC. After completion of the reaction, the reaction mixture was quenched with saturated NaHCO$_3$ solution and the product was extracted with DCM. The combined organic layer was dried over anhydrous Na$_2$SO$_4$ and concentrated under reduced pressure. The crude compound was purified by silica gel column chromatography (15% EtOAc/hexane) to afford racemic 162 (0.878 g, 78%) as a colorless thick oil.

Chiral Preparative SFC Details for 162(+) and 162(−)

The enantiomers were separated by supercritical fluid chromatography (Chiralpak IA, 250×30 mm, 5; Mobile Phase: A—CO$_2$; B—0.1% NH$_3$ in Methanol; Gradient Elution 10-20% B, 8 min, 20% hold 5 min, 20-30% in 3 min; Flow rate: 80.0 mL/min) to obtain 162(+) (100 mg) and 162(−) (100 mg).

162(+): $^1$H NMR (400 MHz, DMSO-d6): δ 8.88-8.83 (m, 3H), 7.64-7.39 (m, 3H), 7.17 (t, J=8.8 Hz, 2H), 5.44-5.38 (m, 1H), 4.19-4.09 (m, 2H), 3.92-3.87 (m, 1H), 3.82-3.79 (m, 1H); LC-MS: m/z 434.0 [M+H]$^+$; HPLC: 98.72%; C-HPLC: 100.00% (RT: 4.16); SOR: +95.67, Solvent: Methanol, Path length: 10 mm, Concentration: 0.245 w/v %.

162(−): $^1$H NMR (400 MHz, DMSO-d6): δ 8.88-8.83 (m, 3H), 7.64-7.39 (m, 3H), 7.17 (t, J=8.8 Hz, 2H), 5.43-5.38 (m, 1H), 4.19-4.09 (m, 2H), 3.92-3.87 (m, 1H), 3.82-3.79 (m, 1H); LC-MS: m/z 434.1 [M+H]$^+$; HPLC: 99.49%; C-HPLC: 99.77% (RT: 4.79); SOR: −70.03, Solvent: Methanol, Path length: 10 mm, Concentration: 0.305 w/v %.

Examples 163(+) and 163(−)

5-(5-(difluoromethyl)-1,3,4-oxadiazol-2-yl)-N-(1-(2,4-difluorophenyl)-2-(2,2,2-trifluoroethoxy)ethyl)pyrimidin-2-amine (163(+) and 163(−))

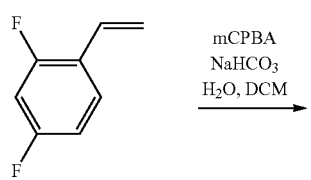

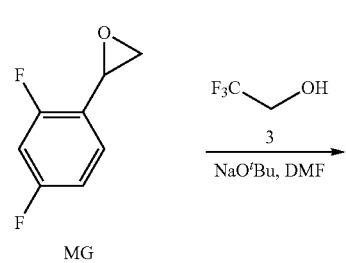

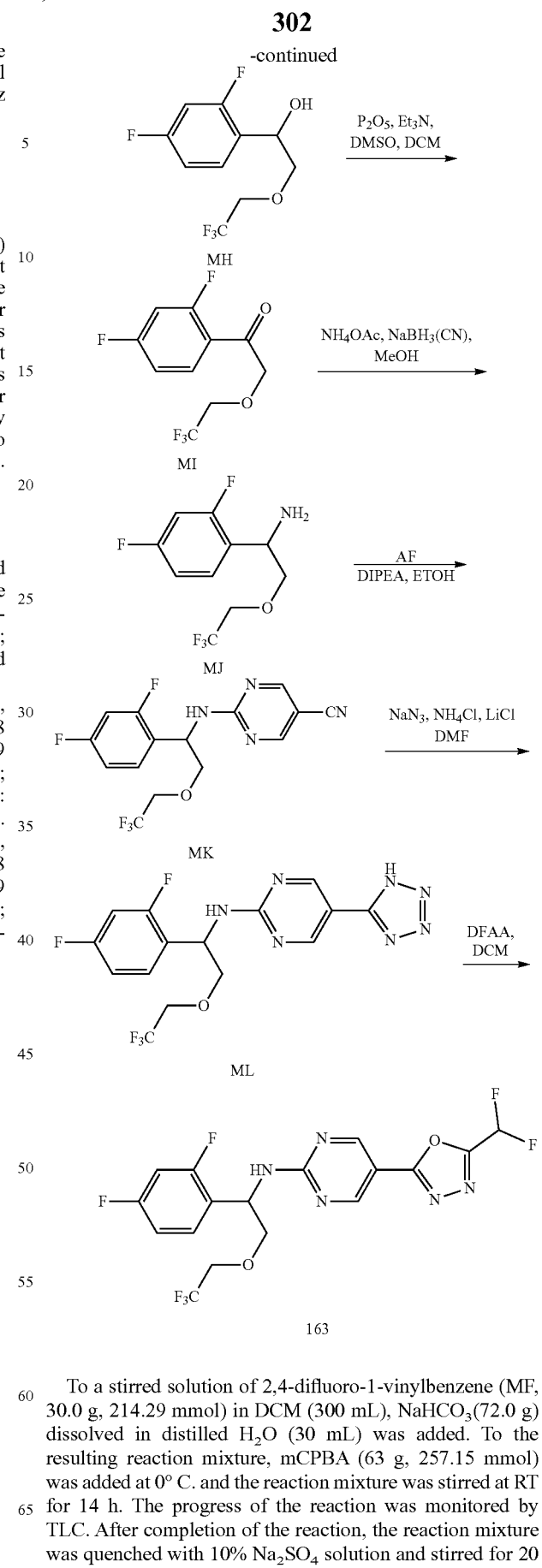

To a stirred solution of 2,4-difluoro-1-vinylbenzene (MF, 30.0 g, 214.29 mmol) in DCM (300 mL), NaHCO$_3$ (72.0 g) dissolved in distilled H$_2$O (30 mL) was added. To the resulting reaction mixture, mCPBA (63 g, 257.15 mmol) was added at 0° C. and the reaction mixture was stirred at RT for 14 h. The progress of the reaction was monitored by TLC. After completion of the reaction, the reaction mixture was quenched with 10% Na$_2$SO$_4$ solution and stirred for 20 min. The organic layer was separated, washed with saturated NaHCO$_3$ solution and brine, dried over anhydrous Na$_2$SO$_4$ and concentrated under reduced pressure. The crude compound was purified by silica gel column chromatography (10% DCM/hexane) to afford compound MG (7.5 g, 22.5%) as a colorless oil. $^1$H NMR (400 MHz, CDCl$_3$): δ 7.20-7.14 (m, 1H), 6.95-6.80 (m, 2H), 4.11 (t, J=3.2 Hz, 1H), 3.19-3.17 (m, 1H), 2.79-2.77 (m, 1H).

1-(2,4-difluorophenyl)-2-(2,2,2-trifluoroethoxy) ethan-1-ol (MH)

To a stirred solution of compound MG (7.5 g, 48.08 mmol) in DMF (80 mL), 2,2,2-trifluoroethan-1-ol (38.4 g, 384.64 mmol) was added followed by NaO$^t$Bu (1.1 g, 11.44 mmol) and the reaction mixture was stirred at 100° C. for 18 h. The progress of the reaction was monitored by TLC. After completion of the reaction, the reaction mixture was quenched with water and extracted with diethyl-ether. The organic layer was dried over anhydrous Na$_2$SO$_4$ and concentrated under reduced pressure. The crude compound was purified by silica gel column chromatography (20% DCM/hexane) to afford compound MH (5.0 g, 41.0%) as an off-white solid. $^1$H NMR (400 MHz, CDCl$_3$): δ 7.57-7.51 (m, 1H), 6.92 (t, J=8.4 Hz, 1H), 6.86-6.79 (m, 1H), 5.23-5.21 (m, 1H), 4.01-3.91 (m, 2H), 3.87-3.84 (m, 1H), 3.63 (t, J=9.0 Hz, 1H), 2.74 (d, J=3.6 Hz, 1H).

1-(2,4-difluorophenyl)-2-(2,2,2-trifluoroethoxy) ethan-1-one (MI)

To a stirred solution of compound MH (3.0 g, 11.72 mmol) in DCM (30 mL) and DMSO (10 mL), P$_2$O$_5$ (4.9 g, 35.16 mmol) was added at 0° C. followed by TEA (8.4 mL, 58.60 mmol) and the reaction mixture was stirred at RT for 16 h. The progress of the reaction was monitored by TLC. After completion of the reaction, the reaction mixture was quenched with water. The organic layer was separated, washed with 1N HCl solution, dried over anhydrous Na$_2$SO$_4$ and concentrated under reduced pressure. The crude compound was purified by silica gel column chromatography (30% DCM/hexane) to afford compound MI (2.5 g, 86.0%) as an off-white solid. $^1$H NMR (400 MHz, CDCl$_3$): δ 8.09-8.03 (m, 1H), 7.07-7.02 (m, 1H), 6.95-6.90 (m, 1H), 4.845 (d, J=4.0 Hz, 2H), 4.10-4.03 (m, 2H).

1-(2,4-difluorophenyl)-2-(2,2,2-trifluoroethoxy) ethan-1-amine (MJ)

To a stirred solution of compound MI (2.0 g, 7.87 mmol) in MeOH (30 mL), ammonium acetate (12.1 g, 157.4 mmol) was added and the reaction mixture was stirred at RT for 10 min. To the resulting reaction mixture NaBH$_3$CN (1.3 g, 21.25 mmol) was added and the reaction mixture was stirred at 70° C. for 16 h. The progress of the reaction was monitored by TLC. After completion of the reaction, the reaction mixture was concentrated under reduced pressure. The residue was diluted with water and basified with 4M NaOH solution. The aqueous layer was extracted with EtOAc. The combined organic layer was dried over anhydrous Na$_2$SO$_4$ and concentrated under reduced pressure. The crude compound was dissolved in 4M HCl in EtOAc and stirred at RT for 15 min. The reaction mixture was concentrated under reduced pressure and the residue was triturated with diethyl ether to afford compound MJ (1.5 g, 75.0%) as an off white solid. This compound was used as such for the next reaction. $^1$H NMR (400 MHz, DMSO-d6): δ 8.86 (brs, 2H), 7.82-7.76 (m, 1H), 7.40-7.34 (m, 1H), 7.26-7.22 (m, 1H), 4.69 (t, J=6.4 Hz, 1H), 4.21-4.14 (m, 2H), 4.07-4.03 (m, 1H), 3.97-3.93 (m, 1H); LC-MS: m/z 255.95 [M+H]$^+$.

2-((1-(2,4-difluorophenyl)-2-(2,2,2-trifluoroethoxy) ethyl)amino)pyrimidine-5-carbonitrile (MK)

To a stirred solution of compound MJ (1.0 g, 3.92 mmol) and 2-chloropyrimidine-5-carbonitrile (AF, 0.60 g, 4.31 mmol) in EtOH (20 mL), DIPEA (3.6 mL, 19.60 mmol) was added and the reaction mixture was stirred at 70° C. for 16 h. The progress of the reaction was monitored by TLC. After completion of the reaction, the reaction mixture was concentrated under reduced pressure. The crude compound was purified by silica gel column chromatography (15% EtOAc/hexane) to afford compound MK (1.0 g, 71.5%) as a yellow thick oil. $^1$H NMR (400 MHz, DMSO-d6): δ 8.97 (d, J=8.4 Hz, 1H), 8.71 (s, 2H), 7.55-7.49 (m, 1H), 7.26-7.21 (m, 1H), 7.12-7.07 (m, 1H), 5.59-5.53 (m, 1H), 4.15-4.08 (m, 2H), 3.93-3.88 (m, 1H), 3.82-3.78 (m, 1H); LC-MS: m/z 359.10 [M+H]$^+$.

N-(1-(2,4-difluorophenyl)-2-(2,2,2-trifluoroethoxy) ethyl)-5-(1H-tetrazol-5-yl)pyrimidin-2-amine (ML)

To a stirred solution of compound MK (1.0 g, 2.79 mmol) in DMF (10 mL), NaN$_3$ (0.91 g, 13.95 mmol), NH$_4$Cl (0.75 g, 13.95 mmol) and LiCl (0.01 g, 0.28 mmol) were added and the reaction mixture was stirred at 100° C. for 16 h. The progress of the reaction was monitored by TLC. After completion of the reaction, the reaction mixture was concentrated under reduced pressure. The residue was quenched with ice water and the product was extracted with EtOAc. The combined organic layer was dried over anhydrous Na$_2$SO$_4$ and concentrated under reduced pressure to afford compound ML (1.1 g, crude) as an off white solid which was used as such for the next reaction. LC-MS: m/z 402.10 [M+H]$^+$.

5-(5-(difluoromethyl)-1,3,4-oxadiazol-2-yl)-N-(1-(2, 4-difluorophenyl)-2-(2,2,2-trifluoroethoxy)ethyl) pyrimidin-2-amine (163)

To a stirred solution of compound ML (1.1 g, 2.73 mmol) in DCM (15 mL), DFAA (2.3 g, 13.68 mmol) was added at 0° C. and the reaction was stirred at RT for 16 h. The progress of the reaction was monitored by TLC. After completion of the reaction, the reaction mixture was quenched with saturated NaHCO$_3$ solution and extracted with DCM. The combined organic layer was dried over anhydrous Na$_2$SO$_4$ and concentrated under reduced pressure. The crude compound was purified by silica gel column chromatography (20% EtOAc/hexane) to afford racemic 163 (0.85 g, 71%) as a colorless sticky oil.

Chiral Preparative HPLC Details for 163(+) and 163(−)

The enantiomers were separated by normal-phase preparative high performance liquid chromatography (Chiralpak IA, 250×30 mm, 5; Mobile Phase: A; n-Hexane/B; 0.1% NH3 in Ethanol; Isocratic Elution 18% B; Flow rate: 32.0 mL/min) to obtain 163(+) (100 mg) and 163(−) (100 mg).
163(+): $^1$H NMR (400 MHz, DMSO-d6): δ 8.90-8.87 (m, 3H), 7.65-7.39 (m, 2H), 7.28-7.22 (m, 1H), 7.13-7.09 (m, 1H), 5.66-5.61 (m, 1H), 4.17-4.10 (m, 2H), 3.95-3.90 (m, 1H), 3.85-3.81 (m, 1H); LC-MS: m/z 452.15 [M+H]$^+$;

HPLC: 99.48%; C-HPLC: 99.84% (RT: 9.73); SOR: +86.19, Solvent: Methanol, Path length: 100 mm, Concentration: 0.26 w/v %.

163(−): $^1$H NMR (400 MHz, DMSO-d6): δ 8.90-8.87 (m, 3H), 7.65-7.39 (m, 2H), 7.28-7.22 (m, 1H), 7.13-7.09 (m, 1H), 5.66-5.61 (m, 1H), 4.17-4.10 (m, 2H), 3.95-3.90 (m, 1H), 3.85-3.81 (m, 1H); LC-MS: m/z 452.10 [M+H]$^+$; HPLC: 99.63%; C-HPLC: 99.58% (RT: 12.87); SOR: −85.91, Solvent: Methanol, Path length: 100 mm, Concentration: 0.265 w/v %.

Examples 164(+) and 164(−)

N-(2-((5-(5-(difluoromethyl)-1,3,4-oxadiazol-2-yl) pyrimidin-2-yl)amino)-2-(4-fluorophenyl)ethyl)-N-(2,2,2-trifluoroethyl)ethanesulfonamide (164(+) and 164(−))

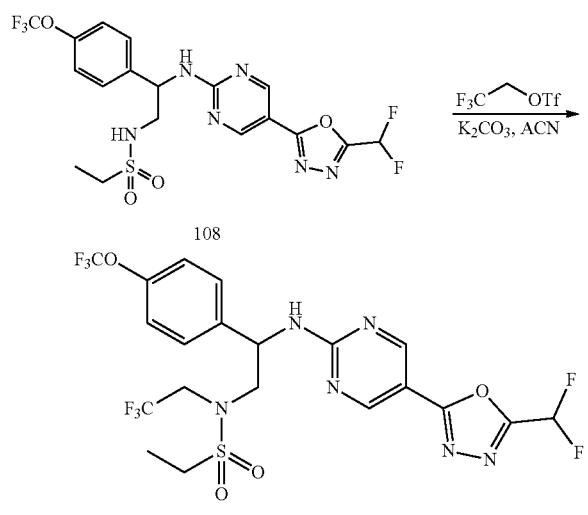

N-(2-((5-(5-(difluoromethyl)-1,3,4-oxadiazol-2-yl) pyrimidin-2-yl)amino)-2-(4-fluorophenyl)ethyl)-N-(2,2,2-trifluoroethyl)ethanesulfonamide (164)

To a stirred solution of compound 108 (1.3 g, 2.94 mmol) in ACN (50 mL), K$_2$CO$_3$ (1.2 g, 8.82 mmol), 2,2,2-trifluoroethyl trifluoromethanesulfonate (0.68 g, 2.94 mmol) were added and the reaction mixture was stirred at 80° C. for 5 h. The progress of the reaction was monitored by TLC. After completion of the reaction, the reaction mixture was filtered through celite and washed with EtOAc. The combined organic layer was dried over anhydrous Na$_2$SO$_4$ and concentrated under reduced pressure. The crude product was purified by silica gel column chromatography (1-2% MeOH/DCM) to afford racemic 164 (0.5 g, 33.0%).

Chiral Preparative HPLC Details for 164(+) and 164(−)

The enantiomers were separated by normal-phase preparative high performance liquid chromatography (Chiralpak IA, 250×30 mm, 5; Mobile Phase: A—n-Hexane+0.1% NH$_3$; B—Ethanol; Isocratic Elution 65% B; Flow rate: 30.0 mL/min) to obtain 164(+) (195 mg) and 164(−) (190 mg).

164(+): $^1$H NMR (400 MHz, DMSO-d6): δ 8.89 (d, J=11.6 Hz, 2H), 8.68 (d, J=9.2 Hz, 1H), 7.65-7.39 (m, 3H), 7.21 (t, J=9.0 Hz, 2H), 5.58-5.52 (m, 1H), 4.28-4.09 (m, 2H), 3.75-3.72 (m, 1H), 3.63-3.58 (m, 1H), 3.24-3.14 (m, 2H), 1.13 (t, J=7.4 Hz, 3H); LC-MS: m/z 525.20 [M+H]$^+$; HPLC: 98.31%; C-HPLC: 99.73% (RT: 15.96); SOR: +68.40, Solvent: Methanol, Path length: 10 mm, Concentration: 0.305 w/v %.

164(−): $^1$H NMR (400 MHz, DMSO-d6): δ 8.89 (d, J=11.6 Hz, 2H), 8.68 (d, J=8.8 Hz, 1H), 7.65-7.39 (m, 3H), 7.21 (t, J=8.8 Hz, 2H), 5.58-5.53 (m, 1H), 4.28-4.09 (m, 2H), 3.75-3.69 (m, 1H), 3.63-3.58 (m, 1H), 3.24-3.12 (m, 2H), 1.13 (t, J=7.2 Hz, 3H); LC-MS: m/z 525.20 [M+H]$^+$; HPLC: 98.99%; C-HPLC: 99.25% (RT: 12.01); SOR: −69.27, Solvent: Methanol, Path length: 50 mm, Concentration: 0.32 w/v %.

Examples 165(+) and 165(−)

N-(2-((5-(5-(difluoromethyl)-1,3,4-oxadiazol-2-yl) pyrimidin-2-yl)amino)-2-(4-fluorophenyl)ethyl)-N-(2,2,2-trifluoroethyl)cyclopropanesulfonamide (165(+) and 165(−))

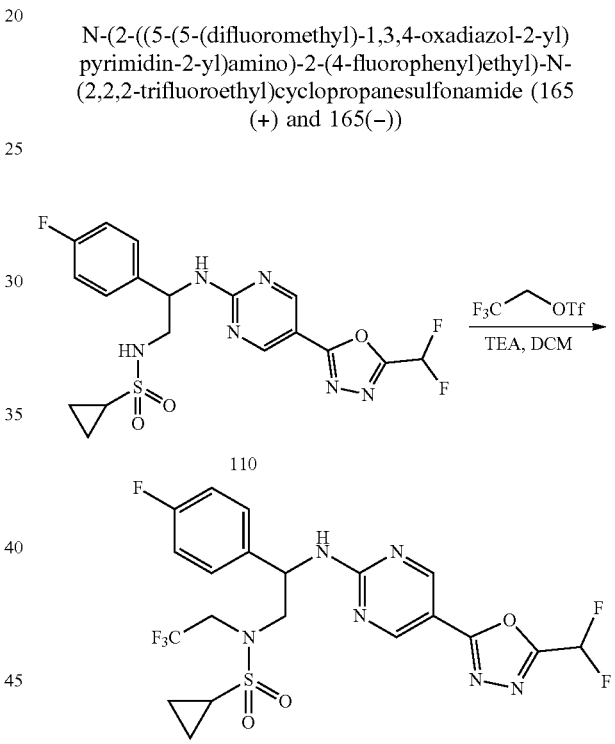

N-(2-((5-(5-(difluoromethyl)-1,3,4-oxadiazol-2-yl) pyrimidin-2-yl)amino)-2-(4-fluorophenyl)ethyl)-N-(2,2,2-trifluoroethyl)cyclopropanesulfonamide (165)

To a stirred solution of compound 110 (1.5 g, 3.30 mmol) in ACN (10 mL), K$_2$CO$_3$ (1.4 g, 9.91 mmol), 2,2,2-trifluoroethyl trifluoromethanesulfonate (1.1 g, 4.95 mmol) were added and the reaction mixture was stirred at 80° C. for 8 h. The progress of the reaction was monitored by TLC. After completion of the reaction, the reaction mixture was filtered through celite and washed with EtOAc. Water was added to the filtrate and aqueous layer was extracted with EtOAc. The combined organic layer was dried over anhydrous Na$_2$SO$_4$ and concentrated under reduced pressure. The crude product was purified by silica gel column chromatography (20% EtOAc/hexane) to afford racemic 165 (0.95 g, 54.0%).

Chiral Preparative HPLC Details for 165(+) and 165(−)

The enantiomers were separated by normal-phase preparative high performance liquid chromatography (Chiralpak IA, 250×30 mm, 5; Mobile Phase: A—n-Hexane+0.1% $NH_3$; B—Isopropyl alcohol; Isocratic Elution 15% B; Flow rate: 32.0 mL/min) to obtain 165(+) (110 mg) and 165(−) (110 mg).

165 (+): $^1$H NMR (400 MHz, DMSO-d6): δ 8.88 (d, J=10.4 Hz, 2H), 8.69 (d, J=9.2 Hz, 1H), 7.65-7.39 (m, 3H), 7.20 (t, J=8.8 Hz, 2H), 5.62-5.56 (m, 1H), 4.27-4.09 (m, 2H), 3.78-3.62 (m, 2H), 2.72-2.67 (m, 1H), 1.04-1.01 (m, 2H), 0.99-0.93 (m, 2H); LC-MS: m/z 537.15 [M+H]$^+$; HPLC: 95.64%; C-HPLC: 99.25% (RT: 12.62); SOR: +67.65, Solvent: Methanol, Path length: 10 mm, Concentration: 0.29 w/v %.

165 (−): $^1$H NMR (400 MHz, DMSO-d6): δ 8.88 (d, J=10.4 Hz, 2H), 8.69 (d, J=9.2 Hz, 1H), 7.65-7.39 (m, 3H), 7.20 (t, J=8.8 Hz, 2H), 5.62-5.56 (m, 1H), 4.27-4.02 (m, 2H), 3.78-3.62 (m, 2H), 3.73-3.67 (m, 1H), 1.07-1.01 (m, 2H), 0.99-0.93 (m, 2H); LC-MS: m/z 537.20 [M+H]$^+$; HPLC: 97.89%; C-HPLC: 98.71% (RT: 15.21); SOR: −66.00, Solvent: Methanol, Path length: 10 mm, Concentration: 0.31 w/v %.

Examples 166(+) and 166(−)

N-(2-((5-(5-(difluoromethyl)-1,3,4-oxadiazol-2-yl)pyrimidin-2-yl)amino)-2-(4-fluorophenyl)ethyl)-N-methylacetamide (166(+) and 166(−))

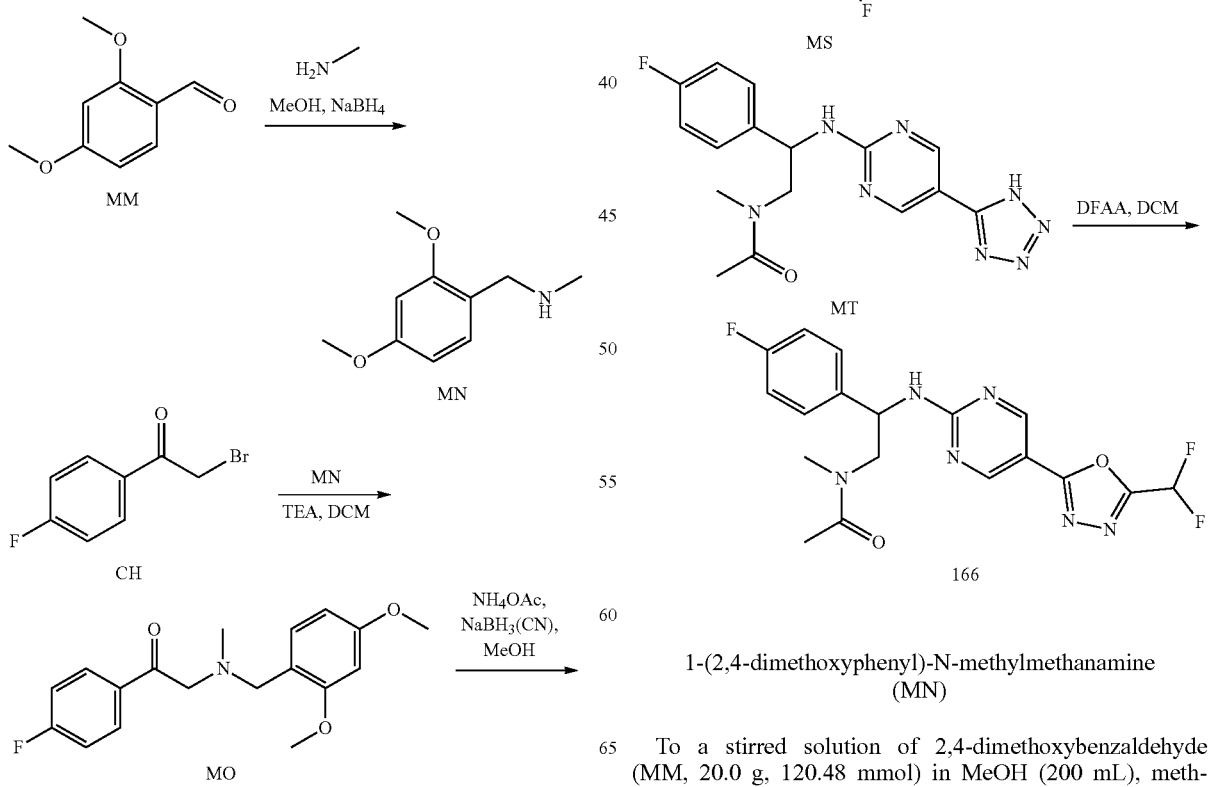

1-(2,4-dimethoxyphenyl)-N-methylmethanamine (MN)

To a stirred solution of 2,4-dimethoxybenzaldehyde (MM, 20.0 g, 120.48 mmol) in MeOH (200 mL), methanamine (33% in MeOH, 15.0 g, 481.90 mmol) was added at 0° C. and the reaction mixture was stirred at RT for 1 h. To the resulting reaction mixture, NaBH$_4$ (5.5 g, 144.57 mmol) was added portion wise at 0° C. and the reaction mixture was stirred at RT for 12 h. The progress of the reaction was monitored by TLC. After completion of the reaction, the reaction mixture was acidified with dilute HCl (200 mL) and MeOH was distilled out under reduced pressure. The residue was diluted with water and basified with dilute NaOH solution (80 mL). The aqueous layer was extracted with EtOAc (5×200 mL). The combined organic layer was dried over anhydrous Na$_2$SO$_4$ and concentrated under reduced pressure. The crude compound was purified by silica gel column chromatography (50-80% EtOAc/hexane) to afford compound MN (20.0 g, 92.0%) as a light yellow liquid. $^1$H NMR (400 MHz, DMSO-d6): δ 7.14 (d, J=8.4 Hz, 1H), 6.51 (brs, 1H), 6.47-6.45 (m, 1H), 3.74 (d, J=8.0 Hz, 6H), 3.53 (s, 2H), 2.24 (s, 3H); LC-MS: m/z 181.80 [M+H]$^+$.

2-((2,4-dimethoxybenzyl)(methyl)amino)-1-(4-fluorophenyl)ethan-1-one (MO)

To a stirred solution of compound MN (15.0 g, 82.87 mmol) in DCM (250 mL), triethylamine (11.0 mL, 82.87 mmol) was added at 0° C. followed by drop wise addition of 2-bromo-1-(4-fluorophenyl)ethan-1-one (CH, 18.0 g, 82.87 mmol) for 30 min and the reaction mixture was stirred at RT for 3 h. The progress of the reaction was monitored by TLC. After completion of the reaction, the reaction mixture was diluted with water (500 mL) and extracted with DCM (5×200 mL). The combined organic layer was dried over anhydrous Na$_2$SO$_4$ and concentrated under reduced pressure. The crude compound was purified by silica gel column chromatography (40% EtOAc/hexane) to afford compound MO (20.0 g, 76.0%) as a yellow semi solid. $^1$H NMR (400 MHz, DMSO-d6): δ 8.06-8.03 (m, 2H), 7.34-7.28 (m, 2H), 7.13 (d, J=8.4 Hz, 1H), 6.53-6.46 (m, 2H), 3.74 (brs, 6H), 3.67 (s, 2H), 3.53 (s, 2H), 2.16 (s, 3H); LC-MS: m/z 318.20 [M+H]$^+$.

N$^1$-(2,4-dimethoxybenzyl)-2-(4-fluorophenyl)-N-methylethane-1,2-diamine (MP)

To a stirred solution of compound MO (20.0 g, 63.09 mmol) in MeOH (300 mL), ammonium acetate (97.2 g, 1261.80 mmol) was added at 0° C. and the reaction mixture was stirred for 20 min. To the resulting reaction mixture, NaBH$_3$CN (10.9 g, 170.34 mmol) was added portion wise and the reaction mixture was stirred at 70° C. for 12 h. The progress of the reaction was monitored by TLC. After completion of the reaction, the reaction mixture was concentrated under reduced pressure. The residue was diluted with water and basified with dilute NaOH solution. The aqueous layer was extracted with EtOAc (5×200 mL). The combined organic layer was dried over anhydrous Na$_2$SO$_4$ and concentrated under reduced pressure. The crude compound was purified by silica gel column chromatography (70-80% EtOAc/hexane) to afford compound MP (14.2 g, 71.0%) as a brown liquid. $^1$H NMR (400 MHz, DMSO-d6): δ 7.47-7.43 (m, 2H), 7.19 (t, J=9.0 Hz, 2H), 7.12 (d, J=8.4 Hz, 1H), 6.54 (brs, 1H), 6.48-6.46 (m, 1H), 4.29-4.26 (m, 1H), 3.73 (brs, 6H), 3.60-3.57 (m, 1H), 3.39-3.36 (m, 1H), 2.59-2.54 (m, 1H), 2.46-2.40 (m, 1H), 2.16 (s, 3H); LC-MS: m/z 319.15 [M+H]$^+$.

2-((2-((2,4-dimethoxybenzyl)(methyl)amino)-1-(4-fluorophenyl)ethyl)amino)pyrimidine-5-carbonitrile (MQ)

To a stirred solution of compound MP (14.0 g, 44.02 mmol) in EtOH (140 mL), DIPEA (33.0 mL, 176.08 mmol) and 2-chloropyrimidine-5-carbonitrile (AF, 6.1 g, 44.02 mmol) were added and the reaction mixture was stirred at 80° C. for 12 h. The progress of the reaction was monitored by TLC. After completion of the reaction, the reaction mixture was concentrated under reduced pressure. The crude compound was purified by silica gel column chromatography (15-60% EtOAc/hexane) to afford compound MQ (6.5 g, 35.0%) as a light yellow semi solid. $^1$H NMR (400 MHz, DMSO-d6): δ 8.66-8.63 (m, 3H), 7.41-7.38 (m, 2H), 7.12 (t, J=8.8 Hz, 2H), 6.96 (d, J=8.4 Hz, 1H), 6.49 (brs, 1H), 6.40-6.38 (m, 1H), 5.24-5.21 (m, 1H), 3.71 (d, J=13.6 Hz, 6H), 3.54-3.51 (m, 1H), 3.43-3.40 (m, 1H), 2.81-2.75 (m, 1H), 2.62-2.57 (m, 1H), 2.13 (s, 3H); LC-MS: m/z 422.20 [M+H]$^+$.

2-((1-(4-fluorophenyl)-2-(methylamino)ethyl)amino) pyrimidine-5-carbonitrile (MR)

To compound MQ (5.0 g, 11.87 mmol), TFA (10 mL) was added at RT and the reaction mixture was stirred at 60° C. for 12 h. The progress of the reaction was monitored by TLC. After completion of the reaction, the reaction mixture was concentrated under reduced pressure. The crude compound was triturated with diethyl-ether to afford compound MR (4.0 g, crude) as a green solid. LC-MS: m/z 272.00 [M+H]$^+$.

N-(2-((5-cyanopyrimidin-2-yl)amino)-2-(4-fluorophenyl)ethyl)-N-methylacetamide (MS)

To a stirred solution of compound MR (2.0 g, 7.38 mmol) in DMF (20 mL), DIPEA (2.85 g, 22.14 mmol), acetic acid (0.89 g, 14.76 mmol) and HATU (3.36 g, 8.85 mmol) were added and the reaction mixture was stirred at RT for 16 h. The progress of the reaction was monitored by TLC. After completion of the reaction, the reaction mixture was diluted with water (200 mL) and extracted with EtOAc (5×200 mL). The organic layer was dried over anhydrous Na$_2$SO$_4$ and concentrated under reduced pressure. The crude compound was purified by silica gel column chromatography (30% EtOAc/hexane) to afford compound MS (1.1 g, 48.0%) as a brown liquid. LC-MS: m/z 314.15 [M+H]$^+$.

N-(2-((5-(1H-tetrazol-5-yl)pyrimidin-2-yl)amino)-2-(4-fluorophenyl)ethyl)-N-methylacetamide (MT)

To a stirred solution of compound MS (1.0 g, 3.19 mmol) in DMF (10 mL), NaN$_3$ (1.03 g, 15.97 mmol), NH$_4$Cl (0.86 g, 15.97 mmol), LiCl (0.20 g) were added and the reaction mixture was stirred at 100° C. for 12 h. The progress of the reaction was monitored by TLC. After completion of the reaction, the reaction mixture was concentrated under reduced pressure. The residue was quenched with ice-water, acidified with dilute HCl solution and extracted with EtOAc (3×100 mL). The combined organic layer was dried over anhydrous Na$_2$SO$_4$ and concentrated under reduced pressure to afford compound MT (1.0 g, 88.5%) as a brown liquid which was used as such for the next reaction. LC-MS: m/z 357.00 [M+H]$^+$.

N-(2-((5-(5-(difluoromethyl)-1,3,4-oxadiazol-2-yl) pyrimidin-2-yl)amino)-2-(4-fluorophenyl)ethyl)-N-methylacetamide (166)

To a stirred solution of compound MT (1.0 g, 2.80 mmol) in DCM (20 mL), DFAA (2.44 g, 14.04 mmol) was added at 0° C. and the reaction was stirred at RT for 36 h. The progress of the reaction was monitored by TLC. After completion of the reaction, the reaction mixture was diluted with water (200 mL) and extracted with DCM (5×200 mL). The combined organic layer was dried over anhydrous $Na_2SO_4$ and concentrated under reduced pressure. The crude compound was purified by silica gel column chromatography (90% EtOAc/hexane) to afford racemic 166 (0.11 g, 10%) as a yellow solid.

Chiral Preparative SFC Details for 166(+) and 166(−)

The enantiomers were separated by supercritical fluid chromatography (Chiralpak IA, 250×30 mm, 5µ; Mobile Phase: A—$CO_2$; B—0.1% $NH_3$ in Methanol; Gradient Elution 10-20% B in 2 min, 20% B hold 7 min, 20-25% B in 3 min, 25-40% B in 4 min, 40% B hold 5 min; Flow rate: 80.0 mL/min) to obtain 166(+) (22 mg) and 166(−) (20 mg).

166(+): $^1$H NMR (400 MHz, DMSO-d6): δ 8.90-8.83 (m, 2H), 8.69 (d, J=8.8 Hz, 1H), 7.64-7.39 (m, 3H), 7.23-7.14 (m, 2H), 5.53-5.38 (m, 1H), 3.72-3.54 (m, 2H), 2.85 (d, J=37.2 Hz, 3H), 1.91 (d, J=6.8 Hz, 3H); LC-MS: m/z 407.15 [M+H]$^+$; HPLC: 98.96%; C-HPLC: 100.00% (RT: 5.21); SOR: +96.24, Solvent: Methanol, Path length: 100 mm, Concentration: 0.25 w/v %.

166(−): $^1$H NMR (400 MHz, DMSO-d6): δ 8.90-8.83 (m, 2H), 8.69 (d, J=8.8 Hz, 1H), 7.64-7.39 (m, 3H), 7.23-7.14 (m, 2H), 5.51-5.40 (m, 1H), 3.72-3.54 (m, 2H), 2.85 (d, J=37.2 Hz, 3H), 1.91 (d, J=6.4 Hz, 3H); LC-MS: m/z 407.15 [M+H]$^+$; HPLC: 99.66%; C-HPLC: 98.57% (RT: 6.06); SOR: −75.48, Solvent: Methanol, Path length: 100 mm, Concentration: 0.25 w/v %.

Examples 167(+) and 167(−)

N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)acetamide (167(+) and 167(−))

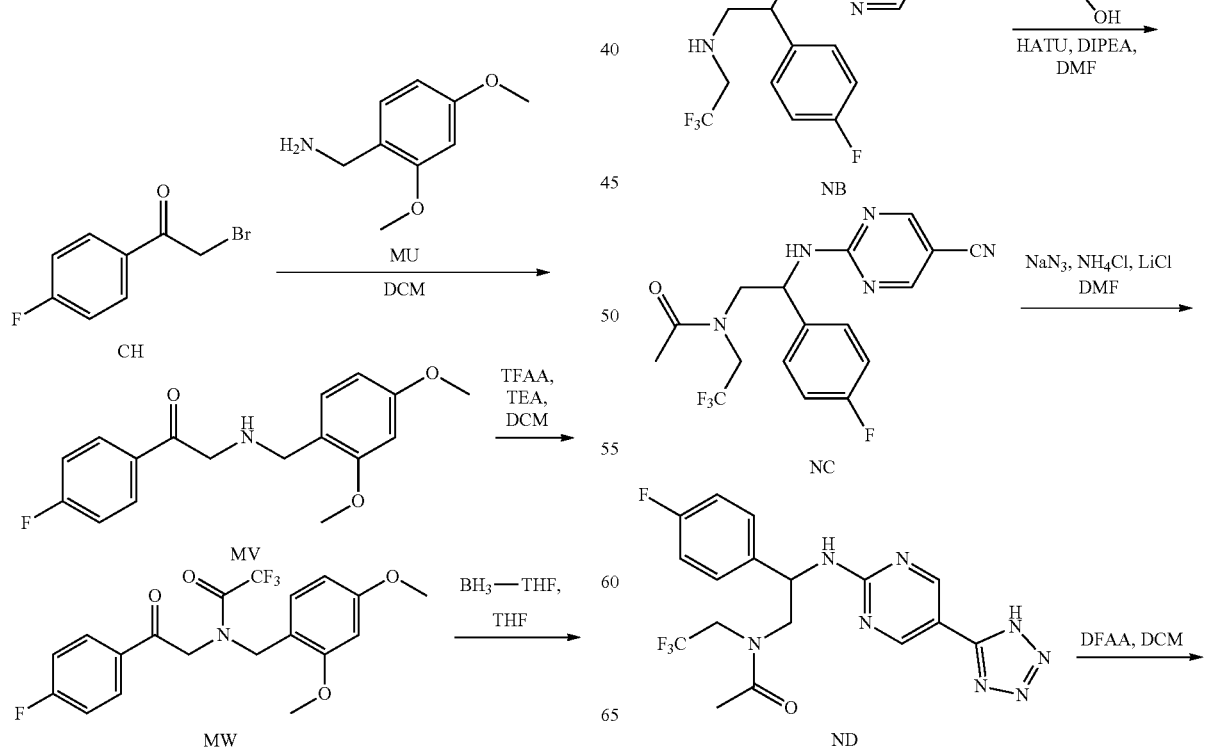

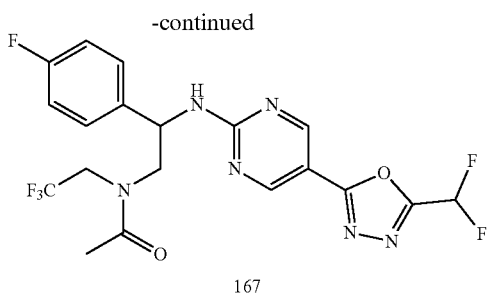

167

2-((2,4-dimethoxybenzyl)amino)-1-(4-fluorophenyl)ethan-1-one (MV)

To a stirred solution of (2,4-dimethoxyphenyl)methanamine (MU, 13.9 mL, 92.16 mmol) in DCM (1 L), 2-bromo-1-(4-fluorophenyl)ethan-1-one (CH, 10.0 g, 46.00 mmol) was added at 0° C. slowly over 15 min and the reaction mixture was stirred at RT for 2 h. The progress of the reaction was monitored by TLC. After completion of the reaction, the reaction mixture was quenched with saturated NH$_4$Cl solution and extracted with DCM (2×400 mL). The combined organic layer was washed with saturated NH$_4$Cl solution (200 mL) and brine (200 mL) and concentrated under reduced pressure at 40-45° C. The crude compound was dissolved in EtOAc (200 mL) and 4M HCl in EtOAc (14 mL) was added slowly at 0° C. The organic phase was concentrated under reduced pressure. The solid compound was washed with diethyl ether (2×50 mL) to afford compound MV (8.0 g, 57.0%) as an off-white solid. $^1$H NMR (400 MHz, DMSO-d6): 69.26 (brs, 2H), 8.11-8.07 (m, 2H), 7.44 (t, J=8.8 Hz, 2H), 7.38 (d, J=8.4 Hz, 1H), 6.61-6.56 (m, 2H), 4.66 (s, 2H), 4.11 (s, 2H), 3.78 (s, 3H), 3.73 (s, 3H); LC-MS: m/z 304.10 [M+H]$^+$.

N-(2,4-dimethoxybenzyl)-2,2,2-trifluoro-N-(2-(4-fluorophenyl)-2-oxoethyl)acetamide (MW)

To a stirred solution of compound MV (8.0 g, 26.40 mmol) in DCM (160 mL), triethylamine (13.4 mL, 79.20 mmol) was added at 0° C. followed by slow addition of trifluoro acetic anhydride (4.4 mL, 31.68 mmol) over 10 min and the reaction mixture was stirred at RT for 2 h. The progress of the reaction was monitored by TLC. After completion of the reaction, the reaction mixture was quenched with ice water (500 mL) and extracted with DCM (2×500 mL). The combined organic layer was dried over anhydrous Na$_2$SO$_4$ and concentrated under reduced pressure to afford compound MW (6.5 g, 62.0%) as a sticky light brown semi solid which was used as such for the next reaction. $^1$H NMR (400 MHz, DMSO-d6): δ 8.12-8.03 (m, 2H), 7.41-7.34 (m, 2H), 7.12 (t, J=7.6 Hz, 1H), 6.57-6.49 (m, 2H), 5.02 (s, 1H), 4.82 (s, 1H), 4.55 (d, J=28.4 Hz, 2H), 3.74 (s, 3H), 3.64 (d, J=30.0 Hz, 3H); LC-MS: m/z 422.10 [M+Na]$^+$.

2-((2,4-dimethoxybenzyl)(2,2,2-trifluoroethyl)amino)-1-(4-fluorophenyl)ethan-1-ol (MX)

To a stirred solution of compound MW (6.5 g, 16.29 mmol) in dry THF (100 mL), BH$_3$-THF solution (1M, 40.7 mL, 40.73 mmol) was added drop wise at 0° C. The reaction mixture was stirred at RT for 30 min followed by stirring at 60° C. for 8 h. The progress of the reaction was monitored by TLC. After completion of the reaction, the reaction mixture was slowly quenched with MeOH (100 mL) at 0° C. The reaction mixture was concentrated under reduced pressure.

The crude residue was diluted with saturated NH$_4$Cl solution and extracted with DCM. The combined organic layer was dried over anhydrous Na$_2$SO$_4$ and concentrated under reduced pressure to afford compound MX (5.0 g, 79.0%) as a sticky colorless semi solid which was used as such for the next reaction. $^1$H NMR (400 MHz, DMSO-d6): δ 7.31-7.27 (m, 2H), 7.11 (t, J=9.2 Hz, 3H), 6.54 (s, 1H), 6.47-6.45 (m, 1H), 5.14 (d, J=3.6 Hz, 1H), 4.73-4.71 (m, 1H), 3.77-3.75 (m, 8H), 3.44-3.66 (m, 2H), 2.74-2.67 (m, 2H); LC-MS: m/z 410.15 [M+Na]$^+$.

2-((2,4-dimethoxybenzyl)(2,2,2-trifluoroethyl)amino)-1-(4-fluorophenyl)ethan-1-one (MY)

To a stirred solution of compound MX (5.0 g, 12.91 mmol) in DCM (250 mL), DMP reagent (10.9 g, 25.83 mmol) was added at 0° C. and the reaction mixture was stirred at RT for 12 h. The progress of the reaction was monitored by TLC. After completion of the reaction, the reaction mixture was filtered through celite and washed with DCM. The filtrate was concentrated and purified by silica gel column chromatography (10% EtOAc/hexane) to afford compound MY (4.0 g, 80.0%) as a colorless sticky solid. $^1$H NMR (400 MHz, DMSO-d6): δ 7.99-7.95 (m, 2H), 7.32 (t, J=8.8 Hz, 2H), 7.14 (d, J=7.6 Hz, 1H), 6.49-6.47 (m, 2H), 4.11 (s, 2H), 3.86 (s, 2H), 3.73 (s, 3H), 3.57-3.52 (m, 5H).

N1-(2,4-dimethoxybenzyl)-2-(4-fluorophenyl)-N1-(2,2,2-trifluoroethyl)ethane-1,2-diamine (MZ)

To a stirred solution of compound MY (4.0 g, 10.38 mmol) in MeOH (100 mL), ammonium acetate (15.9 g, 207.70 mmol) was added and the reaction mixture was stirred at RT for 20 min. To the resulting reaction mixture, sodium cyanoborohydride (1.6 g, 25.95 mmol) was added portion wise and the reaction mixture was stirred at 65-75° C. for 12 h. The progress of the reaction was monitored by TLC. After completion of the reaction, the reaction mixture was concentrated under reduced pressure. The crude thick solid residue was quenched with ice water (100 mL) and basified with dilute NaOH solution to pH 8-10. The aqueous layer was extracted with DCM (2×200 mL). The combined organic layer was dried over anhydrous Na$_2$SO$_4$ and concentrated under reduced pressure to afford compound MZ (3.0 g, 75.0%) as a light brown thick liquid which was used as such for the next reaction. LC-MS: m/z 387.30 [M+H]$^+$.

2-((2-((2,4-dimethoxybenzyl)(2,2,2-trifluoroethyl)amino)-1-(4-fluorophenyl)ethyl)amino)pyrimidine-5-carbonitrile (NA)

To a stirred solution of compound MZ (3.0 g, 7.77 mmol) in EtOH (50 mL), DIPEA (3.9 mL, 23.31 mmol) and 2-chloropyrimidine-5-carbonitrile (AF, 1.3 g, 9.32 mmol) were added and the reaction mixture was stirred at RT for 12 h. The progress of the reaction was monitored by TLC. After completion of the reaction, the reaction mixture was concentrated under reduced pressure.

The crude compound was purified by silica gel column chromatography (15% EtOAc/hexane) to afford compound NA (2.9 g, 76.0%) as a light brown sticky viscous liquid. $^1$H NMR (400 MHz, DMSO-d6): δ 8.66-8.62 (m, 3H), 7.36-7.33 (m, 2H), 7.11 (t, J=8.8 Hz, 2H), 7.02 (d, J=8.0 Hz, 1H), 6.50 (s, 1H), 6.40-6.37 (m, 1H), 5.16-5.12 (m, 1H), 3.79 (s, 2H), 3.72 (d, J=8.8 Hz, 6H), 3.46-3.37 (m, 1H), 3.06-3.00 (m, 1H), 2.92-2.87 (m, 1H) (1H merged in solvent peak).

2-((1-(4-fluorophenyl)-2-((2,2,2-trifluoroethyl) amino)ethyl)amino)pyrimidine-5-carbonitrile (NB)

To compound NA (5.0 g, 10.22 mmol), TFA (10 mL) was added at 0° C. and the reaction mixture was stirred at RT for 2 h. The progress of the reaction was monitored by TLC. After completion of the reaction, the reaction mixture was concentrated under reduced pressure to obtain dark brown colored solid. The crude compound was triturated with n-pentane (3×30 mL) to afford compound NB (4.6 g, crude) as gray solid. $^1$H NMR (400 MHz, DMSO-d6): δ 8.80 (d, J=8.4 Hz, 1H), 8.70 (d, J=6.4 Hz, 2H), 7.45-7.41 (m, 2H), 7.17 (t, J=8.8 Hz, 2H), 5.29-5.24 (m, 1H), 3.80-3.74 (m, 1H), 3.62-3.58 (m, 2H), 3.24-3.18 (m, 1H), 3.10-3.06 (m, 1H); LC-MS: m/z 340.00 [M+H]$^+$.

N-(2-((5-cyanopyrimidin-2-yl)amino)-2-(4-fluorophenyl)ethyl)-N-(2,2,2-trifluoroethyl)acetamide (NC)

To a stirred solution of compound NB (2.0 g, 5.90 mmol) in DMF (20 mL), DIPEA (3 mL, 17.69 mmol), acetic acid (0.70 g, 11.79 mmol) and HATU (2.60 g, 7.07 mmol) were added and the reaction mixture was stirred at 75-80° C. for 12 h. The progress of the reaction was monitored by TLC. After completion of the reaction, the reaction mixture was quenched with ice water and extracted with EtOAc (2×100 mL). The combined organic layer was washed with cold saturated NH$_4$Cl solution (2×100 mL) and brine (2×100 mL), dried over anhydrous Na$_2$SO$_4$ and concentrated under reduced pressure. The crude compound was purified by Combiflash (19% EtOAc/hexane) to afford compound NC (0.9 g, 40.0%) as a light brown sticky liquid. $^1$H NMR (400 MHz, DMSO-d6): δ 8.89 (d, J=9.6 Hz, 1H), 8.77-8.68 (m, 2H), 7.58-7.55 (m, 1H), 7.45-7.41 (m, 1H), 7.25-7.17 (m, 2H), 5.57-5.47 (m, 1H), 4.33-4.26 (m, 1H), 4.20-4.11 (m, 1H), 3.78-3.72 (m, 1H), 3.59-3.53 (m, 1H), 2.70 (s, 3H); LC-MS: m/z 382.05 [M+H]$^+$.

N-(2-((5-(1H-tetrazol-5-yl)pyrimidin-2-yl)amino)-2-(4-fluorophenyl)ethyl)-N-(2,2,2-trifluoroethyl)acetamide (ND)

To a stirred solution of compound NC (0.90 g, 2.36 mmol) in DMF (10 mL), NaN$_3$ (0.77 g, 11.80 mmol), NH$_4$Cl (0.64 g, 11.80 mmol), LiCl (0.27 g) were added and the reaction mixture was stirred at 100° C. for 12 h. The progress of the reaction was monitored by TLC. After completion of the reaction, the reaction mixture was concentrated under reduced pressure. The residue was quenched with ice-water (20 mL), acidified with dilute HCl solution to pH 3-4 and extracted with DCM (2×100 mL). The combined organic layer was dried over anhydrous Na$_2$SO$_4$ and concentrated under reduced pressure to afford compound ND (0.9 g, crude) as a pale yellow sticky solid which was used as such for the next reaction. LC-MS: m/z 425.15 [M+H]$^+$.

N-(2-((5-(5-(difluoromethyl)-1,3,4-oxadiazol-2-yl) pyrimidin-2-yl)amino)-2-(4-fluorophenyl)ethyl)-N-(2,2,2-trifluoroethyl)acetamide (167)

To a stirred solution of compound ND (0.9 g, 2.00 mmol) in DCM (30 mL), DFAA (2.1 mL, 2.00 mmol) was added at 0° C. over 10 min and the reaction was stirred at RT for 12 h. The progress of the reaction was monitored by TLC. After completion of the reaction, the reaction mixture was quenched with ice water and pH was adjusted to 7 by adding saturated NaHCO$_3$ solution.

Aqueous layer was extracted with DCM. The combined organic layer was dried over anhydrous Na$_2$SO$_4$ and concentrated under reduced pressure. The crude compound was purified by combiflash column chromatography (35% EtOAc/hexane) to afford racemic 167 (0.5 g, 53%) as an off-white solid.

Chiral Preparative SFC Details for 167(+) and 167(−)

The enantiomers were separated by supercritical fluid chromatography (Chiralpak IG, 250×30 mm, 5; Mobile Phase: A—CO$_2$; B—0.1% NH$_3$ in Methanol; Gradient Elution 15-25% B over 3 min, 25% B hold 8 min, 25-35% B over 6 min; Flow rate: 80.0 mL/min) to obtain 167(+) (138 mg) and 167(−) (134 mg).

167(+): $^1$H NMR (400 MHz, DMSO-d6): δ 8.91-8.68 (m, 3H), 7.65-7.40 (m, 3H), 7.25-7.17 (m, 2H), 5.65-5.51 (m, 1H), 4.35-4.24 (m, 1H), 4.23-4.11 (m, 1H), 3.82-3.54 (m, 2H), 2.05 (d, J=28.8 Hz, 3H); LC-MS: m/z 475.20 [M+H]$^+$; HPLC: 98.81%; C-HPLC: 99.10% (RT: 6.15); SOR: +106.25, Solvent: Methanol, Path length: 100 mm, Concentration: 0.36 w/v %.

167(−): $^1$H NMR (400 MHz, DMSO-d6): δ 8.91-8.68 (m, 3H), 7.65-7.40 (m, 3H), 7.25-7.17 (m, 2H), 5.65-5.51 (m, 1H), 4.35-4.11 (m, 2H), 3.82-3.54 (m, 2H), 2.05 (d, J=28.8 Hz, 3H); LC-MS: m/z 475.10 [M+H]$^+$; HPLC: 98.45%; C-HPLC: 98.30% (RT: 6.66); SOR: −103.50, Solvent: Methanol, Path length: 100 mm, Concentration: 0.305 w/v %.

Examples 168(+) and 168(−)

N-(2-((5-(5-(difluoromethyl)-1,3,4-oxadiazol-2-yl) pyrimidin-2-yl)amino)-2-(4-fluorophenyl)ethyl)cyclopropanecarboxamide (168(+) and 168(−))

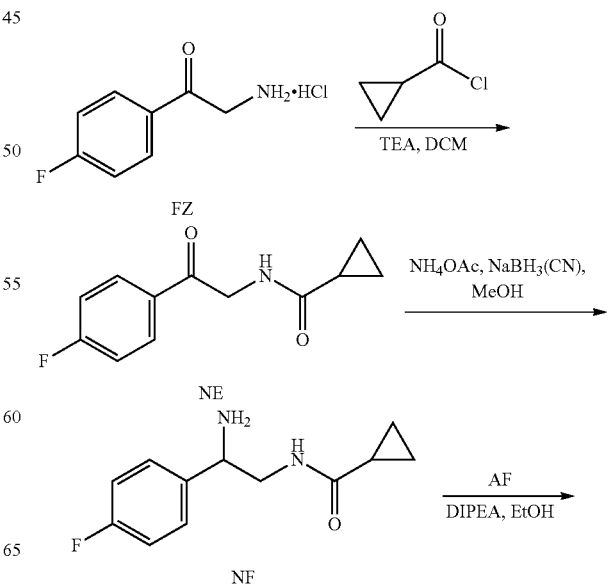

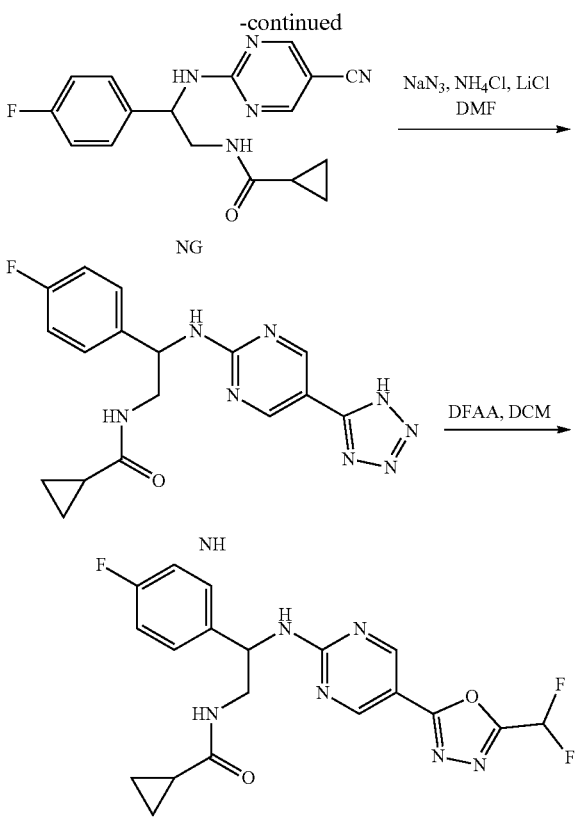

N-(2-(4-fluorophenyl)-2-oxoethyl)cyclopropanecarboxamide (NE)

To a stirred solution of 2-Amino-4-fluoroacetophenone hydrochloride (FZ, 5.0 g, 26.45 mmol) in DCM (50 mL), triethylamine (10.5 mL, 79.35 mmol) was added at 0° C. and the reaction mixture was stirred for 10 min. To the resulting reaction mixture cyclopropanecarbonyl chloride (2.6 mL, 29.10 mmol) was added slowly at 0° C. and stirred at the same temperature for 30 min followed by at RT for 30 min. The progress of the reaction was monitored by TLC. After completion of the reaction, the reaction mixture was diluted with water and extracted with DCM. The combined organic layer was washed with brine, dried over anhydrous $Na_2SO_4$ and concentrated under reduced pressure. The crude compound was triturated with diethyl ether to afford compound NE (5.0 g, 85%) as an off white solid. $^1$H NMR (400 MHz, DMSO-d6): δ 8.44 (t, J=5.4 Hz, 1H), 8.08-8.05 (m, 2H), 7.37 (t, J=8.8 Hz, 2H), 4.61 (d, J=6.0 Hz, 2H), 1.75-1.69 (m, 1H), 0.69-0.67 (m, 4H); LC-MS: m/z 222.00 [M+H]$^+$.

N-(2-amino-2-(4-fluorophenyl)ethyl)cyclopropanecarboxamide (NF)

To a stirred solution of compound NE (5.0 g, 22.62 mmol) in MeOH (100 mL), ammonium acetate (34.8 g, 452.40 mmol) and $NaBH_3CN$ (3.8 g, 61.00 mmol) were added and the reaction mixture was stirred at 70° C. for 12 h. The progress of the reaction was monitored by TLC. After completion of the reaction, the reaction mixture was concentrated under reduced pressure. The residue was diluted with water and basified with 10% NaOH to pH 8-9. The aqueous layer was extracted with DCM (250 mL×2). The combined organic layer was washed with brine, dried over anhydrous $Na_2SO_4$ and concentrated under reduced pressure to afford compound NF (3.2 g, 63.0%) as a light brown viscous liquid. LC-MS: m/z 223.05 [M+H]$^+$.

N-(2-((5-cyanopyrimidin-2-yl)amino)-2-(4-fluorophenyl)ethyl)cyclopropanecarboxamide (NG)

To a stirred solution of compound NF (3.2 g, 14.40 mmol) and 2-chloropyrimidine-5-carbonitrile (AF, 2.2 g, 15.80 mmol) in EtOH (50 mL), DIPEA (7.3 mL, 43.20 mmol) was added in a sealed tube and the reaction mixture was stirred at 90° C. for 1 h. The progress of the reaction was monitored by TLC. After completion of the reaction, the precipitated solid was filtered. The filtrate was concentrated under reduced pressure. The residue was diluted with water and extracted with DCM. The combined organic layer was washed with brine, dried over anhydrous $Na_2SO_4$ and concentrated under reduced pressure. The crude compound was triturated with n-pentane to afford compound NG (3.0 g, 65.0%) as an off white solid. $^1$H NMR (400 MHz, DMSO-d6): δ 8.71 (d, J=2.8 Hz, 1H), 8.63 (d, J=2.8 Hz, 1H), 8.55 (d, J=8.4 Hz, 1H), 8.34-8.29 (m, 1H), 7.35-7.32 (m, 2H), 7.13 (t, J=8.8 Hz, 2H), 5.15-5.09 (m, 1H), 3.68-3.56 (m, 2H), 1.60-1.52 (m, 1H), 0.68-0.59 (m, 4H); LC-MS: m/z 326.20 [M+H]$^+$.

N-(2-((5-(1H-tetrazol-5-yl)pyrimidin-2-yl)amino)-2-(4-fluorophenyl)ethyl)cyclopropanecarboxamide (NH)

To a stirred solution of compound NG (3.0 g, 9.23 mmol) in DMF (30 mL), $NaN_3$ (2.9 g, 46.15 mmol), $NH_4Cl$ (2.5 g, 46.15 mmol) and LiCl (0.9 g) were added and the reaction mixture was stirred at 100° C. for 12 h. The progress of the reaction was monitored by TLC. After completion of the reaction, the reaction mixture was concentrated under reduced pressure. The residue was quenched with ice-water and acidified with 6N HCl solution to pH 2-3. Aqueous layer was extracted with 10% MeOH/DCM (100 mL×3). The combined organic layer was dried over anhydrous $Na_2SO_4$ and concentrated under reduced pressure to afford compound NH (2.1 g, 63.0%) as a light brown thick liquid which was used as such for the next reaction. $^1$H NMR (400 MHz, DMSO-d6): δ 16.67 (brs, 1H), 8.82 (d, J=19.6 Hz, 2H), 8.41 (d, J=8.0 Hz, 1H), 8.23 (brs, 1H), 7.44-7.40 (m, 2H), 7.17-7.12 (m, 2H), 5.23-5.18 (m, 1H), 3.51-3.39 (m, 2H), 1.55-1.49 (m, 1H), 0.64-0.60 (m, 4H); LC-MS: m/z 369.15 [M+H]$^+$.

N-(2-((5-(5-(difluoromethyl)-1,3,4-oxadiazol-2-yl)pyrimidin-2-yl)amino)-2-(4-fluorophenyl)ethyl)cyclopropanecarboxamide (168)

To a stirred solution of compound NH (2.0 g, 5.43 mmol) in DCM (40 mL), DFAA (3.1 mL, 27.17 mmol) was added at 0° C. and the reaction was stirred at RT for 12 h. The progress of the reaction was monitored by TLC. After completion of the reaction, the reaction mixture was quenched with cold saturated $NaHCO_3$ solution. Aqueous layer was extracted with DCM. The combined organic layer was dried over anhydrous $Na_2SO_4$ and concentrated under reduced pressure. The crude compound was purified by flash column chromatography (40% EtOAc/hexane) to afford racemic 168 (1.5 g, 68.0%) as an off white solid.

Chiral Preparative SFC and HPLC Details for 168(+) and 168(−)

The enantiomers were separated in two steps. First, by supercritical fluid chromatography (Chiralpak IG, 250×30 mm, 5; Mobile Phase: A—CO$_2$; B—0.1% NH$_3$ in Methanol; Gradient Elution 25-35% B, 1 min, 35% hold 12 min, 35-40% in 3 min; Flow rate: 80.0 mL/min) then by normal-phase preparative high performance liquid chromatography (Chiralpak IG, 250×30 mm, 5; Mobile Phase: A—n-Hexane+0.1% NH$_3$; B—Isopropyl alcohol; Isocratic Elution 30% B; Flow rate: 32.0 mL/min) to obtain 168(+) (75 mg) and 168(−) (75 mg).

168(+): $^1$H NMR (400 MHz, DMSO-d6): δ 8.85 (d, J=17.6 Hz, 2H), 8.71 (d, J=8.0 Hz, 1H), 8.25 (t, J=5.4 Hz, 1H), 7.64-7.39 (m, 3H), 7.16 (t, J=8.8 Hz, 2H), 5.27-5.21 (m, 1H), 3.51-3.41 (m, 2H), 1.53-1.48 (m, 1H), 0.66-0.58 (m, 4H); LC-MS: m/z 419.00 [M+H]$^+$; HPLC: 96.88%; C-HPLC: 97.83% (RT: 7.42); SOR: +107.29, Solvent: Methanol, Path length: 10 mm, Concentration: 0.362 w/v %.

168(−): $^1$H NMR (400 MHz, DMSO-d6): δ 8.85 (d, J=16.8 Hz, 2H), 8.71 (d, J=8.4 Hz, 1H), 8.24 (t, J=5.6 Hz, 1H), 7.64-7.39 (m, 3H), 7.16 (t, J=9.0 Hz, 2H), 5.27-5.21 (m, 1H), 3.50-3.39 (m, 2H), 1.55-1.48 (m, 1H), 0.65-0.58 (m, 4H); LC-MS: m/z 419.00 [M+H]$^+$; HPLC: 97.44%; C-HPLC: 99.57% (RT: 8.10); SOR: −108.59, Solvent: Methanol, Path length: 10 mm, Concentration: 0.284 w/v %.

Examples 169(+) and 169(−)

N-(2-((5-(5-(difluoromethyl)-1,3,4-oxadiazol-2-yl)pyrimidin-2-yl)amino)-2-(4-fluorophenyl)ethyl)-N-methylcyclopropanecarboxamide (169(+) and 169(−))

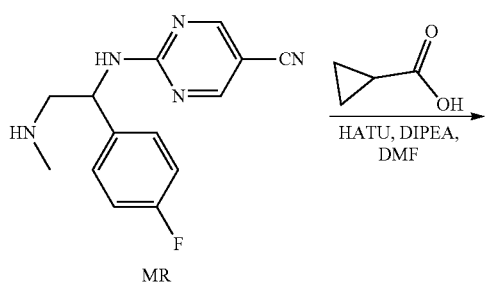

MR

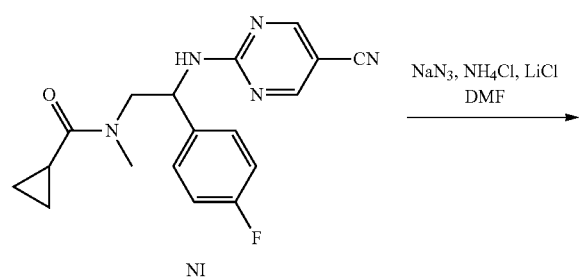

NI

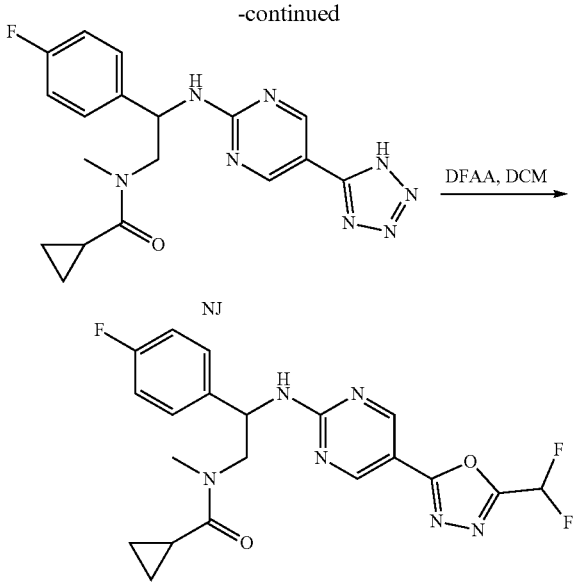

169

N-(2-((5-cyanopyrimidin-2-yl)amino)-2-(4-fluorophenyl)ethyl)-N-methylcyclopropanecarboxamide (NI)

To a stirred solution of compound MR (2.0 g, 7.38 mmol) in DMF (20 mL), DIPEA (2.85 g, 22.14 mmol), cyclopropanecarboxylic acid (1.27 g, 14.76 mmol) and HATU (3.36 g, 8.85 mmol) were added and the reaction mixture was stirred at RT for 16 h. The progress of the reaction was monitored by TLC. After completion of the reaction, the reaction mixture was diluted with water (200 mL) and extracted with EtOAc (5×200 mL). The organic layer was dried over anhydrous Na$_2$SO$_4$ and concentrated under reduced pressure. The crude compound was purified by silica gel column chromatography (38% EtOAc/hexane) to afford compound NI (1.24 g, 50.0%) as a brown liquid. LC-MS: m/z 340.15 [M+H]$^+$.

N-(2-((5-(1H-tetrazol-5-yl)pyrimidin-2-yl)amino)-2-(4-fluorophenyl)ethyl)-N-methylcyclopropanecarboxamide (NJ)

To a stirred solution of compound NI (1.2 g, 3.53 mmol) in DMF (10 mL), NaN$_3$ (1.15 g, 17.69 mmol), NH$_4$Cl (0.96 g, 17.69 mmol), LiCl (0.20 g) were added and the reaction mixture was stirred at 100° C. for 12 h. The progress of the reaction was monitored by TLC. After completion of the reaction, the reaction mixture was concentrated under reduced pressure. The residue was quenched with ice-water, acidified with 6N HCl solution and extracted with EtOAc (5×100 mL). The combined organic layer was dried over anhydrous Na$_2$SO$_4$ and concentrated under reduced pressure to afford compound NJ (1.2 g, 89.0%) as a light brown liquid which was used as such for the next reaction. LC-MS: m/z 383.10 [M+H]$^+$.

N-(2-((5-(5-(difluoromethyl)-1,3,4-oxadiazol-2-yl)pyrimidin-2-yl)amino)-2-(4-fluorophenyl)ethyl)-N-methylcyclopropanecarboxamide (169)

To a stirred solution of compound NJ (1.2 g, 3.14 mmol) in DCM (30 mL), DFAA (2.73 g, 15.70 mmol) was added at 0° C. and the reaction was stirred at RT for 36 h. The progress of the reaction was monitored by TLC. After completion of the reaction, the reaction mixture was diluted with water (200 mL) and extracted with DCM (5×100 mL). The combined organic layer was dried over anhydrous Na$_2$SO$_4$ and concentrated under reduced pressure. The crude compound was purified by silica gel column chromatography (60-80% EtOAc/hexane) to afford racemic 169 (0.17 g, 12.5%) as a yellow solid.

Chiral Preparative SFC Details for 169(+) and 169(−)

The enantiomers were separated by supercritical fluid chromatography (Chiralpak IG, 250×30 mm, 5; Mobile Phase: A—CO$_2$; B—0.1% NH$_3$ in Methanol; Gradient Elution 40% B hold 3 min, 40-45% B in 4 min, 45-50% B in 2 min, 50% B hold 15 min; Flow rate: 80.0 mL/min) to obtain 169(+) (50 mg) and 169(−) (50 mg).

169(+): $^1$H NMR (400 MHz, DMSO-d6): δ 8.89-8.79 (m, 2H), 8.67 (d, J=8.8 Hz, 1H), 7.64-7.38 (m, 3H), 7.21-7.14 (m, 2H), 5.54-5.41 (m, 1H), 3.94-3.79 (m, 1H), 3.69-3.58 (m, 1H), 3.06 (s, 2H), 2.79 (s, 1H), 1.92-1.78 (m, 1H), 0.67-0.54 (m, 4H); LC-MS: m/z 433.20 [M+H]$^+$; HPLC: 97.39%; C-HPLC: 99.98% (RT: 4.27); SOR: +69.90, Solvent: Methanol, Path length: 100 mm, Concentration: 0.25 w/v %.

169(−): $^1$H NMR (400 MHz, DMSO-d6): δ 8.89-8.79 (m, 2H), 8.67 (d, J=8.4 Hz, 1H), 7.64-7.38 (m, 3H), 7.21-7.14 (m, 2H), 5.54-5.39 (m, 1H), 3.93-3.79 (m, 1H), 3.69-3.58 (m, 1H), 3.06 (s, 2H), 2.79 (s, 1H), 1.92-1.78 (m, 1H), 0.67-0.54 (m, 4H); LC-MS: m/z 433.15 [M+H]$^+$; HPLC: 99.62%; C-HPLC: 99.51% (RT: 8.49); SOR: −71.52, Solvent: Methanol, Path length: 100 mm, Concentration: 0.25 w/v %.

Examples 170(+) and 170(−)

N-(2-((5-(5-(difluoromethyl)-1,3,4-oxadiazol-2-yl)pyrimidin-2-yl)amino)-2-(4-fluorophenyl)ethyl)-N-(2,2,2-trifluoroethyl)cyclopropanecarboxamide (170(+) and 170(−))

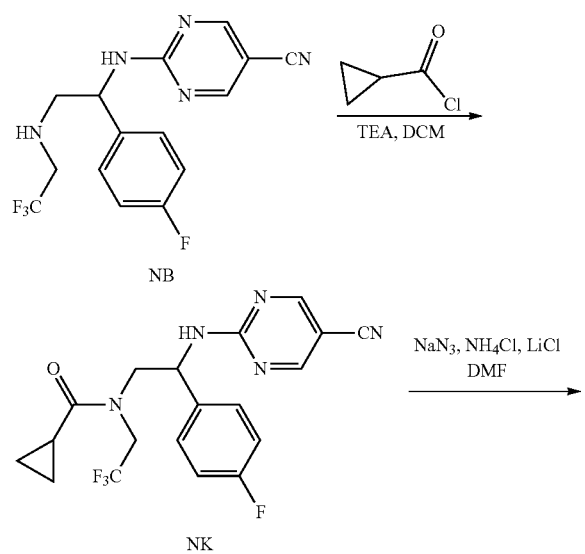

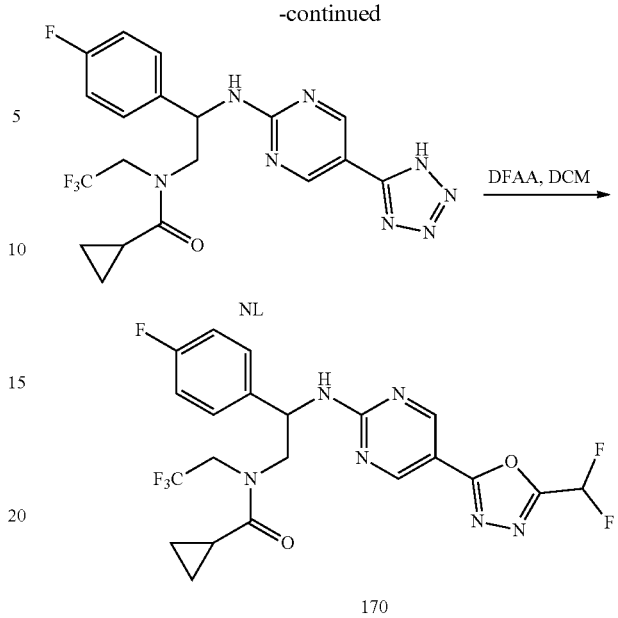

N-(2-((5-cyanopyrimidin-2-yl)amino)-2-(4-fluorophenyl)ethyl)-N-(2,2,2-trifluoroethyl)cyclopropanecarboxamide (NK)

To a stirred solution of compound NB (0.50 g, 1.47 mmol) in DCM (20 mL), triethylamine (0.58 mL, 4.42 mmol) was added at 0° C. followed by cyclopropanecarbonyl chloride (0.16 mL, 1.76 mmol) very slowly and the reaction mixture was stirred at the same temperature for 3 h. The progress of the reaction was monitored by TLC. After completion of the reaction, the reaction mixture was quenched with ice water and extracted with DCM. The combined organic layer was dried over anhydrous Na$_2$SO$_4$ and concentrated under reduced pressure. The crude compound was purified by Combiflash (15% EtOAc/hexane) to afford compound NK (0.34 g, 56.0%) as a light brown sticky semi solid. $^1$H NMR (400 MHz, DMSO-d6): δ 8.86-8.84-8.03 (m, 1H), 8.76-8.67 (m, 2H), 7.55-7.51 (m, 1H), 7.43-7.40 (m, 1H), 7.23-7.16 (m, 2H), 5.66-5.47 (m, 1H), 4.58-4.38 (m, 1H), 4.18-4.11 (m, 1H), 4.00-3.91 (m, 1H), 3.76-3.56 (m, 1H, 2.12-1.94 (m, 1H), 0.81-0.67 (m, 4H); LC-MS: m/z 408.15 [M+H]$^+$.

N-(2-((5-(1H-tetrazol-5-yl)pyrimidin-2-yl)amino)-2-(4-fluorophenyl)ethyl)-N-(2,2,2-trifluoroethyl)cyclopropanecarboxamide (NL)

To a stirred solution of compound NK (1.30 g, 3.19 mmol) in DMF (10 mL), NaN$_3$ (1.03 g, 15.90 mmol), NH$_4$Cl (0.86 g, 15.90 mmol), LiCl (0.40 g) were added and the reaction mixture was stirred at 100° C. for 6 h. The progress of the reaction was monitored by TLC. After completion of the reaction, the reaction mixture was concentrated under reduced pressure. The residue was quenched with ice-water (20 mL), acidified with dilute HCl solution to pH 2-3 and extracted with DCM (2×200 mL). The combined organic layer was dried over anhydrous Na$_2$SO$_4$ and concentrated under reduced pressure to afford compound NL (1.5 g, crude) as a light brown sticky liquid which was used as such for the next reaction. LC-MS: m/z 451.15 [M+H]$^+$.

N-(2-((5-(5-(difluoromethyl)-1,3,4-oxadiazol-2-yl) pyrimidin-2-yl)amino)-2-(4-fluorophenyl)ethyl)-N-(2,2,2-trifluoroethyl)cyclopropanecarboxamide (170)

To a stirred solution of compound NL (1.5 g, 3.33 mmol) in DCM (50 mL), DFAA (3.6 mL, 33.30 mmol) was added at 0° C. over 10 min and the reaction was stirred at RT for 12 h. The progress of the reaction was monitored by TLC. After completion of the reaction, the reaction mixture was quenched with ice water (20 mL) and pH was adjusted to 7 by adding saturated NaHCO₃ solution. Aqueous layer was extracted with DCM. The combined organic layer was dried over anhydrous Na₂SO₄ and concentrated under reduced pressure. The crude compound was purified by combiflash column chromatography (30% EtOAc/hexane) to afford racemic 170 (1.0 g, 62.5%) as an off-white solid.

Chiral Preparative SFC Details for 170(+) and 170(−)

The enantiomers were separated by supercritical fluid chromatography (Chiralpak IG, 250×30 mm, 5; Mobile Phase: A—CO₂; B—0.1% NH₃ in Methanol; Gradient Elution 20-30% B over 3 min, 30% B hold 5 min, 30-40% B over 6 min; Flow rate: 80.0 mL/min) to obtain 170(+) (128 mg) and 170(−) (118 mg).

170(+): $^1$H NMR (400 MHz, DMSO-d6): δ 8.85 (s, 2H), 8.47 (brs, 1H), 7.58-7.32 (m, 3H), 7.17 (t, J=8.8 Hz, 2H), 5.64 (brs, 1H), 4.30 (brs, 2H), 3.92 (brs, 2H), 2.02 (brs, 1H), 0.77 (s, 4H); LC-MS: m/z 501.15 [M+H]⁺; HPLC: 99.43%; C-HPLC: 99.73% (RT: 5.75); SOR: +96.58, Solvent: Methanol, Path length: 100 mm, Concentration: 0.48 w/v %.

170(−): $^1$H NMR (400 MHz, DMSO-d6): δ 8.85 (s, 2H), 8.46 (brs, 1H), 7.58-7.32 (m, 3H), 7.17 (t, J=8.8 Hz, 2H), 5.65 (brs, 1H), 4.29 (brs, 2H), 3.91 (brs, 2H), 2.02 (brs, 1H), 0.77 (s, 4H); LC-MS: m/z 501.20 [M+H]*; HPLC: 98.95%; C-HPLC: 98.78% (RT: 7.57); SOR: −87.52, Solvent: Methanol, Path length: 100 mm, Concentration: 0.485 w/v %.

Examples 171(+) and 171(−)

N-(2-((5-(5-(difluoromethyl)-1,3,4-oxadiazol-2-yl) pyrimidin-2-yl)amino)-2-(3,4-difluorophenyl)ethyl) methanesulfonamide (171(+) and 171(−))

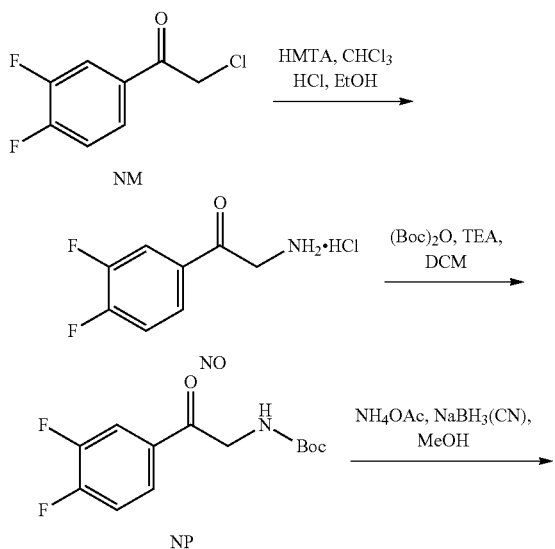

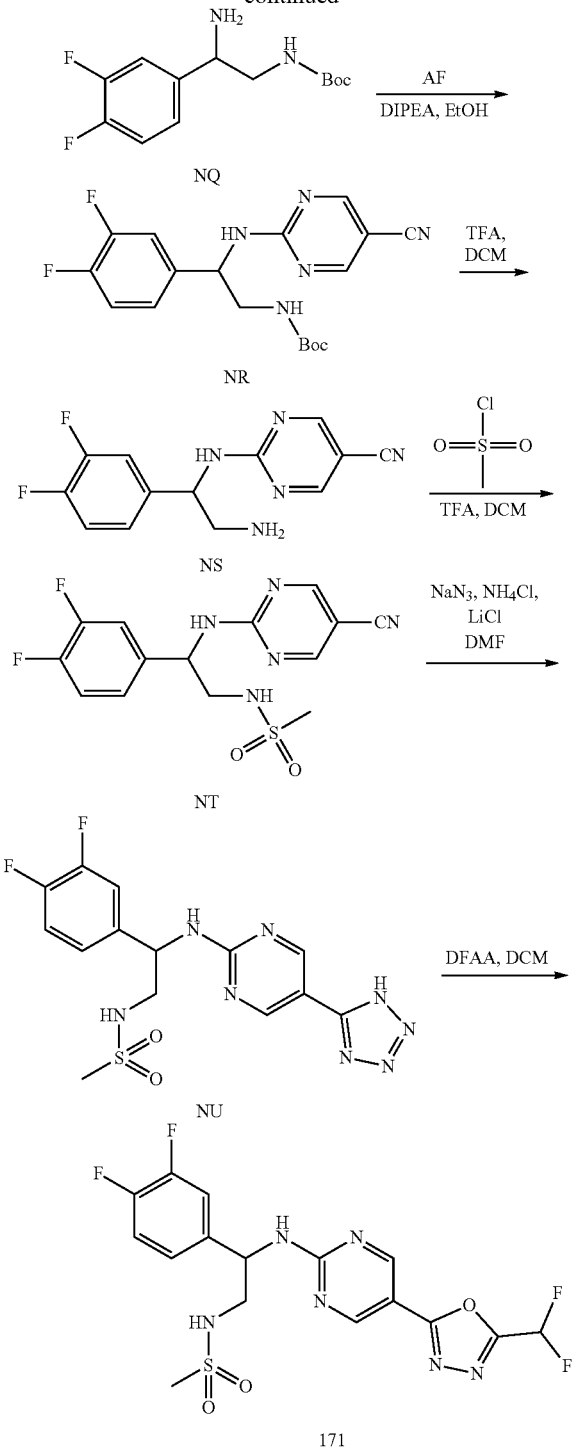

2-amino-1-(3,4-difluorophenyl)ethan-1-one hydrochloride (NO)

To a stirred solution of 2-chloro-1-(3,4-difluorophenyl) ethan-1-one (NM, 10.0 g, 52.46 mmol) in CHCl₃ (100 mL), HMTA (11.0 mL, 78.69 mmol) was added and the reaction mixture was stirred at RT for 12 h. The precipitated white solid was filtered and dried under high vacuum. To the stirred residue in EtOH (25 mL) was added conc. HCl (10 mL) drop wise at 0° C. and the reaction mixture was stirred at RT for 12 h. The progress of the reaction was monitored by TLC. After completion of the reaction, the reaction mixture was concentrated under reduced pressure. The crude compound was triturated with diethyl ether (50 mL) and hexane (100 mL×2) to afford compound NO (8.1 g, 90.0%) as an off-white solid. LC-MS: m/z 172.15 [M+1]$^+$.

tert-butyl (2-(3,4-difluorophenyl)-2-oxoethyl)carbamate (NP)

To a stirred solution of compound NO (8.0 g, 46.78 mmol) in DCM (100 mL), triethylamine (25.2 mL, 187.13 mmol) was added followed by di-ert-butyl dicarbonate (15.3 g, 70.17 mmol) at 0° C. and the reaction mixture was stirred at RT for 12 h. The progress of the reaction was monitored by TLC. After completion of the reaction, the reaction mixture was diluted with water (300 mL) and extracted with DCM (200 mL×5). The combined organic layer was dried over anhydrous $Na_2SO_4$ and concentrated under reduced pressure. The crude compound was purified by silica gel column chromatography (20-50% EtOAc/hexane) to afford compound NP (7.0 g, 55.0%) as a yellow solid. $^1$H NMR (400 MHz, DMSO-d6): δ 8.03 (t, J=9.6 Hz, 1H), 7.88 (brs, 1H), 7.65-7.59 (m, 1H), 7.13 (brs, 1H), 4.42 (d, J=6.0 Hz, 2H), 1.39 (s, 9H); LC-MS: m/z 172.00 [M+1-boc]$^+$.

tert-butyl (2-amino-2-(3,4-difluorophenyl)ethyl)carbamate (NQ)

To a stirred solution of compound NP (7.0 g, 25.83 mmol) in MeOH (80 mL), ammonium acetate (39.8 g, 516.60 mmol) was added at 0° C. and the reaction mixture was stirred for 1 h. To the resulting reaction mixture, $NaBH_3CN$ (4.5 g, 69.74 mmol) was added and the reaction mixture was stirred at 70° C. for 12 h. The progress of the reaction was monitored by TLC. After completion of the reaction, the reaction mixture was concentrated under reduced pressure. The residue was basified with 10% NaOH solution (300 mL) and extracted with EtOAc (200 mL×5). The organic layer was dried over anhydrous $Na_2SO_4$ and concentrated under reduced pressure. The crude compound was purified by silica gel column chromatography (10% MeOH/DCM) to afford compound NQ (4.0 g, 37.0%) as a brown liquid. LC-MS: m/z 273.00 [M+H]$^+$.

tert-butyl (2-((5-cyanopyrimidin-2-yl)amino)-2-(3,4-difluorophenyl)ethyl)carbamate (NR)

To a stirred solution of compound NQ (4.0 g, 14.70 mmol) in EtOH (40 mL), DIPEA (7.6 g, 58.82 mmol) was added followed by 2-chloropyrimidine-5-carbonitrile (AF, 2.0 g, 14.70 mmol) and the reaction mixture was stirred at 80° C. for 12 h. The progress of the reaction was monitored by TLC. After completion of the reaction, the reaction mixture was concentrated under reduced pressure. The crude product was purified by silica gel column chromatography (20% EtOAc/hexane) to afford compound NR (1.1 g, 20.0%) as a light yellow semi solid. $^1$H NMR (400 MHz, DMSO-d6): δ 8.73-8.62 (m, 3H), 7.40-7.33 (m, 2H), 7.17 (brs, 1H), 6.97 (brs, 1H), 5.19-5.14 (m, 1H), 1.36 (s, 9H) (2H merged in solvent peak); LC-MS: m/z 376.10 [M+H]$^+$.

2-((2-amino-1-(3,4-difluorophenyl)ethyl)amino)pyrimidine-5-carbonitrile (NS)

To a stirred solution of compound NR (1.1 g, 2.93 mmol) in DCM (10 mL), TFA (3 mL) was added at 0° C. and the reaction mixture was stirred at RT for 1 h. The progress of the reaction was monitored by TLC. After completion of the reaction, the reaction mixture was concentrated under reduced pressure to afford compound NS (1.0 g, crude) as a yellow solid. LC-MS: m/z 276.10 [M+H]$^+$.

N-(2-((5-cyanopyrimidin-2-yl)amino)-2-(3,4-difluorophenyl)ethyl)methanesulfonamide (NT)

To a stirred solution of compound NS (1.0 g, 3.63 mmol) in DCM (15 mL), triethyl amine (1.5 g, 14.51 mmol) was added followed by methanesulfonyl chloride (0.62 g, 5.45 mmol) at 0° C. and the reaction mixture was stirred at the same temperature for 30 min. The progress of the reaction was monitored by TLC. After completion of the reaction, the reaction mixture was diluted with water (200 mL) and extracted with DCM (200 mL×5). The organic layer was dried over anhydrous $Na_2SO_4$ and concentrated under reduced pressure. The crude product was purified by silica gel column chromatography (50% EtOAc/hexane) to afford compound NT (0.51 g, 40.0%) as a yellow solid. $^1$H NMR (400 MHz, DMSO-d6): δ 8.75 (d, J=8.8 Hz, 1H), 8.71 (s, 2H), 7.49-7.37 (m, 2H), 7.27-7.24 (m, 2H), 5.23-5.17 (m, 1H), 3.41-3.37 (m, 1H), 3.33-3.26 (m, 1H), 2.86 (s, 3H); LC-MS: m/z 354.00 [M+H]$^+$.

N-(2-((5-(1H-tetrazol-5-yl)pyrimidin-2-yl)amino)-2-(3,4-difluorophenyl)ethyl)methanesulfonamide (NU)

To a stirred solution of compound NT (0.50 g, 1.41 mmol) in DMF (10 mL), $NaN_3$ (0.46 g, 7.08 mmol), $NH_4Cl$ (0.38 g, 7.08 mmol), LiCl (0.10 g) were added and the reaction mixture was stirred at 100° C. for 16 h. The progress of the reaction was monitored by TLC. After completion of the reaction, the reaction mixture was concentrated under reduced pressure. The residue was diluted with water (100 mL), acidified with 6N HCl solution and extracted with 10% MeOH/DCM (100 mL×5). The combined organic layer was dried over anhydrous $Na_2SO_4$ and concentrated under reduced pressure to afford compound NU (0.50 g, 90.0%) as a brown liquid which was used as such for the next reaction. LC-MS: m/z 396.9 [M+H]$^+$.

N-(2-((5-(5-(difluoromethyl)-1,3,4-oxadiazol-2-yl)pyrimidin-2-yl)amino)-2-(3,4-difluorophenyl)ethyl)methanesulfonamide (171)

To a stirred solution of compound NU (0.50 g, 1.26 mmol) in DCM (10 mL), DFAA (0.88 g, 5.05 mmol) was added at 0° C. and the reaction was stirred at RT for 12 h. The progress of the reaction was monitored by TLC. After completion of the reaction, the reaction mixture was diluted with water (100 mL) and extracted with DCM (100 mL×5). The organic layer was dried over anhydrous $Na_2SO_4$ and concentrated under reduced pressure. The crude compound was purified by silica gel column chromatography (50-70% EtOAc/hexane) to afford racemic 171 (0.4 g, 71.0%) as an off-white solid.

Chiral Preparative SFC Details for 171(+) and 171(−)

The enantiomers were separated by supercritical fluid chromatography (Chiralpak IG, 250×30 mm, 5; Mobile Phase: A—$CO_2$; B—0.1% $NH_3$ in Methanol; Gradient Elution 20-30% B, 3 min, hold 6 min, 30-35% B, 5 min, 35-45%

B, 4 min, 45-50% B, 4 min; Flow rate: 80.0 mL/min) to obtain 171(+) (40 mg) and 171(−) (40 mg).

171(+): ¹H NMR (400 MHz, DMSO-d6): δ 8.89 (d, J=12.4 Hz, 2H), 8.66 (d, J=8.0 Hz, 1H), 7.65-7.38 (m, 3H), 7.28 (brs, 2H), 5.30-5.24 (m, 1H), 3.43-3.34 (m, 1H), 2.86 (s, 3H) (1H merged in solvent peak); LC-MS: m/z 447.15 [M+H]⁺; HPLC: 99.67%; C-HPLC: 98.40% (RT: 8.16); SOR: +70.88, Solvent: Methanol, Path length: 10 mm, Concentration: 0.25 w/v %.

171(−): ¹H NMR (400 MHz, DMSO-d6): δ 8.89 (d, J=12.0 Hz, 2H), 8.66 (d, J=8.8 Hz, 1H), 7.65-7.38 (m, 3H), 7.28 (brs, 2H), 5.30-5.24 (m, 1H), 3.43-3.35 (m, 1H), 2.86 (s, 3H) (1H merged in solvent peak); LC-MS: m/z 447.15 [M+H]⁺; HPLC: 99.68%; C-HPLC: 100.00% (RT: 7.54); SOR: −66.56, Solvent: Methanol, Path length: 10 mm, Concentration: 0.25 w/v %.

Examples 172A

N-(2-((5-(5-(difluoromethyl)-1,3,4-oxadiazol-2-yl)pyrimidin-2-yl)amino)-2-(3,4-difluorophenyl)ethyl)-N-(2,2,2-trifluoroethyl)methanesulfonamide (172A)

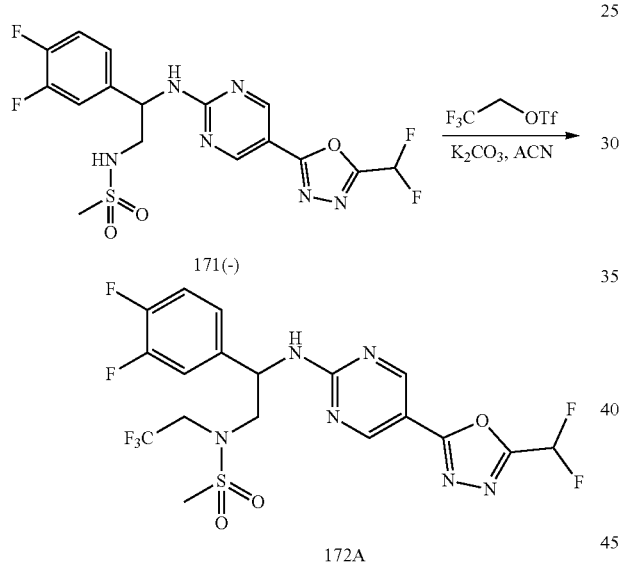

N-(2-((5-(5-(difluoromethyl)-1,3,4-oxadiazol-2-yl)pyrimidin-2-yl)amino)-2-(3,4-difluorophenyl)ethyl)-N-(2,2,2-trifluoroethyl)methanesulfonamide (172A)

To a stirred solution of 171(−) (0.03 g, 0.08 mmol) in ACN (5 mL), K₂CO₃ (0.05 g, 0.38 mmol) and 2,2,2-trifluoroethyl trifluoromethanesulfonate (0.12 g, 0.53 mmol) were added and the reaction mixture was stirred at 80° C. for 24 h. The progress of the reaction was monitored by TLC and LCMS. After completion of the reaction, the reaction mixture was filtered and the filtrate was concentrated under reduced pressure. The crude product was purified by silica gel column chromatography (30% EtOAc/hexane) to afford 172A (0.013 g, 32.5%) as a pale yellow solid. ¹H NMR (400 MHz, DMSO-d6): δ 8.90 (d, J=14.8 Hz, 2H), 8.63 (d, J=8.8 Hz, 1H), 7.65-7.40 (m, 3H), 7.32 (brs, 1H), 5.58-5.51 (m, 1H), 4.24-4.10 (m, 2H), 3.74-3.59 (m, 2H), 3.04 (s, 3H); LC-MS: m/z 529.15 [M+H]⁺; HPLC: 99.58%; C-HPLC: 99.99% (RT: 5.87).

Examples 172B

N-(2-((5-(5-(difluoromethyl)-1,3,4-oxadiazol-2-yl)pyrimidin-2-yl)amino)-2-(3,4-difluorophenyl)ethyl)-N-(2,2,2-trifluoroethyl)methanesulfonamide (172B)

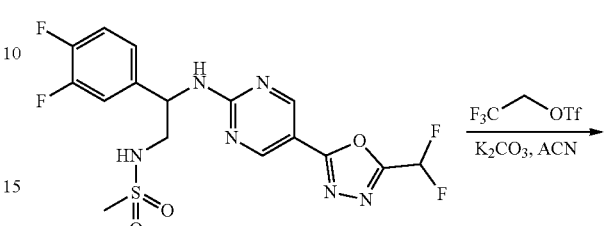

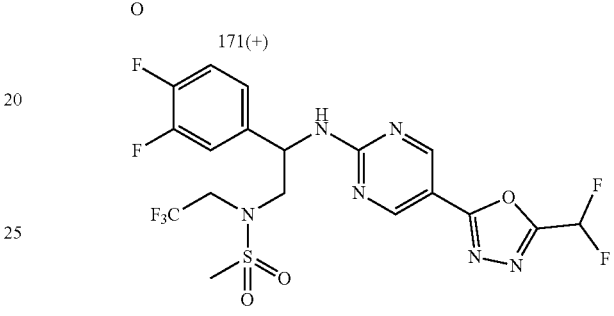

N-(2-((5-(5-(difluoromethyl)-1,3,4-oxadiazol-2-yl)pyrimidin-2-yl)amino)-2-(3,4-difluorophenyl)ethyl)-N-(2,2,2-trifluoroethyl)methanesulfonamide (172B)

To a stirred solution of 171(+) (0.05 g, 0.10 mmol) in ACN (5 mL), K₂CO₃ (0.07 g, 0.50 mmol) and 2,2,2-trifluoroethyl trifluoromethanesulfonate (0.16 g, 0.71 mmol) were added and the reaction mixture was stirred at 80° C. for 24 h. The progress of the reaction was monitored by TLC and LCMS. After completion of the reaction, the reaction mixture was filtered and the filtrate was concentrated under reduced pressure. The crude product was purified by silica gel column chromatography (28% EtOAc/hexane) to afford 172B (0.018 g, 34.0%) as a pale yellow solid. ¹H NMR (400 MHz, DMSO-d6): δ 8.90 (d, J=15.2 Hz, 2H), 8.63 (d, J=8.8 Hz, 1H), 7.65-7.40 (m, 3H), 7.32 (brs, 1H), 5.58-5.51 (m, 1H), 4.24-4.10 (m, 2H), 3.74-3.59 (m, 2H), 3.04 (s, 3H); LC-MS: m/z 529.15 [M+H]⁺; HPLC: 99.52%; C-HPLC: 99.31% (RT: 6.33).

Examples 173(+) and 173(−)

N-(2-(4-chlorophenyl)-2-((5-(5-(difluoromethyl)-1,3,4-oxadiazol-2-yl)pyrimidin-2-yl)amino)ethyl)methanesulfonamide (173(+) and 173(−))

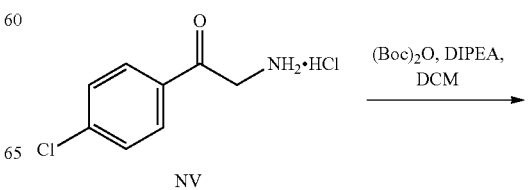

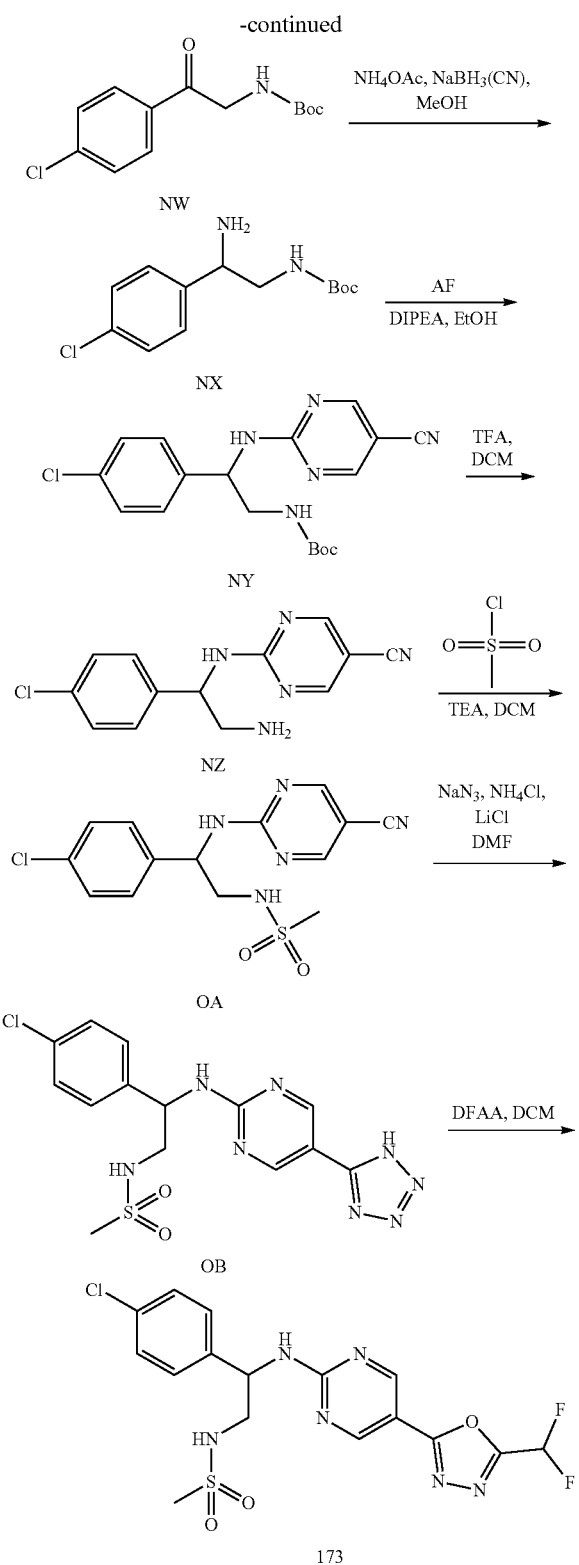

tert-butyl (2-(4-chlorophenyl)-2-oxoethyl)carbamate (NW)

To a stirred solution of 2-Amino-4-chloroacetophenone hydrochloride (NV, 5.0 g, 24.27 mmol) in DCM (100 mL), DIPEA (13.0 mL, 72.81 mmol), di-tert-butyl dicarbonate (6.7 mL, 29.12 mmol) were added at 0° C. and the reaction mixture was stirred at RT for 3 h. The progress of the reaction was monitored by TLC. After completion of the reaction, the reaction mixture was diluted with water. The aqueous layer was extracted with DCM (250 mL×2). The combined organic layer was dried over anhydrous $Na_2SO_4$ and concentrated under reduced pressure to afford compound NW (6.1 g, 94.0%) as an off-white solid which was used as such for the next reaction. $^1$H NMR (400 MHz, DMSO-d6): δ 7.95 (d, J=8.4 Hz, 2H), 7.58 (d, J=8.4 Hz, 2H), 7.07 (t, J=5.6 Hz, 1H), 4.39 (d, J=5.6 Hz, 2H), 1.36 (s, 9H); LC-MS: m/z 169.95 [M+1-boc]$^+$.

tert-butyl (2-amino-2-(4-chlorophenyl)ethyl)carbamate (NX)

To a stirred solution of compound NW (5.0 g, 18.58 mmol) in MeOH (125 mL), ammonium acetate (28.6 g, 371.60 mmol) $NaBH_3CN$ (3.2 g, 50.18 mmol) were added and the reaction mixture was stirred at 80° C. for 2 h. The progress of the reaction was monitored by TLC and LCMS. After completion of the reaction, the reaction mixture was concentrated under reduced pressure. The residue was diluted with water and basified with saturated NaOH solution to pH 9-10. The aqueous layer was extracted with EtOAc (200 mL×3). The combined organic layer was dried over anhydrous $Na_2SO_4$ and concentrated under reduced pressure to afford compound NX (4.9 g, crude) as a yellow semi solid which was used as such for the next reaction. $^1$H NMR (400 MHz, DMSO-d6): δ 7.38-7.25 (m, 5H), 6.82-6.79 (m, 1H), 3.86 (t, J=6.6 Hz, 1H), 3.12-3.00 (m, 1H), 2.97-2.91 (m, 1H), 1.34 (s, 9H); LC-MS: m/z 271.05 [M+H]$^+$.

tert-butyl (2-(4-chlorophenyl)-2-((5-cyanopyrimidin-2-yl)amino)ethyl)carbamate (NY)

To a stirred solution of compound NX (4.9 g, 18.14 mmol) and 2-chloropyrimidine-5-carbonitrile (2.5 g, 18.14 mmol) in EtOH (100 mL), DIPEA (9.8 mL, 54.42 mmol) was added and the reaction mixture was stirred at 80° C. for 12 h. The progress of the reaction was monitored by TLC and LCMS. After completion of the reaction, the reaction mixture was concentrated under reduced pressure. The residue was diluted with water and extracted with EtOAc (200 mL×3). The combined organic layer was dried over anhydrous $Na_2SO_4$ and concentrated under reduced pressure. The crude product was purified by silica gel column chromatography (15-30% EtOAc/hexane) to afford compound NY (5.0 g, 74.0%) as an off-white solid. LC-MS: m/z 374.15 [M+H]$^+$.

2-((2-amino-1-(4-chlorophenyl)ethyl)amino)pyrimidine-5-carbonitrile (NZ)

To a stirred solution of compound NY (5.0 g, 13.40 mmol) in DCM (50 mL), TFA (15.5, 134.00 mL) was added at 0° C. and the reaction mixture was stirred at RT for 16 h. The progress of the reaction was monitored by TLC. After completion of the reaction, the reaction mixture was concentrated under reduced pressure. The obtained crude was triturated with diethyl ether to afford compound NZ (4.0 g, 81.0%) as a yellow solid. LC-MS: m/z 274.10 [M+H]$^+$.

N-(2-(4-chlorophenyl)-2-((5-cyanopyrimidin-2-yl)amino)ethyl)methanesulfonamide (OA)

To a stirred solution of compound NZ (4.0 g, 14.65 mmol) in DCM (100 mL), triethyl amine (6.2 mL, 43.95 mmol), methanesulfonyl chloride (7, 0.96 mL, 14.65 mmol) were added at 0° C. and the reaction mixture was stirred at same temperature for 30 min. The progress of the reaction was monitored by TLC. After completion of the reaction, the reaction mixture was diluted with water and extracted with DCM (200 mL×3). The combined organic layer was dried over anhydrous $Na_2SO_4$ and concentrated under reduced pressure. The crude product was purified by silica gel column chromatography (15-30% EtOAc/hexane) to afford compound OA (2.6 g, 58.0%) as an off-white solid. $^1H$ NMR (400 MHz, DMSO-d6): δ 8.79 (d, J=8.8 Hz, 1H), 8.71-8.67 (m, 2H), 7.44-7.38 (m, 4H), 7.24 (brs, 1H), 5.20-5.16 (m, 1H), 3.39-3.36 (m, 1H), 2.84 (s, 3H) (1H merged in solvent peak); LC-MS: m/z 352.10 $[M+H]^+$.

N-(2-((5-(1H-tetrazol-5-yl)pyrimidin-2-yl)amino)-2-(4-chlorophenyl)ethyl)methanesulfonamide (OB)

To a stirred solution of compound OA (2.0 g, 5.69 mmol) in DMF (20 mL), $NaN_3$ (1.85 g, 28.49 mmol), $NH_4Cl$ (1.50 g, 28.49 mmol), LiCl (0.24 g, 5.69 mmol) were added and the reaction mixture was stirred at 100° C. for 16 h. The progress of the reaction was monitored by TLC and LCMS. After completion of the reaction, the reaction mixture was diluted with cold water and acidified with 6N HCl solution to pH 4-5. The aqueous layer was extracted with EtOAc (300 mL×3). The combined organic layer was dried over anhydrous $Na_2SO_4$ and concentrated under reduced pressure to afford compound OB (1.9 g, 85.0%) as a yellow solid which was used as such for the next reaction. $^1H$ NMR (400 MHz, DMSO-d6): δ 16.75 (brs, 1H), 8.84 (brs, 2H), 8.41 (d, J=8.8 Hz, 1H), 7.47-7.36 (m, 4H), 7.24 (t, J=5.8 Hz, 1H), 5.25-5.20 (m, 1H), 3.42-3.38 (m, 2H), 2.84 (s, 3H); LC-MS: m/z 395.10 $[M+H]^+$.

N-(2-(4-chlorophenyl)-2-((5-(5-(difluoromethyl)-1,3,4-oxadiazol-2-yl)pyrimidin-2-yl)amino)ethyl)methanesulfonamide (173)

To a stirred solution of compound OB (1.9 g, 4.82 mmol) in DCM (30 mL) was added DFAA (1.3 g, 7.23 mmol) at 0° C. and the reaction was stirred at RT for 16 h. The progress of the reaction was monitored by TLC and LCMS. After completion of the reaction, the reaction mixture was diluted with water and extracted with DCM (300 mL×3). The combined organic layer was dried over anhydrous $Na_2SO_4$ and concentrated under reduced pressure. The crude compound was purified by silica gel column chromatography (10-40% EtOAc/hexane) to afford racemic 173 (1.5 g, 70.0%) as an off-white solid.

Chiral Preparative HPLC Details for 173(+) and 173(−)

The enantiomers were separated by normal-phase preparative high performance liquid chromatography (Chiralpak IC, 250×30 mm, 5; Mobile Phase: A-MTBE; B-Ethanol; Isocratic Elution 5% B; Flow rate: 30.0 mL/min) to obtain 173(+) (550 mg) and 173(−) (515 mg).

173(+): $^1H$ NMR (400 MHz, DMSO-d6): δ 8.87 (d, J=14.8 Hz, 2H), 8.72 (d, J=8.8 Hz, 1H), 7.65-7.27 (m, 6H), 5.28-5.23 (m, 1H), 3.43-3.37 (m, 1H), 2.85 (s, 3H) (1H merged in solvent peak); LC-MS: m/z 445.10 $[M+H]^+$; HPLC: 99.89%; C-HPLC: 99.77% (RT: 7.37); SOR: +120.12, Solvent: Methanol, Path length: 10 mm, Concentration: 0.315 w/v %.

173(−): $^1H$ NMR (400 MHz, DMSO-d6): δ 8.87 (d, J=14.8 Hz, 2H), 8.72 (d, J=8.4 Hz, 1H), 7.65-7.39 (m, 5H), 7.27 (brs, 1H), 5.28-5.23 (m, 1H), 3.42-3.37 (m, 1H), 2.85 (s, 3H) (1H merged in solvent peak); LC-MS: m/z 445.05 $[M+H]^+$; HPLC: 99.73%; C-HPLC: 99.78% (RT: 5.78); SOR: −141.62, Solvent: Methanol, Path length: 10 mm, Concentration: 0.32 w/v %.

Example 174(+)

N-(2-(4-chlorophenyl)-2-((5-(5-(difluoromethyl)-1,3,4-oxadiazol-2-yl)pyrimidin-2-yl)amino)ethyl)-N-(2,2,2-trifluoroethyl)methanesulfonamide (174(+))

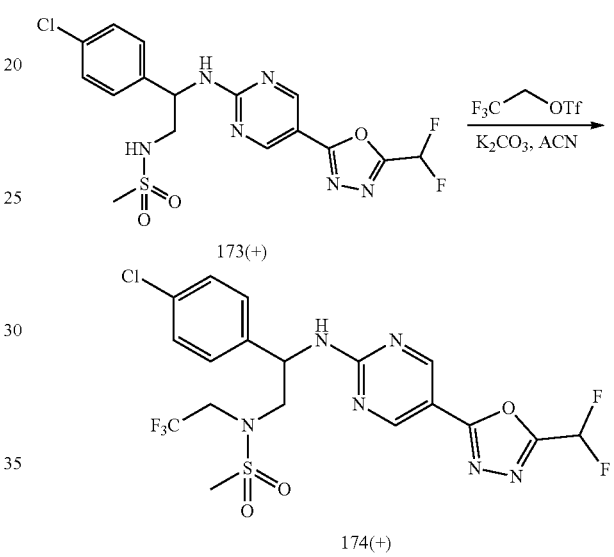

N-(2-(4-chlorophenyl)-2-((5-(5-(difluoromethyl)-1,3,4-oxadiazol-2-yl)pyrimidin-2-yl)amino)ethyl)-N-(2,2,2-trifluoroethyl)methanesulfonamide (174(+))

To a stirred solution of 173(+) (0.25 g, 0.56 mmol) in ACN (10 mL), $K_2CO_3$ (0.24 g, 1.68 mmol), 2,2,2-trifluoroethyl trifluoromethanesulfonate (0.20 mL, 1.40 mmol) were added and the reaction mixture was stirred at 80° C. for 12 h. The progress of the reaction was monitored by TLC and LCMS. After completion of the reaction, the reaction mixture was concentrated under reduced pressure. The residue was diluted with water and extracted with EtOAc (100 mL×2). The combined organic layer was dried over anhydrous $Na_2SO_4$ and concentrated under reduced pressure. The crude product was purified by silica gel column chromatography (10-30% EtOAc/hexane) to afford 174(+) (0.205 g, 70.0%) as a pale yellow solid. $^1H$ NMR (400 MHz, DMSO-d6): δ 8.89 (d, J=16.0 Hz, 2H), 8.68 (d, J=9.2 Hz, 1H), 7.65-7.39 (m, 5H), 5.57-5.51 (m, 1H), 4.25-4.09 (m, 2H), 3.73-3.61 (m, 2H), 3.03 (s, 3H); LC-MS: m/z 527.10 $[M+H]^+$; HPLC: 99.47%; C-HPLC: 99.64% (RT: 10.89); SOR: +113.00, Solvent: Methanol, Path length: 10 mm, Concentration: 0.306 w/v %.

Examples 174(−)

N-(2-(4-chlorophenyl)-2-((5-(5-(difluoromethyl)-1,3,4-oxadiazol-2-yl)pyrimidin-2-yl)amino)ethyl)-N-(2,2,2-trifluoroethyl)methanesulfonamide (174(−))

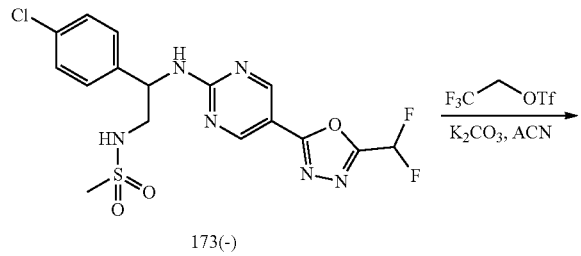

N-(2-(4-chlorophenyl)-2-((5-(5-(difluoromethyl)-1,3,4-oxadiazol-2-yl)pyrimidin-2-yl)amino)ethyl)-N-(2,2,2-trifluoroethyl)methanesulfonamide (174(−))

To a stirred solution of 173(−) (0.20 g, 0.45 mmol) in ACN (10 mL), K$_2$CO$_3$ (0.19 g, 1.35 mmol) and 2,2,2-trifluoroethyl trifluoromethanesulfonate (1, 0.16 mL, 1.12 mmol) were added and the reaction mixture was stirred at 80° C. for 12 h. The progress of the reaction was monitored by TLC and LCMS. After completion of the reaction, the reaction mixture was concentrated under reduced pressure. The residue was diluted with water and extracted with EtOAc (100 mL×2).

The combined organic layer was dried over anhydrous Na$_2$SO$_4$ and concentrated under reduced pressure. The crude product was purified by silica gel column chromatography (10-30% EtOAc/hexane) to afford 174(−) (0.126 g, 53.0%) as a pale yellow solid. $^1$H NMR (400 MHz, DMSO-d6): δ 8.88 (d, J=15.6 Hz, 2H), 8.68 (d, J=9.2 Hz, 1H), 7.64-7.39 (m, 5H), 5.56-5.50 (m, 1H), 4.25-4.08 (m, 2H), 3.73-3.60 (m, 2H), 3.02 (s, 3H); LC-MS: m/z 526.90 [M+H]$^+$; HPLC: 98.18%; C-HPLC: 99.73% (RT: 9.07); SOR: −81.11, Solvent: Methanol, Path length: 10 mm, Concentration: 0.27 w/v %.

Examples 175(+) and 175(−)

5-(5-(difluoromethyl)-1,3,4-oxadiazol-2-yl)-N-(1-(4-fluorophenyl)-2-(4-(trifluoromethyl)-1H-imidazol-1-yl)ethyl)pyrimidin-2-amine (175(+) and 175(−))

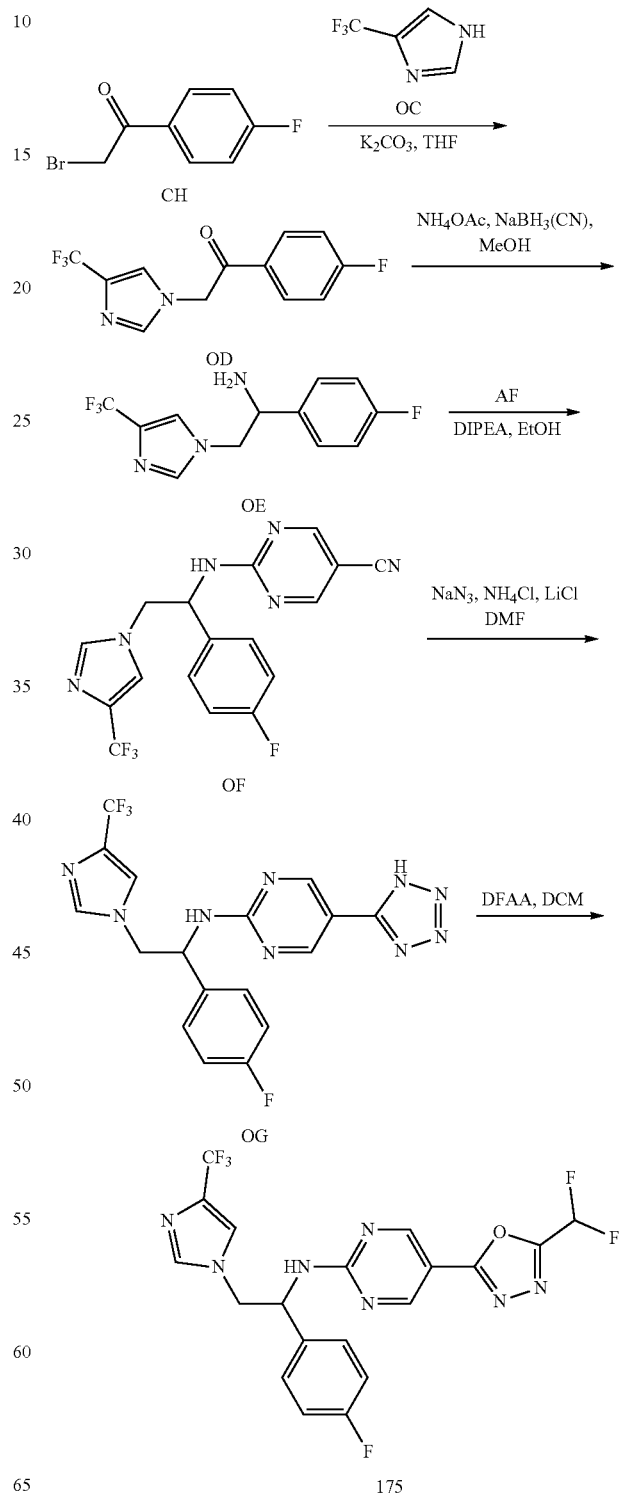

1-(4-fluorophenyl)-2-(4-(trifluoromethyl)-1H-imidazol-1-yl)ethan-1-one (OD)

To a stirred solution of 4-(trifluoromethyl)-1H-imidazole (OC, 0.94 g, 6.91 mmol) in THF (20 mL), $K_2CO_3$ (1.14 g, 8.29 mmol) was added and the reaction mixture was stirred at RT for 15 min. To the resulting reaction mixture, 2-bromo-1-(4-fluorophenyl)ethan-1-one (CH, 1.50 g, 6.91 mmol) was added and the reaction mixture was stirred at RT for 16 h. The progress of the reaction was monitored by TLC. After completion of the reaction, the reaction mixture was filtered through celite. The filtrate was concentrated under reduced pressure. The crude compound was purified by silica gel column chromatography (40% EtOAc/hexane) to afford compound OD (1.2 g, 67.0%) as an off-white solid. $^1$H NMR (400 MHz, DMSO-d6): δ 8.14-8.10 (m, 2H), 7.76 (d, J=17.2 Hz, 2H), 7.44 (t, J=8.8 Hz, 2H), 5.80 (s, 2H); LC-MS: m/z 272.95 $[M+H]^+$.

1-(4-fluorophenyl)-2-(4-(trifluoromethyl)-1H-imidazol-1-yl)ethan-1-amine (OE)

To a stirred solution of compound OD (1.20 g, 4.41 mmol) in MeOH (20 mL), ammonium acetate (6.8 g, 88.20 mmol) was added and the reaction mixture was stirred at RT for 20 min. To the resulting reaction mixture, $NaBH_3CN$ (0.75 g, 11.91 mmol) was added and the reaction mixture was stirred at 80° C. for 16 h. The progress of the reaction was monitored by TLC. After completion of the reaction, the reaction mixture was cooled to RT and concentrated under reduced pressure. The residue was diluted with 10% NaOH solution and extracted with EtOAc. The combined organic layer was dried over anhydrous $Na_2SO_4$ and concentrated under reduced pressure to afford compound OE (0.8 g, crude) as an off-white solid which was used as such for the next reaction. LC-MS: m/z 273.90 $[M+H]^+$.

2-((1-(4-fluorophenyl)-2-(4-(trifluoromethyl)-1H-imidazol-1-yl)ethyl)amino)pyrimidine-5-carbonitrile (OF)

To a stirred solution of compound OE (0.80 g, 2.93 mmol) and 2-chloropyrimidine-5-carbonitrile (AF, 0.45 g, 3.22 mmol) in EtOH (10 mL), DIPEA (2.7 mL, 14.65 mmol) was added and the reaction mixture was stirred at 85° C. for 16 h. The progress of the reaction was monitored by TLC. After completion of the reaction, the reaction mixture was concentrated under reduced pressure. The crude product was purified by silica gel column chromatography (40% EtOAc/hexane) to afford compound OF (0.82 g, 74.5%) as an off-white solid. $^1$H NMR (400 MHz, DMSO-d6): δ 9.01 (d, J=8.8 Hz, 1H), 8.64 (d, J=22.8 Hz, 2H), 7.85 (d, J=18.0 Hz, 2H), 7.55-7.47 (m, 2H), 7.24-7.18 (m, 2H), 5.54-5.51 (m, 1H), 4.40-4.32 (m, 2H); LC-MS: m/z 376.8 $[M+H]^+$.

N-(1-(4-fluorophenyl)-2-(4-(trifluoromethyl)-1H-imidazol-1-yl)ethyl)-5-(1H-tetrazol-5-yl)pyrimidin-2-amine (OG)

To a stirred solution of compound OF (0.82 g, 2.18 mmol) in DMF (10 mL), $NaN_3$ (0.71 g, 10.90 mmol), $NH_4Cl$ (0.58 g, 10.90 mmol) and LiCl (0.07 g) were added and the reaction mixture was stirred at 100° C. for 16 h. The progress of the reaction was monitored by TLC. After completion of the reaction, the reaction mixture was concentrated under reduced pressure. The residue was diluted with 1N HCl and the aqueous layer was extracted with EtOAc. The combined organic layer was dried over anhydrous $Na_2SO_4$ and concentrated under reduced pressure to afford compound OG (0.65 g, crude) as an off-white solid which was used as such for the next reaction. LC-MS: m/z 420.05 $[M+H]^+$.

5-(5-(difluoromethyl)-1,3,4-oxadiazol-2-yl)-N-(1-(4-fluorophenyl)-2-(4-(trifluoromethyl)-1H-imidazol-1-yl)ethyl)pyrimidin-2-amine (175)

To a stirred solution of compound OG (0.65 g, 1.55 mmol) in DCM (20 mL), DFAA (0.67 g, 3.87 mmol) was added and the reaction was stirred at RT for 16 h. The progress of the reaction was monitored by TLC. After completion of the reaction, the reaction mixture was quenched with saturated $NaHCO_3$ solution and the product was extracted with DCM. The combined organic layer was dried over anhydrous $Na_2SO_4$ and concentrated under reduced pressure. The crude compound was purified by silica gel column chromatography (20% EtOAc/hexane) to afford racemic 175 (0.4 0 g, 55.0%) as an off-white solid.

Chiral Preparative SFC Details for 175(+) and 175(−)

The enantiomers were separated by supercritical fluid chromatography (Chiralpak IA, 250×30 mm, 5; Mobile Phase: A—$CO_2$; B—0.1% $NH_3$ in Methanol; Gradient Elution 10-25% B over 1 min, 25-30% B over 7 min, 30% B hold for 4 min, 30-35% B over 2 min, 35-50% B over 4 min; Flow rate: 80.0 mL/min) to obtain 175(+) (60 mg) and 175(−) (60 mg).

175(+): $^1$H NMR (400 MHz, DMSO-d6): δ 8.94 (d, J=8.8 Hz, 1H), 8.86 (brs, 1H), 8.77 (brs, 1H), 7.88 (d, J=21.6 Hz, 2H), 7.64-7.38 (m, 3H), 7.23 (t, J=8.8 Hz, 2H), 5.61-5.55 (m, 1H), 4.44-4.32 (m, 2H); LC-MS: m/z 470.15 $[M+H]^+$; HPLC: 97.24%; C-HPLC: 98.95% (RT: 5.18); SOR: +70.22, Solvent: Methanol, Path length: 100 mm, Concentration: 0.25 w/v %.

175(−): $^1$H NMR (400 MHz, DMSO-d6): δ 8.94 (d, J=9.2 Hz, 1H), 8.86 (brs, 1H), 8.76 (brs, 1H), 7.88 (d, J=21.6 Hz, 2H), 7.63-7.38 (m, 3H), 7.23 (t, J=8.6 Hz, 2H), 5.61-5.55 (m, 1H), 4.44-4.32 (m, 2H); LC-MS: m/z 470.15 $[M+H]^+$; HPLC: 97.11%; C-HPLC: 99.35% (RT: 5.85); SOR: −72.35, Solvent: Methanol, Path length: 100 mm, Concentration: 0.25 w/v %.

Examples 176(+) and 176(−)

5-(5-(difluoromethyl)-1,3,4-oxadiazol-2-yl)-N-(1-(4-fluorophenyl)-2-(4-(trifluoromethyl)-1H-pyrazol-1-yl)ethyl)pyrimidin-2-amine (176(+) and 176(−))

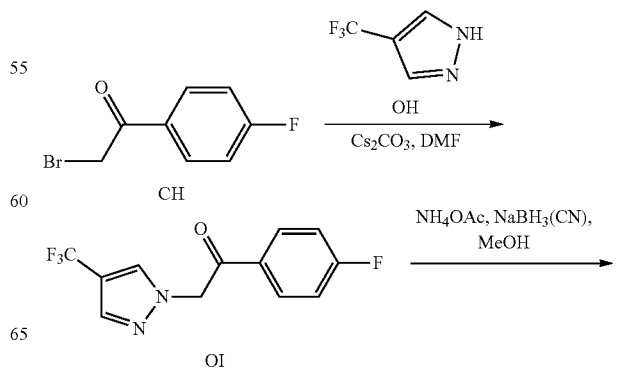

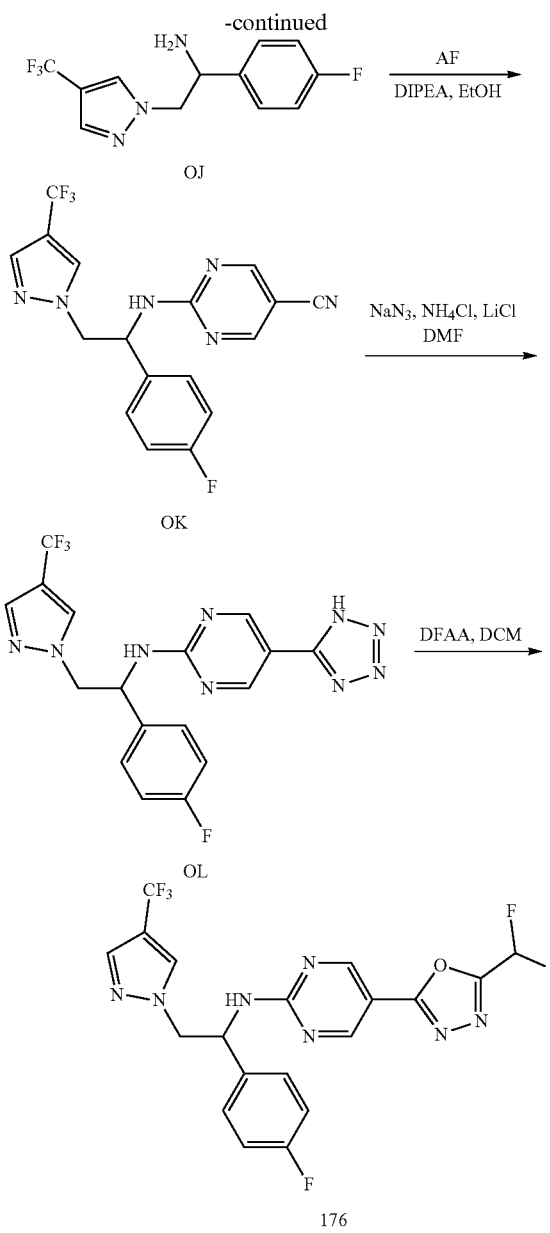

1-(4-fluorophenyl)-2-(4-(trifluoromethyl)-1H-pyrazol-1-yl)ethan-1-one (OI)

To a stirred solution of 4-(trifluoromethyl)-1H-pyrazole (OH, 2.5 g, 18.43 mmol) in DMF (50 mL), Cs$_2$CO$_3$ (9.0 g, 27.64 mmol) was added followed by 2-bromo-1-(4-fluorophenyl)ethan-1-one (CH, 4.0 g, 18.43 mmol) and the reaction mixture was stirred at RT for 1 h. The progress of the reaction was monitored by TLC. After completion of the reaction, the reaction mixture was diluted with ice water and the aqueous layer was extracted with EtOAc. The combined organic layer was dried over anhydrous Na$_2$SO$_4$ and concentrated under reduced pressure. The crude compound was purified by silica gel column chromatography (40% EtOAc/hexane) to afford compound OI (3.0 g, 60.0%) as a light yellow solid. $^1$H NMR (400 MHz, DMSO-d6): δ 8.35 (s, 1H), 8.16-8.12 (m, 2H), 7.95 (s, 1H), 7.45 (t, J=8.8 Hz, 2H), 5.95 (s, 2H); LC-MS: m/z 273.00 [M+H]$^+$.

1-(4-fluorophenyl)-2-(4-(trifluoromethyl)-1H-pyrazol-1-yl)ethan-1-amine (OJ)

To a stirred solution of compound OI (3.0 g, 11 mmol) in MeOH (150 mL), ammonium acetate (17.0 g, 220 mmol) was added followed by NaBH$_3$CN (2.1 g, 33 mmol) at RT and the reaction mixture was stirred at 80° C. for 16 h. The progress of the reaction was monitored by TLC. After completion of the reaction, the reaction mixture was cooled to RT and concentrated under reduced pressure. The residue was diluted with NaHCO$_3$ solution and extracted with DCM. The combined organic layer was dried over anhydrous Na$_2$SO$_4$ and concentrated under reduced pressure. The crude compound was purified by silica gel column chromatography (5% MeOH/DCM) to afford compound OJ (2.3 g, 76.5%) as an off-white solid. LC-MS: m/z 274.2 [M+H]$^+$.

2-((1-(4-fluorophenyl)-2-(4-(trifluoromethyl)-1H-pyrazol-1-yl)ethyl)amino)pyrimidine-5-carbonitrile (OK)

To a stirred solution of compound OJ (2.3 g, 8.42 mmol) and 2-chloropyrimidine-5-carbonitrile (AF, 1.2 g, 8.42 mmol) in EtOH (100 mL), DIPEA (3.7 mL, 21.06 mmol) was added and the reaction mixture was stirred at 80° C. for 2 h. The progress of the reaction was monitored by TLC. After completion of the reaction, the reaction mixture was concentrated under reduced pressure. The residue was dissolved in EtOAc and washed with water and brine. The organic layer was dried over anhydrous Na$_2$SO$_4$ and concentrated under reduced pressure. The crude product was purified by silica gel column chromatography (50% EtOAc/hexane) to afford compound OK (2.5 g, 79.0%) as a light yellow solid. $^1$H NMR (400 MHz, DMSO-d6): δ 8.99 (d, J=8.8 Hz, 1H), 8.64 (d, J=9.6 Hz, 2H), 8.29 (s, 1H), 7.86 (s, 1H), 7.47-7.44 (m, 2H), 7.18 (t, J=8.8 Hz, 2H), 5.67-5.61 (m, 1H), 4.58-4.48 (m, 2H); LC-MS: m/z 377.2 [M+H]$^+$.

N-(1-(4-fluorophenyl)-2-(4-(trifluoromethyl)-1H-pyrazol-1-yl)ethyl)-5-(1H-tetrazol-5-yl)pyrimidin-2-amine (OL)

To a stirred solution of compound OK (2.0 g, 5.31 mmol) in DMF (50 mL), NaN$_3$ (1.03 g, 15.95 mmol), NH$_4$Cl (0.85 g, 15.95 mmol) and LiCl (0.22 g, 5.31) were added in a sealed tube and the reaction mixture was stirred at 100° C. for 16 h. The progress of the reaction was monitored by TLC. After completion of the reaction, the reaction mixture was concentrated under reduced pressure. The residue was diluted with 1N HCl, aqueous layer was extracted with 10% MeOH/DCM. The combined organic layer was dried over anhydrous Na$_2$SO$_4$ and concentrated under reduced pressure to afford compound OL (2.2 g, crude) as a light yellow sticky oil which was used as such for the next reaction. $^1$H NMR (400 MHz, DMSO-d6): δ 8.80 (brs, 1H), 8.62 (d, J=8.8 Hz, 1H), 8.30 (s, 1H), 7.95 (s, 2H), 7.86 (s, 1H), 7.50-7.47 (m, 2H), 7.18 (t, J=8.8 Hz, 2H), 5.71-5.64 (m, 1H), 4.60-4.51 (m, 2H); LC-MS: m/z 420.1 [M+H]$^+$.

5-(5-(difluoromethyl)-1,3,4-oxadiazol-2-yl)-N-(1-(4-fluorophenyl)-2-(4-(trifluoromethyl)-1H-pyrazol-1-yl)ethyl)pyrimidin-2-amine (176)

To a stirred solution of compound OL (2.2 g, 5.25 mmol) in DCM (100 mL), DFAA (1.82 mL, 15.75 mmol) was added and the reaction was stirred at RT for 16 h. The progress of the reaction was monitored by TLC. After completion of the reaction, the reaction mixture was quenched with saturated NaHCO₃ solution and the product was extracted with DCM. The combined organic layer was dried over anhydrous Na₂SO₄ and concentrated under reduced pressure. The crude compound was purified by silica gel column chromatography (10% MeOH/DCM) to afford racemic 176 (1.0 g, 52%) as an off-white solid.

Chiral Preparative SFC Details for 176(+) and 176(−)

The enantiomers were separated by supercritical fluid chromatography (Chiralpak IG, 250×30 mm, 5; Mobile Phase: A—CO₂; B—0.1% NH₃ in Methanol; Gradient Elution 15-30% B in 2 min, 30% B hold 4 min, 30-35% B in 4 min, 35-45% B in 5 min; Flow rate: 80.0 mL/min) to obtain 176(+) (150 mg) and 176(−) (150 mg).

176(+): ¹H NMR (400 MHz, DMSO-d6): δ 8.90 (d, J=9.2 Hz, 1H), 8.82 (d, J=22 Hz, 2H), 8.31 (s, 1H), 7.86 (s, 1H), 7.64-7.38 (m, 3H), 7.19 (t, J=8.8 Hz, 2H), 5.75-5.68 (m, 1H), 4.57-4.54 (m, 2H); LC-MS: m/z 470.15 [M+H]⁺; HPLC: 99.55%; C-HPLC: 99.73% (RT: 6.77); SOR: +52.33, Solvent: Methanol, Path length: 100 mm, Concentration: 0.29 w/v %.

176(−): ¹H NMR (400 MHz, DMSO-d6): δ 8.90 (d, J=9.2 Hz, 1H), 8.82 (d, J=22 Hz, 2H), 8.31 (s, 1H), 7.86 (s, 1H), 7.64-7.38 (m, 3H), 7.19 (t, J=8.8 Hz, 2H), 5.75-5.68 (m, 1H), 4.57-4.54 (m, 2H); LC-MS: m/z 470.15 [M+H]⁺; HPLC: 99.65%; C-HPLC: 99.10% (RT: 8.03); SOR: −63.29, Solvent: Methanol, Path length: 100 mm, Concentration: 0.3 w/v %.

Examples 177(+) and 177(−)

1-(2-((5-(5-(difluoromethyl)-1,3,4-oxadiazol-2-yl)pyrimidin-2-yl)amino)-2-(4-fluorophenyl)ethyl)pyrrolidin-2-one (177(+) and 177(−))

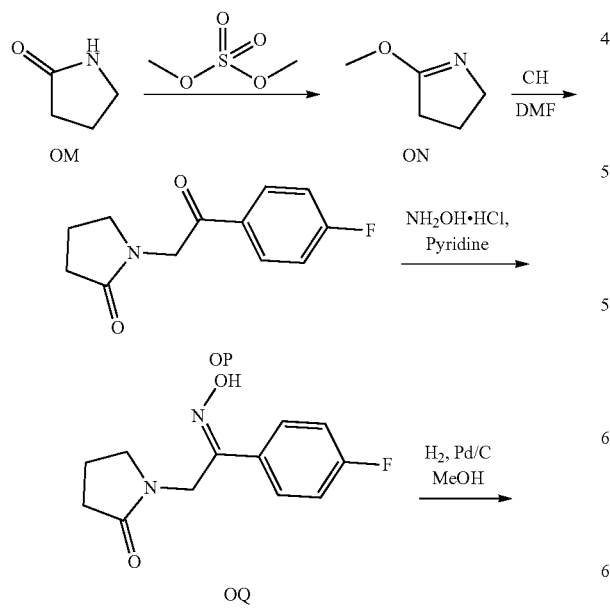

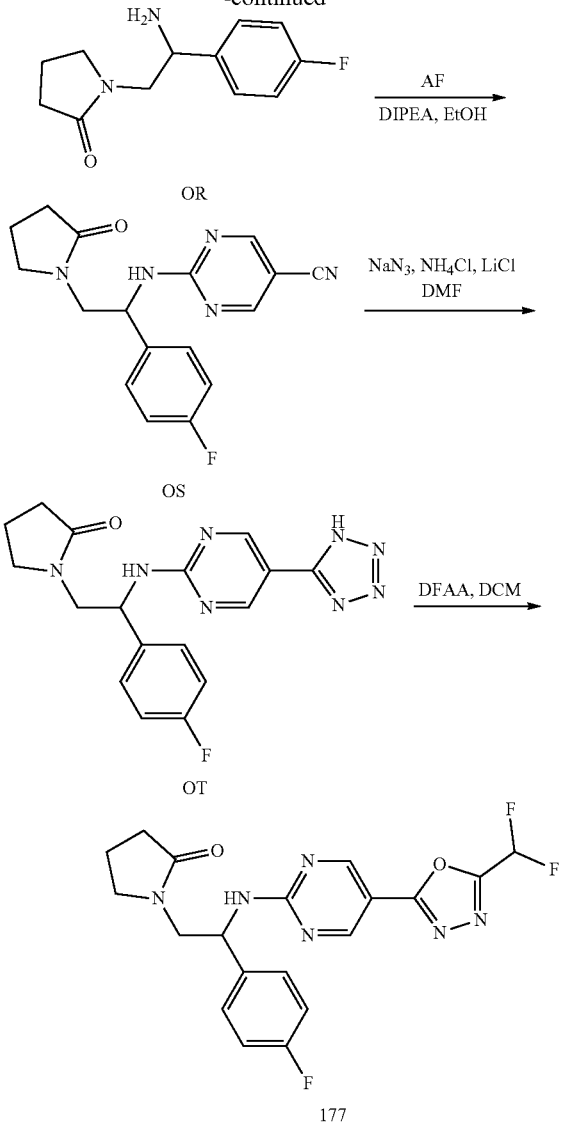

5-methoxy-3,4-dihydro-2H-pyrrole (ON)

Pyrrolidin-2-one (OM, 20.0 g, 235.00 mmol) was added to dimethyl sulfate (22.8 mL, 235.0 mmol) and the resulting reaction mixture was stirred at 60° C. for 16 h. The progress of the reaction was monitored by TLC. After completion of reaction, the reaction mixture was cooled and poured into saturated K₂CO₃ solution (200 ml) and stirred for 30 min. The aqueous layer was extracted with diethyl ether (3×100 mL). The combined organic layer was dried over anhydrous Na₂SO₄ and concentrated under reduced pressure to afford compound ON (14.0 g, 60.0%) as a brown liquid which was used as such for the next reaction.

1-(2-(4-fluorophenyl)-2-oxoethyl)pyrrolidin-2-one (OP)

To a stirred solution of 2-bromo-1-(4-fluorophenyl)ethan-1-one (CH, 5.5 g, 25.0 mmol) in DMF (30 mL), compound ON (5.0 g, 51.0 mmol) was added at RT and the reaction mixture was stirred at 50° C. for 16 h. The progress of the reaction was monitored by TLC. After completion of reaction, the reaction mixture was diluted with water and extracted with EtOAc (500 mL). The organic layer was dried over anhydrous $Na_2SO_4$ and concentrated under reduced pressure. The crude compound was purified by silica gel column chromatography (60% EtOAc/hexane) to afford compound OP (4.5 g, 80.0%) as an off-white solid. $^1$H NMR (400 MHz, DMSO-d6): δ 8.10-8.07 (m, 2H), 7.39 (t, J=8.8 Hz, 2H), 4.76 (s, 2H), 3.39 (t, J=7.0 Hz, 2H), 2.30 (t, J=8.0 Hz, 2H), 2.04-1.96 (m, 2H); LC-MS: m/z 221.95 $[M+H]^+$.

(E)-1-(2-(4-fluorophenyl)-2-(hydroxyimino)ethyl) pyrrolidin-2-one (OQ)

To a stirred solution of compound OP (4.5 g, 20.0 mmol) in pyridine (40 mL), hydroxylamine hydrochloride (2.8 g, 41.0 mmol) was added and the reaction mixture was stirred at RT for 16 h. The progress of the reaction was monitored by TLC. After completion of reaction, the reaction mixture was diluted with EtOAc and washed with 1N HCl solution. The organic layer was dried over anhydrous $Na_2SO_4$ and concentrated under reduced pressure to afford compound OQ (4.5 g, 94.0%) as an off-white solid which was used as such for the next reaction. $^1$H NMR (400 MHz, DMSO-d6): δ 11.68 (s, 1H), 7.69-7.66 (m, 2H), 7.21 (t, J=8.8 Hz, 2H), 4.49 (s, 2H), 3.14 (t, J=7.0 Hz, 2H), 2.15 (t, J=7.8 Hz, 2H), 1.81-1.74 (m, 2H); LC-MS: m/z 237.0 $[M+H]^+$.

1-(2-amino-2-(4-fluorophenyl)ethyl)pyrrolidin-2-one (OR)

To a stirred solution of compound OQ (4.5 g, 19.00 mmol) in MeOH (50 mL), Pd/C (1.0 g) was added and the reaction mixture was stirred at RT for 16 h under $H_2$ balloon pressure. The progress of the reaction was monitored by TLC. After completion of reaction, the reaction mixture was filtered through celite and washed with MeOH. The filtrate was concentrated under reduced pressure. The crude compound was purified by silica gel column chromatography (80% EtOAc/hexane) to afford compound OR (3.5 g, 83.0%) as a light brown sticky solid. $^1$H NMR (400 MHz, DMSO-d6): δ 7.42-7.38 (m, 2H), 7.15-7.10 (m, 2H), 4.05 (t, J=7.2 Hz, 1H), 3.37-3.27 (m, 2H), 3.18-3.10 (m, 2H), 2.33 (brs, 2H), 2.20-2.09 (m, 2H), 1.86-1.79 (m, 2H); LC-MS: m/z 223.05 $[M+H]^+$.

2-((1-(4-fluorophenyl)-2-(2-oxopyrrolidin-1-yl) ethyl)amino)pyrimidine-5-carbonitrile (OS)

To a stirred solution of compound OR (2.0 g, 9.0 mmol) in EtOH (30 mL), DIPEA (8.3 mL, 45.0 mmol) was added followed by 2-chloropyrimidine-5-carbonitrile (AF, 1.3 g, 9.0 mmol) and the reaction mixture was stirred at RT for 16 h. The progress of the reaction was monitored by TLC. After completion of reaction, the reaction mixture was concentrated under reduced pressure. The crude compound was purified by silica gel column chromatography (40% EtOAc/hexane) to afford compound OS (2.0 g, 69.0%) as an off-white solid. $^1$H NMR (400 MHz, DMSO-d6): δ 8.83 (d, J=8.8 Hz, 1H), 8.68 (s, 2H), 7.47-7.44 (m, 2H), 7.16 (t, J=8.8 Hz, 2H), 5.36-5.30 (m, 1H), 3.54 (d, J=7.6 Hz, 2H), 3.31-3.26 (m, 1H), 3.20-3.14 (m, 1H), 2.12 (t, J=8.0 Hz, 2H), 1.82-1.74 (m, 2H); LC-MS: m/z 326.10 $[M+H]^+$.

1-(2-((5-(1H-tetrazol-5-yl)pyrimidin-2-yl)amino)-2-(4-fluorophenyl)ethyl)pyrrolidin-2-one (OT)

To a stirred solution of compound OS (1.5 g, 4.60 mmol) in DMF (15 mL), $NaN_3$ (1.5 g, 23.0 mmol), $NH_4Cl$ (1.2 g, 23.0 mmol) and LiCl (0.3 g) were added and the reaction mixture was stirred at 100° C. for 16 h. The progress of the reaction was monitored by TLC. After completion of reaction, the reaction mixture was concentrated under reduced pressure. The residue was quenched with ice cold water and acidified with 1N HCl solution to pH 3-4. The precipitated solid was filtered, washed with cold water and dried under reduced pressure to afford compound OT (1.5 g, 88.0%) as an off white solid which was used as such for the next reaction. LC-MS: m/z 369.10 $[M+H]^+$.

1-(2-((5-(5-(difluoromethyl)-1,3,4-oxadiazol-2-yl) pyrimidin-2-yl)amino)-2-(4-fluorophenyl)ethyl)pyrrolidin-2-one (171)

To a stirred solution of compound OT (1.0 g, 2.70 mmol) in DCM (15 mL), DFAA (0.95 mL, 5.40 mmol) was added and the reaction was stirred at RT for 16 h. The progress of the reaction was monitored by TLC. After completion of reaction, the reaction mixture was diluted with DCM and washed with water. The combined organic layer was dried over anhydrous $Na_2SO_4$ and concentrated under reduced pressure. The crude compound was purified by silica gel column chromatography (40% EtOAc/hexane) to afford 177 (0.70 g, 61.5%) as an off-white solid.

Chiral Preparative HPLC Details for 176(+) and 176(−)

The enantiomers were separated by chiral preparative HPLC (Shimadzu Preparative LC, 250×30 mm, 5; Mobile Phase: A—n-Hexane; B—0.1% $NH_3$ in EtOH:MeOH (20:80); Isocratic Elution 50% B; Flow rate: 30.0 mL/min) to obtain 177(+) (80 mg) and 177(−) (80 mg).

177(+): $^1$H NMR (400 MHz, DMSO-d6): δ 8.86 (d, J=10.0 Hz, 2H), 8.77 (d, J=8.8 Hz, 1H), 7.65-7.39 (m, 3H), 7.17 (t, J=8.8 Hz, 2H), 5.42-5.37 (m, 1H), 3.56 (d, J=7.6 Hz, 2H), 3.33-3.29 (m, 1H), 3.23-3.17 (m, 1H), 2.12 (t, J=8.0 Hz, 2H), 1.82-1.75 (m, 2H); LC-MS: m/z 419.20 $[M+H]^+$; HPLC: 95.56%; C-HPLC: 99.04% (RT: 7.40); SOR: +83.75, Solvent: Methanol, Path length: 100 mm, Concentration: 0.255 w/v %.

177(−): $^1$H NMR (400 MHz, DMSO-d6): δ 8.86 (d, J=11.2 Hz, 2H), 8.77 (d, J=8.8 Hz, 1H), 7.65-7.39 (m, 3H), 7.17 (t, J=8.8 Hz, 2H), 5.42-5.37 (m, 1H), 3.56 (d, J=7.2 Hz, 2H), 3.33-3.29 (m, 1H), 3.23-3.17 (m, 1H), 2.12 (t, J=8.4 Hz, 2H), 1.82-1.75 (m, 2H); LC-MS: m/z 419.15 $[M+H]^+$; HPLC: 94.35%; C-HPLC: 98.31% (RT: 9.55); SOR: −94.58, Solvent: Methanol, Path length: 100 mm, Concentration: 0.275 w/v %.

Examples 79-102, 104-107, and 114

Examples 79-102, 104-107, and 114 were prepared in a manner analogous to the synthetic processes (and respective appropriate reagents and intermediates) used for the preparation of other compounds exemplified herein.

Example 185: Analytical Methods

HPLC Method A Specifications
Column: X-Select CSH C18 (4.6×150 mm, 3.5 m)
Mobile Phase A-Acetonitrile; Mobile Phase B—5% Acetonitrile+0.1% Formic acid+water
Injection Volume: 5.0 μL; Flow Rate: 1.0 mL/minute Gradient program: 95% B for 1 min, 95% B to 0% B in 8 minute, hold till 12 min, at 15.0 min B concentration is 95% up to 18 min.

HPLC Method B Specifications
  Column: X-Bridge C18 (4.6×150 mm, 3.5 m)
  Mobile Phase A—Acetonitrile; Mobile Phase B—0.1% Ammonia in water
  Injection Volume: 5.0 μL; Flow Rate: 1.2 mL/minute
  Gradient program: 98% B to 15% B in 6 min, hold till 8 min, at 9 min B concentration is 0% hold up to 12 min, at 14 min B concentration is 98% hold up to 18 min.

SFC Method C Specifications
  Column: Chiralpak IA (4.6×250 mm, 5.0 m)
  Mobile Phase A—Supercritical $CO_2$; Mobile Phase B—0.1% Ammonia in methanol
  Flow Rate: 3.0 mL/minute
  Isocratic program: 15% B for 10 min.

HPLC Method D Specifications
  Column: YMC CIRALART CELLULOSE_SC (4.6×250 mm, 5.0 m)
  Mobile Phase A—0.1% TFA in MTBE; Mobile Phase B Isopropyl alcohol
  Flow Rate: 1.0 mL/minute
  Isocratic program: 10% B for 20 min.

HPLC Method E Specifications
  Column: YMC CHIRAL AMYLOSE-SA, 250 mm*4.6 mm, 5 u
  Mobile Phase:
  A: n-HEXANE+0.1% DEA
  B: DCM:MeOH(50:50)
  Flow rate: 1.0 mL/min
  Isocratic: 30% B SFC Method F Specifications
  Column: Chiralpak IA, 250 mm*4.6 mm, 5 u
  Mobile Phase:
  A: $CO_2$
  B: 0.1% NH3+Methanol
  Flow rate: 3.0 mL/min
  Isocratic: 20% B HPLC Method G Specifications
  Column: Chiralpak-IG (4.6×250 mm, 5 m)
  Mobile Phase A—n-Hexane+0.1% TFA; Mobile Phase B—Isopropyl alcohol
  Injection Volume: 10.0 μL; Flow Rate: 1.0 mL/minute
  Isocratic: 15% B HPLC Method H Specifications
  Column: Chiralpak-IA (4.6×250 mm, 5 m)
  Mobile Phase A—n-Hexane+0.1% DEA; Mobile Phase B—Ethanol
  Flow Rate: 1.0 mL/minute
  Isocratic: 25% B SFC Method I Specifications
  Column: Chiralpak IG, 250 mm*4.6 mm, 5 u
  Mobile Phase:
  A: $CO_2$
  B: 0.1% NH3+Methanol
  Flow rate: 3.0 mL/min
  Isocratic: 50% B SFC Method J Specifications
  Column: Chiralpak IA, 250 mm*4.6 mm, 5 u
  Mobile Phase:
  A: $CO_2$
  B: 0.1% NH3+Methanol
  Flow rate: 3.0 mL/min
  Gradient: 10-40% over 5 min, 40% B for 4 min, 40-10% B over 1 min, hold 10% B for 2 min SFC Method K Specifications
  Column: Chiralpak IG, 250 mm*4.6 mm, 5 u
  Mobile Phase:
  A: $CO_2$
  B: 0.1% NH3+Methanol
  Flow rate: 3.0 mL/min
  Gradient: 10-40% over 5 min, 40% B for 4 min, 40-10% B over 1 min, hold 10% B for 2 min HPLC Method L Specifications
  Column: YMC CHIRAL AMYLOSE-SA, 250 mm*4.6 mm, 5 u
  Mobile Phase:
  A: n-HEXANE+0.1% DEA
  B: DCM:MeOH(50:50)
  Flow rate: 1.0 mL/min
  Isocratic: 40% B Example 186: Metalloenzyme Activity All enzymatic reactions were conducted in duplicate at room temperature for 17 hours in a 50 μl mixture containing HDAC assay buffer (50 mM Tris-HCl, pH 7.4, 137 mM NaCl, 2.7 mM KCl, 0.05% Tween 20, 5 μg BSA), an HDAC substrate, an HDAC enzyme, and a test compound. Compound dilution was prepared ten-fold higher than the final concentration of the compounds with 10% DMSO in HDAC assay buffer and 5 μl of the dilution was added to a 50 μl reaction so that the final concentration of DMSO is 1% in all of reactions. After enzymatic reactions, 50 μl of HDAC Developer was added to each well and the plate was incubated at room temperature for an additional 20 minutes. Fluorescence intensity was measured at an excitation of 360 nm and an emission of 460 nm using a Tecan Infinite M1000 or Biotek Synergy microplate reader. The fluorescent intensity data were analyzed using the computer software, Graphpad Prism. In the absence of the compound, the fluorescent intensity (Ft) in each data set was defined as 100% activity. In the absence of HDAC, the fluorescent intensity (Fb) in each data set was defined as 0% activity. The percent activity in the presence of each compound was calculated according to the following equation: % activity=(F−Fb)/(Ft−Fb), where F=the fluorescent intensity in the presence of the compound.

The values of % activity versus a series of compound concentrations were then plotted using non-linear regression analysis of Sigmoidal dose-response curve generated with the equation Y=B+(T−B)/1+10((Log EC50−X)×Hill Slope), where Y=percent activity, B=minimum percent activity, T=maximum percent activity, X=logarithm of compound and Hill Slope=slope factor or Hill coefficient. The $IC_{50}$ value was determined by the concentration causing a half-maximal percent activity.

HDAC1 enzymatic assays contained 0.5 ng HDAC1 and 10 uM of HDAC substrate. HDAC2 enzymatic assays contained 0.5 ng HDAC2 and 10 uM of HDAC substrate. HDAC3 enzymatic assays contained 0.4 ng HDAC3/NCOR2 and 10 uM of HDAC substrate. HDAC4 enzymatic assays contained 0.02 ng HDAC4 and 2 uM of HDAC substrate. HDAC5 enzymatic assays contained 0.5 ng HDAC5 and 2 uM of HDAC substrate. HDAC6 enzymatic assays contained 2 ng HDAC6 and 10 uM of HDAC substrate. HDAC7 enzymatic assays contained 0.05 ng HDAC7 and 2 uM of HDAC substrate. HDAC8 enzymatic assays contained 5 ng HDAC8 and 2 uM of HDAC substrate. HDAC9 enzymatic assays contained Ing HDAC9 and 2 uM of HDAC substrate. HDAC10 enzymatic assays contained 75 ng HDAC10 and 10 uM of HDAC substrate. HDAC11 enzymatic assays contained 5 ng HDAC11 and 2 uM of HDAC substrate.

Example 187: Mouse Pharmacokinetics

A dose of 5 mg/kg in an appropriate formulation was administered by oral gavage to fasted male Swiss Albino mice (n=3), and the plasma was collected at 0, 0.25, 0.5, 1, 2, 4, 8, and 24 h. Plasma levels were measured by HPLC/MS/MS methods and the pharmacokinetic parameters were determined for individual animals from plasma concentration-time data using noncompartmental model 200-202 in Phoenix WinNonlin 6.3.

TABLE 1

HDAC6 and HDAC1 activity

| Ex. # | Human HDAC6 IC50 (μM) | Human HDAC1 IC50 (μM) | HPLC Retention Time (Min)$^a$ | LC-MS (M + H) | Structure |
|---|---|---|---|---|---|
| 1 | 0.21 | >30 | 9.12 | 348.05 | 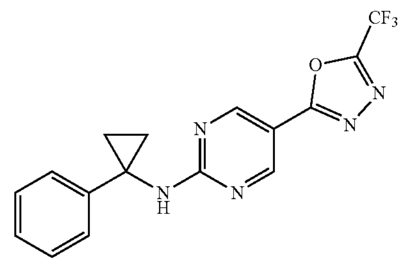 [SMILES: FC(F)(F)c1nnc(-c2cnc(NC3(c4ccccc4)CC3)nc2)o1] |
| 2 | 0.39 | >30 | 9.29 | 336.05 | 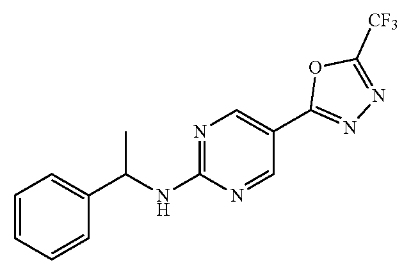 [SMILES: CC(Nc1ncc(-c2nnc(C(F)(F)F)o2)cn1)c1ccccc1] |
| 3 | 0.23 | >30 | 5.53 | 337.05 | 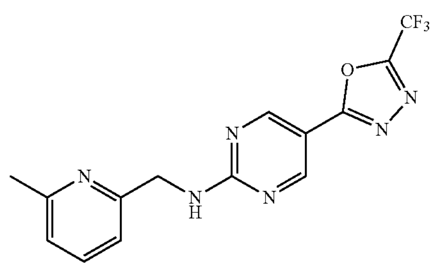 [SMILES: Cc1cccc(CNc2ncc(-c3nnc(C(F)(F)F)o3)cn2)n1] |
| 4 | 0.023 | >30 | 8.19 | 330.1 | 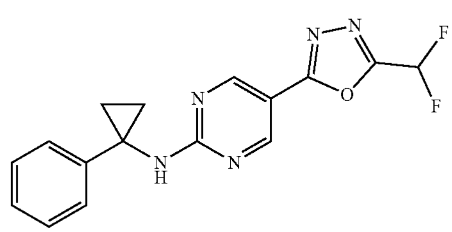 [SMILES: FC(F)c1nnc(-c2cnc(NC3(c4ccccc4)CC3)nc2)o1] |
| 5 | 0.034 | >100 | 8.72 | 348.1 | 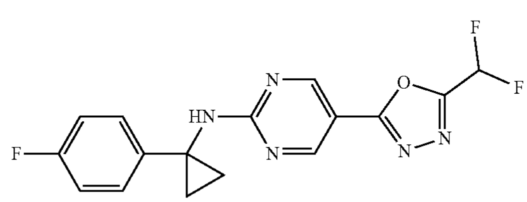 [SMILES: Fc1ccc(C2(Nc3ncc(-c4nnc(C(F)F)o4)cn3)CC2)cc1] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 6 | 0.057 | >30 | 8.37 | 317.95 | 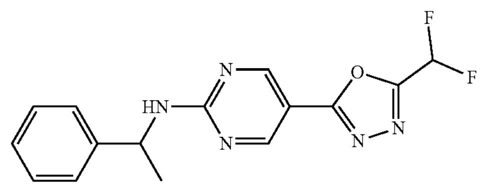 [SMILES: CC(Nc1ncc(-c2nnc(C(F)F)o2)cn1)c1ccccc1] |
| 7 | 1.7 | >30 | 9.09 | 380.1 | 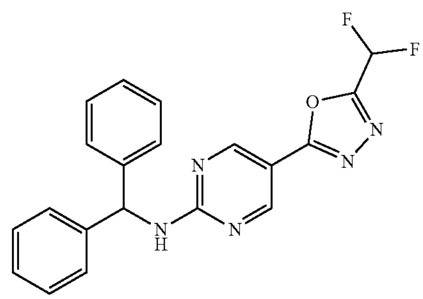 [SMILES: FC(F)c1nnc(-c2cnc(NC(c3ccccc3)c3ccccc3)nc2)o1] |
| 8 | 9 | >30 | 9.19 | 362 | 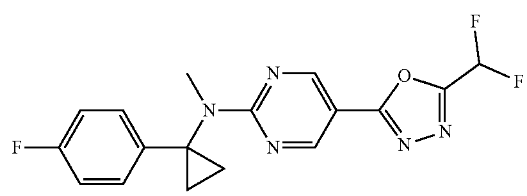 [SMILES: CN(c1ncc(-c2nnc(C(F)F)o2)cn1)C1(c2ccc(F)cc2)CC1] |
| 9 | 0.038 | >30 | 8.81 | 350 | 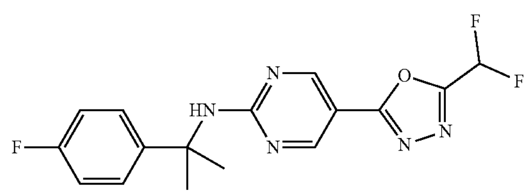 [SMILES: CC(C)(Nc1ncc(-c2nnc(C(F)F)o2)cn1)c1ccc(F)cc1] |
| 10 | 0.009 | >100 | 8.78 | 366.03 | 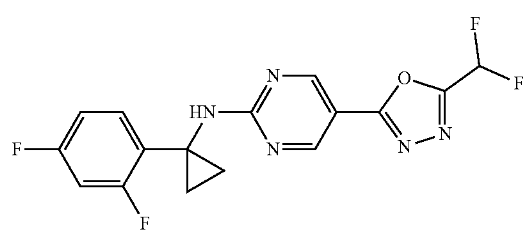 [SMILES: Fc1ccc(C2(Nc3ncc(-c4nnc(C(F)F)o4)cn3)CC2)c(F)c1] |
| 11 | 0.006 | >100 | 8.59 | 366 | 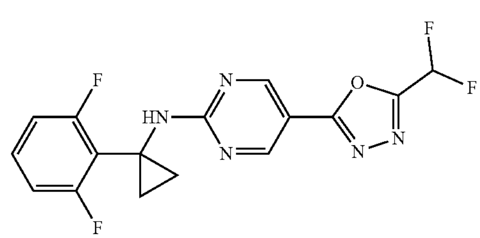 [SMILES: Fc1cccc(F)c1C1(Nc2ncc(-c3nnc(C(F)F)o3)cn2)CC1] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 12 | 0.21 | >30 | 9.22 | 331.08 | 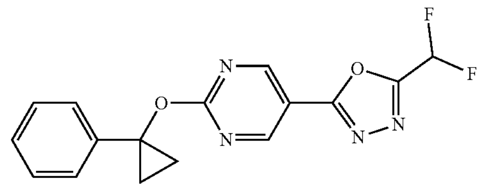 [SMILES: FC(F)c1nnc(-c2cnc(OC3(c4ccccc4)CC3)nc2)o1] |
| 13 | 0.036 | >30 | 8.88 | 403.97 | 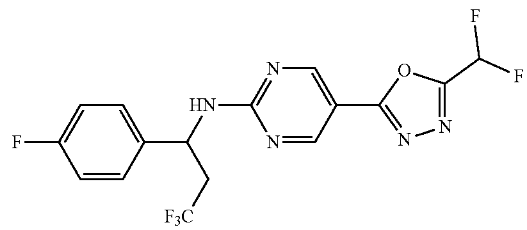 |
| 13(+) | 0.03 | >30 | 3.74[c] | 404.3 | |
| 13(−) | 0.55 | >30 | 4.72[c] | 404.3 | |
| 14 | >30 | >30 | 9.83 | 424.07 | 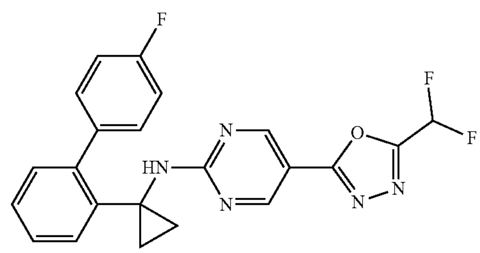 [SMILES: Fc1ccc(-c2ccccc2C2(Nc3ncc(-c4nnc(C(F)F)o4)cn3)CC2)cc1] |
| 15 | 0.074 | >30 | 8.75 | 390 | 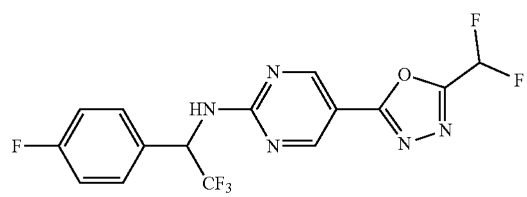 [SMILES: Fc1ccc(C(Nc2ncc(-c3nnc(C(F)F)o3)cn2)C(F)(F)F)cc1] |
| 16 | 0.095 | >30 | 9.21 | 424.05 | 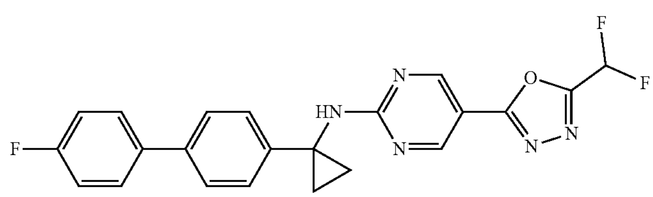 [SMILES: Fc1ccc(-c2ccc(C3(Nc4ncc(-c5nnc(C(F)F)o5)cn4)CC3)cc2)cc1] |
| 17 | 0.16 | >30 | 9.04 | 467.14 | 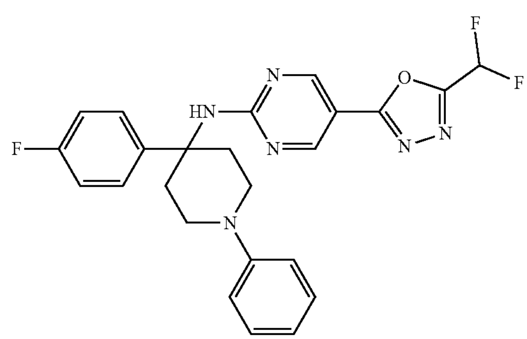 [SMILES: Fc1ccc(C2(Nc3ncc(-c4nnc(C(F)F)o4)cn3)CCN(c3ccccc3)CC2)cc1] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 18 | 0.058 | >30 | 9.19 | 424.07 | 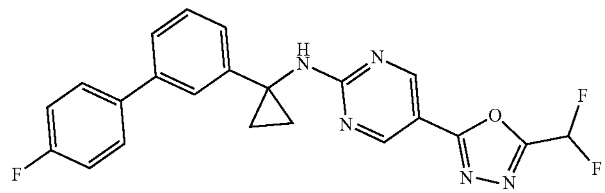 [SMILES: Fc1ccc(-c2cccc(C3(Nc4ncc(-c5nnc(C(F)F)o5)cn4)CC3)c2)cc1] |
| 19 | 0.047 | >30 | 9.26 | 428.07 | 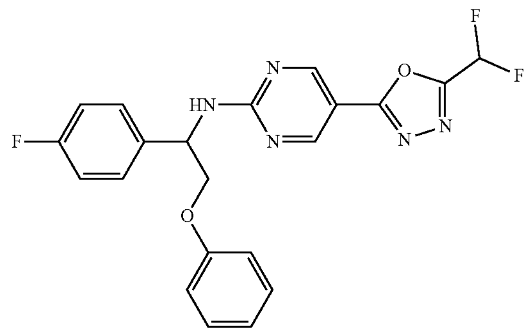 [SMILES: Fc1ccc(C(COc2ccccc2)Nc2ncc(-c3nnc(C(F)F)o3)cn2)cc1] |
| 20 | 0.033 | >30 | 8.44 | 336 | 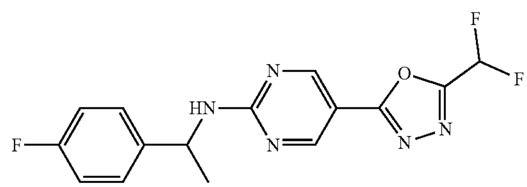 [SMILES: CC(Nc1ncc(-c2nnc(C(F)F)o2)cn1)c1ccc(F)cc1] |
| 20(+) | 0.021 | >30 | 3.52[c] | 336.3 | |
| 20(−) | >1 | >30 | 7.17[c] | 336.25 | |
| 21 | 0.077 | >30 | 8.23 | 366.1 | 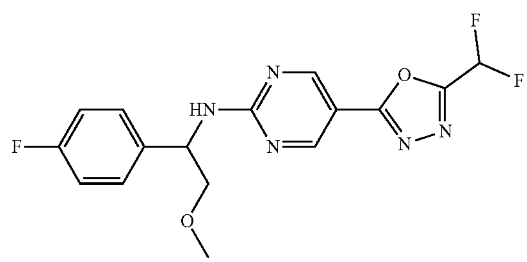 [SMILES: COCC(Nc1ncc(-c2nnc(C(F)F)o2)cn1)c1ccc(F)cc1] |
| 22 | 0.071 | >30 | 8.83 | 350.06 | 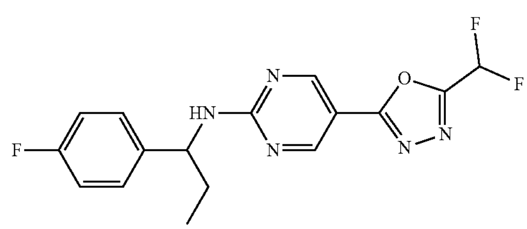 [SMILES: CCC(Nc1ncc(-c2nnc(C(F)F)o2)cn1)c1ccc(F)cc1] |
| 23 | 0.1 | >30 | 9.23 | 364.17 | 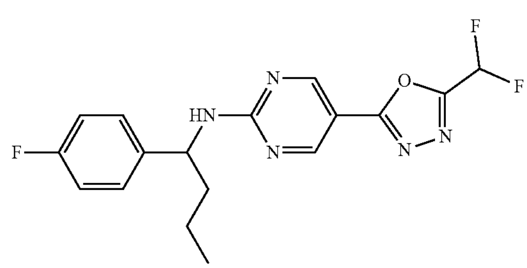 [SMILES: CCCC(Nc1ncc(-c2nnc(C(F)F)o2)cn1)c1ccc(F)cc1] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 24 | 0.095 | >30 | 9.11 | 364 | 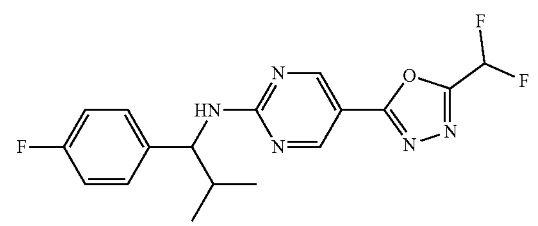 [SMILES: CC(C)C(Nc1ncc(-c2nnc(C(F)F)o2)cn1)c1ccc(F)cc1] |
| 25 | >1 | >30 | 7.19 | 356.05 | 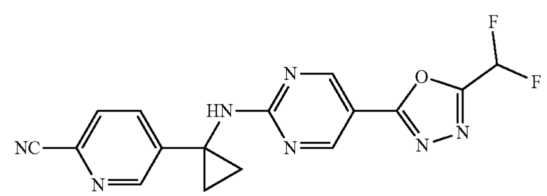 [SMILES: N#Cc1ccc(C2(Nc3ncc(-c4nnc(C(F)F)o4)cn3)CC2)cn1] |
| 26 | 0.14 | >30 | 7.45 | 431 (M − H) | 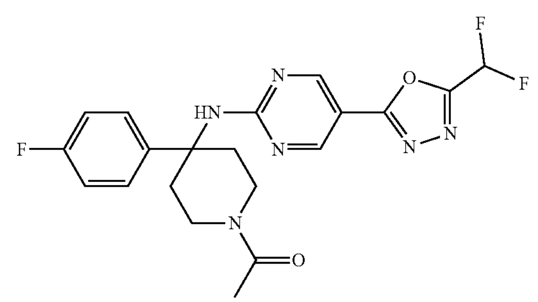 [SMILES: CC(=O)N1CCC(Nc2ncc(-c3nnc(C(F)F)o3)cn2)(c2ccc(F)cc2)CC1] |
| 27 | 0.074 | >30 | 9.32 | 336.14 | 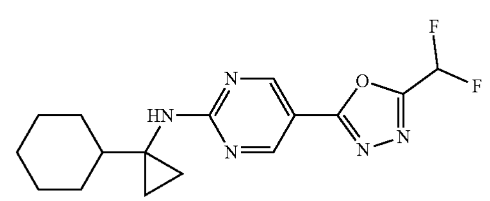 [SMILES: FC(F)c1nnc(-c2cnc(NC3(C4CCCCC4)CC3)nc2)o1] |
| 28 | 0.61 | >30 | 8.3 | 296 | 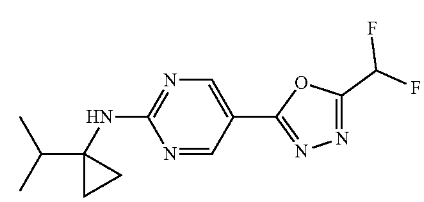 [SMILES: CC(C)C1(Nc2ncc(-c3nnc(C(F)F)o3)cn2)CC1] |
| 29 | 0.45 | >30 | 8.8 | 347.95 | 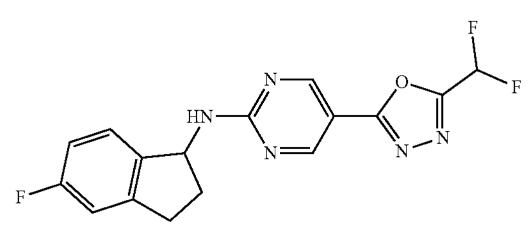 [SMILES: Fc1ccc2c(c1)CCC2Nc1ncc(-c2nnc(C(F)F)o2)cn1] |

TABLE 1-continued

HDAC6 and HDAC1 activity

| Ex. # | Human HDAC6 IC50 (μM) | Human HDAC1 IC50 (μM) | HPLC Retention Time (Min)$^a$ | LC-MS (M + H) | Structure |
|---|---|---|---|---|---|
| 30 | 0.77 | >30 | 7.52 | 435.05 | 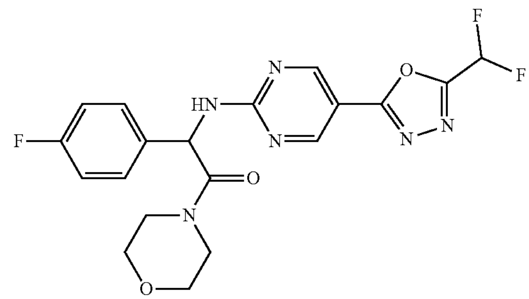 [SMILES: O=C(C(Nc1ncc(-c2nnc(C(F)F)o2)cn1)c1ccc(F)cc1)N1CCOCC1] |
| 31 | 0.12 | >30 | 7.55 | 337 | 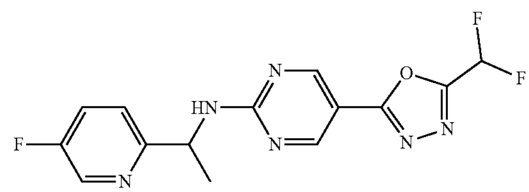 [SMILES: CC(Nc1ncc(-c2nnc(C(F)F)o2)cn1)c1ccc(F)cn1] |
| 32 | 0.059 | >30 | 8.46 | 395.95 | 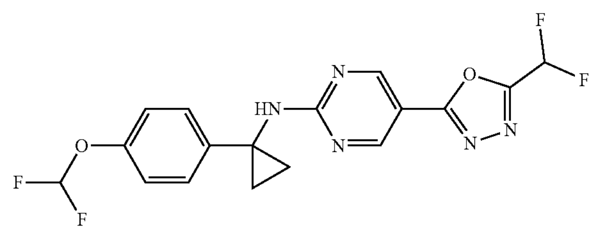 [SMILES: FC(F)Oc1ccc(C2(Nc3ncc(-c4nnc(C(F)F)o4)cn3)CC2)cc1] |
| 33 | 0.029 | >30 | 8.69 | 413.95 | 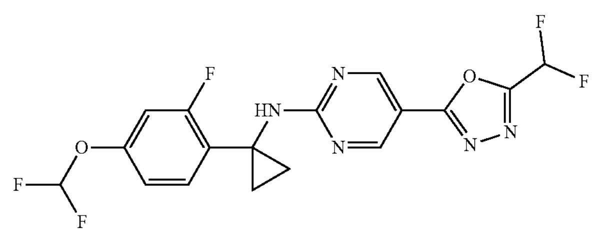 [SMILES: Fc1cc(OC(F)F)ccc1C1(Nc2ncc(-c3nnc(C(F)F)o3)cn2)CC1] |
| 34 | 0.79 | >30 | 9.15 | 362 | 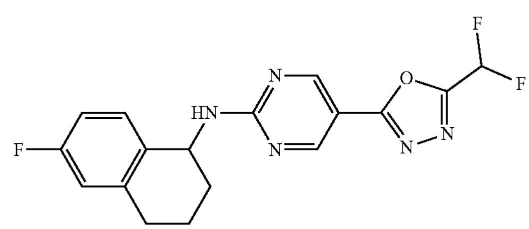 [SMILES: Fc1ccc2c(c1)CCCC2Nc1ncc(-c2nnc(C(F)F)o2)cn1] |
| 35 | 0.17 | >30 | 8.42 | 441.11 | 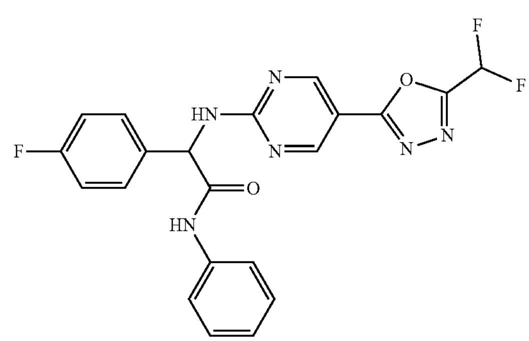 [SMILES: O=C(Nc1ccccc1)C(Nc1ncc(-c2nnc(C(F)F)o2)cn1)c1ccc(F)cc1] |

TABLE 1-continued

HDAC6 and HDAC1 activity

| Ex. # | Human HDAC6 IC50 (μM) | Human HDAC1 IC50 (μM) | HPLC Retention Time (Min)ᵃ | LC-MS (M + H) | Structure |
|---|---|---|---|---|---|
| 36 | 0.064 | >30 | 8.74 | 362.1 | 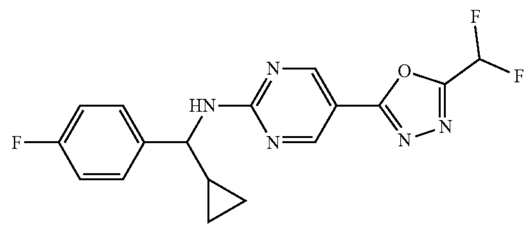 [SMILES: Fc1ccc(C(Nc2ncc(-c3nnc(C(F)F)o3)cn2)C2CC2)cc1] |
| 37 | 0.18 | >30 | 9.12 | 426.1 | 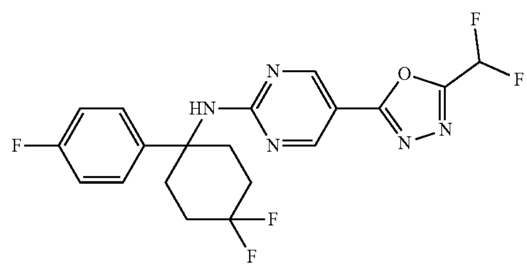 [SMILES: Fc1ccc(C2(Nc3ncc(-c4nnc(C(F)F)o4)cn3)CCC(F)(F)CC2)cc1] |
| 38 | 0.029 | >30 | 7.49 | 429.05 | 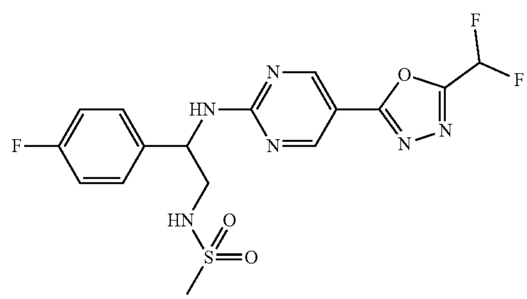 [SMILES: CS(=O)(=O)NCC(Nc1ncc(-c2nnc(C(F)F)o2)cn1)c1ccc(F)cc1] |
| 38(+) | 0.015 | >30 | 9.18ᶜ | 429.3 | |
| 38(−) | 0.32 | >30 | 6.86ᶜ | 429.1 | |
| 39 | 0.05 | >30 | 8.31 | 491.05 | 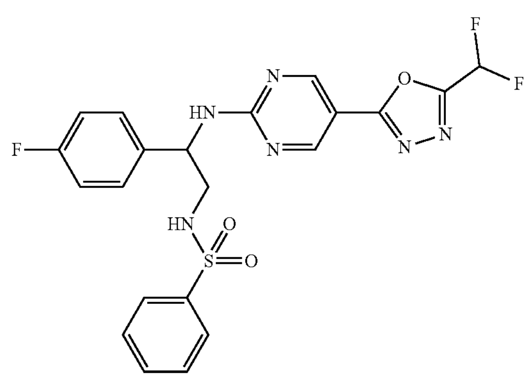 [SMILES: O=S(=O)(NCC(Nc1ncc(-c2nnc(C(F)F)o2)cn1)c1ccc(F)cc1)c1ccccc1] |
| 40 | 0.22 | >30 | 9.6 | 378.05 | 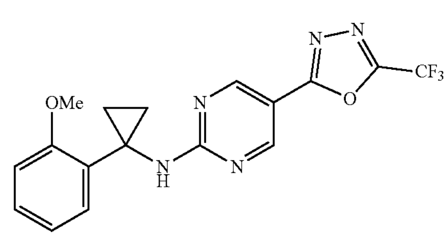 [SMILES: COc1ccccc1C1(Nc2ncc(-c3nnc(C(F)(F)F)o3)cn2)CC1] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 41 | 0.25 | >30 | 9.3 | 378.1 | 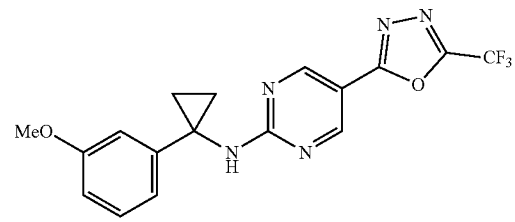 [SMILES: COc1cccc(C2(Nc3ncc(-c4nnc(C(F)(F)F)o4)cn3)CC2)c1] |
| 42 | 0.25 | >30 | 9.03 | 378.05 | 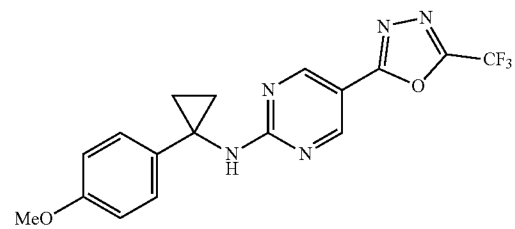 [SMILES: COc1ccc(C2(Nc3ncc(-c4nnc(C(F)(F)F)o4)cn3)CC2)cc1] |
| 43 | 0.039 | >30 | 8.19 | 359.95 | 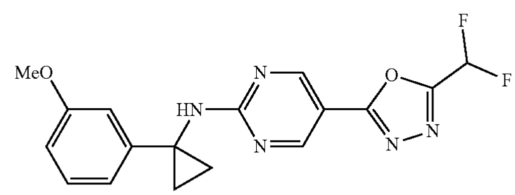 [SMILES: COc1cccc(C2(Nc3ncc(-c4nnc(C(F)F)o4)cn3)CC2)c1] |
| 44 | 0.044 | >30 | 8.54 | 360.15 | 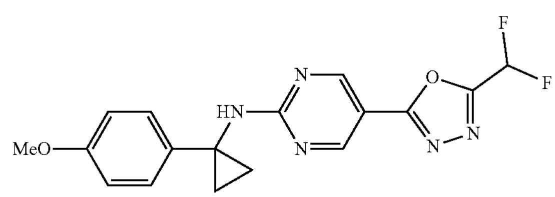 [SMILES: COc1ccc(C2(Nc3ncc(-c4nnc(C(F)F)o4)cn3)CC2)cc1] |
| 45 | 0.064 | >30 | 9.2 | 398.15 | 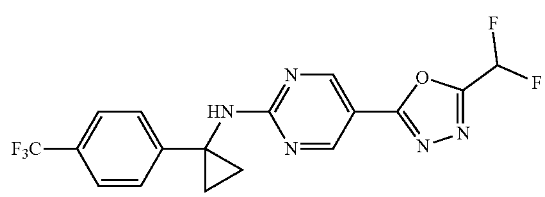 [SMILES: FC(F)c1nnc(-c2cnc(NC3(c4ccc(C(F)(F)F)cc4)CC3)nc2)o1] |
| 46 | 0.023 | >30 | 8.66 | 360 | 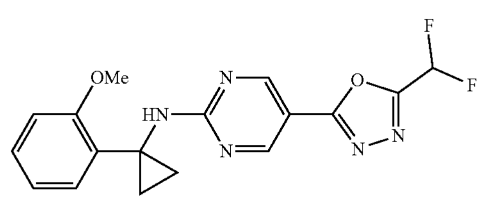 |
| 47 | 0.027 | >30 | 9.43 | 410.05 | 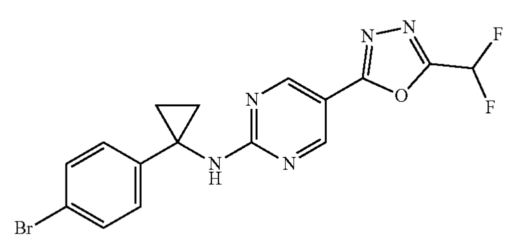 [SMILES: FC(F)c1nnc(-c2cnc(NC3(c4ccc(Br)cc4)CC3)nc2)o1] |

TABLE 1-continued

HDAC6 and HDAC1 activity

| Ex. # | Human HDAC6 IC50 (μM) | Human HDAC1 IC50 (μM) | HPLC Retention Time (Min)^a | LC-MS (M + H) | Structure |
|---|---|---|---|---|---|
| 48 | 0.046 | >30 | 8.01 | 355.1 | 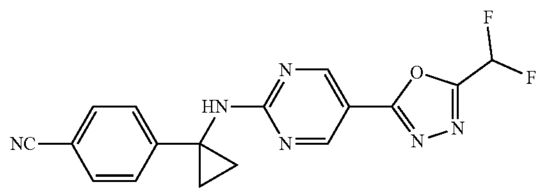 |
| 49 | 0.016 | >30 | 9.36 | 398.05 | 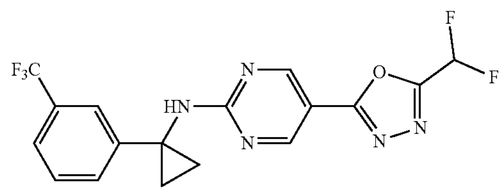 [SMILES: FC(F)c1nnc(-c2cnc(NC3(c4cccc(C(F)(F)F)c4)CC3)nc2)o1] |
| 50 | 0.03 | >30 | 9.07 | 363.9 | 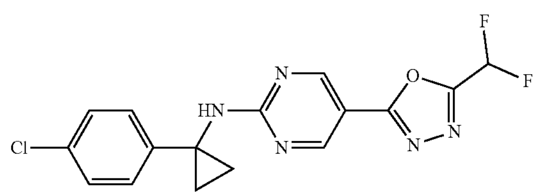 |
| 51 | 0.015 | >30 | 9.03 | 363.9 | 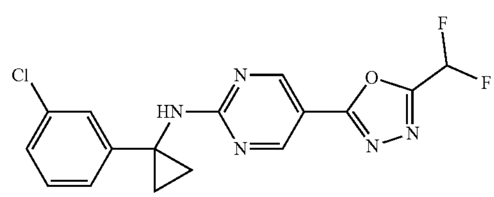 [SMILES: FC(F)c1nnc(-c2cnc(NC3(c4cccc(Cl)c4)CC3)nc2)o1] |
| 52 | 0.006 | >30 | 9.46 | 363.95 | 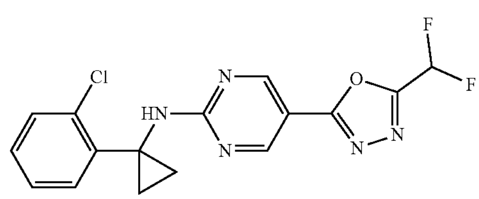 |
| 53 | 0.023 | >30 | 8.94 | 414 | 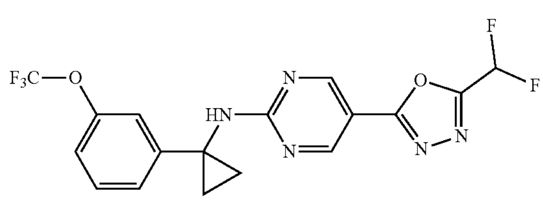 [SMILES: FC(F)c1nnc(-c2cnc(NC3(c4cccc(OC(F)(F)F)c4)CC3)nc2)o1] |
| 54 | 0.022 | >30 | 9.1 | 413.9 | 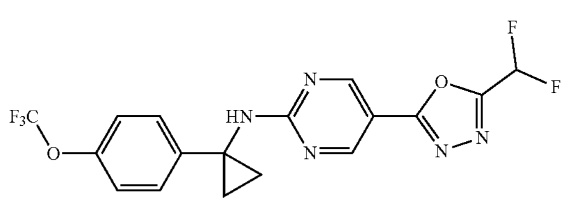 [SMILES: FC(F)c1nnc(-c2cnc(NC3(c4ccc(OC(F)(F)F)cc4)CC3)nc2)o1] |

TABLE 1-continued
HDAC6 and HDAC1 activity
| Ex. # | Human HDAC6 IC50 (μM) | Human HDAC1 IC50 (μM) | HPLC Retention Time (Min)<i>a</i> | LC-MS (M + H) | Structure |
|---|---|---|---|---|---|
| 55 | 0.02 | >30 | 9.22 | 413.9 | 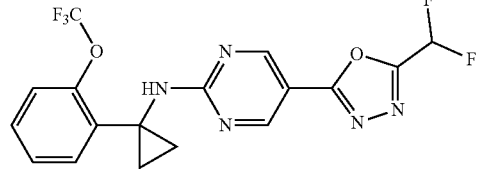 |
| 56 | 0.006 | >100 | 8.5 | 347.99 | 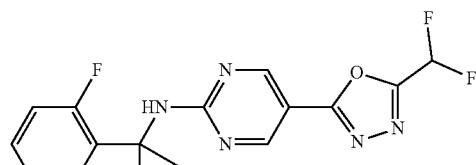 |
| 57 | 0.015 | >100 | 6.86 | 347.99 | 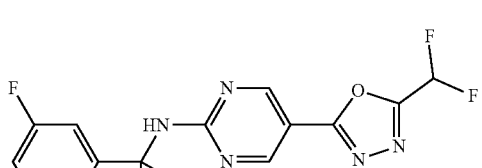 |
| 58 | 0.04 | >30 | 9.29 | 398 | 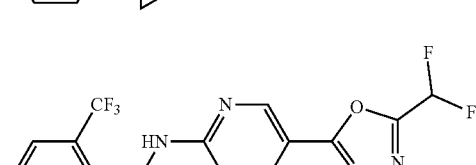 |
| 59 | 0.021 | >30 | 8.39 | 366 | 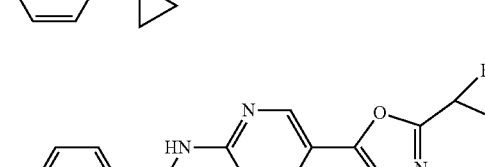 |
| 60 | 0.022 | >30 | 8.61 | 365.95 | 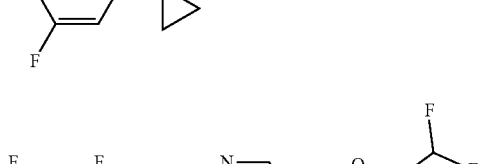 |
| 61 | 0.022 | >30 | 8.6 | 366 | 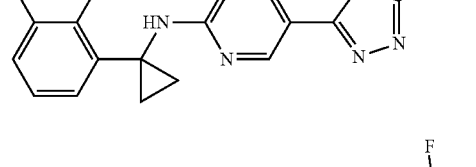 |

TABLE 1-continued

HDAC6 and HDAC1 activity

| Ex. # | Human HDAC6 IC50 (μM) | Human HDAC1 IC50 (μM) | HPLC Retention Time (Min)$^a$ | LC-MS (M + H) | Structure |
|---|---|---|---|---|---|
| 62 | 0.008 | >30 | 9.19 | 382.01 | 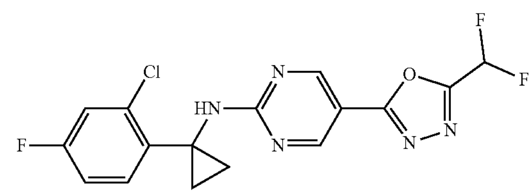 |
| 63 | 0.088 | >30 | 9.34 | 416.02 | 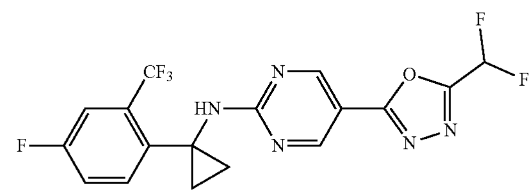 [SMILES: Fc1ccc(C2(Nc3ncc(-c4nnc(C(F)F)o4)cn3)CC2)c(Cl)c1] |
| 64 | 0.028 | >30 | 7.72 | 410.9 | 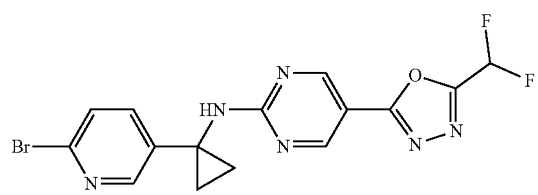 [SMILES: FC(F)c1nnc(-c2cnc(NC3(c4ccc(Br)nc4)CC3)nc2)o1] |
| 65 | 0.39 | >30 | 4.49 | 331 | 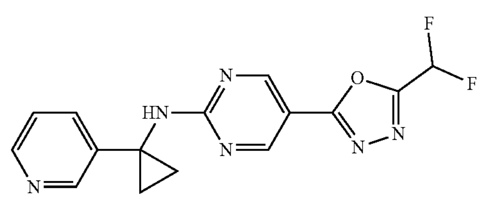 [SMILES: FC(F)c1nnc(-c2cnc(NC3(c4cccnc4)CC3)nc2)o1] |
| 66 | 0.042 | >30 | 9.11 | 382.01 | 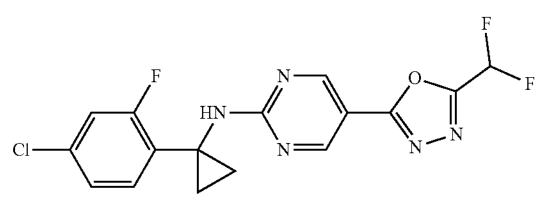 [SMILES: Fc1cc(Cl)ccc1C1(Nc2ncc(-c3nnc(C(F)F)o3)cn2)CC1] |
| 67 | 0.19 | >30 | 7.59 | 348.95 | 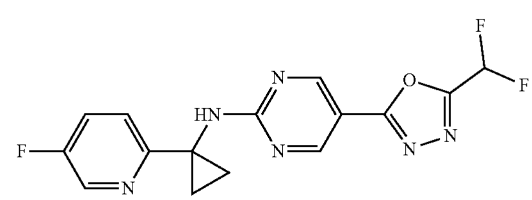 |
| 68 | 0.1 | >30 | 8.66 | 428.05 | 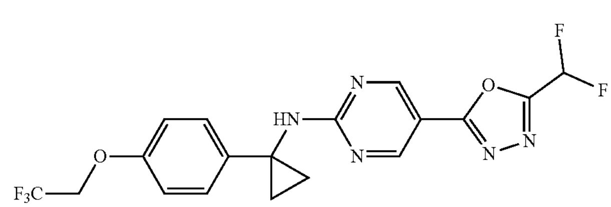 [SMILES: FC(F)c1nnc(-c2cnc(NC3(c4ccc(OCC(F)(F)F)cc4)CC3)nc2)o1] |

TABLE 1-continued

HDAC6 and HDAC1 activity

| Ex. # | Human HDAC6 IC50 (µM) | Human HDAC1 IC50 (µM) | HPLC Retention Time (Min)$^a$ | LC-MS (M + H) | Structure |
|---|---|---|---|---|---|
| 69 | 0.13 | >30 | 7.2 | 437.05 | 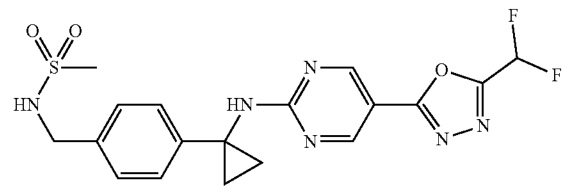 [SMILES: CS(=O)(=O)NCc1ccc(C2(Nc3ncc(-c4nnc(C(F)F)o4)cn3)CC2)cc1] |
| 70 | 0.1 | >30 | 9.26 | 431.95 | 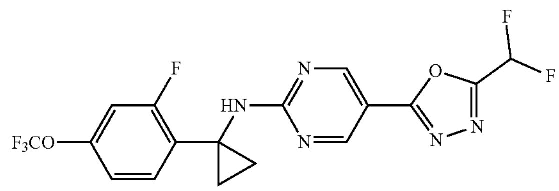 [SMILES: Fc1cc(OC(F)(F)F)ccc1C1(Nc2ncc(-c3nnc(C(F)F)o3)cn2)CC1] |
| 71 | 0.1 | >30 | 9.21 | 416.08 | 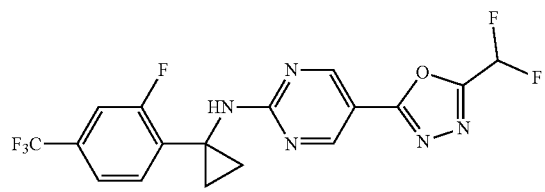 |
| 72 | 0.035 | >30 | 8.38 | 366 | 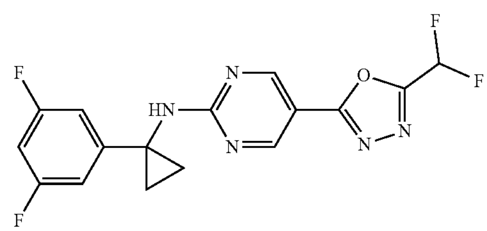 [SMILES: Fc1cc(F)cc(C2(Nc3ncc(-c4nnc(C(F)F)o4)cn3)CC2)c1] |
| 73 | 0.017 | >30 | 8.97 | 382 | 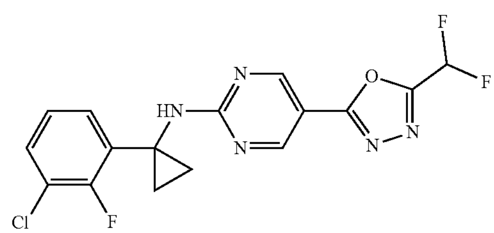 [SMILES: Fc1c(Cl)cccc1C1(Nc2ncc(-c3nnc(C(F)F)o3)cn2)CC1] |
| 74 | 0.019 | >30 | 8.73 | 384.07 | 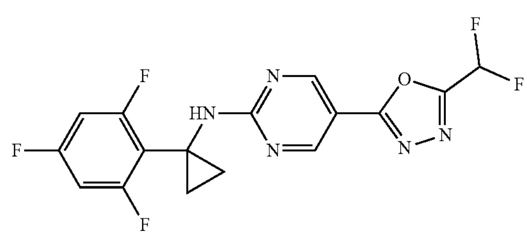 |
| 75 | 0.038 | >30 | 9.2 | 432.06 | 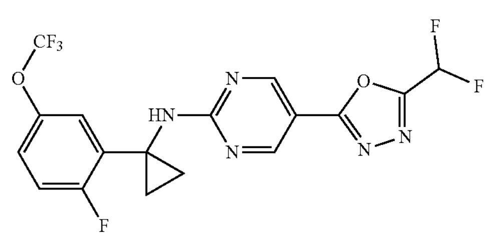 [SMILES: Fc1ccc(OC(F)(F)F)cc1C1(Nc2ncc(-c3nnc(C(F)F)o3)cn2)CC1] |

TABLE 1-continued

HDAC6 and HDAC1 activity

| Ex. # | Human HDAC6 IC50 (μM) | Human HDAC1 IC50 (μM) | HPLC Retention Time (Min)$^a$ | LC-MS (M + H) | Structure |
|---|---|---|---|---|---|
| 76 | 0.014 | >30 | 9.08 | 382.01 | 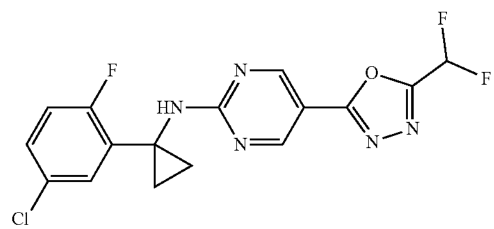 [SMILES: Fc1ccc(Cl)cc1C1(Nc2ncc(-c3nnc(C(F)F)o3)cn2)CC1] |
| 77 | 0.028 | >30 | 9.47 | 378 | 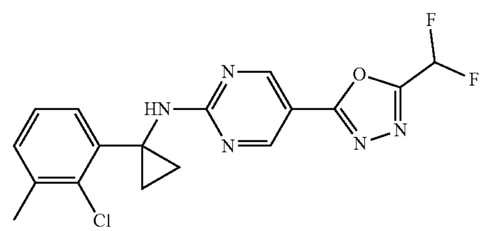 [SMILES: Cc1cccc(C2(Nc3ncc(-c4nnc(C(F)F)o4)cn3)CC2)c1Cl] |
| 78 | 0.047 | >30 | 9.35 | 393.1 | 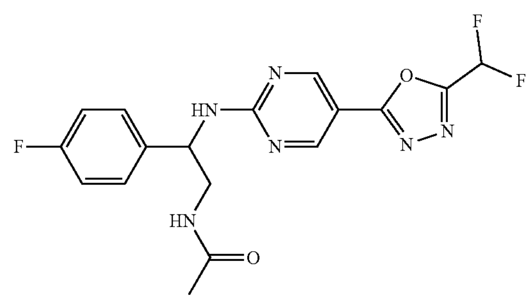 [SMILES: CC(=O)NCC(Nc1ncc(-c2nnc(C(F)F)o2)cn1)c1ccc(F)cc1] |
| 78(+) | 0.048 | >30 | 7.23 | 393.1 | |
| 78(−) | 0.42 | >30 | 7.24 | 393.1 | |
| 79 | 0.076 | >30 | 8.08 | 455.1 | 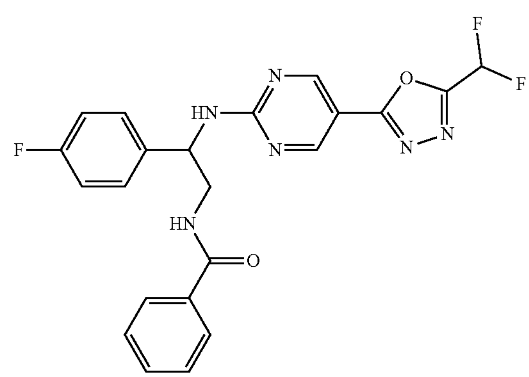 [SMILES: O=C(NCC(Nc1ncc(-c2nnc(C(F)F)o2)cn1)c1ccc(F)cc1)c1ccccc1] |
| 80 | 0.023 | >30 | 8.99 | 382.1 | 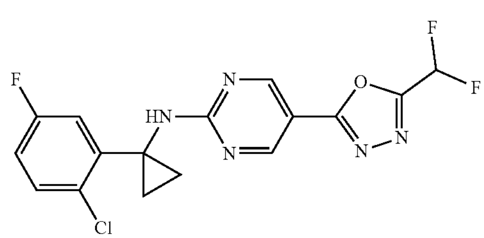 [SMILES: Fc1ccc(Cl)c(C2(Nc3ncc(-c4nnc(C(F)F)o4)cn3)CC2)c1] |

TABLE 1-continued

HDAC6 and HDAC1 activity

| Ex. # | Human HDAC6 IC50 (μM) | Human HDAC1 IC50 (μM) | HPLC Retention Time (Min)$^a$ | LC-MS (M + H) | Structure |
|---|---|---|---|---|---|
| 81 | 0.21 | >30 | 9.45 | 432.1 | 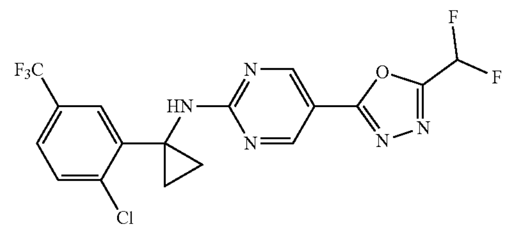 [SMILES: FC(F)c1nnc(-c2cnc(NC3(c4cc(C(F)(F)F)ccc4Cl)CC3)nc2)o1] |
| 82 | 0.035 | >30 | 7.47 | 409 | 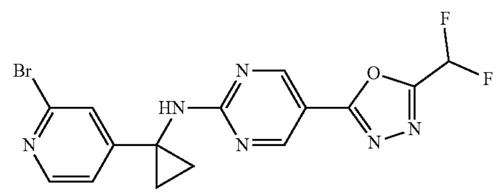 |
| 83 | 0.16 | >30 | 7.15 | 356.05 | 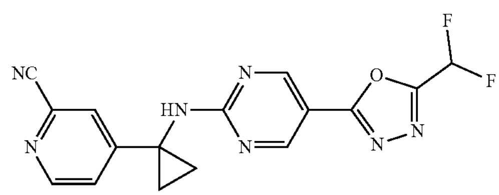 [SMILES: N#Cc1cc(C2(Nc3ncc(-c4nnc(C(F)F)o4)cn3)CC2)ccn1] |
| 84 | 0.077 | >30 | 9.25 | 446.15 | 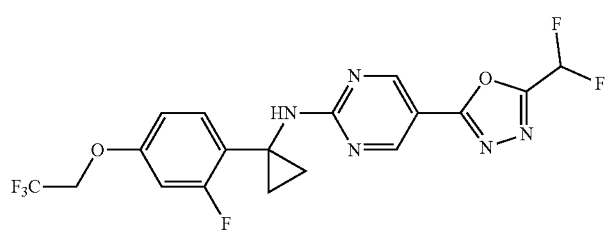 [SMILES: Fc1cc(OCC(F)(F)F)ccc1C1(Nc2ncc(-c3nnc(C(F)F)o3)cn2)CC1] |
| 85 | 0.062 | >30 | 9.41 | 432.05 | 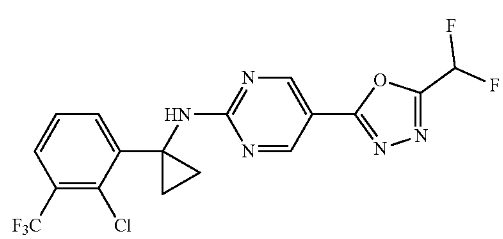 [SMILES: FC(F)c1nnc(-c2cnc(NC3(c4cccc(C(F)(F)F)c4Cl)CC3)nc2)o1] |
| 86 | 0.028 | >30 | 9.22 | 430.05 | 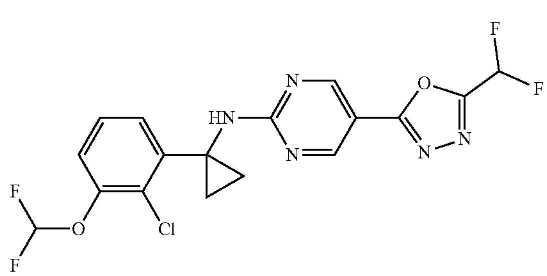 [SMILES: FC(F)Oc1cccc(C2(Nc3ncc(-c4nnc(C(F)F)o4)cn3)CC2)c1Cl] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 87 | 0.12 | >30 | 9.41 | 462.05 | 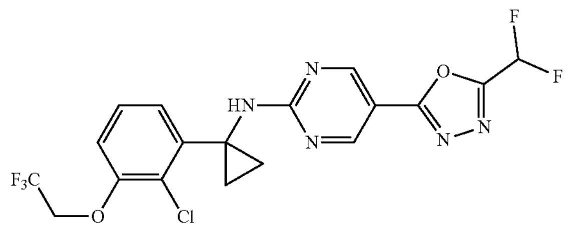 [SMILES: FC(F)c1nnc(-c2cnc(NC3(c4cccc(OCC(F)(F)F)c4Cl)CC3)nc2)o1] |
| 88 | 0.029 | >30 | 9 | 362.1 | 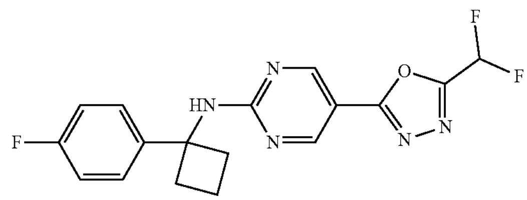 [SMILES: Fc1ccc(C2(Nc3ncc(-c4nnc(C(F)F)o4)cn3)CCC2)cc1] |
| 89 | 0.1 | >30 | 9.39 | 462 | 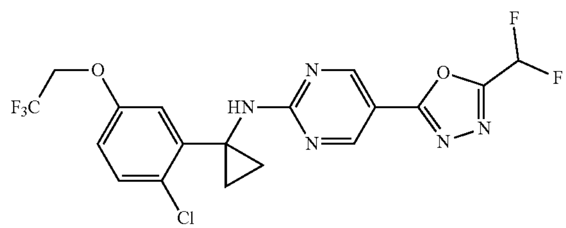 [SMILES: FC(F)c1nnc(-c2cnc(NC3(c4cc(OCC(F)(F)F)ccc4Cl)CC3)nc2)o1] |
| 90 | 0.035 | >30 | 9.45 | 378.1 | 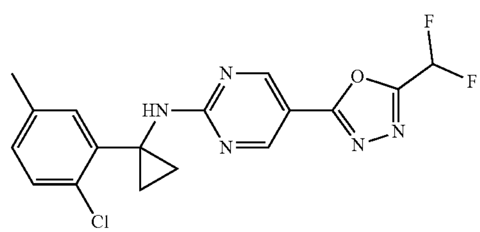 [SMILES: Cc1ccc(Cl)c(C2(Nc3ncc(-c4nnc(C(F)F)o4)cn3)CC2)c1] |
| 91 | 0.021 | >30 | 9.07 | 382.05 | 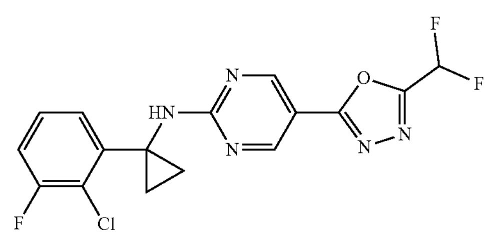 [SMILES: Fc1cccc(C2(Nc3ncc(-c4nnc(C(F)F)o4)cn3)CC2)c1Cl] |
| 92 | | | | | 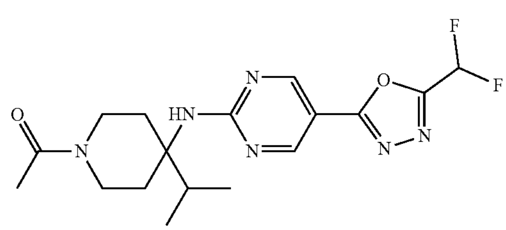 [SMILES: CC(=O)N1CCC(Nc2ncc(-c3nnc(C(F)F)o3)cn2)(C(C)C)CC1] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 93 | 0.043 | >30 | 6.39 | 384.05 | 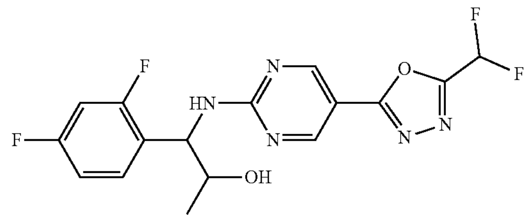 [SMILES: CC(O)C(Nc1ncc(-c2nnc(C(F)F)o2)cn1)c1ccc(F)cc1F] |
| 94 | | | | | 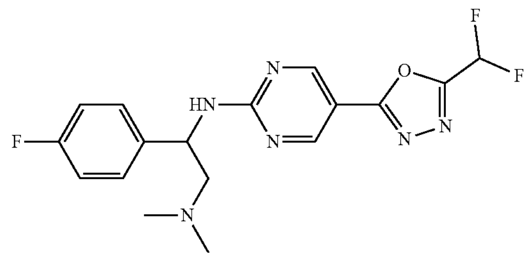 [SMILES: CN(C)CC(Nc1ncc(-c2nnc(C(F)F)o2)cn1)c1ccc(F)cc1] |
| 95 | | | | | 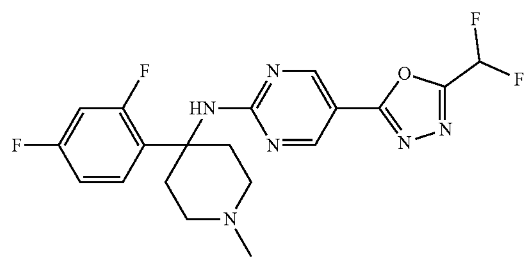 [SMILES: CN1CCC(Nc2ncc(-c3nnc(C(F)F)o3)cn2)(c2ccc(F)cc2F)CC1] |
| 96 | 0.058 | >30 | 5.81 | 351.1 | 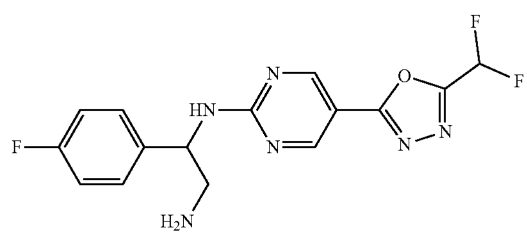 [SMILES: NCC(Nc1ncc(-c2nnc(C(F)F)o2)cn1)c1ccc(F)cc1] |
| 97 | 0.034 | >30 | 8.99 | 368.05 | 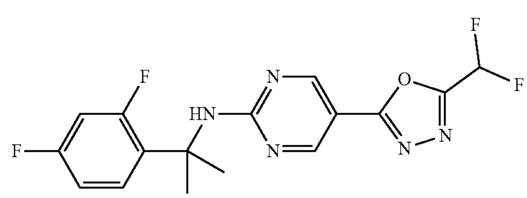 [SMILES: CC(C)(Nc1ncc(-c2nnc(C(F)F)o2)cn1)c1ccc(F)cc1F] |
| 98 | 0.016 | >30 | 8.98 | 368.05 | 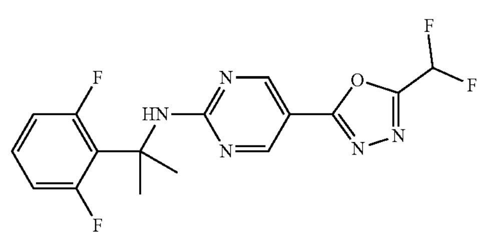 [SMILES: CC(C)(Nc1ncc(-c2nnc(C(F)F)o2)cn1)c1c(F)cccc1F] |

TABLE 1-continued

| | | | HDAC6 and HDAC1 activity | | |
|---|---|---|---|---|---|
| Ex. # | Human HDAC6 IC50 (μM) | Human HDAC1 IC50 (μM) | HPLC Retention Time (Min)[a] | LC-MS (M + H) | Structure |
| 99-R | 0.028 | >30 | 8.63 | 354.05 | |
| 99-S | >1 | >30 | 8.66 | 354.05 | |
| 100(+) | 0.013 | >30 | 3.47[d] | 354.25 | |
| 100(−) | >1 | >30 | 4.8[d] | 354.25 | |
| 101(+) | 0.022 | >30 | 11.2[g] | 422.1 | |
| 101(−) | 0.71 | >30 | 9.3[g] | 422.1 | |

TABLE 1-continued
HDAC6 and HDAC1 activity
| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 102 | 0.092 | >30 | 8.88 | 422.05 | 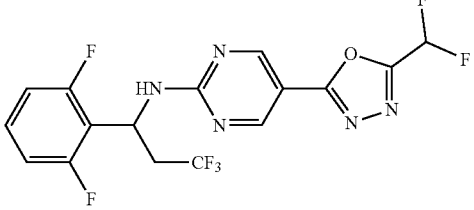 |
| 103(+) | 0.016 | >30 | 12.12[e] | 447.15 | 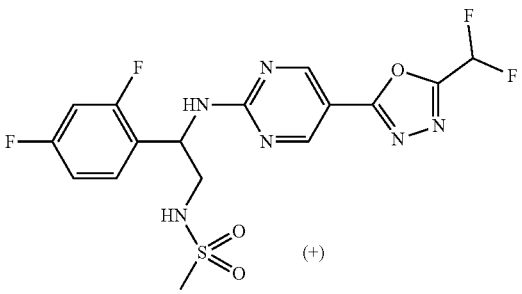 [SMILES: CS(=O)(=O)NCC(Nc1ncc(-c2nnc(C(F)F)o2)cn1)c1ccc(F)cc1F] |
| 103(−) | 0.65 | >30 | 10.06[e] | 447.15 | 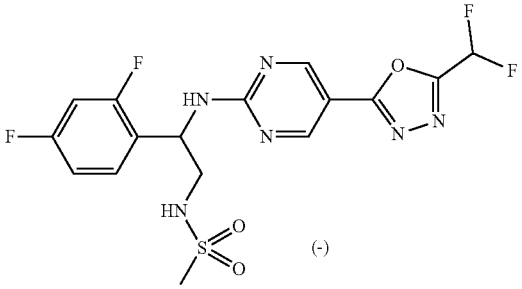 [SMILES: CS(=O)(=O)NCC(Nc1ncc(-c2nnc(C(F)F)o2)cn1)c1ccc(F)cc1F] |
| 104 | | | | | 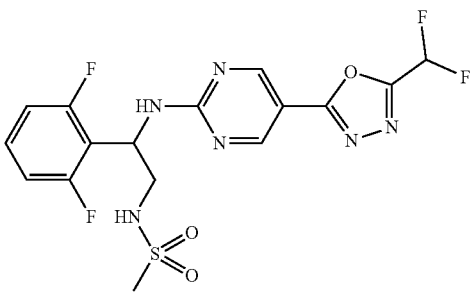 [SMILES: CS(=O)(=O)NCC(Nc1ncc(-c2nnc(C(F)F)o2)cn1)c1c(F)cccc1F] |
| 105 | | | | | 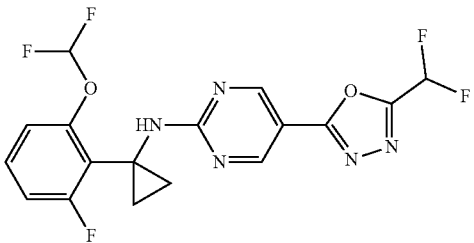 [SMILES: Fc1cccc(OC(F)F)c1C1(Nc2ncc(-c3nnc(C(F)F)o3)cn2)CC1] |

TABLE 1-continued

HDAC6 and HDAC1 activity

| Ex. # | Human HDAC6 IC50 (μM) | Human HDAC1 IC50 (μM) | HPLC Retention Time (Min)<sup>a</sup> | LC-MS (M + H) | Structure |
|---|---|---|---|---|---|
| 106 | 0.016 | >30 | 8.74 | 396.35 | 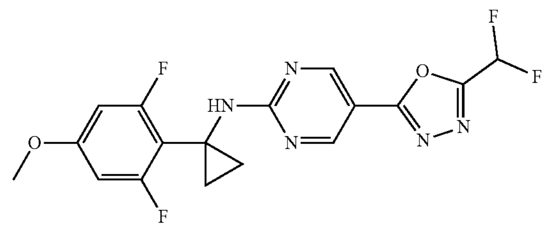 [SMILES: COc1cc(F)c(C2(Nc3ncc(-c4nnc(C(F)F)o4)cn3)CC2)c(F)c1] |
| 107 | | | | | 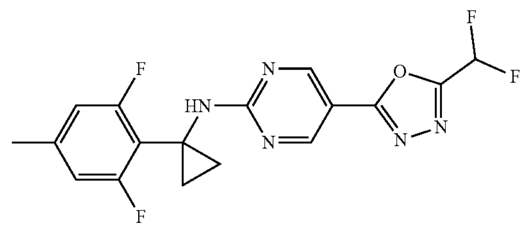 [SMILES: Cc1cc(F)c(C2(Nc3ncc(-c4nnc(C(F)F)o4)cn3)CC2)c(F)c1] |
| 108 | 0.027 | >30 | 7.66 | 443.15 | 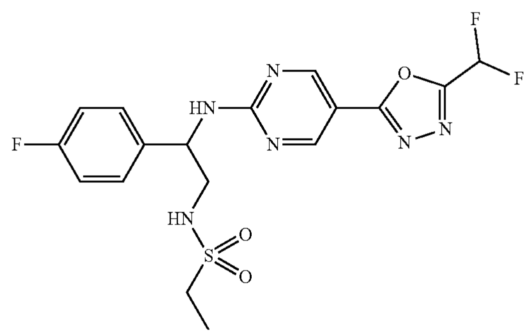 [SMILES: CCS(=O)(=O)NCC(Nc1ncc(-c2nnc(C(F)F)o2)cn1)c1ccc(F)cc1] |
| 109 | 0.037 | >30 | 8.02 | 457.05 | 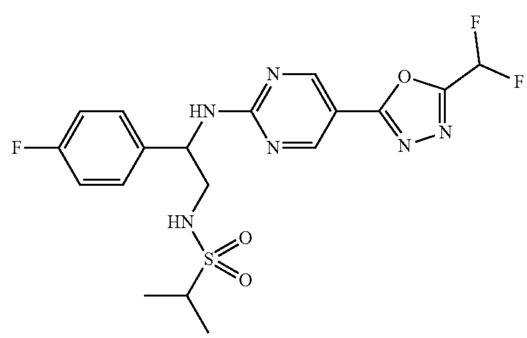 [SMILES: CC(C)S(=O)(=O)NCC(Nc1ncc(-c2nnc(C(F)F)o2)cn1)c1ccc(F)cc1] |
| 110 | 0.028 | >30 | 7.79 | 455.4 | 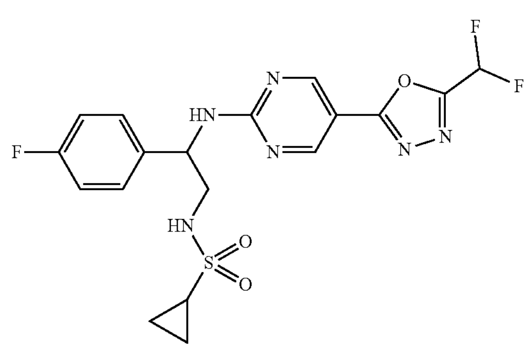 [SMILES: O=S(=O)(NCC(Nc1ncc(-c2nnc(C(F)F)o2)cn1)c1ccc(F)cc1)C1CC1] |

TABLE 1-continued

HDAC6 and HDAC1 activity

| Ex. # | Human HDAC6 IC50 (µM) | Human HDAC1 IC50 (µM) | HPLC Retention Time (Min)[a] | LC-MS (M + H) | Structure |
|---|---|---|---|---|---|
| 111 | 0.032 | >30 | 8.07 | 457.45 | 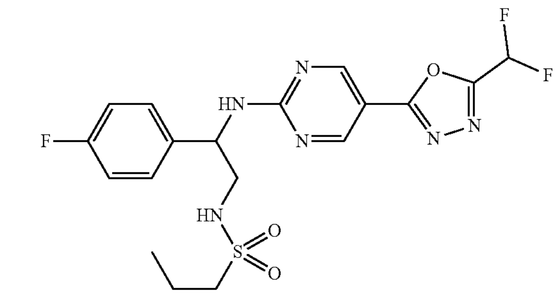 [SMILES: CCCS(=O)(=O)NCC(Nc1ncc(-c2nnc(C(F)F)o2)cn1)c1ccc(F)cc1] |
| 112 | 0.032 | >30 | 8.39 | 471.15 | 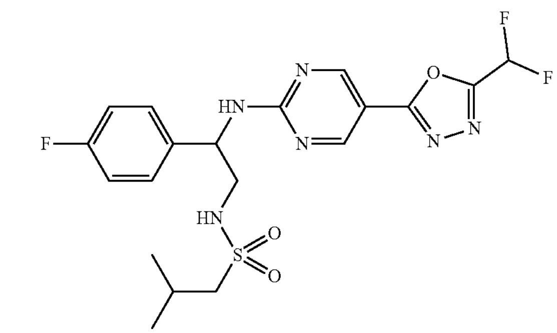 [SMILES: CC(C)CS(=O)(=O)NCC(Nc1ncc(-c2nnc(C(F)F)o2)cn1)c1ccc(F)cc1] |
| 113 | 0.021 | >30 | 7.94 | 443.05 | 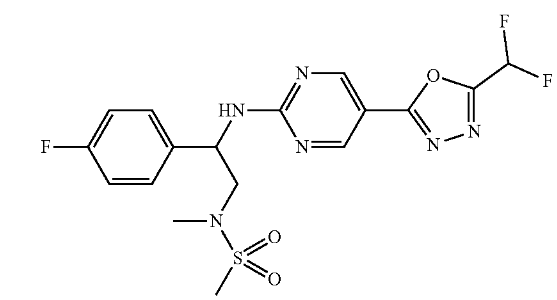 [SMILES: CN(CC(Nc1ncc(-c2nnc(C(F)F)o2)cn1)c1ccc(F)cc1)S(C)(=O)=O] |
| 114 | 0.05 | >30 | 8.19 | 447.05 | 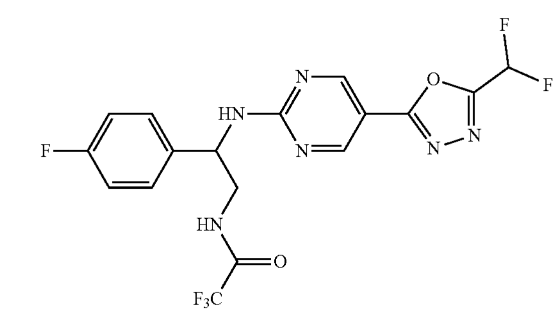 [SMILES: O=C(NCC(Nc1ncc(-c2nnc(C(F)F)o2)cn1)c1ccc(F)cc1)C(F)(F)F] |
| 115(+) | 0.018 | >30 | 9.47[e] | 477.2 | 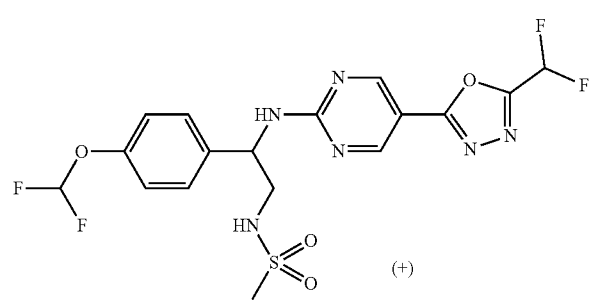 [SMILES: CS(=O)(=O)NCC(Nc1ncc(-c2nnc(C(F)F)o2)cn1)c1ccc(OC(F)F)cc1] |

TABLE 1-continued
HDAC6 and HDAC1 activity
| Ex. # | Human HDAC6 IC50 (µM) | Human HDAC1 IC50 (µM) | HPLC Retention Time (Min)[a] | LC-MS (M + H) | Structure |
|---|---|---|---|---|---|
| 115(−) | 0.37 | >30 | 10.9[e] | 477.1 | 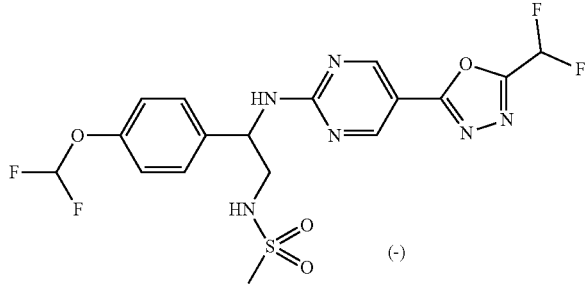 (−) |
| 116(+) | 0.017 | >30 | 13.7[e] | 495.15 | 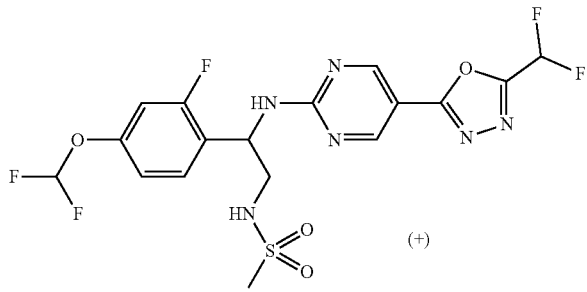 [SMILES: CS(=O)(=O)NCC(Nc1ncc(-c2nnc(C(F)F)o2)cn1)c1ccc(OC(F)F)cc1F] (+) |
| 116(−) | 0.26 | >30 | 11.36[e] | 495.15 | 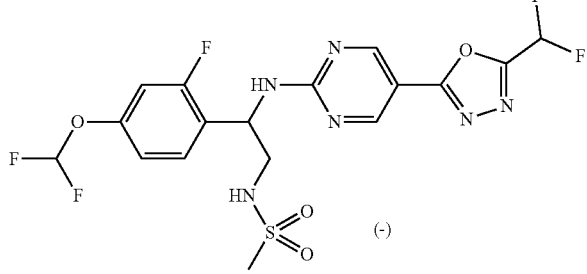 (−) |
| 117 | | | | | 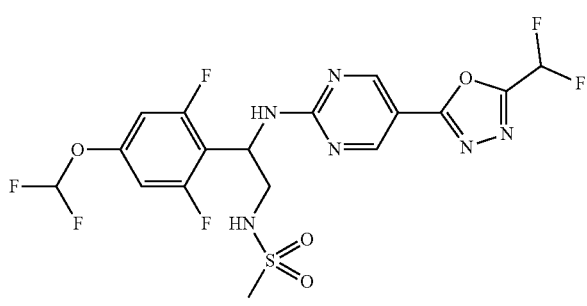 [SMILES: CS(=O)(=O)NCC(Nc1ncc(-c2nnc(C(F)F)o2)cn1)c1c(F)cc(OC(F)F)cc1F] |
| 118 | 0.072 | >30 | 8.56 | 511.15 | 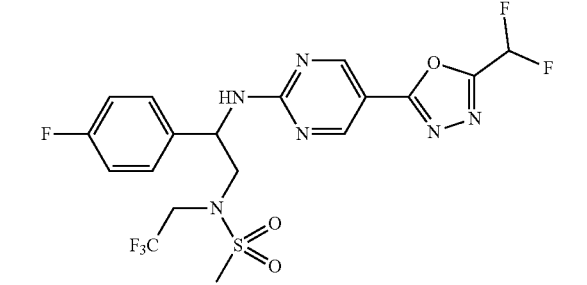 [SMILES: CS(=O)(=O)N(CC(Nc1ncc(-c2nnc(C(F)F)o2)cn1)c1ccc(F)cc1)CC(F)(F)F] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 118(+) | 0.029 | >30 | 19.55[d] | 511.15 | |
| 119 | | | | | 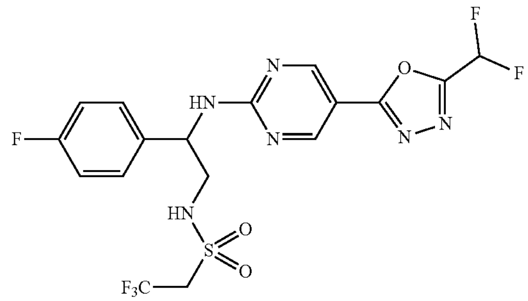 [SMILES: O=S(=O)(CC(F)(F)F)NCC(Nc1ncc(-c2nnc(C(F)F)o2)cn1)c1ccc(F)cc1] |
| 120(+) | 0.037 | >30 | 6.83[e] | 455.2 | 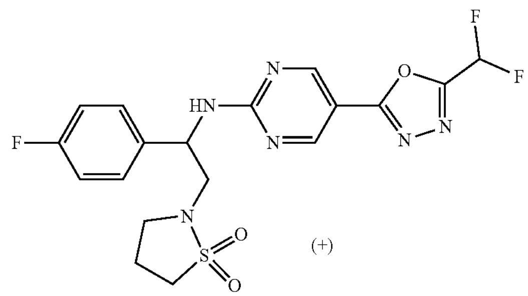 [SMILES: O=S1(=O)CCCN1CC(Nc1ncc(-c2nnc(C(F)F)o2)cn1)c1ccc(F)cc1] |
| 120(−) | 0.15 | >30 | 5.92[e] | 455.2 | 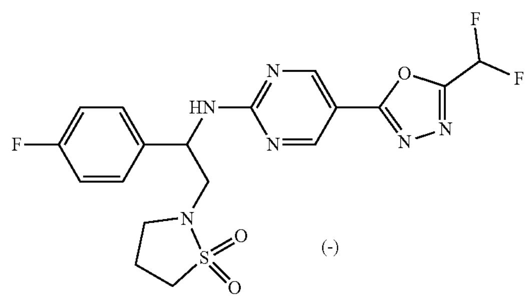 [SMILES: O=S1(=O)CCCN1CC(Nc1ncc(-c2nnc(C(F)F)o2)cn1)c1ccc(F)cc1] |
| 121 | | | | | 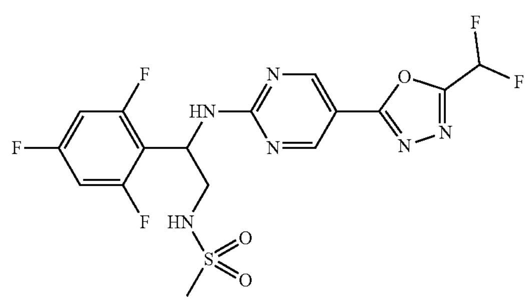 [SMILES: CS(=O)(=O)NCC(Nc1ncc(-c2nnc(C(F)F)o2)cn1)c1c(F)cc(F)cc1F] |
| 122(+) | 0.031 | >30 | 13.25[f] | 495.15 | 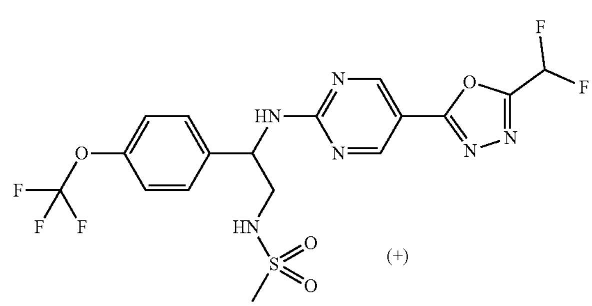 [SMILES: CS(=O)(=O)NCC(Nc1ncc(-c2nnc(C(F)F)o2)cn1)c1ccc(OC(F)(F)F)cc1] |

TABLE 1-continued
HDAC6 and HDAC1 activity
| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 122(−) | 0.84 | >30 | 11.27[f] | 495.15 | 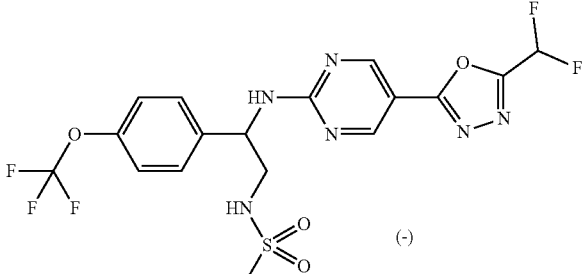 (−) |
| 123(+) | 1.1 | >30 | 3.94[f] | 375.1 | 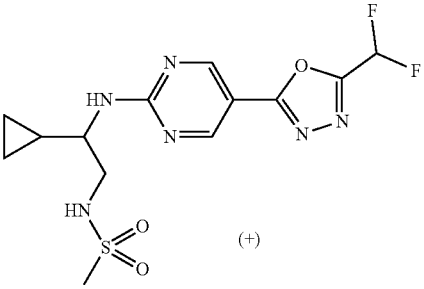 [SMILES: CS(=O)(=O)NCC(Nc1ncc(-c2nnc(C(F)F)o2)cn1)C1CC1] (+) |
| 123(−) | 1.1 | >30 | 4.82[f] | 375.1 | 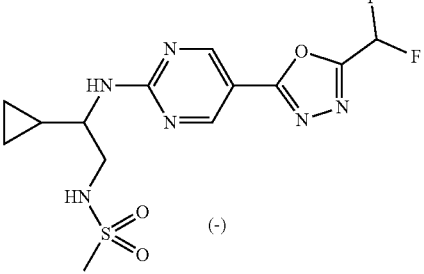 (−) |
| 124 | | | | | 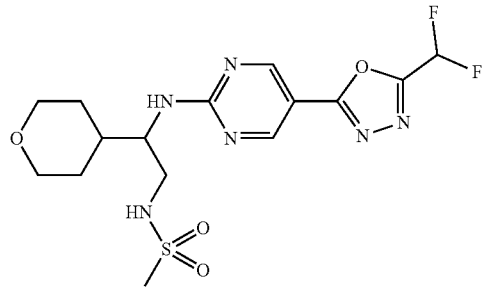 [SMILES: CS(=O)(=O)NCC(Nc1ncc(-c2nnc(C(F)F)o2)cn1)C1CCOCC1] |
| 125 | 0.026 | >30 | 6.25[b] | 443.15 | 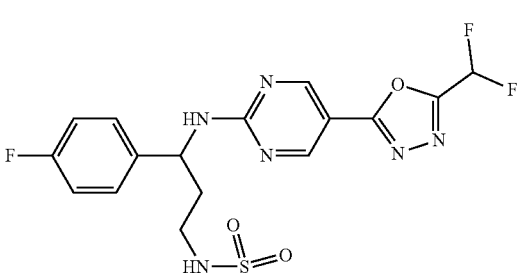 |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 126 | | | | | 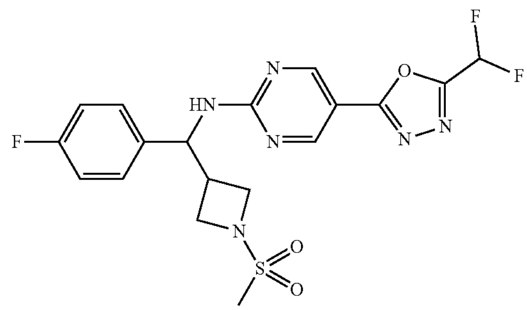 [SMILES: CS(=O)(=O)N1CC(C(Nc2ncc(-c3nnc(C(F)F)o3)cn2)c2ccc(F)cc2)C1] |
| 127A | 0.045 | >30 | 7.68 | 443.1 | 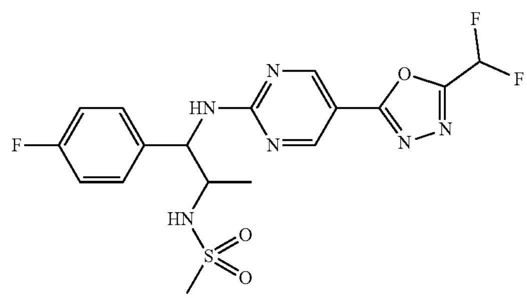 [SMILES: CC(NS(C)(=O)=O)C(Nc1ncc(-c2nnc(C(F)F)o2)cn1)c1ccc(F)cc1] |
| 127B | 0.049 | >30 | 7.79 | 443.1 | 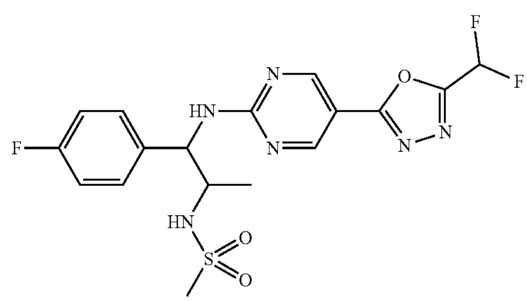 [SMILES: CC(NS(C)(=O)=O)C(Nc1ncc(-c2nnc(C(F)F)o2)cn1)c1ccc(F)cc1] |
| 128 | 0.13 | >30 | 8.22 | 491.15 | 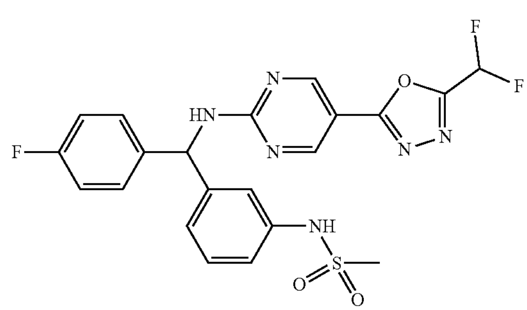 [SMILES: CS(=O)(=O)Nc1cccc(C(Nc2ncc(-c3nnc(C(F)F)o3)cn2)c2ccc(F)cc2)c1] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 129 | 0.25 | >30 | 8.16 | 491.15 | 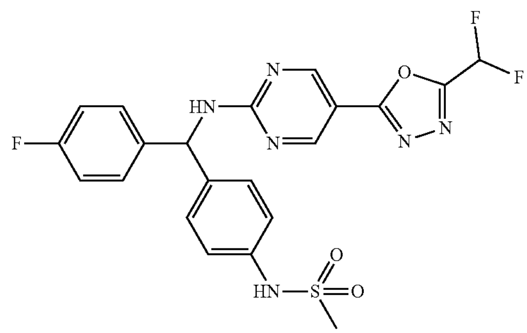 [SMILES: CS(=O)(=O)Nc1ccc(C(Nc2ncc(-c3nnc(C(F)F)o3)cn2)c2ccc(F)cc2)cc1] |
| 130 | 0.19 | >30 | 8.28 | 491.15 | 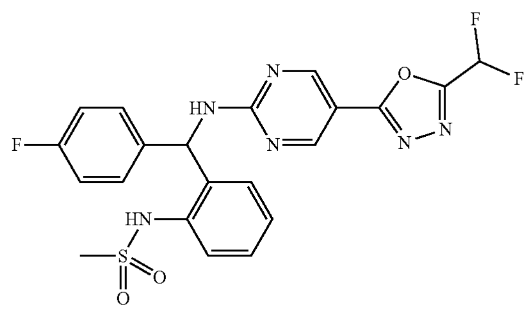 [SMILES: CS(=O)(=O)Nc1ccccc1C(Nc1ncc(-c2nnc(C(F)F)o2)cn1)c1ccc(F)cc1] |
| 131 | 0.058 | >30 | 8.74 | 505.1 | 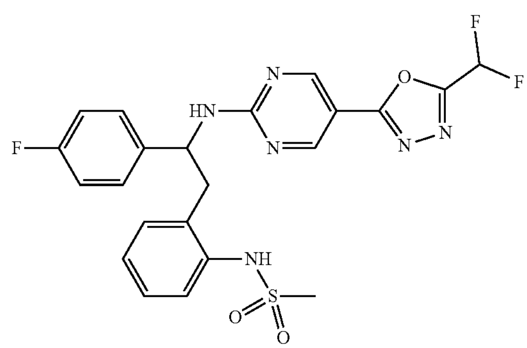 [SMILES: CS(=O)(=O)Nc1ccccc1CC(Nc1ncc(-c2nnc(C(F)F)o2)cn1)c1ccc(F)cc1] |
| 132 | 0.083 | >30 | 8.31 | 505.2 | 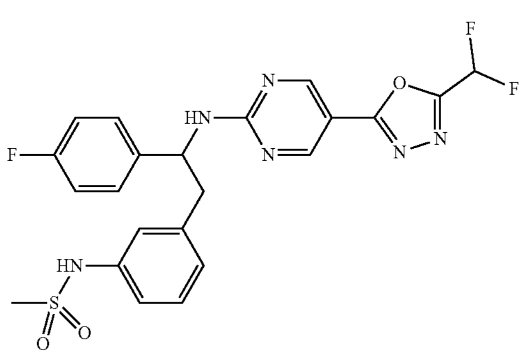 [SMILES: CS(=O)(=O)Nc1cccc(CC(Nc2ncc(-c3nnc(C(F)F)o3)cn2)c2ccc(F)cc2)c1] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 133 | 0.33 | >30 | 8.23 | 505.2 | 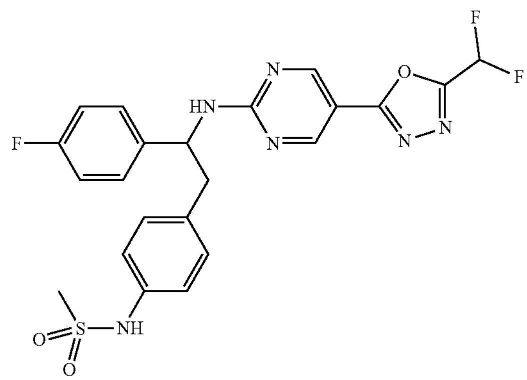 [SMILES: CS(=O)(=O)Nc1ccc(CC(Nc2ncc(-c3nnc(C(F)F)o3)cn2)c2ccc(F)cc2)cc1] |
| 134A | 0.22 | >30 | 8.93 | 410.25 | 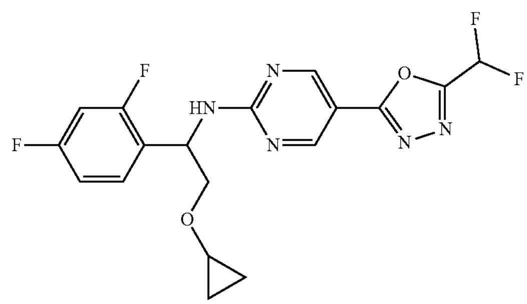 [SMILES: Fc1ccc(C(COC2CC2)Nc2ncc(-c3nnc(C(F)F)o3)cn2)c(F)c1] |
| 134B | 0.061 | >30 | 8.93 | 410.25 | 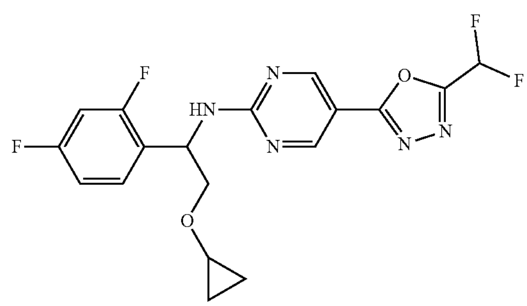 [SMILES: Fc1ccc(C(COC2CC2)Nc2ncc(-c3nnc(C(F)F)o3)cn2)c(F)c1] |
| 135(+) | | | | | 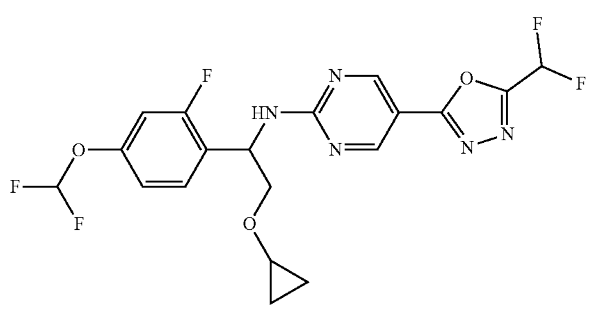 [SMILES: Fc1cc(OC(F)F)ccc1C(COC1CC1)Nc1ncc(-c2nnc(C(F)F)o2)cn1] |

TABLE 1-continued
HDAC6 and HDAC1 activity
| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 135(−) | | | | | 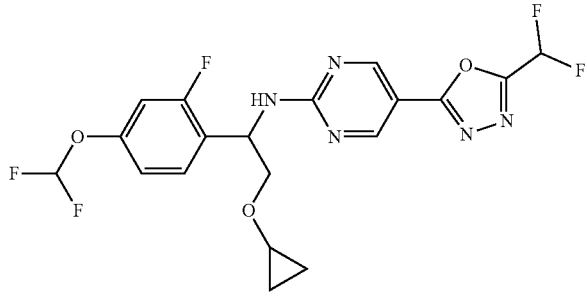 [SMILES: Fc1cc(OC(F)F)ccc1C(COC1CC1)Nc1ncc(-c2nnc(C(F)F)o2)cn1] |
| 136(+) | | | | | 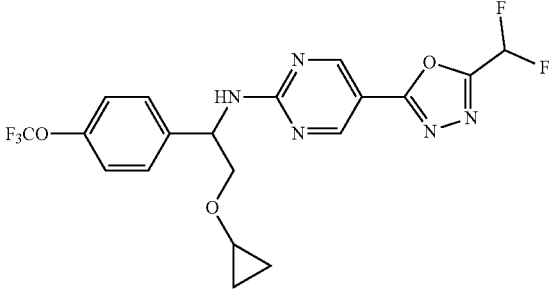 [SMILES: FC(F)c1nnc(-c2cnc(NC(COC3CC3)c3ccc(OC(F)(F)F)cc3)nc2)o1] |
| 136(−) | | | | | 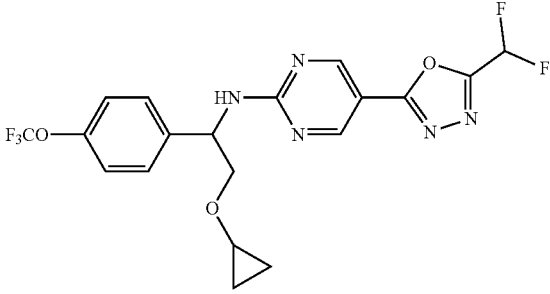 [SMILES: FC(F)c1nnc(-c2cnc(NC(COC3CC3)c3ccc(OC(F)(F)F)cc3)nc2)o1] |
| 137(+) | 0.041 | >30 | 8.98[e] | 461.15 | 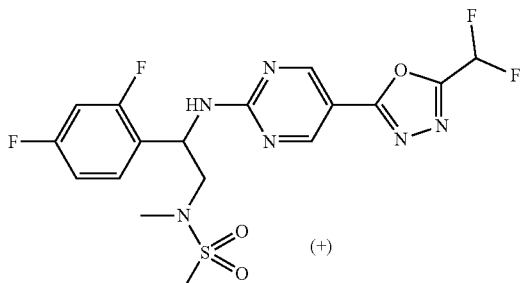 |
| 138(+) | 0.075 | >30 | 7.13[e] | 529.6 | 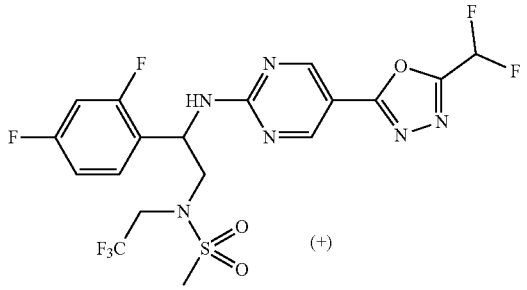 [SMILES: CS(=O)(=O)N(CC(Nc1ncc(-c2nnc(C(F)F)o2)cn1)c1ccc(F)cc1F)CC(F)(F)F] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 139(+) | 0.033 | >30 | 12.47[e] | 461.2 | 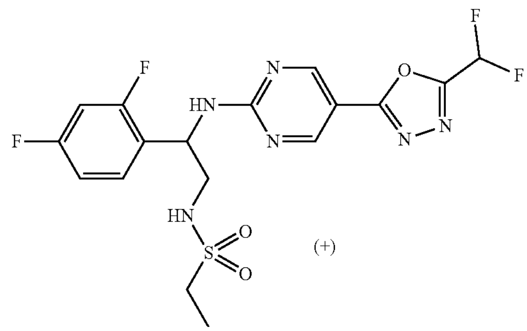 [SMILES: CCS(=O)(=O)NCC(Nc1ncc(-c2nnc(C(F)F)o2)cn1)c1ccc(F)cc1F] |
| 140(+) | 0.058 | >30 | 7.53[e] | 475.05 | 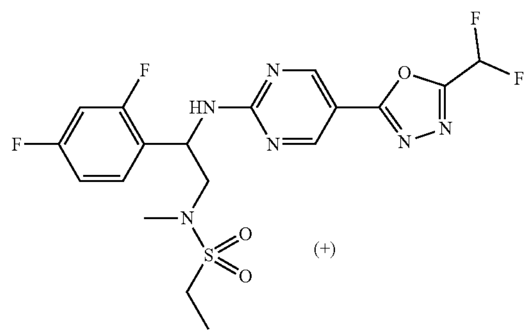 [SMILES: CCS(=O)(=O)N(C)CC(Nc1ncc(-c2nnc(C(F)F)o2)cn1)c1ccc(F)cc1F] |
| 141(+) | 0.13 | >30 | 6.19[e] | 543.15 | 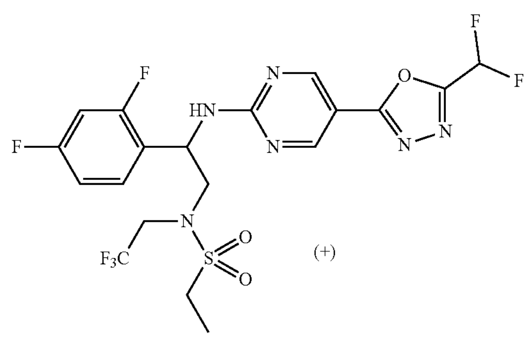 [SMILES: CCS(=O)(=O)N(CC(Nc1ncc(-c2nnc(C(F)F)o2)cn1)c1ccc(F)cc1F)CC(F)(F)F] |
| 142(+) | 0.035 | >30 | 12.37[e] | 473.15 | 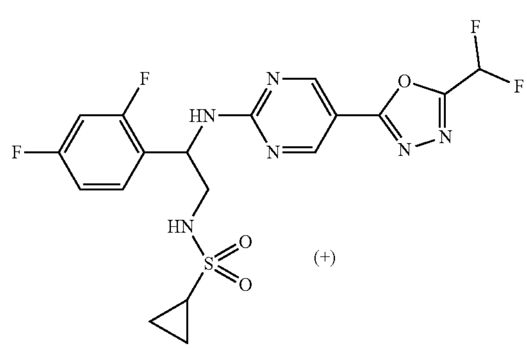 [SMILES: O=S(=O)(NCC(Nc1ncc(-c2nnc(C(F)F)o2)cn1)c1ccc(F)cc1F)C1CC1] |

TABLE 1-continued
HDAC6 and HDAC1 activity
| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 143(+) | 0.053 | >30 | 6.97[e] | 487.15 | 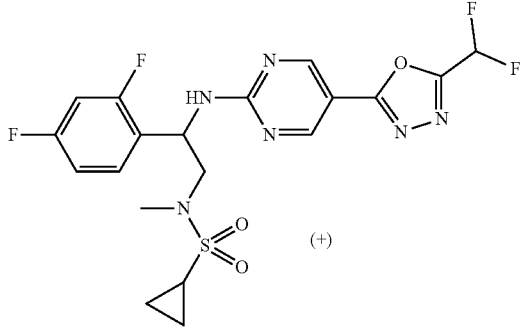 [SMILES: CN(CC(Nc1ncc(-c2nnc(C(F)F)o2)cn1)c1ccc(F)cc1F)S(=O)(=O)C1CC1] |
| 144(+) | 0.16 | >30 | 6.41[e] | 555.2 | 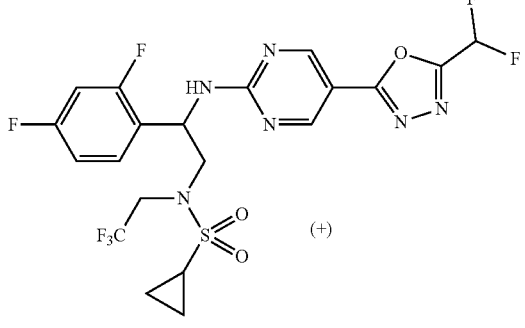 |
| 145(+) | 0.041 | >30 | 9.11[e] | 509.1 | 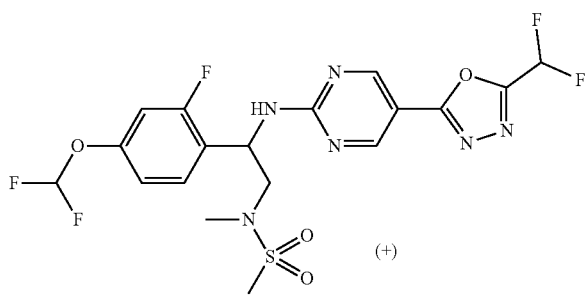 [SMILES: CN(CC(Nc1ncc(-c2nnc(C(F)F)o2)cn1)c1ccc(OC(F)F)cc1F)S(C)(=O)=O] |
| 146(+) | 0.14 | >30 | 9.2[e] | 577.15 | 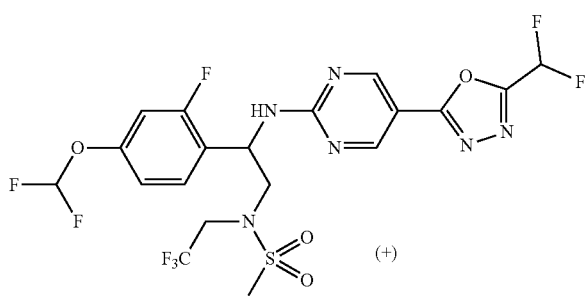 [SMILES: CS(=O)(=O)N(CC(Nc1ncc(-c2nnc(C(F)F)o2)cn1)c1ccc(OC(F)F)cc1F)CC(F)(F)F] |

TABLE 1-continued

HDAC6 and HDAC1 activity

| Ex. # | Human HDAC6 IC50 (μM) | Human HDAC1 IC50 (μM) | HPLC Retention Time (Min)$^a$ | LC-MS (M + H) | Structure |
|---|---|---|---|---|---|
| 147(+) | 0.018 | >30 | 10.15$^e$ | 509.15 | (+) |
| 148(+) | 0.019 | >30 | 7.42$^e$ | 523.2 | (+) |
| 149(+) | 0.2 | >30 | 6.44$^e$ | 591.1 | (+) |
| 150(+) | 0.023 | >30 | 11.19$^e$ | 521.1 | (+) |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 151(+) | 0.085 | >30 | 8.45[e] | 535.15 | 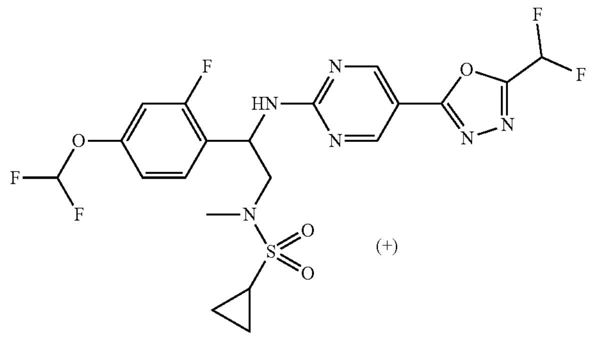 [SMILES: CN(CC(Nc1ncc(-c2nnc(C(F)F)o2)cn1)c1ccc(OC(F)F)cc1F)S(=O)(=O)C1CC1] |
| 152(+) | 0.28 | >30 | 7.2[e] | 603.1 | 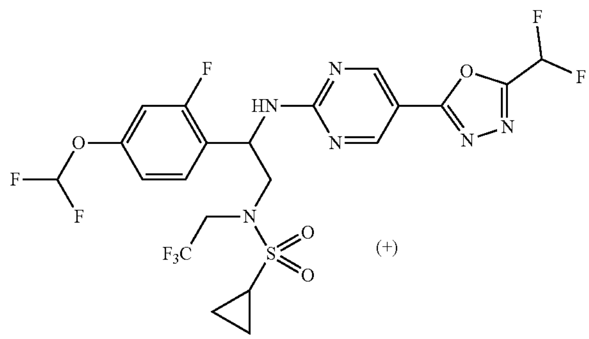 [SMILES: O=S(=O)(C1CC1)N(CC(Nc1ncc(-c2nnc(C(F)F)o2)cn1)c1ccc(OC(F)F)cc1F)CC(F)(F)F] |
| 153(+) | 0.02 | >30 | 8.91[e] | 509.1 | 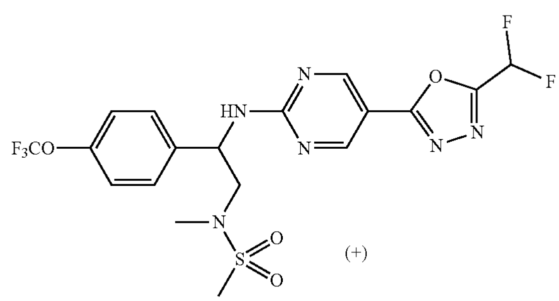 [SMILES: CN(CC(Nc1ncc(-c2nnc(C(F)F)o2)cn1)c1ccc(OC(F)(F)F)cc1)S(C)(=O)=O] |
| 154(+) | 0.26 | >30 | 5.88[e] | 577.05 | 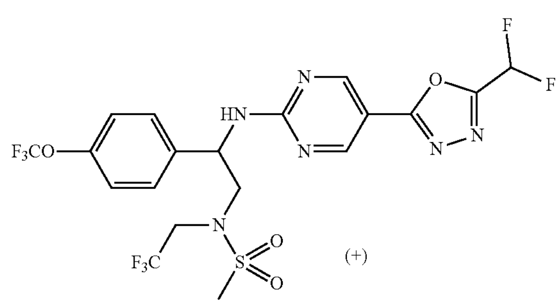 [SMILES: CS(=O)(=O)N(CC(Nc1ncc(-c2nnc(C(F)F)o2)cn1)c1ccc(OC(F)(F)F)cc1)CC(F)(F)F] |

TABLE 1-continued
HDAC6 and HDAC1 activity
| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 155(+) | 0.05 | >30 | 11.94[e] | 509.15 | 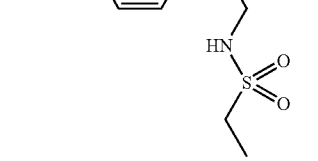 |
| 156(+) | 0.076 | >30 | 7.79[e] | 523.15 | 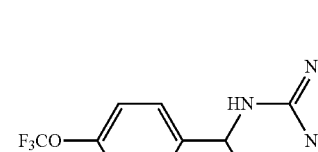 |
| 157(+) | 0.44 | >30 | 7.11[e] | 591.05 | 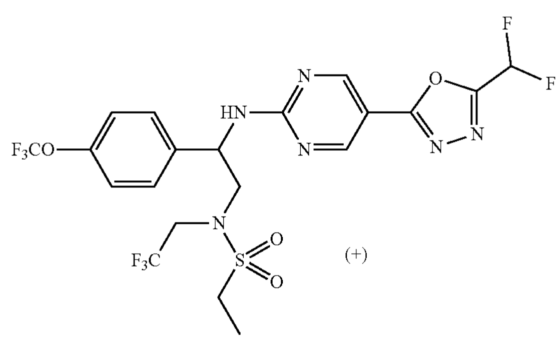 [SMILES: CCS(=O)(=O)N(CC(Nc1ncc(-c2nnc(C(F)F)o2)cn1)c1ccc(OC(F)(F)F)cc1)CC(F)(F)F] |
| 158(+) | 0.051 | >30 | 12[e] | 521.15 | 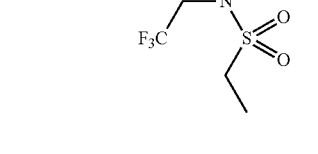 |

TABLE 1-continued
HDAC6 and HDAC1 activity
| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 159(+) | 0.09 | >30 | 7.61[e] | 535.15 | 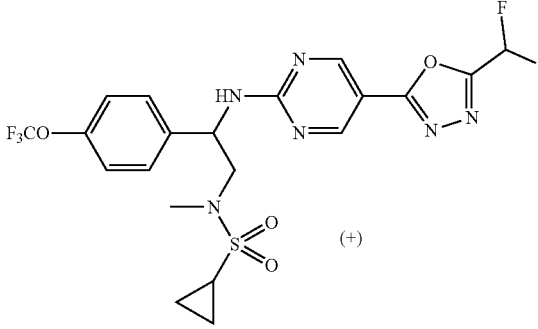 |
| 160(+) | 0.58 | >30 | 7.2[e] | 603.25 | 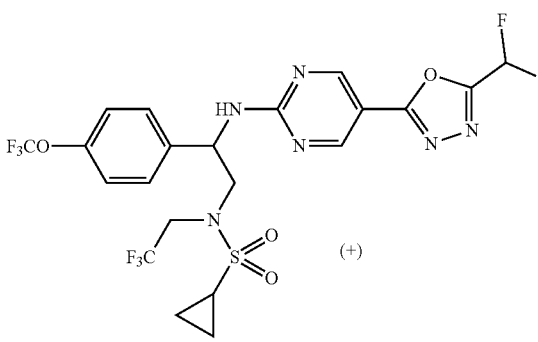 |
| 161(+) | 0.043 | >30 | 7.48 | 414.10 | 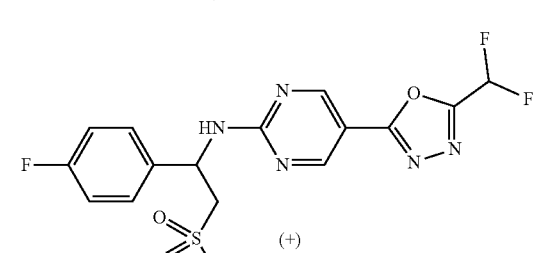 |
| 161(−) | 0.87 | >30 | 7.48 | 414.10 | 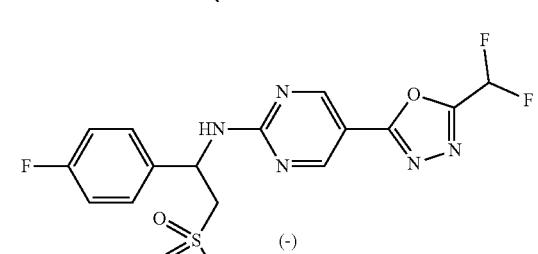 |
| 162(+) | 0.13 | >30 | 8.76 | 434.0 | 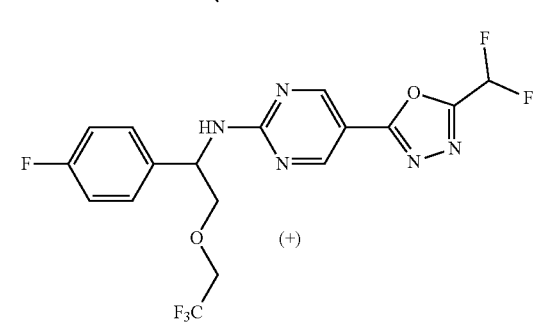 |

TABLE 1-continued
| | | HDAC6 and HDAC1 activity | | | |
|---|---|---|---|---|---|
| Ex. # | Human HDAC6 IC50 (μM) | Human HDAC1 IC50 (μM) | HPLC Retention Time (Min)[a] | LC-MS (M + H) | Structure |
| 162(−) | 0.3 | >30 | 8.76 | 434.0 | 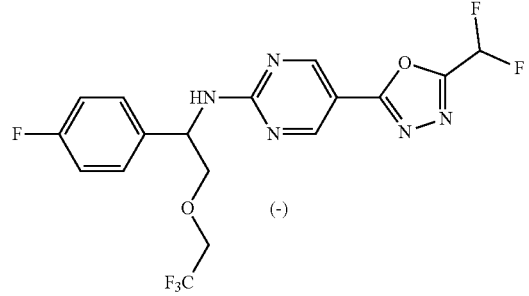 [SMILES: Fc1ccc(C(COCC(F)(F)F)Nc2ncc(-c3nnc(C(F)F)o3)cn2)cc1] |
| 163(+) | 0.11 | >30 | 9.73[h] | 452.15 | 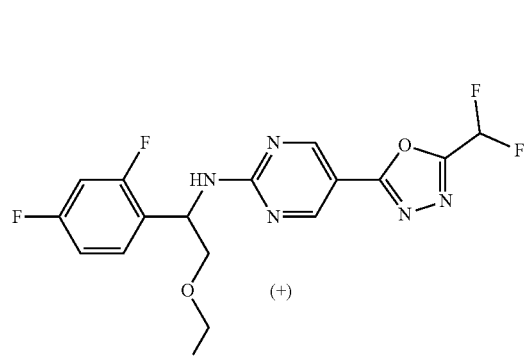 |
| 163(−) | 0.41 | >30 | 12.87[h] | 452.1 | 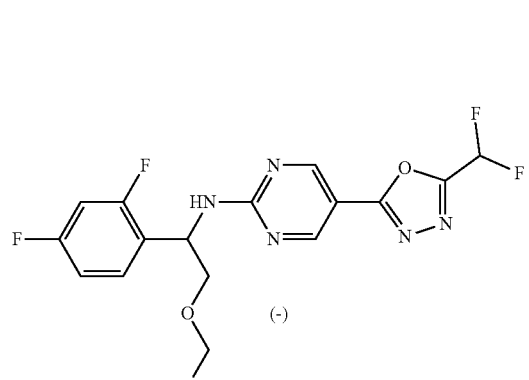 |
| 164(+) | 0.11 | >30 | 8.79 | 525.20 | 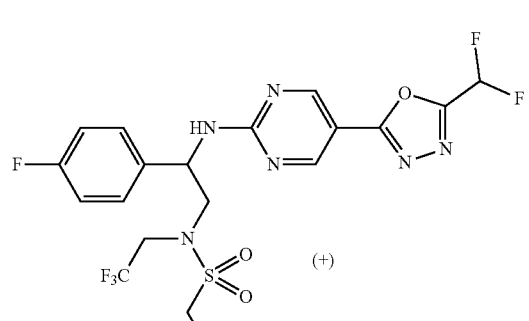 |

TABLE 1-continued
HDAC6 and HDAC1 activity
| Ex. # | Human HDAC6 IC50 (µM) | Human HDAC1 IC50 (µM) | HPLC Retention Time (Min)[a] | LC-MS (M + H) | Structure |
|---|---|---|---|---|---|
| 164(−) | 0.23 | >30 | 8.79 | 525.20 | 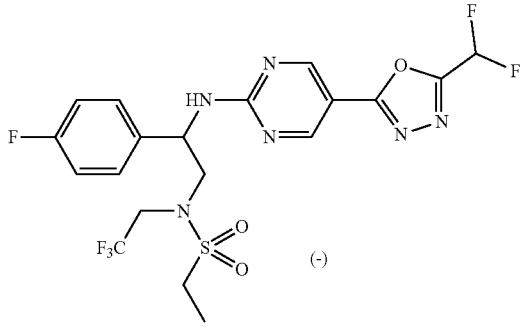 [SMILES: CCS(=O)(=O)N(CC(Nc1ncc(-c2nnc(C(F)F)o2)cn1)c1ccc(F)cc1)CC(F)(F)F] (−) |
| 165(+) | 0.11 | >30 | 8.84 | 537.15 | 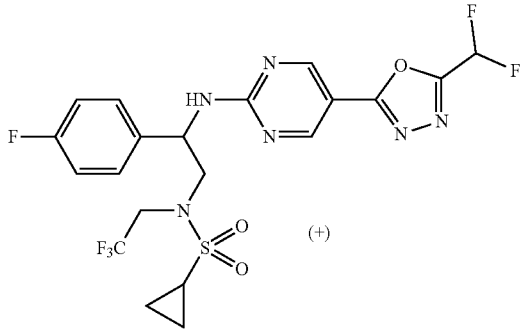 [SMILES: O=S(=O)(C1CC1)N(CC(Nc1ncc(-c2nnc(C(F)F)o2)cn1)c1ccc(F)cc1)CC(F)(F)F] (+) |
| 165(−) | 0.16 | >30 | 8.84 | 537.15 | 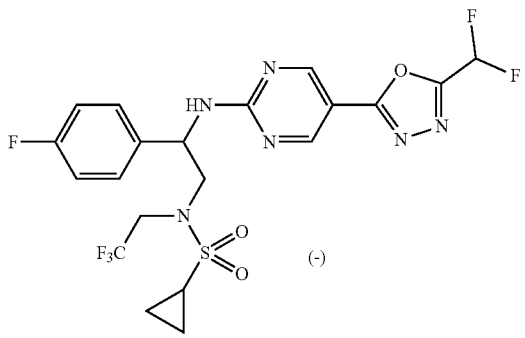 [SMILES: O=S(=O)(C1CC1)N(CC(Nc1ncc(-c2nnc(C(F)F)o2)cn1)c1ccc(F)cc1)CC(F)(F)F] (−) |
| 166(+) | 0.093 | >30 | 5.21[f] | 407.15 | 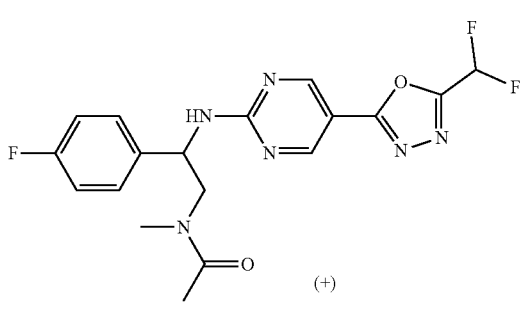 [SMILES: CC(=O)N(C)CC(Nc1ncc(-c2nnc(C(F)F)o2)cn1)c1ccc(F)cc1] (+) |

TABLE 1-continued
HDAC6 and HDAC1 activity
| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 166(−) | 0.36 | >30 | 6.06[f] | 407.15 | 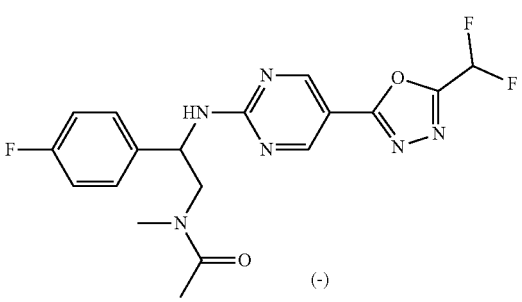 [SMILES: CC(=O)N(C)CC(Nc1ncc(-c2nnc(C(F)F)o2)cn1)c1ccc(F)cc1] (−) |
| 167(+) | 0.11 | >30 | 6.15[k] | 475.2 | 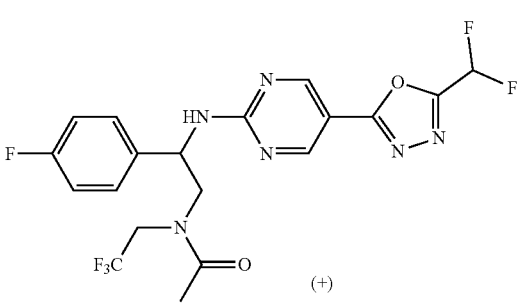 [SMILES: CC(=O)N(CC(Nc1ncc(-c2nnc(C(F)F)o2)cn1)c1ccc(F)cc1)CC(F)(F)F] (+) |
| 167(−) | 0.69 | >30 | 6.66[k] | 475.1 | 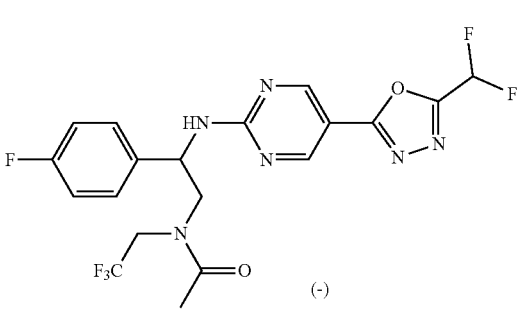 [SMILES: CC(=O)N(CC(Nc1ncc(-c2nnc(C(F)F)o2)cn1)c1ccc(F)cc1)CC(F)(F)F] (−) |
| 168(+) | 0.029 | >30 | 7.64 | 419 | 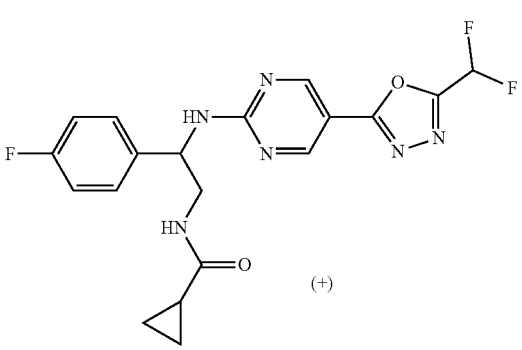 [SMILES: O=C(NCC(Nc1ncc(-c2nnc(C(F)F)o2)cn1)c1ccc(F)cc1)C1CC1] (+) |

TABLE 1-continued
HDAC6 and HDAC1 activity
| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 168(−) | 0.75 | >30 | 7.64 | 419 | 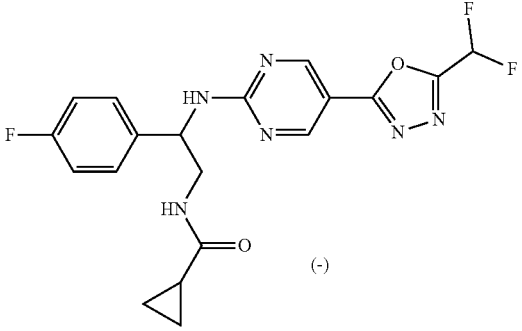 |
| 169(+) | 0.077 | >30 | 4.27[i] | 433.2 | 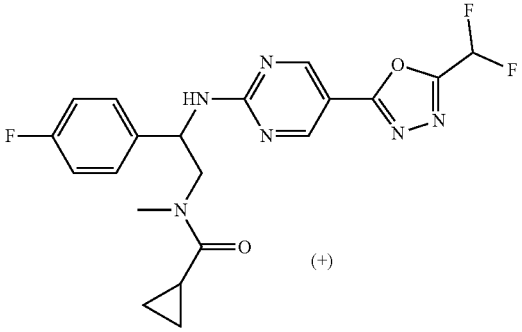 [SMILES: CN(CC(Nc1ncc(-c2nnc(C(F)F)o2)cn1)c1ccc(F)cc1)C(=O)C1CC1] |
| 169(−) | 1.1 | >30 | 8.49[i] | 433.15 | 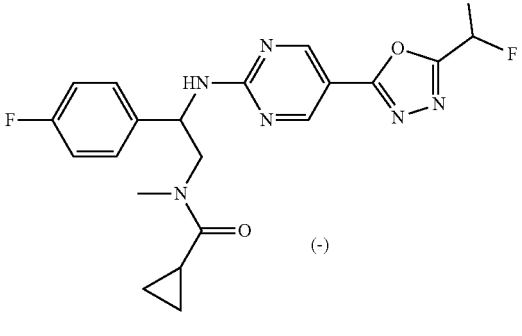 |
| 170(+) | 0.16 | >30 | 5.75[k] | 501.15 | 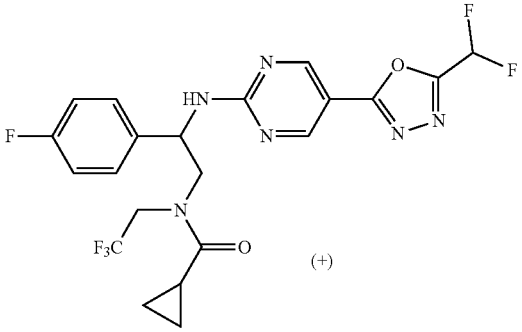 [SMILES: O=C(C1CC1)N(CC(Nc1ncc(-c2nnc(C(F)F)o2)cn1)c1ccc(F)cc1)CC(F)(F)F] |

TABLE 1-continued
HDAC6 and HDAC1 activity
| Ex. # | Human HDAC6 IC50 (μM) | Human HDAC1 IC50 (μM) | HPLC Retention Time (Min)<sup>a</sup> | LC-MS (M + H) | Structure |
|---|---|---|---|---|---|
| 170(−) | 1 | >30 | 7.57[k] | 501.2 | 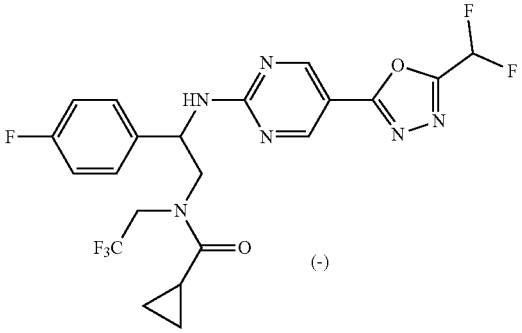 [SMILES: O=C(C1CC1)N(CC(Nc1ncc(-c2nnc(C(F)F)o2)cn1)c1ccc(F)cc1)CC(F)(F)F] (−) |
| 171(+) | 0.23 | >30 | 8.16[k] | 447.15 | 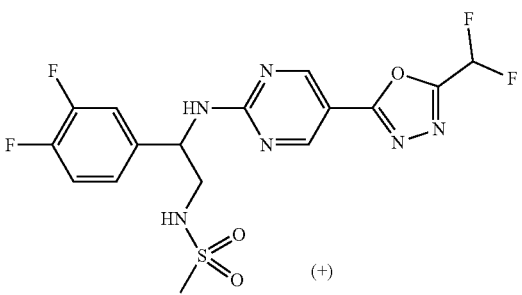 [SMILES: CS(=O)(=O)NCC(Nc1ncc(-c2nnc(C(F)F)o2)cn1)c1ccc(F)c(F)c1] (+) |
| 171(−) | 0.59 | >30 | 7.54[k] | 447.15 | 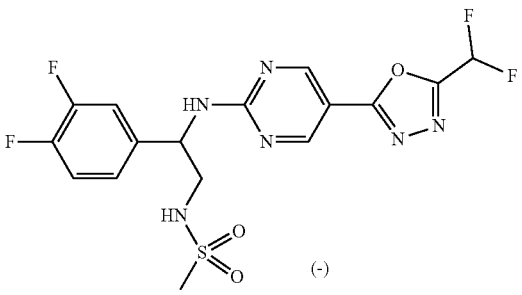 [SMILES: CS(=O)(=O)NCC(Nc1ncc(-c2nnc(C(F)F)o2)cn1)c1ccc(F)c(F)c1] (−) |
| 172(A) | 0.32 | >30 | 5.87[k] | 529.15 | 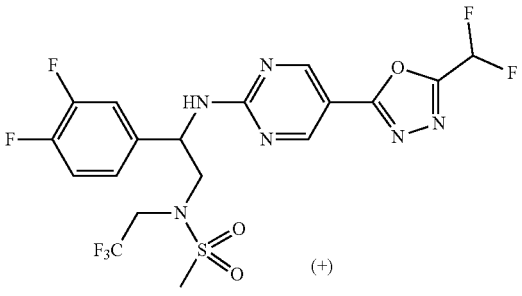 [SMILES: CS(=O)(=O)N(CC(Nc1ncc(-c2nnc(C(F)F)o2)cn1)c1ccc(F)c(F)c1)CC(F)(F)F] (+) |
| 172(B) | 0.086 | >30 | 6.33[k] | 529.15 | 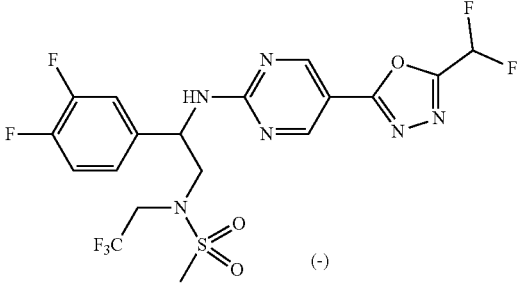 [SMILES: CS(=O)(=O)N(CC(Nc1ncc(-c2nnc(C(F)F)o2)cn1)c1ccc(F)c(F)c1)CC(F)(F)F] (−) |

TABLE 1-continued
HDAC6 and HDAC1 activity
| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 173(+) | 0.024 | >30 | 7.94 | 445.10 | 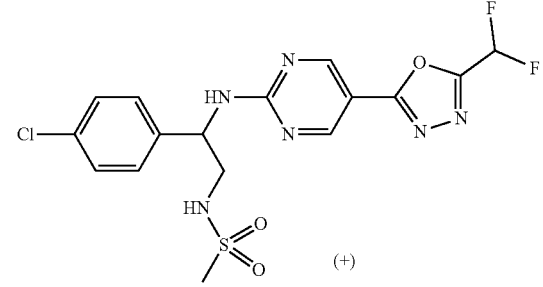 [SMILES: CS(=O)(=O)NCC(Nc1ncc(-c2nnc(C(F)F)o2)cn1)c1ccc(Cl)cc1] (+) |
| 173(−) | 0.49 | >30 | 7.95 | 445.10 | 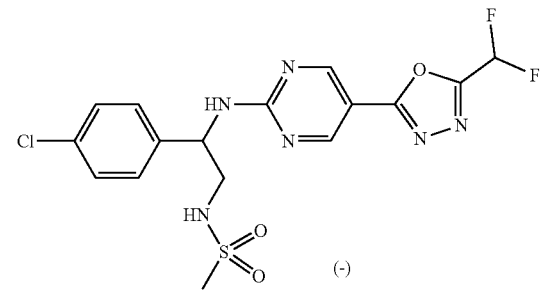 [SMILES: CS(=O)(=O)NCC(Nc1ncc(-c2nnc(C(F)F)o2)cn1)c1ccc(Cl)cc1] (−) |
| 174(+) | 0.17 | >30 | 8.95 | 527.1 | 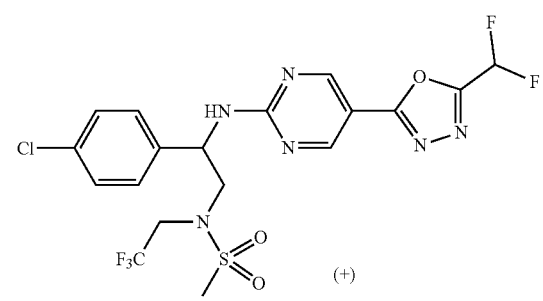 [SMILES: CS(=O)(=O)N(CC(Nc1ncc(-c2nnc(C(F)F)o2)cn1)c1ccc(Cl)cc1)CC(F)(F)F] (+) |
| 174(−) | 0.11 | >30 | 8.96 | 527.1 | 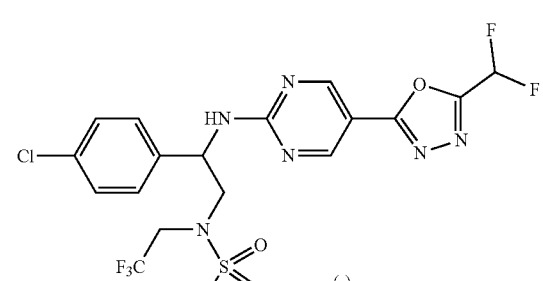 (−) |

TABLE 1-continued
HDAC6 and HDAC1 activity
| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 175(+) | 0.16 | >30 | 5.18[j] | 470.15 | 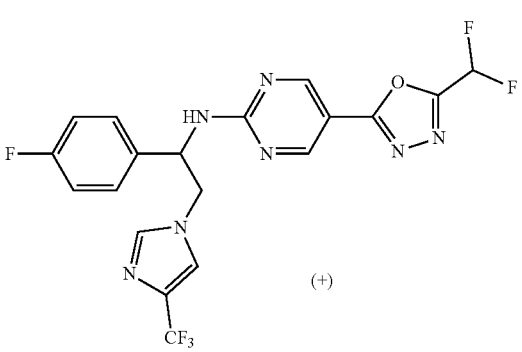 [SMILES: Fc1ccc(C(Cn2cnc(C(F)(F)F)c2)Nc2ncc(-c3nnc(C(F)F)o3)cn2)cc1] (+) |
| 175(−) | 1.5 | >30 | 5.85[j] | 470.15 | 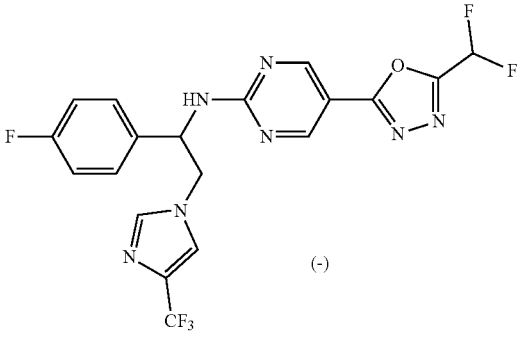 (−) |
| 176(+) | 0.16 | >30 | 6.77[k] | 470.15 | 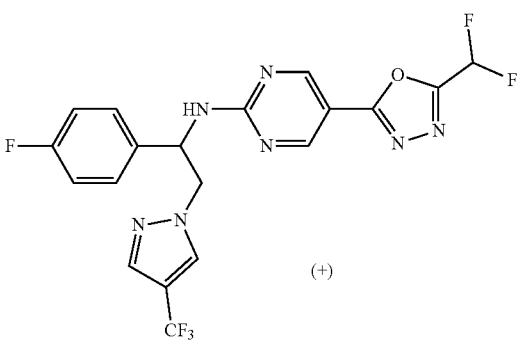 [SMILES: Fc1ccc(C(Cn2ccc(C(F)(F)F)c2)Nc2ncc(-c3nnc(C(F)F)o3)cn2)cc1] (+) |
| 176(−) | 1.5 | >30 | 8.03[k] | 470.15 | 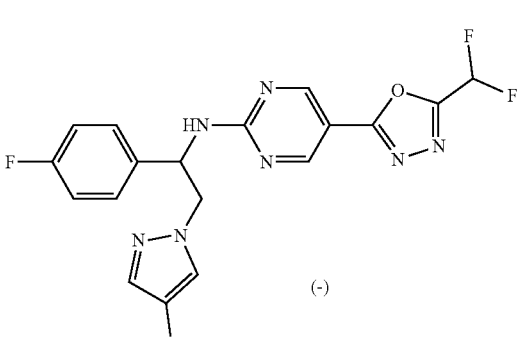 (−) |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 177(−) | 0.076 | >30 | 7.4[1] | 419.2 | (−) |
| 177(+) | 0.11 | >30 | 9.55[1] | 419.15 | (+) |
| 178(−) | | | | | (−) |
| 178(+) | | | | | (+) |
| 179 | | | | | 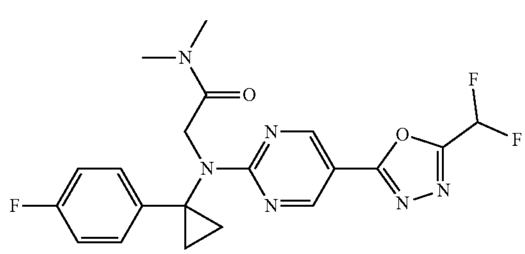 [SMILES: CN(C)C(=O)CN(c1ncc(-c2nnc(C(F)F)o2)cn1)C1(c2ccc(F)cc2)CC1] |

TABLE 1-continued

HDAC6 and HDAC1 activity

| Ex. # | Human HDAC6 IC50 (μM) | Human HDAC1 IC50 (μM) | HPLC Retention Time (Min)[a] | LC-MS (M + H) | Structure |
|---|---|---|---|---|---|
| 180 | | | | | 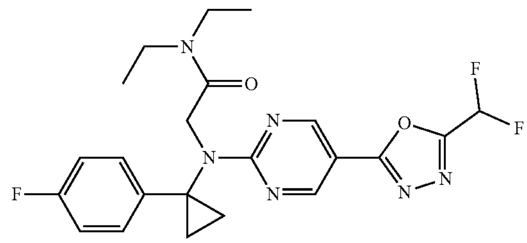 [SMILES: CCN(CC)C(=O)CN(c1ncc(-c2nnc(C(F)F)o2)cn1)C1(c2ccc(F)cc2)CC1] |
| 181 | | | | | 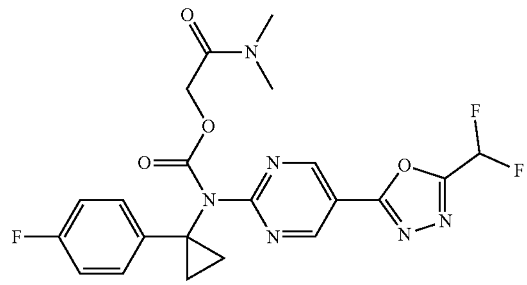 [SMILES: CN(C)C(=O)COC(=O)N(c1ncc(-c2nnc(C(F)F)o2)cn1)C1(c2ccc(F)cc2)CC1] |
| 182 | | | | | 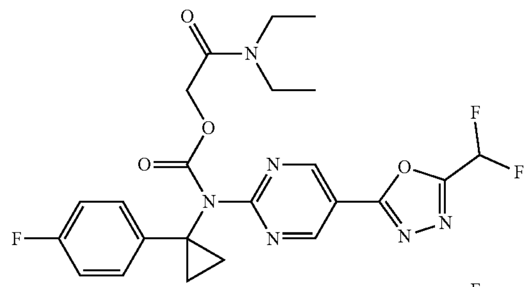 |
| 183 | | | | | 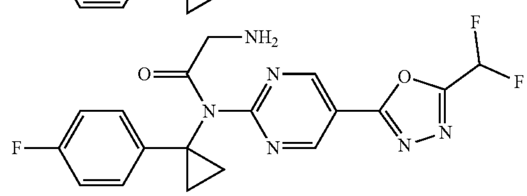 |
| 184 | | | | | 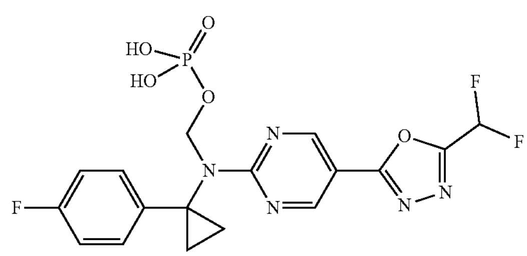 [SMILES: O=P(O)(O)OCN(c1ncc(-c2nnc(C(F)F)o2)cn1)C1(c2ccc(F)cc2)CC1] |

[a] HPLC Method A;
[b] HPLC Method B;
[c] SFC Method C;
[d] HPLC Method D;
[e] HPLC Method E;
[f] HPLC Method F;
[g] HPLC Method G;
[h] HPLC Method H;
[i] HPLC Method I;
[j] HPLC Method J;
[k] HPLC Method K;
[l] HPLC Method L The results in Table 1 demonstrate that compounds of Formula I have potent activity against HDAC6, and most compounds of Formula I have significant selectivity for inhibiting HDAC6 over HDAC1. Selected examples were further evaluated for selectivity versus all other HDAC isoforms. Table 2 shows that all of the evaluated compounds of Formula I have significant selectivity for inhibiting HDAC6 over all other isoforms of HDAC, with selectivity as high as 5000-fold.

TABLE 2

HDAC selectivity profile of selected examples

| Ex | HDAC Enzyme IC$_{50}$ (µM) | | | | | | | | | | |
|---|---|---|---|---|---|---|---|---|---|---|---|
| | 1 | 2 | 3 | 4 | 5 | 6 | 7 | 8 | 9 | 10 | 11 |
| 4 | >30 | >30 | >30 | >30 | >30 | 0.023 | >30 | >30 | >30 | >30 | >30 |
| 5 | >100 | >30 | >30 | >30 | >30 | 0.034 | >30 | >30 | >30 | >30 | >30 |
| 9 | >30 | >30 | >30 | >30 | >30 | 0.038 | >30 | >30 | >30 | >30 | >30 |
| 11 | >100 | >30 | >30 | >30 | >30 | 0.006 | >30 | >30 | >30 | >30 | >30 |
| 13 | >30 | >30 | >30 | >30 | >30 | 0.036 | >30 | >30 | >30 | >30 | >30 |
| 38(+) | >30 | >30 | >30 | >30 | >30 | 0.015 | 16.7 | >30 | >30 | >30 | >30 |
| 62 | >30 | >30 | >30 | >30 | >30 | 0.008 | >30 | >30 | >30 | >30 | >30 |
| 99-R | >30 | >30 | >30 | >30 | >30 | 0.028 | >30 | >30 | >30 | >30 | >30 |
| 110 | >30 | >30 | >30 | >30 | >30 | 0.028 | >30 | >30 | >30 | >30 | >30 |
| 115(+) | >30 | >30 | >30 | 10.7 | >30 | 0.018 | 11.9 | >30 | >30 | >30 | >30 |
| 118(+) | >30 | >30 | >30 | >30 | >30 | 0.029 | >30 | >30 | >30 | >30 | >30 |
| 122(+) | >30 | >30 | >30 | 8.4 | >30 | 0.031 | 26.7 | >30 | >30 | >30 | >30 |
| 161(+) | >30 | >30 | >30 | >30 | >30 | 0.043 | >30 | >30 | >30 | >30 | >30 |
| 168(+) | >30 | >30 | >30 | 13.8 | >30 | 0.029 | 24.4 | >30 | >30 | >30 | >30 |

Comparison Examples were also prepared. Table 3 shows that replacing the 1,3,4-oxadiazole of compounds of the disclosure with a 1,2,4-oxadiazole results in compounds that show significantly decreased inhibition of HDAC6 and/or a significant loss of selectivity for HDAC6 over many other HDAC isoforms. In addition, replacement of the 1,3,4-oxadiazole moiety with a hydroxamic acid moiety, which are common in many known HDAC inhibitors, results in a significant loss in selectivity over HDAC1. Taken together, these results demonstrate that the compounds of the disclosure, characterized by having a 1,3,4-oxadiazole, have surprising potency and selectivity for inhibition of HDAC6, and possess the potential for significant therapeutic utility.

TABLE 3

Comparison Results

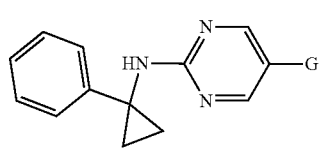

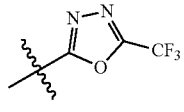 [SMILES: *c1nnc(C(F)(F)F)o1]

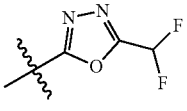 [SMILES: *c1nnc(C(F)F)o1]

| G | hydroxamic acid | 1,2,4-oxadiazole CF$_3$ | 1,2,4-oxadiazole CHF$_2$ | Ex 1 | Ex 4 |
|---|---|---|---|---|---|
| HDAC1 IC$_{50}$ (µM) | 0.086 | | >30 | >30 | >30 |
| HDAC2 IC$_{50}$ (µM) | 13 | | | >30 | >30 |
| HDAC3 IC$_{50}$ (µM) | 4.1 | | | >30 | >30 |
| HDAC4 IC$_{50}$ (µM) | 0.013 | | | >30 | >30 |
| HDAC5 IC$_{50}$ (µM) | 0.25 | | | >30 | >30 |
| HDAC6 IC$_{50}$ (µM) | <0.0015 | 0.15 | 2.9 | 0.21 | 0.023 |
| HDAC7 IC$_{50}$ (µM) | 0.020 | | | >30 | >30 |
| HDAC8 IC$_{50}$ (µM) | >30 | | | >30 | >30 |
| HDAC9 IC$_{50}$ (µM) | 0.077 | | | >30 | >30 |
| HDAC10 IC$_{50}$ (µM) | 6.4 | | | >30 | >30 |
| HDAC11 IC$_{50}$ (µM) | >30 | | | >30 | >30 |

In addition, several exemplary compounds were administered to mice in single, oral dose pharmacokinetic experiments. The results in Table 4 demonstrate that compounds of the disclosure have advantageous pharmacokinetic profiles. All of the exemplary compounds evaluated possess a superior Cmax over that of ricolinostat, a moderately selective clinical HDAC6 hydroxamate-based inhibitor. In addition, all but one of the exemplary compounds evaluated possess a superior half-life over that of ricolinostat.

TABLE 4

Oral, Single Dose Mouse PK Results at 5 mg/kg

| Example | Half-life (h) | Cmax (ng/mL) |
|---|---|---|
| Ricolinostat[a] | 2.7 | 47 |
| 38(+)[b] | 2.7 | 1111 |
| 103(+)[b] | 3.2 | 2373 |
| 108[b] | 2.3 | 2123 |
| 109[b] | 3.4 | 678 |
| 110[b] | 4.3 | 830 |
| 113(+)[b] | 3.5 | 1357 |
| 115(+)[b] | 4.3 | 656 |
| 116(+)[b] | 4.5 | 1006 |
| 118(+)[b] | 23.2 | 697 |
| 122(+)[b] | 18.4 | 2930 |
| 142(+)[b] | 4.1 | 2533 |
| 150(+)[c] | 9.3 | 3388 |
| 171(+)[c] | 3.3 | 2593 |
| 173(+)[c] | 5.6 | 2823 |

[a]20% CremEL in H20;
[b]1% CMC in water;
[c]2% DMSO, 0.2% Tween80, 97.8% of 1% CMC.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:
1. A compound of Formula I-c

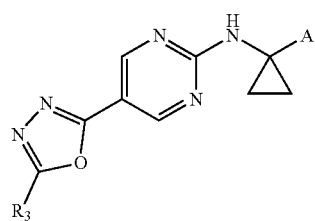

I-c or a pharmaceutically acceptable salt thereof; wherein:
$R^3$ is haloalkyl or —$OR^g$;
A is aryl, heteroaryl, cycloalkyl, heterocycloalkyl, arylalkyl, or alkyl, wherein each A is optionally substituted with 1-3 independent substituents $R^5$;
each occurrence of $R^5$ is, independently, halogen, cyano, alkyl, haloalkyl, —$NR^aR^b$, —$NHSO_2R^c$, —$(CH_2)_nNR^aR^b$, —$(CH_2)_nC(O)NR^aR^b$, —$(CH_2)_nNR^dSO_2R^d$, —$S(O)R^d$, —$S(O)_2R^d$, —$CO_2R^e$, —$COR^f$, —$(CR^eR^f)_nOR^f$, —$OR^f$, or aryl substituted with 0-3 independent halogen, —$NR^aR^b$, —$NHSO_2R^c$, —$(CH_2)_nNR^aR^b$, —$(CH_2)C(O)NR^aR^b$, —$(CH_2)_nNR^dSO_2R^d$, —$S(O)R^d$, —$S(O)_2R^d$, —$CO_2R^e$, —$COR^f$, —$(CR^eR^f)_nOR^f$, or —$OR^f$; or two occurrences of $R^5$, together with the atoms to which they are attached, form a cycloalkyl, heterocycloalkyl, aryl, or heteroaryl ring;
each n is independently 1, 2, 3, 4, 5, 6, 7, 8, 9, or 10;
each occurrence of $R^a$, $R^b$, $R^c$, $R^d$, $R^e$, and $R^f$ is, independently, hydrogen, acyl, alkoxyalkyl, alkyl, alkenyl, alkynyl, heteroalkyl, haloalkyl, cycloalkyl, heterocycloalkyl, aryl, heteroaryl, arylalkyl, heteroarylalkyl, heterocycloalkylalkyl, a nitrogen protecting group when attached to a nitrogen atom, or an oxygen protecting group when attached to an oxygen atom; or $R^a$ and $R^b$ together with the atoms to which they are attached form a heterocycloalkyl ring; or $R^e$ and $R^f$ together with the atoms to which they are attached form a cycloalkyl ring; or 2 instances of $R^d$ together with the atoms to which they are attached form a heterocycloalkyl ring; and
$R^g$ is haloalkyl;
provided that the compound is further characterized by one or more of the following:
$R^3$ is —$CH_2F$;
A is cycloalkyl, heterocycloalkyl, arylalkyl, or alkyl, wherein each A is optionally substituted with 1-3 independent substituents $R^5$;
A is heteroaryl substituted with 1-3 independent substituents $R^5$;
A is phenyl substituted with 1-3 independent substituents $R^5$ and at least one $R^5$ is not Cl, F, —$CF_3$, or methoxy; or
A is an aryl other than phenyl, optionally substituted with 1-3 independent substituents $R^5$.

2. The compound of claim 1, or a pharmaceutically acceptable salt thereof, wherein: $R^3$ is —$CF_3$, —$CHF_2$, or —$CH_2F$.

3. The compound of claim 2, or a pharmaceutically acceptable salt thereof, wherein:
each $R^5$ is, independently, halogen, cyano, alkyl, haloalkyl, —$NR^aR^b$, or —$OR^f$; and $R^f$ is hydrogen, alkyl, or haloalkyl.

4. The compound of claim 3, or a pharmaceutically acceptable salt thereof, wherein: each occurrence of $R^a$, $R^b$, and $R^f$ is, independently, hydrogen, alkyl, or haloalkyl.

5. The compound of claim 4, or a pharmaceutically acceptable salt thereof, wherein:
A is cycloalkyl, heterocycloalkyl, arylalkyl, or alkyl, wherein each A is optionally substituted with 1-3 independent substituents $R^5$.

6. The compound of claim 4, or a pharmaceutically acceptable salt thereof, wherein:
A is heteroaryl substituted with 1-3 independent substituents $R^5$.

7. The compound of claim 4, or a pharmaceutically acceptable salt thereof, wherein:
A is substituted with 1-3 independent substituents $R^5$ and at least one $R^5$ is not Cl, F, —$CF_3$, or methoxy.

8. The compound of claim 2, or a pharmaceutically acceptable salt thereof, wherein:

each R⁵ is phenyl substituted with 0-3 independent halogen, —NRᵃRᵇ, or —ORᶠ; and each occurrence of Rᵃ, Rᵇ, and Rᶠ is, independently, hydrogen, alkyl, or haloalkyl.

9. The compound of claim 1, or a pharmaceutically acceptable salt thereof, wherein:
each occurrence of R⁵ is, independently, halogen, cyano, alkyl, haloalkyl, or —ORᶠ; and Rᶠ is alkyl, or haloalkyl.

10. The compound of claim 2, or a pharmaceutically acceptable salt thereof, wherein:
each occurrence of R⁵ is halogen, cyano, methyl optionally substituted with one or more halogen, or methoxy optionally substituted with one or more halogen.

11. The compound of claim 10, or a pharmaceutically acceptable salt thereof, wherein:
A is aryl or heteroaryl.

12. The compound of claim 11, wherein: A is pyridinyl.

13. The compound of claim 11, wherein: A is phenyl.

14. The compound of claim 1, or a pharmaceutically acceptable salt thereof, wherein:
R³ is —CF₃, —CHF₂, or —CH₂F;
A is phenyl substituted with 1-3 independent substituents R⁵; and
at least one occurrence of R⁵ is cyano, alkyl, or —ORᶠ; and Rᶠ is hydrogen, alkyl, or haloalkyl.

15. A method of selectively inhibiting histone deacetylase 6 (HDAC6) activity in vivo over a histone deacetylase enzyme selected from the group consisting of: HDAC2, HDAC3, HDAC4, HDAC5, HDAC7, HDAC8, HDAC9, HDAC10 and HDAC11, the method administering a compound of Formula I-c:

I-c or a pharmaceutically acceptable salt thereof, to a subject; wherein
R³ is —CF₂H;
A is phenyl or pyridyl optionally substituted with 1-3 independent substituents R⁵; and
each occurrence of R⁵ is halogen, cyano, methyl optionally substituted with one or more halogen, or methoxy optionally substituted with one or more halogen.

16. The method of claim 15, wherein each occurrence of R⁵ is, independently, Cl, F, methyl optionally substituted with one or more F, or methoxy optionally substituted with one or more F.

17. The method of claim 15, wherein each occurrence of R⁵ is, independently, F or —CF₃.

18. The method of claim 15, wherein the compound is Compound 4 or a pharmaceutically acceptable salt thereof, (4)

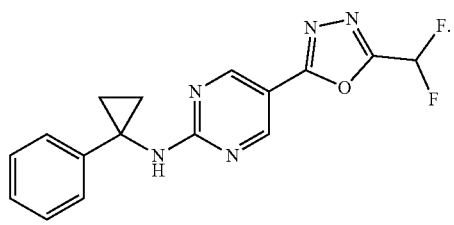

19. The method of claim 15, wherein the compound is Compound 5 or a pharmaceutically acceptable salt thereof, (5)

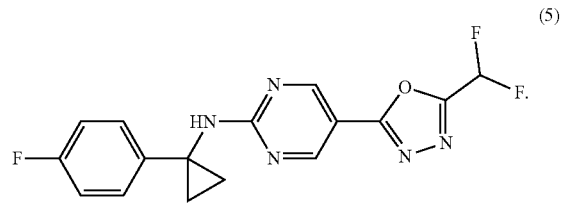 [SMILES: Fc1ccc(C2(Nc3ncc(-c4nnc(C(F)F)o4)cn3)CC2)cc1]

20. The method of claim 15, wherein the compound is Compound 11 or a pharmaceutically acceptable salt thereof.

(11)

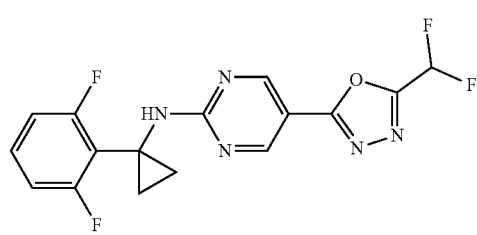

21. The method of claim 15, wherein the compound is Compound 63 or a pharmaceutically acceptable salt thereof, (63)

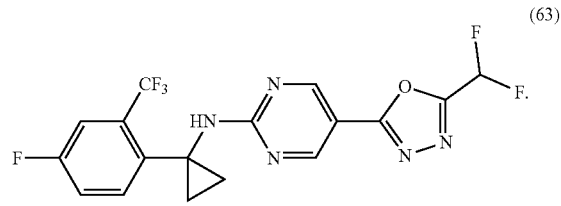 [SMILES: Fc1ccc(C2(Nc3ncc(-c4nnc(C(F)F)o4)cn3)CC2)c(C(F)(F)F)c1]

* * * * *